(12) United States Patent
Kim et al.

(10) Patent No.: US 9,481,682 B2
(45) Date of Patent: Nov. 1, 2016

(54) SUBSTITUTED BENZAMIDES AND SUBSTITUTED PYRIDINECARBOXAMIDES AS BTK INHIBITORS

(71) Applicant: MERCK SHARP & DOHME CORP., Rahway, NJ (US)

(72) Inventors: Ronald M. Kim, Summit, NJ (US); Jian Liu, Edison, NJ (US); Xiaolei Gao, Bridgewater, NJ (US); Sobhana Babu Boga, Scotch Plains, NJ (US); Deodialsingh Guiadeen, Chesterfield, NJ (US); Joseph A. Kozlowski, Summit, NJ (US); Wensheng Yu, Edison, NJ (US); Rajan Anand, Fanwood, NJ (US); Younong Yu, East Brunswick, NJ (US); Oleg B. Selyutin, West Windsor, NJ (US); Ying-Duo Gao, Holmdel, NJ (US); Hao Wu, Shanghai (CN); Shilan Liu, Shanghai (CN); Chundao Yang, Shanghai (CN); Hongjian Wang, Shanghai (CN)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/762,954

(22) PCT Filed: Jan. 22, 2014

(86) PCT No.: PCT/CN2014/000082
§ 371 (c)(1),
(2) Date: Jul. 23, 2015

(87) PCT Pub. No.: WO2014/114185
PCT Pub. Date: Jul. 31, 2014

(65) Prior Publication Data
US 2015/0353570 A1    Dec. 10, 2015

(30) Foreign Application Priority Data

Jan. 23, 2013  (WO) ................ PCT/CN2013/070876
Jan. 9, 2014   (CN) .......................... 2014 1 0010914

(51) Int. Cl.
*A61K 31/4985* (2006.01)
*A61K 31/4427* (2006.01)
(Continued)

(52) U.S. Cl.
CPC ......... *C07D 491/048* (2013.01); *A61K 31/497* (2013.01); *A61K 31/4985* (2013.01); *A61K 31/506* (2013.01); *A61K 31/519* (2013.01); *A61K 31/5365* (2013.01);
(Continued)

(58) Field of Classification Search
CPC ..................... A61K 31/4427; A61K 31/4985; C07D 213/81; C07D 241/38

USPC .................... 514/249, 354; 544/350; 546/323
See application file for complete search history.

(56) References Cited

U.S. PATENT DOCUMENTS

| 2008/0076921 A1 | 3/2008 | Honigberg et al. |
| 2014/0206681 A1* | 7/2014 | Kim ..................... A61K 31/519 514/230.5 |

FOREIGN PATENT DOCUMENTS

| WO | WO2005014599 | 2/2005 |
| WO | WO2005037836 A2 | 4/2005 |

(Continued)

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*

(Continued)

*Primary Examiner* — Douglas M Willis
(74) *Attorney, Agent, or Firm* — Matthew A. Leff; John C. Todaro

(57) ABSTRACT

The present invention provides Bruton's Tyrosine Kinase (Btk) inhibitor compounds according to Formula I or a pharmaceutically acceptable salt thereof or to pharmaceutical compositions comprising these compounds and to their use in therapy. In particular, the present invention relates to the use of Btk inhibitor compounds in the treatment of Btk mediated disorders.

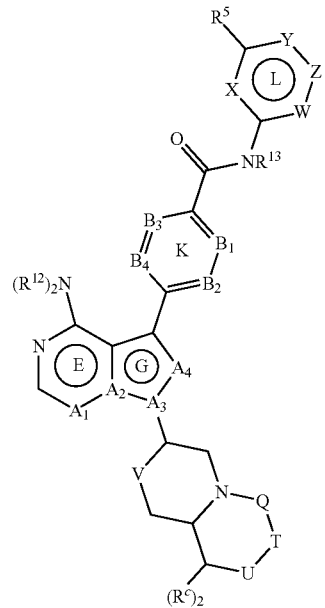

Formula I

23 Claims, No Drawings

(51) Int. Cl.
| | |
|---|---|
| *C07D 241/38* | (2006.01) |
| *C07D 213/81* | (2006.01) |
| *C07D 491/048* | (2006.01) |
| *A61K 31/497* | (2006.01) |
| *A61K 31/519* | (2006.01) |
| *C07D 487/04* | (2006.01) |
| *C07D 519/00* | (2006.01) |
| *A61K 31/506* | (2006.01) |
| *A61K 31/5365* | (2006.01) |
| *A61K 31/5383* | (2006.01) |
| *A61K 45/06* | (2006.01) |
| *C07D 455/02* | (2006.01) |
| *C07D 471/04* | (2006.01) |
| *C07D 498/04* | (2006.01) |

(52) U.S. Cl.
CPC .......... *A61K 31/5383* (2013.01); *A61K 45/06* (2013.01); *C07D 455/02* (2013.01); *C07D 471/04* (2013.01); *C07D 487/04* (2013.01); *C07D 498/04* (2013.01); *C07D 519/00* (2013.01)

(56) References Cited

FOREIGN PATENT DOCUMENTS

| | | |
|---|---|---|
| WO | WO2007064883 A2 | 6/2007 |
| WO | WO2007064993 A2 | 6/2007 |
| WO | WO2008121742 | 10/2008 |
| WO | WO2011095556 A1 | 8/2011 |
| WO | WO2011153514 A1 | 12/2011 |
| WO | WO2013010380 A1 | 1/2013 |
| WO | WO2013010868 | 1/2013 |
| WO | WO2013010869 | 1/2013 |
| WO | WO2014113932 | 7/2014 |
| WO | WO2014116504 | 7/2014 |

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

SUBSTITUTED BENZAMIDES AND SUBSTITUTED PYRIDINECARBOXAMIDES AS BTK INHIBITORS

FIELD OF THE INVENTION

The present invention relates to Btk inhibitor compounds, to pharmaceutical compositions comprising these compounds and to their use in therapy. In particular, the present invention relates to the use of Btk inhibitor compounds in the treatment of Bruton's Tyrosine Kinase (Btk) mediated disorders.

BACKGROUND OF THE INVENTION

B lymphocyte activation is key in the generation of adaptive immune responses. Derailed B lymphocyte activation is a hallmark of many autoimmune diseases and modulation of this immune response is therefore of therapeutic interest. Recently the success of B cell therapies in autoimmune diseases has been established. Treatment of rheumatoid arthritis (RA) patients with Rituximab (anti-CD20 therapy) is an accepted clinical therapy. More recent clinical trial studies show that treatment with Rituximab also ameliorates disease symptoms in relapsing remitting multiple sclerosis (RRMS) and systemic lupus erythematosus (SLE) patients. This success supports the potential for future therapies in autoimmune diseases targeting B cell immunity.

Bruton's tyrosine kinase (Btk) is a Tec family non-receptor protein kinase, expressed in B cells and myeloid cells. The function of Btk in signaling pathways activated by the engagement of the B cell receptor (BCR) and FcεR1 on mast cells is well established. In addition, a function for Btk as a downstream target in Toll like receptor signaling was suggested. Functional mutations in Btk in human results in the primary immunodeficiency disease called XLA which is characterized by a defect in B cell development with a block between pro- and pre-B cell stage. This results in an almost complete absence of B lymphocytes in human causing a pronounced reduction of serum immunoglobulin of all classes. These finding support the key role for Btk in the regulation of the production of auto-antibodies in autoimmune diseases. In addition, regulation of Btk may affect BCR-induced production of pro-inflammatory cytokines and chemokines by B cells, indicating a broad potential for Btk in the treatment of autoimmune diseases.

With the regulatory role reported for Btk in FcεR-mediated mast cell activation, Btk inhibitors may also show potential in the treatment of allergic responses [Gilfillan et al., Immunological Reviews 288 (2009) pp 149-169].

Furthermore, Btk is also reported to be implicated in RANKL-induced osteoclast differentiation [Shinohara et al, Cell 132 (2008) pp 794-806] and therefore may also be of interest for the treatment of bone resorption disorders.

Other diseases with an important role for dysfunctional B cells are B cell malignancies. Indeed anti-CD20 therapy is used effectively in the clinic for the treatment of follicular lymphoma, diffuse large B-cell lymphoma and chronic lymphocytic leukemia [Lim et al, Haematologica, 95 (2010) pp 135-143]. The reported role for Btk in the regulation of B cell proliferation and apoptosis of B cells indicates there is potential for Btk inhibitors in the treatment of B cell lymphomas as well. Inhibition of Btk seems to be relevant in particular for B cell lymphomas due to chronic active BCR signaling [Davis et al, Nature, 463 (2010) pp 88-94].

Some classes of Btk inhibitor compounds have been described as kinase inhibitors, e.g. Imidazo[1,5-f][1,2,4]triazine compounds have been described in WO2005097800 and WO2007064993; Imidazo[1,5-a]pyrazine compounds have been described in WO2005037836 and WO2001019828 as IGF-1R enzyme inhibitors.

Some of the Btk inhibitors reported are not selective over Src-family kinases. With dramatic adverse effects reported for knockouts of Src-family kinases, especially for double and triple knockouts, this is seen as prohibitive for the development of Btk inhibitors that are not selective over the Src-family kinases.

Both Lyn-deficient and Fyn-deficient mice exhibit autoimmunity mimicking the phenotype of human lupus nephritis. In addition, Fyn-deficient mice also show pronounced neurological defects. Lyn knockout mice also show an allergic-like phenotype, indicating Lyn as a broad negative regulator of the IgE-mediated allergic response by controlling mast cell responsiveness and allergy-associated traits [Odom et al, J. Exp. Med., 199 (2004) pp 1491-1502]. Furthermore, aged Lyn knock-out mice develop severe splenomegaly (myeloid expansion) and disseminated monocyte/macrophage tumors [Harder et al, Immunity, 15 (2001) pp 603-615]. These observations are in line with hyperresponsive B cells, mast cells and myeloid cells, and increased Ig levels observed in Lyn-deficient mice. Female Src knockout mice are infertile due to reduced follicle development and ovulation [Roby et al, Endocrine, 26 (2005) pp 169-176]. The double knockouts $Src^{-/-}Fyn^{-/-}$ and $Src^{-/-}Yes^{-/-}$ show a severe phenotype with effects on movement and breathing. The triple knockouts $Src^{-/-}Fyn^{-/-}Yes^{-/-}$ die at day 9.5 [Klinghoffer et al, EMBO J., 18 (1999) pp 2459-2471]. For the double knockout $Src^{-/-}Hck^{-/-}$, two thirds of the mice die at birth, with surviving mice developing osteopetrosis, extramedullary hematopoieseis, anemia, leukopenia [Lowell et al, Blood, 87 (1996) pp 1780-1792].

Hence, an inhibitor that inhibits multiple or all kinases of the Src-family kinases simultaneously may cause serious adverse effects.

SUMMARY OF THE INVENTION

The present invention provides compounds which inhibit Btk activity, their use for treatment of Btk mediated diseases and disorders, in particular autoimmune diseases and inflammatory diseases, as well as pharmaceutical compositions comprising such compounds and pharmaceutical carriers.

DETAILED DESCRIPTION

The object of the present invention is to provide Bruton's Tyrosine Kinase (Btk)inhibitor compounds, to pharmaceutical compositions comprising these compounds and to their use in therapy. In particular, the present invention relates to the use of Btk inhibitor compounds in the treatment of Btk mediated disorders.

More specifically, the present invention provides Btk inhibitor compounds according to Formula I, or pharmaceutically acceptable salts thereof Formula I

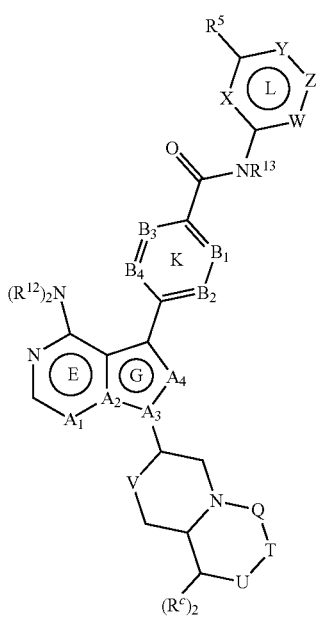

wherein:

$A_1$, $A_2$, $A_3$, and $A_4$ are independently C, CH, $CR^{11}$ or N and bicyclic ring system E-G is selected from the group consisting of:

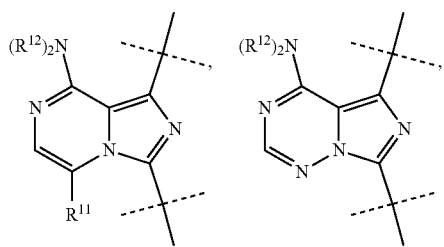

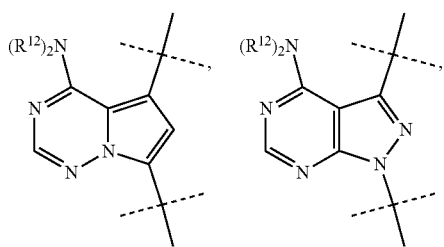

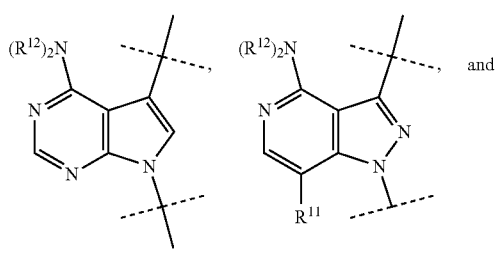

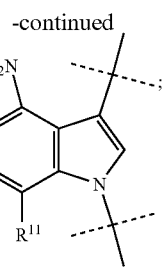

$R^{11}$ is independently selected from the group consisting of:
a) deuterium,
b) H,
c) halogen,
d) cyano,
e) $C^2H_3$,
f) —COOH,
g) —$CO_2$(1-6C)alkyl,
h) —CO(1-6C)alkyl,
i) —CONH(1-6C)alkoxy,
j) —CONH(1-6C)alkyl,
k) —CONdi(1-6C)alkyl,
l) (1-6C)alkyl,
m) (3-7C)cycloalkyl,
n) (1-6C)alkoxy,
o) aryl,
p) (1-5C)heteroaryl,
q) (2-6C)alkenyl,
r) (2-6C)alkynyl, and
s) (4-7C)heterocycloalkyl, $R^{11}$ is optionally substituted with one or more groups selected from: halogen, (1-6C)alkyl, (1-5C)alkoxy, hydroxyl, or oxo;

$R^{12}$ is independently selected from the group consisting of: H, (1-3C)alkyl, (1-3C)alkylNHC(O), (1-3C)alkylOC(O), and (1-3C)alkylC(O);

$R^{13}$ is independently selected from the group consisting of: H and (1-4C)alkoxy;

wherein in aromatic ring K
$B_1$ is N or $C(R^7)$;
$B_2$ is N or $C(R^8)$;
$B_3$ is N or $C(R^9)$;
$B_4$ is N or $C(R^{10})$;

$R^7$ is H, halogen, OH, (1-3C)alkyl, (1-6C)alkoxy, (3-6C)cycloalkoxy, (1-5C)heterocycloalkoxy, halo(1-3C)alkyl, or CN; wherein $R^7$ may optionally be substituted with one, two or three halogens, OH, (2-4C)alkynyl, —C(O)$NH_2$, —C(O)OH, or —C(O)(1-4C)alkyl;

$R^8$ is H, halogen, OH, (1-3C)alkyl, (1-6C)alkoxy, (3-6C)cycloalkoxy, (1-5C)heterocycloalkoxy, halo(1-3C)alkyl, or CN; wherein $R^8$ may optionally be substituted with one, two or three halogens, OH, (2-4C)alkynyl, —C(O)$NH_2$, —C(O)OH, or —C(O)(1-4C)alkyl;

$R^9$ is H, halogen, OH, (1-3C)alkyl, (1-6C)alkoxy, (3-6C)cycloalkoxy, (1-5C)heterocycloalkoxy, halo(1-3C)alkyl, or CN; wherein $R^9$ may optionally be substituted with one, two or three halogens, OH, (2-4C)alkynyl, —C(O)$NH_2$, —C(O)OH, or —C(O)(1-4C)alkyl;

$R^{10}$ is H, halogen, OH, (1-3C)alkyl, (1-6C)alkoxy, (3-6C)cycloalkoxy, (1-5C)heterocycloalkoxy, halo(1-3C)alkyl, or CN; wherein $R^{10}$ may optionally be substituted with one, two or three halogens, OH, (2-4C)alkynyl, —C(O)$NH_2$, —C(O)OH, or —C(O)(1-4C)alkyl;

wherein in heteroaromatic ring L

W is CH, N or S;

X is $C(R^{6a})$, N, O or S;

Y is $C(R^6)$, $N(R^{6b})$, O or S;

Z is $C(R^{6a})$, N or a bond;

$R^5$ is H, halogen, cyano, (1-4C)alkyl, (1-5C)alkoxy, (3-6C)cycloalkyl, (3-6C)cycloalkoxy, or —C(O)O(1-3C)alkyl; wherein $R^5$ may optionally be substituted with one, two or three halogens, OH, or (1-3C)alkoxy; or $R^5$ is aryl, (1-5C)heteroaryl or (2-6C)heterocycloalkyl, wherein $R^5$ may optionally be substituted with halogen, (1-6C)alkyl, or (1-3C)alkoxy;

$R^6$ is H, halogen, cyano, (1-6C)alkyl, or (1-6C)alkoxy; wherein $R^6$ may optionally be substituted with one, two or three halogen or cyano;

$R^{6a}$ is H, (1-4C)alkyl or (3-6C)cycloalkyl;

$R^{6b}$ is H, (1-3C)alkyl, (3-6C)cycloalkyl, or —C(O)O(1-4C)alkyl; or $R^5$ and $R^6$ together can form a carbocyclic or heterocyclic 5- to 6-membered ring, and optionally be unsaturated or aromatic; or $R^5$ and $R^6$ together can form (3-7C)cycloalkenyl or (2-6C)heterocycloalkenyl; each optionally substituted with (1-3C)alkyl or with one or more halogen;

Q is C=O, $C(R^f)_2$ or $C=N(R^h)$;

T is $C(R^e)_2$, O, $NR^e$, or a bond;

U is $C(R^d)_2$, O, or $NR^d$;

V is $C(R^g)_2$, O, or a bond;

$R^c$, $R^d$, $R^e$, and $R^f$ are each independently selected from H, halogen, (1-6C)alkyl, hydroxyl, (1-6C)alkenyl, or —C(O)$R^z$, wherein $R^z$ is independently selected from (1-5C)heteroaryl, aryl and hydroxyl; any alkyl group of $R^c$, $R^d$, $R^e$, or $R^f$ may optionally be substituted with hydroxy, —C(O)(1-3C)alkoxy or —C(O)OH;

$R^g$ is independently selected from H, halogen, (1-6C)alkyl, (1-6C)alkoxy, halo(1-6C)alkyl, or hydroxyl;

$R^h$ is independently selected from H or CN;

with the proviso that:

1) up to 2 atoms of X, Y, and Z can simultaneously be a heteroatom;

2) when one atom selected from X or Y is O or S, then Z is a bond and the other atom selected from X or Y cannot be O or S;

3) when Z is CH or N, then Y is $C(R^6)$ or N and X is CH, or N;

4) in ring K, up to 2 of $B_1$, $B_2$, $B_3$ and $B_4$ can be N;

5) when Q is $C(R^f)_2$, then T is $C(R^e)$;

6) when T is $NR^e$, then $R^e$ is not halogen; and 7) when U is $NR^d$, then $R^d$ is not halogen.

In another aspect, the invention relates to a compound having Formula II, or pharmaceutically acceptable salts thereof,

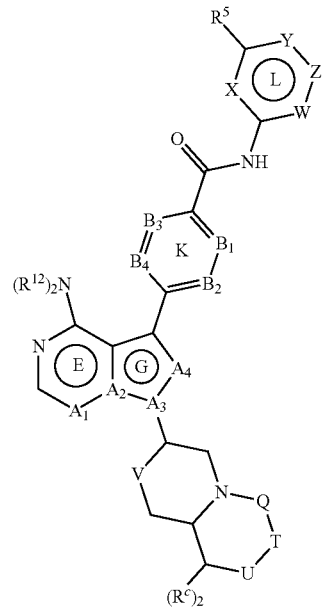

Formula II wherein:

$A_1$, $A_2$, $A_3$, and $A_4$ are independently C, CH, $CR^{11}$ or N and bicyclic ring system E-G is selected from the group consisting of:

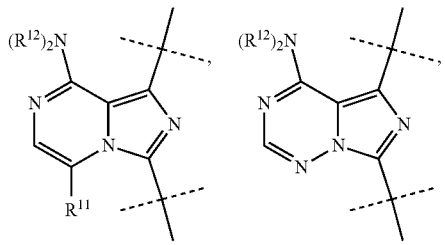

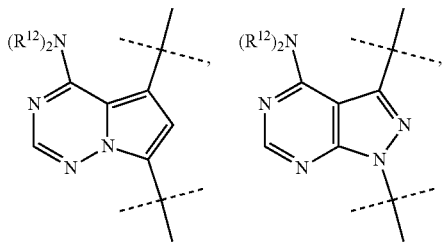

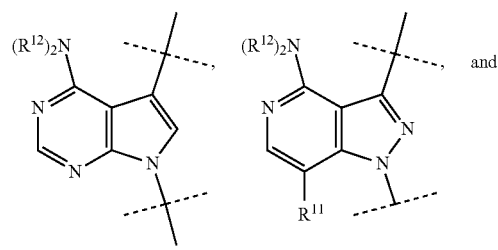

and

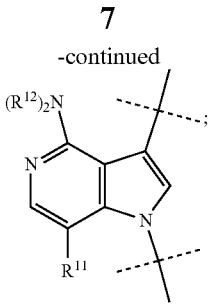

R¹¹ is independently selected from the group consisting of:
  a) deuterium,
  b) H,
  c) halogen,
  d) cyano,
  e) $C_2H_3$,
  f) COOH,
  g) $CO_2$(1-6C)alkyl,
  h) CO(1-6C)alkyl,
  i) CONH(1-6C)alkoxy,
  j) CONH(1-6C)alkyl,
  k) CONdi(1-6C)alkyl,
  l) (1-6C)alkyl,
  m) (3-7C)cycloalkyl,
  n) (1-6C)alkoxy,
  o) (6-10C)aryl,
  p) (1-5C)heteroaryl,
  q) (2-6C)alkenyl,
  r) (2-6C)alkynyl, and
  s) (4-7C)heterocycloalkyl, R¹¹ is optionally substituted with one or more groups selected from: halogen, (1-6C)alkyl, (1-5C)alkoxy, hydroxyl, or oxo;

R¹² is independently selected from the group consisting of H, (1-3C)alkyl, (1-3C)alkylNHC(O), and (1-3C)alkylOC(O);

wherein in aromatic ring K
$B_1$ is N or $C(R^7)$;
$B_2$ is N or $C(R^8)$;
$B_3$ is N or $C(R^9)$;
$B_4$ is N or $C(R^{10})$;
$R^7$ is H, halogen, OH, (1-3C)alkyl, (1-3C)alkoxy or halo(1-3C)alkyl, CN; any alkoxy may optionally be substituted with one, two or three halogen;
$R^8$ is H, halogen, OH, (1-3C)alkyl, (1-3C)alkoxy or halo(1-3C)alkyl, CN; any alkoxy may optionally be substituted with one, two or three halogen;
$R^9$ is H, halogen, OH, (1-3C)alkyl, (1-3C)alkoxy or halo(1-3C)alkyl, CN; any alkoxy may optionally be substituted with one, two or three halogen;
$R^{10}$ is H, halogen, OH, (1-3C)alkyl, (1-3C)alkoxy or halo(1-3C)alkyl, CN; any alkoxy may optionally be substituted with one, two or three halogen;

wherein in heteroaromatic ring L
W is CH or N;
X is CH, N, O or S;
Y is $C(R^6)$, N, O or S;
Z is CH, N or a bond;
$R^5$ is H, halogen, cyano, (1-4C)alkyl, (1-5C)alkoxy, (3-6C)cycloalkyl or (3-6C)cycloalkoxy; any alkyl, alkoxy, cycloalkyl or cycloalkocy of $R^5$ may optionally be substituted with one, two or three halogen; or $R^5$ is (6-1C)aryl, (1-5C)heteroaryl or (2-6C)heterocycloalkyl, the aryl or heterocycloalkyl of which may optionally be substituted with halogen, (1-6C)alkyl, (1-3C)alkoxy;
$R^6$ is H, halogen, cyano, (1-6C)alkyl, or (1-6C)alkoxy, any alkyl or alkoxy of $R^6$ may optionally be substituted with one, two or three halogen or cyano; or
$R^5$ and $R^6$ together can form a carbocyclic or heterocyclic 5 to 6-membered ring, and optionally be unsaturated or aromatic; or $R^5$ and $R^6$ together can form (3-7C)cycloalkenyl or (2-6C)heterocycloalkenyl; each optionally substituted with (1-3C)alkyl or with one or more halogen;
Q is C=O or $C(R^f)_2$;
T is $C(R^e)_2$, O, $NR^e$, or a bond;
U is $C(R^d)_2$, O, or $NR^d$;
V is $C(R^g)_2$, O, or a bond;
$R^c$, $R^d$, $R^e$, and $R^f$ are each independently selected from H, halogen, (1-6C)alkyl, and hydroxyl; any alkyl group of $R^c$, $R^d$, $R^e$, or $R^f$ may optionally be substituted with hydroxyl;
$R^g$ is independently selected from H, halogen, (1-6C)alkyl, (1-6C)alkoxy, halo(1-6C)alkyl, and hydroxyl;
with the proviso that:
  1) up to 2 atoms of X, Y, and Z can simultaneously be a heteroatom;
  2) when one atom selected from X, Y is O or S, then Z is a bond and the other atom selected from X, Y cannot be O or S;
  3) when Z is CH or N, then Y is $C(R^6)$ or N and X is C, or N;
  4) in ring K, up to 2 of $B_1$, $B_2$, $B_3$ and $B_4$ can be N; and
  5) when Q is $C(R^f)_2$, then T is $C(R^e)_2$.

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "alkoxy", etc.

As used herein, and throughout this disclosure, the following terms, unless otherwise indicated, shall be understood to have the following meanings:

Halogen means fluorine, chlorine, bromine or iodine. Fluorine, chlorine or bromine being preferred halogens; fluorine or chlorine being more preferred.

The term "alkyl," as used herein, refers to an aliphatic hydrocarbon group having one of its hydrogen atoms replaced with a bond having the specified number of carbon atoms. In different embodiments, an alkyl group contains, for example, from 1 to 6 carbon atoms (1-6C)Alkyl or from 1 to 3 carbon atoms (1-3C)Alkyl. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

Unless specified otherwise, "alkyl" includes both branched- and straight-chain saturated aliphatic hydrocarbon groups, including all isomers, having the specified number of carbon atoms; for example, "(1-6C)Alkyl" includes all of the hexyl alkyl and pentyl alkyl isomers as well as n-, iso-, sec- and t-butyl, n- and isopropyl, ethyl and methyl. "Alkylene" refers to both branched- and straight-chain saturated aliphatic hydrocarbon groups, including all isomers, having the specified number of carbons, and having two terminal end chain attachments; for example, the term "A-C$_4$alkylene-B" represents, for example, A-CH$_2$—CH$_2$—CH$_2$—CH$_2$—B, A-CH$_2$—CH$_2$—CH(CH$_3$)—CH$_2$—B, A-CH$_2$—CH(CH$_2$CH$_3$)—B, A-CH$_2$—C(CH$_3$)(CH$_3$)—B, and the like.

Haloalkyl means a branched or unbranched alkyl group having the recited number of carbon atoms, in which one and up to all hydrogen atoms are replaced by a halogen; halogen is as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo. For example, a halo(1-3C)alkyl means a branched or unbranched alkyl group having 1, 2, or 3 carbon atoms, in which at least one hydrogen atom is replaced by a halogen. Examples of "haloalkyl" include, but are not limited to, fluoromethyl, difluoromethyl, trifluoromethyl, 1-fluoroethyl, 2-fluoroethyl, 2,2-difluoroethyl, 2,2,2-trifluoroethyl, and perfluoro-n-propyl.

Alkoxy means an alkoxy group having the recited number of carbon atoms, the alkyl moiety having the same meaning as previously defined, e.g., "Alkoxy" refers to an alkyl-O— group represented by a linear or branched alkyl group of indicated number of carbon atoms attached through an oxygen bridge; for example "(1-6C)Alkoxy" includes —OCH$_3$, —OCH$_2$CH$_3$, —OCH(CH$_3$)$_2$, —O(CH$_2$)$_5$CH$_3$, and the like.

Cycloalkoxy means a cycloalkyl group having the recited number of carbon atoms, with the same meaning as previously defined, attached via a ring carbon atom to an exocyclic oxygen atom, such as cyclopropoxyl, cyclobutoxyl, or cyclopentoxyl. "Cycloalkoxy" refers to a cycloalkyl-O— group represented by a cycloalkyl group of indicated number of carbon atoms attached through an oxygen bridge; for example "(3-6C)cycloalkoxy" includes —O-cyclopropyl, —O-cyclobutyl, —O-cyclopentyl, or —O-cyclohexyl.

Heterocycloalkoxy means a cycloalkyl group having the recited number of carbon atoms, and 1-3 heteroatoms selected from N, O and/or S, with the same meaning as previously defined, attached via a ring carbon atom to an exocyclic oxygen atom.

Unless otherwise specifically noted as only "unsubstituted" or only "substituted", alkyl groups are unsubstituted or substituted with 1 to 3 substituents on each carbon atom.

Alkenyl means a branched or unbranched group having the recited number of carbon atoms, wherein a double bond exists between two carbon atoms, such as ethenyl, 2-propenyl, isobutenyl, 2-butenyl, and n-pentenyl.

Alkynyl means a branched or unbranched group having the recited number of carbon atoms, wherein a triple bond exists between two carbon atoms, such as ethynyl, propynyl, 2-propynyl, n-butynyl, 2-butynyl, n-pentynyl, isopentynyl, isohexynyl or n-hexynyl.

The term "carbocyclic" means a hydrocarbon ring having the specified number of carbon atoms, the ring being saturated, unsaturated or aromatic.

The term "cycloalkyl" means a cyclic ring of an alkane having the specified total ring carbon atoms; for example, "(3-6C)Cycloalkyl" includes cyclopropyl, cyclobutyl, cyclopentyl, or cyclohexyl.

The term "heterocycloalkyl" means a ring having the specified number of carbon atoms, the ring being saturated, unsaturated or aromatic. Heterocycloalkyl may be a 4-8 membered monocyclic or 8-10 membered bicyclic ring having 1-5 heteroatoms. Preferably 2-5 carbon atoms, more preferably 3-5 carbon atoms, and 1-3 heteroatoms selected from N, O and/or S, which may be attached via a nitrogen atom, if feasible, or a carbon atom. Preferred number of heteroatoms is one or two. Preferred heteroatoms are N or O. For example, "(1-3C)heterocycloalkyl" includes heterocycloalkyl with 1-3 carbon atoms, such as piperidine, morpholine, pyrrolidine and piperazine. Heterocycloalkyl includes, but is not limited to (1-5C)Heterocycloalkyl, (1-6C)Heterocycloalkyl, (2-5C)Heterocycloalkyl, (2-6C)Heterocycloalkyl, and (3-7C)Heterocycloalkyl. Heterocycloalkyl includes "heterocycloalkenyl". Heterocycloalkenyl means an unsaturated ring having the specified number of carbon atoms. For example, "(2-6C)heterocycloalkenyl" includes a heterocycloalkenyl with 2, 3, 4, 5 or 6 carbon atoms. Heterocycloalkyl also includes "heteroaryl". Heteroaryl is a 5-6 membered monocyclic aromatic ring or a fused bicyclic aromatic ring having 6-10 members, and 1-6 heteroatoms selected from N, O or S. Preferred heteroaryl groups are tetrazolyl, imidazolyl, thiadiazolyl, pyridyl, pyrimidyl, triazinyl, thiazolyl, oxazolyl, isoxazolyl, pyrazolyl, thiadiazolyl, isothiadiazolyl, thienyl, furyl, quinoline, isoquinoline and indole.

The term "heterocyclic" and "heterocycloalkyl" have the same meaning.

Cycloalkenyl means a cycloalkyl group having the recited number of carbon atoms, preferably 3-7 carbon atoms, and a double bond between at least two of the carbon atoms. For example, "(3-7C)cycloalkenyl" includes a cycloalkenyl with 3, 4, 5, 6 or 7 carbon atoms. Preferred cycloalkenyl groups are cyclopentenyl or cyclohexenyl.

Aryl means an aromatic hydrocarbon ring having between 6-10 carbon atoms, that may be a monocyclic aromatic ring or a fused bicyclic aromatic ring, such asphenyl, naphthyl, tetrahydronaphthyl or indenyl. The preferred aryl group is phenyl.

Di[alkyl]amino means an amino group, disubstituted with alkyl group(s), each independently containing the recited number of carbon atoms and having the same meaning as previously defined. Preferred di[alkyl]amino group is dimethylamino.

Hydroxyalkyl means an alkyl group as previously defined, substituted with a hydroxyl group.

Cycloalkyl(1-4C)alkyl means an alkyl group having 1-4 carbon atoms with the same meaning as previously defined, substituted with a cycloalkyl group having the recited number of carbon atoms as previously defined.

Cycloalkoxy(1-4C)alkyl means an alkyl group having 1-4 carbon atoms with the same meaning as previously defined, substituted with a cycloalkoxy group having the recited number of carbon atoms as previously defined. The cycloalkoxy group is linked via the exocyclic oxygen to the alkyl group.

Aryl(1-6C)alkyl means an alkyl group having 1-6 carbon atoms with the same meaning as previously defined, substituted with a aryl group having the recited number of carbon atoms as previously defined.

Heteroaryl(1-6C)alkyl means an alkyl group having 1-6 carbon atoms with the same meaning as previously defined, substituted with a heteroaryl group having the recited number of carbon atoms as previously defined.

Heterocycloalkyl(1-6C)alkyl means an alkyl group having 1-6 carbon atoms with the same meaning as previously defined, substituted with a heterocycloalkyl group having the recited number of carbon atoms as previously defined.

Alkoxy(1-6C)alkyl means an alkyl group having 1-6 carbon atoms with the same meaning as previously defined, substituted with an alkoxy group the alkyl moiety of which having the recited number of carbon atoms as previously defined. Examples of "alkoxyalkyl" include, but are not limited to, methoxymethyl, 1-methoxyethyl, 2-ethoxyethyl, and 1,1-dimethoxyethyl.

When, in the definition of a substituent, is indicated that "all of the alkyl groups" of said substituent are optionally substituted, this also includes the alkyl moiety of an alkoxy group.

A circle in a ring of Formula I indicates that the ring is aromatic or that it has the requisite number of double bonds to complete the valence.

Depending on the ring formed, the nitrogen, if present in T, U, W, X, Y or Z, may carry a hydrogen.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means that the group may or may not be substituted with the specified groups, radicals or moieties.

The term pharmaceutically acceptable salt is well known in the art. It may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

The compounds of this invention include the prodrugs, hydrates or solvates of the compounds. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The term "effective amount" as used herein, refers to an amount of the compound of Formula (I), (II), (Ia), (Ib), (Ic), (Id), (Iai), (Ibi), (Ici), (Idi), (Ie), (If) or (Ig), and/or an additional therapeutic agent, or a composition thereof, that is effective in producing the desired therapeutic, ameliorative, inhibitory or preventative effect when administered to a subject suffering from a BTK-mediated disease or disorder. In the combination therapies of the present invention, as effective amount can refer to each individual agent or to the combination as a whole, wherein the amounts of all agents administered are together effective, but wherein the component agent of the combination may not be present individually in an effective amount.

A "subject" is a human or non-human mammal. In one embodiment, a subject is a human.

It should be noted that any carbon as well as heteroatom with unsatisfied valences in the text, schemes, examples and tables herein is assumed to have the sufficient number of hydrogen atom(s) to satisfy the valences.

In the above definitions with multifunctional groups, the attachment point is at the last group, unless otherwise specified on the substituent group by a dash. A dash on the substituent group would then represent the point of attachment.

Aspects of the Invention

In one aspect the invention relates to a compound according to Formula I or II, wherein ring K is defined as:
$B_1$ is $C(R^7)$, $B_2$ is $C(R^8)$, $B_3$ is $C(R^9)$, and $B_4$ is $C(R^{10})$; or
$B_1$ is N, $B_2$ is N, $B_3$ is $C(R^9)$, and $B_4$ is $C(R^{10})$; or
$B_1$ is N, $B_2$ is $C(R^8)$, $B_3$ is N, and $B_4$ is $C(R^{10})$; or
$B_1$ is N, $B_2$ is $C(R^8)$, $B_3$ is $C(R^9)$, and $B_4$ is N; or
$B_1$ is $C(R^7)$, $B_2$ is $C(R^8)$, $B_3$ is N, and $B_4$ is N; or
$B_1$ is $C(R^7)$, $B_2$ is N, $B_3$ is $C(R^9)$, and $B_4$ is N.

In another aspect the invention relates to a compound of Formula I or II, wherein ring K is defined as: $B_1$ is $C(R^7)$, $B_2$ is $C(R^8)$, $B_3$ is $C(R^9)$, and $B_4$ is $C(R^{10})$, and wherein $R^7$, $R^8$, $R^9$ and $R^{10}$ each are H, halogen, (1-3C)alkyl, (1-3C) alkoxy or halo(1-3C)alkyl; any alkoxy may optionally be substituted with one, two or three halogen;

In yet another aspect the invention relates to a compound according to FormulaI or II, wherein ring L is selected from the group consisting of phenyl, pyridyl, pyrimidyl, pyridazyl, triazinyl, thiazolyl, oxazolyl, isoxazolyl, pyrazolyl, imidazolyl, thiadiazolyl, and isothiazolyl.

In yet another aspect the invention relates to a compound according to FormulaI or II, wherein the ring system L is selected from the group consisting of:

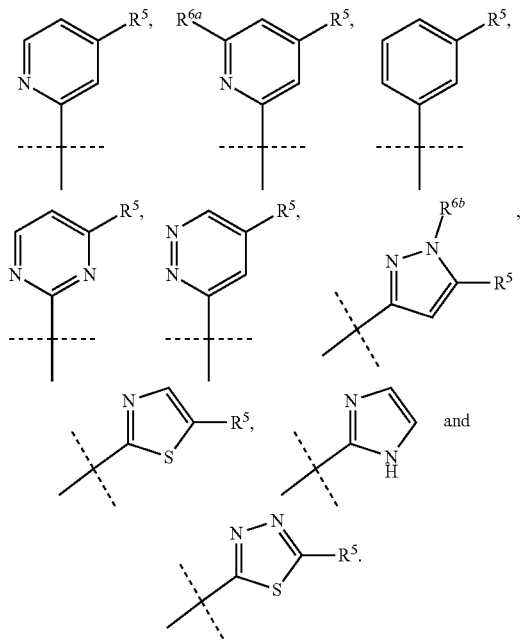

In yet another aspect the invention relates to a compound according to FormulaI or II wherein ring L is selected from the group consisting of pyridyl, pyrimidyl, and thiazolyl. In a preferred aspect, ring L is pyridyl.

In another aspect the invention relates to a compound according to Formula I or II wherein $R^5$ is selected from the group consisting of hydrogen, fluorine, chlorine, CN, cyclopropyl, cyclobutyl, oxetanyl, (1-3C)alkyl, (1-5C)alkoxy, and (1-5C)cycloalkoxy; the alkyl, alkoxy, cycloalkyl and cycloalkoxy of which are optionally substituted with one or more halogen.

In another aspect the invention relates to a compound according to Formula I or II wherein $R^5$ is selected from the group consisting of hydrogen, fluorine, methyl, ethyl, propyl, cyclopropyl, cyclobutyl, cyclopropoxyl, and trifluoromethyl.

In yet another aspect the invention relates to a compound according to Formula I or II wherein $R^{11}$ is selected from the group consisting of H, $^2$H, F, Cl, Br, methyl, $C^2H_3$, ethyl, cyclopropyl and vinyl. In one embodiment, $R^{11}$ is H or halogen. In another embodiment $R^{11}$ is halogen. In a preferred embodiment, $R^{11}$ is F or Cl.

In yet another aspect the invention relates to a compound according to Formula I or II wherein $A_1$-$A_4$ are C or N and bicyclic ring system E-G is selected from the group consisting of

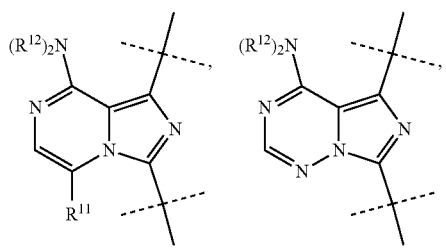

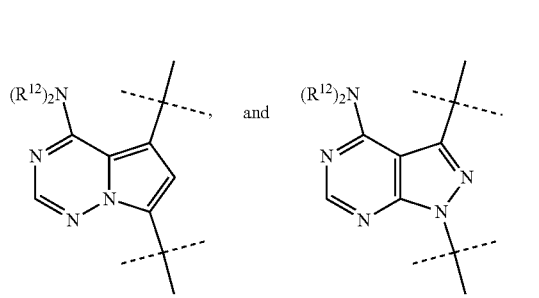

and

Preferably, $R^{12}$ is H.

In yet another aspect the invention relates to a compound according to Formula I or II wherein $A_1$-$A_4$ are C or N and bicyclic ring system E-G is

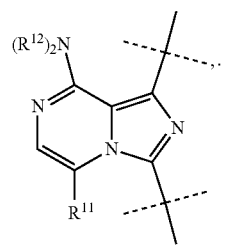

In one aspect of the invention relating to the compound according to Formula I or II, the invention relates to a compound having Formula Ia

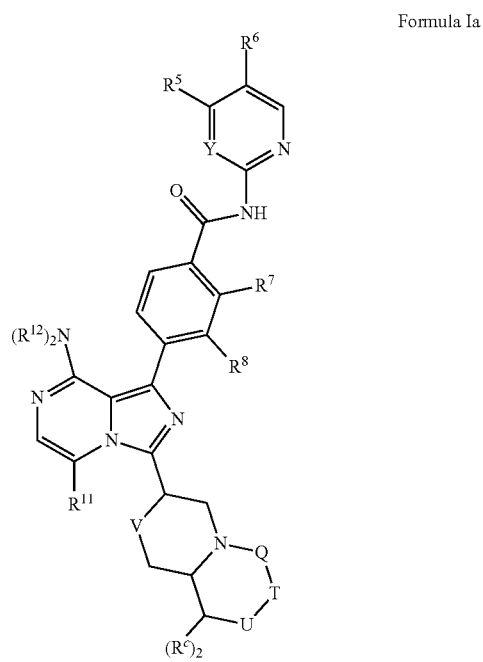

Formula Ia or a pharmaceutically acceptable salt thereof.

In another aspect of the invention relating to the compound according to Formula I or II, the invention relates to a compound having Formula Ib

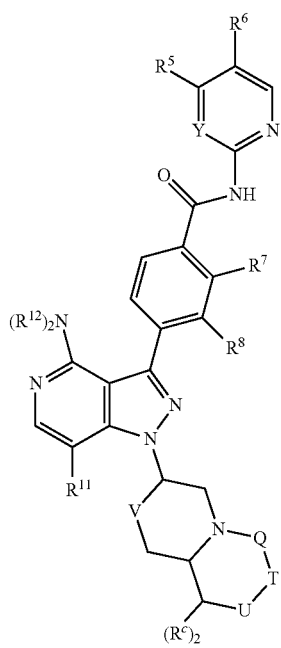

Formula Ib or a pharmaceutically acceptable salt thereof.

In another aspect of the invention relating to the compound according to Formula I or II, the invention relates to a compound having Formula Ic Formula Ic

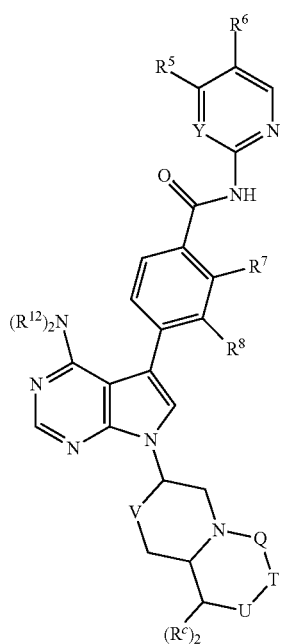

or a pharmaceutically acceptable salt thereof.

In yet another aspect of the invention relating to the compound according to Formula I or II, the invention relates to a compound having Formula Id Formula Id

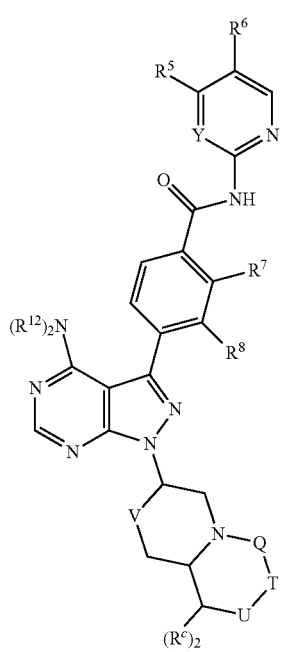

or a pharmaceutically acceptable salt thereof.

In one aspect of the invention relating to the compound according to Formula I or II, the invention relates to a compound having Formula Iai Formula Iai

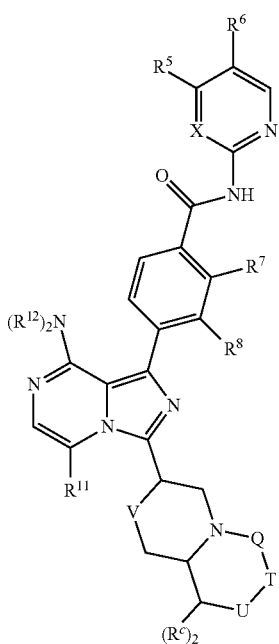

or a pharmaceutically acceptable salt thereof. In a preferred embodiment, $R^6$, $R^7$ and R are each hydrogen.

In another aspect of the invention relating to the compound according to Formula I or II, the invention relates to a compound having Formula Ibi Formula Ibi

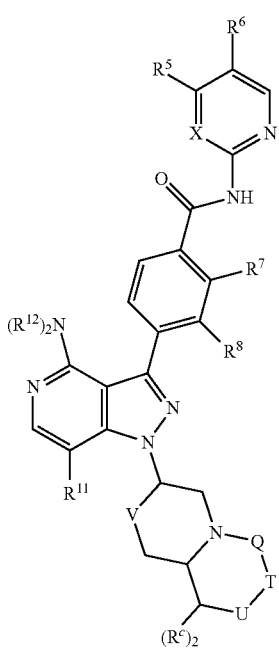

or a pharmaceutically acceptable salt thereof.

In another aspect of the invention relating to the compound according to Formula I or II, the invention relates to a compound having Formula Ici

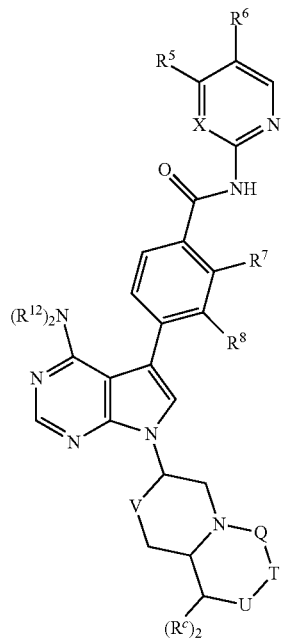

Formula Ici or a pharmaceutically acceptable salt thereof.

In another aspect of the invention relating to the compound according to Formula I or II, the invention relates to a compound having Formula Idi

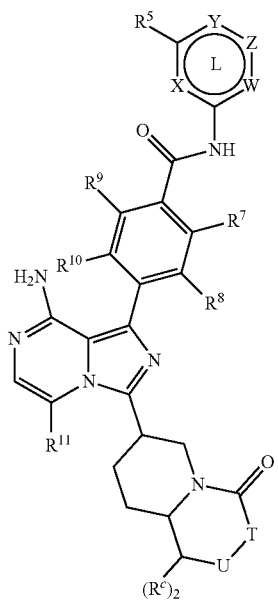

Formula Ie or a pharmaceutically acceptable salt thereof. In one embodiment of the compound of Formula 1e, $R^7$, $R^8$, $R^9$, and $R^{10}$ are independently selected from H, halogen, or (1-3C)alkoxy;

$R^1$ is H, halogen or (1-3C)alkyl, wherein the alkyl is optionally substituted with one, two or three halogen;

$R^c$ is H or $CH_3$; and $R^d$ is H or $CH_3$.

In another aspect of the invention relating to the compound according to Formula Ie, the invention relates to a compound having Formula If Formula Idi or a pharmaceutically acceptable salt thereof.

In another aspect of the invention relating to the compound according to Formula I or II, the invention relates to a compound having Formula 1e

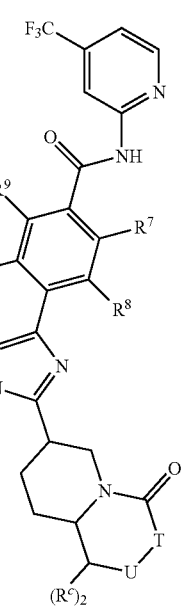

Formula 1f or a pharmaceutically acceptable salt thereof.

In another aspect of the invention relating to the compound according to Formula Ie, the invention relates to a compound having Formula 1g Formula Ig

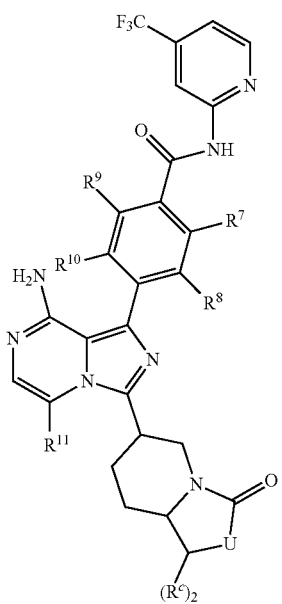

or a pharmaceutically acceptable salt thereof.

In a preferred embodiment of the above-mentioned aspects of the invention, $R^{11}$ is halogen.

The invention also relates to those compounds wherein all specific definitions for $A_1$-$A_4$, $B_1$-$B_4$, Q, T, U, V, W, X, Y, Z, $R^3$, $R^4$, $R^5$, $R^6$, $R^{6a}$, $R^{6b}$, $R^7$, $R^8$, $R^9$, $R^{10}$, $R^{11}$, $R^{12}$, $R^{13}$, $R^c$, $R^d$, $R^e$, $R^f$, $R^g$, $R^h$, and $R^z$ and all substituent groups in the various aspects of the inventions defined here above occur in any combination within the definition of the Btk inhibitor compounds of Formula I, II, Ia, Ib, Ic, Id, Ie, If, Ig, Iai, Ibi, Ici, Idi, or pharmaceutically acceptable salts thereof.

Non-limiting examples of the compounds of the present invention include:

4-{8-amino-3-[(6S,8aS)-3-oxohexahydro[1,3]oxazolo[3,4-a]pyridin-6-yl]imidazo[1,5-a]pyrazin-1-yl}-N-[4-(trifluoromethyl)pyridin-2-yl]benzamide;

4-{8-amino-3-[(6R,8aR)-3-oxohexahydro[1,3]oxazolo[3,4-a]pyridin-6-yl]imidazo[1,5-a]pyrazin-1-yl}-N-[4-(trifluoromethyl)pyridin-2-yl]benzamide;

4-{8-amino-3-[(6R,8aS)-2-methyl-3-oxooctahydroimidazo[1,5-a]pyridin-6-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[4-(cyclopropyloxy)pyridin-2-yl]benzamide;

4-{8-amino-3-[(6R,8aS)-3-oxooctahydroindolizin-6-yl]imidazo[1,5-a]pyrazin-1-yl}-N-pyridin-2-ylbenzamide;

4-{8-amino-3-[(6S,8aR)-3-oxooctahydroindolizin-6-yl]imidazo[1,5-a]pyrazin-1-yl}-N-(4-cyclobutylpyridin-2-yl)benzamide;

4-{8-amino-3-[(6R,8aS)-3-oxooctahydroindolizin-6-yl]imidazo[1,5-a]pyrazin-1-yl}-N-(5-methyl-1,3-thiazol-2-yl)benzamide;

4-{8-amino-3-[(6S,8aR)-3-oxooctahydroindolizin-6-yl]imidazo[1,5-a]pyrazin-1-yl}-N-pyridin-2-ylbenzamide;

4-{8-amino-3-[(6S,8aS)-3-oxooctahydroindolizin-6-yl]imidazo[1,5-a]pyrazin-1-yl}-N-[4-(trifluoromethyl)pyridin-2-yl]benzamide;

4-{8-amino-3-[(6R,8aR)-3-oxooctahydroindolizin-6-yl]imidazo[1,5-a]pyrazin-1-yl}-N-[4-(trifluoromethyl)pyridin-2-yl]benzamide;

4-{8-amino-3-[(6R,8aS)-3-oxohexahydro[1,3]oxazolo[3,4-a]pyridin-6-yl]imidazo[1,5-a]pyrazin-1-yl}-N-[4-(trifluoromethyl)pyridin-2-yl]benzamide;

4-{8-amino-3-[(6S,8aR)-3-oxohexahydro[1,3]oxazolo[3,4-a]pyridin-6-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[4-(difluoromethyl)pyridin-2-yl]-3-fluorobenzamide;

4-{8-amino-3-[(6R,8aS)-3-oxooctahydroindolizin-6-yl]imidazo[1,5-a]pyrazin-1-yl}-N-(4-cyanopyridin-2-yl)-3-fluorobenzamide;

4-{8-amino-3-[(6R,8aS)-3-oxooctahydroindolizin-6-yl]imidazo[1,5-a]pyrazin-1-yl}-N-(4-cyclopropylpyridin-2-yl)-3-fluorobenzamide;

4-{8-amino-3-[(6R,8aS)-3-oxooctahydroindolizin-6-yl]imidazo[1,5-a]pyrazin-1-yl}-N-[4-(difluoromethyl)pyridin-2-yl]benzamide;

4-{8-amino-3-[(6R,8aS)-3-oxooctahydroindolizin-6-yl]imidazo[1,5-a]pyrazin-1-yl}-N-(4-ethylpyridin-2-yl)benzamide;

4-{8-amino-3-[(6R,8aS)-3-oxooctahydroindolizin-6-yl]imidazo[1,5-a]pyrazin-1-yl}-N-(4-cyclopropylpyridin-2-yl)benzamide;

4-{8-amino-3-[(6R,8aS)-3-oxooctahydroindolizin-6-yl]imidazo[1,5-a]pyrazin-1-yl}-N-[4-(trifluoromethyl)pyrimidin-2-yl]benzamide;

4-{8-amino-3-[(6R,8aS)-3-oxooctahydroindolizin-6-yl]imidazo[1,5-a]pyrazin-1-yl}-N-[4-(1,1-difluoroethyl)pyridin-2-yl]-3-fluorobenzamide;

4-{8-amino-3-[(6R,8aS)-3-oxooctahydroindolizin-6-yl]imidazo[1,5-a]pyrazin-1-yl}-2-methyl-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-fluoro-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-2-fluoro-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[4-(1,1-difluoroethyl)pyridin-2-yl]-2-fluorobenzamide;

4-{8-amino-3-[(6R,8aS)-3-oxooctahydroindolizin-6-yl]imidazo[1,5-a]pyrazin-1-yl}-N-[4-(difluoromethyl)pyridin-2-yl]-2-fluorobenzamide;

4-{8-amino-3-[(6R,8aS)-3-oxooctahydroindolizin-6-yl]imidazo[1,5-a]pyrazin-1-yl}-N-(4-cyclopropylpyridin-2-yl)-2-fluorobenzamide;

4-{8-amino-3-[(6R,8aS)-3-oxooctahydroindolizin-6-yl]imidazo[1,5-a]pyrazin-1-yl}-N-(4-cyclopropylpyridin-2-yl)-2-methylbenzamide;

4-{8-amino-3-[(6R,8aS)-3-oxooctahydroindolizin-6-yl]imidazo[1,5-a]pyrazin-1-yl}-N-[4-(3-fluorooxetan-3-yl)pyridin-2-yl]benzamide;

4-{8-amino-3-[(6R,8aS)-3-oxooctahydroindolizin-6-yl]imidazo[1,5-a]pyrazin-1-yl}-N-[4-(1-fluoro-1-methylethyl)pyridin-2-yl]benzamide;

4-{8-amino-3-[(1R,6R,8aS)-1-methyl-3-oxohexahydro[1,3]oxazolo[3,4-a]pyridin-6-yl]imidazo[1,5-a]pyrazin-1-yl}-3-fluoro-N-[4-(trifluoromethyl)pyridin-2-yl]benzamide;

4-{8-amino-3-[(1R,6R,8aS)-1-methyl-3-oxohexahydro[1,3]oxazolo[3,4-a]pyridin-6-yl]imidazo[1,5-a]pyrazin-1-yl}-N-(4-cyclopropylpyridin-2-yl)-3-fluorobenzamide;

4-{8-amino-3-[(1S,6R,8aS)-1-methyl-3-oxohexahydro[1,3]
oxazolo[3,4-a]pyridin-6-yl]imidazo[1,5-a]pyrazin-1-yl}-
3-fluoro-N-[4-(trifluoromethyl)pyridin-2-yl]benzamide;

4-{8-amino-3-[(6R,8aS)-3-oxooctahydroindolizin-6-yl]imi-
dazo[1,5-a]pyrazin-1-yl}-N-(4-cyanopyridin-2-yl)-2-
fluorobenzamide;

4-{8-amino-3-[(6R,8aS)-3-oxooctahydroindolizin-6-yl]imi-
dazo[1,5-a]pyrazin-1-yl}-N-(4-cyanopyridin-2-yl)-3-
methoxybenzamide;

4-{8-amino-3-[(6R,8aS)-3-oxooctahydroindolizin-6-yl]imi-
dazo[1,5-a]pyrazin-1-yl}-N-(4-cyanopyridin-2-yl)-2-
methylbenzamide;

4-{8-amino-3-[(1 S,6R,8aS)-1-methyl-3-oxohexahydro[1,3]
oxazolo[3,4-a]pyridin-6-yl]imidazo[1,5-a]pyrazin-1-yl}-
N-(4-cyclopropylpyridin-2-yl)-3-fluorobenzamide;

4-{8-amino-3-[(6R,8aS)-3-oxooctahydroindolizin-6-yl]imi-
dazo[1,5-a]pyrazin-1-yl}-N-(4-cyclopropylpyridin-2-yl)-
3-methoxybenzamide;

4-{8-amino-3-[(7R,9aS)-4-oxooctahydropyrido[2,1-c][1,4]
oxazin-7-yl]imidazo[1,5-a]pyrazin-1-yl}-3-fluoro-N-[4-
(trifluoromethyl)pyridin-2-yl]benzamide;

4-{8-amino-3-[(7R,9aS)-4-oxooctahydro-2H-pyrido[1,2-a]
pyrazin-7-yl]imidazo[1,5-a]pyrazin-1-yl}-N-[4-(trifluo-
romethyl)pyridin-2-yl]benzamide;

4-{8-amino-3-[(7S,9aR)-4-oxooctahydro-2H-pyrido[1,2-a]
pyrazin-7-yl]imidazo[1,5-a]pyrazin-1-yl}-N-[4-(trifluo-
romethyl)pyridin-2-yl]benzamide;

4-{8-amino-3-[(6R,8aS)-3-oxooctahydroindolizin-6-yl]imi-
dazo[1,5-a]pyrazin-1-yl}-2-chloro-N-[4-(trifluorom-
ethyl)pyridin-2-yl]benzamide;

4-{8-amino-3-[(6R,8aS)-3-oxooctahydroindolizin-6-yl]imi-
dazo[1,5-a]pyrazin-1-yl}-N-[4-(cyclopropyloxy)pyridin-
2-yl]-3-fluorobenzamide;

4-{8-amino-3-[(3 S,9aS)-6-oxooctahydro-2H-quinolizin-3-
yl]imidazo[1,5-a]pyrazin-1-yl}-3-fluoro-N-[4-(trifluo-
romethyl)pyridin-2-yl]benzamide;

4-{8-amino-3-[(3R,9aR)-6-oxooctahydro-2H-quinolizin-3-
yl]imidazo[1,5-a]pyrazin-1-yl}-3-fluoro-N-[4-(trifluo-
romethyl)pyridin-2-yl]benzamide;

4-{8-amino-3-[(1 S,6R,8aS)-1-methyl-3-oxohexahydro[1,3]
oxazolo[3,4-a]pyridin-6-yl]imidazo[1,5-a]pyrazin-1-yl}-
N-(4-cyclopropylpyridin-2-yl)benzamide;

4-{8-amino-3-[(1R,6R,8aS)-1-methyl-3-oxohexahydro[1,3]
oxazolo[3,4-a]pyridin-6-yl]imidazo[1,5-a]pyrazin-1-yl}-
N-(4-cyclopropylpyridin-2-yl)benzamide;

4-{8-amino-3-[(1 S,6R,8aS)-1-methyl-3-oxohexahydro[1,3]
oxazolo[3,4-a]pyridin-6-yl]imidazo[1,5-a]pyrazin-1-yl}-
N-[4-(trifluoromethyl)pyridin-2-yl]benzamide;

4-{8-amino-3-[(1R,6R,8aS)-1-methyl-3-oxohexahydro[1,3]
oxazolo[3,4-a]pyridin-6-yl]imidazo[1,5-a]pyrazin-1-yl}-
N-[4-(trifluoromethyl)pyridin-2-yl]benzamide;

4-{8-amino-3-[(7R,9aS)-2-methyl-4-oxooctahydro-2H-
pyrido[1,2-a]pyrazin-7-yl]imidazo[1,5-a]pyrazin-1-yl}-
N-[4-(trifluoromethyl)pyridin-2-yl]benzamide;

4-{8-amino-3-[(7S,9aR)-2-methyl-4-oxooctahydro-2H-
pyrido[1,2-a]pyrazin-7-yl]imidazo[1,5-a]pyrazin-1-yl}-
N-[4-(trifluoromethyl)pyridin-2-yl]benzamide;

4-{8-amino-3-[(6R,8aS)-1,1-dimethyl-3-oxohexahydro[1,3]
oxazolo[3,4-a]pyridin-6-yl]imidazo[1,5-a]pyrazin-1-yl}-
N-[4-(trifluoromethyl)pyridin-2-yl]benzamide;

4-{8-amino-3-[(1R,6R,8aS)-1-methyl-3-oxohexahydro[1,3]
oxazolo[3,4-a]pyridin-6-yl]imidazo[1,5-a]pyrazin-1-yl}-
N-(4-cyclopropylpyridin-2-yl)-3-methoxybenzamide;

4-{8-amino-3-[(7R,9aR)-4-oxooctahydro-2H-pyrido[1,2-a]
pyrazin-7-yl]imidazo[1,5-a]pyrazin-1-yl}-N-[4-(trifluo-
romethyl)pyridin-2-yl]benzamide;

4-{8-amino-3-[(7R,9aS)-octahydropyrido[2,1-c][1,4]ox-
azin-7-yl]imidazo[1,5-a]pyrazin-1-yl}-N-[4-(trifluorom-
ethyl)pyridin-2-yl]benzamide;

4-{8-amino-3-[(7S,9aR)-octahydropyrido[2,1-c][1,4]ox-
azin-7-yl]imidazo[1,5-a]pyrazin-1-yl}-N-[4-(trifluorom-
ethyl)pyridin-2-yl]benzamide;

4-{8-amino-3-[(7S,9aS)-4-oxooctahydro-2H-pyrido[1,2-a]
pyrazin-7-yl]imidazo[1,5-a]pyrazin-1-yl}-N-[4-(trifluo-
romethyl)pyridin-2-yl]benzamide;

4-{8-amino-3-[(2S,6S,8aR)-2-hydroxy-3-oxooctahydroin-
dolizin-6-yl]imidazo[1,5-a]pyrazin-1-yl}-N-[4-(trifluo-
romethyl)pyridin-2-yl]benzamide;

4-{8-amino-3-[(2R,6R,8aS)-2-hydroxy-3-oxooctahydroin-
dolizin-6-yl]imidazo[1,5-a]pyrazin-1-yl}-N-[4-(trifluo-
romethyl)pyridin-2-yl]benzamide;

4-{8-(methylamino)-3-[(6R,8aS)-3-oxooctahydroindolizin-
6-yl]imidazo[1,5-a]pyrazin-1-yl}-N-[4-(trifluoromethyl)
pyridin-2-yl]benzamide;

4-{8-[(ethylcarbamoyl)amino]-3-[(6R,8aS)-3-oxooctahy-
droindolizin-6-yl]imidazo[1,5-a]pyrazin-1-yl}-N-[4-(trif-
luoromethyl)pyridin-2-yl]benzamide;

4-{8-amino-3-[(1R,6R,8aS)-1-methyl-3-oxooctahydroin-
dolizin-6-yl]imidazo[1,5-a]pyrazin-1-yl}-N-[4-(trifluo-
romethyl)pyridin-2-yl]benzamide;

4-{8-amino-3-[(1S,6R,8aR)-1-methyl-3-oxooctahydroin-
dolizin-6-yl]imidazo[1,5-a]pyrazin-1-yl}-N-[4-(trifluo-
romethyl)pyridin-2-yl]benzamide;

4-{8-amino-3-[(1 S,6R,8aR)-1-methyl-3-oxooctahydroin-
dolizin-6-yl]imidazo[1,5-a]pyrazin-1-yl}-N-[4-(trifluo-
romethyl)pyridin-2-yl]benzamide;

4-{8-amino-3-[(1R,6R,8aS)-1-methyl-3-oxooctahydroin-
dolizin-6-yl]imidazo[1,5-a]pyrazin-1-yl}-N-[4-(trifluo-
romethyl)pyridin-2-yl]benzamide;

4-{8-amino-3-[(7R,9aS)-2-(2-hydroxyethyl)-4-oxoocta-
hydro-2H-pyrido[1,2-a]pyrazin-7-yl]imidazo[1,5-a]
pyrazin-1-yl}-N-[4-(trifluoromethyl)pyridin-2-yl]benz-
amide;

4-{8-amino-3-[(2R,6S,8aR)-2-hydroxy-3-oxooctahydroin-
dolizin-6-yl]imidazo[1,5-a]pyrazin-1-yl}-N-[4-(trifluo-
romethyl)pyridin-2-yl]benzamide;

4-{8-amino-3-[(2S,6R,8aS)-2-hydroxy-3-oxooctahydroin-
dolizin-6-yl]imidazo[1,5-a]pyrazin-1-yl}-N-[4-(trifluo-
romethyl)pyridin-2-yl]benzamide;

4-{8-amino-3-[(6R,8aS)-3-oxooctahydroindolizin-6-yl]imi-
dazo[1,5-a]pyrazin-1-yl}-3-ethoxy-N-[4-(trifluorom-
ethyl)pyridin-2-yl]benzamide;

4-{8-amino-3-[(6R,8aS)-3-oxooctahydroindolizin-6-yl]imi-
dazo[1,5-a]pyrazin-1-yl}-3-(benzyloxy)-N-[4-(trifluo-
romethyl)pyridin-2-yl]benzamide;

4-{8-amino-3-[(6R,8aS)-3-oxooctahydroindolizin-6-yl]imi-
dazo[1,5-a]pyrazin-1-yl}-3-(difluoromethoxy)-N-[4-(trif-
luoromethyl)pyridin-2-yl]benzamide;

4-{8-amino-3-[(2S,6R,8aR)-2-hydroxy-3-oxooctahydroin-
dolizin-6-yl]imidazo[1,5-a]pyrazin-1-yl}-N-[4-(trifluo-
romethyl)pyridin-2-yl]benzamide;

4-{8-amino-3-[(2R,6S,8aS)-2-hydroxy-3-oxooctahydroin-
dolizin-6-yl]imidazo[1,5-a]pyrazin-1-yl}-N-[4-(trifluo-
romethyl)pyridin-2-yl]benzamide;

4-{8-amino-3-[(2R,6S,8aS)-2-hydroxy-3-oxooctahydroin-
dolizin-6-yl]imidazo[1,5-a]pyrazin-1-yl}-N-[4-(trifluo-
romethyl)pyridin-2-yl]benzamide;

4-{8-amino-3-[(2S,6R,8aR)-2-hydroxy-3-oxooctahydroin-
dolizin-6-yl]imidazo[1,5-a]pyrazin-1-yl}-N-[4-(trifluo-
romethyl)pyridin-2-yl]benzamide;

4-{8-amino-3-[(6R,8aR)-3-oxotetrahydro-1H-[1,3]oxazolo
[4,3-c][1,4]oxazin-6-yl]imidazo[1,5-a]pyrazin-1-yl}-N-
[4-(trifluoromethyl)pyridin-2-yl]benzamide;

4-{8-amino-3-[(3R,7R,9aS)-3-methyl-4-oxooctahydro-pyrido[2,1-c][1,4]oxazin-7-yl]imidazo[1,5-a]pyrazin-1-yl}-N-[4-(trifluoromethyl)pyridin-2-yl]benzamide;

4-{8-amino-3-[(3E,6R,8aS)-3-(cyanoimino)octahydroindolizin-6-yl]imidazo[1,5-a]pyrazin-1-yl}-N-[4-(trifluoromethyl)pyridin-2-yl]benzamide;

methyl{3-[(6R,8aS)-3-oxooctahydroindolizin-6-yl]-1-(4-{[4-(trifluoromethyl)pyridin-2-yl]carbamoyl}phenyl)imidazo[1,5-a]pyrazin-8-yl}carbamate;

4-{8-amino-3-[(7R,9aS)-2-ethyl-4-oxooctahydro-2H-pyrido[1,2-a]pyrazin-7-yl]imidazo[1,5-a]pyrazin-1-yl}-N-[4-(trifluoromethyl)pyridin-2-yl]benzamide;

4-{8-amino-3-[(7R,9aS)-2-(1-methylethyl)-4-oxooctahydro-2H-pyrido[1,2-a]pyrazin-7-yl]imidazo[1,5-a]pyrazin-1-yl}-N-[4-(trifluoromethyl)pyridin-2-yl]benzamide;

methyl{(7R,9aS)-7-[8-amino-1-(4-{[4-(trifluoromethyl)pyridin-2-yl]carbamoyl}phenyl)imidazo[1,5-a]pyrazin-3-yl]-4-oxooctahydro-2H-pyrido[1,2-a]pyrazin-2-yl}acetate;

4-{8-amino-3-[(4aS,7R)-2-methyl-1-oxooctahydro-1H-pyrido[1,2-c]pyrimidin-7-yl]imidazo[1,5-a]pyrazin-1-yl}-N-[4-(trifluoromethyl)pyridin-2-yl]benzamide;

4-{8-amino-3-[(4aR,7S)-2-methyl-1-oxooctahydro-1H-pyrido[1,2-c]pyrimidin-7-yl]imidazo[1,5-a]pyrazin-1-yl}-N-[4-(trifluoromethyl)pyridin-2-yl]benzamide;

4-{8-amino-3-[(7R,9aS)-4-oxo-2-(pyridin-4-ylcarbonyl)octahydro-2H-pyrido[1,2-a]pyrazin-7-yl]imidazo[1,5-a]pyrazin-1-yl}-3-methoxy-N-[4-(trifluoromethyl)pyridin-2-yl]benzamide;

2-{(7R,9aS)-7-[8-amino-1-(4-{[4-(trifluoromethyl)pyridin-2-yl]carbamoyl}phenyl)imidazo[1,5-a]pyrazin-3-yl]-4-oxooctahydro-2H-pyrido[1,2-a]pyrazin-2-yl}-2-methylpropanoic acid;

4-{8-amino-3-[(6R,8aS)-octahydroindolizin-6-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-methoxy-N-[4-(trifluoromethyl)pyridin-2-yl]benzamide;

4-{8-amino-3-[(1R,6R,8aS)-1-methyl-3-oxohexahydro[1,3]oxazolo[3,4-a]pyridin-6-yl]imidazo[1,5-a]pyrazin-1-yl}-3-methoxy-N-[4-(trifluoromethyl)pyridin-2-yl]benzamide;

4-{8-amino-3-[(6R,8aS)-1,1-dimethyl-3-oxohexahydro[1,3]oxazolo[3,4-a]pyridin-6-yl]imidazo[1,5-a]pyrazin-1-yl}-3-methoxy-N-[4-(trifluoromethyl)pyridin-2-yl]benzamide;

4-{8-amino-3-[(3R,8aR)-6-oxohexahydro-1H-pyrrolo[2,1-c][1,4]oxazin-3-yl]imidazo[1,5-a]pyrazin-1-yl}-3-methoxy-N-[4-(trifluoromethyl)pyridin-2-yl]benzamide;

4-{8-amino-3-[(4aS,7R)-1-oxohexahydro-3H-pyrido[1,2-c][1,3]oxazin-7-yl]imidazo[1,5-a]pyrazin-1-yl}-N-[4-(trifluoromethyl)pyridin-2-yl]benzamide;

4-{8-amino-3-[(4aR,7S)-1-oxohexahydro-3H-pyrido[1,2-c][1,3]oxazin-7-yl]imidazo[1,5-a]pyrazin-1-yl}-N-[4-(trifluoromethyl)pyridin-2-yl]benzamide;

4-{8-amino-3-[(6S,8aR)-2,2-dimethyl-3-oxooctahydroindolizin-6-yl]imidazo[1,5-a]pyrazin-1-yl}-N-[4-(trifluoromethyl)pyridin-2-yl]benzamide;

4-{8-amino-3-[(6R,8aS)-2,2-dimethyl-3-oxooctahydroindolizin-6-yl]imidazo[1,5-a]pyrazin-1-yl}-N-[4-(trifluoromethyl)pyridin-2-yl]benzamide;

4-{8-amino-3-[(1 S,6R,8aS)-3-imino-1-methylhexahydro[1,3]oxazolo[3,4-a]pyridin-6-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[4-(1-hydroxyethyl)pyridin-2-yl]benzamide;

4-{8-amino-3-[(6R,8aS)-3-oxooctahydroindolizin-6-yl]imidazo[1,5-a]pyrazin-1-yl}-N-[4-(1-hydroxy-1-methylethyl)pyridin-2-yl]benzamide;

4-{8-amino-3-[(6R,8aS)-3-oxooctahydroindolizin-6-yl]imidazo[1,5-a]pyrazin-1-yl}-N-[4-(1-methoxyethyl)pyridin-2-yl]benzamide;

4-{8-amino-3-[(6R,8aS)-2,2-dimethyl-3-oxooctahydroindolizin-6-yl]imidazo[1,5-a]pyrazin-1-yl}-3-methoxy-N-[4-(trifluoromethyl)pyridin-2-yl]benzamide;

4-{8-amino-3-[(6S,8aR)-2,2-dimethyl-3-oxooctahydroindolizin-6-yl]imidazo[1,5-a]pyrazin-1-yl}-3-methoxy-N-[4-(trifluoromethyl)pyridin-2-yl]benzamide;

4-{8-amino-3-[(7R,9aS)-4-oxo-2-(pyridin-4-ylcarbonyl)octahydro-2H-pyrido[1,2-a]pyrazin-7-yl]imidazo[1,5-a]pyrazin-1-yl}-N-[4-(trifluoromethyl)pyridin-2-yl]benzamide;

methyl 2-{[(4-{8-amino-3-[(6R,8aS)-3-oxooctahydroindolizin-6-yl]imidazo[1,5-a]pyrazin-1-yl}phenyl)carbonyl]amino}pyridine-4-carboxylate;

4-{8-amino-3-[(6R,8aS)-3-oxooctahydroindolizin-6-yl]imidazo[1,5-a]pyrazin-1-yl}-N-[5-(trifluoromethyl)pyridazin-3-yl]benzamide;

4-{8-amino-3-[(7R,9aS)-4-oxo-2-(phenylcarbonyl)octahydro-2H-pyrido[1,2-a]pyrazin-7-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-isoquinolin-3-ylbenzamide;

4-{8-amino-3-[(3R,8aR)-6-oxohexahydro-1H-pyrrolo[2,1-c][1,4]oxazin-3-yl]imidazo[1,5-a]pyrazin-1-yl}-N-[4-(trifluoromethyl)pyridin-2-yl]benzamide;

{(7R,9aS)-7-[8-amino-1-(4-{[4-(trifluoromethyl)pyridin-2-yl]carbamoyl}phenyl)imidazo[1,5-a]pyrazin-3-yl]-4-oxooctahydro-2H-pyrido[1,2-a]pyrazin-2-yl}acetic acid;

4-{8-amino-3-[(1 S,6R,8aS)-1-ethenyl-3-oxohexahydro[1,3]oxazolo[3,4-a]pyridin-6-yl]imidazo[1,5-a]pyrazin-1-yl}-N-[4-(trifluoromethyl)pyridin-2-yl]benzamide;

4-{8-amino-3-[(1R,6R,8aS)-1-ethenyl-3-oxohexahydro[1,3]oxazolo[3,4-a]pyridin-6-yl]imidazo[1,5-a]pyrazin-1-yl}-N-[4-(trifluoromethyl)pyridin-2-yl]benzamide;

4-{8-amino-3-[(4aR,7R)-2-methyl-1-oxooctahydro-1H-pyrido[1,2-c]pyrimidin-7-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-chloro-N-[4-(trifluoromethyl)pyridin-2-yl]benzamide;

4-{8-amino-3-[(6R,8aS)-2,2-dimethyl-3-oxooctahydroindolizin-6-yl]imidazo[1,5-a]pyrazin-1-yl}-3-ethoxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(1,1-difluoroethyl)-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-5-ethoxy-2-fluoro-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-3-[(~2~H_3_)methyloxy]-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[5-cyano-4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-hydroxy-N-[4-(trifluoromethyl)pyridin-2-yl]benzamide;

5-{8-amino-3-[(6R,8aS)-3-oxooctahydroindolizin-6-yl]imidazo[1,5-a]pyrazin-1-yl}-N-[4-(trifluoromethyl)pyridin-2-yl]pyridine-2-carboxamide;

4-{8-amino-3-[(6R,8aS)-3-oxooctahydroindolizin-6-yl]imidazo[1,5-a]pyrazin-1-yl}-N-[6-methyl-4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(cyclopropyloxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[3-methyl-4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-cyano-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N~1~-[4-(trifluoromethyl)pyridin-2-yl]benzene-1,3-dicarboxamide;

4-{8-amino-3-[(6R,8aS)-3-oxooctahydroindolizin-6-yl]imidazo[1,5-a]pyrazin-1-yl}-N-[6-(1-methylethyl)-4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[6-cyclobutyl-4-(trifluoromethyl)pyridin-2-yl]benzamide;

2-{8-amino-3-[(6R,8aS)-3-oxooctahydroindolizin-6-yl]imidazo[1,5-a]pyrazin-1-yl}-5-{[4-(trifluoromethyl)pyridin-2-yl]carbamoyl}benzoic acid;

4-{8-amino-5-chloro-3-[(6R,8aS)-3-oxooctahydroindolizin-6-yl]imidazo[1,5-a]pyrazin-1-yl}-3-ethoxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-(6-methoxypyridin-2-yl)benzamide;

4-{8-amino-3-[(6R,8aS)-3-oxooctahydroindolizin-6-yl]imidazo[1,5-a]pyrazin-1-yl}-2-fluoro-5-methoxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-2-fluoro-5-methoxy-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-5-ethoxy-2-fluoro-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-fluoro-5-methoxy-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-N-(4-cyclopropylpyridin-2-yl)-5-ethoxy-2-fluorobenzamide;

4-{8-amino-3-[(6R,8aS)-3-oxooctahydroindolizin-6-yl]imidazo[1,5-a]pyrazin-1-yl}-N-(4-cyclopropylpyridin-2-yl)-5-ethoxy-2-fluorobenzamide;

4-{8-amino-3-[(6R,8aS)-3-oxooctahydroindolizin-6-yl]imidazo[1,5-a]pyrazin-1-yl}-3-(cyclohexyloxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(1-methylethoxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(cyclobutyloxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(cyclopentyloxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(2,2-dimethylpropoxy)-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-methoxy-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-(cyclopropyloxy)-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-(cyclopropyloxy)-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-3-(cyclopropyloxy)-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-3-(cyclopropyloxy)-N-(4-cyclopropylpyridin-2-yl)benzamide;

4-{8-amino-3-[(6R,8aS)-3-oxooctahydroindolizin-6-yl]imidazo[1,5-a]pyrazin-1-yl}-3-(cyclopropyloxy)-N-(4-cyclopropylpyridin-2-yl)benzamide;

4-{8-amino-3-[(6R,8aS)-3-oxooctahydroindolizin-6-yl]imidazo[1,5-a]pyrazin-1-yl}-3-(azetidin-3-yloxy)-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-5-(cyclopropyloxy)-2-fluoro-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-5-ethoxy-2-fluoro-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-5-ethoxy-2-fluoro-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-N-(5-methyl-1,3-thiazol-2-yl)benzamide;

2-{8-amino-3-[(6R,8aS)-3-oxooctahydroindolizin-6-yl]imidazo[1,5-a]pyrazin-1-yl}-5-{[4-(trifluoromethyl)pyridin-2-yl]carbamoyl}phenyl acetate;

4-{8-(acetylamino)-3-[(6R,8aS)-3-oxooctahydroindolizin-6-yl]imidazo[1,5-a]pyrazin-1-yl}-3-hydroxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-hydroxy-N-(2-methoxyethyl)-N-[4-(trifluoromethyl)pyridin-2-yl]benzamide;

4-{8-amino-5-chloro-3-[(6R,8aS)-3-oxooctahydroindolizin-6-yl]imidazol[1,5-a]pyrazin-1-yl}-3-ethoxy-N-(5-methyl-1,3-thiazol-2-yl)benzamide;

4-{8-amino-3-[(6R,8aS)-3-oxooctahydroindolizin-6-yl]imidazo[1,5-a]pyrazin-1-yl}-3-ethoxy-N-(5-methyl-1,3-thiazol-2-yl)benzamide;

4-{8-amino-5-fluoro-3-[(6R,8aS)-3-oxooctahydroindolizin-6-yl]imidazo[1,5-a]pyrazin-1-yl}-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-3-ethoxy-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-3-methoxy-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide;

4-{8-amino-5-fluoro-3-[(6R,8aS)-3-oxooctahydroindolizin-6-yl]imidazo[1,5-a]pyrazin-1-yl}-3-ethoxy-N-(5-methyl-1,3-thiazol-2-yl)benzamide;

4-{8-amino-5-fluoro-3-[(6R,8aS)-3-oxooctahydroindolizin-6-yl]imidazo[1,5-a]pyrazin-1-yl}-3-hydroxy-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-3-fluoro-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-N-(4-cyclopropylpyridin-2-yl)-3-fluorobenzamide;

4-{8-amino-5-fluoro-3-[(6R,8aS)-3-oxooctahydroindolizin-6-yl]imidazo[1,5-a]pyrazin-1-yl}-N-(4-cyclopropylpyridin-2-yl)benzamide;

4-{8-amino-5-fluoro-3-[(6R,8aS)-3-oxooctahydroindolizin-6-yl]imidazo[1,5-a]pyrazin-1-yl}-5-ethoxy-2-fluoro-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[3-(trifluoromethyl)-1H-pyrazol-5-yl]benzamide;

4-{8-amino-3-[(6R,8aS)-3-oxooctahydroindolizin-6-yl]imidazo[1,5-a]pyrazin-1-yl}-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-N-1H-imidazol-2-ylbenzamide;

4-{8-amino-3-[(6R,8aS)-3-oxooctahydroindolizin-6-yl]imidazo[1,5-a]pyrazin-1-yl}-N-[5-(trifluoromethyl)isoxazol-3-yl]benzamide;

4-{8-amino-3-[(6R,8aS)-3-oxooctahydroindolizin-6-yl]imidazo[1,5-a]pyrazin-1-yl}-N-[3-(trifluoromethyl)isoxazol-5-yl]benzamide;

4-{8-amino-3-[(6R,8aS)-3-oxooctahydroindolizin-6-yl]imidazo[1,5-a]pyrazin-1-yl}-N-(1,5-dimethyl-1H-pyrazol-3-yl)benzamide;

4-{8-amino-3-[(6R,8aS)-3-oxooctahydroindolizin-6-yl]imidazo[1,5-a]pyrazin-1-yl}-N-(3-methyl-1,2,4-thiadiazol-5-yl)benzamide;

4-{8-amino-3-[(6R,8aS)-3-oxooctahydroindolizin-6-yl]imidazo[1,5-a]pyrazin-1-yl}-N-[4-(trifluoromethyl)-1H-imidazol-2-yl]benzamide;

4-{8-amino-3-[(6R,8aS)-3-oxooctahydroindolizin-6-yl]imidazo[1,5-a]pyrazin-1-yl}-N-(3-ethyl-1,2,4-thiadiazol-5-yl)benzamide;

4-{8-amino-3-[(6R,8aS)-3-oxooctahydroindolizin-6-yl]imidazo[1,5-a]pyrazin-1-yl}-N-[3-(1-methylethyl)-1,2,4-thiadiazol-5-yl]benzamide;

4-{8-amino-3-[(6R,8aS)-3-oxooctahydroindolizin-6-yl]imidazo[1,5-a]pyrazin-1-yl}-N-[1-cyclopentyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-N-(5-cyclopropyl-1-methyl-1H-pyrazol-3-yl)benzamide;

4-{8-amino-3-[(6R,8aS)-3-oxooctahydroindolizin-6-yl]imidazo[1,5-a]pyrazin-1-yl}-N-(5-methyl-1,3,4-thiadiazol-2-yl)benzamide;

4-{8-amino-5-chloro-3-[(6R,8aS)-3-oxooctahydroindolizin-6-yl]imidazo[1,5-a]pyrazin-1-yl}-N-[1-methyl-5-(trifluoromethyl)-1H-pyrazol-3-yl]benzamide;

ethyl 2-{[(4-{8-amino-3-[(6R,8aS)-3-oxooctahydroindolizin-6-yl]imidazo[1,5-a]pyrazin-1-yl}phenyl)carbonyl]amino}-4-(trifluoromethyl)-1,3-oxazole-5-carboxylate;

4-{8-amino-3-[(6R,8aS)-3-oxooctahydroindolizin-6-yl]imidazo[1,5-a]pyrazin-1-yl}-N-[1-ethyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-3-methyl-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-3-methyl-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-methoxy-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-3-methoxy-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-3-chloro-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-3-chloro-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-5-chloro-2-fluoro-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-5-chloro-2-fluoro-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-chloro-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-chloro-N-(5-methyl-1,3-thiazol-2-yl)benzamide;

4-{8-amino-5-chloro-3-[(6R,8aS)-3-oxooctahydroindolizin-6-yl]imidazo[1,5-a]pyrazin-1-yl}-3-chloro-N-(5-methyl-1,3-thiazol-2-yl)benzamide;

4-{8-amino-5-chloro-3-[(6R,8aS)-3-oxooctahydroindolizin-6-yl]imidazo[1,5-a]pyrazin-1-yl}-2-fluoro-5-methyl-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-2-fluoro-5-methyl-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(2-methoxyethoxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(2-hydroxyethoxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(2-ethoxyethoxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-methoxy-N-(5-methyl-1,3-thiazol-2-yl)benzamide;

4-{8-amino-5-chloro-3-[(6R,8aS)-3-oxooctahydroindolizin-6-yl]imidazo[1,5-a]pyrazin-1-yl}-3-methoxy-N-(5-methyl-1,3-thiazol-2-yl)benzamide;

4-{8-amino-3-[(6R,8aS)-3-oxooctahydroindolizin-6-yl]imidazo[1,5-a]pyrazin-1-yl}-3-(but-3-yn-1-yloxy)-N-[4-(trifluoromethyl)pyridin-2-yl]benzamide;

4-{8-amino-5-methyl-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide;

4-{8-amino-3-[(6R,8aS)-3-oxooctahydroindolizin-6-yl]-5-(trifluoromethyl)imidazo[1,5-a]pyrazin-1-yl}-3-ethoxy-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-N-(4-ethylpyridin-2-yl)-3-methoxybenzamide;

4-{8-amino-5-chloro-3-[(6R,8aS)-3-oxooctahydroindolizin-6-yl]imidazo[1,5-a]pyrazin-1-yl}-3-methoxy-N-(4-methoxypyridin-2-yl)benzamide;

4-{8-amino-5-chloro-3-[(6R,8aS)-3-oxooctahydroindolizin-6-yl]imidazo[1,5-a]pyrazin-1-yl}-N-(4-cyclobutylpyridin-2-yl)-3-methoxybenzamide;

4-{8-amino-5-chloro-3-[(6R,8aS)-3-oxooctahydroindolizin-6-yl]imidazo[1,5-a]pyrazin-1-yl}-3-methoxy-N-(5-methylpyridin-2-yl)benzamide;

4-{8-amino-3-[(6R,8aS)-3-oxooctahydroindolizin-6-yl]-5-(trifluoromethyl)imidazo[1,5-a]pyrazin-1-yl}-3-chloro-N-[4-(trifluoromethyl)pyridin-2-yl]benzamide;

4-{8-amino-3-[(6R,8aS)-3-oxooctahydroindolizin-6-yl]-5-(trifluoromethyl)imidazo[1,5-a]pyrazin-1-yl}-N-(4-cyclopropylpyridin-2-yl)-3-fluorobenzamide;

4-{8-amino-3-[(6R,8aS)-3-oxooctahydroindolizin-6-yl]-5-(trifluoromethyl)imidazo[1,5-a]pyrazin-1-yl}-3-methoxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-fluoro-5-methyl-N-[4-(trifluoromethyl)pyridin-2-yl]benzamide;

4-{8-amino-3-[(6R,8aS)-3-oxooctahydroindolizin-6-yl]-5-(trifluoromethyl)imidazo[1,5-a]pyrazin-1-yl}-3-ethoxy-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-3-(1,1-difluoroethoxy)-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-fluoro-5-methoxy-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-2-chloro-5-methoxy-N-[4-(trifluoromethyl)pyridin-2-yl]benzamide;

4-{8-amino-3-[(6R,8aS)-2,2-dimethyl-3-oxooctahydroindolizin-6-yl]imidazo[1,5-a]pyrazin-1-yl}-3-fluoro-5-methoxy-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-3-fluoro-5-methoxy-N-[4-(trifluoromethyl)pyridin-2-yl]benzamide;

4-(8-amino-5-fluoro-3-((6R,8aS)-3-oxooctahydroindolizin-6-yl)imidazo[1,5-a]pyrazin-1-yl)-3-ethoxy-5-fluoro-N-(4-(trifluoromethyl)pyridin-2-yl)benzamide;

4-(8-amino-3-((6R,8aS)-1,1-dimethyl-3-oxooctahydroindolizin-6-yl)imidazo[1,5-a]pyrazin-1-yl)-3-ethoxy-N-(4-(trifluoromethyl)pyridin-2-yl)benzamide; and 4-(8-amino-3-((6R,8aS)-1,1-dimethyl-3-oxooctahydroindolizin-6-yl)imidazo[1,5-a]pyrazin-1-yl)-3-ethoxy-5-fluoro-N-(4-(trifluoromethyl)pyridin-2-yl)benzamide, or pharmaceutically acceptable salts thereof.

In a preferred embodiment of the invention, the compound according to Formula I, or a pharmaceutically acceptable salt thereof, is selected from the group consisting of:

4-{8-amino-3-[(6R,8aS)-3-oxooctahydroindolizin-6-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-ethoxy-N-[4-(trifluoromethyl)pyridin-2-yl]benzamide;

4-{8-amino-3-[(6R,8aS)-1,1-dimethyl-3-oxohexahydro[1,3]oxazolo[3,4-a]pyridin-6-yl]imidazo[1,5-a]pyrazin-1-yl}-3-methoxy-N-[4-(trifluoromethyl)pyridin-2-yl]benzamide;

4-{8-amino-3-[(6S,8aR)-2,2-dimethyl-3-oxooctahydroindolizin-6-yl]imidazo[1,5-a]pyrazin-1-yl}-N-[4-(trifluoromethyl)pyridin-2-yl]benzamide;

4-{8-amino-3-[(6R,8aS)-2,2-dimethyl-3-oxooctahydroindolizin-6-yl]imidazo[1,5-a]pyrazin-1-yl}-3-methoxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-methoxy-N-[4-(trifluoromethyl)pyridin-2-yl]benzamide;

4-{8-amino-3-[(6R,8aS)-2,2-dimethyl-3-oxooctahydroindolizin-6-yl]imidazo[1,5-a]pyrazin-1-yl}-3-ethoxy-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-5-ethoxy-2-fluoro-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-3-ethoxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-fluoro-5-methoxy-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-3-methoxy-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-3-ethoxy-N-[4-(trifluoromethyl)pyridin-2-yl]benzamide;

4-{8-amino-3-[(6R,8aS)-3-oxooctahydroindolizin-6-yl]-5-(trifluoromethyl)imidazo[1,5-a]pyrazin-1-yl}-3-ethoxy-N-[4-(trifluoromethyl)pyridin-2-yl]benzamide; and 4-(8-amino-5-fluoro-3-((6R,8aS)-3-oxooctahydroindolizin-6-yl)imidazo[1,5-a]pyrazin-1-yl)-3-ethoxy-5-fluoro-N-(4-(trifluoromethyl)pyridin-2-yl)benzamide.

The Btk inhibitor compounds of the invention having Formula I or II inhibit the Btk kinase activity. All compounds of the invention have an $EC_{50}$ of 10 μM or lower. In another aspect the invention relates to compounds of Formula I which have an $EC_{50}$ of less than 100 nM. In yet another aspect the invention relates to compounds of Formula I or II which have an $EC_{50}$ of less than 10 nM.

The term $EC_{50}$ means the concentration of the test compound that is required for 50% inhibition of its maximum effect in vitro.

In another aspect the invention relates to compounds of Formula I or II or pharmaceutically acceptable salts thereof, which have an $IC_{50}$ of less than 100 nM. In yet another aspect the invention relates to the compounds of Formula I or II or pharmaceutically acceptable salts thereof, which have an $IC_{50}$ of less than 10 nM.

The term $IC_{50}$ means the concentration of the test compound that is required for 50% inhibition of its maximum effect in vitro.

BTK enzymatic activity was determined with the LANCE (Lanthanide Chelate Excite) TR-FRET (Time-resolved fluorescence resonance energy transfer) assay. In this assay, the potency ($IC_{50}$) of each compound was determined from an eleven point (1:3 serial dilution; final compound concentration range in assay from 1 μM to 0.017 nM) titration curve using the following outlined procedure. To each well of a black non-binding surface Corning 384-well microplate (Corning Catalog #3820), 5 nL of compound (2000 fold dilution in final assay volume of 10 μL) was dispensed, followed by the addition of 7.5 μL of 1× kinase buffer (50 mM Hepes 7.5, 10 mM $MgCl_2$, 0.01% Brij-35, 1 mM EGTA, 0.05% BSA & 1 mM DTT) containing 10.18 pg/μL (133.3 pM) of BTK enzyme (recombinant protein from baculovirus-transfected Sf9 cells: full-length BTK, 6HIS-tag cleaved). Following a 60 minute compound & enzyme incubation, each reaction was initiated by the addition of 2.5 μL 1× kinase buffer containing 8 μM biotinylated "A5" peptide (Biotin-EQEDEPEGDYFEWLE-NH2) (SEQ ID NO: 1), and 100 μM ATP. The final reaction in each well of 10 μL consists of 100 pM hBTK, 2 μM biotin-A5-peptide, and 25 μM ATP. Phosphorylation reactions were allowed to proceed for 120 minutes. Reactions were immediately quenched by the addition of 20 uL of 1× quench buffer (15 mM EDTA, 25 mM Hepes 7.3, and 0.1% Triton X-100) containing detection reagents (0.626 nM of LANCE-Eu-W1024-anti-phosphoTyrosine antibody, PerkinElmer and 86.8 nM of Streptavidin-conjugated Dylight 650, Dyomics/ThermoFisher Scientific). After 60 minutes incubation with detection reagents, reaction plates were read on a PerkinElmer EnVision plate reader using standard TR-FRET protocol. Briefly, excitation of donor molecules (Eu-chelate: anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). $IC_{50}$ values were determined by 4 parameter robust fit of TR-FRET ratio values vs. ($Log_{10}$) compound concentrations.

The Btk activity can also be determined in B cell lines such as Ramos cells or in primary cell assays, e.g. PBMC or whole blood from human, monkey, rat or mouse or isolated splenocytes from monkey, rat or mouse. Inhibition of Btk activity can be investigated measuring anti-IgM-induced MIP 1β production (Ramos, PBMC, splenocytes), $H_2O_2$-induced Btk and PLCγ2 phosphorylation (Ramos cells), or anti-IgM-induced B cell proliferation or CD86 expression on primary B cells (PBMC and splenocytes).

Regulation of Btk activity can also be determined on human, monkey, rat or mouse mast cells following activation FceR induced degranulation, cytokine production and CD63 induced cell surface expression.

Furthermore, regulation of Btk activity can be determined on CD14+ monocytes differentiated following treatment with M-CSF to osteoclasts and activated with RANKL.

Activity of Btk inhibitors can be investigated in mouse splenocytes following administration in vivo. In a typical experiment mice can be euthanized 3 h following compound administration. Spleens can be extracted from the treated mice for splenocyte isolation. Splenocytes can be plated in 96 well culture plates and stimulated with anti-IgM, without further addition of compounds. Anti-IgM-induced B cell stimulation and inhibition thereof by Btk inhibitors can be measured by B cell proliferation, MIP1β production or CD86 expression on CD19+ splenocyte B cells.

Efficacy of Btk inhibitors can also be investigated in the mouse collagen induced arthritis model using a therapeutic protocol with start of treatment following onset of disease, measuring disease score, X-ray analysis of bone destruction, cartilage breakdown and histology of joints Efficacy of Btk inhibitors on the regulation of activated mast cells can be investigated in vivo using the passive cutaneous anaphylaxis model.

The effect of Btk inhibitors on bone resorption in vivo can be investigated using the rat OVX model. In this model ovariectomized animals develop symptoms of osteoporosis that may be regulated using a Btk inhibitor.

The compounds of Formula I can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds having Formula I or the pharmaceutically acceptable salts or solvates thereof may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

One or more compounds of the invention having Formula I or the pharmaceutically acceptable salts or solvates thereof may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula I (e.g. those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herinbelow, by substituting an appropriate isotopically labeled reagent for a non-isotopically labeled reagent.

The compounds having Formula I and pharmaceutical compositions thereof can be used to treat or prevent a variety of conditions, diseases or disorders mediated by Bruton's Tyrosine kinase (Btk). Such conditions, diseases or disorders include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g. precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors, myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula (I) and salts, solvates and physiologically functional derivatives thereof for use in therapy, and particularly in the treatment of diseases and conditions mediated by inappropriate Btk activity.

The inappropriate Btk activity referred to herein is any Btk activity that deviates from the normal Btk activity expected in a particular mammalian subject. Inappropriate Btk activity may take the form of, for instance, an abnormal increase in activity, or an aberration in the timing and or control of Btk activity. Such inappropriate activity may result then, for example, from overexpression or mutation of the protein kinase leading to inappropriate or uncontrolled activation.

In a further embodiment, the present invention is directed to methods of regulating, modulating, or inhibiting Btk for the prevention and/or treatment of disorders related to unregulated or inappropriate Btk activity.

In a further embodiment, the present invention provides a method of treatment of a mammal suffering from a disorder mediated by Btk activity, which comprises administering to said mammal an effective amount of a compound of Formula (I) or a pharmaceutically acceptable salt, solvate, or a physiologically functional derivative thereof.

In a further embodiment, the present invention provides for the use of a compound of Formula (I), or a pharmaceutically acceptable salt or solvate thereof, or a physiologically functional derivative thereof, in the preparation of a medicament for the treatment of a disorder mediated by Btk activity.

In a further embodiment said disorder mediated by Btk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Btk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

A further aspect of the invention resides in the use of a compound of Formula I or a pharmaceutically acceptable salt thereof for the manufacture of a medicament to be used for the treatment of Btk-mediated diseases or Btk-mediated conditions.

A further aspect of the invention resides in the use of a compound of Formula I or a pharmaceutically acceptable salt thereof for the manufacture of a medicament to be used for the treatment of chronic B cell disorders in which T cells play a prominent role.

In yet another aspect the invention resides in the use of a compound of Formula I or a pharmaceutically acceptable salt thereof for the manufacture of a medicament to be used for the treatment of Btk-mediated diseases or conditions. These include, but are not limited to, the treatment of B cell lymphomas resulting from chronic active B cell receptor signaling.

Thus, the compounds according to the invention may be used in therapies to treat or prevent diseases Bruton's Tyrosine Kinase (Btk) mediated disorders. Btk mediated disorders or Btk mediated condition as used herein, mean any disease state or other deleterious condition in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that may be treated or prevented with the compounds of the present invention include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), Goodpasture's syndrome, (and associated glomerulonephritis and pulmonary hemorrhage), atherosclerosis, autoimmune hematologic disorders (e.g. hemolytic anemia, aplastic anemia, idiopathic thrombocytopenia, chronic idiopathic thrombocytopenic purpura (ITP), and neutropenia), autoimmune gastritis, and autoimmune inflammatory bowel diseases (e.g. ulcerative colitis and Crohn's disease), irritable bowel syndrome, host versus graft disease, allograft rejection, chronic thyroiditis, Graves' disease, Sjorgren's disease, scleroderma, diabetes (type I and type II), active hepatitis (acute and chronic), pancreatitis, primary billiary cirrhosis, myasthenia gravis, multiple sclerosis, systemic lupus erythematosis, psoriasis, atopic dermatitis, dermatomyositis, contact dermatitis, eczema, skin sunburns, vasculitis (e.g. Behcet's disease), ANCA-associated and other vasculitudes, chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, Addison's disease, Parkinson's disease, Alzheimer's disease, diabetes, septic shock, myasthenia gravis, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Allergies that may be treated or prevented include, among others, allergies to foods, food additives, insect poisons, dust mites, pollen, animal materials and contact allergens, type I hypersensitivity allergic asthma, allergic rhinitis, allergic conjunctivitis.

Infectious diseases that may be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that may be treated or prevented include, among others, osteoporosis, osteoarthritis, traumatic arthritis, gouty arthritis and bone disorders related with multiple myeloma.

Proliferative diseases that may be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell, ALL in particular.

In particular the compounds of Formula I or pharmaceutically acceptable salts may be used for the treatment of B cell lymphomas resulting from chronic active B cell receptor signaling.

Included herein are methods of treatment and/or pharmaceutical compositions in which at least one compound of Formula I or a pharmaceutically acceptable salt thereof is administered in combination with at least one other additional therapeutically active agent. The other additional therapeutically active agent is an anti-inflammatory agent, an immunosuppressant agent, or a chemotherapeutic agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory agent is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant agent, such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic agents, in particular, drugs that induce apoptosis. Examples of other chemotherapeutic agents that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. J. Exp. Med. 2005 201(11):1837-1852).

While it is possible that, for use in therapy, a compound of Formula (I), as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of Formula (I) and salts, solvates and physiological functional derivatives thereof, and one or more pharmaceutically acceptable carriers, diluents, or excipients. The compounds of the Formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula (I), or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of the Formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, Chronic Obstructive Pulmonary disease (COPD) or Acute Respiratory Distress Syndrome (ARDS).

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula (I) is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula (I) or salt or solvate thereof (preferably in particle-size-reduced form, e.g. in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula (I) or salt thereof. The lactose is preferably lactose hydrate e.g. lactose monohydrate and/or is preferably inhalation-grade and/or fine-grade lactose.

Preferably, the particle size of the lactose is defined by 90% or more (by weight or by volume) of the lactose particles being less than 1000 microns (micrometres) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurized aerosols, nebulizers or insufflators.

For pharmaceutical compositions suitable and/or adapted for intranasal administration, the compound of Formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The invention further includes a pharmaceutical composition of a compound of Formula I or pharmaceutically acceptable salts thereof, as hereinbefore described, in combination with packaging material suitable for said composition, said packaging material including instructions for the use of the composition for the use as hereinbefore described.

The following are examples of representative pharmaceutical dosage forms for the compounds of this invention:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the particular compound having Formula I, the nature of the formulation, and the route of administration, and will ultimately be at the discretion of the attendant physician or veterinarian. However, an effective amount of a compound of Formula (I) for the treatment of diseases or conditions associated with inappropriate Btk activity, will generally be in the range of 5 μg to 100 mg/kg body weight of recipient (mammal) per day and more usually in the range of 5 μg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula (I) per se.

In general parenteral administration requires lower dosages than other methods of administration which are more dependent upon absorption. However, a dosage for humans preferably contains 0.0001-25 mg of a compound of Formula I or pharmaceutically acceptable salts thereof per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

The present invention also relates to a pharmaceutical composition comprising a compound of Formula I or pharmaceutically acceptable salt thereof in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition comprising at least one compound of Formula I or pharmaceutically acceptable salts thereof in combination with at least one other therapeutically active agent.

Compounds of the present invention, and their salts and solvates, and physiologically functional derivatives thereof, may be employed alone or in combination with other therapeutic agents for the treatment of Btk mediated diseases and conditions associated with inappropriate Btk activity. Combination therapies according to the present invention thus comprise the administration of at least one compound of Formula (I) or a pharmaceutically acceptable salt or solvate thereof, or a physiologically functional derivative thereof, and the use of at least one other pharmaceutically active agent. The compound(s) of Formula (I) and the other pharmaceutically active agent(s) may be administered together or separately and, when administered separately this may occur simultaneously or sequentially in any order. The amounts of the compound(s) of Formula (I) and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of Formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2), p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for "triple combination" therapy, comprising a compound of Formula (I) or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of Formula (I) or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol).

For the treatment of cancer a compound of Formula I may be combined with one or more of an anticancer agents. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxyl)phenoxy)propoxy)-2-ethyl-chromane-2-carboxylic acid (disclosed in U.S. Ser. No. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF 1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diariziidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP 1350, BNPI 1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)-ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP 1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of Formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a;

interferon alfa-2b; irinotecan; ixabepilone; lapatinib; lenalidomide; letrozole; leucovorin; leuprolide acetate; levamisole; lomustine; mechlorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

General Synthesis

The 8-amino-imidazo[1,5-a]pyrazine, 4-amino-imidazo[1,5-f][1,2,4]triazine, 4-amino-pyrazolo[3,4-d]pyrimidine and 4-amino-pyrrolo[1,2-f][1,2,4]triazine derivatives of the present invention can be prepared by methods well known in the art of organic chemistry. See, for example, J. March, 'Advanced Organic Chemistry' 4th Edition, John Wiley and Sons. During these synthetic sequences, it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 3rd Edition, John Wiley and Sons, 1999. The protective groups are optionally removed at a convenient subsequent stage using methods well known in the art.

The products of the reactions are optionally isolated and purified, if desired, using conventional techniques including, but not limited to, filtration, distillation, crystallization, chromatography, and the like. Such materials are optionally characterized using conventional means, including physical constants and spectral data.

The 8-amino-imidazo[1,5-a]pyrazine compounds of formula I, wherein $R^5$, $R^c$, $R^d$, $R^e$, and $R^f$, have the previously defined meanings, can be prepared by the general synthetic route shown in Scheme I.

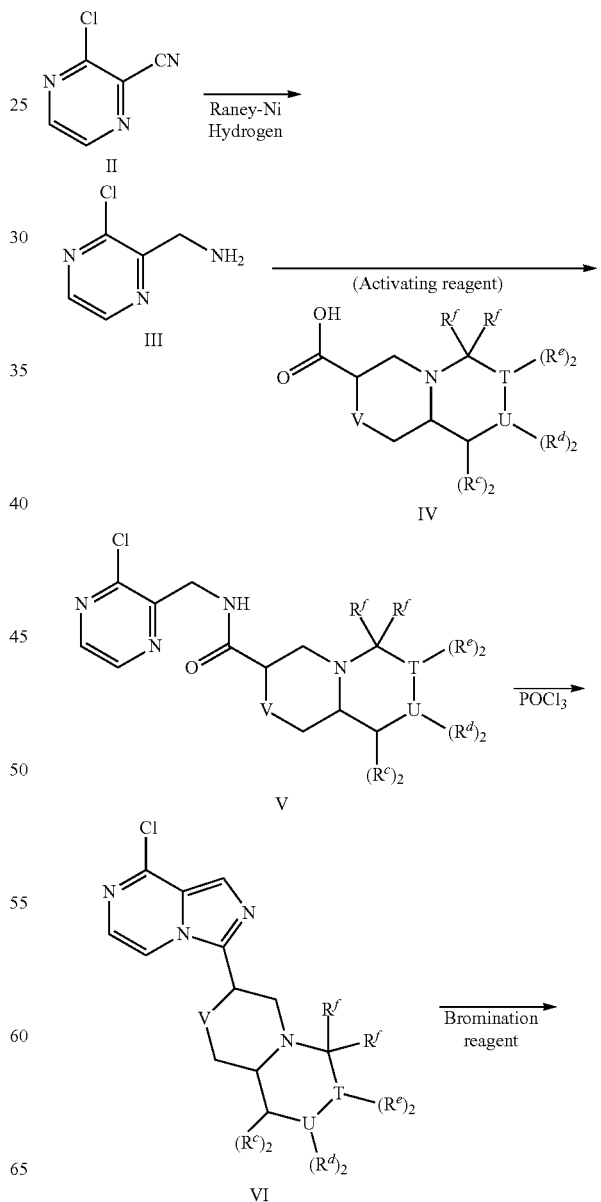

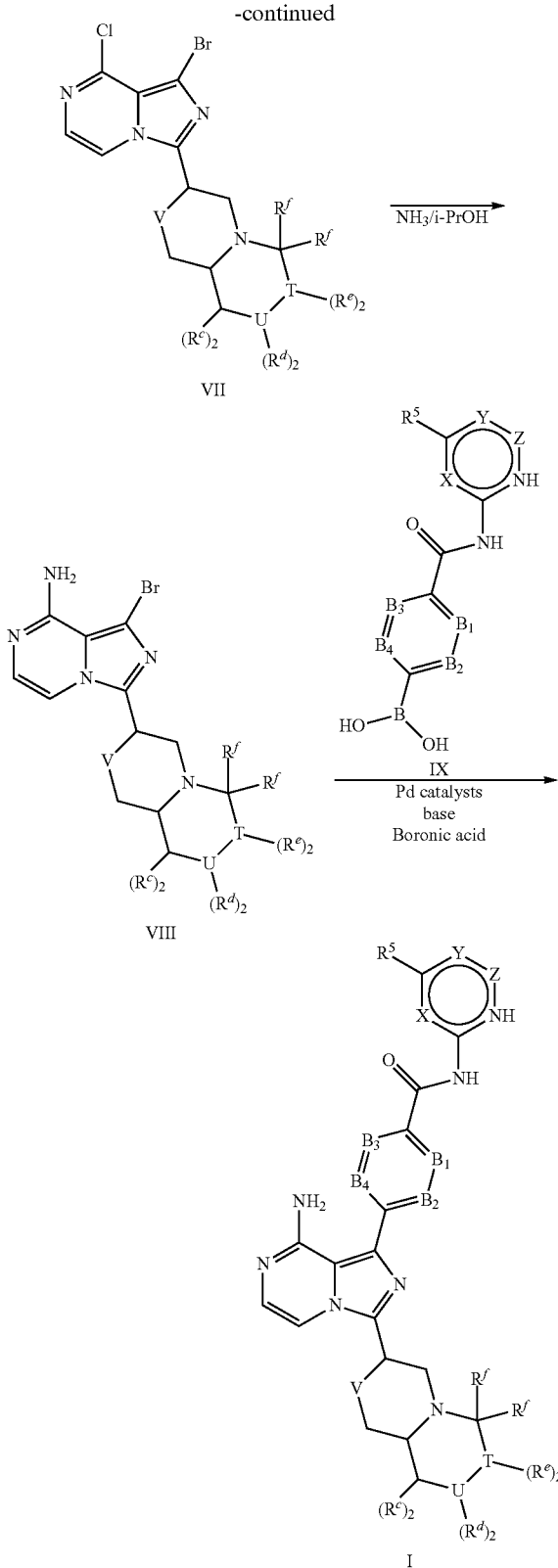

(IV). The reaction of IV can be carried out in a solvent such as DMF, THF or DCM in the presence of a base such as DIPEA, N-methylmorpholine, 4-DMAP or triethylamine and in the presence of a coupling reagent such as PyBOP, TBTU, EDCI or HATU to form N-((3-chloropyrazin-2-yl)methyl)amide (V). Cyclisation chloropyrazine (V) can be performed using condensation reagents like phosphorousoxychloride under heating conditions to provide the 8-chloroimidazo[1,5-a]pyrazine derivatives VI. Subsequent bromination can be accomplished using bromine or N-bromosuccinimide in a suitable solvent like DCM or DMF at appropriate temperature to obtain compounds of formula VII. 8-Aminoimidazo[1,5-a]pyrazine derivatives (VIII) can be prepared from compounds of formula VII using ammonia(gas) in isopropanol at elevated temperature in a pressure vessel (>4 atm). Compounds of formula I can be prepared from compounds of formula VIII using an appropriate boronic acid or pinacol ester (IX), in the presence of a suitable palladium catalyst system, for example bis(diphenylphosphino)ferrocene palladium(II)chloride complex or tetrakis(triphenylphosphine)palladium(0) in the presence of an inorganic base like potassium carbonate, cesium carbonate or potassium phosphate in a suitable solvent system like combinations of dioxane and water. Palladium catalysts and conditions to form either the pinacol esters or to couple the boronic acids or pinacol esters with the 1-bromoimidazo[1,5-a]pyrazin-8-amine are well known to the skilled organic chemist—see, for example, Ei-ichi Negishi (Editor), Armin de Meijere (Associate Editor), Handbook of Organopalladium Chemistry for Organic Synthesis, John Wiley and Sons, 2002. The bicyclic carboxylic compounds like IV can be readily prepared using methods well known to the skilled organic chemist, illustrated in schemes.

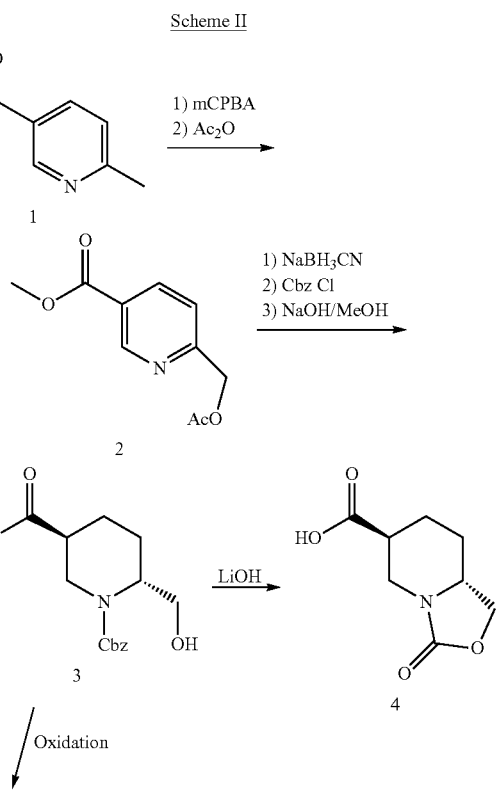

Scheme II

Reduction of 3-chloropyrazine-2-carbonitrile (II) can be accomplished by hydrogenation in the presence of a suitable catalyst system and solvent, for example Raney-Nickel ethanol to provide (3-chloropyrazin-2-yl)methanamine (III). This can then be reacted with the bicyclic carboxylic acid

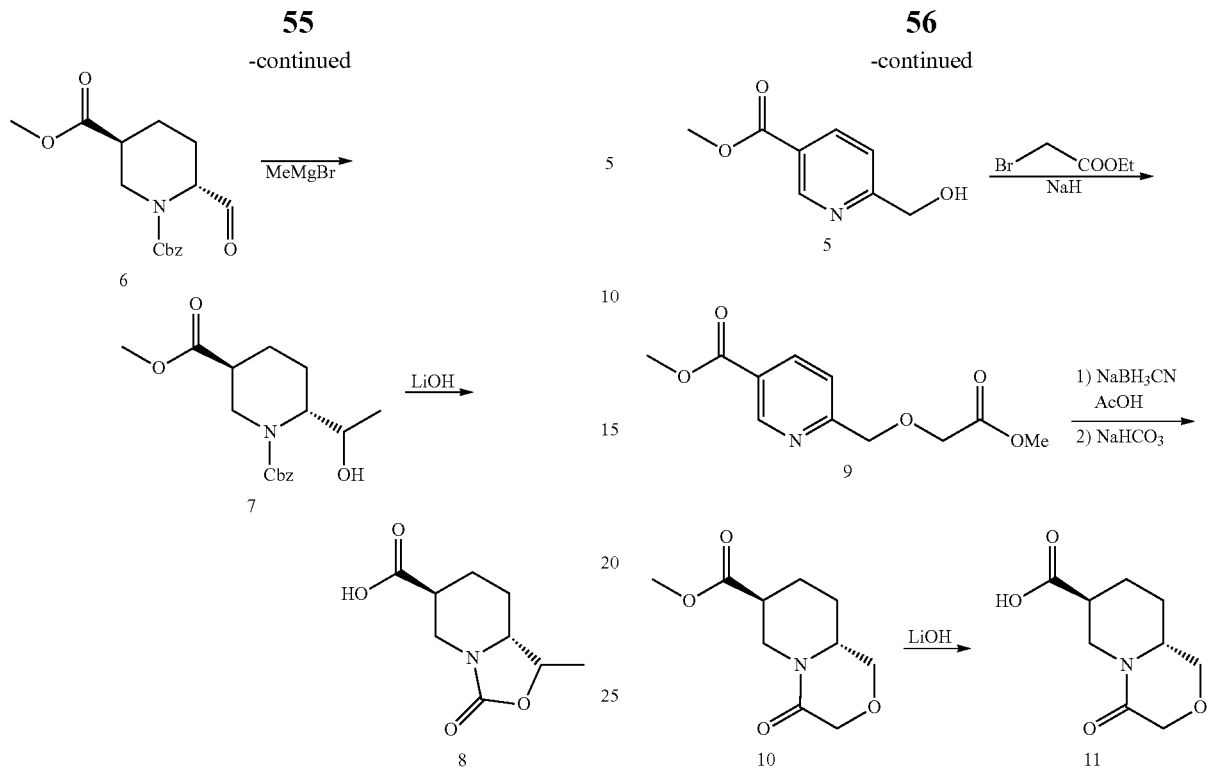

Most of this bicyclic carboxylic compounds can be prepared from the common starting material methyl 2-methyl-5-pyridinecarboxylate (1). Scheme II shows the preparation of compound 4 and 5. Compound 1 was converted to 2 by oxidation using mCPBA to N-oxide, followed by treatment with acetic anhydride to rearrange to acetate. The pyridine ring in 2 was then saturated with sodiumcyanoborohydride, followed by protection of the amine with Cbz with treatment of CbzCl under basic conditions such as TEA, and finally hydrolysis of the acetate to using sodium hydroxide in methanol with water to provide compound 3. Compound 3 was then treated with lithium hydroxide in tetrahydrofuran with water, the carbamate was formed along with the hydrolysis of the ester to acid provided bicyclic acid compound 4. The hydroxy in intermediate 3 is oxidized to aldehyde 6 using oxidation conditions such as TPAP/NMO. Methyl magnesium bromide addition to the aldehyde provides the secondary alcohol 7 which is converted to the carbamate 8 using the same basic condition, lithium hydroxide in tetrahydrofuran with water.

The intermediate 2 was converted to hydroxymethylpyridine-5-carboxylate 5; and then the hydroxyl can be alkylated by ethyl 2-bromoacetate to compound under sodium hydride as base in THF to provide compound 9. The reductive condition described before using sodium cyanoborohydride to saturate the pyridine ring, followed by treatment with base for the lactam formation generated compound 10. Finally, the methyl ester was hydrolyzed to acid 11.

Scheme IV

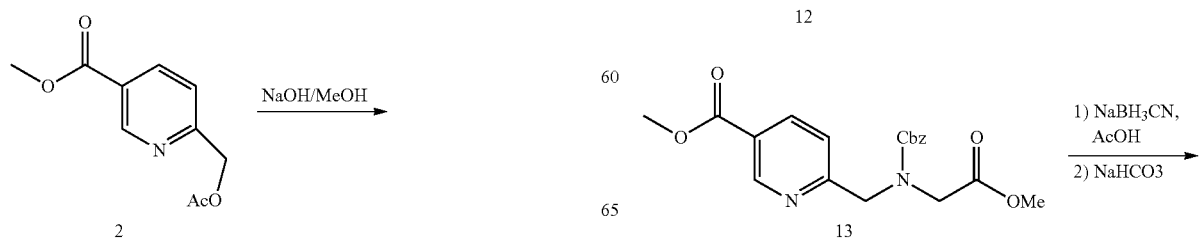

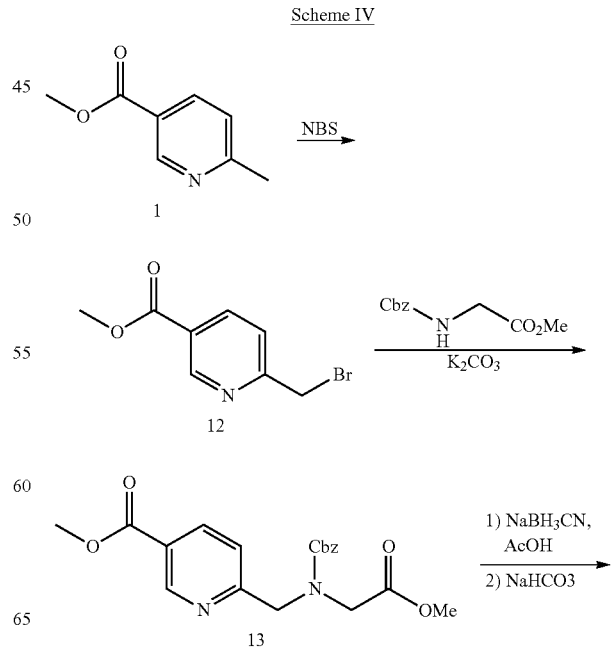

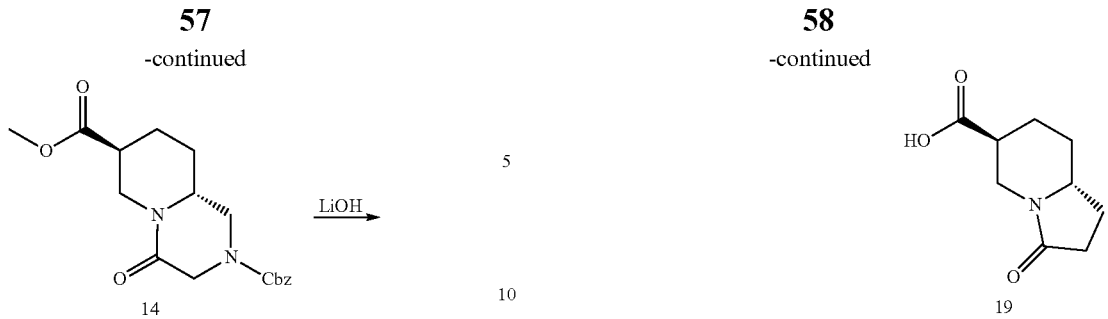

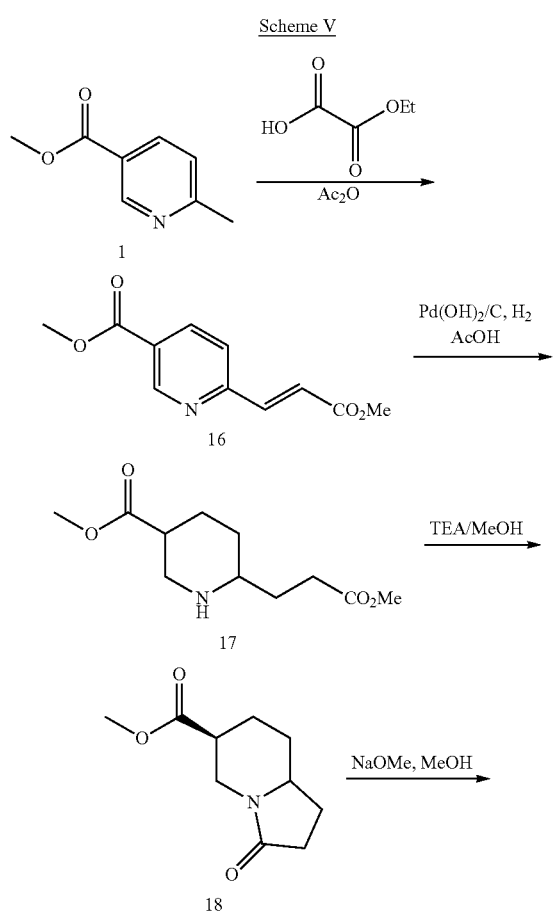

Scheme IV shows the preparation of bicyclic acid 15. The common starting material 1 was bromoated using NBS to benzylic bromide 12. The benzylic bromide was used to alkylate methyl N-Cbz-glycineester to 13. The pyridine was reduced using the same condition, followed by lactam formation to 14 and hydrolysis of ester to acid 15.

The bicyclic acid 19 was prepared using the synthetic scheme V. The common starting material 1 reacted with ethyl oxazylate in acetic anhydride with heating to provide the 1,2-unsaturated ester 16. Hydrogenation using palladium hydroxide on carbon as catalyst in acetic acid reduces the pyridine to piperidine 17. When 17 was treated with base such as triethyl amine in methanol, the lactam 18 was formed. The methyl ester is hydrolyzed by treatment with sodium methoxide in methanol to trans bicyclic acid 19.

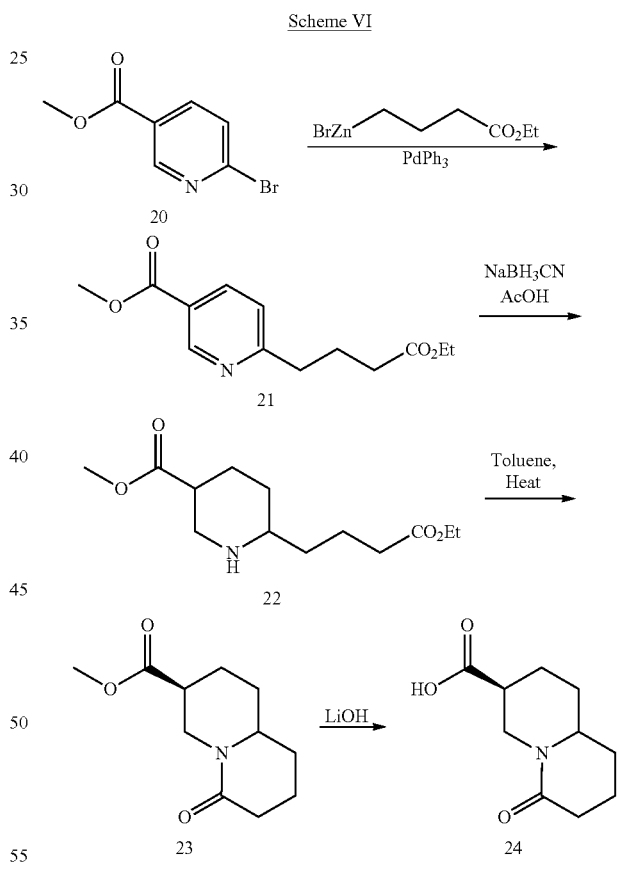

Scheme VI illustrates the preparation of bicyclic acid 24. Niggishi coupling of methyl 6-bromonicotinate 20 with (4-ethoxy-4-oxobutyl)zinc(II) bromide catalyzed with palladium provides compound 21. The pyridine ring is then reduced using sodium cyanoborohydride in acetic acid to 22, followed by ring closure by heating in toluene to lactam 23. Hydrolysis of the ester provided 24. Substituted bicyclic acid 19 and 24 are prepared in the similar ways described in Schemes V and VI.

The present invention also includes within its scope all stereoisomeric forms of the Btk inhibitor compounds according to the present invention resulting, for example, because of configurational or geometrical isomerism. Such stereoisomeric forms are enantiomers, diastereoisomers, cis and trans isomers etc. For example where azepane-2-carboxylic acid is used as amino acid, there exists a mixture of two enantiomers. In the case of the individual stereoisomers of compounds of Formula I or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in *Chirality in Industry* (edited by A. N. Collins, G. N. Sheldrake and J. Crosby, 1992; John Wiley). Likewise methods for synthesis of geometrical isomers are also well known in the art.

The Btk inhibitor compounds of the present invention, which can be in the form of a free base, may be isolated from the reaction mixture in the form of a pharmaceutically acceptable salt. The pharmaceutically acceptable salts may also be obtained by treating the free base of Formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The Btk inhibitor compounds of the present invention may also exist as amorphous solids. Multiple crystalline forms are also possible. All the physical forms are included within the scope of the present invention.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

The invention is illustrated by the following examples.

Examples

The following examples are illustrative embodiments of the invention, not limiting the scope of the invention in any way. Reagents are commercially available or are prepared according to procedures in the literature.

Mass Spectrometry: Electron Spray spectra were recorded on the Applied Biosystems API-165 single quad mass spectrometer in alternating positive and negative ion mode using Flow Injection. The mass range was 120-2000 Da. and scanned with a step rate of 0.2 Da. and the capillary voltage was set to 5000 V. $N_2$ gas was used for nebulisation.

LC-MS spectrometer (Waters) Detector: PDA (200-320 nm), Mass detector: ZQ and Eluent: A: acetonitrile with 0.05% trifluoroacetic acid, B: acetonitrile/water=1/9 (v/v) with 0.05% trifluoroacetic acid.

| Method A: LC-MS | |
|---|---|
| Column | Agilent TC-C18, 50 × 2.1 mm, 5 μm |
| Mobile Phase | A: $H_2O$ (0.1% TFA) |
| | B: MeCN (0.05% TFA) |
| | Stop Time: 4.5 min |

| Gradient | Time (min) | B % |
|---|---|---|
| | 0 | 1 |
| | 0.4 | 1 |
| | 3.4 | 90 |
| | 3.9 | 100 |
| | 3.91 | 1 |

| | |
|---|---|
| Sample injection volume | 2 μl |
| Flow Rate | 0.8 ml/min |
| Wavelength | 220 nm |
| Oven Tem. | 50° C. |
| MS polarity | ESI POS |

| Method B: LC-MS |
|---|
| Sample Info: Easy-Access Method: '1-Short_TFA_Pos' |
| Method Info: B222 Column Agilent SBC (3.0 × 50 mm, 1.8 μm); |
| Flow 1.0 mL/min; |
| solvent A: $H_2O$-0.1% TFA; |
| solvent B: MeCN-0.1% TFA; |
| GRADIENT TABLE: 0 min: 10% B, 0.3 min: 10% B, 1.5 min: 95% B, 2.70 min: 95% B, 2.76 min: 10% B |
| stop time 3.60 min, PostTime 0.70 min. |

| Method C: LC-MS |
|---|
| Sample Info: Easy-Access Method: '1_Fast' |
| Method Info: A330 Column Agilent Zorbax SB-C18 (2.1 × 30 mm, 3.5 μm); |
| Flow 2.0 mL/min; |
| solvent A: $H_2O$-0.1% TFA; |
| solvent B: MeCN-0.1% TFA; |
| GRADIENT TABLE: 0.01 min: 10% B, 1.01 min: 95% B, 1.37 min: 95% B, 1.38 min: 10% B, |
| stop time 1.7 min, PostTime = OFF |

| Method D: LC-MS |
|---|
| Mobile Phase: 0.1% TFA in MeCN and 0.1% TFA in Water |
| Column: Xterra 2.1 × 20 mm 3.5 μm IS or SunFire |
| Flow rate = 1.5 mL/min |
| Injection Volume = 5 μL |
| Column Heater = 50° C. |
| Run time = 4 min |
| Flow rate = 1.5 mL/min |
| Injection Volume = 5 μL |

| Gradient: | | |
|---|---|---|
| Time | % A | % B |
| 0.00 | 95 | 5 |
| 3.00 | 5 | 95 |
| 3.25 | 2 | 98 |
| 3.26 | 95 | 5 |

| Method E: LC-MS |
|---|
| Mobile Phase: A: 0.1% TFA in MeCN and B: 0.1% TFA in Water |
| Column: Xterra 2.1 × 20 mm 3.5 μm IS or SunFire |
| Flow rate = 1.5 mL/min |
| Injection Volume = 5 μL |
| Column Heater = 50° C. |

Run time = 2 min
Flow rate = 1.5 mL/min
Injection Volume = 5 µL

Gradient:

| Time | % A | % B |
|---|---|---|
| 0.00 | 95 | 5 |
| 0.75 | 5 | 95 |
| 1.25 | 2 | 98 |
| 1.26 | 95 | 5 |

Method F: LC-MS

Acquity UPLC BEH-C18 (2.1 × 50 mm, 1.7 µm); Flow 1 mL/min.
5%-100% MeCN in 1.4 min
0.1% $NH_3$
Preparative HPLC was conducted on a column (50 × 10 mm ID, 5 µm, Xterra Prep MS C18) at a flow rate of 5 ml/min, injection volume 500 µl, at room temperature and UV Detection at 210 nm.

The following abbreviations are used throughout the application with respect to chemical terminology:
HATU O-(7-Azabenzotriazol-1-yl)-1,1,3,3-tetramethyluroniumhexafluoro phosphate
Cbz Benzyloxycarbonyl
D Deuterated hydrogen
DMF N,N-Dimethylformamide
DCM Dichloromethane
EA Ethyl acetate
EtOAc Ethyl acetate
DIPEA N,N-Diisopropylethylamine
THF Tetrahydrofuran
EtOH Ethanol
EDCI.HCl 1-(3-Dimethylaminopropyl)-3-ethylcarbodiimide hydrochloride
4-DMAP 4-Dimethylaminopyridine
PyBOP O-Benzotriazole-1-yl-oxy-trispyrrolidinophosphonium hexafluorophosphate
TBTU O-Benzotriazol-1-yl-N,N,N',N-tetramethyluronium tetrafluoroborate
HBr Hydrogen bromide
HCl Hydrogen chloride
HOAc Acetic acid
$POCl_3$ Phosphorous oxychloride
HPLC High Pressure Liquid Chromatography
UPLC Ultra Performance Liquid Chromatography
LiHMDS Lithium hexamethyldisilazide
MeOH Methanol
DCM Dichloromethane
n-BuLi n-Butyllithium
$CO_2$ Carbondioxide
$NaHCO_3$ Sodium bicarbonate
$K_3PO_4$ Potassium phosphate
$P(Cy)_3$ Tricyclohexylphosphine
$Pd(OAc)_2$ Palladium(II) acetate
$Na_2SO_4$ Sodium sulfate
$Na_2CO_3$ Sodium carbonate
DAST Diethylaminosulfur trifluoride
$Cs_2CO_3$ Cesium carbonate
$Et_2O$ Diethylether
$Na_2S_2O_3$ Sodium thiosulfate
$Na_2S_2O_4$ Sodium hydrosulfite
$NaCNBH_3$ Sodium cyanoborohydride
$NH_4Cl$ Ammonium chloride
$MgSO_4$ Magnesium sulfate
LiOH Lithium hydroxide
IPA Isopropylamine
TFA Trifluoroacetic acid
Cbz-Cl Benzylchloroformate
PE Petroleum ether
EA Ethyl acetate
NaHMDS Sodium hexamethyldisilazide
10% Pd/C 10% Palladium on carbon
TEA Triethylamine
CDI 1,1'-Carbonyl diimidazole
DMI 1,3-Dimethyl-2-imidazolidinone
NBS N-Bromosuccinimide
i-PrOH 2-Propanol
$K_2CO_3$ Potassium carbonate
$Pd(dppf)Cl_2$ 1,1'-Bis(diphenylphosphino)ferrocene palladium (II) chloride, complex with dichloromethane
$Et_3N$ Triethylamine
2-BuOH 2-Butanol
LCMS Liquid Chromatography/Mass Spectrometry
MeCN Acetonitrile
$NH_3$ Ammonia
$CD_3I$ Trideuteromethyl iodide
$CD_3OD$ Tetradeuteromethanol
$CH_3I$ Iodomethane
$CBr_4$ Carbon tetrabromide
Tris-HCl Tris(hydroxymethyl)aminomethane hydrochloride
$MgCl_2$ Magnesium chloride
$NaN_3$ Sodium azide
DTT Dithiothreitol
DMSO Dimethyl sulfoxide
IMAP Immobilized Metal Ion Affinity-Based Fluorescence Polarization
ATP Adenosine triphosphate
$MnCl_2$ Manganese(II) chloride
DMA Dimethylacetamide
IPA Isopropyl alcohol
TPP triphenylphosphine
DIAD Diisopropyl azodicarboxylate
DMB 2,4-dimethoxybenzyl
DCE Dichloroethane
DEAD Diethyl azodicarboxylate
ACN Acetonitrile
Ret. Time Retention Time
RT (rt) Room Temperature
Aq Aqueous
EtOH Ethanol
MPLC Medium Pressure Liquid Chromoatography
Xantphos 4,5-Bis(diphenylphosphino)-9,9-dimethylxanthene
X-phos 2-Dicyclohexylphosphino-2',4',6'-triisopropylbiphenyl

INTERMEDIATES

Intermediate 1

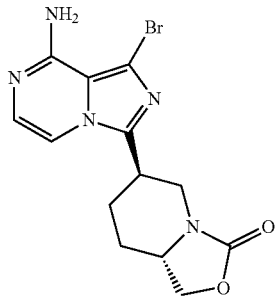 [SMILES: Nc1nccn2c([C@@H]3CC[C@H]4COC(=O)N4C3)nc(Br)c12]

(6R,8aS)-6-(8-amino-1-bromoimidazo[1,5-a]pyrazin-3-yl)tetrahydro-1H-oxazolo[3,4-a]pyridin-3(5H)-one

(a) trans-1-benzyl 3-methyl 6-(acetoxymethyl)piperidine-1,3-dicarboxylate

To a solution of methyl 6-(acetoxymethyl)nicotinate (75 g, 358.5 mmol) in AcOH (1000 mL) was added NaBH$_3$CN (45.2 g, 717 mmol) portionwise at rt. The solution was stirred overnight. The reaction mixture was concentrated under reduced pressure and the residue was dissolved in H$_2$O (770 mL) and the pH was adjusted to 8 with aqueous NaHCO$_3$. The resulting mixture was cooled to 0° C., to which Cbz-Cl (122 g, 716 mmol) was added dropwise. The mixture was stirred at rt overnight and extracted with DCM (2×500 mL). The organic layer was dried over Na$_2$SO$_4$ and concentrated in vacuo and the residue was purified by column chromatography with silica gel eluted by 5~30% ethyl acetate in petroleum ether (60-90 fraction) preparative HPLC to give to trans-1-benzyl 3-methyl 6-(acetoxymethyl)piperidine-1,3-dicarboxylate (42 g, 33.6% yield) MS: M/Z (M+1): 349.9. Retention Time: 1.053.

(b) trans-1-benzyl 3-methyl 6-(hydroxymethyl)piperidine-1,3-dicarboxylate

To a solution of trans-1-benzyl 3-methyl 6-(acetoxymethyl)piperidine-1,3-dicarboxylate (8.8 g, 25.2 mmol) in MeOH (88 mL) was added HCl (2.2 ml, 12M). The resulting solution was stirred at reflux overnight and cooled to rt. After removal of solvent in vacuo, the residue was purified by chromatography to give 4.3 g of trans-1-benzyl 3-methyl 6-(hydroxymethyl)piperidine-1,3-dicarboxylate. $^1$HNMR (400 MHz, CD$_3$OD) δ=7.39 (s, 5H), 5.15 (s, 2H), 4.38-4.26 (m, 2H), 3.73-3.67 (m, 4H), 3.66-3.58 (m, 1H), 2.97 (br. s, 1H), 2.48 (tt, J=4.1, 11.8 Hz, 1H), 1.98-1.84 (m, 1H), 1.78-1.57 (m, 1H).

(c) (3S,6R)-1-benzyl 3-methyl 6-(hydroxymethyl)piperidine-1,3-dicarboxylate & (3R,6S)-1-benzyl 3-methyl 6-(hydroxymethyl)piperidine-1,3-dicarboxylate 4.3 g of trans-1-Benzyl 3-methyl 6-(hydroxymethyl)piperidine-1,3-dicarboxylate was resolved with chiral HPLC to give two enantiomers. (Instrument: Thar 200; Column: AD 250 mm×50 mm, 5 um; Mobile phase: A: Supercritical CO$_2$, B: MeOH, A:B=85:15 at 160 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) 1.3 g of (3S,6R)-1-benzyl 3-methyl 6-(hydroxymethyl)piperidine-1,3-dicarboxylate(E1) was obtained followed by 1.1 g of (3R,6S)-1-benzyl 3-methyl 6-(hydroxymethyl)piperidine-1,3-dicarboxylate (E2).

(d)(3S,6R)-1-((benzyloxy)carbonyl)-6-(hydroxymethyl)piperidine-3-carboxylic acid To a mixture of (3S,6R)-1-benzyl 3-methyl 6-(hydroxymethyl)piperidine-1,3-dicarboxylate (1.0 g, 3.25 mmol) in MeOH/H$_2$O (6 mL/3 mL) was added Lithium hydroxide monohydrate (273 mg, 6.5 mmol). The reaction mixture was stirred at 25° C. overnight. The mixture was concentrated in vacuo, acidified by 1N HCl to pH 5~6, and then extracted with EA. The organic layer was washed with brine, dried over Na$_2$SO$_4$, and concentrated in vacuo to give (3S,6R)-1-((benzyloxy)carbonyl)-6-(hydroxymethyl)piperidine-3-carboxylic acid (780 mg, 81.8% yield). $^1$HNMR (400 MHz, CD$_3$OD): δ=7.32~7.40 (m, 5H), 5.16 (s, 2H), 4.30~4.36 (m, 2H), 3.60~3.73 (m, 2H), 2.93~3.02 (m, 1H), 2.39~2.46 (m, 1H), 1.89~1.97 (m, 2H), 1.59~1.77 (m, 2H).

(e) (6S,8aR)-3-oxohexahydro-1H-oxazolo[3,4-a]pyridine-6-carboxylic acid

A mixture of (3S,6R)-1-benzyl 3-methyl 6-(hydroxymethyl)piperidine-1,3-dicarboxylate (2.7 g, 8.785 mmol) in tetrahydrofuran/H$_2$O (30 mL) was added LiOH (737 mg, 17.57 mmol). The mixture was stirred at room temperature for 1 hour. The reaction mixture was extracted with ethyl acetate (100 mL) 1 time and the aqueous layer was lyophilized to give (6S,8aR)-3-oxohexahydro-1H-oxazolo[3,4-a]pyridine-6-carboxylic acid (1.6 g, 100% yield). MS (ESI): M/Z (M+1): 186.07.

(f) (6S,8aR)-N-((3-chloropyrazin-2-yl)methyl)-3-oxohexahydro-1H-oxazolo[3,4-a]pyridine-6-carboxamide A mixture of (6S,8aR)-3-oxohexahydro-1H-oxazolo[3,4-a]pyridine-6-carboxylic acid (1 g, 5.4 mmol) in dichloromethane (10 mL) was added triethylamine(1 g, 5.4 mmol) and isobutyl chloroformate (590 mg, 4.32 mmol) at 0° C. The mixture was stirred at room temperature for 2 hours. (3-Chloro-pyrazin-2-yl)-methylamine (966 mg, 5.39 mmol) was added portionwise, followed by another 3 eq triethylamine. The mixture was stirred at room temperature for 3 hours. The reaction mixture was concentrated in vacuo and purified on silica gel chromatography (PE: THF=50%~100%) to afford (6S,8aR)-N-((3-chloropyrazin-2-yl)methyl)-3-oxohexahydro-1H-oxazolo[3,4-a]pyridine-6-carboxamide (230 mg, 14% yield). $^1$HNMR(400 MHz, DMSO-d6): δ=8.64 (d, J=6.4 Hz, 1 H), 8.61 (t, J=5.6 Hz, 1 H), 8.44 (d, J=6.0 Hz, 1 H), 4.53~4.49 (m, 2 H), 4.37 (t, J=8.0 Hz, 1 H), 3.92~3.88 (m, 1 H), 2.91 (J=12.0 Hz, 1 H), 2.42~2.33 (m, 1 H), 1.93 (d, J=13.2 Hz, 1 H), 1.86~1.81 (m, 1 H), 1.63~1.52 (m, 1 H), 1.30~1.23 (m, 1 H). MS (ESI): M/Z (M+1): 311.08.

(g) (6R,8aS)-6-(8-chloroimidazo[1,5-a]pyrazin-3-l)tetrahydro-1H-oxazolo[3,4-a]pyridin-3(5H)-one A mixture of (6S,8aR)-N-((3-chloropyrazin-2-yl)methyl)-3-oxohexahydro-1H-oxazolo[3,4-a]pyridine-6-carboxamide (290 mg, 0.932 mmol) in CH3CN (5 mL) was added POCl$_3$ (715 mg, 4.66 mmol) at 0° C. The mixture was stirred at 30° C. for 15 hours. The reaction mixture was poured into ice water, basified by NaHCO$_3$ and extracted with dichloromethane/propan-2-ol (3:1, 30 mL×3). The combined organic layers were washed with brine, dried over anhydrous sodium sulfate, concentrated in vacuo to afford (6R,8aS)-6-(8-chloroimidazo[1,5-a]pyrazin-3-yl)tetrahydro-1H-oxazolo[3,4-a]pyridin-3(5H)-one (270 mg, 98% yield).
$^1$HNMR(400 MHz, CDCl$_3$): δ=7.81 (s, 1H), 7.71 (d, J=5.6 Hz, 1 H), 7.38 (d, J=4.8 Hz, 1 H), 4.49 (t, J=8.0 Hz, 1 H), 4.14~4.11 (m, 1 H), 4.10~4.02 (m, 1 H), 3.89~3.82 (m, 1 H), 3.29~3.23 (m, 1 H), 3.20~3.12 (m, 1 H), 2.27~2.20 (m, 2 H), 2.17~2.03 (m, 2 H). MS (ESI): M/Z (M+1): 293.07.

(h) (6R,8aS)-6-(1-bromo-8-chloroimidazo[1,5-a]pyrazin-3-yl)tetrahydro-1H-oxazolo[3,4-a]pyridin-3(5H)-one A mixture of (6R,8aS)-6-(8-chloroimidazo[1,5-a]pyrazin-3-yl)tetrahydro-1H-oxazolo[3,4-a]pyridin-3(5H)-one (270 mg, 0.922 mmol) in DMF (3 mL) was added 1-bromopyrrolidine-2,5-dione (181 mg, 1.015 mmol). The mixture was stirred at room temperature for 1 hour and quenched with saturated sodium bicarbonate. The resulting mixture was extracted with ethyl acetate and the combined organic layers were washed with brine, dried over anhydrous sodium sulfate and concentrated in vacuo to give (6R,8aS)-6-(1-bromo-8-chloroimidazo[1,5-a]pyrazin-3-yl)tetrahydro-1H-oxazolo[3,4-a]pyridin-3(5H)-one (310 mg, 90% yield). $^1$HNMR (400 MHz, DMSO-d6): δ=8.47~8.46 (d, J=4 Hz, 1 H), 7.44~7.45 (d, J=4 Hz, 1 H), 4.46~4.40 (m, 2 H), 3.98~3.95 (m, 1 H), 3.88~3.83 (m, 2H), 3.27~3.21 (t, J=12 Hz, 1 H), 2.07~2.04 (d, J=12 Hz, 1 H), 1.93~1.89 (m, 1 H), 1.76~1.67 (m, 1 H), 1.59~1.47 (m, 4 H). MS (ESI): M/Z (M+1): 371.

(i) (6R,8aS)-6-(8-amino-1-bromoimidazo[1,5-a]pyrazin-3-yl)tetrahydro-1H-oxazolo[3,4-a]pyridin-3(5H)-one A mixture of (6R,8aS)-6-(1-bromo-8-chloroimidazo[1,5-a]pyrazin-3-yl)tetrahydro-1H-oxazolo[3,4-a]pyridin-3(5H)-one (30 mg, 0.08 mmol) in NH$_4$OH/i-PrOH (3 mL/3 mL) was stirred at 100° C. in a sealed tube for 7 h. The reaction mixture was cooled to room temperature and concentrated in vacuo to afford (6R,8aS)-6-(8-amino-1-bromoimidazo[1,5-a]pyrazin-3-yl)tetrahydro-1H-oxazolo[3,4-a]pyridin-3(5H)-one (10 mg, 35% yield). MS (ESI): M/Z (M+1)=352.03.

Intermediate 2

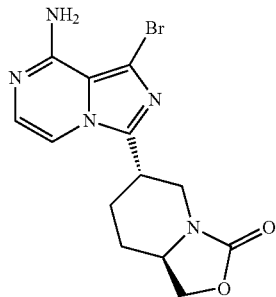 [SMILES: Nc1nccn2c([C@H]3CC[C@@H]4COC(=O)N4C3)nc(Br)c12]

(6S,8aR)-6-(8-amino-1-bromoimidazo[1,5-a]pyrazin-3-yl)tetrahydro-1H-oxazolo[3,4-a]pyridin-3(5H)-one (a) (6R,8aS)-3-oxohexahydro-1H-oxazolo[3,4-a]pyridine-6-carboxylic acid To a mixture of (3R,6S)-1-benzyl 3-methyl 6-(hydroxymethyl)piperidine-1,3-dicarboxylate (2.7 g, 8.785 mmol) in tetrahydrofuran/H$_2$O (1:1, 30 mL) was added LiOH (737 mg g, 17.57 mmol). The resulting mixture was stirred at room temperature for 1 hour and extracted with ethyl acetate (100 mL). The aqueous layer was lyophilized to give (6R,8aS)-3-oxohexahydro-1H-oxazolo[3,4-a]pyridine-6-carboxylic acid (1.6 g, 100% yield). $^1$HNMR (400 MHz, DMSO-d6): δ=12.62 (s, 1 H), 4.36 (t, J=8.4 Hz, 1 H), 3.89~3.74 (m, 1 H), 3.70~3.63 (m, 1 H), 2.90~2.84 (m, 1 H), 2.37~2.29 (m, 1 H), 2.07~2.03 (m, 1 H), 1.85~1.82 (m, 1 H), 1.55~1.40 (m, 1 H), 1.37~1.22 (m, 1 H). MS (ESI): M/Z (M+1): 185.8.

(b) (6R,8aS)-N-((3-chloropyrazin-2-yl)methyl)-3-oxohexahydro-1H-oxazolo[3,4-a]pyridine-6-carboxamide To a mixture of (6R,8aS)-3-oxohexahydro-1H-oxazolo[3,4-a]pyridine-6-carboxylic acid (150 mg, 0.810 mmol) in dichloromethane (5 mL) was added triethylamine(344 mg, 3.24 mmol) and isobutyl chloroformate(116 mg, 0.851 mmol) at 0° C. The mixture was stirred at room temperature for 2 hours, to which (3-Chloro-pyrazin-2-yl)-methylamine (145 mg, 0.810 mmol) was added portionwise, followed by another 3 eq triethylamine. The mixture was stirred at room temperature for additional 3 hours. The reaction mixture was concentrated in vacuo and purified by silica gel chromatography (PE:THF=50%~100%) to afford (6R,8aS)-N-((3-chloropyrazin-2-yl)methyl)-3-oxohexahydro-1H-oxazolo[3,4-a]pyridine-6-carboxamide(40 mg, 16% yield). MS (EI): M/Z (M+1): 311.1.

(c) (6S,8aR)-6-(8-chloroimidazo[1,5-a]pyrazin-3-yl)tetrahydro-1H-oxazolo[3,4-a]pyridin-3 (5H)-one To a mixture of (6R,8aS)-N-((3-chloropyrazin-2-yl)methyl)-3-oxohexahydro-1H-oxazolo[3,4-a]pyridine-6-carboxamide(60 mg, 0.205 mmol) in CH$_3$CN (3 mL) was added POCl$_3$ (157 mg, 1 mmol) at 0° C. The mixture was stirred at 30° C. for 15 hours. The reaction mixture was poured into ice water, basified by solid NaHCO$_3$ and extracted with dichloromethane/Propan-2-ol (3:1, 20 mL×3). The combined organic layers were washed with brine, dried over anhydrous sodium sulfate, concentrated to afford (6S,8aR)-6-(8-chloroimidazo[1,5-a]pyrazin-3-yl)tetrahydro-1H-oxazolo[3,4-a]pyridin-3(5H)-one(50 mg, 88% yield). MS (EI): M/Z (M+1): 293.00.

(d) (6S,8aR)-6-(1-bromo-8-chloroimidazo[1,5-a]pyrazin-3-yl)tetrahydro-1H-oxazolo[3,4-a]pyridin-3(5H)-one To a mixture of (6S,8aR)-6-(8-chloroimidazo[1,5-a]pyrazin-3-yl)tetrahydro-1H-oxazolo[3,4-a]pyridin-3(5H)-one(50 mg, 0.17 mmol) in DMF (3 mL) was added 1-bromopyrrolidine-2,5-dione (34.2 mg, 0.192 mmol). The mixture was stirred at room temperature for 1 hour and quenched with saturated sodium bicarbonate. The resulting mixture was extracted with ethyl acetate, the combined organic layer was washed with brine (10 mL×3), dried over anhydrous sodium sulfate and concentrated to give (6S,8aR)-6-(1-bromo-8-chloroimidazo[1,5-a]pyrazin-3-yl)tetrahydro-1H-oxazolo[3,4-a]pyridin-3(5H)-one(80 mg, 100% yield). $^1$HNMR(400 MHz, DMSO-d6): δ=8.47~8.46 (d, J=4 Hz, 1 H), 7.45~7.44 (d, J=4 Hz, 1 H), 4.46~4.40 (m, 2 H), 3.98~3.95 (m, 1 H), 3.88~3.83 (m, 2 H), 3.27~3.21 (t, J=12 Hz, 1 H), 2.07~2.04 (d, J=12 Hz, 1 H), 1.93~1.89 (m, 1 H), 1.76~1.67 (m, 1 H), 1.60~1.47 (m, 1 H). (ESI): M/Z (M+1): M/Z (M+3) 372.9: (M+1) 371=10:7.5

(e) (6S,8aR)-6-(8-amino-1-bromoimidazo[1,5-a]pyrazin-3-yl)tetrahydro-1H-oxazolo[3,4-a]pyridin-3(5H)-one A mixture of (6S,8aR)-6-(1-bromo-8-chloroimidazo[1,5-a]pyrazin-3-yl)tetrahydro-1H-oxazolo[3,4-a]pyridin-3(5H)-one (80 mg, 0.215 mmol) in NH$_4$OH/i-PrOH (4 mL/4 mL) was stirred at 100° C. in sealed tube for 7 hours. The reaction mixture was cooled to room temperature and concentrated in vacuo to afford crude product which was purified by prep- TLC to give (6S,8aR)-6-(8-amino-1-bromoimidazo[1,5-a]pyrazin-3-yl)tetrahydro-1H-oxazolo[3,4-a]pyridin-3(5H)-one (20 mg, 27% yield). MS (ESI): M/Z (M+1)=352.03.

Intermediate 3

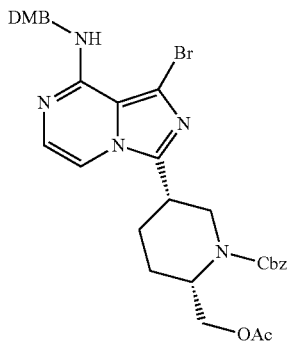

(2S,5S)-benzyl 2-(acetoxymethyl)-5-(1-bromo-8-((2,4-dimethoxybenzyl)amino)-imidazo[1,5-a]pyrazin-3-yl)piperidine-1-carboxylate (a) trans-1-benzyl 3-methyl 6-(acetoxymethyl)piperidine-1,3-dicarboxylate To a solution of methyl 6-(acetoxymethyl)nicotinate (75 g, 358.5 mmol) in AcOH (1000 ml) was added NaBH₃CN (45.2 g, 717 mmol) portionwise at rt. The solution was stirred overnight. The reaction mixture was concentrated under reduced pressure and the residue was dissolved in H₂O (770 ml) and the pH was adjusted to 8 with aqueous NaHCO₃. The resulting mixture was cooled to 0° C., to which Cbz-Cl (122 g, 716 mmol) was added dropwise. The mixture was stirred at rt overnight and extracted with DCM (2×500 mL). The organic layer was dried over Na₂SO₄ and concentrated in vacuo. The residue was purified by column chromatography with silica gel eluted by 5-30% ethyl acetate in petroleum ether (60-90 fraction) preparative HPLC to give to trans-1-benzyl 3-methyl 6-(acetoxymethyl)piperidine-1,3-dicarboxylate (42 g, 33.6% yield). MS: M/Z (M+1): 349.9. Retention Time: 1.053 min.

(b) trans-1-benzyl 3-methyl 6-(hydroxymethyl)piperidine-1,3-dicarboxylate

To a solution of trans-1-benzyl 3-methyl 6-(acetoxymethyl)piperidine-1,3-dicarboxylate (8.8 g, 25.2 mmol) in MeOH (88 ml) was added HCl (2.2 ml, 12M). The resulting solution was stirred at reflux overnight. After this cooled to r.t and removal of the solvent in vacuo, the residue was purified by chromatography on silica gel to give 4.3 g of trans-1-benzyl 3-methyl 6-(hydroxymethyl)piperidine-1,3-dicarboxylate. ¹HNMR (400 MHz, CD3OD) δ=7.39 (s, 5H), 5.15 (s, 2H), 4.38-4.26 (m, 2H), 3.73-3.67 (m, 4H), 3.66-3.58 (m, 1H), 2.97 (br. s, 1H), 2.48 (tt, J=4.1, 11.8 Hz, 1H), 1.98-1.84 (m, 1H), 1.78-1.57 (m, 1H).

(c) (3S,6S)-1-benzyl 3-methyl 6-(hydroxymethyl)piperidine-1,3-dicarboxylate & (3R,6R)-1-benzyl 3-methyl 6-(hydroxymethyl)piperidine-1,3-dicarboxylate 4.3 g of trans-1-benzyl 3-methyl 6-(hydroxymethyl)piperidine-1,3-dicarboxylate was resolved with chiral HPLC to give two enantiomers. (Instrument: Thar 200; Column: AD 250 mm*50 mm, 5 um; Mobile phase: A: Supercritical CO₂, B: MeOH, A:B=85:15 at 160 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) 1.3 g of (3S,6S)-1-benzyl 3-methyl 6-(hydroxymethyl)-piperidine-1,3-dicarboxylate was obtained followed by 1.1 g of (3R,6R)-1-benzyl 3-methyl 6-(hydroxymethyl)piperidine-1,3-dicarboxylate.

(d) (3S,6S)-1-((benzyloxy)carbonyl)-6-(hydroxymethyl)piperidine-3-carboxylic acid To a mixture of (3S,6S)-1-benzyl 3-methyl 6-(hydroxymethyl)piperidine-1,3-dicarboxylate (1.0 g, 3.25 mmol) in MeOH/H₂O (6 mL/3 mL) was added Lithium hydroxide monohydrate (273 mg, 6.5 mmol). The reaction mixture was stirred at 25° C. overnight. The mixture was concentrated in vacuo, acidified with IN HCl to pH 5~6, and extracted with EA. The organic layer was washed with brine, dried over Na₂SO₄, concentrated in vacuo to give (3S,6S)-1-((benzyloxy)carbonyl)-6-(hydroxymethyl)piperidine-3-carboxylic acid (780 mg, 81.8% yield). ¹HNMR (400 MHz, CD₃OD): δ=7.32~7.40 (m, 5 H), 5.16 (s, 2 H), 4.30~4.36 (m, 2 H), 3.60~3.73 (m, 2 H), 2.93~3.02 (m, 1 H), 2.39~2.46 (m, 1 H), 1.89~1.97 (m, 2 H), 1.59~1.77 (m, 2 H).

(e) (2S,5R)-benzyl 5-(((3-chloropyrazin-2-yl)methyl)carbamoyl)-2-(hydroxymethyl)piperidine-1-carboxylate To a solution of (3S,6S)-1-((benzyloxy)carbonyl)-6-(hydroxymethyl)piperidine-3-carboxylic acid (0.78 g, 2.66 mmol) in 20 mL of DMF was added HATU (1.21 g, 3.2 mmol). After stirring for 30 min under N₂, (3-Chloropyrazin-2-yl) methanamine hydrochloride (0.48 g, 2.66 mol) and Et₃N (0.8 g, 7.98 mmol) was added. The reaction mixture was stirred at room temperature for 12 hours under N₂. The mixture was partitioned between EA and water. The organic layer was washed with 1 N HCl and water, dried over sodium sulfate, filtered and concentrated in vacuo. The residue was purified by silica gel column chromatography to afford (2S,5R)-benzyl 5-(((3-chloropyrazin-2-yl)methyl)carbamoyl)-2-(hydroxymethyl)piperidine-1-carboxylate (0.7 g, 63.0% yield). ¹HNMR (400 MHz, CD₃OD): δ=8.50~8.54 (m, 1 H), 8.35 (d, J=2.4 Hz, 1 H), 7.31~7.41 (m, 5 H), 5.16 (s, 2 H), 4.63 (s, 2 H), 4.34~4.38 (m, 1 H), 4.21~4.25 (m, 1 H), 3.72~3.77 (m, 1 H), 3.63~3.67 (m, 1 H), 3.01~3.07 (m, 1 H), 2.46~2.54 (m, 1 H), 1.80~1.93 (m, 3 H), 1.61~1.71 (m, 1 H). MS (ESI): M/Z (M+1): 419.1.

(f) (2S,5R)-benzyl 2-(acetoxymethyl)-5-(((3-chloropyrazin-2-yl)methyl)-carbamoyl)piperidine-1-carboxylate To a mixture of (2S,5R)-benzyl 5-(((3-chloropyrazin-2-yl)methyl)carbamoyl)-2-(hydroxymethyl)piperidine-1-carboxylate (500 mg, 1.2 mmol) in 4 mL of DCM was added acetyl chloride (141 mg, 1.8 mmol) and pyridine (190 mg, 2.4 mmol). The reaction mixture was stirred at 25° C. overnight. The mixture was poured into aq. NH₄Cl, and extracted with DCM. The organic layer was dried over Na₂SO₄, concentrated in vacuo and purified by flash chromatography to give (2S,5R)-benzyl 2-(acetoxymethyl)-5-(((3-chloropyrazin-2-yl)methyl)carbamoyl)piperidine-1-carboxylate (240 mg 43.6% yield). ¹HNMR (400 MHz, CD₃OD): δ=8.31~8.50 (m, 2 H), 7.29~7.36 (m, 5 H), 5.10~5.15 (m, 2 H), 4.55~4.61 (m, 3 H), 4.12~4.38 (m, 3 H), 3.04~3.14 (m, 1 H), 2.46~2.54 (m, 1 H), 1.66~1.86 (m, 7 H). MS (ESI): M/Z (M+1): 461.0.

(g) (2R,5R)-benzyl 2-(acetoxymethyl)-5-(1-bromo-8-((2,4-dimethoxybenzyl)amino)imidazo[1,5-a]pyrazin-3-yl)piperidine-1-carboxylate (2S,5R)-benzyl 2-(acetoxymethyl)-5-(((3-chloropyrazin-2-yl)methyl)-carbamoyl)piperidine-1-carboxylate (100 mg, 0.22 mmol) was converted to the title compound (90 mg) using procedures analogous to those described for synthesis of Intermediate 19, steps h. $^1$HNMR (400 MHz, CDCl$_3$): δ=7.34-7.38 (m, 5 H), 7.10-7.14 (m, 1 H), 6.90~6.99 (m, 1 H), 6.74~6.76 (m, 1 H), 6.43-6.50 (m, 2 H), 5.11~5.23 (m, 2 H), 4.65-4.71 (m, 3 H), 4.18-4.39 (m, 3 H), 3.88 (s, 3 H), 3.80 (s, 3 H), 2.98-3.24 (m, 2 H), 1.81-1.98 (m, 7 H). MS (ESI): M/Z (M/M+2=1/1) 652.1/654.1.

Intermediate 4

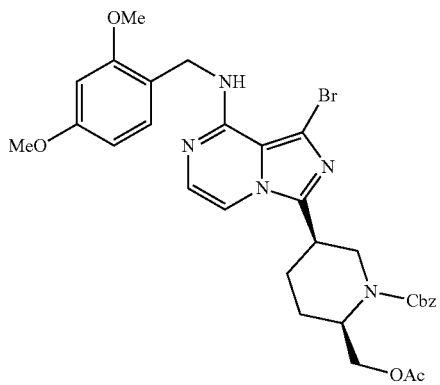 [SMILES: COc1ccc(CNc2nccn3c([C@@H]4CC[C@H](COC(C)=O)N(C(=O)OCc5ccccc5)C4)nc(Br)c23)c(OC)c1]

(2R,5R)-benzyl 2-(acetoxymethyl)-5-(1-bromo-8-((2,4-dimethoxybenzyl)amino)-imidazo[1,5-a]pyrazin-3-yl)piperidine-1-carboxylate The title compound (90 mg) was prepared using from SM using analogous procedures as Intermediate 19. $^1$HNMR (400 MHz, CDCl$_3$): δ=7.34~7.38 (m, 5 H), 7.10~7.14 (m, 1 H), 6.90~6.99 (m, 1 H), 6.74~6.76 (m, 1 H), 6.43~6.50 (m, 2 H), 5.11~5.23 (m, 2 H), 4.65~4.71 (m, 3 H), 4.18~4.39 (m, 3 H), 3.88 (s, 3 H), 3.80 (s, 3 H), 2.98~3.24 (m, 2H), 1.81~1.98 (m, 7 H). MS (ESI): M/Z (M/M+2=1/1) 652.1/654.1.

Intermediate 5

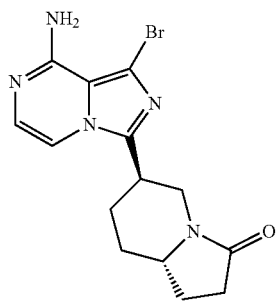 [SMILES: Nc1nccn2c([C@@H]3CC[C@H]4CCC(=O)N4C3)nc(Br)c12]

(6R,8aS)-6-(8-amino-1-bromoimidazo[1,5-a]pyrazin-3-yl)hexahydroindolizin-3 (2H)-one (a) (E)-methyl 6-(3-ethoxy-3-oxoprop-1-en-1-yl)nicotinate A 1 L flask containing mixture of ethyl 2-oxoacetate (155 g, 0.76 mol) and methyl 6-methylnicotinate (50 g, 0.33 mol) in 300 mL of acetic anhydride was refluxed at 130° C. for two days and concentrated in vacuo. The resultant crude was purified by silica gel chromatography (eluent: 20% EA/hex) to afford (E)-methyl 6-(3-ethoxy-3-oxoprop-1-en-1-yl)nicotinate (57 g, 0.242 mol, 73% yield). LCMS data: Ret. time.=1.42 min, m/z 236 (M+H)$^+$; $^1$HNMR (CDCl$_3$, 500 Hz): 9.24 (1H, d, J=2 Hz); 8.333 (1H, dd J=6 Hz); 7.20 (1H, d, J=16 Hz); 7.511 (1H, d, J=8 Hz); 7.042 (1H, d, J=15.5 Hz); 4.310 (q, J=7 Hz); 3.988 (3H, s), 1.366 (3H, t, J=7 Hz).

(b) Ethyl 6-(3-ethoxy-3-oxopropyl)piperidine-3-carboxylate

To a 500 ml vessel charged with (E)-methyl 6-(3-ethoxy-3-oxoprop-1-en-1-yl)nicotinate (10 g) in acetic acid (100 mL) was added palladium hydroxide on carbon (20%, 2.5 g). The vessel was loaded on ParShaker and the mixture was exposed to hydrogen at 40 psi for 18 hours. The catalyst was filtered under nitrogen stream and washed with ethyl acetate. The filtrate was then concentrated in vacuo to afford methyl 6-(3-ethoxy-3-oxopropyl)piperidine-3-carboxylate. LCMS data: Ret. time 0.22 min; m/z 244.3 (M+H)$^+$.

(c) Methyl 3-oxooctahydroindolizine-6-carboxylate

Methyl 6-(3-ethoxy-3-oxopropyl)piperidine-3-carboxylate (103.5 g, 0.425 mol) was refluxed in a mixture of TEA (100 ml, 0717 mol) and MeOH (500 ml) for 18 h and concentrated in vacuo. The residue was purified by silica gel chromatography (eluent: 3% 2N NH$_3$ in MeOH/DCM) to afford a mixture of cis/trans isomers methyl 3-oxooctahydroindolizine-6-carboxylate (94 g, 4/1 ratio). LCMS data: Ret. time 1.07 min; m/z 198 (M+H)$^+$.

(d) Trans 3-oxooctahydroindolizine-6-carboxylic acid

A solution of methyl 3-oxooctahydroindolizine-6-carboxylate (94 g, 477 mmol) in methanol (1000 mL) was heated from rt to 50° C. While the solution was being heated, 25% NaOMe in methanol (215 mL, 940 mmol) was added in one portion. The reaction mixture was stirred at 50° C. for 4.5 h and concentrated in vacuo to afford a solid. This solid was dissolved in water (300 mL), resulting in the formation of a gray solid. This solid was filtered off, and the filtrate was then reconcentrated (water bath at 60° C.) to provide a white solid. This 60° C. solid was dissolved in water (100 mL) and cooled in an ice bath. Once the solution had reached 5° C., aq. 6 M HCl (165 mL, 990 mmol) was added dropwise while maintaining the temperature below 23° C. Solids formed as the addition continued. This mixture was stirred for ~30 min while the solution cooled to 5° C., and then it was filtered. The isolated solid was washed with cold water and then dried under a nitrogen flush overnight to afford the mixture of enantiomers trans 3-oxooctahydroindolizine-6-carboxylic acid (66.44 g, 363 mmol, 76% yield) as a white solid. LCMS data: Ret. time 0.92 min; m/z 184.12 (M+H)$^+$. $^1$HNMR (CDCl$_3$, 500 MHz, ppm): 9.42 (1H, br), 4.38 (1H, ddd, J=13.2, 4.1, 1.6 Hz), 3.44 (1H, m), 2.76 (1H, t, J=12.7 Hz), 2.42 (3H, m), 2.24 (2H, m), 1.97 (1H, ddd, J=13.2, 6.8, 3.3 Hz), 1.61 (2H, m), 1.23 (1H, M).

(e) (6R,8aS) 3-oxooctahydroindolizine-6-carboxylic acid and (6S,8aR) 3-oxooctahydroindolizine-6-carboxylic acid The two enantiomers of trans 3-oxooctahydroindolizine-6-carboxylic acid were separated on Chiral HPLC (IC column, 4.6×150 mm, 50% IPA+TFA/CO$_2$, 2.5 ml/min. 100 bar, 35° C.) to give (6S,8aR)-3-oxooctahydroindolizine-6-carboxylic acid (E1, Ret. time=3.1 min, >99% ee) followed by (6R,8aS)-3-oxooctahydroindolizine-6-carboxylic acid (E2, Ret. time=4.2 min, >99% ee).

(f) (6R,8aS)-N-((3-chloropyrazin-2-yl)methyl)-3-oxooctahydroindolizine-6-carboxamide HATU (15.91 g, 41.8 mmol) was added to a stirred, cooled 0° C. mixture of (6R,8aS)-3-oxooctahydroindolizine-6-carboxylic acid (7.3 g, 39.8 mmol), (3-chloropyrazin-2-yl)methanamine hydrochloride (7.89 g, 43.8 mmol) and DIPEA (10.44 ml, 59.8 mmol) in CH$_2$Cl$_2$ (25 ml) and the mixture was stirred at room temperature for 1 h. and then concentrated. The residue was purified by column chromatography on silica gel (Isco 240 g silica gel), eluting with CH$_2$Cl$_2$/MeOH (50/1) to give (6R,8aS)-N-((3-chloropyrazin-2-yl)methyl)-3-oxooctahydroindolizine-6-carboxamide (11.15 g, 36.1 mmol, 91% yield) as a white solid. LC-MS: Ret. time 1.09 min; m/z 309.11 (M+H)$^+$; $^1$HNMR (CDCl$_3$, 500 Hz): 8.38 (1H, d, J=2 Hz), 8.25 (1H, d, J=2 Hz), 7.37 (1H, dd, J=4 and 4.5 Hz), 4.56-4.72 (2H, m, 1), 4.29 (1H, dd, J=13 and 4.5 Hz), 3.42-3.47 (m, 1), 2.81 (1H, t, J=13 Hz), 2.35 (2H, t, J=8 Hz), 2.17-2.23 (1H, m), 2.04 (1H, d, J=13.5 Hz), 1.94-1.96 (1H, m), 1.74-1.82 (1H, m), 1.55-1.62 (1H, m), 1.16-1.24 (1H, m).

(g) (6R,8aS)-6-(8-chloroimidazo[1,5-a]pyrazin-3-yl)hexahydroindolizin-3 (2H)-one POCl$_3$ (5.85 ml, 62.7 mmol) was added to a stirred, cooled 0° C. mixture of (6R,8aS)-N-((3-chloropyrazin-2-yl)methyl)-3-oxooctahydroindolizine-6-carboxamide (3228.2 mg, 10.46 mmol) in Acetonitrile (20 ml), to which DMF (0.810 ml, 10.46 mmol) was added. The mixture was stirred at room temperature for overnight, and poured into iced water, to which powdered NaHCO$_3$ was added until pH~8. The mixture was extracted with DCM, dried over MgSO$_4$, filtered and concentrated. The residue was purified by column chromatography on silica gel (ISCO, 40 g), eluting with CH$_2$Cl$_2$/MeOH (25/1) to give (6R,8aS)-6-(8-chloroimidazo[1,5-a]pyrazin-3-yl)hexahydroindolizin-3(2H)-one (1.9981 g, 6.87 mmol, 65.7% yield) as a colorless oil. Ret. time 1.15 min; m/z 291.12 (M+H)$^+$; $^1$HNMR (CDCl$_3$, 500 Hz): 7.72 (1H, d, J=4.5 Hz), 7.39 (1H, d, J=5 Hz), 4.40-4.42 (1H, m), 3.62-3.67 (1H, m), 3.03-3.08 (2H, m), 2.11-2.51 (8H, m), 1.70-1.77 (1H, m), 1.39-1.46 (1H, m).

(h) (6R,8aS)-6-(1-bromo-8-chloroimidazo[1,5-a]pyrazin-3-yl)hexahydroindolizin-3 (2H)-one NBS (1.468 g, 8.25 mmol) was added to a stirred mixture of (6R,8aS)-6-(8-chloroimidazo[1,5-a]pyrazin-3-yl)hexahydroindolizin-3(2H)-one (1.9981 g, 6.87 mmol) in acetonitrile (25 ml) and the mixture was stirred at room temperature for 1 h. The reaction was quenched with sat. NaHCO$_3$, extracted with DCM, dried and concentrated in vacuo. The residue was purified by column chromatography on silica gel (ISCO gold 40 g), eluting with CH$_2$Cl$_2$/MeOH (40/1) to give (6R,8aS)-6-(1-bromo-8-chloroimidazo[1,5-a]pyrazin-3-yl)hexahydroindolizin-3(2H)-one (2.2 g, 5.95 mmol, 87% yield) as a white solid. Ret. time 1.24 min; m/z 368.97 and 370.98 (M+H)$^+$.

(i) (6R,8aS)-6-(8-amino-1-bromoimidazo[1,5-a]pyrazin-3-yl)hexahydroindolizin-3 (2H)-one A stirred mixture of (6R,8aS)-6-(1-bromo-8-chloroimidazo[1,5-a]pyrazin-3-yl)hexahydroindolizin-3(2H)-one (2.2109 g, 5.98 mmol) in 100 mL of 2N NH$_3$ in 2-propanol was heated in a sealed tube at 120° C. for 24 h. and concentrated in vacuo. The residue was purified by column chromatography on silica gel (ISCO, 80 g), eluting with CH$_2$Cl$_2$/MeOH(15/1) to afford (6R,8aS)-6-(8-amino-1-bromoimidazo[1,5-a]pyrazin-3-yl)hexahydroindolizin-3(2H)-one (2.04 g, 5.84 mmol, 98% yield) as a white solid. Ret. time 1.16 min; m/z 350.0 and 352.0 (M+H)$^+$.

Intermediate 6

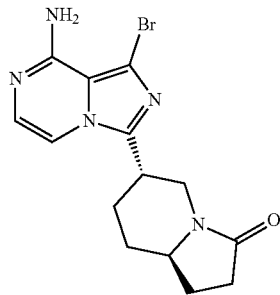 [SMILES: Nc1nccn2c([C@H]3CC[C@@H]4CCC(=O)N4C3)nc(Br)c12]

(6S,8aR)-6-(8-amino-1-bromoimidazo[1,5-a]pyrazin-3-yl)hexahydroindolizin-3 (2H)-one The title compound (6S,8aR)-6-(8-amino-1-bromoimidazo[1,5-a]pyrazin-3-yl) hexahydroindolizin-3(2H)-one was prepared using the same steps of Intermediate 5 (f-I) using (6S,8aR)-3-oxooctahydroindolizine-6-carboxylic acid (Intermediate 5, step e) as the starting material.

Intermediate 7

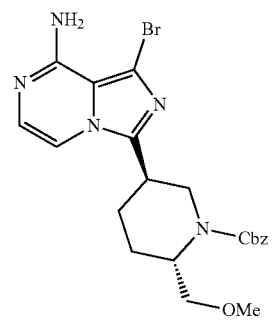 [SMILES: COC[C@@H]1CC[C@@H](c2nc(Br)c3c(N)nccn23)CN1C(=O)OCc1ccccc1]

4-(8-amino-3-((6R,8aS)-2-methyl-3-oxooctahydroimidazo[1,5-a]pyridin-6-yl)imidazo[1,5-a]pyrazin-1-yl)-N-(4-(trifluoromethyl)pyridin-2-yl)benzamide (a) (3S,6R)-1-benzyl 3-methyl 6-(methoxymethyl)piperidine-1,3-dicarboxylate N1,N1,N8,N8-tetramethylnaphthalene-1,8-diamine (3.66 g, 17.08 mmol) and Me$_3$OBF$_4$ (2.52 g, 17.08 mmol) was added to a solution of (3S,6R)-1-benzyl 3-methyl 6-(hydroxymethyl)piperidine-1,3-dicarboxylate (1.75 g, 5.69 mmol) in dichloromethane (18 mL) at room temperature. After stirring for 1 hour, saturated NaHCO$_3$ solution was added and filtered, the filtrate was extracted with dichloromethane (200 mL×3), the combined organic layers were washed with brine, dried over sodium sulfate, filtered and concentrated to afford the crude product, which was purified by silica gel column chromatography(PE:THF=50%~100%) to give (3S,6R)-1-benzyl 3-methyl 6-(methoxymethyl)piperidine-1,3-dicarboxylate (1.5 g, 82% yield). $^1$HNMR (400 MHz, CD$_3$OD): δ=7.41-7.27 (m, 5H), 5.21-5.13 (m, 1H), 5.10-5.03 (m, 1H), 4.46 (d, J=14.1 Hz, 1H), 4.39 (q, J=6.5 Hz, 1H), 3.65-3.55 (m, 4H), 3.49-3.42 (m, 1H), 3.35-3.28 (m, 6H), 3.18 (dd, J=4.0, 14.1 Hz, 1H), 2.67 (br. s, 1H), 2.03-1.96 (m, 1H), 1.90-1.74 (m, 2H), 1.64-1.57 (m, 1H). MS (EI): M/Z (M+1): 322.16

(b) (3S,6R)-1-((benzyloxy)carbonyl)-6-(methoxymethyl)piperidine-3-carboxylic acid A mixture of (3S,6R)-1-benzyl 3-methyl 6-(methoxymethyl)piperidine-1,3-dicarboxylate (1.54 g, 4.79 mmol) and LiOH (0.605 g, 14.4 mmol) in tetrahydrofuran/H$_2$O (150 mL, 1:1) was stirred at room temperature for 2 hours. The reaction mixture was extracted with ethyl acetate and the aqueous layer was acidified with 1 N HCl, extracted with ethyl acetate (100 mL×3). the combined organic layers were washed with brine, dried over sodium sulfate, filtered and concentrated to afford (3S,6R)-1-((benzyloxy)carbonyl)-6-(methoxymethyl)piperidine-3-carboxylic acid (1.5 g, 100% yield). $^1$HNMR (400 MHz, CDCl$_3$): δ=7.41-7.24 (m, 5H), 5.24-5.18 (m, 1H), 5.13-5.06 (m, 1H), 4.56 (d, J=14.1 Hz, 1H), 4.43 (d, J=5.3 Hz, 1H), 3.55-3.43 (m, 2H), 3.15 (dd, J=4.0, 14.1 Hz, 1H), 2.67 (br. s, 1H), 2.10 (s, 1H), 1.89-1.80 (m, 2H), 1.72-1.63 (m, 1H). MS (EI): M/Z (M+1): 308.14

(c)(2R,5S)-benzyl5-(((3-chloropyrazin-2-yl)methyl)carbamoyl)-2-(methoxymethyl)piperidine-1-carboxylate A mixture of (3S,6R)-1-((benzyloxy)carbonyl)-6-(methoxymethyl)piperidine-3-carboxylic acid (1.5 g, 4.88 mmol), (3-chloropyrazin-2-yl)methanamine (0.875 g, 4.88 mmol), HATU (2 g, 5.4 mmol) and triethylamine (1.97 g, 19.52 mmol) in dichloromethane (20 mL) was stirred at room temperature for 12 hours. The mixture was concentrated to afford the crude product, which was purified by silica gel column chromatography(PE:EA=100%~60%) to give (2R,5S)-benzyl 5-(((3-chloropyrazin-2-yl)methyl)carbamoyl)-2-(methoxymethyl)piperidine-1-carboxylate (2.0 g, 95% yield). $^1$HNMR (400 MHz, CDCl$_3$): δ=8.26 (d, J=2.5 Hz, 1H), 8.22 (s, 1H), 7.26 (s, 6H), 5.19-5.11 (m, 1H), 5.07-5.01 (m, 1H), 4.67 (d, J=16.8 Hz, 1H), 4.52-4.40 (m, 3H), 3.63-3.57 (m, 1H), 3.54-3.47 (m, 1H), 3.36 (s, 3H), 3.28 (dd, J=3.4, 14.9 Hz, 1H), 2.63 (br. s, 1H), 2.18 (d, J=12.8 Hz, 1H), 1.93-1.75 (m, 2H), 1.66 (d, J=2.3 Hz, 1H). MS (EI): M/Z (M+1): 433.16

(d)(2S,5R)-benzyl5-(8-chloroimidazo[1,5-a]pyrazin-3-yl)-2-(methoxymethyl)piperidine-1-carboxylate To a mixture of (2R,5S)-benzyl5-(((3-chloropyrazin-2-yl)methyl)carbamoyl)-2-(methoxymethyl)piperidine-1-carboxylate (60 mg, 0.138 mmol) in CH$_3$CN (3 mL) was added POCl$_3$ (106 mg, 0.69 mmol) at 0° C. The mixture was stirred at 30° C. for 15 hours. The reaction mixture was poured into ice water, basified with NaHCO$_3$ and extracted with dichloromethane/Propan-2-ol (3:1, 10 mL×3). The combined organic layers were washed with brine, dried over anhydrous sodium sulfate, concentrated to afford (2S,5R)-benzyl5-(8-chloroimidazo[1,5-a]pyrazin-3-yl)-2-(methoxymethyl)piperidine-1-carboxylate (57 mg, 98% yield).

$^1$HNMR (400 MHz, CDCl$_3$): δ=7.72 (s, 1H), 7.46 (d, J=5.0 Hz, 1H), 7.32-7.28 (m, 3H), 7.20 (d, J=4.8 Hz, 1H), 7.14 (br. s, 2H), 4.96 (s, 2H), 4.36 (t, J=5.4 Hz, 1H), 4.12 (d, J=14.1 Hz, 1H), 3.75-3.67 (m, 1H), 3.64-3.56 (m, 2H), 3.32-3.24 (m, 2H), 2.47-2.36 (m, 1H), 2.29-2.11 (m, 2H), 1.76-1.67 (m, 1H). MS (EI): M/Z (M+1): 415.15.

(e)(2S,5R)-benzyl5-(1-bromo-8-chloroimidazo[1,5-a]pyrazin-3-yl)-2-(methoxymethyl)piperidine-1-carboxylate A mixture of (2S,5R)-benzyl5-(8-chloroimidazo[1,5-a]pyrazin-3-yl)-2-(methoxymethyl)piperidine-1-carboxylate (1 g, 2.4 mmol) in CH$_3$CN (10 mL) was added 1-bromopyrrolidine-2,5-dione (0.5 g, 2.65 mmol). The mixture was stirred at room temperature for 1 hour. The reaction mixture was quenched with water and extracted with dichloromethane. The combined organic layer was washed with brine 3, dried over anhydrous sodium sulfate and concentrated in vacuo to give (2S,5R)-benzyl5-(1-bromo-8-chloroimidazo[1,5-a]pyrazin-3-yl)-2-(methoxymethyl)piperidine-1-carboxylate (1.2 g, yield 100%). $^1$HNMR (400 MHz, CDCl$_3$): δ=7.43 (d, J=4.8 Hz, 1H), 7.34-7.29 (m, 3H), 7.18 (d, J=4.8 Hz, 3H), 4.99 (s, 2H), 4.33 (quin, J=5.8 Hz, 1H), 4.06 (dd, J=3.4, 13.9 Hz, 1H), 3.70 (dd, J=6.3, 9.8 Hz, 1H), 3.64-3.60 (m, 1H), 3.37 (s, 3H), 2.77 (s, 2H), 2.43-2.33 (m, 1H), 2.28-2.19 (m, 1H), 2.19-2.09 (m, 1H), 1.74-1.65 (m, 1H). MS (EI): M/Z (M+1): 493.06.

(f)(2S,5R)-benzyl5-(8-amino-1-bromoimidazo[1,5-a]pyrazin-3-yl)-2-(methoxymethyl)piperidine-1-carboxylate A mixture of (2S,5R)-benzyl5-(1-bromo-8-chloroimidazo[1,5-a]pyrazin-3-yl)-2-(methoxymethyl)piperidine-1-carboxylate (60 mg, 0.096 mmol) in NH$_4$OH/i-PrOH (3 mL: 3 mL) was stirred at 100° C. in a sealed tube for 7 hours. The reaction mixture was cooled to room temperature and concentrated in vacuo to afford (2S,5R)-benzyl 5-(8-amino-1-bromoimidazo[1,5-a]pyrazin-3-yl)-2-(methoxymethyl)piperidine-1-carboxylate (40 mg, 89% yield).MS (EI): M/Z (M+1): 474.11.

Intermediate 8

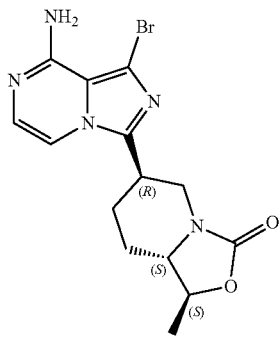

(1S,6R,8aS)-6-(8-amino-1-bromoimidazo[1,5-a]pyrazin-3-yl)-1-methyltetrahydro-1H-oxazolor[3,4-a]pyridine-3(5H)-one

(a) (3R,6S)-1-benzyl 3-methyl 6-(1-hydroxyethyl)piperidine-1,3-dicarboxylate To a solution of (3R,6S)-1-benzyl 3-methyl 6-formylpiperidine-1,3-dicarboxylate (12.4 g, 40.7 mmol) in dry THF (190 mL) at −78° C. was added methylmagnesium bromide (19 ml, 3 Min THF) dropwise. The reaction mixture was stirred at −78° C. for 2 hrs and quenched with aq. NH₄Cl. The resulting mixture was diluted with DCM (100 mL) and H₂O (100 mL), the organic layer was washed with brine (100 mL), dried over Na₂SO₄, and concentrated in vacuo The crude product was purified by column chromatography on silica gel eluted with PE/EA (100-40%) to give (3R,6S)-1-benzyl-3-methyl 6-(1-hydroxyethyl)piperidine-1,3-dicarboxylate (6.5 g, yield 50.0%). $^1$HNMR (400 MHz, CD$_3$OD): δ=7.41-7.26 (m, 5H), 5.19-5.04 (m, 2H), 4.51-4.42 (m, 1H), 4.05-3.88 (m, 1H), 3.55 (br. s, 3H), 3.10 (d, J=9.8 Hz, 1H), 2.66 (br. s, 1H), 1.99-1.82 (m, 3H), 1.77-1.56 (m, 1H), 1.19 (d, J=6.0 Hz, 1H), 1.08 (d, J=6.0 Hz, 2H).MS (ESI): M/Z (M+1): 322.4.

(b) (6R,8aS)-1-methyl-3-oxohexahydro-1H-oxazolo[3,4-a]pyridine-6-carboxylic acid To a solution of (3R,6S)-1-benzyl 3-methyl 6-(1-hydroxyethyl)piperidine-1,3-dicarboxylate (6.5 g, 20.2 mmol) in THF/H₂O (1/1, 150 ml) was added lithium hydroxide monohydrate (1.7 g, 40.4 mmol) portionwise. The resulting solution was stirred at 25° C. for 12 hrs under N₂. The reaction was acidified to pH 5-6 with HCl, then dried by lyophilization to give a solid. The solid was extracted by DCM, then the organic layer was concentrated in vacuo to afford (6R,8aS)-1-methyl-3-oxohexahydro-1H-oxazolo[3,4-a]pyridine-6-carboxylic acid (3 g, yield 75%). $^1$HNMR (400 MHz, CD$_3$OD): δ=4.76 (quin, J=6.9 Hz, 1H), 4.29 (quin, J=6.3 Hz, 1H), 4.00 (dtd, J=1.5, 4.9, 13.2 Hz, 1H), 3.77-3.64 (m, 1H), 3.31-3.27 (m, 1H), 3.06-2.87 (m, 1H), 2.53-2.36 (m, 1H), 2.32-2.17 (m, 1H), 2.04-1.93 (m, 1H), 1.73 (qd, J=3.3, 12.5 Hz, 1H), 1.68-1.45 (m, 2H), 1.44-1.32 (m, 3H). MS (ESI): M/Z (M+1): 200.1.

(c) (6R,8aS)-N-((3-chloropyrazin-2-yl)methyl)-1-methyl-3-oxohexahydro-1H-oxazolo[3,4-a]pyridine-6-carboxamide To a solution of (6R,8aS)-1-methyl-3-oxohexahydro-1H-oxazolo[3,4-a]pyridine-6-carboxylic acid (600 mg, 3.02 mmol) in dry DCM (12 mL) at 5° C. was added oxalyl dichloride (1.15 g, 9.04 mmol) dropwise followed by DMF (3 drops). The reaction mixture was stirred at 30° C. for 2 h and concentrated by rotary evaporation The crude product was dissolved in DCM (3 ml), to which a solution of (3-chloropyrazin-2-yl)methanamine (594 mg, 3.32 mmol) TEA (640 mg, 6.04 mmol) in DCM (10 ml) was added and the resulting mixture was stirred at 30° C. for 12 hrs. The reaction was diluted with DCM (20 mL) and H₂O (20 mL), the organic layer was washed with brine (20 mL), dried over Na₂SO₄ and concentrated in vacuo. The crude product was purified by column chromatography on silica gel eluted with PE/THF (100%-40%) to give (6R,8aS)-N-((3-chloropyrazin-2-yl)methyl)-1-methyl-3-oxohexahydro-1H-oxazolo[3,4-a]pyridine-6-carboxamide (800 mg, 55.3% yield). $^1$HNMR (400 MHz, CD$_3$OD): δ=8.55 (d, J=2.5 Hz, 1H), 8.36 (d, J=2.5 Hz, 1H), 4.77 (quin, J=6.8 Hz, 1H), 4.65 (s, 2H), 4.30 (quin, J=6.2 Hz, 1H), 3.98-3.90 (m, 1H), 3.78-3.70 (m, 1H), 3.12-3.00 (m, 1H), 2.51 (ttd, J=4.1, 12.1, 16.0 Hz, 1H), 2.19-2.07 (m, 1H), 2.00 (dd, J=3.5, 13.1 Hz, 1H), 1.81-1.66 (m, 2H), 1.55-1.39 (m, 3H), 1.35 (d, J=6.5 Hz, 2H). MS (ESI): M/Z (M+1): 325.1.

(d) (6R,8aS)-6-(8-chloroimidazo[1,5-a]pyrazin-3-yl)-1-methyltetrahydro-1H-oxazolo[3,4-a]pyridin-3(5H)-one To a solution of (6R,8aS)-N-((3-chloropyrazin-2-yl)methyl)-1-methyl-3-oxohexahydro-1H-oxazolo[3,4-a]pyridine-6-carboxamide (700 mg, 2.16 mmol) in anhydrous acetonitrile (10 mL) cooled in an ice water bath was added POCl₃ (1.6 g, 10.77 mmol) followed by DMF (160 mg, 2.16 mmol). The resulting mixture was stirred at 25° C. for 12 h. The reaction was poured into an ice-water mixture, neutralized with powdered sodium bicarbonate and extracted with DCM (20 mL×3). The organic layer was washed with brine (30 mL), dried over Na₂SO₄, and concentrated in vacuo to give (6R,8aS)-6-(8-chloroimidazo[1,5-a]pyrazin-3-yl)-1-methyltetrahydro-1H-oxazolo[3,4-a]pyridin-3(5H)-one (630 mg, 95% yield). $^1$HNMR (400 MHz, CD$_3$OD): δ=8.26-8.20 (m, 1H), 7.85 (s, 1H), 7.39 (d, J=5.0 Hz, 1H), 4.84-4.76 (m, 1H), 4.36 (quin, J=6.2 Hz, 1H), 4.07-3.97 (m, 1H), 3.87 (ddd, J=3.6, 7.7, 11.7 Hz, 1H), 3.54-3.33 (m, 2H), 2.30-2.14 (m, 1H), 2.10-1.78 (m, 3H), 1.77-1.54 (m, 1H), 1.47-1.38 (m, 3H). MS (ESI): M/Z (M+1): 306.1.

(e) (6R,8aS)-6-(1-bromo-8-chloroimidazo[1,5-a]pyrazin-3-yl)-1-methyltetrahydro-1H-oxazolo[3,4-a]pyridin-3(5H)-one To a solution of (6R,8aS)-6-(8-chloroimidazo[1,5-a]pyrazin-3-yl)-1-methyltetrahydro-1H-oxazolo[3,4-a]pyridin-3(5H)-one (50 mg, 0.163 mmol) in anhydrous DMF (1 mL) was added NBS (30.5 mg, 0.17 mmol), and the resulting mixture was stirred for 2 hrs, and poured into ice-water (10 mL). Sat. NaHCO₃ was added to the stirred mixture, which was then filtered and the cake was dissolved with ethyl acetate (50 mL), washed with H₂O (30 mL×10). The organic layer was washed with brine (30 mL), dried over Na₂SO₄, and concentrated in vacuo to afford (6R,8aS)-6-(1-bromo-8-chloroimidazo[1,5-a]pyrazin-3-yl)-1-methyltetrahydro-1H-oxazolo[3,4-a]pyridin-3(5H)-one (56 mg, 89.2% yield). $^1$HNMR (400 MHz, CD$_3$OD): δ=8.21 (d, J=5.0 Hz, 1H), 7.36 (d, J=5.3 Hz, 1H), 4.82-4.79 (m, 1H), 4.60 (s, 1H), 4.01 (d, J=10.5 Hz, 1H), 3.86 (ddd, J=3.6, 7.9, 11.8 Hz, 1H), 3.33 (br. s, 1H), 2.22 (d, J=14.1 Hz, 1H), 1.96-1.85 (m, 1H), 1.83-1.77 (m, 1H), 1.70 (dt, J=3.4, 12.5 Hz, 1H), 1.39 (d, J=6.5 Hz, 3H). MS (ESI): M/Z (M+2): 386.8.

(f) (6R,8aS)-6-(8-amino-1-bromoimidazo[1,5-a]pyrazin-3-yl)-1-methyltetrahydro-1H-oxazolo[3,4-a]pyridin-3(5H)-one To a solution of (6R,8aS)-6-(1-bromo-8-chloroimidazo[1,5-a]pyrazin-3-yl)-1-methyltetrahydro-1H-oxazolo[3,4-a]pyridin-3(5H)-one (400 mg, 1.04 mmol) in i-PrOH (4 mL) was added ammonia hydrate (4 mL), and the resulting mixture was heated at 100° C. for 12 hrs and concentrated to afford (6R,8aS)-6-(8-amino-1-bromoimidazo[1,5-a]pyrazin-3-yl)-1-methyltetrahydro-1H-oxazolo[3,4-a]pyridin-3(5H)-one (400 mg). MS (ESI): M/Z (M+2): 367.9; Retention time: 0.548 min.

(g) (1S,6R,8aS)-6-(8-amino-1-bromoimidazo[1,5-a]pyrazin-3-yl)-1-methyltetrahydro-1H-oxazolo[3,4-a]pyridin-3(5H)-one (6R,8aS)-6-(8-amino-1-bromoimidazo[1,5-a]pyrazin-3-yl)-1-methyltetrahydro-1H-oxazolo[3,4-a]pyridin-3(5H)-one (400 mg, 1.1 mmol) was separated by chiral separation to afford ((1 S,6R,8aS)-6-(8-amino-1-bromoimidazo[1,5-a]pyrazin-3-yl)-1-methyl tetrahydro-1H-oxazolo[3,4-a]pyridin-3(5H)-one, (Retention time: 7.46 min), (100 mg, 52.6% yield) followed by ((1R,6R,8aS)-6-(8-amino-1-bromoimidazo[1,5-a]pyrazin-3-yl)-1-methyltetrahydro-1H-oxazolo[3,4-a]pyridin-3(5H)-one (Intermediate 9). Separation condition: Instrument: Berger MultiGram™ SFC, Mettler Toledo Co, Ltd; Column: AS 250 mm×30 mm, 5 um; Mobile phase: A: Supercritical CO₂, B: MeOH (0.05% NH₄OH), A:B=73:27 at 60 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.

(6R,8aS)-6-(8-amino-1-bromoimidazo[1,5-a]pyrazin-3-yl)-1-methyltetrahydro-1H-oxazolo[3,4-a]pyridin-3(5H)-one ¹HNMR (400 MHz, CD₃OD): δ=7.59 (d, J=5.0 Hz, 1H), 6.98 (d, J=5.0 Hz, 1H), 4.60 (br. s, 1H), 4.35 (t, J=6.1 Hz, 1H), 3.97 (dd, J=2.9, 12.7 Hz, 1H), 3.49-3.41 (m, 1H), 3.27-3.16 (m, 1H), 2.15 (d, J=12.5 Hz, 1H), 2.09-2.01 (m, 1H), 1.91-1.79 (m, 1H), 1.65-1.53 (m, 1H), 1.45 (d, J=6.3 Hz, 3H). MS (ESI): M/Z (M+2): 367.9.

Intermediate 9

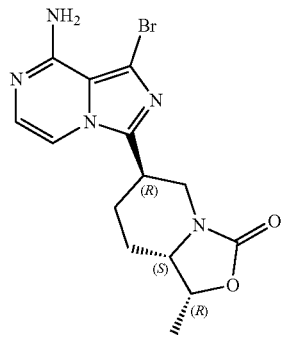

(1R,6R,8aS)-6-(8-amino-1-bromoimidazo[1,5-a]pyrazin-3-yl)-1-methyltetrahydro-1H-oxazolo[3,4-a]pyridin-3(5H)-one (1R,6R,8aS)-6-(8-amino-1-bromoimidazo[1,5-a]pyrazin-3-yl)-1-methyltetrahydro-1H-oxazolo[3,4-a]pyridin-3(5H)-one was isolated as pek 2 as described in Intermediate 8, step g. (¹HNMR (400 MHz, CD₃OD): δ=7.58 (d, J=5.0 Hz, 1H), 6.98 (d, J=5.3 Hz, 1H), 4.60 (br. s, 1H), 3.97 (d, J=8.5 Hz, 1H), 3.89-3.78 (m, 1H), 3.28-3.17 (m, 2H), 2.20 (d, J=13.6 Hz, 1H), 1.88 (d, J=13.8 Hz, 1H), 1.82-1.75 (m, 1H), 1.69 (dt, J=3.4, 12.5 Hz, 1H), 1.38 (d, J=6.5 Hz, 3H). MS (ESI): M/Z (M+2): 367.9.

Intermediates 10E1 and 10E2

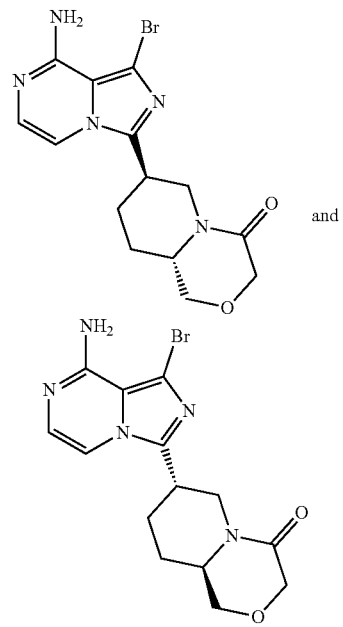

(7R,9aS)-7-(8-amino-1-bromoimidazo[1,5-a]pyrazin-3-yl)hexahydropyrido[2,1-c][1,4]oxazin-4(3H)-one & (7S,9aR)-7-(8-amino-1-bromoimidazo[1,5-a]pyrazin-3-yl)hexahydropyrido[2,1-c][1,4]oxazin-4(3H)-one a) methyl 6-((2-ethoxy-2-oxoethoxy)methyl)nicotinate To a solution of methyl 6-(hydroxymethyl)nicotinate (15.0 g, 89.7 mmol) in tetrahydrofuran (300 mL) was added NaH (4.7 g, 10.4 mmol, 60%) in one portion at 0° C. After 30 min, ethyl 2-bromoacetate (14.9 mL, 134.6 mmol) was added to the reaction mixture. The reaction mixture was heated to 70° C. overnight and quenched with saturated NaHCO₃ and extracted with ethyl acetate (150 mL×3). The combined organic layers were washed with brine, dried over sodium sulfate, filtered and concentrated in vacuo to afford the crude product, which was purified by silica gel column chromatography (EA:PE=10%~70%) to give methyl 6-((2-ethoxy-2-oxoethoxy)methyl)nicotinate (12.0 g, 53.1% yield). ¹HNMR (400 MHz, CDCl₃): δ=9.12 (d, J=1.5 Hz, 1H), 8.29 (dd, J=8.2, 2.1 Hz, 1H), 7.60 (d, J=8.0 Hz, 1H), 4.79 (s, 2H), 4.20-4.25 (m, 4H), 3.93 (s, 3H), 1.25-1.30 ppm (m, 3H). MS (ESI): M/Z (M+1): 253.9.

b) trans-methyl 4-oxooctahydropyrido[2,1-c][1,4]oxazine-7-carboxylate

To a solution of methyl 6-((2-ethoxy-2-oxoethoxy)methyl)nicotinate (8.0 g, 31.6 mmol) in AcOH (100 ml) was added NaBH$_3$CN(6.0 g, 94.8 mmol) portionwise at 0° C. and the reaction mixture was stirred at rt overnight. The reaction mixture was concentrated in vacuo and the residue was dissolved in H$_2$O (100 ml) and basified with aqueous NaHCO$_3$ to pH 8. The reaction mixture was extracted with EA (100 mL×3). The organic layer was dried over Na$_2$SO$_4$ and concentrated in vacuo. The residue was dissolved into MeOH (300 ml) and the resulting mixture was refluxed for 4 h and concentrated in vacuo to afford the crude product, which was purified by silica gel column chromatography (THF:PE=10%~80%) to give trans-methyl 4-oxooctahydro-pyrido[2,1-c][1,4]oxazine-7-carboxylate (2.55 g, 41.1% yield). $^1$HNMR (400 MHz, CDCl$_3$): δ=4.85-4.97 (m, 1H), 4.05-4.19 (m, 2H), 3.96 (dd, J=11.9, 4.4 Hz, 1H), 3.67 (s, 3H), 3.50 (dd, J=11.9, 6.9 Hz, 1H), 3.36 (qd, J=7.3, 4.1 Hz, 1H), 2.52-2.62 (m, 1H), 2.43 (tt, J=12.0, 3.8 Hz, 1H), 2.18 (dt, J=13.5, 2.4 Hz, 1H), 1.69-1.82 (m, 1H), 1.55-1.67 (m, 1H), 1.33-1.46 ppm (m, 1H). MS (ESI): M/Z (M+1): 213.9.

c) trans-4-oxooctahydropyrido[2,1-c][1,4]oxazine-7-carboxylic acid

To a solution of methyl 4-oxooctahydropyrido[2,1-c][1,4]oxazine-7-carboxylate (2.55 g, 12.0 mmol) in tetrahydrofuran (100 mL) was added a solution of lithium hydroxide monohydrate (1.0 g) in H$_2$O (24 mL) and the reaction mixture was stirred at room temperature overnight under N$_2$ atmosphere. The organic layer was evaporated under vacuum. The aqueous layer was acidified to pH 2 with 2M HCl and lyophilized to afford the crude trans-4-oxooctahydropyrido[2,1-c][1,4]oxazine-7-carboxylic acid (2.2 g, 92.4% yield), which was used in next step without purification. $^1$HNMR (400 MHz, D$_2$O): δ=3.86-4.01 (m, 2H), 3.67 (dd, J=11.2, 3.4 Hz, 1H), 3.51 (dd, J=11.3, 7.8 Hz, 2H), 3.23-3.33 (m, 1H), 2.90-2.99 (m, 1H), 2.52-2.63 (m, 1H), 2.11 (d, J=10.0 Hz, 1H), 1.82-1.92 (m, 1H), 1.44-1.62 ppm (m, 2H). MS (ESI): M/Z (M+1): 199.9.

d) trans-N-((3-chloropyrazin-2-yl)methyl)-4-oxooctahydropyrido[2,1-c][1,4]oxazine-7-carboxamide A mixture of trans-4-oxooctahydropyrido[2,1-c][1,4]oxazine-7-carboxylic acid (2.2 g, 11.0 mmol), (3-chloropyrazin-2-yl)methanamine hydrochloride (2.2 g, 3.70 mmol), HATU (6.3 g, 16.6 mmol) and triethylamine (4.7 mL, 33.1 mmol) in dichloromethane (100 mL) was stirred at room temperature for 4 hours. The reaction mixture was washed with water (150 mL) and extracted with dichloromethane (50 mL×3) and the combined organic layers were concentrated in vacuo to afford the crude product, which was purified by silica gel column chromatography (THF:PE=10%~100%) to give trans-N-((3-chloropyrazin-2-yl)methyl)-4-oxooctahydropyrido[2,1-c][1,4]oxazine-7-carboxamide (2.1 g, 58.3% yield). $^1$HNMR (400 MHz, CD$_3$OD): δ=8.54 (d, J=2.4 Hz, 1H), 8.34 (d, J=2.3 Hz, 1H), 4.74 (dt, J=12.9, 1.9 Hz, 1H), 4.60-4.67 (m, 2H), 4.11 (s, 2H), 4.02 (dd, J=11.9, 4.3 Hz, 1H), 3.56-3.65 (m, 2H), 3.43-3.53 (m, 1H), 2.67-2.76 (m, 1H), 2.49 (tt, J=11.8, 3.7 Hz, 1H), 2.05-2.15 (m, 1H), 1.77-1.88 (m, 2H), 1.50 ppm (dd, J=11.8, 3.9 Hz, 1H). MS (ESI): M/Z (M+1): 325.1.

e) trans-7-(8-chloroimidazo[1,5-a]pyrazin-3-yl)hexahydropyrido[2,1-c][1,4]oxazin-4(3H)-one To a solution of trans-N-((3-chloropyrazin-2-yl)methyl)-4-oxooctahydropyrido[2,1-c][1,4]oxazine-7-carboxamide (1.3 g, 4.0 mmol) in anhydrous dichloromethane (100 mL) at 0° C. was added dimethylformamide (52 uL, 0.68 mmol), pyridine (3.25 mL, 40.0 mmol) and followed by POCl$_3$ (1.82 mL, 20.0 mmol). The resulting mixture was stirred at 25° C. for 5 h under a stream of nitrogen. The reaction mixture was poured into an ice-water mixture, neutralized with powdered sodium bicarbonate and extracted with DCM. The organic layer was washed with brine, dried over anhydrous Na$_2$SO$_4$ and concentrated under vacuum to give a crude product. The crude product was purified by column chromatography on silica gel eluting with (THF:PE=10%~100%) to give trans-7-(8-chloroimidazo[1,5-a]pyrazin-3-yl)hexahydropyrido[2,1-c][1,4]oxazin-4(3H)-one (0.40 g, yield 33.3%). $^1$H NMR (400 MHz, CDCl$_3$) δ=7.81 (s, 1H), 7.72 (dd, J=5.0, 0.8 Hz, 1H), 7.37 (d, J=5.0 Hz, 1H), 4.93 (dt, J=13.3, 2.1 Hz, 1H), 4.20 (d, J=4.0 Hz, 2H), 4.07 (dd, J=12.0, 4.3 Hz, 1H), 3.66 (dd, J=12.0, 6.0 Hz, 1H), 3.52-3.60 (m, 1H), 3.07-3.17 (m, 1H), 2.78-2.89 (m, 1H), 2.17-2.28 (m, 2H), 1.92 (dq, J=13.4, 3.2 Hz, 1H), 1.62-1.70 ppm (m, 1H). MS (ESI): M/Z (M+1): 307.1.

f) trans-7-(1-bromo-8-chloroimidazo[1,5-a]pyrazin-3-yl)hexahydropyrido[2,1-c][1,4]oxazin-4(3H)-one N-bromosuccinimide (0.26 g, 1.43 mmol) was added to a solution of trans-7-(8-chloroimidazo[1,5-a]pyrazin-3-yl)hexahydropyrido[2,1-c][1,4]oxazin-4(3H)-one (0.40 g, 1.30 mmol) in dimethylformamide (4 mL) and stirred at 25° C. for 2 h under a stream of nitrogen. The reaction was quenched with aqueous NaHCO$_3$(40 mL), and extracted with EA (20 mL×3). The combined organic phase was washed with water(10 mL*5),followed by brine(10 mL). The organic phase was dried over anhydrous Na$_2$SO$_4$ and concentrated under vacuum to afford trans-7-(1-bromo-8-chloroimidazo[1,5-a]pyrazin-3-yl) hexahydropyrido[2,1-c][1,4]oxazin-4(3H)-one (0.50 g, yield 100%). $^1$H NMR (400 MHz, CD$_3$OD) δ=8.20 (d, J=5.0 Hz, 1H), 7.36 (d, J=5.3 Hz, 1H), 4.77-4.82 (m, 1H), 4.15 (s, 2H), 4.08 (dd, J=11.5, 4.0 Hz, 1H), 3.58-3.75 (m, 3H), 2.95 (t, J=12.4 Hz, 1H), 2.15-2.24 (m, 1H), 1.94-2.03 (m, 1H), 1.91 (d, J=3.3 Hz, 1H), 1.64-1.78 ppm (m, 1H). MS (ESI): M/Z (M/M+2=1/1) 385.0/387.0.

g) trans-7-(8-amino-1-bromoimidazo[1,5-a]pyrazin-3-yl)hexahydropyrido[2,1-c][1,4]oxazin-4(3H)-one Trans-7-(1-bromo-8-chloroimidazo[1,5-a]pyrazin-3-yl)hexahydropyrido[2,1-c][1,4]oxazin-4(3H)-one (0.50 g, 1.30 mmol) was dissolved in NH$_4$OH (6 mL) and i-PrOH (6 mL) and stirred at 110° C. for 12 h in a sealed tube. Then the reaction was cooled and concentrated at reduced pressure to afford 0.47 g of trans-7-(8-amino-1-bromoimidazo[1,5-a]pyrazin-3-yl)hexahydropyrido[2,1-c][1,4]oxazin-4(3H)-one, which was used directly in the next step without further purification. MS (ESI): M/Z (M/M+2=10/8) 366.0/368.0. (R.T.: 0.29)

h) (7R,9aS)-7-(8-amino-1-bromoimidazo[1,5-a]pyrazin-3-yl)hexahydropyrido[2,1-c][1,4]oxazin-4(3H)-one Trans-7-(8-amino-1-bromoimidazo[1,5-a]pyrazin-3-yl)hexahydropyrido[2,1-c][1,4]oxazin-4(3H)-one(0.47 g, 1.3 mmol) were separated by chiral separation (Instrument: Berger MultiGram™ SFC, Mettler Toledo Co, Ltd; Column: OD 250 mm*30 mm, 5 um; Mobile phase: A: Supercritical $CO_2$, B: MeOH, A:B=65:35 at 50 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to obtain the compounds E1: ((7R,9aS)-7-(8-amino-1-bromoimidazo[1,5-a]pyrazin-3-yl)hexahydropyrido[2,1-c][1,4]oxazin-4(3H)-one, (Ret. time=6.29 min), 0.21 g, 44.7%). $^1$H NMR (400 MHz, CD$_3$OD) δ=7.60 (d, J=5.5 Hz, 1H), 7.00 (d, J=5.0 Hz, 1H), 4.80 (dt, J=12.8, 1.9 Hz, 1H), 4.16 (s, 2H), 4.09 (dd, J=11.5, 4.0 Hz, 1H), 3.64-3.68 (m, 1H), 3.57 (br. s, 1H), 3.22-3.30 (m, 1H), 2.91 (t, J=12.5 Hz, 1H), 2.20 (d, J=13.1 Hz, 1H), 1.87-2.00 (m, 2H), 1.67-1.77 ppm (m, 1H).MS (ESI): M/Z (M+1): 367.2.

(7S,9aR)-7-(8-amino-1-bromoimidazo[1,5-a]pyrazin-3-yl)hexahydropyrido[2,1-c][1,4]oxazin-4(3H)-one Intermediate 10E2: ((7S,9aR)-7-(8-amino-1-bromoimidazo[1,5-a]pyrazin-3-yl)hexahydropyrido[2,1-c][1,4]oxazin-4(3H)-one (Ret. time=6.83 min), 0.17 g, 36.1%) was prepared by following the procedure of intermediate 11. $^1$H NMR (400 MHz, CD$_3$OD)) δ=7.60 (d, J=5.5 Hz, 1H), 7.00 (d, J=5.0 Hz, 1H), 4.80 (dt, J=12.8, 1.9 Hz, 1H), 4.16 (s, 2H), 4.09 (dd, J=11.5, 4.0 Hz, 1H), 3.64-3.68 (m, 1H), 3.57 (br. s, 1H), 3.22-3.30 (m, 1H), 2.91 (t, J=12.5 Hz, 1H), 2.20 (d, J=13.1 Hz, 1H), 1.87-2.00 (m, 2H), 1.67-1.77 ppm (m, 1H).MS (ESI): M/Z (M+1): 367.2.

Intermediate 11

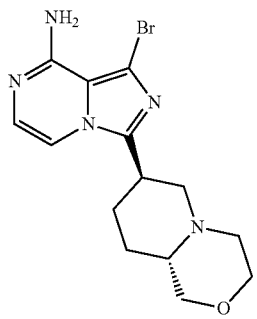 [SMILES: Nc1nccn2c([C@@H]3CC[C@H]4COCCN4C3)nc(Br)c12]

1-bromo-3-((7R,9aS)-octahydropyrido[2,1-c][1,4]oxazin-7-yl)imidazo[1,5-a]pyrazin-8-amine To a solution of (7R,9aS)-7-(8-amino-1-bromoimidazo[1,5-a]pyrazin-3-yl)hexahydropyrido[2,1-c][1,4]oxazin-4(3H)-one (80 mg, 0.22 mmol) in 10 mL of THF was added 10 M of BH$_3$.SMe$_2$ (0.11 mL, 1.09 mmol) at 0° C. and stirred at room temperature overnight. Then the reaction mixture was quenched with MeOH and concentrated under vacuum to afford the crude product (60 mg, 78.0%), which was used in the next step without purification. $^1$H NMR (400 MHz, DMSO-d6): δ=7.83 (d, J=5.8 Hz, 1H), 7.67 (d, J=5.0 Hz, 1H), 6.97 (d, J=5.0 Hz, 1H), 6.91 (d, J=5.8 Hz, 1H), 4.12 (d, J=5.0 Hz, 1H), 3.75 (d, J=10.0 Hz, 1H), 3.69-3.60 (m, 1H), 3.51 (t, J=10.5 Hz, 1H), 3.10 (t, J=10.5 Hz, 1H), 2.89 (d, J=9.5 Hz, 1H), 2.61 (d, J=10.8 Hz, 1H), 2.38-2.16 (m, 2H), 2.05-1.91 (m, 2H), 1.61-1.47 (m, 2H), 1.31-1.17 (m, 1H). MS (ESI): M/Z (M+1): 353.1.

Intermediate 12

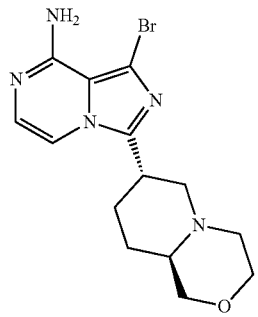 [SMILES: Nc1nccn2c([C@H]3CC[C@@H]4COCCN4C3)nc(Br)c12]

1-bromo-3-((7S,9aR)-octahydropyrido[2,1-c][1,4]oxazin-7-yl)imidazo[1,5-a]pyrazin-8-amine The procedure is as shown in Intermediate 11 (7S,9aR)-7-(8-amino-1-bromoimidazo[1,5-a]pyrazin-3-yl)hexahydropyrido[2,1-c][1,4]oxazin-4(3H)-one was reduced by BH$_3$.SMe$_2$ to give 1-bromo-3-((7S,9aR)-octahydropyrido[2,1-c][1,4]oxazin-7-yl)imidazo[1,5-a]pyrazin-8-amine (30 mg, 52.0%) as a colorless oil. 1H NMR (400 MHz, DMSO-d6) δ=7.83 (d, J=5.8 Hz, 1H), 7.67 (d, J=5.0 Hz, 1H), 6.97 (d, J=5.0 Hz, 1H), 6.91 (d, J=5.8 Hz, 1H), 4.12 (d, J=5.0 Hz, 1H), 3.75 (d, J=10.0 Hz, 1H), 3.69-3.60 (m, 1H), 3.51 (t, J=10.5 Hz, 1H), 3.10 (t, J=10.5 Hz, 1H), 2.89 (d, J=9.5 Hz, 1H), 2.61 (d, J=10.8 Hz, 1H), 2.38-2.16 (m, 2H), 2.05-1.91 (m, 2H), 1.61-1.47 (m, 2H), 1.31-1.17 (m, 1H). MS (ESI): M/Z (M+1): 353.1.

Intermediate 13

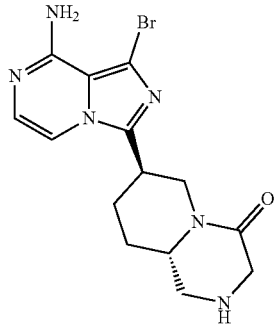 [SMILES: Nc1nccn2c([C@@H]3CC[C@H]4CNCC(=O)N4C3)nc(Br)c12]

(7R,9aS)-7-(8-amino-1-bromoimidazo[1,5-a]pyrazin-3-yl)hexahydro-1H-pyrido[1,2-a]pyrazin-4(6H)-one (a) methyl 6-(bromomethyl)nicotinate To a solution of methyl 6-methylnicotinate (30 g, 197 mmol) and NBS (52.7 g, 296 mmol) in CCl$_4$ (300 mL) was added AIBN (3 g). Then the reaction mixture was heated to 80° C. and stirred overnight. Then the reaction mixture was cooled and filtered, and the filtrate was concentrated under vacuum to give a crude residue. The crude residue was purified by silica gel column chromatography (PE/EA=5/1) to give methyl 6-(bromomethyl)nicotinate (10 g, yield 22.2%). $^1$H NMR (400 MHz, CDCl$_3$) δ=9.17 (d, J=1.5 Hz, 1H), 8.30 (dd, J=2.0, 8.0 Hz, 1H), 7.54 (d, J=8.0 Hz, 1H), 4.58 (s, 2H), 3.96 (s, 3H).

(b) methyl 6-((((benzyloxy)carbonyl)(2-methoxy-2-oxoethyl)amino)methyl)nicotinate To a solution of methyl 6-(bromomethyl)nicotinate (10 g, 43 mmol) and methyl 2-(((benzyloxy)carbonyl)amino)acetate (14.5 g, 65 mmol) in DMF (200 mL) was added K$_2$CO$_3$ (29.6 g, 215 mmol). Then the mixture was stirred at room temperature overnight. Then the reaction mixture was poured into water and extracted with EA (200 ml*3). The combined organic phase was washed with brine (500 mL) and dried over anhydrous Na$_2$SO$_4$ and filtered. The filtrate was concentrated under vacuum, and purified by silica gel column chromatography (PE/EA=2/1) to give methyl 6-((((benzyloxy)carbonyl)(2-methoxy-2-oxoethyl)amino) methyl)nicotinate (2.7 g, yield 16.8%). $^1$H NMR (400 MHz, CDCl$_3$) δ=9.11 (dd, J=1.5, 6.0 Hz, 1H), 8.30-8.13 (m, 1H), 7.47 (d, J=8.0 Hz, 1H), 7.35-7.25 (m, 5H), 5.17 (d, J=5.3 Hz, 2H), 4.73 (d, J=14.3 Hz, 2H), 4.19-4.10 (m, 2H), 3.95 (d, J=1.8 Hz, 3H), 3.74-3.61 (m, 3H).

(c) (trans)-2-benzyl 7-methyl 4-oxohexahydro-1H-pyrido[1,2-a]pyrazine-2,7(6H)-dicarboxylate To a solution of methyl 6-((((benzyloxy)carbonyl)(2-methoxy-2-oxoethyl)amino)methyl)nicotinate (2.5 g, 6.7 mmol) in AcOH (25 mL) was added NaBH$_3$CN(1.3 g, 20 mmol) in portions at 10° C. The solution was stirred overnight at room temperature. The reaction mixture was concentrated under reduced pressure to give a crude residue. The residue was dissolved in H$_2$O (50 ml) and aqueous NaHCO$_3$ was added to achieve pH=8. The mixture was then extracted with EA (50 ml*3). The combined organic phase was washed with brine (100 mL), dried over anhydrous Na$_2$SO$_4$ and concentrated under vacuum to give a crude of methyl 6-((((benzyloxy)carbonyl)(2-methoxy-2-oxoethyl)amino)methyl)piperidine-3-carboxylate (2.8 g). The crude of methyl 6-((((benzyloxy)carbonyl)(2-methoxy-2-oxoethyl)amino)methyl)piperidine-3-carboxylate (2.8 g, 7.9 mmol) in MeOH (30 mL) was stirred at 70° C. for 12 h under a stream of nitrogen. Then the mixture was concentrated under vacuum and the residue purified by silica gel column chromatography (PE/THF=1/1) to give (trans)-2-benzyl 7-methyl 4-oxohexahydro-1H-pyrido[1,2-a]pyrazine-2,7 (6H)-dicarboxylate (2 g, yield 74%). $^1$H NMR (400 MHz, CD$_3$OD) δ=7.49-7.24 (m, 5H), 5.16 (d, J=3.3 Hz, 2H), 4.86-4.78 (m, 1H), 4.22-4.03 (m, 2H), 3.98-3.87 (m, 1H), 3.70 (s, 3H), 3.43 (d, J=8.8 Hz, 2H), 2.69-2.56 (m, 1H), 2.45 (tt, J=3.9, 12.1 Hz, 1H), 2.15 (d, J=13.1 Hz, 1H), 1.81 (dd, J=2.5, 4.5 Hz, 1H), 1.74-1.58 (m, 1H).

(d)(trans)-2-((benzyloxyl)carbonyl)-4-oxooctahydro-1H-pyrido[1,2-a]pyrazine-7-carboxylic acid To a solution of (trans)-2-benzyl 7-methyl 4-oxohexahydro-1H-pyrido[1,2-a]pyrazine-2,7(6H)-dicarboxylate (1.2 g, 3.5 mmol) in THF/H$_2$O (1:1, 20 ml) was added LiOH.H$_2$O (290 mg, 7.0 mmol) portionwise. The resulting solution was stirred at 25° C. for 12 h under N$_2$. The reaction was acidified to pH=5 with HCl (1M), and then extracted with DCM/i-PrOH (4/1, 30 mL*10). The combined organic layers were washed with brine, dried over sodium sulfate, filtered and concentrated to give (trans)-2-((benzyloxy)carbonyl)-4-oxooctahydro-1H-pyrido[1,2-a]pyrazine-7-carboxylic acid (700 mg, yield 92.1%). $^1$H NMR (400 MHz, CD$_3$OD) δ=7.46-7.27 (m, 5H), 5.23-5.06 (m, 2H), 4.25-4.16 (m, 1H), 4.08-3.99 (m, 1H), 3.87 (dd, J=10.0, 15.3 Hz, 1H), 3.63 (dd, J=2.9, 12.4 Hz, 1H), 3.02 (t, J=12.7 Hz, 1H), 2.80 (tt, J=4.0, 12.2 Hz, 1H), 2.29 (d, J=10.5 Hz, 1H), 2.10-1.93 (m, 2H), 1.77-1.52 (m, 2H).

(e) (trans)-benzyl 7-(((3-chloropyrazin-2-yl)methyl) carbamoyl)-4-oxohexahydro-1H-pyrido[1,2-a]pyrazine-2(6H)-carboxylate A mixture of (trans)-2-((benzyloxy)carbonyl)-4-oxooctahydro-1H-pyrido[1,2-a]pyrazine-7-carboxylic acid (1.3 g, 3.9 mmol), (3-chloropyrazin-2-yl)methanamine hydrochloride (840 mg, 4.7 mmol), HATU (2.2 g, 5.8 mmol) and TEA (1.6 g, 15.6 mmol) in DMF (20 mL) was stirred at 25° C. for overnight. Then the reaction mixture was poured into water and extracted with EA (50 ml*3). The combined organic phase was washed with brine (100 mL), dried over Na$_2$SO$_4$, concentrated under vacuum to give the crude residue, which was purified by silica gel column chromatography (PE/THF=1/3) to give (trans)-benzyl 7-(((3-chloropyrazin-2-yl)methyl)carbamoyl)-4-oxohexahydro-1H-pyrido[1,2-a]pyrazine-2(6H)-carboxylate (600 mg, yield 35.3%). $^1$H NMR (400 MHz, CD$_3$OD) δ=8.52 (d, J=2.5 Hz, 1H), 8.33 (d, J=2.3 Hz, 1H), 7.40-7.29 (m, 5H), 5.15 (br. s, 2H), 4.77-4.67 (m, 1H), 4.12 (br. s, 1H), 3.96-3.85 (m, 1H), 3.48 (br. s, 2H), 2.71 (t, J=12.5 Hz, 1H), 2.52-2.36 (m, 1H), 2.11-1.97 (m, 2H), 1.90-1.71 (m, 2H).

(f)(trans)-benzyl 7-(8-chloroimidazo[1,5-a]pyrazin-3-yl)-4-oxohexahydro-1H-pyrido[1,2-a]pyrazine-2 (6H)-carboxylate To a solution of (trans)-benzyl 7-(((3-chloropyrazin-2-yl) methyl)carbamoyl)-4-oxohexahydro-1H-pyrido[1,2-a]pyrazine-2(6H)-carboxylate (0.5 g, 1.1 mmol) in DCM (15 mL) was added DMF (13 mg, 0.18 mmol) and pyridine (0.88 mL, 11 mmol). Then to this solution was added POCl$_3$(0.52 mL, 5.5 mmol) at 0° C. and stirred for 6 h. The reaction mixture was poured into an ice-water mixture, neutralized with powdered sodium bicarbonate, and extracted with DCM(30 mL*10). The organic layer was washed with brine, dried over anhydrous sodium sulfate, filtered and concentrated to give (trans)-benzyl-7-(8-chloroimidazo[1,5-a]pyrazin-3-yl)-4-oxohexahydro-1H-pyrido[1,2-a]pyrazine-2(6H)-carboxylate (300 mg, yield 62.5%). $^1$H NMR (400 MHz, CD$_3$OD) δ=8.18 (d, J=4.5 Hz, 1H), 7.85 (s, 1H), 7.38 (dd, J=3.6, 5.6 Hz, 5H), 7.33 (dd, J=3.0, 5.8 Hz, 1H), 5.17 (br. s, 2H), 4.84-4.75 (m, 1H), 4.19 (br. s, 2H), 3.99-3.84 (m, 1H), 3.72 (t, J=6.7 Hz, 1H), 3.63 (br. s, 2H), 3.03-2.93 (m, 1H), 2.23-2.16 (m, 1H), 1.64 (d, J=12.0 Hz, 1H), 1.40 (s, 1H).

(g)(trans)-benzyl 7-(1-bromo-8-chloroimidazo[1,5-a]pyrazin-3-yl)-4-oxohexahydro-1H-pyrido[1,2-a] pyrazine-2(6H)-carboxylate N-bromosuccinimide (146 mg, 0.82 mmol) was added to a solution of benzyl 7-(8-chloroimidazo[1,5-a]pyrazin-3-yl)-4-oxohexahydro-1H-pyrido[1,2-a]pyrazine-2(6H)-carboxylate (300 mg, 0.68 mmol) in DMF (6 mL) and stirred at 25° C. for 2 h under N$_2$. The reaction was quenched with NaHCO$_3$ and H$_2$O, and extracted with EA (20 mL*3). The organic layer was washed with water (40 mL*3), and with brine, dried over anhydrous Na₂SO₄, and concentrated to afford (trans)-benzyl7-(1-bromo-8-chloroimidazo[1,5-a]pyrazin-3-yl)-4-oxohexahydro-1H-pyrido[1,2-a]pyrazine-2(6H)-carboxylate (300 mg, yield 88.2%). ¹H NMR (400 MHz, CD₃OD) δ=8.19 (dd, J=0.8, 5.0 Hz, 1H), 7.86 (d, J=0.8 Hz, 1H), 7.42-7.35 (m, 5H), 5.19 (br. s, 2H), 4.83 (ddd, J=2.0, 4.0, 13.1 Hz, 1H), 4.21 (br. s, 2H), 4.01-3.89 (m, 1H), 3.64 (br. s, 2H), 2.98 (t, J=12.4 Hz, 1H), 2.22 (d, J=14.8 Hz, 1H), 2.11-1.89 (m, 2H), 1.66 (d, J=8.0 Hz, 1H).

(h)(7R,9aS)-benzyl 7-(8-amino-1-bromoimidazo[1,5-a]pyrazin-3-yl)-4-oxohexahydro-1H-pyrido[1,2-a]pyrazine-2(6H)-carboxylate (Trans)-benzyl 7-(1-bromo-8-chloroimidazo[1,5-a]pyrazin-3-yl)-4-oxohexahydro-1H-pyrido[1,2-a]pyrazine-2(6H)-carboxylate (300 mg, 0.6 mmol) was dissolved in NH₄OH (7 mL) and i-PrOH (7 mL) and stirred at 100° C. for 12 h in a sealed tube. Then the reaction was cooled and concentrated under reduced pressure to afford 300 mg of (trans)-benzyl 7-(8-amino-1-bromoimidazo[1,5-a]pyrazin-3-yl)-4-oxohexahydro-1H-pyrido[1,2-a]pyrazine-2(6H)-carboxylate (crude), which was purified by chiral HPLC to give (7R,9aS)-benzyl 7-(8-amino-1-bromoimidazo[1,5-a]pyrazin-3-yl)-4-oxohexahydro-1H-pyrido[1,2-a]pyrazine-2(6H)-carboxylate(0.1 g, 33.3%). (ESI): M/Z (M+1): M/Z (M+3) 501: (M+1) 499=10:8 (Condition: 5-95AB_1.5 min; R.T.: 0.756). The chiral HPLC condition was [Instrument: Thar 80; Column: AS250 mm*20 mm, 20 um; Mobile phase: A: Supercritical CO₂, B: MeOH, A:B=55:45 at 80 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm].

(i)(7R,9aS)-7-(8-amino-1-bromoimidazo[1,5-a]pyrazin-3-yl)hexahydro-1H-pyrido[1,2-a]pyrazin-4(6H)-one (7R,9aS)-benzyl 7-(8-amino-1-bromoimidazo[1,5-a]pyrazin-3-yl)-4-oxohexa hydro-1H-pyrido[1,2-a]pyrazine-2(6H)-carboxylate (100 mg, 0.2 mmol) in HBr/HOAc (2 mL) was stirred at room temperature for 0.5 h. Isopropyl alcohol (5 mL) was then added to the reaction mixture and filtered. The filter cake was added to water (20 mL), and adjusted to pH=9 with solid NaHCO₃. The mixture was then extracted with DCM/i-PrOH (3/1, 10 mL*3). The organic layer was washed with brine, dried over anhydrous Na₂SO₄, and concentrated under vacuum to afford (7R,9aS)-7-(8-amino-1-bromoimidazo[1,5-a]pyrazin-3-yl)hexahydro-1H-pyrido[1,2-a]pyrazin-4(6H)-one(60 mg, yield 82.2%). ¹H NMR (400 MHz, CD₃OD) δ=7.57 (d, J=5.3 Hz, 1H), 7.00 (d, J=5.0 Hz, 1H), 4.86-4.71 (m, 1H), 3.58-3.47 (m, 1H), 3.43 (d, J=4.3 Hz, 1H), 3.29-3.14 (m, 2H), 2.89-2.74 (m, 2H), 2.16 (d, J=13.6 Hz, 1H), 2.00-1.85 (m, 2H), 1.72-1.58 (m, 1H).

Intermediate 14

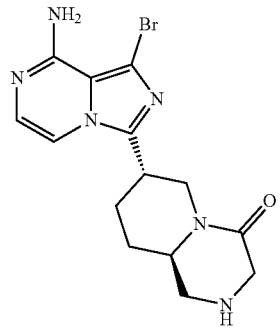 [SMILES: Nc1nccn2c([C@H]3CC[C@@H]4CNCC(=O)N4C3)nc(Br)c12]

(7S,9aR)-7-(8-amino-1-bromoimidazo[1,5-a]pyrazin-3-yl)hexahydro-1H-pyrido[1,2-a]pyrazin-4(6H)-one (a) (7S,9aR)-benzyl 7-(8-amino-1-bromoimidazo[1,5-a]pyrazin-3-yl)-4-oxohexahydro-1H-pyrido[1,2-a]pyrazine-2(6H)-carboxylate (Trans)-benzyl 7-(1-bromo-8-chloroimidazo[1,5-a]pyrazin-3-yl)-4-oxohexahydro-1H-pyrido[1,2-a]pyrazine-2(6H)-carboxylate (300 mg, 0.6 mmol) was dissolved in NH₄OH (7 mL) and i-PrOH (7 mL) and stirred at 100° C. for 12 h in a sealed tube. Then the reaction mixture was cooled and concentrated under reduced pressure to afford 300 mg of (trans)-benzyl 7-(8-amino-1-bromoimidazo[1,5-a]pyrazin-3-yl)-4-oxohexahydro-1H-pyrido[1,2-a]pyrazine-2(6H)-carboxylate (crude), which was purified by chiral HPLC to give (7S,9aR)-benzyl 7-(8-amino-1-bromoimidazo[1,5-a]pyrazin-3-yl)-4-oxohexahydro-1H-pyrido[1,2-a]pyrazine-2(6H)-carboxylate (60 mg, 20%). (ESI): M/Z (M+1): M/Z (M+3) 501: (M+1) 499=10:8 (Condition: 5-95AB_1.5 min; R.T.: 0.760). The chiral HPLC condition was [Instrument: Thar 80; Column: AS250 mm*20 mm, 20 um; Mobile phase: A: Supercritical CO₂, B: MeOH, A:B=55:45 at 80 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm].

(b) (7S,9aR)-7-(8-amino-1-bromoimidazo[1,5-a]pyrazin-3-yl)hexahydro-1H-pyrido[1,2-a]pyrazin-4(6H)-one (7S,9aR)-benzyl 7-(8-amino-1-bromoimidazo[1,5-a]pyrazin-3-yl)-4-oxohexahydro-1H-pyrido[1,2-a]pyrazine-2(6H)-carboxylate (60 mg, 0.12 mmol) was dissolved in HBr/HOAc (2 mL) and stirred at room temperature for 0.5 h. Isopropyl alcohol (5 mL) was added to the mixture and filtered. The filter cake was added to water (20 mL), and adjusted to pH=9 with solid NaHCO₃. The mixture was then extracted with DCM/i-PrOH (3/1, 10 mL*3). The organic layer was washed with brine, dried over Na₂SO₄, and concentrated under vacuum to afford (7S,9aR)-7-(8-amino-1-bromoimidazo[1,5-a]pyrazin-3-yl)hexahydro-1H-pyrido[1,2-a]pyrazin-4(6H)-one(40 mg, yield 90.9%). (ESI): M/Z (M+1): M/Z (M+3) 367: (M+1) 365=10:8 (Condition 5-95AB_1.5 min; R.T.: 0.142).

Intermediate 15

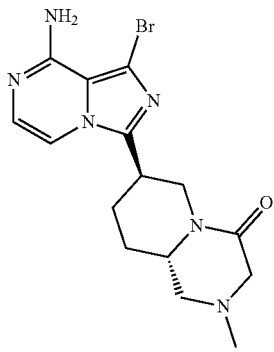 [SMILES: CN1CC(=O)N2C[C@H](c3nc(Br)c4c(N)nccn34)CC[C@H]2C1]

(7R,9aS)-7-(8-amino-1-bromoimidazo[1,5-a]pyrazin-3-yl)-2-methylhexahydro-1H-pyrido[1,2-a]pyrazin-4(6H)-one To a solution of (7R,9aS)-7-(8-amino-1-bromoimidazo[1,5-a]pyrazin-3-yl) hexahydro-1H-pyrido[1,2-a]pyrazin-4(6H)-one (200 mg, 0.55 mmol) in methanol (16 mL) was added formaldehyde (37%, 2.8 mL), NaBH$_3$CN (340 mg, 5.48 mmol) and HOAc (5.2 mL). Then the mixture was stirred at 25° C. for 2 h. Then the reaction mixture was added to water (30 mL) and adjusted to pH=9 with solid NaHCO$_3$. The mixture was then extracted with DCM (20 mL*3). The organic layer was washed with brine, dried over Na$_2$SO$_4$, concentrated under vacuum to afford (7R,9aS)-7-(8-amino-1-bromoimidazo[1,5-a]pyrazin-3-yl)-2-methylhexahydro-1H-pyrido[1,2-a]pyrazin-4(6H)-one (0.1 g, yield 48.15%). $^1$H NMR (400 MHz, CD$_3$OD) δ=7.57 (d, J=5.3 Hz, 1H), 6.99 (d, J=5.0 Hz, 1H), 4.83-4.75 (m, 1H), 3.19 (d, J=16.6 Hz, 2H), 3.07-2.95 (m, 2H), 2.86 (t, J=12.4 Hz, 1H), 2.43 (dd, J=7.3, 12.0 Hz, 1H), 2.35 (s, 3H), 2.16 (d, J=13.1 Hz, 1H), 2.03-1.87 (m, 2H), 1.76-1.58 (m, 1H).

Intermediate 16

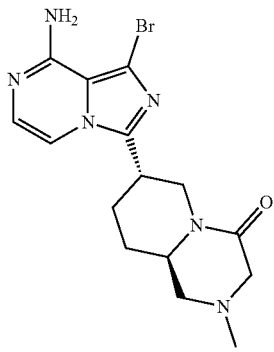 [SMILES: CN1CC(=O)N2C[C@@H](c3nc(Br)c4c(N)nccn34)CC[C@@H]2C1]

(7S,9aR)-7-(8-amino-1-bromoimidazo[1,5-a]pyrazin-3-yl)-2-methylhexahydro-1H-pyrido[1,2-a]pyrazin-4(6H)-one To a solution of (7S,9aR)-7-(8-amino-1-bromoimidazo[1,5-a]pyrazin-3-yl) hexahydro-1H-pyrido[1,2-a]pyrazin-4(6H)-one (200 mg, 0.55 mmol) in methanol (16 mL) was added formaldehyde (37%, 2.8 mL), NaBH$_3$CN (340 mg, 5.48 mmol) and HOAc (5.2 mL). The mixture was stirred at 25° C. for 2 h. Then the reaction mixture was added to water (30 mL), and adjusted to pH=9 with solid NaHCO$_3$. The mixture was extracted with DCM (20 mL*3). The organic layer was washed with brine, dried over anhydrous Na$_2$SO$_4$ and concentrated under vacuum to afford (7S,9aR)-7-(8-amino-1-bromoimidazo[1,5-a]pyrazin-3-yl)-2-methylhexahydro-1H-pyrido[1,2-a]pyrazin-4(6H)-one (0.08 g, yield 38.5%). $^1$H NMR (400 MHz, CD$_3$OD) δ=7.57 (d, J=5.3 Hz, 1H), 6.99 (d, J=5.0 Hz, 1H), 4.84-4.72 (m, 1H), 3.65-3.51 (m, 1H), 3.27-3.13 (m, 2H), 3.07-2.94 (m, 2H), 2.86 (t, J=12.5 Hz, 1H), 2.44 (dd, J=7.5, 12.3 Hz, 1H), 2.35 (s, 3H), 2.03-1.88 (m, 2H), 1.76-1.60 (m, 1H).

Intermediates 17E and 17E2

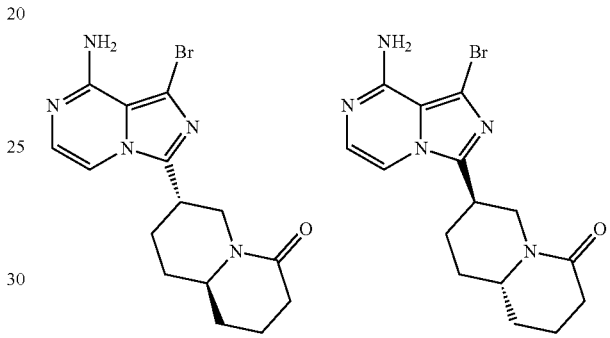

(7S,9aS)-7-(8-amino-1-bromoimidazo[1,5-a]pyrazin-3-yl)hexahydro-1H-quinolizin-4(6H)-one, and (7R,9aR)-7-(8-amino-1-bromoimidazo[1,5-a]pyrazin-3-yl)hexahydro-1H-quinolizin-4(6H)-one (a) methyl 6-(4-ethoxy-4-oxobutyl)nicotinate To the solution of methyl 6-bromonicotinate (7.2 g, 35.32 mmol) in anhydrous THF (200 mL) was added Pd(PPh$_3$)$_4$ (1.92 g, 1.66 mmol), followed by (4-ethoxy-4-oxobutyl)zinc (II) bromide (100 mL, 49.99 mmol). The resulting mixture was stirred at room temperature overnight. The mixture was quenched with sat. aq. NH$_4$Cl and H$_2$O (200 mL) and extracted with EA (35 mL*3). The combined organic phase was dried over sodium sulfate, filtered, concentrated to give a crude product. The crude was purified by column chromatography on silica gel eluting with PE/EA (0-60%) to give methyl 6-(4-ethoxy-4-oxobutyl)nicotinate (5.4 g, 43%) as a light yellow oil. $^1$H NMR (400 MHz, CDCl$_3$) δ=9.13 (d, J=1.5 Hz, 1H), 8.20 (dd, J=2.3, 8.0 Hz, 1H), 7.39-6.98 (m, 1H), 4.12 (q, J=7.0 Hz, 2H), 3.94 (s, 3H), 2.96-2.72 (m, 2H), 2.36 (t, J=7.3 Hz, 2H), 2.15-1.98 (m, 2H), 1.25 (t, J=7.2 Hz, 3H).

(b) methyl 6-(4-ethoxy-4-oxobutyl)piperidine-3-carboxylate

To the solution of methyl 6-(4-ethoxy-4-oxobutyl)nicotinate (5.4 g, 21.51 mmol) in AcOH (60 mL) was added NaBCH$_3$ (4.06 g, 64.54 mmol) at 10° C. The mixture was stirred at room temperature overnight. The mixture was concentrated under vacuum. The residue was basified to pH 7-8 with NaHCO$_3$, and H$_2$O (150 mL) and extracted with DCM/i-PrOH (3:1) (25 mL*3). The combined organic layers were washed with brine, dried over sodium sulfate, filtered and concentrated to give methyl 6-(4-ethoxy-4-oxobutyl) piperidine-3-carboxylate (5.3 g, 95.49%) as a yellow oil. $^1$H NMR (400 MHz, CDCl$_3$) δ=6.58 (br. s, 1H), 4.18-4.07 (m, 2H), 3.74-3.61 (m, 3H), 3.28-3.10 (m, 1H), 2.99-2.83 (m, 2H), 2.43-2.30 (m, 2H), 2.04 (s, 3H), 1.81-1.47 (m, 6H), 1.32-1.21 (m, 3H).

(c) (racemic)-methyl 6-oxooctahydro-1H-quinolizine-3-carboxylate

The solution of methyl 6-(4-ethoxy-4-oxobutyl)piperidine-3-carboxylate (5.3 g, 20.62 mmol) in toluene (80 mL) was refluxed for 6 h. The mixture was concentrated under vacuum and the residue was purified by Prep_HPLC to give (trans)-methyl 6-oxooctahydro-1H-quinolizine-3-carboxylate (1.87 g) as a yellow oil. $^1$H NMR (400 MHz, CDCl$_3$) δ=5.04-4.95 (m, 1H), 3.72-3.65 (m, 3H), 3.34-3.21 (m, 1H), 2.59-2.33 (m, 4H), 2.21-2.11 (m, 1H), 2.09-1.99 (m, 1H), 1.89-1.77 (m, 2H), 1.73-1.60 (m, 2H), 1.60-1.48 (m, 1H), 1.45-1.33 (m, 1H).

(d) (trans)-6-oxooctahydro-1H-quinolizine-3-carboxylic acid

LiOH (0.89 g, 21.30 mmol) was added to the solution of (trans)-methyl 6-oxooctahydro-1H-quinolizine-3-carboxylate (1.8 g, 8.52 mmol) in THF (20 mL) and H$_2$O (20 mL). The mixture was stirred at room temperature for 2 h. The mixture was then acidified to pH 5-6 and partitioned with H$_2$O (50 mL) and DCM/i-PrOH (3:1) (15 mL*3). The combined organic layers were washed with brine, dried over anhydrous sodium sulfate, filtered and concentrated to give (trans)-6-oxooctahydro-1H-quinolizine-3-carboxylic acid (0.92 g, 84.49%) as a white solid. $^1$H NMR (400 MHz, CHLOROFORM-d) δ=5.08-4.98 (m, 1H), 3.32-3.20 (m, 1H), 2.58-2.40 (m, 3H), 2.39-2.30 (m, 1H), 2.18 (d, J=13.1 Hz, 1H), 2.08-1.98 (m, 1H), 1.88-1.77 (m, 2H), 1.73-1.62 (m, 2H), 1.57-1.46 (m, 1H), 1.44-1.35 (m, 1H).

(e) (trans)-N-((3-chloropyrazin-2-yl)methyl)-6-oxooctahydro-1H-quinolizine-3-carboxamide A mixture of (trans)-6-oxooctahydro-1H-quinolizine-3-carboxylic acid (520 mg, 2.64 mmol), (3-chloropyrazin-2-yl)methanamine hydrochloride (570 mg, 3.17 mmol), HATU (1.50 g, 3.95 mmol) and TEA (0.79 g, 7.91 mmol) in DCM (13 mL) was stirred at 25° C. overnight. The mixture was quenched with H$_2$O (40 mL) and extracted with DCM (15 mL*3). The combined organic layers were dried over anhydrous sodium sulfate, filtered and concentrated to give a crude product. The crude product was purified by column chromatography on silica gel eluting with PE/THF (0-60%) to give (trans)-N-((3-chloropyrazin-2-yl)methyl)-6-oxooctahydro-1H-quinolizine-3-carboxamide (0.7 g, 82.35%) as a light yellow solid. $^1$H NMR (400 MHz, CDCl3) δ=8.53-8.41 (m, 1H), 8.33 (d, J=2.5 Hz, 1H), 6.96 (br. s, 1H), 5.08-4.88 (m, 1H), 4.73-4.61 (m, 2H), 3.40-3.26 (m, 1H), 2.72-2.57 (m, 1H), 2.47-2.28 (m, 3H), 2.12-2.00 (m, 2H), 1.89-1.77 (m, 4H), 1.73-1.62 (m, 1H), 1.58-1.47 (m, 1H).

(f) (trans)-7-(8-chloroimidazo[1,5-a]pyrazin-3-yl) hexahydro-1H-quinolizin-4(6H)-one To a solution of (trans)-N-((3-chloropyrazin-2-yl) methyl)-6-oxooctahydro-1H-quinolizine-3-carboxamide (1.16 g, 3.6 mmol) in anhydrous DCM (18 mL) at 0° C. was added dimethylformamide (44.7 mg, 0.61 mmol), Pyridine (2.84 g, 36 mmoL), and followed by POCl$_3$ (2.71 g, 18.0 mmol). The resulting mixture was stirred at 0° C. for 3 h. The reaction was poured to an ice-water mixture, neutralized with powdered sodium bicarbonate and extracted with DCM (10 mL*3). The organic layer was washed with brine, dried over Na$_2$SO$_4$ and concentrated to dryness under vacuum. The crude product was purified by column chromatography on silica gel eluting with PE/THF (0-80%) to give(trans)-7-(8-chloroimidazo[1,5-a]pyrazin-3-yl)hexahydro-1H-quinolizin-4(6H)-one (0.34 g, 31.1%) as a white solid. $^1$H NMR (400 MHz, CDCl$_3$) δ=7.85-7.74 (m, 2H), 7.36 (d, J=5.0 Hz, 1H), 5.01 (td, J=2.3, 13.1 Hz, 1H), 3.54-3.40 (m, 1H), 3.15-2.99 (m, 1H), 2.75-2.64 (m, 1H), 2.53-2.32 (m, 2H), 2.26-2.19 (m, 2H), 2.17-2.07 (m, 1H), 2.00-1.85 (m, 2H), 1.82-1.70 (m, 1H), 1.66-1.62 (m, 1H), 1.59-1.52 (m, 1H).

(g) (trans)-7-(1-bromo-8-chloroimidazo[1,5-a] pyrazin-3-yl)hexahydro-1H-quinolizin-4(6H)-one N-bromosuccinimide (265.5 mg, 1.5 mmol) was added to a solution of (trans)-7-(8-chloroimidazo[1,5-a]pyrazin-3-yl) hexahydro-1H-quinolizin-4(6H)-one (380 mg, 1.25 mmol) in DMF (8 mL) and stirred at 25° C. for 2 h under a stream of N$_2$. The reaction was partitioned with H$_2$O (35 mL) and EA (10 mL*3). The organic layer was washed with brine, dried over anhydrous Na$_2$SO$_4$ and concentrated to dryness under vacuum to afford (trans)-7-(1-bromo-8-chloroimidazo [1,5-a]pyrazin-3-yl) hexahydro-1H-quinolizin-4(6H)-one (445 mg, 92.7%) as a light yellow solid. $^1$H NMR (400 MHz, CDCl$_3$) δ=7.76 (d, J=5.3 Hz, 1H), 7.34 (d, J=5.0 Hz, 1H), 5.03-4.91 (m, 1H), 3.45 (dtd, J=2.6, 6.2, 11.8 Hz, 1H), 3.08-2.95 (m, 1H), 2.74-2.61 (m, 1H), 2.50-2.32 (m, 2H), 2.30-2.07 (m, 3H), 1.98-1.83 (m, 2H), 1.81-1.69 (m, 1H), 1.66-1.62 (m, 1H), 1.58-1.49 (m, 1H).

(h) (trans)-7-(8-amino-1-bromoimidazo[1,5-a] pyrazin-3-yl)hexahydro-1H-quinolizin-4(6H)-one (Trans)-7-(1-bromo-8-chloroimidazo[1,5-a]pyrazin-3-yl) hexahydro-1H-quinolizin-4(6H)-one) (355 mg, 0.92 mol) was dissolved in NH$_4$OH (5 mL) and i-PrOH (5 mL) and stirred at 100° C. for 12 h in a sealed tube. Then the reaction was cooled to room temperature and concentrated under reduced pressure to give (trans)-7-(8-amino-1-bromoimidazo[1,5-a]pyrazin-3-yl) hexahydro-1H-quinolizin-4(6H)-one (310 mg, 91.9%) as a yellow solid. MS (ESI): M/Z (M+1): 365.7.

(i) (7S,9aS)-7-(8-amino-1-bromoimidazo[1,5-a] pyrazin-3-yl)hexahydro-1H-quinolizin-4(6H)-one (Trans)-7-(8-amino-1-bromoimidazo[1,5-a]pyrazin-3-yl) hexahydro-1H-quinolizin-4(6H)-one was purified by SFC to give (7S,9aS)-7-(8-amino-1-bromoimidazo[1,5-a]pyrazin-3-yl)hexahydro-1H-quinolizin-4(6H)-one (55 mg, 17.7%) (Ret. time=7.07 min) as a yellow solid material. The chiral HPLC condition was [Instrument: Thar 200; Column: OJ 250 mm*20 mm, 20 um; Mobile phase: A: Supercritical CO$_2$, B: EtOH (0.05% NH$_3$H$_2$O), A:B=80:20 at 70 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm. 1H NMR (400 MHz, CDCl$_3$) δ=7.30 (d, J=5.0 Hz, 1H), 7.04 (d, J=5.0 Hz, 1H), 5.72 (br. s, 2H), 5.04-4.93 (m, 1H), 3.41 (d, J=10.3 Hz, 1H), 3.04-

2.89 (m, 1H), 2.66 (t, J=12.3 Hz, 1H), 2.47-2.31 (m, 2H), 2.19-2.05 (m, 2H), 2.03-1.91 (m, 2H), 1.80-1.47 (m, 4H).

(7S,9aS)-7-((3S)-8-amino-1-bromo-3,8a-dihydroimidazo[1,5-a]pyrazin-3-yl)hexahydro-1H-quinolizin-4(6H)-one (E2) (Trans)-7-(8-amino-1-bromoimidazo[1,5-a]pyrazin-3-yl)hexahydro-1H-quinolizin-4(6H)-one was purified by SFC to give (7S,9aS)-7-((3S)-8-amino-1-bromo-3,8a-dihydroimidazo[1,5-a]pyrazin-3-yl)hexahydro-1H-quinolizin-4(6H)-one (70 mg, 22.6%) (Rt=6.15 min) as a yellow solid. 1H NMR (400 MHz, CDCl₃) δ=7.30 (d, J=5.0 Hz, 1H), 7.04 (d, J=5.0 Hz, 1H), 5.72 (br. s, 2H), 5.04-4.93 (m, 1H), 3.41 (d, J=10.3 Hz, 1H), 3.04-2.89 (m, 1H), 2.66 (t, J=12.3 Hz, 1H), 2.47-2.31 (m, 2H), 2.19-2.05 (m, 2H), 2.03-1.91 (m, 2H), 1.80-1.47 (m, 4H).

Intermediate 18

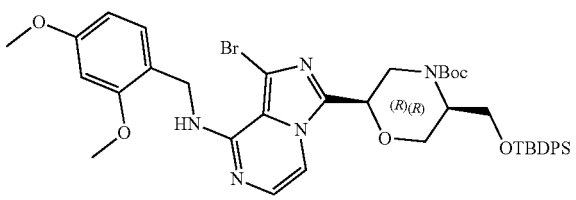

(2R,5R)-tert-butyl 2-(1-bromo-8-((2,4-dimethoxybenzyl)amino)imidazo[1,5-a]pyrazin-3-yl)-5-(((tert-butyldiphenylsilyl)oxy)methyl)morpholine-4-carboxylate (a) (S)-methyl 2-(benzylamino)-3-((tert-butyldiphenylsilyl)oxy)propanoate (S)-methyl 2-(benzylamino)-3-hydroxypropanoate (5 g, 23.9 mmol) was dissolved in 100 mL of CH₂Cl₂. NEt3 (2.9 g, 28.7 mmol) was added followed by a catalytic amount of DMAP (0.15 g, (1.2 mmol). The reaction mixture was cooled to 0° C. and TBS-Cl (6.9 g, 25.09 mmol) was added. The mixture was then warmed to rt and stirred for overnight. The mixture was quenched with water (100 mL) and extracted with CH₂Cl₂ (100 mL). The organic layer was washed with sat. NH₄Cl, dried over Na₂SO₄ and concentrated to give (S)-methyl 2-(benzylamino)-3-((tert-butyldiphenylsilyl)oxy) propanoate (10.2 g, 95%). LCMS: [M+H]⁺: 448.13; Ret. time=2.01 min, 4 min).Used as such for the next step without any further purification.

(b) (R)-2-(benzylamino)-3-((tert-butyldiphenylsilyl)oxy)propan-1-ol

To (S)-methyl 2-(benzylamino)-3-((tert-butyldiphenylsilyl)oxy)propanoate (5 g, 11.17 mmol) in 100 mL of THF was added MeOH (0.5 ml) followed by 2.0 M LiBH₄ in THF (6.7 mL). The reaction mixture was stirred at rt for 16 hrs and then quenched with slow addition of sat. aq. NH₄Cl (100 mL). The mixture was extracted with EtOAc(3×100 mL), dried over anhydrous Na₂SO₄, filtered and concentrated to give (R)-2-(benzylamino)-3-((tert-butyldiphenylsilyl)oxy) propan-1-ol (4.4 g, 94%). LCMS: [M+H]⁺: 422.20; Ret. time=1.22 min). Used as such for the next step without any further purification.

(c) ((2R,5R)-4-benzyl-5-(((tert-butyldiphenylsilyl)oxy)methyl)morpholin-2-yl) methanol (R)-2-(benzylamino)-3-((tert-butyldiphenylsilyl)oxy)propan-1-ol (6 g, 14.3 mmol) was dissolved in 100 mL toluene, (S)-(+)-epichlorohydrin(1.58 g, 17.2 mmol) was added and followed then by the slow addition of lithium perchlorate (1.82 g, 17.2 mmol) over 30 min. The reaction was stirred at rt for 48 h. A solution of sodium methoxide (25 wt % in CH₃OH) 25 mL was then added and the mixture was stirred for 3 days. Saturated aq. NH₄Cl (100 mL) was added, and the product was extracted with EtOAc (3×100 mL). The combined organics were washed with brine, dried over anhydrous MgSO₄, filtered, and evaporated to dryness to give the crude product, which was purified by chromatography eluting with 20-50% EtOAc in hexanes to afford product ((2R,5R)-4-benzyl-5-(((tert-butyldiphenylsilyl)oxy)methyl)morpholin-2-yl)methanol (2.6 g, 38%). LCMS: [M+H]⁺:476.17, Ret. time=1.15 min,).

(d) (2R,5R)-tert-butyl 5-(((tert-butyldiphenylsilyl)oxy)methyl)-2-(hydroxymethyl) morpholine-4-carboxylate ((2R,5R)-4-benzyl-5-(((tert-butyldiphenylsilyl)oxy)methyl)morpholin-2-yl)methanol (4 g, 8.41 mmol) was dissolved in 100 mL Ethanol at 20° C., BOC₂O (2.2 g, 10.09 mmol) added followed by Et₃N (0.86 g, 8.41 mmol). The reaction mixture was degassed with N₂ for ~10 min. Pd(OH)2 (1.2 g, 1.68 mmol) was added slowly and degassed with N₂ for another 10 min. The reaction was hydrogenated with the Parr apparatus at 45-50 psi of H₂O/N (20 hrs). The mixture was then purged with N₂, filtered on a pad of celite, and rinsed with EtOH (200 mL). The filtrate was concentrated to dryness to give a residue. The residue was dissolved in EtOAc (200 ml) and washed with water (150 mL×2). The organic phase was dried over MgSO₄, filtered and concentrated under vacuum to afford a crude product, which was column purified on silica gel using 5-20% MeOH in DCM to give (2R,5R)-tert-butyl 5-(((tert-butyldiphenylsilyl)oxy)methyl)-2-(hydroxymethyl) morpholine-4-carboxylate (2.6 g, 64%). LCMS: [M+H]⁺: 486.11, Ret. time=1.43 min, LC-MS method E).

(e) (2R,5R)-tert-butyl 5-(((tert-butyldiphenylsilyl)oxy)methyl)-2-(((3-chloro pyrazin-2-yl)methyl)carbamoyl)morpholine-4-carboxylate (2R,5R)-tert-butyl 5-(((tert-butyldiphenylsilyl)oxy)methyl)-2-(hydroxymethyl) morpholine-4-carboxylate (2 g, 4.12 mmol) was dissolved in 100 mL CH₂Cl₂ and cooled to 0° C. TEMPO(0.13 g, 0.82 mmol) was added, followed by (diacetoxyiodo)benzene (2.65 g, 8.24 mmol). The ice bath was removed, and the reaction was allowed to warm to room temperature and stirred overnight. The mixture was diluted with 200 mL ethyl acetate and washed with 10% Na₂S₂O₃, aq. satd. NaHCO₃, and brine. The organic phase was dried with Na₂SO₄, filtered and concentrated to give (2R,5R)-4-(tert-butoxycarbonyl)-5-(((tert-butyl diphenylsilyl)oxy) methyl)morpholine-2-carboxylic acid (1.36 g, 66%). LCMS: [M–H]⁺: 498.23 Ret. time=1.33 min, LC-MS method E). Used as such for the next step without any further purification.

(2R,5R)-4-(tert-butoxycarbonyl)-5-(((tert-butyldiphenylsilyl)oxy)methyl)morpholine-2-carboxylic acid (1.5 g, 3.0 mmol) and (3-chloropyrazin-2-yl)methanamine. HCl salt (0.54 g, 3.0 mmol) were dissolved in DMF 100 mL. To the reaction mixture was added Et$_3$N (0.76 g, 6.0 mmol) followed by slow addition of HATU (1.37 g, 3.6 mmol) at 0° C. The reaction was stirred at rt for 1 day under a stream of nitrogen and then quenched with sat. NaHCO$_3$ (100 mL) and extracted with EtOAc(2×150 mL). The combined organic layer was washed with water (200 mL), brine (200 mL), dried over anhydrous Na$_2$SO$_4$, filtered, and evaporated. The crude residue was subjected to column purification using 20-50% EtOAc/Hex. to give (2R,5R)-tert-butyl 5-(((tert-butyldiphenylsilyl)oxy)methyl)-2-(((3-chloropyrazin-2-yl)methyl)carbamoyl)morpholine-4-carboxylate (0.86 g, 46%). LCMS: [M-Boc+H]$^+$:525.25 Ret. time=2.74 min, LC-MS method E).

(f) (2R,5R)-tert-butyl 5-(((tert-butyldiphenylsilyl)oxy)methyl)-2-(8-chloro imidazo[1,5-a]pyrazin-3-yl)morpholine-4-carboxylate (2R,5R)-tert-butyl 5-(((tert-butyldiphenylsilyl)oxy)methyl)-2-(((3-chloropyrazin-2-yl)methyl)carbamoyl)morpholine-4-carboxylate (1.2 g, 1.92 mmol) was dissolved in 1:1 (25 mL) mixture of acetonitrile:DMF. POCl$_3$ (0.613 mL, 6.72 mmol) was added slowly at 0° C. The reaction mixture was stirred at 40° C. for 45 mins under a stream of nitrogen. The reaction was cooled in an ice bath and poured into AMMONIUM HYDROXIDE (40 mL) solution cooled in an ice bath. The resultant mixture was extracted with EtOAc (3×50 mL), dried over anhydrous Na$_2$SO$_4$, filtered, and evaporated to give crude product, which was column purified (using 20-30% EtOAc in hex) to give (2R,5R)-tert-butyl 5-(((tert-butyldiphenylsilyl)oxy)methyl)-2-(8-chloroimidazo[1,5-a]pyrazin-3-yl)morpholine-4-carboxylate product 1 (0.57 g, 49%). LCMS: [M-Boc+H]$^+$: 507.11; Ret. time=1.40 min, LC-MS method E.

(g) (2R,5R)-tert-butyl 2-(1-bromo-8-chloroimidazo[1,5-a]pyrazin-3-yl)-5-(((tert-butyldiphenylsilyl)oxy)methyl)morpholine-4-carboxylate To (2R,5R)-tert-butyl 5-(((tert-butyldiphenylsilyl)oxy)methyl)-2-(8-chloroimidazo[1,5-a]pyrazin-3-yl)morpholine-4-carboxylate (0.5 g, 0.82 mmol) in 10 mL DMF at 0° C., was added N-BROMOSUCCINIMIDE (0.15 g, 0.82 mmol) and stirred for 1 h at r.t. The reaction was quenched with 1M. Na$_2$S$_2$O$_3$ (aq) solution (20 mL) and extracted with EtOAc (3×25 mL). The organic phase was dried with Na$_2$SO$_4$ and concentrated to dryness to give the product (2R,5R)-tert-butyl 2-(1-bromo-8-chloroimidazo[1,5-a]pyrazin-3-yl)-5-(((tert-butyldiphenylsilyl)oxy)methyl)morpholine-4-carboxylate (0.496 g, 88%).Taken to next step without purification. LCMS: [M-Boc+H]$^+$: 587.04; Ret. time=1.42 min, LC-MS method E).

(h) (2R,5R)-tert-butyl 2-(1-bromo-8-((2,4-dimethoxybenzyl)amino)imidazo[1,5-a]pyrazin-3-yl)-5-(((tert-butyldiphenylsilyl)oxy)methyl)morpholine-4-carboxylate (2R,5R)-tert-butyl 2-(1-bromo-8-chloroimidazo[1,5-a]pyrazin-3-yl)-5-(((tert-butyl diphenylsilyl)oxy)methyl)morpholine-4-carboxylate (0.5 g, 0.729 mmol), (2,4-dimethoxyphenyl)methanamine (0.25 g, 1.46 mmol) and N-ethyl-N-isopropylpropan-2-amine (0.283 g, 2.186 mmol) were dissolved in 20 mL 1,4-dioxane stirred at r.t for overnight. Another 1 equiv. of (2,4-dimethoxyphenyl)methanamine was added and heated to 50° C. and stirred for one more overnight. The reaction mixture was then concentrated under vacuum to give the crude (2R,5R)-tert-butyl 2-(1-bromo-8-((2,4-dimethoxybenzyl)amino)imidazo[1,5-a]pyrazin-3-yl)-5-(((tert-butyldiphenylsilyl)oxy)methyl)morpholine-4-carboxylate(0.516 g, 87%). LCMS: [M+H]$^+$: 818.31, Ret. time=1.28 min, LC-MS method E).

Intermediate 19

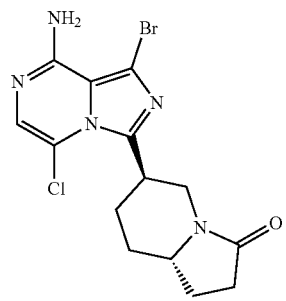 [SMILES: Nc1ncc(Cl)n2c([C@@H]3CC[C@H]4CCC(=O)N4C3)nc(Br)c12]

(6R,8aS)-6-(8-amino-1-bromo-5-chloroimidazo[1,5-a]pyrazin-3-yl)hexahydroindolizin-3 (2H)-one N-chlorosuccinimide (1.906 g, 14.28 mmol) was added to a stirred mixture of (6R,8aS)-6-(8-amino-1-bromoimidazo[1,5-a]pyrazin-3-yl)hexahydroindolizin-3 (2H)-one (Intermediate 6, 5 g, 14.28 mmol) in acetic acid (50 mL) and the mixture was stirred at 80° C. for 1 h, the reaction mixture was concentrated. The residue was purified by column chromatography on silica gel (ISCO, 80 g), eluting with 5% MeOH (2N NH3)/methylene chloride to give (6R,8aS)-6-(8-amino-1-bromo-5-chloroimidazo[1,5-a]pyrazin-3-yl) hexahydroindolizin-3(2H)-one (4.9 g, 12.74 mmol, 89% yield) as a white solid. LCMS [M+H]$^+$: found 386.

Intermediate 20

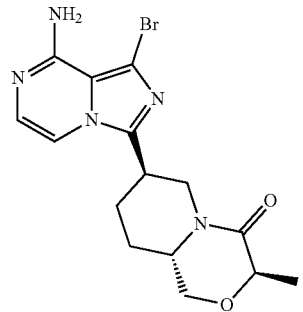 [SMILES: C[C@H]1OC[C@@H]2CC[C@@H](c3nc(Br)c4c(N)nccn34)CN2C1=O]

7-(8-Amino-1-bromo-imidazo[1,5-a]pyrazin-3-yl)-3-methyl-hexahydro-pyrido[2,1-c][1,4]oxazin-4-one (a) (3R,6S)-methyl 6-(((tert-butyldimethylsilyl)oxy)methyl)piperidine-3-carboxylate To a solution of (3R,6S)-methyl 6-(hydroxymethyl)piperidine-3-carboxylate (0.1 g, 0.58 mmol) in DMF (1.0 mL) was added tert-butylchlorodimethylsilane (130.5 mg, 0.87 mmol) and 4H-imidazole (118 mg, 1.73 mmol) at 0° C.

under N₂ atmosphere. The resulting mixture was stirred at 20° C. for 2 hrs. Then the reaction mixture was quenched with H₂O (3 mL) and extracted with ethyl acetate (5 mL×3), the organic layers were washed with brine (10 mL), dried over Na₂SO₄, and evaporated to get the crude product, which was purified with flash chromatography (PE/THF=20-60%) to give (3R,6S)-methyl 6-(((tert-butyldimethylsilyl)oxy)methyl)piperidine-3-carboxylate (90 mg, yield: 54.2%). ¹H NMR (400 MHz, CDCl₃) δ=3.66 (s, 3H), 3.57 (dd, J=3.8, 9.8 Hz, 1H), 3.40 (dd, J=7.7, 9.7 Hz, 1H), 3.36-3.29 (m, 1H), 2.70 (t, J=11.5 Hz, 1H), 2.58 (tdd, J=3.6, 7.3, 10.6 Hz, 1H), 2.45 (tt, J=3.9, 11.7 Hz, 1H), 2.13-2.09 (m, 1H), 1.64-1.56 (m, 1H), 1.55-1.46 (m, 1H), 1.21-1.08 (m, 1H), 0.88 (s, 9H), 0.04 (s, 6H).

(b) (3R,6S)-methyl 6-(((tert-butyldimethylsilyl)oxy)methyl)-1-((R)-2-chloropropanoyl)piperidine-3-carboxylate To a solution of (3R,6S)-methyl 6-(((tert-butyldimethylsilyl)oxy)methyl)piperidine-3-carboxylate (80 mg, 0.278 mmol) in DCM (2 mL) was added triethylamine (0.078 ml, 0.556 mmol) and 2-chloropropionyl chloride (0.03 ml, 0.278 mmol) in DCM (0.5 mL) at 0° C. under N₂ atmosphere. The resulting mixture was stirred at 0° C. for 40 min. The reaction mixture was quenched with methanol (1 mL), and then diluted with DCM (5 mL) and H₂O (5 mL). The organic layer was washed with brine (5 mL), dried over Na₂SO₄, evaporated, and purified by flash chromatography (PE/EA=20~50%) to give (3R,6S)-methyl 6-(((tert-butyldimethylsilyl)oxy)methyl)-1-((R)-2-chloropropanoyl)piperidine-3-carboxylate (60 mg, yield: 57%). ¹H NMR (400 MHz, CDCl₃) δ=5.04-4.90 (m, 1H), 4.75 (q, J=6.4 Hz, 1H), 4.51 (br. s, 1H), 4.23 (d, J=14.3 Hz, 1H), 3.89-3.76 (m, 1H), 3.68 (s, 3H), 3.63 (dd, J=4.6, 10.2 Hz, 1H), 3.55-3.49 (m, 1H), 3.42 (dd, J=4.1, 14.4 Hz, 1H), 2.81 (dd, J=4.0, 14.1 Hz, 1H), 2.68 (d, J=3.8 Hz, 1H), 2.15-2.04 (m, 1H), 2.03-1.95 (m, 1H), 1.89-1.80 (m, 1H), 1.63 (dd, J=6.4, 17.2 Hz, 4H), 1.51 (d, J=13.6 Hz, 1H), 0.86 (d, J=12.0 Hz, 9H), 0.07-0.02 (m, 6H).

(c) (3R,6S)-methyl 1-((R)-2-chloropropanoyl)-6-(hydroxymethyl)piperidine-3-carboxylate To a solution of (3R,6S)-methyl 6-(((tert-butyldimethylsilyl)oxy)methyl)-1-((R)-2-chloropropanoyl)piperidine-3-carboxylate (100 mg, 0.26 mmol) in THF (2 mL) was added tetrabutylammonium fluoride (83.01 mg, 0.32 mmol) under N₂ atmosphere. The resulting mixture was stirred for 60 min. H₂O (2 mL) was added, and the mixture was extracted with ethyl acetate (5 mL×2), the organic layer was washed with brine (5 mL), dried over Na₂SO₄, evaporated and purified by flash chromatography (PE/THF=20~60%) to get (3R,6S)-methyl 1-((R)-2-chloropropanoyl)-6-(hydroxymethyl)piperidine-3-carboxylate (40 mg, yield: 57.7%). ¹H NMR (400 MHz, CDCl₃) δ=5.00 (q, J=6.3 Hz, 1H), 4.85-4.56 (m, 1H), 4.23 (d, J=14.6 Hz, 1H), 3.99-3.78 (m, 1H), 3.76-3.54 (m, 4H), 3.40 (dd, J=3.9, 14.7 Hz, 1H), 2.72 (br. s, 1H), 2.43-2.23 (m, 1H), 2.08-1.99 (m, 1H), 1.98-1.82 (m, 1H), 1.68 (d, J=6.5 Hz, 4H).

(d) (3S,7R,9aS)-methyl 3-methyl-4-oxooctahydropyrido[2,1-c][1,4]oxazine-7-carboxylate To a solution of (3R,6S)-methyl 1-((R)-2-chloropropanoyl)-6-(hydroxymethyl)piperidine-3-carboxylate (260 mg, 0.99 mmol) in anhydrous THF (13 mL) was added NaH (47.3 mg, 1.18 mmol) at 0° C. under N₂ atmosphere. The resulting mixture was stirred at 20° C. for 2 hrs. The reaction mixture was quenched with sat. aq. NaHCO₃ (5 mL), extracted with ethyl acetate (10 mL×3), the organic layer was washed with brine (10 mL), dried over Na₂SO₄, evaporated, and purified by flash chromatography (PE/THF=10~60%) to give (3S,7R,9aS)-methyl 3-methyl-4-oxooctahydropyrido[2,1-c][1,4]oxazine-7-carboxylate (160 mg, yield: 71.4%). 1H NMR (400 MHz, CDCl₃) δ=4.90 (ddd, J=2.0, 4.1, 13.0 Hz, 1H), 4.18 (q, J=6.9 Hz, 1H), 3.91 (dd, J=4.1, 12.2 Hz, 1H), 3.74 (dd, J=3.0, 12.0 Hz, 1H), 3.69 (s, 3H), 3.30-3.23 (m, 1H), 2.67-2.55 (m, 1H), 2.46 (tdd, J=3.9, 7.7, 15.6 Hz, 1H), 2.26-2.19 (m, 1H), 1.77-1.65 (m, 3H), 1.46 (d, J=6.8 Hz, 3H).

(e) (3S,7R,9aS)-3-methyl-4-oxooctahydropyrido[2,1-c][1,4]oxazine-7-carboxylic acid To a solution of (3S,7R,9aS)-methyl 3-methyl-4-oxooctahydropyrido[2,1-c][1,4]oxazine-7-carboxylate (170 mg, 0.75 mmol) in THF (3.4 mL) was added a solution of LiOH.H2O (63 mg, 1.5 mmol) in H2O (0.85 mL) under N2 atmosphere. The resulting mixture was stirred at 20° C. for 12 hrs. Then the mixture was evaporated, and dissolved with H2O (2 mL), acidified with 1M of HCl to pH 3-4. Then the mixture was separated by prep-HPLC to afford (3S,7R,9aS)-3-methyl-4-oxooctahydropyrido[2,1-c][1,4]oxazine-7-carboxylic acid(90 mg, yield: 56.4%). ¹H NMR (400 MHz, METHANOL-d₄) δ=4.78 (ddd, J=1.9, 4.1, 13.1 Hz, 1H), 4.16 (q, J=6.8 Hz, 1H), 3.93 (dd, J=4.3, 12.3 Hz, 1H), 3.75 (dd, J=2.8, 12.3 Hz, 1H), 3.38-3.32 (m, 1H), 2.66 (t, J=12.4 Hz, 1H), 2.44-2.32 (m, 1H), 2.27-2.16 (m, 1H), 1.80-1.65 (m, 3H), 1.39 (d, J=6.8 Hz, 3H).

(f) (3S,7R,9aS)-N-((3-chloropyrazin-2-yl)methyl)-3-methyl-4-oxooctahydropyrido[2,1-c][1,4]oxazine-7-carboxamide To a solution of (3S,7R,9aS)-3-methyl-4-oxooctahydropyrido[2,1-c][1,4]oxazine-7-carboxylic acid (55 mg, 0.26 mmol) in anhydrous DCM (1 mL) was added oxalyl dichloride (0.068 mL, 0.77 mmol) in DCM (0.5 mL) at 0° C. under N2 atmosphere, and followed by 1 drop of DMF. The resulting mixture was stirred at 0° C. for 2 hrs. The reaction mixture was evaporated, dissolved with DCM (0.5 mL), and added to a solution of (3-chloropyrazin-2-yl)methanamine hydrochloride (56.1 mg, 0.31 mmol), and triethylamine (0.079 mL, 0.57 mmol) in DCM (1 mL), at 0° C. under N2 atmosphere, and the mixture was stirred for 12 hrs at 15° C. Then the mixture was diluted with DCM (5 mL), and H2O (5 mL). The organic layer was washed with brine (5 mL), dried over Na2SO4, evaporated to get the crude product, which was then purified by prep-TLC (PE/THF=1:1) to give (3S,7R,9aS)-N-((3-chloropyrazin-2-yl)methyl)-3-methyl-4-oxooctahydropyrido[2,1-c][1,4]oxazine-7-carboxamide (55 mg, yield: 62.9%). ¹H NMR (400 MHz, CDCl₃) δ=8.42 (d, J=2.5 Hz, 1H), 8.29 (d, J=2.5 Hz, 1H), 7.17 (br. s, 1H), 4.76-4.57 (m, 2H), 4.16 (q, J=6.9 Hz, 1H), 3.92 (dd, J=4.1, 12.2 Hz, 1H), 3.74 (dd, J=2.5, 12.0 Hz, 1H), 3.37-3.25 (m, 1H), 2.73 (t, J=12.3 Hz, 1H), 2.42 (tt, J=4.0, 11.8 Hz, 1H), 2.18-2.03 (m, 2H), 1.99-1.84 (m, 1H), 1.79-1.68 (m, 2H), 1.44 (d, J=7.0 Hz, 3H).

(g) (3R,7R,9aS)-7-(8-chloroimidazo[1,5-a]pyrazin-3-yl)-3-methylhexahydropyrido[2,1-c][1,4]oxazin-4(3H)-one To a solution of (3S,7R,9aS)-N-((3-chloropyrazin-2-yl)methyl)-3-methyl-4-oxooctahydropyrido[2,1-c][1,4]oxazine-7-carboxamide(180 mg, 0.53 mmol) in DCM (2.5 mL) was added DMF (6.6 mg, 0.09 mmol), pyridine (0.43 mL, 5.31 mmol), and followed by POCl3 (0.25 mL, 2.66 mmol) in DCM (0.5 mL) at 0° C., and stirred at 0° C. for 5 hrs. Then the mixture was poured into an ice-aq. NaHCO3 (15 mL), extracted with ethyl acetate (5 mL*3), the organic layers were washed with brine (5 mL), dried over Na2SO4, evaporated to get the crude product, which was then purified by prep-TLC (PE/THF=1:1) to afford (3R,7R,9aS)-7-(8-chloroimidazo[1,5-a]pyrazin-3-yl)-3-methylhexahydropyrido[2,1-c][1,4]oxazin-4(3H)-one(120 mg, yield: 70.4%). ¹H NMR (400 MHz, CHLOROFORM-d) δ=7.80 (s, 1H), 7.78 (d, J=5.0 Hz, 1H), 7.37 (d, J=5.0 Hz, 1H), 4.89 (dd, J=3.5, 13.1 Hz, 1H), 4.22 (q, J=6.8 Hz, 1H), 4.03 (dd, J=4.0, 12.0 Hz, 1H), 3.83 (dd, J=2.3, 12.3 Hz, 1H), 3.50-3.43 (m, 1H), 3.15-3.06 (m, 1H), 2.86-2.75 (m, 1H), 2.33-2.25 (m, 2H), 1.99-1.86 (m, 2H), 1.52 (d, J=6.8 Hz, 3H).

(h) (3R,7R,9aS)-7-(1-bromo-8-chloroimidazo[1,5-a]pyrazin-3-yl)-3-methylhexahydropyrido[2,1-c][1,4]oxazin-4(3H)-one To a solution of (3R,7R,9aS)-7-(8-chloroimidazo[1,5-a]pyrazin-3-yl)-3-methylhexahydropyrido[2,1-c][1,4]oxazin-4(3H)-one (120 mg, 0.374 mmol) in anhydrous DMF (5 mL) was added NBS (73.2 mg, 0.411 mmol) under N2 atmosphere, and stirred at 10° C. for 90 min. LCMS showed that the reaction was complete, then the mixture was poured into an ice-water (10 mL), and extracted with EA (10 mL×3), the organic layers were then washed with H2O (10 mL×8), brine (10 mL), dried over Na2SO4, and evaporated to get (3R,7R,9aS)-7-(1-bromo-8-chloroimidazo[1,5-a]pyrazin-3-yl)-3-methylhexahydropyrido[2,1-c][1,4]oxazin-4(3H)-one (360 mg, yield: 86%), which was used for next step directly without purification. ¹H NMR (400 MHz, CHLOROFORM-d) δ=7.76 (d, J=5.0 Hz, 1H), 7.36 (d, J=5.0 Hz, 1H), 4.89-4.82 (m, 1H), 4.22 (q, J=6.7 Hz, 1H), 4.03 (dd, J=3.9, 12.2 Hz, 1H), 3.83 (dd, J=2.1, 12.2 Hz, 1H), 3.48-3.40 (m, 1H), 3.13-3.01 (m, 1H), 2.84-2.74 (m, 1H), 2.37-2.20 (m, 2H), 2.00-1.84 (m, 2H), 1.52 (s, 3H).

(i) (3R,7R,9aS)-7-(8-amino-1-bromoimidazo[1,5-a]pyrazin-3-yl)-3-methylhexahydropyrido[2,1-c][1,4]oxazin-4(3H)-one A mixture of (3R,7R,9aS)-7-(1-bromo-8-chloroimidazo[1,5-a]pyrazin-3-yl)-3-methylhexahydropyrido[2,1-c][1,4]oxazin-4(3H)-one (120 mg, 0.3 mmol) in i-PrOH/NH4OH (3 mL, 1:1) was heated in a 30 mL of sealed tube at 100° C. for 12 hrs. LCMS showed that the reaction was complete, then the mixture was evaporated to get the crude product, which was then dissolved with H2O (10 mL), extracted with DCM/i-PrOH (10 mL×3, 3:1). The organic layer was washed with brine (10 mL), dried over Na2SO4, and evaporated to get (3R,7R,9aS)-7-(8-amino-1-bromoimidazo[1,5-a]pyrazin-3-yl)-3-methylhexahydropyrido[2,1-c][1,4]oxazin-4(3H)-one (110 mg, yield: 96%). 1H NMR (400 MHz, DMSO-d6) δ=7.64 (d, J=5.3 Hz, 1H), 7.03 (d, J=5.0 Hz, 1H), 6.69 (br. s, 2H), 4.57 (td, J=1.9, 12.8 Hz, 1H), 4.15 (q, J=6.9 Hz, 1H), 3.92 (dd, J=4.1, 12.2 Hz, 1H), 3.74 (dd, J=2.5, 12.0 Hz, 1H), 3.48 (d, J=5.8 Hz, 1H), 3.16 (tdd, J=3.9, 7.6, 11.2 Hz, 1H), 2.83 (t, J=12.2 Hz, 1H), 2.15-2.03 (m, 1H), 1.84-1.71 (m, 3H), 1.34 (d, J=7.0 Hz, 3H).

Intermediate 21

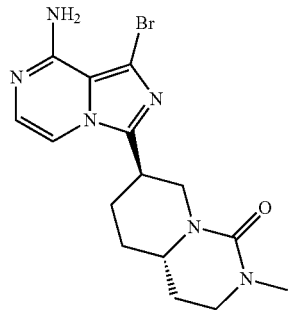 [SMILES: CN1CC[C@@H]2CC[C@@H](c3nc(Br)c4c(N)nccn34)CN2C1=O]

Trans-7-(8-amino-1-bromoimidazo[1,5-a]pyrazin-3-yl)-2-methloctahydro-1H-pyrido[1,2-c]pyrimidin-1-one (a) methyl 6-vinylnicotinate To a solution of methyl 6-bromonicotinate (10 g, 46.5 mmol) in i-PrOH (100 mL) was added potassium vinyltrifluoroborate (12.4 g, 93 mmol), Et3N (14.1 g, 140 mmol), and Pd(dppf)Cl2.DCM (1.1 g). The mixture was stirred at 100° C. for 2 h under nitrogen. The reaction was complete detected by TLC. The mixture was concentrated and the residue was purified by column chromatography on silica gel eluted with PE/EA=15/1 to give methyl 6-vinylnicotinate (7.2 g, 95%). ¹H-NMR (CDCl3, 400 MHz) δ 3.94 (s, 3H), 5.55 (d, J=12.0 Hz, 1 H), 6.36 (d, J=20.0 Hz, 1 H), 6.85 (dd, J=17.41, 10.76 Hz, 1 H), 7.39 (d, J=8.22 Hz, 1 H), 8.23 (dd, J=8.22, 2.35 Hz, 1 H), 9.15 (d, J=1.56 Hz, 1 H).

(b) methyl 6-(2-((2,4-dimethoxybenzyl)amino)ethyl)nicotinate

To a solution of methyl 6-vinylnicotinate (7.2 g, 44.2 mmol) in MeOH (50 mL) was added (2,4-dimethoxyphenyl)methanamine (14.7 g, 88.3 mmol) and AcOH (50 mL). The mixture was heated to reflux overnight. The mixture was concentrated, basified with aq. NaHCO3 and extracted with EA. The organic layer was dried and concentrated. The residue was purified by column chromatography on silica gel eluted with PE/EA=3/1 to give methyl 6-(2-((2,4-dimethoxybenzyl)amino)ethyl)nicotinate (4 g, 27%).

(c) methyl 6-(2-((2,4-dimethoxybenzyl)amino)ethyl)piperidine-3-carboxylate

To a solution of methyl 6-(2-((2,4-dimethoxybenzyl)amino)ethyl)nicotinate (3.6 g, 10.9 mmol) in AcOH (80 mL) was added NaBH3CN (2.74 g, 43.6 mmol). The mixture was stirred at room temperature for 1 h, then heated to 70° C. and stirred overnight. The solvent was evaporated and the residue was dissolved in MeOH. The solution was alkalified with NaHCO3 solution and purified by column chromatography on silica gel eluted with DCM/MeOH=20/1 to give methyl 6-(2-((2,4-dimethoxybenzyl)amino)ethyl)piperidine-3-carboxylate (crude 4.1 g).

MS-ESI(m/z): 337 (M+1)+ (LC-MS method C; Ret. time: 0.847 min).

(d) methyl 2-(2,4-dimethoxybenzyl)-1-oxoocta-hydro-1H-pyrido[1,2-c]pyrimidine-7-carboxylate To a solution of methyl 6-(2-((2,4-dimethoxybenzyl)amino)ethyl)piperidine-3-carboxylate (4 g, 11.9 mmol) in THF (130 mL) was added CDI (3.8 g, 23.8 mmol). The mixture was stirred at 70° C. for 6 h. The mixture was concentrated in vacuo and the residue was purified by column chromatography on silica gel eluted with DCM/THF=30/1 to give trans-(1 g, yield 45%) and cis-(700 mg, yield 32%)methyl 2-(2,4-dimethoxybenzyl)-1-oxoocta-hydro-1H-pyrido[1,2-c]pyrimidine-7-carboxylate.
For trans isomers:
$^1$H NMR (CD$_3$OD, 400 MHz) δ 1.25-1.37 (m, 1 H), 1.50-1.60 (m, 1 H), 1.65-1.77 (m, 2 H), 1.96-2.15 (m, 2 H), 2.40-2.51 (m, 1 H), 2.60 (t, J=12.0 Hz, 1 H), 3.11-3.25 (m, 3 H), 3.67 (s, 3 H), 3.79 (s, 6 H), 4.40-4.56 (m, 2 H), 4.76-4.86 (m, 1 H), 6.38-6.51 (m, 2 H), 7.20 (d, J=8.0 Hz, 1 H).
For cis isomers:
$^1$H NMR (CD$_3$OD, 400 MHz) δ 1.41-1.51 (m, 2 H), 1.58-1.71 (m, 2 H), 1.85-1.94 (m, 1 H), 2.12-2.19 (m, 1 H), 2.56-2.62 (m, 1 H), 2.69-2.75 (m, 1 H), 3.03-3.18 (m, 3 H), 3.62 (s, 3 H), 3.72 (d, J=2.74 Hz, 6 H), 4.32-4.50 (m, 2 H), 4.89-4.95 (m, 1 H), 6.34-6.41 (m, 2 H), 7.12 (d, J=8.0 Hz, 1 H).

(e) trans-methyl 1-oxooctahydro-1H-pyrido[1,2-c]pyrimidine-7-carboxylate

A solution of trans-methyl 2-(2,4-dimethoxybenzyl)-1-oxooctahydro-1H-pyrido[1,2-c]pyrimidine-7-carboxylate (600 mg, 1.6 mmol) in TFA (4 mL) was stirred at 90° C. for 1 h. The solvent was evaporated and the residue was used in next step directly. MS-ESI(m/z): 213 (M+1)+ (LC-MS method C; Ret. time: 0.912 min).

(f) trans-methyl 2-methyl-1-oxooctahydro-1H-pyrido[1,2-c]pyrimidine-7-carboxylate A solution of trans-methyl 1-oxooctahydro-1H-pyrido[1,2-c]pyrimidine-7-carboxylate (1.6 mmol) in THF (30 mL) was cooled to 0-5° C. and NaH (199 mg, 5.0 mmol) was added portionwise. The mixture was stirred at room temperature for 30 min, and then MeI (706 mg, 5.0 mmol) was added. The reaction mixture was stirred at room temperature overnight. The reaction was quenched with H$_2$O (0.5 mL) and the volatiles were evaporated. The residue was used in next step directly.

(g) trans-2-methyl-1-oxooctahydro-1H-pyrido[1,2-c]pyrimidine-7-carboxylic acid To a solution of trans-methyl 2-methyl-1-oxooctahydro-1H-pyrido[1,2-c]pyrimidine-7-carboxylate (1.6 mmol) in MeOH/THF/H$_2$O (10 mL/10 mL/3 mL) was added LiOH*H$_2$O (83 mg, 2.0 mmol). The mixture was stirred at room temperature for 2 h. The volatiles were evaporated and the residue was used in next step directly. MS-ESI(m/z): 213 (M+1)$^+$ (LC-MS method C; Ret. time: 0.917 min).

(h) trans-N-((3-chloropyrazin-2-yl)methyl)-2-methyl-1-oxooctahydro-1H-pyrido[1,2-c]pyramidine-7-carboxamide To a solution of trans-2-methyl-1-oxooctahydro-1H-pyrido[1,2-c]pyrimidine-7-carboxylic acid (1.6 mmol) in DCM (20 mL) was added (3-chloropyrazin-2-yl) methanamine hydrochloride (356 mg, 2.0 mmol), EDC (477 mg, 2.5 mmol), HOBT (336 mg, 2.5 mmol) and TEA (670 mg, 6.6 mmol), and the resulting mixture was stirred at 50° C. overnight. The volatiles were evaporated and the residue was purified by column chromatography on silica gel eluted with DCM/THF=3/1 to give trans-N-((3-chloropyrazin-2-yl)methyl)-2-methyl-1-oxooctahydro-1H-pyrido[1,2-c]pyramidine-7-carboxamide (90 mg, four steps: 17%). $^1$H NMR (CDCl3, 400 MHz) δ 1.24-1.34 (m, 1H), 1.67-1.76 (m, 3 H), 1.92-2.08 (m, 3 H), 2.29-2.38 (m, 1 H), 2.64 (t, J=12.0 Hz, 1 H), 2.87 (s, 3 H), 3.12-3.21 (m, 3 H), 4.59-4.69 (m, 3 H), 6.89-7.01 (m, 1 H), 8.24 (d, J=4.0 Hz, 1 H), 8.37 (d, J=4.0 Hz, 1 H).

(i) trans-7-(8-chloroimidazo[1,5-a]pyrazin-3-yl)-2-methloctahydro-1H-pyrido[1,2-c]pyrimidin-1-one To a solution of trans-N-((3-chloropyrazin-2-yl)methyl)-2-methyl-1-oxooctahydro-1H-pyrido[1,2-c]pyramidine-7-carboxamide (100 mg, 0.3 mmol) in MeCN (20 mL) was added PCl$_5$ (185 mg, 0.9 mmol). The mixture was stirred at 60° C. for 1 h, then another batch of PCl$_5$ (185 mg, 0.9 mmol) was added in portions during a period of 1 h, and the reaction mixture was stirred at 60° C. for further 20 min. The reaction was complete detected by LCMS. After cooling, the reaction solution was treated with DCM and aq. NaHCO$_3$. The organic layer was separated, dried and concentrated. The residue was purified by column chromatography on silica gel eluted with DCM/THF=5/1 to give trans-7-(8-chloroimidazo[1,5-a]pyrazin-3-yl)-2-methyl octahydro-1H-pyrido[1,2-c]pyrimidin-1-one (75 mg, 79%).MS-ESI(m/z): 320 (M+1) (LC-MS method C; Ret. time: 1.073 min).

(j) trans-7-(1-bromo-8-chloroimidazo[1,5-a]pyrazin-3-yl)-2-methyloctahydro-1H-pyrido[1,2-c]pyrimidin-1-one To a solution of trans-7-(8-chloroimidazo[1,5-a]pyrazin-3-yl)-2-methyloctahydro-1H-pyrido[1,2-c]pyrimidin-1-one (75 mg, 0.24 mmol) in DMF (1.5 mL) was added a solution of NBS (46 mg, 0.26 mmol) in DMF (0.5 mL). The mixture was stirred at room temperature for 1 h. The reaction mixture was treated with EA and water, the organic layer was separated, dried and concentrated. The residue was purified by column chromatography on silica gel eluted with DCM/THF=10/1 to give trans-7-(1-bromo-8-chloroimidazo[1,5-a]pyrazin-3-yl)-2-methylocta hydro-1H-pyrido[1,2-c]pyrimidin-1-one (75 mg, 95%). MS-ESI(m/z): 400 (M+1)$^+$ (LC-MS method C; Ret. time: 1.205 min).

(k) trans-7-(8-amino-1-bromoimidazo[1,5-a]pyrazin-3-yl)-2-methyloctahydro-1H-pyrido[1,2-c]pyrimidin-1-one A solution of trans-7-(1-bromo-8-chloroimidazo[1,5-a]pyrazin-3-yl)-2-methyloctahydro-1H-pyrido[1,2-c]pyrimidin-1-one (75 mg, 0.2 mmol) in NH$_3$/i-PrOH (4 mL) was added in 30 mL seal tube, and the mixture was stirred at 100° C. overnight. The mixture was concentrated and the residue was purified by column chromatography on silica gel eluted with DCM/MeOH=30/1 to give the title compound (55 mg, 73%).
MS-ESI (m/z): 379 (M+1)$^+$ (LC-MS method C; Ret. time: 0.934 min).
Same procedure started from cis-methyl-2-(2,4-dimethoxybenzyl)-1-oxooctahydro-1H-pyrido[1,2-c]pyrimidine- 7-carboxylate afforded cis-7-(8-amino-1-bromoimidazo[1,5-a]pyrazin-3-yl)-2-methyloctahydro-1H-pyrido[1,2-c]pyrimidin-1-one. MS-ESI (m/z): 379 (M+1)+ (LC-MS method C; Ret. time: 0.954 min).

Intermediate 22

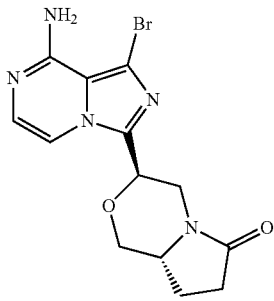 [SMILES: Nc1nccn2c([C@H]3CN4C(=O)CC[C@@H]4CO3)nc(Br)c12]

3-(8-Amino-1-bromo-imidazo[1,5-a]pyrazin-3-yl)-hexahydro-pyrrolo[2,1-c][1,4]oxazin-6-one (a) (R)-5-(((tert-butyldimethylsilyl)oxy)methyl)pyrrolidin-2-one To a solution of (R)-5-(((tert-butyldimethylsilyl)oxy)methyl)pyrrolidin-2-one (25 g, 217.14 mmol) in anhydrous DMF (100 mL) was added TBSCl (49.09 g, 325.72 mmol) and 4H-imidazole (44.35 g, 651.43 mmol). The mixture was stirred at 25° C. for 3 hours. The mixture was quenched by the addition of water (100 mL), the mixture was then extracted with EtOAc (200 mL×4). The combined organic layers were washed with brine (100 mL×5), dried over sodium sulfate, filtered and concentrated to afford the crude product, which was purified on silica gel column chromatograph (THF/PE=5%~30%) to give (R)-5-(((tert-butyldimethylsilyl)oxy)methyl)pyrrolidin-2-one (43 g, yield 86.33%) as a colorless oil. $^1$H NMR (400 MHz, CHLOROFORM-d)=5.80 (s, 1H), 3.76-3.64 (m, 1H), 3.61 (d, J=2.8 Hz, 1H), 3.46-3.41 (m, 1H), 2.37-2.32 (m, 2H), 2.20-2.16 (m, 1H), 1.74-1.70 (m, 1H), 0.88 (s, 9H), 0.06 (s, 6H); (ESI): M/Z (M+1): 230.1 (LC-MS method C; RetTime: 1.466).

(b) (R)-5-(((tert-butyldimethylsilyl)oxy)methyl)-1-((R)-oxiran-2-ylmethyl)pyrrolidin-2-one To a solution of (R)-5-(((tert-butyldimethylsilyl)oxy)methyl)pyrrolidin-2-one (16 g, 69.75 mmol) in anhydrous THF (500 mL) was added NaH (60%, 3.07 g, 76.72 mmol) at 0° C. portionwise. The mixture was stirred at 25° C. for 1 hour, then (S)-2-(chloromethyl)oxirane (7.74 g, 83.70 mmol) was added and the mixture was heated to 80 C stirred for another 10 hours. The mixture was quenched by the addition of sat. NH$_4$Cl (200 mL) at 0° C., the mixture was then extracted with EtOAc (100 mL×4), the combined organic layers were washed with brine (100 mL), dried over sodium sulfate, filtered and concentrated to afford the crude product, which was purified on silica gel column chromatograph (THF/PE=5%~35%) to give (R)-5-(((tert-butyldimethylsilyl)oxy)methyl)-1-((R)-oxiran-2-ylmethyl)pyrrolidin-2-one (4 g, yield 20%) as a colourless oil. $^1$H NMR (400 MHz, CHLOROFORM-d)=4.19 (dd, J=2.8, 14.8, 1H), 3.80-3.77 (m, 2H), 3.60-3.56 (m, 1H), 3.25-3.13 (m, 1H), 3.08-3.00 (m, 1H), 2.77 (d, J=8.8 Hz, 1H), 2.74-2.65 (m, 1H), 2.49-2.41 (m, 1H), 2.40-2.26 (m, 1H), 2.23-2.08 (m, 1H), 1.93-1.82 (m, 1H), 0.87 (s, 9H), 0.04 (s, 6H); (ESI): M/Z (M+1): 286.1 (LC-MS method C; R.T.: 0.804).

(c) (R)-5-(hydroxymethyl)-1-((R)-oxiran-2-ylmethyl)pyrrolidin-2-one

To a solution of (R)-5-(((tert-butyldimethylsilyl)oxy)methyl)-1-((R)-oxiran-2-ylmethyl)pyrrolidin-2-one (2.7 g, 9.46 mmol) in anhydrous THF (30 mL), TBAF (2.97 g, 11.35 mmol) was added portionwise. The reaction mixture was stirred at 25° C. for 2 hrs. The reaction was quenched by water (3 mL), then the mixture was concentrated to afford the crude product, which was purified on silica gel column chromatograph (THF/PE=20%~100%) to give (R)-5-(hydroxymethyl)-1-((R)-oxiran-2-ylmethyl)pyrrolidin-2-one (1 g, yield 61.8%) as a yellow oil. $^1$H NMR (400 MHz, Methanol-d4)=3.99 (dd, J=2.8, 14.8, 1H), 3.90-3.82 (m, 1H), 3.80-3.74 (m, 1H), 3.57-3.53 (m, 1H), 3.07-3.04 (m, 1H), 2.95-2.86 (m, 1H), 2.77-2.75 (m, 1H), 2.58-2.56 (m, 1H), 2.45-2.41 (m, 1H), 2.36-2.30 (m, 1H), 2.22-2.13 (m, 1H), 1.99-1.92 (m, 1H); (ESI): M/Z (M+1): 172.1 (LC-MS method C; R.T.: 0.201).

(d) (3R,8aR)-3-(hydroxymethyl)tetrahydro-1H-pyrrolo[2,1-c][1,4]oxazin-6(7H)-one

Na (1.93 g, 84.12 mmol) was added to EtOH (30 mL) and the mixture was stirred at 25° C. for 40 mins, then a solution of (R)-5-(hydroxymethyl)-1-((R)-oxiran-2-ylmethyl)pyrrolidin-2-one (2.4 g, 8.18 mmol) in anhydrous EtOH (30 mL) was added at 0° C. The mixture was stirred at 25° C. for 16 hours. The mixture was adjusted topH=7 with 1M HCl and concentrated to afford a residue, which was diluted with DCM (100 mL) and stirred for 20 mins. The mixture was filtered and the filtrate was concentrated to give crude (3R,8aR)-3-(hydroxymethyl)tetrahydro-1H-pyrrolo[2,1-c][1,4]oxazin-6(7H)-one (2.4 g, 30% of (3R,8aR)-3-(hydroxymethyl)tetrahydro-1H-pyrrolo[2,1-c][1,4]oxazin-6(7H)-one, yield 30%) as a yellow oil, which was immediately used in the next step. (ESI): M/Z (M+1): 172.1 (LC-MS method C; R.T.: 0.100).

(e) (3R,8aR)-6-oxohexahydro-1H-pyrrolo[2,1-c][1,4]oxazine-3-carboxylic acid

To a solution of (3R,8aR)-3-(hydroxymethyl)tetrahydro-1H-pyrrolo[2,1-c][1,4]oxazin-6(7H)-one (1.1 g, 6.43 mmol) in acetone (50 mL) and Sat.NaHCO$_3$ (15 mL) was added TEMPO (50.2 mg, 0.321 mmol) and NaBr (198.3 mg, 1.93 mol). Then 1,3,5-trichloro-1,3,5-triazinane-2,4,6-trione (3 g, 12.85 mmol) was added portionwise at 0° C. The reaction mixture was stirred at 25° C. for 12 hrs. The reaction was quenched by i-PrOH (20 mL) and stirred for another 60 mins. The mixture was filtered and filtrate was adjust basic to PH=8 with sat.NaHCO3. It was extracted with DCM (100 mL), the aqueous layer was adjust acid to PH=4 with 2M HCl. It was extracted with DCM/i-PrOH (3:1, 100 mL×4), the combined organic layers were washed with brine (30 mL), dried over sodium sulfate, filtered and concentrated to give (3R,8aR)-6-oxohexahydro-1H-pyrrolo[2,1-c][1,4]oxazine-3-carboxylic acid (500 mg, yield 46%) as a yellow oil, which was immediately used in the next step. (ESI): M/Z (M+1): 186.1 (LC-MS method C; R.T.: 0.205)

(f) (3R,8aR)-N-((3-chloropyrazin-2-yl)methyl)-6-oxohexahydro-1H-pyrrolo[2,1-c][1,4]oxazine-3-carboxamide To a solution of (3R,8aR)-6-oxohexahydro-1H-pyrrolo[2,1-c][1,4]oxazine-3-carboxylic acid (600 mg, 3.24 mmoL) in DCM (20 mL) was added isobutyl carbonochloridate (531 mg, 3.56 mmol) and TEA (0.53 mL, 3.78 mmol), the mixture was stirred at 0° C. for 1 hour, then (3-chloropyrazin-2-yl)methanamine hydrochloride (641 mg, 3.56 mmol) and TEA (1.1 mL, 7.56 mmol) was added at 0° C. The mixture was stirred at 25° C. for 3 hours. To the mixture was added water (20 mL) and DCM (50 mL), the mixture was then separated and the aqueous layer was extracted with DCM (50 mL×3), the combined organic layers were washed with brine (20 mL), dried over sodium sulfate, filtered and concentrated to afford the crude product, which was purified on silica gel column chromatograph (MeOH/DCM=0~10%) to give (3R,8aR)-N-((3-chloropyrazin-2-yl)methyl)-6-oxohexahydro-1H-pyrrolo[2,1-c][1,4]oxazine-3-carboxamide (300 mg, yield 29.8%) as a sheer oil. ¹H NMR (400 MHz, CHLOROFORM-d) d=8.50 (d, J=2.5 Hz, 1H), 8.36 (d, J=2.0 Hz, 1H), 7.78 (br. s, 1H), 4.74 (d, J=5.0 Hz, 2H), 4.52 (dd, J=3.1, 13.4 Hz, 1H), 4.23 (dd, J=3.8, 11.3 Hz, 1H), 3.97 (dd, J=3.0, 11.0 Hz, 1H), 3.75 (dtd, J=4.0, 7.3, 10.8 Hz, 1H), 3.30 (t, J=11.0 Hz, 1H), 2.86 (t, J=12.3 Hz, 1H), 2.60-2.43 (m, 2H), 2.29-2.13 (m, 1H), 1.70-1.54 (m, 1H)

(g) (3R,8aR)-3-(8-chloroimidazo[1,5-a]pyrazin-3-yl)tetrahydro-1H-pyrrolo[2,1-c][1,4]oxazin-6(7H)-one To a solution of (3R,8aR)-N-((3-chloropyrazin-2-yl)methyl)-6-oxohexahydro-1H-pyrrolo[2,1-c][1,4]oxazine-3-carboxamide (600 mg, 1.93 mmol) in anhydrous MeCN (15 mL) was added PCl₅ (2 g, 9.65 mmol) at 0° C. The mixture was stirred at 15° C. for 15 hours. The mixture was poured into ice-water, adjust basic with Sat. NaHCO₃, then separated and the aqueous layer was extracted with DCM (50 mL×3), the combined organic layers were washed with brine (20 mL), dried over sodium sulfate, filtered and concentrated to afford the crude product, which was purified on silica gel column chromatography (MeOH/DCM=0~10%) to give (3R,8aR)-3-(8-chloroimidazo[1,5-a]pyrazin-3-yl)tetrahydro-1H-pyrrolo[2,1-c][1,4]oxazin-6(7H)-one (300 mg, yield 53%) as a yellow solid. (ESI): M/Z (M+1): 293.0 (LC-MS method C; R.T.: 0.585)

(h) (3R,8aR)-3-(1-bromo-8-chloroimidazo[1,5-a]pyrazin-3-yl)tetrahydro-1H-pyrrolo[2,1-c][1,4]oxazin-6(7H)-one To a solution of (3R,8aR)-3-(8-chloroimidazo[1,5-a]pyrazin-3-yl)tetrahydro-1H-pyrrolo[2,1-c][1,4]oxazin-6(7H)-one (300 mg, 1.02 mmol) in anhydrous MeCN (10 mL) was added 1-bromopyrrolidine-2,5-dione (219 mg, 1.23 mmol). The mixture was stirred at 25° C. for 1 hour. The mixture was quenched by the addition of water (10 mL) at 0° C., the mixture was then extracted with DCM/i-PrOH (3:1, 30 mL×4), the combined organic layers were washed with brine (10 mL), dried over sodium sulfate, filtered and concentrated to give (3R,8aR)-3-(1-bromo-8-chloroimidazo[1,5-a]pyrazin-3-yl)tetrahydro-1H-pyrrolo[2,1-c][1,4]oxazin-6(7H)-one (320 mg, yield 84%) as a yellow solid, which was immediately used in the next step. (ESI): M/Z (M+1): 370.8 (LC-MS method C; R.T.: 1.133).

(i) (3R,8aR)-3-(8-amino-1-bromoimidazo[1,5-a]pyrazin-3-yl)tetrahydro-1H-pyrrolo[2,1-c][1,4]oxazin-6(7H)-one To a solution of (3R,8aR)-3-(1-bromo-8-chloroimidazo[1,5-a]pyrazin-3-yl)tetrahydro-1H-pyrrolo[2,1-c][1,4]oxazin-6(7H)-one (300 mg, 0.807 mmol) in NH₃.H₂O (4 mL) was added i-PrOH (4 mL). The mixture was stirred at 100° C. for 12 hour under a sealed tube. The mixture was concentrated to give crude (3R,8aR)-3-(8-amino-1-bromoimidazo[1,5-a]pyrazin-3-yl)tetrahydro-1H-pyrrolo[2,1-c][1,4]oxazin-6(7H)-one (250 mg, yield 88%) as a yellow solid, which was immediately used in the next step. (ESI): M/Z (M+1): 351.8 (LC-MS method C; R.T.: 1.239).

Intermediates 22a and 22b

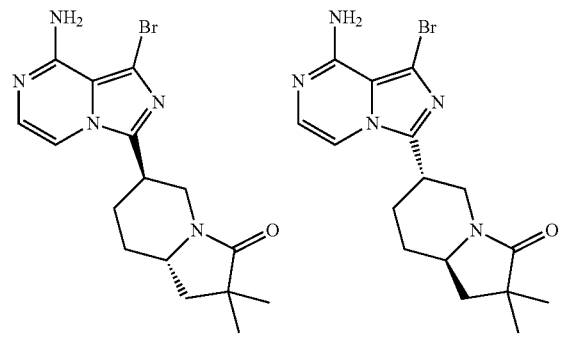 [SMILES: CC1(C)C[C@@H]2CC[C@@H](c3nc(Br)c4c(N)nccn34)CN2C1=O ; CC1(C)C[C@H]2CC[C@H](c3nc(Br)c4c(N)nccn34)CN2C1=O]

6-(8-amino-1-bromoimidazo[1,5-a]pyrazin-3-yl)-2,2-dimethylhexahydroindolizin-3(2H)-one (a) 5-(methoxycarbonyl)-2-methylpyridine 1-oxide A solution of methyl 6-methylnicotinate (15 g, 99.34 mmol) and m-CPBA (18.8 g, 109.3 mmol) in DCM (100 mL) was stirred at room temperature for 4 hours. The reaction mixture was quenched with 200 mL of saturated aqueous Na₂SO₃ and 100 mL of saturated aqueous NaHCO₃. The resulting mixture was extracted with EA (200 mL×3). The combined EA layer was washed with brine and dried over Na₂SO₄. Filtered and the filtrate was concentrated. The residue was purified by column chromatography on silica gel (PE/EtOAc=5/1) to afford 5-(methoxycarbonyl)-2-methylpyridine 1-oxide (12 g, 72%) as a yellow solid. MS-ESI (m/z): 168.2 (M+1)⁺ (LC-MS method C; Ret. time: 0.32 min).

(b) methyl 6-(hydroxymethyl)nicotinate

To a solution of 5-(methoxycarbonyl)-2-methylpyridine 1-oxide (12 g, 72 mmol) in DCM (50 mL) was added TFAA (25 mL) dropwise at 0° C. The mixture was stirred at reflux for 2 hours. The mixture was concentrated and the residue was adjusted to pH 9 with saturated aqueous NaHCO₃. The resulting mixture was extracted with EA. The solvent was removed and the residue was purified by column chromatography on silica gel (PE/EtOAc=1/1) to afford methyl 6-(hydroxymethyl)nicotinate(7 g, 58%).

MS-ESI (m/z): 168.2 (M+1)⁺ (LC-MS method C; Rt: 0.25 min).

(c) methyl 6-formylnicotinate

A mixture of methyl 6-(hydroxymethyl)nicotinate (7 g, 37 mmol) and MnO$_2$ (32.3 g, 372 mmol) in DCM (200 mL) was stirred at 20° C. for 4 hours. The mixture was filtered and the filtrate was concentrated. The residue was purified by column chromatography on silica gel (PE/EtOAc=5/1) to afford methyl 6-formylnicotinate (6 g, 97%).MS-ESI (m/z): 166.2 (M+1)$^+$ (LC-MS method C; Ret. time: 0.36 min).

(d) methyl 6-(1-hydroxy-3-methoxy-2,2-dimethyl-3-oxopropyl)nicotinate

To a stirred solution of 1-methyl-1H-imidazole (296 mg, 3.6 mmol) and anhydrous LiCl (303 mg, 7.2 mmol) in DMF (150 mL) was added methyl 6-formylnicotinate (6 g, 36 mmol) and ((1-methoxy-2-methylprop-1-en-1-yl)oxy)trimethylsilane (9.4 g, 54 mmol) at room temperature under nitrogen atmosphere, and the resulting mixture was stirred for 10 h. The reaction was quenched by the addition of a little amount of 1 N aq HCl. The product was extracted with ethyl acetate twice. The combined organic layer was washed with water and brine, and evaporated to dryness. The residue was purified by column chromatography on silica gel (PE/EtOAc=10/1) to afford methyl 6-(1-hydroxy-3-methoxy-2,2-dimethyl-3-oxopropyl)nicotinate (5.2 g, 53.7%) as a yellow solid.

MS-ESI (m/z): 268.0 (M+1)$^+$ (LC-MS method C; Ret. time: 0.888 min).

(e) methyl 6-(3-methoxy-2,2-dimethyl-1-((methylsulfonyl)oxy)-3-oxopropyl)nicotinate To a mixture of methyl 6-(1-hydroxy-3-methoxy-2,2-dimethyl-3-oxopropyl)nicotinate (5 g, 18.7 mmol) and TEA (3.78 g, 37.5 mmol) in DCM (200 mL) was added MsCl (5.15 g, 21 mmol) under ice-bath. The mixture was stirred at room temperature for 2 hours. The mixture was concentration and the residue was purified by column chromatography on silica gel (PE/EtOAc=10/1) to afford methyl 6-(3-methoxy-2,2-dimethyl-1-((methylsulfonyl)oxy)-3-oxopropyl) nicotinate (4 g, 61.9%) as a yellow solid. MS-ESI (m/z): 346.2 (M+1)$^+$ (LC-MS method C; Ret. time: 1.072 min).

(f) methyl 6-(3-methoxy-2,2-dimethyl-3-oxopropyl)nicotinate

A mixture of methyl 6-(3-methoxy-2,2-dimethyl-1-((methylsulfonyl)oxy)-3-oxopropyl)nicotinate (4 g, 11.6 mmol) and Pd/C (4 g) in MeOH (15 mL) was hydrogenated at room temperature for 2 hours. The mixture was filtered and the filtrate was concentrated, the residue was purified by column chromatography on silica gel (DCM/THF=5/1) to afford methyl 6-(3-methoxy-2,2-dimethyl-3-oxopropyl) nicotinate (2.4 g, 82.4%).MS-ESI (m/z): 252.2 (M+1) (LC-MS method C; Ret. time: 1.059 min).

(g) methyl 2,2-dimethyl-3-oxooctahydroindolizine-6-carboxylate

To a solution of methyl 6-(3-methoxy-2,2-dimethyl-3-oxopropyl)nicotinate (1.2 g, 4.78 mmol) in AcOH (20 mL) was added NaCNBH$_3$ (1.5 g, 24 mmol) in portions. The mixture was stirred at 60° C. for 16 hours. The mixture was concentration and the residue was purified by column chromatography on silica gel PE/THF=10/1) to afford methyl 2,2-dimethyl-3-oxooctahydro indolizine-6-carboxylate (600 mg, 55.8%).

MS-ESI (m/z): 226.0 (M+1)$^+$ (LC-MS method C; Ret. time: 0.918 min).

(h) 2,2-dimethyl-3-oxooctahydroindolizine-6-carboxylic acid

A mixture of methyl 2,2-dimethyl-3-oxooctahydroindolizine-6-carboxylate (530 mg, 2.36 mmol) and LiOH (495 mg, 11.8 mmol) in MeOH/THF/H$_2$O (5 mL/5 mL/2 mL) was stirred at 15° C. for 2 hours. The volatiles were removed and the mixture was adjusted to pH 4 with 1 N HCl. The resulting mixture was extracted with DCM/i-PrOH(10/1). The organic layer was dried over Na$_2$SO$_4$. The solvent was removed to give 2,2-dimethyl-3-oxooctahydroindolizine-6-carboxylic acid (500 mg, 100%), which was used in the next step directly. MS-ESI (m/z): 212.0 (M+1)$^+$ (LC-MS method C; Ret. time: 1.032 min).

(i) N-((3-chloropyrazin-2-yl)methyl)-2,2-dimethyl-3-oxooctahydroindolizine-6-carboxamide To a solution of 2,2-dimethyl-3-oxooctahydroindolizine-6-carboxylic acid (500 mg, 2.4 mmol) and (3-chloropyrazin-2-yl) methanamine(509 mg, 2.83 mmol) in THF (20 mL) was added HATU(1.075 g, 2.8 mmol) and TEA (596 mg, 5.9 mmol). The mixture was stirred at room temperature for 4 hours. Removed the volatiles under reduced pressure, and the rest mixture was extracted with DCM, the combined organic layer was washed with water, brine and dried over anhydrous Na$_2$SO$_4$. The organic layer was concentrated in vacuo and the residue was purified by silica gel column chromatography (PE/THF=10/1) to afford N-((3-chloropyrazin-2-yl)methyl)-2,2-dimethyl-3-oxooctahydroindolizine-6-carboxamide (700 mg, 88.3%).MS-ESI (m/z): 337.2 (M+1) (LC-MS method C; Ret. time: 0.935 min).

(j) 6-(8-chloroimidazo[1,5-a]pyrazin-3-yl)-2,2-dimethylhexahydroindolizin-3 (2H)-one A mixture of N-((3-chloropyrazin-2-yl)methyl)-2,2-dimethyl-3-oxooctahydroindolizine-6-carboxamide (700 mg, 2.08 mmol) and PCl$_5$ (1.5 g, 7.3 mmol) in MeCN (40 mL) was stirred at 60° C. for 4 hours. The mixture was quenched with saturated NaHCO$_3$ solution and extracted with EA. The EA layer was washed with brine and dried over anhydrous Na$_2$SO$_4$. The mixture was filtered and the filtrate was concentrated. The residue was purified by silica gel column chromatography (DCM/THF=10/1) to afford 6-(8-chloroimidazo[1,5-a]pyrazin-3-yl)-2,2-dimethylhexahydroindolizin-3(2H)-one (350 mg, 52.8%). MS-ESI (m/z): 319.2 (M+1) (LC-MS method C; Ret. time: 1.04 min).

(k) 6-(1-bromo-8-chloroimidazo[1,5-a]pyrazin-3-yl)-2,2-dimethylhexahydroindolizin-3 (2H)-one A mixture of 6-(8-chloroimidazo[1,5-a]pyrazin-3-yl)-2,2-dimethylhexahydroindolizin-3(2H)-one (200 mg, 0.63 mmol) and NBS (145 mg, 0.82 mmol) in DMF (5 mL) was stirred at 15° C. for 1 hour. The mixture was treated with water and extracted with EA. The EA layer was washed with brine and dried over anhydrous Na$_2$SO$_4$. Filtered and the filtrate was concentrated. The residue was purified by column chromatography on silica gel (PE/EtOAc=1/1) to afford 6-(1-bromo-8-chloroimidazo[1,5-a]pyrazin-3-yl)-2,2-dimethylhexahydroindolizin-3(2H)-one (200 mg, 79.9%). MS-ESI (m/z): 398.9 (M+1)+ (LC-MS method C; Ret. time: 1.105 min).

(l) 6-(8-amino-1-bromoimidazo[1,5-a]pyrazin-3-yl)-2,2-dimethylhexahydroindolizin-3 (2H)-one A solution of 6-(1-bromo-8-chloroimidazo[1,5-a]pyrazin-3-yl)-2,2-dimethylhexahydroindolizin-3(2H)-one (200 mg, 0.5 mol) in i-PrOH (10 mL) saturated with NH3 was stirred at 80° C. for 16 hours in a 30 mL of sealed tube. The mixture was concentrated and the residue was purified by prep. TLC to give 6-(8-amino-1-bromoimidazo[1,5-a]pyrazin-3-yl)-2,2-dimethylhexahydro indolizin-3(2H)-one (180 mg, 94.3%), which was separated by SFC to only afford two trans-isomers (6R,8aS)-6-(8-amino-1-bromoimidazo[1,5-a]pyrazin-3-yl)-2,2-dimethylhexahydroindolizin-3(2H)-one and (6S,8aR)-6-(8-amino-1-bromoimidazo[1,5-a]pyrazin-3-yl)-2,2-dimethyl hexahydroindolizin-3 (2H)-one.

Intermediate 23

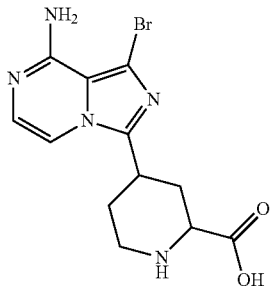 [SMILES: Nc1nccn2c(C3CCNC(C(=O)O)C3)nc(Br)c12]

4-(8-amino-1-(4-((4-(trifluoromethyl)pyridin-2-yl)carbamoyl)phenyl)imidazo[1,5-a]pyrazin-3-yl)piperidine-2-carboxylic acid (a) ethyl isonicotinate To a suspension of isonicotinic acid (5 g, 40.65 mmoL) in EtOH (50 mL) was added concentrated sulfuric acid (3.98 g, 40.65 mmoL) dropwise. After the dropwise addition, the mixture was stirred at 80° C. for 15 hours. To this suspension were added water at 0° C. and adjusted pH=6.5 with NaHCO3. The mixture was extracted with EA (150 mL×3), the combined organic layers were washed with brine (100 mL), dried over sodium sulfate, filtered and concentrated to give ethyl isonicotinate (4 g, yield 67%). 1HNMR (300 MHz, CHLOROFORM-d) δ=8.77 (d, J=5.5 Hz, 2H), 7.90-7.79 (m, 2H), 4.41 (q, J=7.2 Hz, 2H), 1.41 (t, J=7.2 Hz, 3H).

(b) ethyl 2-carbamoylisonicotinate

To a solution of ethyl isonicotinate (4 g, 26.46 mmoL) and concentrated H2SO4(2.6 g, 26.46 mmoL) in formamide (32 mL), 30% H2O2(4.5 g, 39.69 mmoL) and powdered FeSO4.7H2O (11 g, 39.69 mmoL) were separately and simultaneously added over 10 min efficient stirring and cooling in an ice-bath. After complete addition the ice-bath was remove and stirred for 12 h. Trisodium citrate(52.8 mL, 1M) was added and the mixture was brought to Ph=8 by addition of NaHCO3. The mixture was extracted with DCM (100 mL×5), the combined organic layers were washed with brine (50 mL), dried over sodium sulfate, filtered and concentrated to afford the crude product which was recrystallised from EtOH to give ethyl 2-carbamoylisonicotinate (1.3 g, yield 25%). 1H NMR (400 MHz, DMSO-d6) δ=8.85 (dd, J=0.8, 4.8 Hz, 1H), 8.42 (dd, J=0.9, 1.6 Hz, 1H), 8.26 (br. s, 1H), 8.02 (dd, J=1.6, 4.9 Hz, 1H), 7.83 (d, J=1.5 Hz, 1H), 4.43-4.34 (m, 2H), 1.36 (t, J=7.2 Hz, 3H).

(c) ethyl 2-carbamoylpiperidine-4-carboxylate

A mixture of ethyl 2-carbamoylisonicotinate (1.3 g, 6.7 mmoL) was slurried in CH3OH (50 mL), then HCl (0.56 mL, 6.7 mmoL) and PtO2 (0.1 g) were added. The mixture was hydrogenated at 55 psi with stirring for 22 hours. The reaction mixture was filtered and concentrated to afford ethyl 2-carbamoylpiperidine-4-carboxylate (1.3 g, yield: 97%). 1H NMR (400 MHz, METHANOL-d4) δ=4.16 (q, J=7.0 Hz, 2H), 3.89 (dd, J=2.6, 12.9 Hz, 1H), 3.45 (d, J=11.3 Hz, 1H), 3.14-3.00 (m, 1H), 2.85-2.71 (m, 1H), 2.53 (d, J=14.1 Hz, 1H), 2.24-2.11 (m, 1H), 1.83-1.67 (m, 2H), 1.49-1.36 (m, 1H), 1.30-1.18 (m, 3H).

(d) 1-benzyl 4-ethyl 2-carbamoylpiperidine-1,4-dicarboxylate ethyl 2-carbamoylpiperidine-4-carboxylate (200 mg, 1 mol) was slurried in dichloromethane (4 mL) and N-ethyl-N-isopropylpropan-2-amine (387.5 mg, 3 mmol) was added followed by benzyl carbonochloridate (179 mg, 1 mmol) dropwise. The mixture was stirred at 13° C. for 1 hour. The reaction mixture was evaporated to give crude product which purified on silica gel column chromatograph (PE/THF=100%~60%) to give 1-benzyl 4-ethyl 2-carbamoylpiperidine-1,4-dicarboxylate (170 mg, yield 51%). 1HNMR (400 MHz, METHANOL-d4) δ=7.43-7.23 (m, 5H), 5.18-5.06 (m, 2H), 4.52 (t, J=6.0 Hz, 1H), 4.19-4.03 (m, 2H), 3.93-3.82 (m, 1H), 3.51 (t, J=11.7 Hz, 1H), 2.68 (quin, J=5.7 Hz, 1H), 2.48-2.36 (m, 1H), 2.20-2.09 (m, 1H), 2.00 (d, J=9.5 Hz, 1H), 1.85-1.73 (m, 1H), 1.29-1.20 (m, 3H).

(e) 1-benzyl 4-ethyl 2-cyanopiperidine-1,4-dicarboxylate 1-benzyl 4-ethyl 2-carbamoylpiperidine-1,4-dicarboxylate (120 mg, 0.36 mmol) was dissolved in pyridine (2 mL). The mixture was cooled to 0° C. and SOCl2 (254 mg, 2.16 mmol) was added dropwise and left for 12 hours at 13° C. The reaction mixture was concentrated and partitioned between diluted HCl and dichloromethane. The aqueous layer was extracted with dichloromethane (20 mL×3), the combined organic layers were washed with brine (20 mL), dried over sodium sulfate, filtered and concentrated to afford the crude product, which was purified on silica gel column chromatograph (PE/THF=100%~80%) to give 1-benzyl 4-ethyl 2-cyanopiperidine-1,4-dicarboxylate (90 mg, yield 79%). 1HNMR (400 MHz, DMSO-d6) δ=7.42-7.25 (m, 5H), 5.29 (d, J=3.3 Hz, 1H), 5.19-5.05 (m, 1H), 4.10 (qq, J=7.1, 10.7 Hz, 1H), 3.93-3.80 (m, 1H), 3.09 (t, J=12.8 Hz, 1H), 2.92-2.82 (m, 1H), 2.33 (dd, J=1.6, 14.7 Hz, 1H), 2.13-1.98 (m, 2H), 1.66-1.53 (m, 1H), 1.21 (t, J=7.2 Hz, 3H).

(f) 1-((benzyloxy)carbonyl)-2-cyanopiperidine-4-carboxylic acid

To a solution of 1-benzyl 4-ethyl 2-cyanopiperidine-1,4-dicarboxylate (80 g, 0.253 mmoL) in THF/H2O (1:1, 4 mL)

was added LiOH.H₂O (20 mg, 0.476 mmol). The mixture was stirred at 13° C. for 13 hours. The mixture was extracted with DCM (10 mL×1) and the aqueous layer was acidified with 2M HCl, extracted with EA (5 mL×5), the combined organic layers were washed with brine (5 mL), dried over sodium sulfate, filtered and concentrated to give 1-((benzyloxy)carbonyl)-2-cyanopiperidine-4-carboxylic acid (70 mg, yield 95%). 1H NMR (400 MHz, DMSO-d6) δ=12.56 (br. s, 1H), 7.44-7.25 (m, 5H), 5.47 (br. s, 1H), 5.13 (s, 2H), 4.09-4.03 (m, 1H), 2.89 (br. s, 1H), 2.83-2.71 (m, 1H), 2.20-2.09 (m, 1H), 1.94 (br. s, 1H), 1.78-1.65 (m, 1H), 1.40 (dq, J=4.6, 12.8 Hz, 1H).

(g) benzyl 4-(((3-chloropyrazin-2-yl)methyl)carbamoyl)-2-cyanopiperidine-1-carboxylate To a solution of 1-((benzyloxy)carbonyl)-2-cyanopiperidine-4-carboxylic acid (30 mg, 0.104 mmol) in anhydrous DCM (5 mL) was added HATU (43.5 mg, 0.114 mmol), Et3N (31.56 mg, 0.312 mmol) and (3-chloropyrazin-2-yl) methanamine hydrochloride (20.5 mg, 0.114 mmol). The reaction mixture was stirred at 13° C. for 12 hrs. The reaction was quenched by the addition of water (10 mL), then it was extracted with DCM (10 mL×3), the combined organic layers were washed with brine (10 mL), dried over sodium sulfate, filtered and concentrated to afford the crude product, which was purified on silica gel column chromatograph (PE/THF=100%~50%) to give benzyl 4-(((3-chloropyrazin-2-yl)methyl)carbamoyl)-2-cyanopiperidine-1-carboxylate (40 mg, yield 93%). ¹H NMR (400 MHz, METHANOL-d4) δ=8.54 (d, J=2.5 Hz, 1H), 8.35 (d, J=2.5 Hz, 1H), 7.44-7.31 (m, 5H), 5.53 (d, J=4.0 Hz, 1H), 5.21 (d, J=2.5 Hz, 2H), 4.64 (s, 2H), 4.25 (d, J=13.1 Hz, 1H), 2.87-2.84 (m, 1H), 2.88-2.77 (m, 3H), 2.16 (d, J=12.5 Hz, 1H), 2.02-1.91 (m, 2H), 1.66 (dq, J=4.8, 12.9 Hz, 1H).

(h) benzyl 4-(8-chloroimidazo[1,5-a]pyrazin-3-yl)-2-cyanopiperidine-1-carboxylate A mixture of benzyl 4-(((3-chloropyrazin-2-yl)methyl) carbamoyl)-2-cyanopiperidine-1-carboxylate (40 mg, 0.096 mol) in CH3CN (3 mL) was added POCl3(44 mg, 0.287 mmol) and N,N-dimethylformamide (catalytic amount) at 0° C. The mixture was stirred at 17° C. for 10 hours. The reaction mixture was poured into ice water, adjusted basic with NaHCO3 and extracted with dichloromethane (10 mL×3). The combined organic layers were washed with brine(5 mL), dried over anhydrous sodium sulfate, concentrated to afford benzyl 4-(8-chloroimidazo[1,5-a]pyrazin-3-yl)-2-cyanopiperidine-1-carboxylate (30 mg, yield: 79%). ¹H NMR (400 MHz, METHANOL-d4) δ=8.23 (d, J=5.0 Hz, 1H), 7.98 (s, 1H), 7.84 (s, 1H), 7.44-7.31 (m, 6H), 5.63 (t, J=3.6 Hz, 1H), 5.26-5.17 (m, 2H), 4.31 (d, J=14.1 Hz, 1H), 3.71-3.61 (m, 1H), 2.31 (dd, J=4.4, 9.7 Hz, 2H), 2.11 (s, 2H), 1.78 (dq, J=4.6, 12.8 Hz, 1H).

(i) benzyl 4-(1-bromo-8-chloroimidazo[1,5-a] pyrazin-3-yl)-2-cyanopiperidine-1-carboxylate A mixture of benzyl 4-(8-chloroimidazo[1,5-a]pyrazin-3-yl)-2-cyanopiperidine-1-carboxylate (1.5 g, 3.78 mmol) in CH3CN (20 mL) was added 1-Bromo-pyrrolidine-2,5-dione (0.74 g, 4.16 mmol). The mixture was stirred at 15° C. for 1 hour. The reaction mixture was quenched with water and extracted with ethyl acetate(100 mL×3). The combined organic layers were washed with brine (50 mL), dried over anhydrous sodium sulfate and evaporated to give benzyl 4-(1-bromo-8-chloroimidazo[1,5-a]pyrazin-3-yl)-2-cyanopiperidine-1-carboxylate (1.5 g, yield 84%). ¹H NMR (400 MHz, CHLOROFORM-d) δ=7.67 (d, J=5.0 Hz, 1H), 7.45-7.32 (m, 6H), 5.67-5.41 (m, 1H), 5.20 (s, 2H), 4.35 (br. s, 1H), 3.52-3.38 (m, 1H), 3.27 (br. s, 1H), 2.35 (br. s, 1H), 2.26-2.14 (m, 1H), 2.11-1.88 (m, 2H).

(j) benzyl 4-(8-chloroimidazo[1,5-a]pyrazin-3-yl)-2-cyanopiperidine-1-carboxylate A mixture of benzyl 4-(1-bromo-8-chloroimidazo[1,5-a] pyrazin-3-yl)-2-cyanopiperidine-1-carboxylate (900 mg, 1.90 mmol) in NH3.H2O/i-PrOH (30 mL, 3:2) in a sealed tube. The mixture was stirred at 100° C. for 12 hours. The reaction mixture was cooled to 9° C. and concentrated to afford benzyl 4-(8-chloroimidazo[1,5-a]pyrazin-3-yl)-2-cyanopiperidine-1-carboxylate (900 mg, yield 100%).
MS (EI): M/Z (M+1): 454.8.

(k) 4-(8-amino-1-bromoimidazo[1,5-a]pyrazin-3-yl) piperidine-2-carboxylic acid

A mixture of benzyl 4-(8-amino-1-bromoimidazo[1,5-a] pyrazin-3-yl)-2-cyanopiperidine-1-carboxylate (300 mg, 0.66 mmol) in 6M HCl (10 mL) was stirred at 100° C. for 3 hours. The reaction mixture was concentrated to afford crude product which purified by SFC(Column: OJ-H; Co-Solvent: IPA (0.05% DEA); Injection Volume: 2; Total Flow: 2.5) to give (2S,4R)-4-(8-amino-1-bromoimidazo[1, 5-a]pyrazin-3-yl)piperidine-2-carboxylic acid (30 mg), (2R, 4S)-4-(8-amino-1-bromoimidazo[1,5-a]pyrazin-3-yl)piperidine-2-carboxylic acid (22 mg) and (2R,4R)-4-(8-amino-1-bromoimidazo[1,5-a]pyrazin-3-yl)piperidine-2-carboxylic acid (25 mg, total yield: 34.4).
MS (EI): M/Z (M+1): 340.0.

Intermediate 24

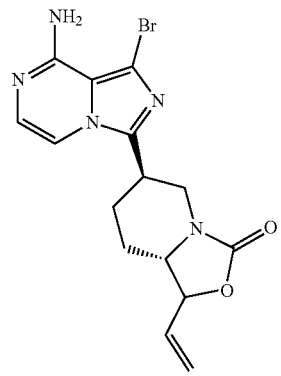 [SMILES: C=CC1OC(=O)N2C[C@H](c3nc(Br)c4c(N)nccn34)CC[C@@H]12]

(6R,8aS)-6-(8-amino-1-bromoimidazo[1,5-a] pyrazin-3-yl)-1-vinyltetrahydro-1H-oxazolo[3,4-a] pyridin-3(5H)-one (a) (3R,6S)-1-benzyl 3-ethyl 6-(1-hydroxyallyl) piperidine-1,3-dicarboxylate To a solution of (3R,6S)-1-benzyl 3-ethyl 6-formylpiperidine-1,3-dicarboxylate (750 mg, 2.46 mmol) in THF (50 mL) was added C2H3MgBr (3.68 mL, 3.68 mmol) at −78° C. and stirred for 3 h under N2 atmosphere. The reaction mixture was poured into aq. NH4Cl (30 mL) and extracted with EA (50 mL×3). The organic layer was contracted in vacou to give the residue which was purified with pre_TLC (PE:EA=1:1) to give the product (3R,6S)-1-benzyl 3-ethyl 6-(1-hydroxyallyl)piperidine-1,3-dicarboxylate (340 mg, yield 41.5%) as a colourless oil. 1HNMR (400 MHz, CHLOROFORM-d): δ=7.39-7.31 (m, 5H), 5.94-5.73 (m, 1H), 5.42-5.00 (m, 5H), 4.46-4.27 (m, 1H), 4.16-4.01 (m, 1H), 3.59 (s, 3H), 2.62 (br. s, 1H), 2.14-1.87 (m, 2H), 1.82-1.74 (m, 1H), 1.62-1.53 (m, 1H).

(b) (6R,8aS)-3-oxo-1-vinylhexahydro-1H-oxazolo[3,4-a]pyridine-6-carboxylic acid

To a solution of (3R,6S)-1-benzyl 3-ethyl 6-(1-hydroxyallyl)piperidine-1,3-dicarboxylate (340 mg, 0.98 mmol) in THF (5 mL) was added 1 M LiOH.H2O (2.94 mL, 2.94 mmol) at −78° C. and stirred at 20° C. for 3 h under N2 atmosphere. TLC (PE: THF=1:1) showed the starting materials was consumed completely. Then the reaction mixture was puted into water (50 mL), washed with EA (50 mL*2). The aqueous layer was acided to PH=2, concentrated in vacuo and purified with pre_HPLC to afford (6R,8aS)-3-oxo-1-vinylhexahydro-1H-oxazolo[3,4-a]pyridine-6-carboxylic acid (160 mg, yield 77.4%) as a colourless oil. 1HNMR (400 MHz, Methanol-d4): δ=6.05-5.88 (m, 1H), 5.53-5.32 (m, 2H), 5.09 (dd, J=6.8, 8.0 Hz, 0.5H), 4.61 (t, J=6.8 Hz, 0.5H), 4.08-3.94 (m, 1H), 3.81 (ddd, J=3.5, 8.2, 11.9 Hz, 0.5H), 3.44 (ddd, J=3.6, 7.0, 11.0 Hz, 0.5H), 3.07-2.91 (m, 1H), 2.55-2.36 (m, 1H), 2.25 (d, J=15.3 Hz, 1H), 2.00 (qd, J=3.2, 12.6 Hz, 1H), 1.73-1.65 (m, 1H), 1.65-1.53 (m, 1H), 1.53-1.35 (m, 1H).

(c)(6R,8aS)-N-((3-chloropyrazin-2-yl)methyl)-3-oxo-1-vinylhexahydro-1H-oxazolo[3,4-a]pyridine-6-carboxamide To a solution of (6R,8aS)-3-oxo-1-vinylhexahydro-1H-oxazolo[3,4-a]pyridine-6-carboxylic acid (60 mg, 0.28 mmol) in DCM (5 mL) was added (COCl)$_2$ (54.1 mg, 0.43 mmol) at 0° C. and stirred at 20° C. for 1 h under N2 atmosphere. The mixture was concentrated in vacuo to give the residue, which was dissolved in THF (2 mL) and followed by (3-chloropyrazin-2-yl)methanamine hydrochloride (76.7 mg, 0.43 mmol) and Et3N (86.2 mg, 0.85 mmol). The mixture was stirred at 20° C. for 5 h. TLC (PE:THF=1:1) showed the starting materials was consumed completely. Then the reaction mixture was poured into water (10 mL), extracted with EA (10 mL×2). The organic layer was concentrated in vacuo and purified with pre-TLC to afford (6R,8aS)-N-((3-chloropyrazin-2-yl)methyl)-3-oxo-1-vinylhexahydro-1H-oxazolo[3,4-a]pyridine-6-carboxamide (30 mg, yield 31.4%) as a white solid. 1HNMR (400 MHz, Methanol-d4): δ=8.53 (dd, J=1.0, 2.5 Hz, 1H), 8.34 (d, J=2.0 Hz, 1H), 6.04-5.88 (m, 1H), 5.50-5.31 (m, 2H), 4.65-4.57 (m, 3H), 3.98-3.89 (m, 1H), 3.83 (ddd, J=3.4, 8.2, 11.8 Hz, 1H), 3.50-3.42 (m, 1H), 2.58-2.42 (m, 1H), 2.10 (dd, J=2.5, 12.8 Hz, 1H), 2.03-1.95 (m, 1H), 1.77-1.63 (m, 2H), 1.53-1.38 (m, 1H).

(d)(6R,8aS)-6-(8-chloroimidazo[1,5-a]pyrazin-3-yl)-1-vinyltetrahydro-1H-oxazolo[3,4-a]pyridin-3(5H)-one To a solution of (6R,8aS)-N-((3-chloropyrazin-2-yl)methyl)-3-oxo-1-vinylhexahydro-1H-oxazolo[3,4-a]pyridine-6-carboxamide (150 mg, 0.45 mmol) in anhydrous acetonitrile (5 mL) was added POCl3 (0.26 mL, 2.67 mmol) and DMF (34 uL) portionwise at 0° C. under an ice-water bath. The resulting mixture was stirred at room temperature for 12 h. The mixture was poured into an ice-water mixture, neutralized with powered sodium bicarbonate (PH=8), extracted with dichloromethane (50 mL×3). The organic layer was contracted in vacuo and tracked with TLC (PE: THF=1:1), purified with pre_TLC to give (6R,8aS)-6-(8-chloroimidazo[1,5-a]pyrazin-3-yl)-1-vinyltetrahydro-1H-oxazolo[3,4-a]pyridin-3(5H)-one (90 mg, yield 63.4%) as a white soiled. 1HNMR (400 MHz, CHLOROFORM-d): δ=7.81 (dd, J=0.8, 2.5 Hz, 1H), 7.73-7.67 (m, 1H), 7.38 (dd, J=2.8, 5.0 Hz, 1H), 6.01-5.83 (m, 1H), 5.60-5.35 (m, 2H), 5.12-5.03 (m, 0.5H), 4.61-4.54 (m, 0.5H), 4.17-4.08 (m, 2H), 3.85 (ddd, J=3.6, 7.8, 11.9 Hz, 0.5H), 3.50 (ddd, J=3.5, 5.6, 11.5 Hz, 0.5H), 3.30-3.19 (m, 1H), 3.18-3.08 (m, 1H), 2.29-2.22 (m, 1H), 2.15-2.10 (m, 1H), 1.82-1.74 (m, 0.5H), 1.62-1.56 (m, 0.5H).

(e)(6R,8aS)-6-(1-bromo-8-chloroimidazo[1,5-a]pyrazin-3-yl)-1-vinyltetrahydro-1H-oxazolo[3,4-a]pyridin-3(5H)-one To a solution of (6R,8aS)-6-(8-chloroimidazo[1,5-a]pyrazin-3-yl)-1-vinyltetrahydro-1H-oxazolo[3,4-a]pyridin-3(5H)-one (90 mg, 0.28 mmol) in anhydrous DMF (4 mL) was added N-bromosuccinimide (55.3 mg, 0.31 mmol) portionwise at 20° C. The resulting mixture was stirred at room temperature for 1 h. The mixture was poured to an ice-water mixture, extracted with dichloromethane (15 mL×3). The organic layer was contracted in vacuo and tracked with TLC (PE:THF=1:1). The residue was purified with flash column to give (6R,8aS)-6-(1-bromo-8-chloroimidazo[1,5-a]pyrazin-3-yl)-1-vinyltetrahydro-1H-oxazolo[3,4-a]pyridin-3 (5H)-one (90 mg, yield 80.1%) as a white solid. $^1$H NMR (400 MHz, METHANOL-d4) δ=8.23 (d, J=5.0 Hz, 1H), 7.90 (d, J=5.3 Hz, 1H), 7.37 (d, J=5.0 Hz, 1H), 7.18 (d, J=5.0 Hz, 1H), 6.00 (ddd, J=6.5, 10.6, 17.3 Hz, 1H), 5.59-5.40 (m, 2H), 5.17 (t, J=6.9 Hz, 1H), 4.07-3.95 (m, 2H), 3.38-3.34 (m, 2H), 2.26-2.15 (m, 1H), 1.97-1.85 (m, 1H), 1.81-1.72 (m, 1H), 1.72-1.60 (m, 1H).

(f)(6R,8aS)-6-(8-amino-1-bromoimidazo[1,5-a]pyrazin-3-yl)-1-vinyltetrahydro-1H-oxazolo[3,4-a]pyridin-3(5H)-one To a solution of (6R,8aS)-6-(1-bromo-8-chloroimidazo[1,5-a]pyrazin-3-yl)-1-vinyltetrahydro-1H-oxazolo[3,4-a]pyridin-3(5H)-one (100 mg, 0.25 mmol) in i_PrOH (2 mL) was added NH$_3$.H2O (2 mL, 25.15 mmol) at 20° C. The resulting mixture was stirred under 50 psi at 110° C. for 10 h in a 100 mL of stealed tube. The mixture was cooled to room temperature and contracted in vacuo to give (6R,8aS)-6-(8-amino-1-bromoimidazo[1,5-a]pyrazin-3-yl)-1-vinyltetrahydro-H-oxazolo[3,4-a]pyridin-3(5H)-one (80 mg, yield 84.1%) as a white solid, which was used to the next step without purification. (ESI): M/Z (M) 378.0: (M+2) 380.0=10:8 (LC-MS method C; R.T.: 0.544).

Intermediate 25a and 25b

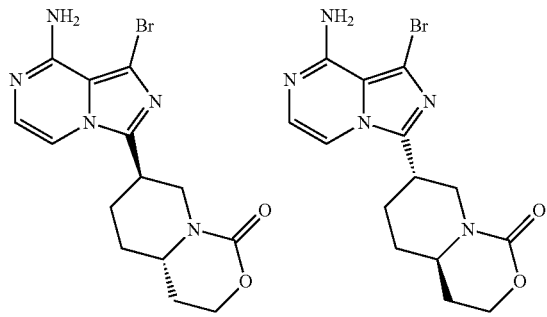 [SMILES: Nc1nccn2c([C@@H]3CC[C@H]4CCOC(=O)N4C3)nc(Br)c12 ; Nc1nccn2c([C@H]3CC[C@@H]4CCOC(=O)N4C3)nc(Br)c12]

7-(8-amino-1-bromoimidazo[1,5-a]pyrazin-3-yl)
hexahydropyrido[1,2-c][1,3]oxazin-1(3H)-one

(a) methyl 6-(oxiran-2-yl)nicotinate

To a solution of methyl 6-vinylnicotinate (20.1 g, 123 mmol) in water/t-BuOH (200 mL/100 mL) was added with NBS (24.1 g, 136 mmol) in portions over 15 min, and the mixture was stirred at 40° C. for 2 h. After cooling to 5° C., the reaction mixture was basified with addition of NaOH solution (5 g in 15 mL of water), and stirred at this temperature for further 30 min, then the mixture was added another NaOH solution (4.9 g in 15 mL of water) in portions during a period of 30 min. The reaction was complete detected by LCMS, and the mixture was treated with EA and water. The organic layer was concentrated to give the crude product, which was used in next step directly without further purification. MS-ESI (m/z): 180 (M+1)$^+$ (LC-MS method C; Ret. time: 0.323 min).

(b) methyl 6-(2-hydroxyethyl)nicotinate

To a solution of methyl 6-(oxiran-2-yl)nicotinate (123 mmol) from above step in EtOH (400 mL) was added Pd/C (10 g) and ammonium formate (31 g, 493 mmol). The mixture was stirred at room temperature for 2 h under nitrogen protection. The reaction was complete detected by TLC. The suspension was filtered through a pad of Celite, and the filtrate was concentrated. The residue was purified by column chromatography on silica gel eluted with PE/EA=1/3 to give methyl 6-(2-hydroxyethyl)nicotinate (10 g, two steps: 45%). $^1$H-NMR (CDCl3, 400 MHz) δ=3.08 (t, J=5.67 Hz, 2 H), 3.93 (s, 3 H), 4.03 (t, J=5.67 Hz, 2 H), 7.25 (d, J=8.0 Hz, 1 H), 8.21 (dd, J=8.02, 2.15 Hz, 1 H), 9.09 (d, J=1.17 Hz, 1 H).

(c) methyl 6-(2-hydroxyethyl)piperidine-3-carboxylate

To a solution of methyl 6-(2-hydroxyethyl)nicotinate (8.9 g, 49.2 mmol) in AcOH (120 mL) was added NaBH$_3$CN (9.3 g, 16.6 mmol) at 0° C. The mixture was heated to 50° C. and stirred overnight. The reaction was complete detected by LCMS. The solvent was evaporated and the residue was treated with aq. NaHCO$_3$ and EA. The product was in aqueous phase, and used in next step directly. MS-ESI (m/z): 188 (M+1)$^+$ (LC-MS method C; Ret. time: 0.13 min).

(d) 1-tert-butyl 3-methyl 6-(2-hydroxyethyl)piperidine-1,3-dicarboxylate

A solution of methyl 6-(2-hydroxyethyl)piperidine-3-carboxylate (49.2 mmol) from the above step in aq. NaHCO$_3$ (500 mL) was added Boc$_2$O (32.2 g, 147.5 mmol) and THF (80 mL). The mixture was stirred at room temperature for 1 h. The reaction was complete detected by LCMS. The reaction mixture was extracted with EA. The organic layer was dried and concentrated. The residue was purified by column chromatography on silica gel eluted with PE/EA=5/1 to give 1-tert-butyl 3-methyl 6-(2-hydroxyethyl)piperidine-1,3-dicarboxylate (8.5 g, two steps: 60%). $^1$H-NMR (CDCl3, 400 MHz) δ 1.45 (s, 9 H), 1.51-1.81 (m, 3 H), 1.83-2.00 (m, 2 H), 2.04-2.11 (m, 1 H), 2.37-2.60 (m, 1 H), 2.72-2.92 (m, 1 H), 3.27-3.42 (m, 1 H), 3.55-3.62 (m, 1 H), 3.69 (s, 3 H), 4.12-4.52 (m, 2 H).

(e) methyl 1-oxooctahydropyrido[1,2-c][1,3]oxazine-7-carboxylate

To a solution of 1-tert-butyl 3-methyl 6-(2-hydroxyethyl)piperidine-1,3-dicarboxylate (6.5 g, 22.6 mmol) in DCM (100 mL) was added TEA (6.9 g, 67.9 mmol) and MsCl (3.9 g, 34.0 mmol). The mixture was stirred at room temperature for 2 h, then heated to 60° C. and stirred overnight. The reaction mixture was treated with DCM and water. The organic layer was dried and concentrated. The residue was purified by column chromatography on silica gel eluted with DCM/THF=5/1 to give methyl 1-oxooctahydropyrido[1,2-c][1,3]oxazine-7-carboxylate (3.4 g, 71%). $^1$H-NMR (CDCl3, 400 MHz) δ 1.30-1.42 (m, 1 H), 1.54-1.64 (m, 1 H), 1.75-1.87 (m, 3 H), 2.12-2.21 (m, 2 H), 2.44-2.53 (m, 1 H), 2.74 (t, J=12.0 Hz, 1 H), 3.25-3.34 (m, 1 H), 3.64-3.70 (m, 3 H), 3.70-3.75 (m, 1 H), 4.10-4.24 (m, 2 H), 4.60-4.72 (m, 1 H).

(f) 1-oxooctahydropyrido[1,2-c][1,3]oxazine-7-carboxylic acid

To a solution of methyl 1-oxooctahydropyrido[1,2-c][1,3]oxazine-7-carboxylate (3.4 g, 16.0 mmol) in THF/MeOH/H$_2$O (30 mL/30 mL/10 mL) was added LiOH*H$_2$O (3.4 g, 80.0 mmol). The mixture was stirred at room temperature for 2 h. The reaction was complete detected by LCMS. The mixture was extracted with EA. The aqueous layer was acidified by 1 M HCl and extracted with DCM. The DCM layer was dried and concentrated to give the product, which was used in next step directly without further purification. MS-ESI (m/z): 200 (M+1) (LC-MS method C; Ret. time: 0.21 min).

(g) N-((3-chloropyrazin-2-yl)methyl)-1-oxooctahydropyrido[1,2-c][1,3]oxazine-7-carboxamide To a solution of 1-oxooctahydropyrido[1,2-c][1,3]oxazine-7-carboxylic acid (3.13 g, 15.7 mmol) in THF (100 mL) was added (3-chloropyrazin-2-yl)methanamine hydrochloride (2.8 g, 15.7 mmol), TEA (4.8 g, 47.2 mmol) and HATU (6 g, 15.7 mmol). The mixture was stirred at room temperature for 2 h. The reaction was complete detected by LCMS. The reaction mixture was treated with DCM and water, the organic layer was dried and concentrated. The residue was purified by column chromatography on silica gel eluted with DCM/THF=5/1 to give N-((3-chloropyrazin-2-yl)methyl)-1-oxooctahydropyrido[1,2-c][1,3]oxazine-7-carboxamide (4.7 g, 92%). H-NMR (CDCl3, 400 MHz) δ

1.40-1.49 (m, 1 H), 1.71-1.92 (m, 3 H), 2.04-2.26 (m, 2 H), 2.43-2.57 (m, 1 H), 2.81-2.97 (m, 1 H), 3.31-3.42 (m, 1 H), 4.13-4.27 (m, 2 H), 4.46-4.56 (m, 1 H), 4.64 (d, J=4.70 Hz, 2 H), 8.29 (d, J=2.35 Hz, 1 H), 8.44 (d, J=2.35 Hz, 1 H).

(h) 7-(8-chloroimidazo[1,5-a]pyrazin-3-yl)hexahydropyrido[1,2-c][1,3]oxazin-1(3H)-one To a solution of N-((3-chloropyrazin-2-yl)methyl)-1-oxooctahydropyrido[1,2-c][1,3]oxazine-7-carboxamide (4.7 g, 14.5 mmol) in MeCN (100 mL) was added PCl₅ (6 g, 29.0 mmol). The mixture was stirred at 60° C. for 1.5 h. The reaction was complete detected by LCMS, and the reaction mixture was treated with DCM and water. The organic layer was dried and concentrated. The residue was purified by column chromatography on silica gel eluted with DCM/THF=5/1 to give 7-(8-chloroimidazo[1,5-a]pyrazin-3-yl)hexahydropyrido[1,2-c][1,3]oxazin-1(3H)-one (2 g, 45%). MS-ESI (m/z): 307 (M+1)⁺ (LC-MS method C; Ret. time: 1.056 min).

(i) 7-(1-bromo-8-chloroimidazo[1,5-a]pyrazin-3-yl)hexahydropyrido[1,2-c][1,3]oxazin-1 (3H)-one To a solution of 7-(8-chloroimidazo[1,5-a]pyrazin-3-yl)hexahydropyrido[1,2-c][1,3]oxazin-1(3H)-one (2.23 g, 7.3 mmol) in DMF (20 mL) was added a solution of NBS (1.35 g, 7.6 mmol) in DMF (10 mL) at 0° C. The mixture was stirred at room temperature for 1 h. The reaction was complete detected by LCMS. The reaction solution was poured into water (200 mL) and filtered. The solid was dissolved with DCM, dried and concentrated to give the product, which was used in next step directly without further purification. MS-ESI (m/z): 385 (M+1)⁺ (LC-MS method C; Ret. time: 1.186 min).

(j) 7-(8-amino-1-bromoimidazo[1,5-a]pyrazin-3-yl)hexahydropyrido[1,2-c][1,3]oxazin-1(3H)-one A solution of 7-(1-bromo-8-chloroimidazo[1,5-a]pyrazin-3-yl)hexahydropyrido[1,2-c][1,3]oxazin-1(3H)-one (1.87 g, 4.8 mmol) in NH₃/i-PrOH (30 mL) was added in 30 mL seal tube, and the mixture was stirred at 110° C. overnight. The reaction mixture was concentrated and the residue was purified by column chromatography on silica gel eluted with DCM/MeOH=50/1 to give 7-(8-amino-1-bromoimidazo[1,5-a]pyrazin-3-yl)hexahydropyrido[1,2-c][1,3]oxazin-1 (3H)-one (1.4 g, 80%), which was separated by SFC to afford two trans-isomers only.

SFC condition: "Column: Chiralcel OJ-H 250×4.6 mm I.D., 5 um Mobile phase: methanol (0.05% DEA) in CO₂ from 5% to 40% Flow rate: 2.35 mL/min Wavelength: 220 nm"

For (4aS,7R)-7-(8-amino-1-bromoimidazo[1,5-a]pyrazin-3-yl)hexahydropyrido[1,2-c][1,3]oxazin-1(3H)-one and (4aR,7S)-7-(8-amino-1-bromoimidazo[1,5-a]pyrazin-3-yl)hexahydropyrido[1,2-c][1,3]oxazin-1(3H)-one:

¹H-NMR (CDCl3,400 MHz) δ 1.43-1.57 (m, 1 H), 1.79-1.92 (m, 1 H), 1.95-2.19 (m, 3 H), 2.20-2.32 (m, 1 H), 2.91 (t, J=12.0 Hz, 1 H), 3.02-3.10 (m, 1 H), 3.37-3.55 (m, 1 H), 4.09-4.34 (m, 2 H), 4.53-4.69 (m, 1 H), 5.93 (br. s, 2 H), 7.02 (d, J=5.09 Hz, 1 H), 7.27 (d, J=5.09 Hz, 1 H).

Same procedure as the preparation of (1S,3R)-3-(8-amino-1-(4-((4-(trifluoromethyl)pyridin-2-yl)carbamoyl)phenyl)imidazo[1,5-a]pyrzin-3-yl)-1-isopropylcyclopentanecarboxylic acid give the following compound:

For 4-(8-amino-3-((4aS,7R)-1-oxooctahydropyrido[1,2-c][1,3]oxazin-7-yl)imidazo[1,5-a]pyrazin-1-yl)-N-(4-(trifluoromethyl)pyridin-2-yl)benzamide:

¹H-NMR (CD₃OD, 400 MHz) δ 1.55-1.71 (m, 1 H), 1.85-2.05 (m, 3 H), 2.20-2.35 (m, 2 H), 3.18 (t, J=12.52 Hz, 1 H), 3.35-3.46 (m, 1 H), 3.51-3.63 (m, 1 H), 4.18-4.37 (m, 2 H), 4.57 (d, J=12.91 Hz, 1 H), 7.04 (d, J=6.26 Hz, 1 H), 7.43 (d, J=4.70 Hz, 1 H), 7.76-8.00 (m, 3 H), 8.17 (d, J=8.22 Hz, 2 H), 8.48-8.70 (m, 2 H).

For 4-(8-amino-3-((4aR,7S)-1-oxooctahydropyrido[1,2-c][1,3]oxazin-7-yl)imidazo[1,5-a]pyrazin-1-yl)-N-(4-(trifluoromethyl)pyridin-2-yl)benzamide:

¹H-NMR (CD₃OD, 400 MHz) δ 1.55-1.71 (m, 1 H), 1.85-2.05 (m, 3 H), 2.20-2.35 (m, 2 H), 3.18 (t, J=12.52 Hz, 1 H), 3.35-3.46 (m, 1 H), 3.51-3.63 (m, 1 H), 4.18-4.37 (m, 2 H), 4.57 (d, J=12.91 Hz, 1 H), 7.04 (d, J=6.26 Hz, 1 H), 7.43 (d, J=4.70 Hz, 1 H), 7.76-8.00 (m, 3 H), 8.17 (d, J=8.22 Hz, 2 H), 8.48-8.70 (m, 2 H).

Intermediate 26

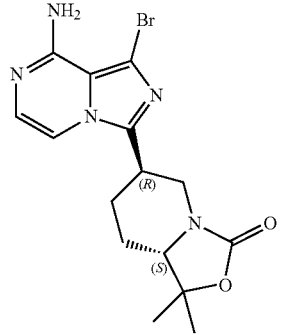

(6R,8aS)-6-(8-amino-1-bromoimidazo[1,5-a]pyrazin-3-yl)-1,1-dimethyltetrahydro-1H-oxazolor[3,4-a]pyridin-3(5H)-one Step 1: (3R,6S)-1-benzyl 3-methyl 6-acetylpiperidine-1,3-dicarboxylate To a solution of (3R,6S)-1-benzyl 3-methyl 6-(1-hydroxyethyl)piperidine-1,3-dicarboxylate (500 mg, 1.56 mmoL) in anhydrous DCM (20 mL) was added Martin's reagent (990 mg, 2.33 mmoL) at 0° C. portion-wise. The mixture was stirred at 0° C. to 25° C. for 3 hours. The mixture was quenched by the addition of a solution of 15% Na2S2O3 in saturated NaHCO3 (20 mL) at 0° C. slowly, the mixture was then separated and the aqueous layer was extracted with DCM (50 mL×4), the combined organic layers were washed with brine (20 mL), dried over sodium sulfate, filtered and concentrated to afford the crude product, which was purified on silica gel column chromatograph (EA/PE=5%~35%) to give (3R,6S)-1-benzyl 3-methyl 6-acetylpiperidine-1,3-dicarboxylate (300 mg, yield 60.38%) as a colorless oil. ¹H NMR (400 MHz, CHLOROFORM-d) δ=7.44-7.27 (m, 5H), 5.30-5.06 (m, 2H), 4.80-4.57 (m, 1H), 4.48 (d, J=13.3 Hz, 1H), 3.78-3.49 (m, 3H), 3.24 (d, J=14.1 Hz, 1H), 2.58 (br. s, 1H), 2.24-1.99 (m, 5H), 1.99-1.84 (m, 1H), 1.63-1.51 (m, 1H).

Step 2: (3R,6S)-1-benzyl 3-methyl 6-(2-hydroxypropan-2-yl)piperidine-1,3-dicarboxylate To a solution of (3R,6S)-1-benzyl 3-methyl 6-acetylpiperidine-1,3-dicarboxylate (0.58 g, 1.82 mmol) in anhydrous THF (10 mL) at −78° C., MeMgBr (3M in ether, 1.82 mL, 0.564 mmol) was added dropwise. The reaction mixture was stirred at −78° C.~25° C. for 4 hrs. The reaction was quenched by saturated ammonium chloride (20 mL), then the mixture was extracted with EA (50 mL×4), the combined organic layers were washed with brine (20 mL), dried over sodium sulfate, filtered and concentrated to afford the crude product, which was purified on silica gel column chromatograph (THF/PE=5%~40%) to give (3R,6S)-1-benzyl 3-methyl 6-(2-hydroxypropan-2-yl)piperidine-1,3-dicarboxylate (200 mg, yield 32.83%) as a colorless oil. (ESI): M/Z (M+1): 336.2 (LC-MS method B; R.T.: 4.316).

Step 3: (6R,8aS)-1,1-dimethyl-3-oxohexahydro-1H-oxazolo[3,4-a]pyridine-6-carboxylic acid To a solution of (3R,6S)-1-benzyl 3-methyl 6-(2-hydroxypropan-2-yl)piperidine-1,3-dicarboxylate (200 mg, 0.596 mmol) in THF/H2O (1:1, 10 mL) was added LiOH (28.56 mg, 1.19 mmol). The mixture was stirred at 25° C. for 3 hours. The mixture was adjust acid to PH=1 with 1M HCl and the mixture was dried via freeze dryer to give the crude product, which was purified by prepared HPLC to give (6R,8aS)-1,1-dimethyl-3-oxohexahydro-1H-oxazolo[3,4-a]pyridine-6-carboxylic acid (100 mg, yield 78.65%) as a white solid. $^1$H NMR (400 MHz, CHLOROFORM-d) δ=3.78 (dd, J=3.6, 12.9 Hz, 1H), 3.27 (dd, J=3.4, 11.7 Hz, 1H), 2.89-2.79 (m, J=12.3, 12.3 Hz, 1H), 2.32 (tdd, J=4.0, 7.9, 15.8 Hz, 1H), 2.09 (d, J=11.8 Hz, 1H), 1.73-1.63 (m, 1H), 1.51-1.28 (m, 5H), 1.24 (s, 3H).

Step 4: (6R,8aS)-N-((3-chloropyrazin-2-yl)methyl)-1,1-dimethyl-3-oxohexahydro-1H-oxazolo[3,4-a]pyridine-6-carboxamide To a solution of (6R,8aS)-1,1-dimethyl-3-oxohexahydro-1H-oxazolo[3,4-a]pyridine-6-carboxylic acid (100 mg, 0.468 mmol) in anhydrous DCM (40 mL) was added (COCl)$_2$ (158.9 mg, 0.469 mmol) at 0° C., then DMF (one drop) was added and the mixture was stirred at 25° C. for 1.5 hrs. The mixture was concentrated in vacuo, which then diluted with DCM (5 mL) was added to a solution of (3-chloropyrazin-2-yl)methanamine hydrochloride (101.32 mg, 0.562 mmol), TEA (94.91 mg, 0.938 mmol) in DCM (10 mL). The mixture was stirred at 25° C. for 3 hrs, The mixture was quenched by the addition of water (10 mL) at 0° C., the mixture was then extracted with DCM (50 mL×3), the combined organic layers were washed with 1M HCl (10 mL), brine (20 mL), dried over sodium sulfate, filtered and concentrated to give (6R,8aS)-N-((3-chloropyrazin-2-yl)methyl)-1,1-dimethyl-3-oxohexahydro-1H-oxazolo[3,4-a]pyridine-6-carboxamide (150 mg, 94.19%) as a colorless oil. $^1$H NMR (400 MHz, CHLOROFORM-d) d=8.46 (d, J=2.5 Hz, 1H), 8.34 (d, J=2.5 Hz, 1H), 6.94 (br. s, 1H), 4.78-4.60 (m, 2H), 4.09 (dd, J=4.1, 12.7 Hz, 1H), 3.26 (dd, J=3.3, 11.8 Hz, 1H), 3.08 (dd, J=11.8, 13.1 Hz, 1H), 2.43 (tt, J=4.1, 11.7 Hz, 1H), 2.16 (d, J=12.5 Hz, 1H), 1.86-1.70 (m, 2H), 1.46 (s, 3H), 1.44-1.38 (m, 1H), 1.35 (s, 3H).

Step 5: (6R,8aS)-6-(8-chloroimidazo[1,5-a]pyrazin-3-yl)-1,1-dimethyltetrahydro-1H-oxazolo[3,4-a]pyridin-3(5H)-one To a solution of (6R,8aS)-N-((3-chloropyrazin-2-yl)methyl)-1,1-dimethyl-3-oxohexahydro-1H-oxazolo[3,4-a]pyridine-6-carboxamide (180 mg, 0.531 mmol) in anhydrous MeCN (5 mL) was added POCl3 (407.33 mg, 2.66 mmol) at 0° C. dropwise. Then DMF (one drop) was added and the mixture was stirred at 25° C. for 15 hours, The mixture was poured into ice-water, adjust basic with Sat. NaHCO3 (20 mL), the mixture was then extracted with EA (20 mL×4), the combined organic layers were washed with brine (10 mL), dried over sodium sulfate, filtered and concentrated to afford the crude product, which was purified on silica gel column chromatograph (THF/PE=5%~50%) to give (6R,8aS)-6-(8-chloroimidazo[1,5-a]pyrazin-3-yl)-1,1-dimethyltetrahydro-1H-oxazolo[3,4-a]pyridin-3(5H)-one (80 mg, yield 46.94%) as a white solid. (ESI): M/Z (M+1): 321.0 (LC-MS method C; R.T.: 0.643).

Step 6: (6R,8aS)-6-(1-bromo-8-chloroimidazo[1,5-a]pyrazin-3-yl)-1,1-dimethyltetrahydro-1H-oxazolo[3,4-a]pyridin-3(5H)-one To a solution of (6R,8aS)-6-(8-chloroimidazo[1,5-a]pyrazin-3-yl)-1,1-dimethyltetrahydro-1H-oxazolo[3,4-a]pyridin-3(5H)-one (80 mg, 0.249 mmol) in anhydrous MeCN (5 mL) was added 1-bromopyrrolidine-2,5-dione (53.27 mg, 0.299 mmol). The mixture was stirred at 25° C. for 2 hour. The mixture was quenched by the addition of H$_2$O (10 mL) at 0° C., the mixture was then extracted with EA (20 mL×4), the combined organic layers were washed with brine (10 mL), dried over sodium sulfate, filtered and concentrated to give (6R,8aS)-6-(1-bromo-8-chloroimidazo[1,5-a]pyrazin-3-yl)-1,1-dimethyltetrahydro-1H-oxazolo[3,4-a]pyridin-3(5H)-one (85 mg, yield 85.28%) as a yellow solid. (ESI): M/Z (M+1): 399.0 (R.T.: 0.723).

Step 7: (6R,8aS)-6-(8-amino-1-bromoimidazo[1,5-a]pyrazin-3-yl)-1,1-dimethyltetrahydro-1H-oxazolo[3,4-a]pyridin-3(5H)-one To a solution of (6R,8aS)-6-(1-bromo-8-chloroimidazo[1,5-a]pyrazin-3-yl)-1,1-dimethyltetrahydro-1H-oxazolo[3,4-a]pyridin-3(5H)-one (85 mg, 0.212 mmol) in NH3H2O (4 mL) was added i-PrOH (4 mL). The mixture was stirred at 100° C. for 12 hour in a sealed tube. The mixture was concentrated to give crude (6R,8aS)-6-(8-amino-1-bromoimidazo[1,5-a]pyrazin-3-yl)-1,1-dimethyltetrahydro-1H-oxazolo[3,4-a]pyridin-3(5H)-one (80.87 mg, yield 100%) as a yellow solid, which without further purification. (ESI): M/Z (M+1): 380.0 (LC-MS method C; R.T.: 0.941).

Intermediate 27

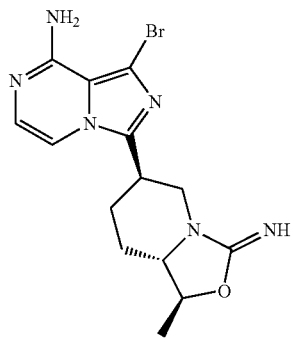 [SMILES: C[C@@H]1OC(=N)N2C[C@H](c3nc(Br)c4c(N)nccn34)CC[C@@H]12]

1-bromo-3-((1 S,6R,8aS)-3-imino-1-methylhexahydro-1H-oxazolo[3,4-a]pyridin-6yl)imidazo[1,5-a]pyrazin-8-amine

Step 1: (S)-1-((2S,5R)-5-(8-amino-1-bromoimidazo[1,5-a]pyrazin-3-yl)piperidin-2-yl)ethanol To the solution of KOH (24 mg, 0.42 mmol) in EtOH (4 mL) was added (1S,6R,8aS)-6-(8-amino-1-bromoimidazo[1,5-a]pyrazin-3-yl)-1-methyltetrahydro-1H-oxazolo[3,4-a]pyridin-3(5H)-one (50 mg, 0.13 mmol). The mixture was refluxed for 18 h. The mixture was partitioned with DCM/i-PrOH (8 mL×4) and H₂O (40 ml). The organic layer was dried over $Na_2SO_4$, filtered, concentrated in vacuo to give (S)-1-((2S,5R)-5-(8-amino-1-bromoimidazo[1,5-a]pyrazin-3-yl)piperidin-2-yl)ethanol (33 mg, 71.7%) as a yellow solid. ¹H NMR (400 MHz, METHANOL-$d_4$) δ=7.55 (d, J=5.0 Hz, 1H), 6.99 (d, J=5.3 Hz, 1H), 3.60-3.52 (m, 1H), 3.28-3.22 (m, 1H), 3.21-3.11 (m, 1H), 2.87 (t, J=11.4 Hz, 1H), 2.52-2.42 (m, 1H), 2.18-2.07 (m, 1H), 1.92-1.77 (m, 2H), 1.40-1.26 (m, 2H), 1.23 (d, J=6.5 Hz, 3H).

Step 2: 1-bromo-3-((1S,6R,8aS)-3-imino-1-methylhexahydro-1H-oxazolo[3,4-a]pyridin-6-yl)imidazo[1,5-a]pyrazin-8-amine To the solution of (S)-1-((2S,5R)-5-(8-amino-1-bromoimidazo[1,5-a]pyrazin-3-yl)piperidin-2-yl)ethanol (33 mg, 0.088 mmol) in DMF (2 mL) at 0° C. was added BrCN (10.27 mg, 0.097 mmol) and $NaHCO_3$ (22.17 mg, 0.264 mmol). The mixture was stirred at r.t. for 1 h. The mixture was partitioned with DCM/i-PrOH (8 mL×8) and H₂O (40 ml). The organic layer was dried over $Na_2SO_4$, filtered, concentrated in vacuo to give 1-bromo-3-((1S,6R,8aS)-3-imino-1-methylhexahydro-1H-oxazolo[3,4-a]pyridin-6-yl)imidazo[1,5-a]pyrazin-8-amine (35 mg, 94.5%) as a yellow solid.

Intermediate 28

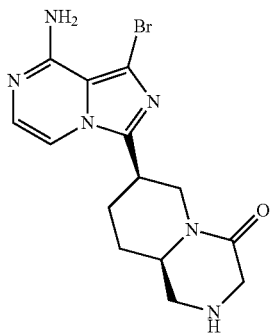 [SMILES: Nc1nccn2c([C@@H]3CC[C@@H]4CNCC(=O)N4C3)nc(Br)c12]

(7R,9aR)-7-(8-amino-1-bromoimidazo[1,5-a]pyrazin-3-yl)hexahydro-1H-pyrido[1,2-a]pyrazin-4(6H)-one

Step 1: (cis)-2-benzyl 7-methyl 4-oxohexahydro-1H-pyrido[1,2-a]pyrazine-2,7(6H)-dicarboxylate To a solution of methyl 6-((((benzyloxy)carbonyl)(2-methoxy-2-oxoethyl)amino)methyl)nicotinate (2.5 g, 6.7 mmol) in AcOH (25 mL) was added $NaBH_3CN$ (1.3 g, 20 mmol) portions at 10° C. The solution was stirred for overnight at room temperature. The reaction mixture was concentrated under reduced pressure to give to residue. The residue was dissolved in H2O (50 ml) was added aqueous NaHCO3 to pH=8, the mixture was extracted with EA (50 ml×3). The combined organic phase was washed with brine (100 mL), dried over Na2SO4, concentrated in vacuo to give crud methyl 6-((((benzyloxy)carbonyl)(2-methoxy-2-oxoethyl)amino)methyl)piperidine-3-carboxylate (2.8 g). The mixture of methyl 6-((((benzyloxy)carbonyl)(2-methoxy-2-oxoethyl)amino)methyl)piperidine-3-carboxylate (2.8 g, 7.9 mmol) in MeOH (30 mL) was stirred at 70° C. for 12 h under N2. Then the mixture was concentrated in vacuo, the residue was purified by silica gel column chromatography (PE/THF=1/1) to give (cis)-2-benzyl 7-methyl 4-oxohexahydro-1H-pyrido[1,2-a]pyrazine-2,7(6H)-dicarboxylate (0.8 g, yield 30%). ¹H NMR (400 MHz, METHANOL-d4) δ=7.38-7.33 (m, 5H), 5.16 (d, J=3.2 Hz, 2H), 4.85-4.80 (m, 1H), 4.15-4.07 (m, 2H), 3.95-3.93 (m, 1H), 3.91-3.70 (m, 3H), 3.44-3.42 (m, 2H), 2.67-2.61 (m, 1H), 2.47-2.44 (m, 1H), 2.17-2.13 (m, 1H), 1.82 (s, 1H), 1.69-1.65 (m, 1H), 1.62-1.42 (m, 1H).

Step 2: (cis)-2-((benzyloxy)carbonyl)-4-oxooctahydro-1H-pyrido[1,2-a]pyrazine-7-carboxylic acid To a solution of (cis)-2-benzyl 7-methyl 4-oxohexahydro-1H-pyrido[1,2-a]pyrazine-2,7(6H)-dicarboxylate (0.8 g, 2.3 mmol) in THF/H2O (1:1, 16 ml) was added LiOH.H2O (200 mg, 4.6 mmol) portionwise. The resulting solution was stirred at 25° C. for 12 h under N2. The reaction was acidified to pH=5 with HCl (1M), then extracted with DCM/i-PrOH (4/1, 30 mL×10). The combined organic layers were washed with brine, dried over sodium sulfate, filtered and concentrated to give (cis)-2-((benzyloxy)carbonyl)-4-oxooctahydro-1H-pyrido[1,2-a]pyrazine-7-carboxylic acid (700 mg, yield 92.1%). ¹H NMR (400 MHz, METHANOL-d4) δ=7.40-7.32 (m, 5H), 5.16-5.14 (m, 2H), 4.18-3.89 (m, 4H), 2.94-2.74 (m, 2H), 2.23-2.20 (m, 1H), 1.93-1.89 (m, 1H), 1.62-1.49 (m, 2H).

Step 3: (cis)-2-((benzyloxy)carbonyl)-4-oxooctahydro-1H-pyrido[1,2-a]pyrazine-7-carboxylic acid A mixture of (cis)-2-((benzyloxy)carbonyl)-4-oxooctahydro-1H-pyrido[1,2-a]pyrazine-7-carboxylic acid (0.7 g, 2.1 mmol), (3-chloropyrazin-2-yl)methanamine hydrochloride (450 mg, 2.5 mmol), HATU (1.2 g, 3.1 mmol) and TEA (0.85 g, 8.4 mmol) in DMF (10 mL) was stirred at 25° C. for overnight. Then the reaction mixture was poured into water, the mixture was extracted with EA (50 ml×3). The combined organic phase was washed with brine (100 mL), dried over Na2SO4, concentrated in vacuo, the residue was purified by silica gel column chromatography (PE/THF=1/3) to give (cis)-benzyl 7-(((3-chloropyrazin-2-yl)methyl)carbamoyl)-4-oxohexahydro-1H-pyrido[1,2-a]pyrazine-2(6H)-carboxylate (440 mg, yield 45.8%).

Step 4: Cis-(7S,9aS)-benzyl7-(8-chloroimidazo[1,5-a]pyrazin-3-yl)-4-oxohexahydro-1H-pyrido[1,2-a]pyrazine-2(6H)-carboxylate To a solution of (7S,9aS)-benzyl 7-(((3-chloropyrazin-2-yl)methyl)carbamoyl)-4-oxohexahydro-1H-pyrido[1,2-a]pyrazine-2(6H)-carboxylate (1.32 g, 2.88 mmol) in anhydrous DCM (15 mL) was added dimethylformamide (35.77 mg, 0.49 mmol), Pyridine (2.27 g, 28.8 mmoL), followed by POCl3 (2.16 g, 14.4 mmol) at an ice-water bath. The resulting mixture was stirred at 20° C. for 3 h. The mixture was poured to an ice-water mixture, neutralized with powered sodium bicarbonate, extracted with DCM (10 mL×3).

The organic layer was washed with brine, dried over Na2SO4, concentrated. The crude product was purified by column chromatography on silica gel eluted with PE/THF (0-80%) to give Cis-(7S,9aS)-benzyl 7-(8-chloroimidazo[1,5-a]pyrazin-3-yl)-4-oxohexahydro-1H-pyrido[1,2-a]pyrazine-2(6H)-carboxylate (0.15 g, 11.8%) as a white solid. $^1$H NMR (400 MHz, CHLOROFORM-d) δ=8.76 (s, 1H), 7.81 (s, 1H), 7.72 (d, J=4.8 Hz, 1H), 7.43-7.28 (m, 5H), 5.62-5.53 (m, 1H), 5.17 (s, 2H), 4.99-4.86 (m, 1H), 4.21 (br. s, 1H), 3.98-3.92 (m, 3H), 3.60-3.49 (m, 1H), 3.16-3.00 (m, 1H), 2.89-2.70 (m, 1H), 2.28-2.20 (m, 1H), 2.08-2.01 (m, 1H), 2.00-1.93 (m, 1H).

Step 5: Cis-(7S,9aS)-benzyl7-(1-bromo-8-chloroimidazo[1,5-a]pyrazin-3-yl)-4-oxohexahydro-1H-pyrido[1,2-a]pyrazine-2(6H)-carboxylate N-bromosuccinimide (86.91 mg, 0.49 mmol) was added to a solution of racemic-(7S,9aS)-benzyl7-(8-chloroimidazo[1,5-a]pyrazin-3-yl)-4-oxohexahydro-1H-pyrido[1,2-a]pyrazine-2(6H)-carboxylate (180 mg, 0.409 mmol) in DMF (5 mL) was stirred at 25° C. for 1.5 h under N2. The reaction was partitioned with H2O (30 mL) and EA (10 mL×3). The organic layer was washed with brine, dried over Na2SO4, concentrated to afford Cis-(7S,9aS)-benzyl 7-(1-bromo-8-chloroimidazo[1,5-a]pyrazin-3-yl)-4-oxohexahydro-1H-pyrido[1,2-a]pyrazine-2(6H)-carboxylate (166 mg, 78.6%) as a light yellow solid. $^1$H NMR (400 MHz, CHLOROFORM-d) δ=7.69 (d, J=5.0 Hz, 1H), 7.46-7.31 (m, 6H), 5.17 (s, 2H), 4.88 (dd, J=2.3, 13.1 Hz, 1H), 4.29-4.16 (m, 1H), 3.98-3.82 (m, 1H), 3.78-3.74 (m, 1H), 3.65-3.61 (m, 1H), 3.60-3.46 (m, 2H), 3.11-2.99 (m, 1H), 2.90-2.71 (m, 1H), 2.30-2.17 (m, 1H), 1.71-1.51 (m, 2H).

Step 6: Cis-(7S,9aS)-benzyl7-(8-amino-1-bromoimidazo[1,5-a]pyrazin-3-yl)-4-oxohexahydro-1H-pyrido[1,2-a]pyrazine-2(6H)-carboxylate To a solution of (7S,9aS)-benzyl 7-(1-bromo-8-chloroimidazo[1,5-a]pyrazin-3-yl)-4-oxohexahydro-1H-pyrido[1,2-a]pyrazine-2(6H)-carboxylate (166 mg, 0.32 mol) in NH4OH (6 mL) and i-PrOH (4 mL) was stirred at 100° C. for 12 h in sealed tube. Then the reaction was concentrated under reduced pressure to give Cis-(7S,9aS)-benzyl 7-(8-amino-1-bromoimidazo[1,5-a]pyrazin-3-yl)-4-oxohexahydro-1H-pyrido[1,2-a]pyrazine-2(6H)-carboxylate (140 mg, 88.05%) as a yellow solid. LCMS: Retention time: 0.692 min, (M+H)+ m/z: 498.9.

(a) (7R,9aR)-benzyl7-(8-amino-1-bromoimidazo[1,5-a]pyrazin-3-yl)-4-oxohexahydro-1H-pyrido[1,2-a]pyrazine-2(6H)-carboxylate The racemic (7S,9aS)-benzyl 7-(8-amino-1-bromoimidazo[1,5-a]pyrazin-3-yl)-4-oxohexahydro-1H-pyrido[1,2-a]pyrazine-2(6H)-carboxylate was purified by SFC to give (7R,9aR)-benzyl 7-(8-amino-1-bromoimidazo[1,5-a]pyrazin-3-yl)-4-oxohexahydro-1H-pyrido[1,2-a]pyrazine-2(6H)-carboxylate (38 mg) (Ret. time=7.07 min) as a yellow solid. The chiral HPLC condition was [Instrument: Thar 80; Column: OD250 mm*20 mm, 10 um; Mobile phase: A: Supercritical CO2, B: EtOH (0.05% NH3H2O), A:B=55:45 at 80 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm]. $^1$H NMR (400 MHz, CHLOROFORM-d) δ=7.44-7.31 (m, 5H), 5.47 (br. s, 1H), 5.16 (s, 2H), 5.00-4.81 (m, 1H), 4.20 (d, J=7.8 Hz, 1H), 3.93 (br. s, 1H), 3.77 (d, J=4.0 Hz, 1H), 3.64 (d, J=4.3 Hz, 1H), 3.52 (br. s, 2H), 3.06-2.94 (m, 1H), 2.84-2.71 (m, 1H), 1.64-1.52 (m, 2H).

(b) (7R,9aR)-7-(8-amino-1-bromoimidazo[1,5-a]pyrazin-3-yl)hexahydro-1H-pyrido[1,2-a]pyrazin-4(6H)-one The solution of (7R,9aR)-benzyl 7-(8-amino-1-bromoimidazo[1,5-a]pyrazin-3-yl)-4-oxohexahydro-1H-pyrido[1,2-a]pyrazine-2(6H)-carboxylate (38 mg, 0.076 mmol) in HBr/AcOH (1.5 mL) was stirred at 20° C. for 40 min. The mixture was recrystallied with 2-isopropoxypropane, The solid was collected and washed with sat.aq.NaHCO3 (30 mL), extracted with DCM (7 mL×3). The organic layer was dried over Na2SO4, concentrated to afford (7R,9aR)-7-(8-amino-1-bromoimidazo[1,5-a]pyrazin-3-yl)hexahydro-1H-pyrido[1,2-a]pyrazin-4(6H)-one (6 mg, 21.5%) as a light yellow solid.

Intermediate 29

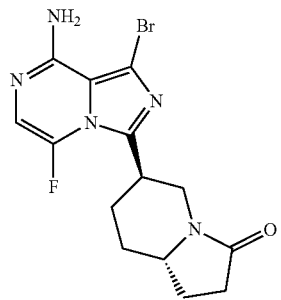 [SMILES: Nc1ncc(F)n2c([C@@H]3CC[C@H]4CCC(=O)N4C3)nc(Br)c12]

(6R,8aS)-6-(8-amino-1-bromo-5-fluoroimidazo[1,5-a]pyrazin-3-yl)hexahydroindolizin-3(2H)-one Step 1: (6R,8aS)-6-(8-amino-1-bromo-5-fluoro-6-methoxy-5,6-dihydroimidazo[1,5-a]pyrazin-3-yl)hexahydroindolizin-3 (2H)-one 1-chloromethyl-4-fluoro-1,4-diazoniabicyclo[2.2.2]octanbis(tetrafluoroborate) (2.62 g, 7.40 mmol) was added to a stirred mixture of(6R,8aS)-6-(8-amino-1-bromoimidazo[1,5-a]pyrazin-3-yl)hexahydroindolizin-3(2H)-one (2.16 g, 6.17 mmol) in MeOH (25 ml) and acetonitrile (25 ml) in 250 ml round bottom flask. The mixture was stirred at room temperature for overnight and then concentrated. The residue was purified by column chromatography on silica gel (ISCO 80 g), eluting with CH2Cl2/MeOH (10/1) to give ((6R,8aS)-6-(8-amino-1-bromo-5-fluoro-6-methoxy-5,6-dihydroimidazo[1,5-a]pyrazin-3-yl)hexahydroindolizin-3 (2H)-one (2.4 g, 6.00 mmol, 97% yield) as a white foam solid.

Step 2: (6R,8aS)-6-(8-amino-1-bromo-5-fluoroimidazo[1,5-a]pyrazin-3-yl)hexahydroindolizin-3 (2H)-one To 20 ml microwave reaction vessel was charged a mixture of (6R,8aS)-6-(8-amino-1-bromo-5-fluoro-6-methoxy-5,6 dihydroimidazo[1,5-a]pyrazin-3-yl)hexahydroindolizin-3(2H)-one (300 mg, 0.750 mmol) in pyridine (8 ml). The mixture was stirred under microwave irradiation at 180° C. for 15 min. and then concentrated. The residue was purified by column chromatography on silica gel (ISCO 80 g), eluting with $CH_2Cl_2$/MeOH (20/1) to give (6R,8aS)-6-(8-amino-1-bromo-5-fluoroimidazo[1,5-a]pyrazin-3-yl)hexahydroindolizin-3(2H)-one (112 mg, 0.304 mmol, 40.6% yield) as a white solid. LC-MS: C14H15BrFN5O, found [M+H]+ 370.0. LC-MS method E Ret. time=0.91 min.

Intermediate 30

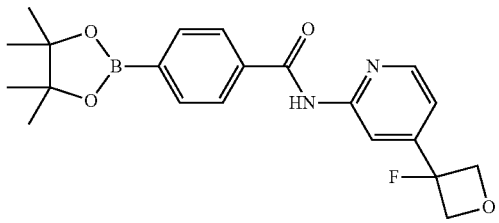 [SMILES: CC1(C)OB(c2ccc(C(=O)Nc3cc(C4(F)COC4)ccn3)cc2)OC1(C)C]

N-(4-(3-fluorooxetan-3-yl)pyridin-2-yl)-4-(4,4,5,5-tetramethyl-1,3,2-dioxaborolan-2-yl)benzamide (a) 3-(2-chloropyridin-4-yl)oxetan-3-ol To a solution of 2-chloro-4-iodopyridine (1.0 g, 4.18 mmol) in anhydrous THF (10 mL) was added n-BuLi (3.34 mL, 8.35 mmol) at −78° C. The mixture was stirred at −78° C. for 20 mins. Then oxetan-3-one (361 mg, 5.01 mmol) was added at −78° C. and the mixture was stirred at −78° C. for 50 mins. The mixture was quenched with saturated $NH_4Cl$ (10 mL) and extracted with ethyl acetate (100 mL×3). The combined organic layers were washed with brine, dried over sodium sulfate, filtered and concentrated to afford the crude product, which was purified on silica gel chromatography (EA:PE=5%~40%) to afford 3-(2-chloropyridin-4-yl)oxetan-3-01(620 mg, yield 86%) as a yellow solid. (ESI): M/Z (M+1): 352 (Condition: 0-60AB_3 MIN; R.T.: 1.303).

(b) 2-chloro-4-(3-fluorooxetan-3-yl)pyridine

To a solution of 3-(2-chloropyridin-4-yl)oxetan-3-ol (650 mg, 3.50 mmol) in dichloromethane (10 mL) was added DAST (847 mg, 5.25 mmol) at −78° C. The resulting mixture was stirred at −78° C. for 3 hrs and then warmed to room temperature and stirred for another 12 hours. The mixture was quenched by the addition of Sat. $NaHCO_3$ and extracted with dichloromethane (50 mL×3). The combined organic layers were washed with brine, dried over sodium sulfate, filtered and concentrated to afford the crude product, which was purified on silica gel chromatography (EA:PE=10%~50%) to give 2-chloro-4-(3-fluorooxetan-3-yl)pyridine(120 mg, yield 18%) as a yellow solid. (ESI): M/Z (M+1): 188.0 (LC-MS method C; R.T.: 0.597).

(c) N-(4-(3-fluorooxetan-3-yl)pyridin-2-yl)-4-(4,4,5,5-tetramethyl-1,3,2-dioxaborolan-2-yl)benzamide To a clear solution of 2-chloro-4-(3-fluorooxetan-3-yl)pyridine(120 mg, 0.64 mmol) and 4-(4,4,5,5-tetramethyl-1,3,2-dioxaborolan-2-yl)benzamide(174 mg, 0.70 mmol) in dioxane (6 mL) was added xant-Phos (catalytic amount) followed by Pd(pddf)Cl₂ (catalytic amount) under a stream of nitrogen. Then the mixture was heated to 100° C. and stirred for 12 hours. The reaction mixture was then cooled to room temperature and filtered. The filtrate was concentrated in vacuum and purified on silica gel chromatography (EA:PE=5% 40%) to give N-(4-(3-fluorooxetan-3-yl)pyridin-2-yl)-4-(4,4,5,5-tetramethyl-1,3,2-dioxaborolan-2-yl)benzamide(70 mg, yield 27%) as a yellow solid. (ESI): M/Z (M+1): 399.1 (LC-MS method C; R.T.: 0.897).

Intermediate 31

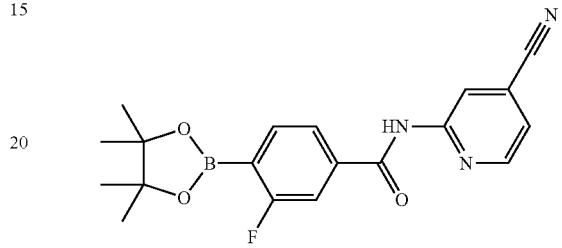

N-(4-cyanopyridin-2-yl)-3-fluoro-4-(4,4,5,5-tetramethyl-1,3,2-dioxaborolan-2-yl)benzamide (a) tert-butyl (4-cyanopyridin-2-yl)carbamate A degassed mixture of 2-chloroisonicotinonitrile (10 g, 72.2 mmol), Carbamic acid tert-butyl ester (10.15 g, 86.6 mmol), $Cs_2CO_3$ (47 g, 144.4 mmol), X-phos (4.3 g, 9.02 mmol) and Pd(OAc)₂ (810 mg, 3.6 mmol) in 150 mL of 1,4-dioxane was stirred at 80° C. for 2.5 hrs under a stream of N₂. The mixture was cooled to room temperature and filtered. The filtrate was concentrated under vacuum to give a crude product, which was purified by silica gel column chromatography (PE:EA=20~50%) to give tert-butyl (4-cyanopyridin-2-yl)carbamate (12.0 g, yield: 76%). ¹HNMR(400 MHz, $CDCl_3$): δ=9.14 (br. s, 1H), 8.46 (dd, J=0.8, 5.3 Hz, 1H), 8.34 (s, 1H), 7.16 (dd, J=1.4, 5.1 Hz, 1H), 1.56 (s, 9H). MS (ESI): M/Z (M+1): 220.1.

(b) 2-aminoisonicotinonitrile

To a solution of tert-butyl (4-cyanopyridin-2-yl)carbamate (6.5 g, 29.6 mmol) in 60 mL of DCM was added 20 mL of trifluoroacetic acid. The reaction was stirred at r.t. for 2 hrs, and then concentrated to dryness under vacuum. Aq. $NaHCO_3$ (10 mL) was added and extracted with EA (20 mL*3). The organic layer was washed with brine (20 mL), dried over $Na_2SO_4$ and concentrated under vacuum to give 3.5 g crude of compound 2-aminoisonicotinonitrile. ¹HNMR(400 MHz, $CDCl_3$): δ=8.20 (d, J=5.3 Hz, 1H), 6.82 (dd, J=1.0, 5.3 Hz, 1H), 6.69 (s, 1H), 4.77 (br. s, 2H). MS (ESI): M/Z (M+1): 120.1.

(c) 4-bromo-N-(4-cyanopyridin-2-yl)-3-fluorobenzamid

To a solution of 4-bromo-3-fluorobenzoic acid (8.2 g, 37.7 mmol) in 80 mL of DCM was added Oxalyl dichloride (14.4 g, 113.1 mmol) and 8 drops of DMF at 0° C. After stirring for 1 h, the mixture was concentrated under vacuum and dissolved in 70 mL of THF, and added to a solution of compound 2-aminoisonicotinonitrile (5.4 g, 45.3 mmol) in 90 mL of THF at 0° C. The reaction was stirred at 30° C. for 12 hrs. The mixture was filtered and the filtrate was concentrated under vacuum to give a crude product. The crude product was purified by silica gel column chromatography (PE:EA=20-60%) to give 4-bromo-N-(4-cyanopyridin-2-yl)-3-fluorobenzamide (4.7 g, yield: 39.2%). $^1$HNMR (300 MHz, DMSO-d6): δ=11.46 (s, 1H), 8.67 (d, J=5.1 Hz, 1H), 8.48 (s, 1H), 8.02 (dd, J=2.0, 9.7 Hz, 1H), 7.94-7.86 (m, 1H), 7.85-7.80 (m, 1H), 7.66 (dd, J=1.3, 4.9 Hz, 1H). MS (ESI): M/Z (M+2): 320.9.

(d) N-(4-cyanopyridin-2-yl)-3-fluoro-4-(4,4,5,5-tetramethyl-1,3,2-dioxaborolan-2-yl)benzamide A degassed mixture of 4-bromo-N-(4-cyanopyridin-2-yl)-3-fluorobenzamide (900 mg, 2.8 mmol), Bispinacolatodiboron (929 mg, 3.65 mmol), KOAc (824 mg, 8.4 mmol), and Pd(dppf)Cl$_2$ (143 mg, 0.2 mmol) in 15 mL of 1,4-dioxane was stirred at 90° C. for 12 hrs under a stream of N$_2$. The mixture was cooled to room temperature and H$_2$O (10 mL) was added. It was then extracted with ethyl acetate (15 mL*3). The organic layers were washed with brine (20 mL), dried over Na$_2$SO$_4$, and concentrated under vacuum to give a crude product, which was purified by silica gel column chromatography (PE:EA=20~80%) to give N-(4-cyanopyridin-2-yl)-3-fluoro-4-(4,4,5,5-tetramethyl-1,3,2-dioxaborolan-2-yl)benzamide (700 mg, yield: 68%).
$^1$HNMR (400 MHz, CDCl$_3$): δ=8.72 (s, 1H), 8.70 (s, 1H), 8.48 (dd, J=0.8, 5.0 Hz, 1H), 7.89 (dd, J=5.8, 7.8 Hz, 1H), 7.66 (dd, J=1.5, 7.5 Hz, 1H), 7.61 (dd, J=1.4, 9.4 Hz, 1H), 7.32 (dd, J=1.3, 5.0 Hz, 1H), 1.39 (s, 12H). MS (ESI): M/Z (M+1): 368.2.

Intermediate 32

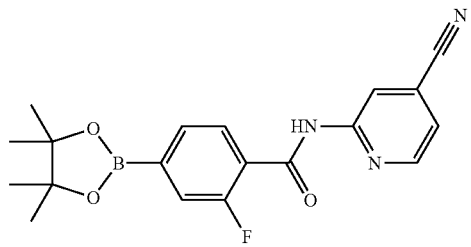 [SMILES: CC1(C)OB(c2ccc(C(=O)Nc3cc(C#N)ccn3)c(F)c2)OC1(C)C]

N-(4-cyanopyridin-2-yl)-2-fluoro-4-(4,4,5,5-tetramethyl-1,3,2-dioxaborolan-2-yl)benzamide (a) 4-bromo-N-(4-cyanopyridin-2-yl)-2-fluorobenzamide To a solution of 4-bromo-2-fluorobenzoic acid (3.03 g, 13.8 mmol) in anhydrous DMF (30 mL) was added HATU (5.25 g, 13.8 mmol), and stirred at 30° C. for 30 min. Tri-ethylamine (3.8 g, 37.8 mmol) was added, followed by 2-aminoisonicotinonitrile (1.5 g, 12.6 mmol. The mixture was stirred at 30° C. for 12 hrs. H$_2$O (50 mL) was added, and the mixture was extracted with ethyl acetate (50 mL*3). The organic layers were washed with brine(20 mL), dried over Na$_2$SO$_4$ evaporated, and purified by flash chromatography (PE:EA=20~60%) to get the compound 4-bromo-N-(4-cyanopyridin-2-yl)-2-fluorobenzamide (1.56 g, yield: 39%).

$^1$HNMR (400 MHz, CDCl$_3$): δ=8.71 (s, 1H), 8.50 (d, J=4.5 Hz, 1H), 8.03 (t, J=8.4 Hz, 1H), 7.89 (t, J=8.2 Hz, 1H), 7.51 (dd, J=1.6, 8.4 Hz, 1H), 7.46-7.42 (m, 1H), 7.33 (dd, J=1.4, 5.1 Hz, 1H). MS (ESI): M/Z (M+2): 320.9.

(b) N-(4-cyanopyridin-2-yl)-2-fluoro-4-(4,4,5,5-tetramethyl-1,3,2-dioxaborolan-2-yl)benzamide A degassed mixture of 4-bromo-N-(4-cyanopyridin-2-yl)-2-fluorobenzamide (1.2 g, 3.7 mmol), Bispinacolatodiboron (1.2 g, 4.8 mmol), KOAc (1.1 g, 11.2 mmol), Cy$_3$P (84 mg, 0.3 mmol), and Pd(OAc)$_2$ (67 mg, 0.3 mmol) in 30 mL of 1,4-dioxane was stirred at 90° C. for 12 hrs. The mixture was cooled to room temperature and H$_2$O (50 mL) added. The mixture was extracted with ethyl acetate (50 mL*3). The organic layer was washed with brine(50 mL), dried over Na$_2$SO$_4$, concentrated under vacuum to give a crude product, which was then purified by flash chromatography (PE:EA=20~60%) to give the compound N-(4-cyanopyridin-2-yl)-3-fluoro-4-(4,4,5,5-tetramethyl-1,3,2-dioxaborolan-2-yl)benzamide (500 mg, yield: 38%). $^1$HNMR (400 MHz, CDCl$_3$): δ=8.72 (s, 1H), 8.49 (d, J=5.0 Hz, 1H), 8.12 (t, J=7.7 Hz, 1H), 7.73 (d, J=7.8 Hz, 1H), 7.62 (d, J=12.0 Hz, 1H), 7.37 (s, 1H), 7.31 (d, J=4.0 Hz, 1H), 1.36 (s, 12H). MS (ESI): M/Z (M+1)$^+$: 368.2.

Intermediate 33

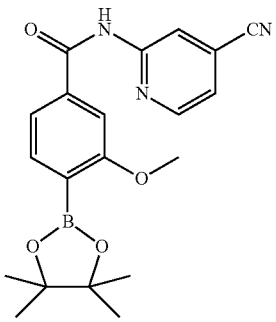 [SMILES: COc1cc(C(=O)Nc2cc(C#N)ccn2)ccc1B1OC(C)(C)C(C)(C)O1]

N-(4-cyanopyridin-2-yl)-3-methoxy-4-(4,4,5,5-tetramethyl-1,3,2-dioxaborolan-2-yl)benzamide (a) 4-bromo-N-(4-cyanopyridin-2-yl)-3-methoxybenzamide To the solution of 2-aminoisonicotinonitrile (1.4 g, 11.75 mmol) in toluene (60 mL) was added Al(Me)$_3$ (5.87 ml, 11.75 mmol) at room temperature. After stirring for 30 min, methyl 4-bromo-3-methoxybenzoate (2.88 g, 11.75 mmol) was added. The reaction was refluxed for 3 h. The mixture was quenched with 1N HCl and partitioned with H$_2$O (45 mL) and EA (10 mL*3). The EA layer was dried, filtered, concentrated, and purified by column chromatography on silica gel (PE:EA=0-60%) to give 4-bromo-N-(4-cyanopyridin-2-yl)-3-methoxybenzamide (2.55 g, 65.38%) as a white solid. $^1$H NMR (400 MHz, CDCl$_3$) δ=8.69 (s, 1H), 8.65 (br. s, 1H), 8.49 (dd, J=0.8, 5.0 Hz, 1H), 7.69 (d, J=8.0 Hz, 1H), 7.51 (d, J=2.0 Hz, 1H), 7.33-7.29 (m, 2H), 4.01 (s, 3H).

(b) N-(4-cyanopyridin-2-yl)-3-methoxy-4-(4,4,5,5-tetramethyl-1,3,2-dioxaborolan-2-yl)benzamide To the solution of 4-bromo-N-(4-cyanopyridin-2-yl)-3-methoxybenzamide (2.55 g, 7.68 mmol) in dioxane (50 ml)

was added 4,4,4',4',5,5,5',5'-octamethyl-2,2'-bi(1,3,2-dioxaborolane) (2.92 g, 11.52 mmol), KOAc (2.25 g, 23.04 mmol), and Pd(dppf)Cl₂ (0.275 g, 0.38 mmol). The mixture was purged with N₂ and stirred at 90° C. for 2 h. The mixture was partitioned with H₂O (85 mL) and EA (20 mL*3). The EA layer was purified by column chromatography on silica gel (PE:EA=0-55%) to give N-(4-cyanopyridin-2-yl)-3-methoxy-4-(4,4,5,5-tetramethyl-1,3,2-dioxaborolan-2-yl)benzamide (0.99 g, 34%) as a white solid. ¹H NMR (400 MHz, CDCl₃) δ=8.83-8.63 (m, 2H), 8.47 (dd, J=0.8, 5.0 Hz, 1H), 7.78 (d, J=7.5 Hz, 1H), 7.45 (d, J=1.3 Hz, 1H), 7.39 (dd, J=1.4, 7.7 Hz, 1H), 7.30 (dd, J=1.3, 5.0 Hz, 1H), 3.93 (s, 3H), 1.38 (s, 12H).

Intermediate 34

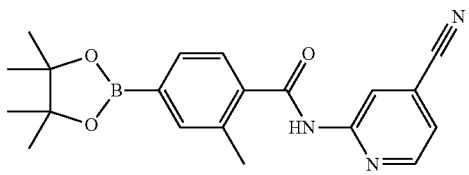 [SMILES: Cc1cc(B2OC(C)(C)C(C)(C)O2)ccc1C(=O)Nc1cc(C#N)ccn1]

N-(4-cyanopyridin-2-yl)-2-methyl-4-(4,4,5,5-tetramethyl-1,3,2-dioxaborolan-2-yl)benzamide 2-methyl-4-(4,4,5,5-tetramethyl-1,3,2-dioxaborolan-2-yl)benzamide (2.4 g, 9.19 mmol) was prepared following the same procedure as in Intermediate 33. To a clear solution of 2-methyl-4-(4,4,5,5-tetramethyl-1,3,2-dioxaborolan-2-yl)benzamide (2.4 g, 9.19 mmol) and 2-chloroisonicotinonitrile (1.4 g, 10.11 mmol) in dioxane (50 mL) was added xantPhos (catalytic amount) followed by Pd(pddf)Cl₂ (336 mg, 0.46 mmol) under a stream of nitrogen. Then the mixture was heated to 100° C. and stirred for 12 hours. The mixture was then cooled to room temperature and filtered. The filtrate was concentrated under vacuum and purified on silica gel chromatography (EA:PE=5%~40%) to give N-(4-cyanopyridin-2-yl)-2-methyl-4-(4,4,5,5-tetramethyl-1,3,2-dioxaborolan-2-yl)benzamide (1.4 g, yield 42%) as a yellow solid. ¹H NMR (400 MHz, CD₃OD) δ=8.58 (s, 1H), 8.53 (d, J=5.0 Hz, 1H), 7.70-7.63 (m, 2H), 7.50 (d, J=7.3 Hz, 1H), 7.43 (dd, J=1.3, 5.0 Hz, 1H), 2.47 (s, 3H), 1.36 (s, 12H).

Intermediate 35

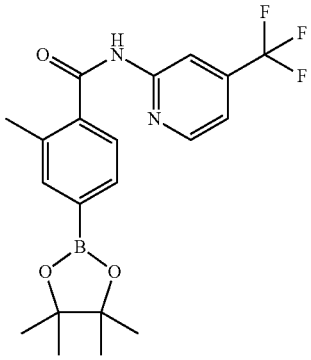 [SMILES: Cc1cc(B2OC(C)(C)C(C)(C)O2)ccc1C(=O)Nc1cc(C(F)(F)F)ccn1]

2-methyl-4-(4,4,5,5-tetramethyl-1,3,2-dioxaborolan-2-yl)-N-(4-(trifluoromethyl)pyridin-2-yl)benzamide (a) 4-bromo-2-methyl-N-(4-(trifluoromethyl)pyridin-2-yl)benzamide To a solution of 4-bromo-2-methylbenzoic acid (5 g, 0.023 mmol) in dichloromethane(50 mL) was added (COCl)₂(8.85 g, 0.069 mmol) at 0° C. The mixture was stirred at room temperature. for 2 hours and then evaporated and dissolved in tetrahydrofuran(100 mL). 4-(trifluoromethyl)pyridin-2-amine (7.5 g, 0.046 mmol) was added portionwise at 0° C. The reaction mixture was stirred at 80° C. overnight. The mixture was cooled to room temperature and filtered the filtrate was concentrated to dryness to give 4-bromo-2-methyl-N-(4-(trifluoromethyl)pyridin-2-yl)benzamide. (6 g, yield 70%). (ESI): M/Z (M+1): M/Z (M+3) 361: (M+1) 359 (LC-MS method C; R.T.: 0.904).

(b) 2-methyl-4-(4,4,5,5-tetramethyl-1,3,2-dioxaborolan-2-yl)-N-(4-(trifluoromethyl)pyridin-2-yl)benzamide To a degassed mixture of 4-bromo-2-methyl-N-(4-(trifluoromethyl)pyridin-2-yl)benzamide (3 g, 8.356 mmol) and 4,4,4',4',5,5,5',5'-octamethyl-2,2'-bi(1,3,2-dioxaborolane) (2.5 g, 9.8 mmol) in dioxane(50 mL) was added Pd(dppf)Cl2(catalytic amount) and KOAc (2.45 g, 25 mmol) under N₂. The mixture was heated to 100° C. and stirred for 3 hour. The reaction mixture was cooled to room temperature and concentrated under vacuum to give a crude product, which was and purified on silica gel chromatography (PE: EA=100%~80%) to afford 2-methyl-4-(4,4,5,5-tetramethyl-1,3,2-dioxaborolan-2-yl)-N-(4-(trifluoromethyl)pyridin-2-yl)benzamide (3 g, yield 88%).

¹H NMR (400 MHz, DMSO-d6): δ=11.31 (s, 1H), 8.63 (d, J=5.3 Hz, 1H), 8.52 (s, 1H), 7.92 (s, 1H), 7.59-7.47 (m, 4H), 2.38 (s, 3H), 1.31-1.27 (m, 13H). MS (ESI): M/Z (M+1): 407.1.

Intermediate 36

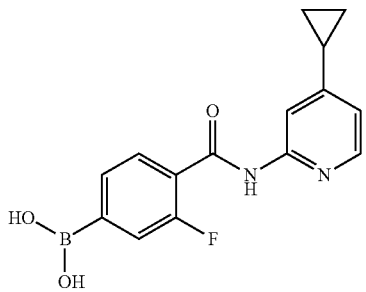 [SMILES: O=C(Nc1cc(C2CC2)ccn1)c1ccc(B(O)O)cc1F]

(4-((4-cyclopropylpyridin-2-yl)carbamoyl)-3-fluorophenyl)boronic acid

To a solution of 4-cyclopropylpyridin-2-amine (0.5 g, 3.7 mmol) and 4-borono-2-fluorobenzoic acid (0.7 g, 4.1 mmol) in 5 mL of DMF was added DIEA (0.95 g, 7.5 mmol). After stirring for 5 min at 0° C., HATU (1.56 g, 4.1 mmol) was added, and the resulting mixture was stirred at room temperature overnight, and then stirred at 80° C. for 5 hours. The reaction mixture was cooled to room temperature and treated with water and extracted with EA. The combined organic layers were washed with brine, dried over anhydrous Na₂SO₄ and concentrated under vacuum to give a crude residue. The residue was purified by column chromatography on silica gel (EA/MeOH=20/1) to afford (4-((4-cyclopropylpyridin-2-yl)carbamoyl)-3-fluorophenyl)boronic acid (0.7 g, yield 63.6%). MS-ESI (m/z): 301 (M+1)+ (LC-MS method C; Ret. time: 0.98 min).

Intermediate 37

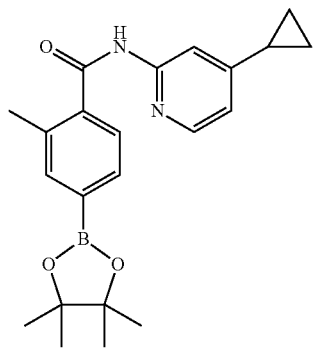 [SMILES: Cc1cc(B2OC(C)(C)C(C)(C)O2)ccc1C(=O)Nc1cc(C2CC2)ccn1]

N-(4-cyclopropylpyridin-2-yl)-2-methyl-4-(4,4,5,5-tetramethyl-1,3,2-dioxaborolan-2-yl)benzamide (a) 4-bromo-2-methylbenzamide To a solution of 4-bromo-2-methylbenzoic acid (8 g, 0.037 mmol) in dichloromethane(80 mL) was added (COCl)₂(9.4 mL) at 0° C. The mixture was stirred at room temperature for 2 hours and then evaporated to dryness under vacuum and dissolved in dichloromethane(80 mL) and added to a solution of NH₄OH (4.2 g, 0.09 mmol) in dichloromethane(20 mL) at 0° C. The reaction mixture was stirred at 25° C. for 1 h and filtered. The filtrate was dried to give 4-bromo-2-methylbenzamide (8 g, yield 100%). (ESI): M/Z (M+1): M/Z (M+3) 216: (M+1) 214 (LC-MS method C; R.T.: 0.647).

(b) 2-methyl-4-(4,4,5,5-tetramethyl-1,3,2-dioxaborolan-2-yl)benzamide

To a degassed mixture of 4-bromo-2-methylbenzamide (5 g, 0.023 mmol) and 4,4,4',4',5,5,5',5'-octamethyl-2,2'-bi(1,3,2-dioxaborolane) (6.5 g, 0.025 mmol) in dioxane(100 mL) was added Pd(dppf)Cl₂(950 mg, 0.002 mmol) and KOAc (6.8 g, 0.069 mmol) under N₂. The mixture was heated to 100° C. and stirred for 3 hours. The reaction mixture was cooled to room temperature and concentrated to dryness under vacuum to give a crude product, which was purified on silica gel chromatography (PE:EA=100%~60%) to afford 2-methyl-4-(4,4,5,5-tetramethyl-1,3,2-dioxaborolan-2-yl)benzamide (3.6 g, yield 60%). ¹H NMR (400 MHz, CD₃OD): δ=7.66-7.59 (m, 1H), 7.41 (d, J=7.5 Hz, 1H), 2.45 (s, 3H), 1.40-1.33 (m, 12H). MS (ESI): M/Z (M+1): 262.1.

(c) N-(4-cyclopropylpyridin-2-yl)-2-methyl-4-(4,4,5,5-tetramethyl-1,3,2-dioxaborolan-2-yl)benzamide To a degassed mixture of 2-methyl-4-(4,4,5,5-tetramethyl-1,3,2-dioxaborolan-2-yl)benzamide (3.5 g, 0.013 mol) and 2-chloro-4-cyclopropylpyridine (2.3 g, 0.015 mol) in dioxane(60 mL) was added Pd₂(dba)₃(614 mg, 0.65 mmol) Xant-phos (700 mg, 0.0013 mol) and Cs₂CO₃ (8.7 g, 0.026 mmol) under N₂. The mixture was stirred at 100° C. for 13 hours. The reaction was cooled to room temperature and concentrated to dryness—under vacuum to give a crude product, which was purified on silica gel chromatography (PE:EA=100%~70%) to afford N-(4-cyclopropylpyridin-2-yl)-2-methyl-4-(4,4,5,5-tetramethyl-1,3,2-dioxaborolan-2-yl)benzamide (1.5 g, yield 30%). ¹H NMR (400 MHz, CD₃OD) δ=8.10 (d, J=5.3 Hz, 1H), 7.93 (s, 1H), 7.70-7.63 (m, 2H), 7.48 (d, J=7.5 Hz, 1H), 6.87 (dd, J=1.4, 5.4 Hz, 1H), 2.46 (s, 4H), 2.02-1.93 (m, 1H), 1.36 (s, 15H), 1.17-1.11 (m, 2H), 0.90-0.83 (m, 2H). MS (ESI): M/Z (M+1): 379.2.

Intermediate 38

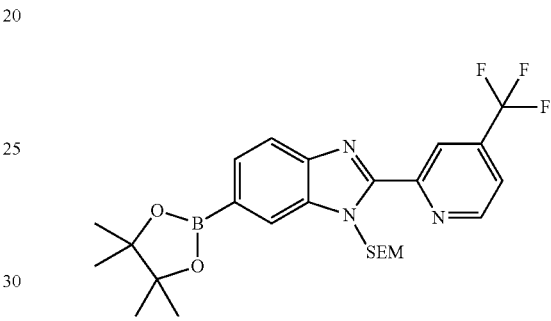

6-(4,4,5,5-tetramethyl-1,3,2-dioxaborolan-2-yl)-2-(4-(trifluoromethyl)pyridin-2-yl)-1-((2-(trimethylsilyl)ethoxy)methyl)-1H-benzo[d]imidazole (a) 4-(trifluoromethyl)-2-vinylpyridine A mixture of 2-chloro-4-(trifluoromethyl)pyridine (10 g, 55.2 mmol), potassium vinyl trifluoroborate (11 g, 82.8 mmol), Pd(dppf)Cl₂(500 mg) and K₂CO₃ (15.2 g, 110.4 mmol) in the mixed solvent of dioxane (150 mL) and H₂O (15 mL) was stirred at 110° C. for 1.5 hrs under a stream of N2. The reaction mixture was cooled to room temperature, filtered and evaporated to give a crude residue. The residue was purified by column chromatography on silica gel eluted with PE:EA=10:1 to afford 4-(trifluoromethyl)-2-vinylpyridine (4.5 g, 47.4%). MS-ESI (m/z): 174.0 (M+1)⁺ (LC-MS method C; Ret. time: 0.94 min).

(b) 4-(trifluoromethyl)picolinaldehyde

To a solution of 4-(trifluoromethyl)-2-vinylpyridine (4.5 g, 25.8 mmol) and OsO₄(60 mg, 2.58 mmol) in THF(50 mL) was added NaIO₄ (11 g, 51.4 mmol). The resulting mixture was stirred at room temperature for 3 hours. The mixture was treated with H₂O and extracted with EA. The EA layer was washed with brine, dried over Na₂SO₄, and filtered. The filtrate was distilled under normal pressure to give the crude 4-(trifluoromethyl)picolinaldehyde, which was used in the next step directly.

MS-ESI (m/z): 176.2 (M+1)⁺ (Acq Method: 10-80AB_2 min; Ret. time: 0.24 min)

(c) 6-bromo-2-(4-(trifluoromethyl)pyridin-2-yl)-1H-benzo[d]imidazole

To a solution of the crude of 4-(trifluoromethyl)picolinaldehyde and 4-bromobenzene-1,2-diamine (4.1 g, 22.7 mmol) in THF (200 mL) was added IBD (15 g, 45.3 mmol) under ice-bath. The mixture was stirred at this temperature for 0.5 hour. The solvent was removed under reduced pressure and the residue was dissolved in EA. The resulting solution was washed with water(30 mL×3), brine and dried over anhydrous Na₂SO₄. The organic phase was concentrated under reduced pressure to give a brick red residue, which was purified by column chromatography on silica gel (PE:EtOAc=5:1) to afford 6-bromo-2-(4-(trifluoromethyl)pyridin-2-yl)-1H-benzo[d]imidazole (4 g, two steps: 45.1%).

MS-ESI (m/z): 342.2 (M+1)$^+$ (LC-MS method C; Ret. time: 1.12 min)

(d) 6-bromo-2-(4-(trifluoromethyl)pyridin-2-yl)-1-((2-(trimethylsilyl)ethoxy)methyl)-1H-benzo[d]imidazole To a solution of 6-bromo-2-(4-(trifluoromethyl)pyridin-2-yl)-1H-benzo[d]imidazole (4 g, 9.3 mmol) in anhydrous THF (50 mL) was added NaH 60% in mineral oil (372 mg, 9.3 mmol) in portions. After the addition was completed, the mixture was stirred at 22° C. for 10 min. To the mixture was added (2-(chloromethoxy)ethyl)trimethylsilane (1.54 g, 9.3 mmol) dropwise, and the resulting mixture was stirred at 22° C. for a further 2 hours. The mixture was treated with water (50 mL) and extracted with EA (50 mL×3). The combined EA layer was washed with brine, dried over anhydrous Na₂SO₄ and concentrated under reduced pressure. The crude product was purified by column chromatography on silica gel (PE:EtOAc=10:1) to afford 6-bromo-2-(4-(trifluoromethyl)pyridin-2-yl)-1-((2-(trimethylsilyl)ethoxy)methyl)-1H-benzo[d]imidazole (4.38 g, 100%).

MS-ESI (m/z): 473.9 (M+1) (LC-MS method C; Ret. time: 1.38 min)

(e) 6-(4,4,5,5-tetramethyl-1,3,2-dioxaborolan-2-yl)-2-(4-(trifluoromethyl)pyridin-2-yl)-1-((2-(trimethylsilyl)ethoxy)methyl)-1H-benzo[d]imidazole A mixture of 6-bromo-2-(4-(trifluoromethyl)pyridin-2-yl)-1-((2-(trimethylsilyl)ethoxy)methyl)-1H-benzo[d]imidazole (4.38 g, 9.3 mmol), 4,4,4',4',5,5,5',5'-octamethyl-2,2'-bi(1,3,2-dioxaborolane) (2.6 g, 10.2 mmol), KOAc (2.23 g, 23.3 mmol), Pd2(dba)3 (446 mg, 0.76 mmol) and TCP (213 mg, 0.76 mmol) in dioxane (100 mL) was stirred at 110° C. for 2 hours under a stream of nitrogen. After cooling to room temperature, the mixture was filtered, and the filtrate was concentrated under vacuum to give a crude residue, which was purified by column chromatography on silica gel (PE:EtOAc=10:1) to afford the title product (4.5 g, 93.2%).

MS-ESI (m/z): 520.2 (M+1)$^+$ (LC-MS method C; Ret. time: 1.178 min)

Intermediate 39

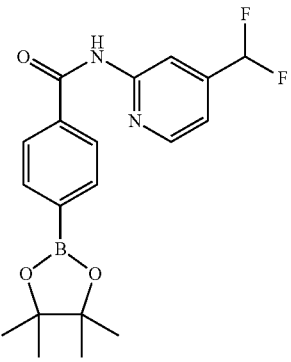 [SMILES: CC1(C)OB(c2ccc(C(=O)Nc3cc(C(F)F)ccn3)cc2)OC1(C)C]

N-(4-(difluoromethyl)pyridin-2-yl)-4-(4,4,5,5-tetramethyl-1,3,2-dioxaborolan-2-yl)benzamide

(a) 2-bromo-4-(difluoromethyl)pyridine

To a solution of 2-bromoisonicotinaldehyde (2 g, 10.752 mmol) in dichloromethane was added DAST(6.613 g, 32.257 mmol) at −78° C. The mixture was warmed to room temperature slowly in 2 hours. The reaction mixture was quenched with saturated sodium bicarbonate and extracted with dichloromethane. The combined organic layer was washed with brine, dried over anhydrous sodium sulfate and evaporated to give 2-bromo-4-(difluoromethyl)pyridine (2 g, yield 90%). $^1$HNMR (400 MHz, CDCl₃): δ=8.52-8.51 (d, J=8.0 Hz, 1 H), 7.63 (s, 1 H), 7.40-7.38 (d, J=8.0 Hz, 1 H), MS (ESI): M/Z (M+1)=207.95.

(b) N-(4-(difluoromethyl)pyridin-2-yl)-4-(4,4,5,5-tetramethyl-1,3,2-dioxaborolan-2-yl)benzamide To a degassed mixture of 4-(4,4,5,5-tetramethyl-1,3,2-dioxaborolan-2-yl)benzamide (1.5 g, 6.07 mmol) and 2-bromo-4-(difluoromethyl)pyridine(1.515 g, 7.284 mmol) in dioxane was added Pd₂(dba)₃(catalytic amount), X-phos (catalytic amount) and Cs₂CO₃ (3.956 g, 12.141 mmol) under N₂ atmosphere. The mixture was stirred at 100° C. overnight. The reaction mixture was cooled to room temperature and filtered. The filtrate was concentrated, and the residue was purified on silic-gel to give N-(4-(difluoromethyl)pyridin-2-yl)-4-(4,4,5,5-tetramethyl-1,3,2-dioxaborolan-2-yl)benzamide (1.8 g, yield 79%).

$^1$HNMR (400 MHz, DMSO-d6): δ=8.55-8.54 (d, J=4 Hz, 1 H), 8.39 (s, 1 H), 8.02~8.00 (d, J=8.0 Hz, 2 H), 7.79-7.77 (d, J=8.0 Hz, 2 H), 7.34-7.33 (d, J=4 Hz, 1 H), 7.29~7.01 (t, J=52 Hz, 1 H), 1.30 (s, 12 H), MS (ESI): M/Z (M+1)=375.16.

Intermediate 40

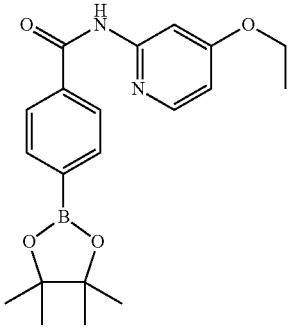 [SMILES: CCOc1ccnc(NC(=O)c2ccc(B3OC(C)(C)C(C)(C)O3)cc2)c1]

N-(4-ethoxypyridin-2-yl)-4-(4,4,5,5-tetramethyl-1,3,2-dioxaborolan-2-yl)benzamide To a degassed mixture of 4-(4,4,5,5-tetramethyl-1,3,2-dioxaborolan-2-yl)benzamide (9.4 g, 38 mmol) and 2-chloro-4-ethoxypyridine (5 g, 31.7 mmol) in dioxane was added Brettphos-prePd (catalytic amount) and $Cs_2CO_3$ (12.3 g, 37.8 mmol) under $N_2$ atmosphere. The mixture was heated to 100° C. and stirred for 3.5 hours. The reaction mixture was cooled to room temperature and filtered. The filtrate was concentrated, and the residue was purified on silic-gel (PE: EA=100%~30%) to give N-(4-ethoxypyridin-2-yl)-4-(4,4,5,5-tetramethyl-1,3,2-dioxaborolan-2-yl)benzamide (8.8 g, yield 75%). $^1$HNMR (400 MHz, $CDCl_3$): δ=8.74 (s, 1 H), 8.05~8.02(m, 1 H), 8.01 (s, 1 H), 7.94~7.89 (m, 4 H), 6.60~6.59 (m, 1 H), 4.20~4.14 (m, 2 H), 1.47~1.43 (m, 3 H), 1.36 (s, 12 H), MS (ESI): M/Z (M+1)=369.19.

Intermediate 41

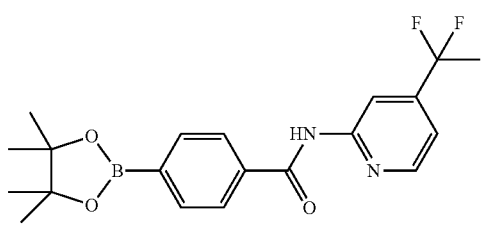 [SMILES: CC(F)(F)c1ccnc(NC(=O)c2ccc(B3OC(C)(C)C(C)(C)O3)cc2)c1]

N-(4-(1,1-difluoroethyl)pyridin-2-yl)-4-(4,4,5,5-tetramethyl-1,3,2-dioxaborolan-2-yl)benzamide (a) 2-bromo-N-methoxy-N-methylisonicotinamide To a solution of 2-bromoisonicotinic acid (40.4 g, 0.2 mol) in 200 mL of dry DMF was added CDI (32.4 g, 0.2 mol) in portions. After stirring for 30 min under $N_2$ atmosphere N,O-methylhydroxylamine hydrochloride (19.5 g, 0.2 mol) was added and the mixture was stirred at room temperature overnight under $N_2$ atmosphere. The mixture was diluted with water and extracted with EtOAc. The combined organic phase was washed with water and brine, dried over $Na_2SO_4$, filtered and concentrated in vacuo to afford a crude residue, which was purified by flash chromatography on silica gel to give compound 2-bromo-N-methoxy-N-methylisonicotinamide (28 g, yield 57%).
$^1$HNMR (400 MHz, DMSO-d6): δ=8.50 (d, J=4.8 Hz, 1 H), 7.79 (s, 1 H), 7.59 (d, J=4.8 Hz, 1 H), 3.56 (s, 3 H), 3.27 (s, 3 H). MS (ESI): M/Z (M/M+2=1/1) 244.7/246.7.

(b) 1-(2-bromopyridin-4-yl)ethanone

To a solution of 2-bromo-N-methoxy-N-methylisonicotinamide (27 g, 0.11 mol) in 200 mL of dry THF was added 3 M MeMgBr (44 mL, 0.132 mol) at −78° C. under $N_2$ atmosphere. The mixture was stirred at −78° C. for 2 hrs under $N_2$, and then quenched with aq.$NH_4Cl$, and extracted with EtOAc. The organic phase was washed with water and brine, dried over $Na_2SO_4$, filtered and concentrated under vacuum to afford a crude residue, which was purified by flash chromatography on silica gel to give 1-(2-bromopyridin-4-yl)ethanone (20 g, yield: 90.9%). $^1$HNMR (400 MHz, DMSO-d6): δ=8.59 (d, J=4.8 Hz, 1 H), 8.01 (s, 1 H), 7.82 (d, J=4.8 Hz, 1 H), 2.61 (s, 3 H).

(c) 2-bromo-4-(1,1-difluoroethyl)pyridine

To a solution of 1-(2-bromopyridin-4-yl)ethanone (20 g, 0.1 mol) in 200 mL of DCM was added DAST (40.3 g, 0.25 mol) at 0° C. The reaction mixture was stirred overnight, and slowly poured into aq. $NaHCO_3$ and extracted with DCM. The organic phases were washed with water and brine, dried over $Na_2SO_4$, filtered and concentrated under vacuum to give a crude residue, which was purified by flash chromatography on silica gel to give 2-bromo-4-(1,1-difluoroethyl)pyridine (18.5 g, yield: 84.1%). $^1$HNMR (400 MHz, DMSO-d6): δ=8.56 (d, J=5.2 Hz, 1 H), 7.86 (s, 1 H), 7.65 (d, J=4.8 Hz, 1 H), 2.00 (t, J=19.2 Hz, 3 H). MS (ESI): M/Z (M/M+2=1/1) 222.0/224.0.

(d) N-(4-(1,1-difluoroethyl)pyridin-2-yl)-4-(4,4,5,5-tetramethyl-1,3,2-dioxaborolan-2-yl)benzamide 2-bromo-4-(1,1-difluoroethyl)pyridine was used to prepare N-(4-(1,1-difluoroethyl)pyridin-2-yl)-4-(4,4,5,5-tetramethyl-1,3,2-dioxaborolan-2-yl)benzamide. The procedure of intermediate 40 was followed. $^1$H NMR (400 MHz, $CDCl_3$) δ=8.73 (s, 1H), 8.56 (s, 1H), 8.38 (d, J=5.3 Hz, 1H), 7.97-7.89 (m, 4H), 7.22 (d, J=5.3 Hz, 1H), 1.96 (t, J=18.3 Hz, 3H), 1.37 (s, 12H).

Intermediate 42

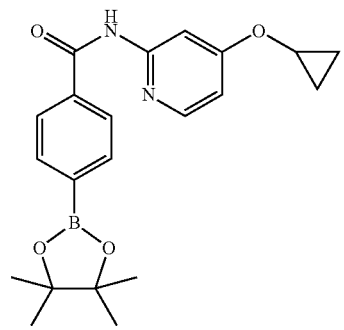 [SMILES: CC1(C)OB(c2ccc(C(=O)Nc3cc(OC4CC4)ccn3)cc2)OC1(C)C]

N-(4-cyclopropoxypyridin-2-yl)-4-(4,4,5,5-tetramethyl-1,3,2-dioxaborolan-2-yl)benzamide (a) 2-chloro-4-cyclopropoxypyridine To a solution of 2-chloropyridin-4-ol (1 g, 7.75 mmol) in DMA (10 ml) was added bromocyclopropane (2.8 g, 23.2 mmol), NaI (1.16 g, 7.75 mmol) and Cs$_2$CO$_3$ (5 g, 15.5 mmol). The mixture was stirred at MW 170° C. for 20 minutes, and then MW 180° C. for 30 minutes. The reaction mixture was extracted with EA. The organic layer was dried and concentrated. The residue was purified by flash column chromatography to give 300 mg of 2-chloro-4-cyclopropoxypyridine.
$^1$H NMR (400 MHz, CDCl$_3$) δ=8.19 (d, J=5.8 Hz, 1H), 7.02 (d, J=2.0 Hz, 1H), 6.87 (dd, J=2.0, 5.8 Hz, 1H), 3.80 (tt, J=3.0, 6.0 Hz, 1H), 0.91-0.75 (m, 4H).

(b) N-(4-cyclopropoxypyridin-2-yl)-4-(4,4,5,5-tetramethyl-1,3,2-dioxaborolan-2-yl)benzamide N-(4-cyclopropoxypyridin-2-yl)-4-(4,4,5,5-tetramethyl-1,3,2-dioxaborolan-2-yl)benzamide was prepared following the procedure of intermediate 40H NMR (400 MHz, CDCl$_3$) δ=9.12 (br. s, 1H), 8.27 (d, J=2.01 Hz, 1H), 8.20 (d, J=5.52 Hz, 1H), 8.07 (d, J=6.02 Hz, 1H), 7.66 (d, J=7.78 Hz, 1H), 7.37 (d, J=7.78 Hz, 1H), 6.62-6.73 (m, 1H), 6.42-6.49 (m, 1H), 3.84-3.94 (m, 1H), 1.37 (s, 12H), 0.78-0.94 (m, 4H).

Intermediate 43

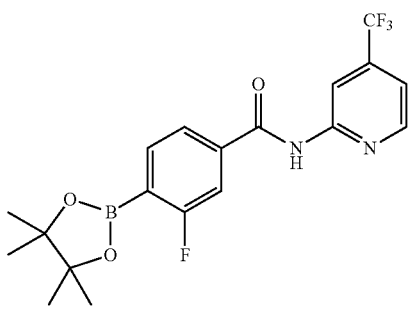 [SMILES: CC1(C)OB(c2ccc(C(=O)Nc3cc(C(F)(F)F)ccn3)cc2F)OC1(C)C]

3-fluoro-4-(4,4,5,5-tetramethyl-1,3,2-dioxaborolan-2-yl)-N-(4-(trifluoromethyl)pyridin-2-yl)benzamide (a) 4-bromo-3-fluoro-N-(4-(trifluoromethyl)pyridin-2-yl)benzamide To a stirring solution of 4-bromo-3-fluorobenzoic acid (19.6 g, 90 mmol), 4-(trifluoromethyl)pyridin-2-amine (16.2 g, 0.1 mol) and TEA (50 mL) in dry THF (300 mL) was added HATU (41.8 g, 0.11 mol) portionwise. The reaction mixture was stirred at room temperature for 20 hrs and at 60° C. for another 40 hrs. The resulting mixture was concentrated in vacuo and the residue was purified by flash chromatograph on silica gel (EA/PE: 5% to 15%) to give compound 4-bromo-3-fluoro-N-(4-(trifluoromethyl)pyridin-2-yl)benzamide. (26.8 g, yield: 82%).

(b) 3-fluoro-4-(4,4,5,5-tetramethyl-1,3,2-dioxaborolan-2-yl)-N-(4-(trifluoromethyl)pyridin-2-yl)benzamide A degassed mixture of 4-bromo-3-fluoro-N-(4-(trifluoromethyl)pyridine-2-yl)benzamide (26.8 g, 74 mmol), Bis(pinacolato)diboron (22.6 g, 90 mmol), TCP (1.24 g, 4.44 mmol), Pd(dba)2 (2.6 g, 4.44 mmol) and KOAc (21.8 g, 220 mmol) in dry dioxane (400 mL) was stirred at 110° C. overnight under N$_2$ atmosphere. After cooling to room temperature, the resulting mixture was filtered and concentrated under vacuum to afford a crude residue. The residue was purified by flash column chromatograph on silica gel (EA/PE: 5% to 20%) to give 3-fluoro-4-(4,4,5,5-tetramethyl-1,3,2-dioxaborolan-2-yl)-N-(4-(trifluoromethyl)pyridin-2-yl)benzamide. (20 g, yield: 66%).

Intermediate 44

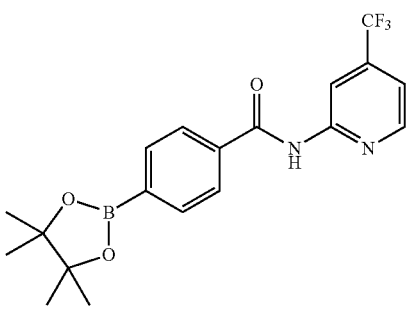 [SMILES: CC1(C)OB(c2ccc(C(=O)Nc3cc(C(F)(F)F)ccn3)cc2)OC1(C)C]

4-(4,4,5,5-Tetramethyl-1,3,2-dioxaborolan-2-yl)-N-(4-(trifluoromethyl)pyridin-2-yl)benzamide This compound was prepared, in an analogues manner as described in Intermediate 43, starting from 4-(trifluoromethyl)pyridin-2-amine and 4-bromobenzoic acid, to afford the title compound 4-(4,4,5,5-Tetramethyl-1,3,2-dioxaborolan-2-yl)-N-(4-(trifluoromethyl)pyridin-2-yl)benzamide.

Intermediate 45

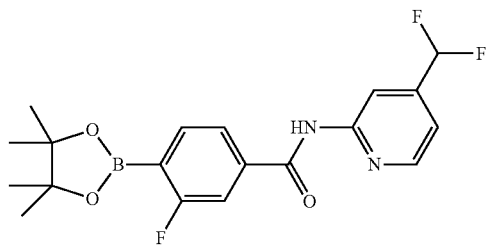 [SMILES: CC1(C)OB(c2ccc(C(=O)Nc3cc(C(F)F)ccn3)cc2F)OC1(C)C]

N-(4-(difluoromethyl)pyridin-2-yl)-3-fluoro-4-(4,4,5,5-tetramethyl-1,3,2-dioxaborolan-2-yl)benzamide (a) tert-butyl (4-(difluoromethyl)pyridin-2-yl)carbamate A degassed mixture of 2-chloro-4-(difluoromethyl)pyridine (6.3 g, 38.5 mmol), Carbamic acid tert-butyl ester (5.4 g, 46.2 mmol), Cs$_2$CO$_3$ (25 g, 77 mmol), X-phos (1.83 g, 3.85 mmol) and Pd(OAc)$_2$ (430 mg, 1.925 mmol) in 40 mL of 1,4-dioxane was stirred at 90° C. for 2 h under a stream of N$_2$. The mixture was concentrated under vacuum to give a crude product, which was purified by silica gel column chromatography to give tert-butyl (4-(difluoromethyl)pyridin-2-yl)carbamate (7.57 g, yield: 80.5%). ¹HNMR (400 MHz, DMSO-d6): δ=10.11 (s, 1H), 8.38 (d, J=5.2 Hz, 1 H), 7.99 (s, 1 H), 7.16 (d, J=4.8 Hz, 1 H), 7.07 (t, J=55.2 Hz, 1 H), 1.46 (s, 9 H).

(b) 4-(difluoromethyl)pyridin-2-amine

To a solution of tert-butyl (4-(difluoromethyl)pyridin-2-yl)carbamate (6.8 g, 27.8 mmol) in 40 mL of DCM was added 20 mL of trifluoroacetic acid. The reaction was stirred at r.t. for 1 h and then concentrated under vacuum. Aq. NaHCO₃ was added and extracted with EA. The organic layer was washed with brine, dried over Na₂SO₄, concentrated to give 4 g crude of compound 4-(difluoromethyl)pyridin-2-amine.
¹HNMR (400 MHz, DMSO-d6): δ=8.00 (d, J=5.2 Hz, 1 H), 6.88 (t, J=55.6 Hz, 1 H), 6.56 (d, J=5.6 Hz, 1 H), 6.54 (s, 1 H), 6.27 (s, 2 H).

(c) 4-bromo-N-(4-(difluoromethyl)pyridin-2-yl)-3-fluorobenzamide

To a solution of 4-bromo-3-fluorobenzoic acid (5 g, 22.8 mmol) in 100 mL of DCM was added Oxalyl dichloride (8.7 g, 68.5 mmol) and 5 drops of DMF at 0° C. After stirring for 1 h, the mixture was concentrated under vacuum and dissolved in 20 mL of THF, and added to a solution of 4-(difluoromethyl)pyridin-2-amine (3.9 g, 27.36 mmol) in 30 mL of THF at 0° C. The reaction was stirred at r.t for 30 min and at 80° C. overnight. After cooling to r.t, the mixture was filtered and the filtrate was concentrated under vacuum to give a crude residue, which was purified by silica gel column chromatography to give 4-bromo-N-(4-(difluoromethyl)pyridin-2-yl)-3-fluorobenzamide (4.9 g, yield: 62.3%). ¹HNMR (400 MHz, DMSO-d6): δ=11.26 (s, 1 H), 8.56 (d, J=4.8 Hz, 1 H), 8.37 (s, 1 H), 8.01 (d, J=10.0 Hz, 1 H), 7.78-7.90 (m, 2 H), 7.35 (d, J=5.2 Hz, 1 H), 7.15 (t, J=55.2 Hz, 1 H). MS (ESI): M/Z (M/M+2=1/1): 344.5/346.5.

(d) N-(4-(difluoromethyl)pyridin-2-yl)-3-fluoro-4-(4,4,5,5-tetramethyl-1,3,2-dioxaborolan-2-yl)benzamide A degassed mixture of 4-bromo-N-(4-(difluoromethyl)pyridin-2-yl)-3-fluorobenzamide (4.9 g, 14.2 mmol), Bispinacolatodiboron (5.4 g, 21.3 mmol), KOAc (4.2 g, 42.6 mmol) and Pd(dppf)Cl₂(1.04 g, 1.42 mmol) in 60 mL of 1,4-dioxane was stirred at 90° C. for 2 h under a stream of N₂. The mixture was concentrated under vacuum to give a crude product, which was purified by silica gel column chromatography to give N-(4-(difluoromethyl)pyridin-2-yl)-3-fluoro-4-(4,4,5,5-tetramethyl-1,3,2-dioxaborolan-2-yl)benzamide (5.4 g, yield: 96.9%). ¹HNMR (400 MHz, DMSO-d6): δ=11.25 (s, 1 H), 8.56 (d, J=4.8 Hz, 1 H), 8.37 (s, 1 H), 7.85 (d, J=7.6 Hz, 1 H), 7.74~7.79 (m, 2 H), 7.35 (d, J=5.2 Hz, 1 H), 7.15 (t, J=55.2 Hz, 1 H), 1.31 (s, 12 H). MS (ESI): M/Z (M+1): 392.9.

Intermediate 46

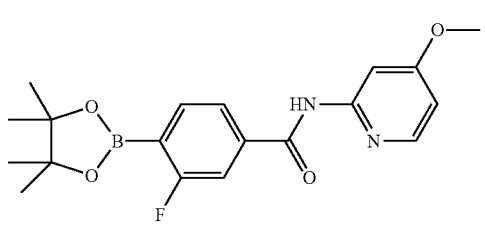

3-fluoro-N-(4-methoxypyridin-2-yl)-4-(4,4,5,5-tetramethyl-1,3,2-dioxaborolan-2-yl)benzamide 1 g of 3-fluoro-N-(4-methoxypyridin-2-yl)-4-(4,4,5,5-tetramethyl-1,3,2-dioxaborolan-2-yl)benzamide was obtained following the same procedure described for Intermediate 44. ¹H NMR (400 MHz, CDCl₃): δ=8.72 (brs, 1 H), 8.07 (d, J=5.6 Hz, 1 H), 8.00 (d, J=2.0 Hz, 1 H), 7.86 (dd, J₁=5.6 Hz, J₂=7.6 Hz, 1 H), 7.59~7.66 (m, 2H), 6.64 (dd, J₁=2.0 Hz, J₂=6.0 Hz, 1 H), 3.91 (s, 3 H), 1.37 (s, 12 H).

Intermediate 47

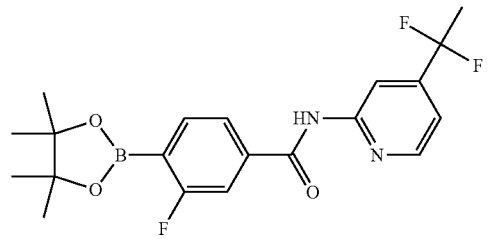 [SMILES: CC(F)(F)c1ccnc(NC(=O)c2ccc(B3OC(C)(C)C(C)(C)O3)c(F)c2)c1]

N-(4-(1,1-difluoroethyl)pyridin-2-yl)-3-fluoro-4-(4,4,5,5-tetramethyl-1,3,2-dioxaborolan-2-yl)benzamide(d)tert-butyl (4-(1,1-difluoroethyl)pyridin-2-yl)carbamate 4 g of N-(4-(1,1-difluoroethyl)pyridin-2-yl)-3-fluoro-4-(4,4,5,5-tetramethyl-1,3,2-dioxaborolan-2-yl)benzamide was obtained following the procedure described for Intermediate 44. ¹H NMR (400 MHz, CDCl₃): δ=9.56 (brs, 1 H), 8.60 (s, 1 H), 8.36 (d, J=5.2 Hz, 1 H), 7.88 (dd, J, =6.0 Hz, J₂=7.6 Hz, 1 H), 7.67-7.76 (m, 2 H), 7.24~7.25 (m, 1 H), 1.96 (t, J=18.4 Hz, 3 H), 1.38 (s, 12 H).

Intermediate 48

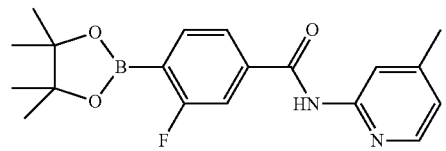

3-fluoro-N-(4-methylpyridin-2-yl)-4-(4,4,5,5-tetramethyl-1,3,2-dioxaborolan-2-yl)benzamide 3-fluoro-N-(4-methylpyridin-2-yl)-4-(4,4,5,5-tetramethyl-1,3,2-dioxaborolan-2-yl)benzamide was prepared following procedure described for Intermediate 44. ¹H NMR (400 MHz, CDCl₃—) delta=8.61 (br, s, 1H), 8.21 (s, 1H), 8.14 (d, J=5.0 Hz, 1H), 7.91-7.82 (m, 1H), 7.62 (dd, J=8.8, 15.8 Hz, 2H), 6.92 (d, J=4.5 Hz, 1H), 2.41 (s, 3H), 1.38 (s, 12H); MS (APCI): m/z (M+1): 357.2.

Intermediate 49

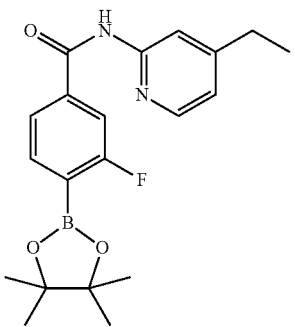 [SMILES: CCc1ccnc(NC(=O)c2ccc(B3OC(C)(C)C(C)(C)O3)c(F)c2)c1]

N-(4-ethylpyridin-2-yl)-3-fluoro-4-(4,4,5,5-tetramethyl-1,3,2-dioxaborolan-2-yl)benzamide N-(4-ethylpyridin-2-yl)-3-fluoro-4-(4,4,5,5-tetramethyl-1,3,2-dioxaborolan-2-yl)benzamide was prepared followed same procedure of intermediate 44. $^1$H NMR (400 MHz, CDCl$_3$): δ=8.81 (s, 1 H), 8.24 (s, 1 H), 8.12~8.11 (d, J=4 Hz, 1 H), 7.86~7.83 (m, 1 H), 7.66~7.59 (m, 2 H), 6.93~6.92 (d, J=4 Hz, 1 H), 2.73~2.67 (m, 2 H), 1.38 (s, 12 H), 1.30~1.26 (t, J=8 Hz, 3 H), MS MS (EI): M/Z (M+1): 371.19.

Intermediate 50

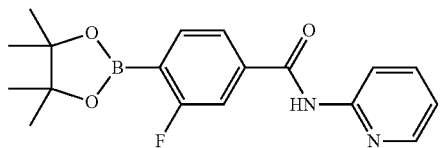

3-fluoro-N-(pyridin-2-yl)-4-(4,4,5,5-tetramethyl-1,3,2-dioxaborolan-2-yl)benzamide 3-fluoro-N-(pyridin-2-yl)-4-(4,4,5,5-tetramethyl-1,3,2-dioxaborolan-2-yl)benzamide was prepared followed the procedure of intermediate 44. $^1$HNMR (400 MHz, CDCl$_3$): δ=8.64 (brs, 1 H), 8.36 (d, J=8.0 Hz, 1 H), 8.28~8.30 (m, 1 H), 7.86 (dd, J$_1$=6.0 Hz, J$_2$=7.6 Hz, 1 H), 7.75~7.79 (m, 1 H), 7.10 (dd, J$_1$=0.8 Hz, J$_2$=5.2 Hz, 1 H), 7.08 (dd, J$_1$=0.8 Hz, J$_2$=5.2 Hz, 1 H), 7.07~7.11 (m, 1 H), 1.38 (s, 12 H).

Intermediate 51

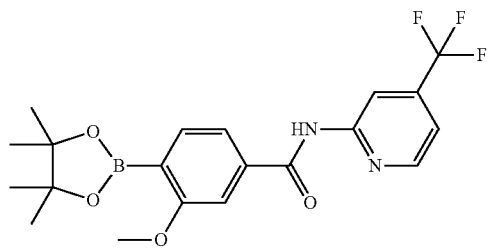 [SMILES: COc1cc(C(=O)Nc2cc(C(F)(F)F)ccn2)ccc1B1OC(C)(C)C(C)(C)O1]

3-methoxy-4-(4,4,5,5-tetramethyl-1,3,2-dioxaborolan-2-yl)-N-(4-(trifluoromethyl)pyridin-2-yl)benzamide (a) 3-methoxy-4-(4,4,5,5-tetramethyl-1,3,2-dioxaborolan-2-yl)benzoic acid A solution of 4-borono-3-methoxybenzoic acid (500 mg, 2.55 mmol) and pinacol (330 mg, 2.79 mmol) in THF (5 ml) and toluene (5 ml) was stirred at 40° C. overnight. After cooling the mixture was partitioned with water and extracted with ethyl acetate three times. The combined organic layers were washed with brine, dried over anhydrous Na$_2$SO$_4$ and concentrated in vacuo. The crude 3-methoxy-4-(4,4,5,5-tetramethyl-1,3,2-dioxaborolan-2-yl)benzoic acid was used in the next step without further purification.

(b) 3-methoxy-4-(4,4,5,5-tetramethyl-1,3,2-dioxaborolan-2-yl)benzoyl chloride

To a solution of 3-methoxy-4-(4,4,5,5-tetramethyl-1,3,2-dioxaborolan-2-yl)benzoic acid (700 mg, 2.52 mmol) in DCM (20 ml) was added 2 drops of DMF, the mixture was cooled to 0° C. under ice-water bath, and followed by the addition of oxalyl dichloride (629 mg, 5.03 mmol). The reaction mixture was stirred at 0° C. for 2 hours. The solvent was concentrated in vacuo, and the crude 3-methoxy-4-(4,4,5,5-tetramethyl-1,3,2-dioxaborolan-2-yl)benzoyl chloride was used in the next step directly.

(c) 3-methoxy-4-(4,4,5,5-tetramethyl-1,3,2-dioxaborolan-2-yl)-N-(4-(trifluoromethyl)pyridin-2-yl)benzamide To a solution of 3-methoxy-4-(4,4,5,5-tetramethyl-1,3,2-dioxaborolan-2-yl)benzoyl chloride (700 mg, 2.36 mmol) in THF (50 ml) was added 4-(trifluoromethyl)pyridin-2-amine (574 mg, 3.55 mmol). The resulting mixture was stirred at 80° C. overnight. The mixture was cooled to room temperature, the volatiles were concentrated in vacuo and the residue was purified by silica gel chromatography (petroleum ether/ethyl acetate=3/1 v/v %) to afford the title compound Intermediate 51(546 mg, three steps: 54.8%). MS-ESI (m/z): 423 (M+1)$^+$ (LC-MS method C; Ret. time: 1.26 min).

Intermediate 52

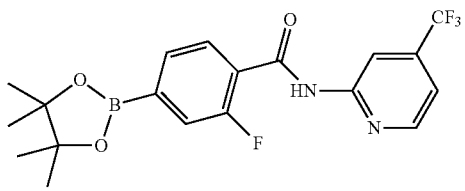 [SMILES: CC1(C)OB(c2ccc(C(=O)Nc3cc(C(F)(F)F)ccn3)c(F)c2)OC1(C)C]

2-fluoro-4-(4,4,5,5-tetramethyl-1,3,2-dioxaborolan-2-yl)-N-(4-(trifluoromethyl)pyridin-2-yl)benzamide This compound was prepared, in an analogues manner as described for Intermediate 44, starting from 4-bromo-2-fluorobenzoic acid, to afford the title compound (74.3%).

MS-ESI (m/z): 411 (M+1) (LC-MS method C; Ret. time: 1.55 min).

¹H NMR (400 MHz, DMSO-d₆) δ=11.41 (s, 1H), 8.66 (d, J=5.1 Hz, 1H), 8.51 (s, 1H), 7.84-7.66 (m, 1H), 7.64-7.51 (m, 2H), 7.45 (d, J=10.2 Hz, 2H), 1.29 (s, 12H).

Intermediate 53

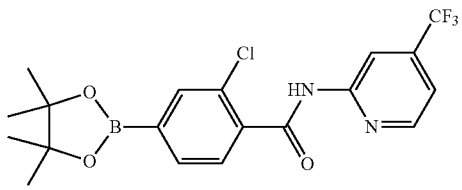 [SMILES: CC1(C)OB(c2ccc(C(=O)Nc3cc(C(F)(F)F)ccn3)c(Cl)c2)OC1(C)C]

2-chloro-4-(4,4,5,5-tetramethyl-1,3,2-dioxaborolan-2-yl)-N-(4-(trifluoromethyl)pyridin-2-yl)benzamide (a) 4-bromo-2-chloro-N-(4-(trifluoromethyl)pyridin-2-yl)benzamide To a solution of methyl 4-bromo-2-chlorobenzoate (1.15 g, 7.1 mmol) in toluene (20 ml) was added dropwise Me₃Al (5 ml, 2 M in toluene, 10 mmol) under nitrogen protection at room temperature. After the addition was completed the mixture was stirred for further 10 min, and 4-(trifluoromethyl)pyridin-2-amine (1.76 g, 7.1 mmol) was added. The resulting mixture was then heated at reflux for 8 h. After cooling the mixture was quenched with water, extracted with ethyl acetate three times. The combined organic layers were washed with brine, dried over anhydrous Na₂SO₄, and concentrated in vacuo. The residue was purified by silica gel chromatography (petroleum ether/ethyl acetate=6/1 v/v %) to give 4-bromo-2-chloro-N-(4-(trifluoromethyl)pyridin-2-yl)benzamide(1.88 g, 67.6%).

(b) 2-chloro-4-(4,4,5,5-tetramethyl-1,3,2-dioxaborolan-2-yl)-N-(4-(trifluoromethyl)pyridin-2-yl)benzamide This compound was prepared, in an analogues manner as described in Intermediate 43 step (b), starting from 6.8 g of 4-bromo-2-chloro-N-(4-(trifluoromethyl)pyridin-2-yl)benzamide, to afford the title compound, Intermediate 53 (3.2 g, 47%).

MS-ESI (m/z): 427 (M+1)⁺ (LC-MS method C; Ret. time: 1.44 min).

¹H NMR (400 MHz, CD₃OD) δ=8.63-8.46 (m, 2H), 7.84-7.69 (m, 2H), 7.58 (s, 1H), 7.40 (br. s, 1H), 1.35 (s, 12H).

Intermediate 54

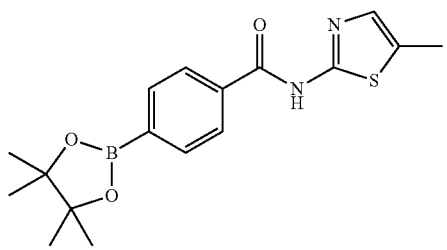

N-(5-Ethylthiazol-2-yl)-4-(4,4,5,5-tetramethyl-1,3,2-dioxaborolan-2-yl)benzamide This compound was prepared, in an analogues manner as described for Intermediate 44, starting from 5-methylthiazol-2-amine, to afford the title compound Intermediate 54.

Intermediate 55

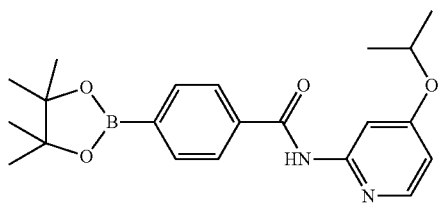 [SMILES: CC(C)Oc1ccnc(NC(=O)c2ccc(B3OC(C)(C)C(C)(C)O3)cc2)c1]

N-(4-isopropoxypyridin-2-yl)-4-(4,4,5,5-tetramethyl-1,3,2-dioxaborolan-2-yl)benzamide (a) 4-bromo-N-(4-isopropoxypyridin-2-yl)benzamide A solution of 4-isopropoxypyridin-2-amine (1.019 g, 6.70 mmol) and DMAP (0.709 g, 5.81 mmol) in MeCN (5.0 ml) under N₂ was treated with 4-bromobenzoyl chloride (1.0 g, 4.47 mmol) dissolved in MeCN (5.0 ml) and the mixture stirred at rt overnight. The mixture was diluted with DCM and washed with water (×2). The aqueous layer was washed with DCM and the combined organics washed with brine, dried (MgSO₄) and concentrated to afford a cream solid. Purification on a 40 g column on the CombiFlash RF, eluting with 0 to 20% EtOAc/Hexane (24 CV) afforded 1.33 g of the title compound as a white solid. m/z(M+2)⁺: 237.01.

(b) N-(4-isopropoxypyridin-2-yl)-4-(4,4,5,5-tetramethyl-1,3,2-dioxaborolan-2-yl)benzamide A 4 ml vial containing 4-bromo-N-(4-isopropoxypyridin-2-yl)benzamide from Step a 1(0.1 g, 0.298 mmol), 4,4,4', 4',5,5,5',5'-octamethyl-2,2'-bi(1,3,2-dioxaborolane) (0.083 g, 0.328 mmol), and Potassium acetate (0.088 g, 0.895 mmol) was treated with Dioxane (1.0 ml), and the mixture degassed with house vacuum and backfilled with N₂ (×2). 2nd generation X-phos precatalyst (0.047 g, 0.060 mmol) as a slurry in dioxane (0.5 ml) under N₂ was then added via a syringe and the resulting cream suspension was then stirred at 70° C. for 2 h. The mixture was dilute with EtOAc, filtered and concentrate. Purification on a 12 g column on the CombiFlash Rf, eluting with 0 to 40% EtOAc/Hexane afforded 70 mg of the Title compound Intermediate 55. m/z (M+1)⁺: 383.22.

Intermediate 56

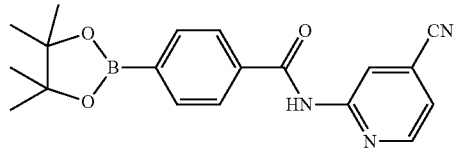 [SMILES: CC1(C)OB(c2ccc(C(=O)Nc3cc(C#N)ccn3)cc2)OC1(C)C]

N-(4-Cyanopyridin-2-yl)-4-(4,4,5,5-tetramethyl-1,3,2-dioxaborolan-2-yl)benzamide This compound was prepared, in an analogous manner as described in Intermediate 55 starting from 2-aminoisonicotinonitrile, to afford the title compound (1.3 g, 99%).

Intermediate 57

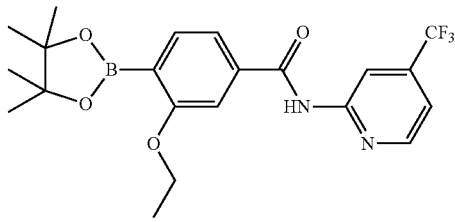 [SMILES: CCOc1cc(C(=O)Nc2cc(C(F)(F)F)ccn2)ccc1B1OC(C)(C)C(C)(C)O1]

3-ethoxy-4-(4,4,5,5-tetramethyl-1,3,2-dioxaborolan-2-yl)-N-(4-(trifluoromethyl)pyridin-2-yl)benzamide Step 1: methyl 4-bromo-3-ethoxybenzoate A suspension of methyl 4-bromo-3-hydroxybenzoate (1.0 g, 4.33 mmol) and powder potassium carbonate (0.658 g, 4.76 mmol) in DMF (4.33 ml) under $N_2$ was treated with iodoethane (0.675 g, 4.33 mmol) via a syringe and the mixture stirred at rt for 2 h. The reaction was quenched with water and extracted with EtOAc (×2). The combined EtOAc layer was washed with water (×2) and brine, dried (MgSO$_4$) and concentrated to afford a white solid. Trituration with ether/hexane followed by filtration afforded 910 mg of the title compound as a white solid. $^1$H NMR, 500 MHz, CDCl3, δ 7.62 (d, J=8.2 Hz, 1H), 7.55 (d, J=1.7 Hz, 1H), 7.52 (dd, J=8.2, 1.8 Hz, 1H), 4.19 (q, J=6.9 Hz, 2H), 3.94 (s, 3H), 1.52 (t, J=7.0 Hz, 3H) ppm.

Step 2: 4-bromo-3-ethoxybenzoic acid

A solution of the title compound from step 1, methyl 4-bromo-3-ethoxybenzoate (900 mg, 3.47 mmol) in THF (9.0 ml) was treated with LiOH (166 mg, 6.95 mmol) dissolved in Water (4.5 ml) followed by MeOH (4.5 ml). The resulting mixture was then stirred at 45° C. for 2 h. The solvent was evaporated and the residue diluted with water. The pH was adjusted to pH 6 with 2 N HCl and the resulting white suspension washed with EtOAc (×2). The organic layer was dried (MgSO$_4$) and concentrated to afford 765 mg of the title compound as a white solid. Calc'd m/z=245.0. Found m/z=247.0 (M+2).

Step 3: 4-bromo-3-ethoxy-N-(4-(trifluoromethyl)pyridin-2-yl)benzamide

A suspension of the title compound from step 2,4-bromo-3-ethoxybenzoic acid, (500 mg, 2.040 mmol), in DCM (5982 μl) under $N_2$ was treated with DMF (55.3 μl, 0.714 mmol) followed by THIONYL CHLORIDE (1489 μl, 20.40 mmol) via a syringe and the mixture stirred at 35° C. for 18 h. The solvent was evaporated and the residue co-evaporated with DCM and toluene (×2). The resulting residue was then diluted with Acetonitrile (5982 μl) and treated with DMAP (324 mg, 2.65 mmol) and 4-(trifluoromethyl)pyridin-2-amine (364 mg, 2.244 mmol). The mixture was then stirred at rt for 3 h. The solvent was evaporated and the residue diluted with EtOAc and washed with water (×2). The combined organics was washed with brine, dried (MgSO$_4$) and concentrated. Purification on the CombiFlash RF MPLC, on a 40 g column, eluting with 0 to 20% EtOAc/Hexane (25 CV) afforded 380 mg of the title compound as a white solid. Calc'd m/z=389.1. Found m/z=391.0 (M+2).

Step 4: 3-ethoxy-4-(4,4,5,5-tetramethyl-1,3,2-dioxaborolan-2-yl)-N-(4-(trifluoromethyl)pyridin-2-yl)benzamide A sealed vial containing the title compound from step 3,4-bromo-3-ethoxy-N-(4-(trifluoromethyl)pyridin-2-yl)benzamide (500 mg, 1.285 mmol), 4,4,4',4',5,5,5',5'-octamethyl-2,2'-bi(1,3,2-dioxaborolane) (359 mg, 1.413 mmol), PdCl2(dppf)-CH$_2$Cl2Adduct (210 mg, 0.257 mmol) and POTASSIUM ACETATE (252 mg, 2.57 mmol) was evacuated and backfilled with $N_2$. Dioxane (6424 μl) was then added via a syringe and the suspension evacuated again and backfilled with $N_2$. The mixture was then stirred at rt for 5 min and then at 75° C. for 4.0 h (dark mixture). The mixture was diluted with EtOAc and filtered. The filtrate was concentrated to afford a brown oil. Purification on the CombiFlash RF MPLC, on a 40 g column, eluting with 0 to 20% EtOAc/Hexane (40 CV) afforded 487 mg of the title compound, Intermediate 5. Calc'd m/z=436.2. Found m/z=437.1 (M+1)+.

Intermediate 58

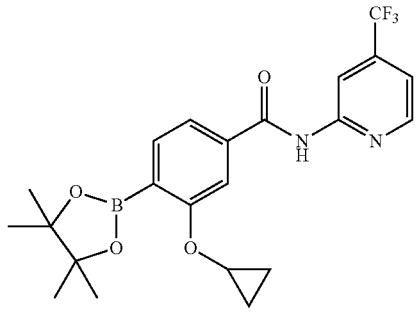 [SMILES: CC1(C)OB(c2ccc(C(=O)Nc3cc(C(F)(F)F)ccn3)cc2OC2CC2)OC1(C)C]

3-cyclopropoxy-4-(4,4,5,5-tetramethyl-1,3,2-dioxaborolan-2-yl)-N-(4-(trifluoromethyl)pyridin-2-yl)benzamide Step 1: 4-bromo-3-cyclopropoxy-N-(4-(trifluoromethyl)pyridin-2-yl)benzamide A solution of 4-bromo-3-cyclopropoxybenzoic acid (1.6 g, 6.22 mmol) and DMF (0.169 ml, 2.178 mmol) in DCM (40.0 mL, 0.156M) was treated with thionyl chloride (4.54 mL, 62.2 mmol) and the mixture stirred at 35° C. for 18 h. The solvent was evaporated and the residue azeotroped (×2) with toluene. The resulting cream solid was then diluted with acetonitrile (10 mL) and treated with DMAP (0.988 g, 8.09 mmol). The mixture was stirred at room temperature for 5 min and 4-(trifluoromethyl)pyridin-2-amine (1.211 g, 7.47 mmol) was added. The mixture was then stirred at 35 C for 15 h. The solvent was evaporated and the residue diluted with DCM and washed with water (2) and brine. The organic layer was dried (MgSO$_4$) and concentrated to afford a cream solid. Crude was purified on Redi Sep Rf filter column on CombiFlash 0-20% Hex/EtOAc. Appropriate fractions collected and concentrated in vacuo to afford 4-bromo-3-cyclopropoxy-N-(4-(trifluoromethyl)pyridin-2-yl)benzamide LC-MS (ES, m/z) C$_{16}$H$_{12}$BrF$_3$N$_2$O$_2$: 401; Found 403[M+H]$^+$.

Step 2: 3-cyclopropoxy-4-(4,4,5,5-tetramethyl-1,3,2-dioxaborolan-2-yl)-N-(4-(trifluoromethyl)pyridin-2-yl)benzamide To a flask was charged with 4-bromo-3-cyclopropoxy-N-(4-(trifluoromethyl)pyridin-2-yl)benzamide (2.19 g, 5.46 mmol), 4,4,4',4',5,5,5',5'-octamethyl-2,2'-bi(1,3,2-dioxaborolane) (1.52 g, 6.0 mmol) potassium acetate (1.6 g, 16.38 mmol), 1,1-bis(diphenylphosphino)ferrocenedichloropalladium(ii) dichloromethane complex (0.399 g, 0.1 mmol) in dioxane (35 mL, 0.156 M). The resulting mixture was degassed and purged with nitrogen for 5 min and stirred at 78° C. overnight. Mixture was filtered and concentrated in vacuo. Residue was purified on RediSep Rf filter column on CombiFlash with 10% MeOH/DCM 0-3% to produce product 3-cyclopropoxy-4-(4,4,5,5-tetramethyl-1,3,2-dioxaborolan-2-yl)-N-(4-(trifluoromethyl)pyridin-2-yl)benzamide. LC-MS (ES, m/z) C$_{22}$H$_{24}$BF$_3$N$_2$O$_4$: 448; Found 449[M+H]$^+$.

Intermediate 59

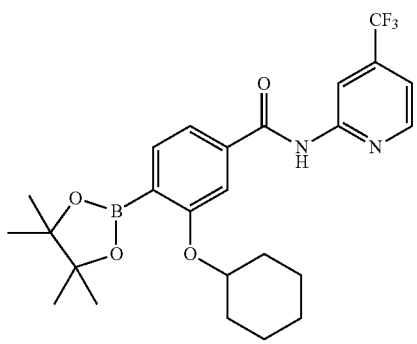 [SMILES: CC1(C)OB(c2ccc(C(=O)Nc3cc(C(F)(F)F)ccn3)cc2OC2CCCCC2)OC1(C)C]

3-(cyclohexyloxy)-4-(4,4,5,5-tetramethyl-1,3,2-dioxaborolan-2-yl)-N-(4-(trifluoromethyl)pyridin-2-yl)benzamide In the same procedure as intermediate 57 by replacing the iodoethane with cyclohexylbromide in step 1, 3-(cyclohexyloxy)-4-(4,4,5,5-tetramethyl-1,3,2-dioxaborolan-2-yl)-N-(4-(trifluoromethyl)pyridin-2-yl)benzamide was prepared. LC-MS (ES, m/z) C$_{25}$H$_{30}$BrF$_3$N$_2$O$_4$: 490; Found: 491[M+H]$^+$.

Intermediate 60

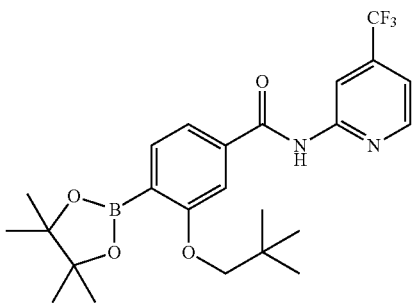 [SMILES: CC(C)(C)COc1cc(C(=O)Nc2cc(C(F)(F)F)ccn2)ccc1B1OC(C)(C)C(C)(C)O1]

3-(neopentyloxy)-4-(4,4,5,5-tetramethyl-1,3,2-dioxaborolan-2-yl)-N-(4-(trifluoromethyl)pyridin-2-yl)benzamide In the same procedure as intermediate 57 by replacing the iodoethane with neopentylbromide in step 1, 3-(neopentyloxy)-4-(4,4,5,5-tetramethyl-1,3,2-dioxaborolan-2-yl)-N-(4-(trifluoromethyl)pyridin-2-yl)benzamide was prepared. LC-MS (ES, m/z) C$_{24}$H$_{30}$BrF$_3$N$_2$O$_4$: 478; Found: 479[M+H]$^+$.

Intermediate 61

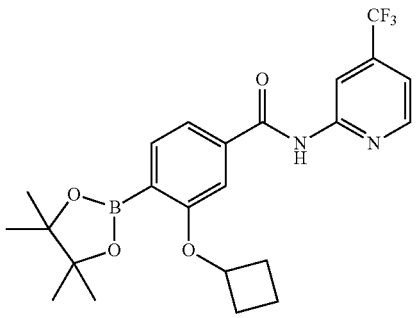 [SMILES: CC1(C)OB(c2ccc(C(=O)Nc3cc(C(F)(F)F)ccn3)cc2OC2CCC2)OC1(C)C]

3-cyclobutoxy-4-(4,4,5,5-tetramethyl-1,3,2-dioxaborolan-2-yl)-N-(4-(trifluoromethyl)pyridin-2-yl)benzamide In the same procedure as intermediate 57 by replacing iodoethane with cyclobutylbromide in step 1, 3-cyclobutoxy-4-(4,4,5,5-tetramethyl-1,3,2-dioxaborolan-2-yl)-N-(4-(trifluoromethyl)pyridin-2-yl)benzamide was prepared. LC-MS (ES, m/z) C$_{23}$H$_{26}$BrF$_3$N$_2$O$_4$: 462; Found: 463 [M+H]$^+$.

Intermediate 62

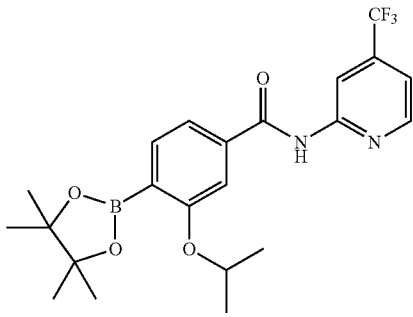 [SMILES: CC(C)Oc1cc(C(=O)Nc2cc(C(F)(F)F)ccn2)ccc1B1OC(C)(C)C(C)(C)O1]

3-isopropoxy-4-(4,4,5,5-tetramethyl-1,3,2-dioxaborolan-2-yl)-N-(4-(trifluoromethyl)pyridin-2-yl)benzamide In the same procedure as intermediate 57 by replacing iodoethane with isopropylbromide in step 1, 2 3-isopropoxy-4-(4,4,5,5-tetramethyl-1,3,2-dioxaborolan-2-yl)-N-(4-(trifluoromethyl)pyridin-2-yl)benzamide was prepared. LC-MS (ES, m/z) $C_{22}H_{26}BrF_3N_2O_4$: 450; Found: 451[M+H]$^+$.

Intermediate 63

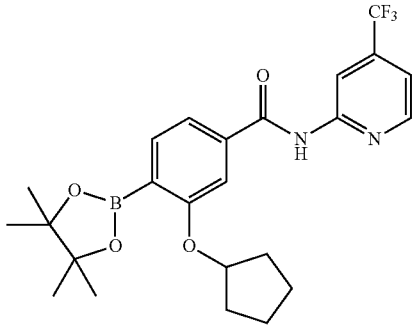 [SMILES: CC1(C)OB(c2ccc(C(=O)Nc3cc(C(F)(F)F)ccn3)cc2OC2CCCC2)OC1(C)C]

3-(cyclopentyloxy)-4-(4,4,5,5-tetramethyl-1,3,2-dioxaborolan-2-yl)-N-(4-(trifluoromethyl)pyridin-2-yl)benzamide In the same procedure as intermediate 57 by replacing iodoethane with cyclopentylbromide in step 1, 3-(cyclopentyloxy)-4-(4,4,5,5-tetramethyl-1,3,2-dioxaborolan-2-yl)-N-(4-(trifluoromethyl)pyridin-2-yl)benzamide was prepared. LC-MS (ES, m/z) $C_{24}H_{28}BrF_3N_2O_4$: 476; Found: 477[M+H]$^+$.

Intermediate 64

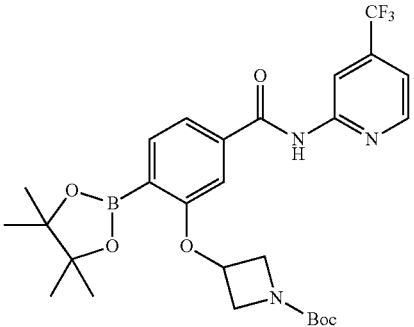 [SMILES: CC(C)(C)OC(=O)N1CC(Oc2cc(C(=O)Nc3cc(C(F)(F)F)ccn3)ccc2B2OC(C)(C)C(C)(C)O2)C1]

tert-butyl 3-(2-(4,4,5,5-tetramethyl-1,3,2-dioxaborolan-2-yl)-5-((4-(trifluoromethyl)pyridin-2-yl)carbamoyl)phenoxy)azetidine-1-carboxylate In the same procedure as intermediate 57 by replacing iodoethane with tert-butyl 3-bromoazetidine-1-carboxylate, tert-butyl 3-(2-(4,4,5,5-tetramethyl-1,3,2-dioxaborolan-2-yl)-5-((4-(trifluoromethyl)pyridin-2-yl)carbamoyl)phenoxy)azetidine-1-carboxylate was prepared. LC-MS (ES, m/z) $C_{27}H_{33}BrF_3N_3O_6$: 563; Found: 564[M+H]$^+$.

Intermediate 65

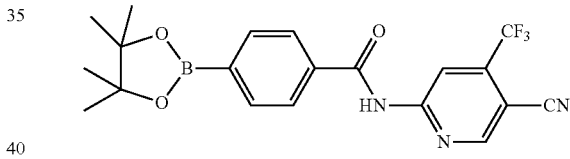

N-(5-cyano-4-(trifluoromethyl)pyridin-2-yl)-4-(4,4,5,5-tetramethyl-1,3,2-dioxaborolan-2-yl)benzamide Step 1: 4-bromo-N-(5-cyano-4-(trifluoromethyl)pyridin-2-yl)benzamide A solution of 6-amino-4-(trifluoromethyl)nicotinonitrile (1.086 g, 5.81 mmol), 4-bromobenzoyl chloride (1.0 g, 4.47 mmol) and DMAP (0.709 g, 5.81 mmol) in Acetonitrile (14.88 ml) was stirred at rt for 16 h. The reaction was diluted with DCM and washed with water. The organic layer was dried (MgSO$_4$) and concentrated. Trituration from DCM (standing o/n) followed by filtration afforded 1.59 g of the title compound as greenish/crean powder. $^1$H NMR, 500 MHz, CDCl3, δ 8.91 (s, 1H), 8.81 (s, 1H), 7.91 (d, J=8.4 Hz, 2H), 7.71 (d, J=8.2 Hz, 2H) ppm.

Step 2: N-(5-cyano-4-(trifluoromethyl)pyridin-2-yl)-4-(4,4,5,5-tetramethyl-1,3,2-dioxaborolan-2-yl)benzamide A round bottom flask containing the title compound from step 1(4-bromo-N-(5-cyano-4-(trifluoromethyl)pyridin-2-yl)benzamide)(500 mg, 1.351 mmol), 4,4,4',4',5,5,5',5'-octamethyl-2,2'-bi(1,3,2-dioxaborolane) (515 mg, 2.026 mmol), and POTASSIUM ACETATE (398 mg, 4.05 mmol) was treated with 1,4 Dioxane (12 ml), evacuated with house vacuum and backfilled with N₂ (×2). 2ND GENERATION XPHOS PRECATALYST (213 mg, 0.270 mmol) as a slurry in 1,4-Dioxane (6 ml) under N₂ was then added via a syringe and the resulting cream suspension was then stirred at 80° C. for 10 h. The mixture was diluted with EtOAc, filtered and the filtrate concentrated. Purification on the CombiFlash Rf MPLC, on a 80 g column eluting with 0 to 10% EtOAc/Hexane afforded 398 mg of the title compound, Intermediate 18 as a cream solid. Calc'd m/z=417.1. Found m/z=418.2. (M+1).

Intermediate 66

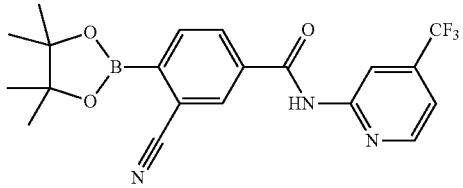 [SMILES: CC1(C)OB(c2ccc(C(=O)Nc3cc(C(F)(F)F)ccn3)cc2C#N)OC1(C)C]

3-cyano-4-(4,4,5,5-tetramethyl-1,3,2-dioxaborolan-2-yl)-N-(4-(trifluoromethyl)pyridin-2-yl)benzamide Step 1: 4-bromo-3-cyano-N-(4-(trifluoromethyl)pyridin-2-yl)benzamide A suspension of 4-bromo-3-cyanobenzoic acid (1.0 g, 4.42 mmol) and N,N-DIMETHYLFORMAMIDE (0.113 g, 1.548 mmol) in DCM (22.12 ml) was treated with THIONYL CHLORIDE (3.23 ml, 44.2 mmol) and the mixture stirred at 35° C. over night. The mixture was concentrated, diluted with DCM and concentrated again. The resulting cream solid was dissolved in toluene and azeothroped (×2). The resulting oil was diluted with MeCN (20 ml) and treated with DMAP (0.703 g, 5.75 mmol). After stirring for 5 min 4-(trifluoromethyl)pyridin-2-amine (0.789 g, 4.87 mmol) was added and the mixture stirred at 60° C. for 5 h. The mixture was diluted with DCM and washed with water (×2). The organic layer was dried (MgSO₄), filtered and concentrated to afford an oil. Purification on the CombiFlash RF, on a 120 g column, eluting with 0 to 20% EtOAc/Hexane afforded 1.1 g of the title compound as a cream solid. Calc'd m/z=370.1. Found m/z=372.0 (M+2).

Step 2: 3-cyano-4-(4,4,5,5-tetramethyl-1,3,2-dioxaborolan-2-yl)-N-(4-(trifluoromethyl)pyridin-2-yl)benzamide A vial containing the title compound from step 1,4-bromo-3-cyano-N-(4-(trifluoromethyl)pyridin-2-yl)benzamide, (100 mg, 0.270 mmol), 4,4,4',4',5,5,5',5'-octamethyl-2,2'-bi(1,3,2-dioxaborolane) (137 mg, 0.540 mmol), PdCl2(dppf)-CH₂Cl₂Adduct (22.06 mg, 0.027 mmol) and POTASSIUM ACETATE (80 mg, 0.811 mmol) was evacuated and backfilled with N₂. Acetonitrile (2702 µl) was then added via a syringe and the suspension evacuated again and backfilled with N₂ (×2). The mixture was then stirred at rt for 5 min and then at 75° C. for 15 h. The mixture was diluted with EtOAc and filtered. The filtrate was concentrated to afford the crude sticky solid title compound. Calc'd m/z=335.0. Found m/z=336.0 (M+1).

Intermediate 67

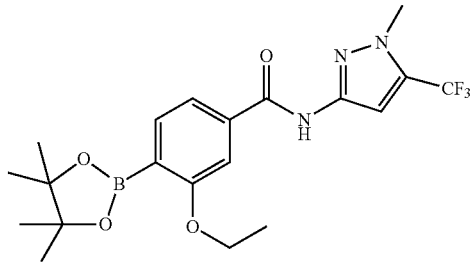 [SMILES: CCOc1cc(C(=O)Nc2cc(C(F)(F)F)n(C)n2)ccc1B1OC(C)(C)C(C)(C)O1]

3-ethoxy-N-(1-methyl-5-(trifluoromethyl)-1H-pyrazol-3-yl)-4-(4,4,5,5-tetramethyl-1,3,2-dioxaborolan-2-yl)benzamide Step 1: 4-bromo-3-ethoxy-N-(1-methyl-5-(trifluoromethyl)-1H-pyrazol-3-yl)benzamide A solution of the title compound from step 2, Intermediate 5,4-bromo-3-ethoxybenzoic acid (5.0 g, 20.40 mmol) in DMF (102 ml) was treated with HATU (8.53 g, 22.44 mmol) and the mixture stirred at rt for 15 min. 1-methyl-5-(trifluoromethyl)-1H-pyrazol-3-amine (3.37 g, 20.40 mmol) was then added followed by DIEA (7.13 ml, 40.8 mmol) and the mixture stirred at rt for 15 h. The mixture was diluted with EtOAc and washed with water (×2). The organic layer was then washed with brine, dried (MgSO₄) and concentrated to afford an oil. Purification on the CombiFlash RF MPLC on a 24 g column, eluting with 0 to 20% EtOAc/Hexane afforded 7.2 g of the desired product as an oil which later solidified. Calc'd m/z=392.1. Found m/z=394.0 (M+2).

Step 2: 3-ethoxy-N-(1-methyl-5-(trifluoromethyl)-1H-pyrazol-3-yl)-4-(4,4,5,5-tetramethyl-1,3,2-dioxaborolan-2-yl)benzamide In a sealed round bottom flask containing the title compound from step 1,4-bromo-3-ethoxy-N-(1-methyl-5-(trifluoromethyl)-1H-pyrazol-3-yl)benzamide, (1000 mg, 2.55 mmol), 4,4,4',4',5,5,5',5'-octamethyl-2,2'-bi(1,3,2-dioxaborolane) (971 mg, 3.82 mmol), PdCl₂(dppf)-CH₂Cl2Adduct (208 mg, 0.255 mmol) and POTASSIUM ACETATE (751 mg, 7.65 mmol) was added 1,4-Dioxane (1.27E+04 µl) under a N₂ atmosphere. The resulting suspension was then degassed (×3) and back filled with N₂. The mixture was then stirred at 80° C. under N₂ for 8 h. The mixture was filtered and the filtrate concentrated. Purification on the CombiFlash RF, on a 80 g column, eluting with 0 to 15% EtOac/Hexane (80 CV) afforded 763 mg of the title compound, Intermediate 30 as an oil which later solidified. Calc'd m/z=439.2. Found m/z=440.2 (M+1).

Intermediate 68

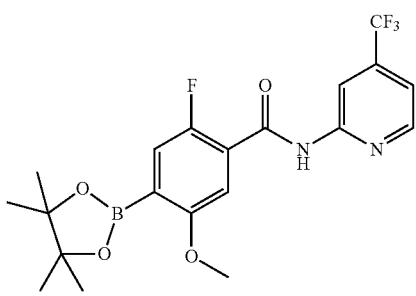 [SMILES: COc1cc(C(=O)Nc2cc(C(F)(F)F)ccn2)c(F)cc1B1OC(C)(C)C(C)(C)O1]

2-fluoro-5-methoxy-4-(4,4,5,5-tetramethyl-1,3,2-dioxaborolan-2-yl)-N-(4-(trifluoromethyl)pyridin-2-yl)benzamide Step 1: 4-bromo-2-fluoro-5-methoxybenzoic acid A solution of 4-bromo-2-fluoro-5-methoxybenzaldehyde (1000 mg, 4.29 mmol) and 2-methylbut-2-ene (1362 µl, 12.87 mmol) in t-BuOH (1.43E+04 µl) was treated slowly via an additional funnel a solution of SODIUM CHLORITE (893 mg, 9.87 mmol) and SODIUM DIHYDROGEN PHOSPHATE (1030 mg, 8.58 mmol) dissolved in Water (1.43E+04 µl) and the mixture stirred at rt for 3 h. The solvent was evaporated and the resulting white solid diluted with sat. Na$_2$CO$_3$ (20 ml) and extracted with ether. The aq layer was acidified with 1 N HCl (pH=4) and extracted with EtOAc (×2). The combined organic layer was dried (MgSO$_4$) and concentrated to afford 940 mg of the title compound as a white solid. Calc'd m/z=249.0. Found m/z 251.0 (M+2).

Step 2: 4-bromo-2-fluoro-5-methoxy-N-(4-(trifluoromethyl)pyridin-2-yl)benzamide

A solution of the title compound from step 1,4-bromo-2-fluoro-5-methoxybenzoic acid (940 mg, 3.77 mmol) and DMF (102 µl, 1.321 mmol) in DCM (9436 µl) was treated with THIONYL CHLORIDE (2755 µl, 37.7 mmol) and the mixture stirred at 35° C. for 18 h. The solvent was evaporated and the residue azotroped (×2) with toluene. The resulting cream solid was then diluted with MeCN (9 ml) and treated with DMAP (599 mg, 4.91 mmol). The mixture was then stirred at rt for 5 min and 4-(trifluoromethyl)pyridin-2-amine (749 mg, 4.53 mmol) was added. The mixture was then stirred at 35 C for 15 h. The solvent was evaporated and the residue diluted with DCM and washed with water (×2) and brine. The combined organic layer was dried (MgSO$_4$) and concentrated to afford a cream solid. Trituration from ether/hexane followed by filtration afforded 0.9 g of the title compound as a cream solid. The filtrated was concentrated and another 0.3 g of the title compound was afforded. Calc'd m/z=393.1. Found m/z 395.0 (M+2).

Step 3: 2-fluoro-5-methoxy-4-(4,4,5,5-tetramethyl-1,3,2-dioxaborolan-2-yl)-N-(4-(trifluoromethyl)pyridin-2-yl)benzamide A sealed vial containing the title compound from step 2,4-bromo-2-fluoro-5-methoxy-N-(4-(trifluoromethyl)pyridin-2-yl)benzamide (200 mg, 0.509 mmol), 4,4,4',4',5,5,5',5'-octamethyl-2,2'-bi(1,3,2-dioxaborolane) (194 mg, 0.763 mmol), POTASSIUM ACETATE (150 mg, 1.526 mmol) and PdCl2(dppf)-CH$_2$Cl$_2$Adduct (41.5 mg, 0.051 mmol) under a N$_2$ atmosphere was treated with 1,4-Dioxane (5087 µl) and immediately evacuated and backfilled with N$_2$ (×3). The resulting red-brown mixture was then stirred at 70° C. for 2 h. The mixture was diluted with EtOAc and filtered. The filtrate was washed with water and brine, dried (MgSO$_4$) and concentrated. Purification on the CombiFlash RF on a 40 g column, eluting with 0 to 30% EtOAc/Hexane afforded 238 mg of the title compound, Intermediate 31 as a white solid. Calc'd m/z=440.2. Found m/z=441.2 (M+1).

Intermediate 69

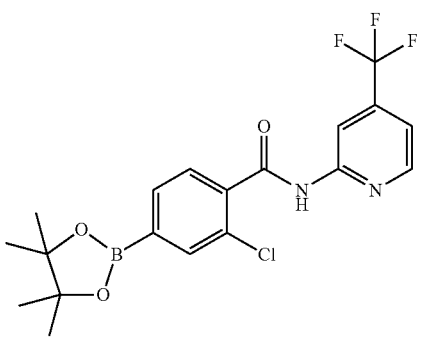 [SMILES: CC1(C)OB(c2ccc(C(=O)Nc3cc(C(F)(F)F)ccn3)c(Cl)c2)OC1(C)C]

2-chloro-4-(4,4,5,5-tetramethyl-1,3,2-dioxaborolan-2-yl)-N-(4-(trifluoromethyl)pyridin-2-yl)benzamide A solution of 2-chloro-4-(4,4,5,5-tetramethyl-1,3,2-dioxaborolan-2-yl)benzoic acid (1.0 g, 3.54 mmol) in DCM (11.80 ml) in a high pressure flask was treated with DMF (0.096 ml, 1.239 mmol) followed by THIONYL CHLORIDE (2.58 ml, 35.4 mmol) and the mixture stirred at 50° C. for 20 h. The mixture was concentrated and azeotroped (×2) with toluene. The resulting oil was then diluted with MeCN (12 ml) and treated with N,N-dimethylpyridin-4-amine (0.476 g, 3.89 mmol) and DMAP (0.432 g, 3.54 mmol) The mixture was then stirred at rt for 20 h. The solvent was evaporated and the residue diluted with DCM and extracted with water and brine (×2). The organic layer was dried (MgSO$_4$) and concentrated to afford an oil. Purification on the CombiFlash Companion MPLC, on a 40 g column eluting with 0 to 25% EtOAc/Hexane afforded 273 mg of the title compound, Intermediate 69, 2-chloro-4-(4,4,5,5-tetramethyl-1,3,2-dioxaborolan-2-yl)-N-(4-(trifluoromethyl)pyridin-2-yl)benzamide. Calc'd m/z=426.6. Found m/z=427.26 (M+1).

Intermediate 70

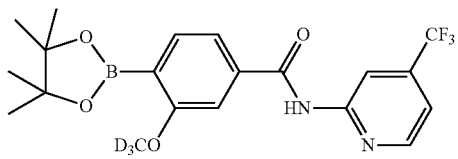

3-D3-methoxy-4-(4,4,5,5-tetramethyl-1,3,2-dioxa-borolan-2-yl)-N-(4-(trifluoromethyl)pyridin-2-yl)benzamide Step 1: methyl 4-bromo-3-D3-methoxybenzoate A suspension of methyl 4-bromo-3-hydroxybenzoate (327 mg, 1.415 mmol) and powder potassium carbonate (215 mg, 1.557 mmol) in DMF (1415 µl) under a $N_2$ atmosphere was treated with IODOMETHANE-D3 (205 mg, 1.415 mmol) via a syringe and the mixture stirred at rt for 2 h. The reaction mixture was quenched with water and extracted with EtOAc (×2). The combined EtOAc layer was washed with water (×2) and brine, dried ($MgSO_4$) and concentrated to afford the title compound as a clear oil (335 mg) which crystallised over night. Calc'd m/z=248.0. Found m/z=248.0, (M).

Step 2: 4-bromo-3-D3-methoxybenzoic acid

A solution of the product from Step 1 (300 mg, 1.209 mmol) in THF (3.0 ml) was treated with LiOH (57.9 mg, 2.418 mmol) dissolved in Water (1.5 ml) followed by MeOH (1.5 ml). The resulting mixture was then stirred at 45° C. for 2 h. The solvent was evaporated and the residue diluted with water. The pH was adjusted to pH 6 with 1 N HCl and the resulting white suspension washed with EtOAc (×2). The combined organic layer was dried ($MgSO_4$) and concentrated to afford 282 mg of the title compound as a white solid. Calc'd m/z=234.0. Found m/z=236 (M, M+2).

Step 3: 4-bromo-3-D3-methoxy-N-(4-(trifluoromethyl)pyridin-2-yl)benzamide

A suspension of the title compound from step 2 (280 mg, 1.196 mmol), in DCM (5982 µl) under $N_2$ was treated with DMF (32.4 µl, 0.419 mmol) followed by THIONYL CHLORIDE (873 µl, 11.96 mmol) via a syringe and the mixture stirred at 35° C. for 15 h. The solvent was evaporated and the residue co-evaporated with DCM and toluene (×2). The resulting residue was then diluted with Acetonitrile (5982 µl) and treated with DMAP (190 mg, 1.555 mmol) and 4-(trifluoromethyl)pyridin-2-amine (213 mg, 1.316 mmol). The mixture was then stirred at rt for 3 h. The solvent was evaporated and the residue diluted with EtOAc and washed with water (×2). The combined organics was washed with brine, dried ($MgSO_4$) and concentrated. The resulting residue was purified on the CombiFlash RF MPLC on a 40 g column eluting with 0 to 20% EtOAc/Hexane (25 CV) to afford 380 mg of the title compound as a white solid. Calc'd m/z=378.1. Found m/z=380.1 (M, M+2).

Step 4: 3-D3methoxy-4-(4,4,5,5-tetramethyl-1,3,2-dioxaborolan-2-yl)-N-(4-(trifluoromethyl)pyridin-2-yl)benzamide A sealed vial containing the title compound from step 3 (365 mg, 0.965 mmol), 4,4,4',4',5,5,5',5'-octamethyl-2,2'-bi(1,3,2-dioxaborolane) (270 mg, 1.062 mmol), PdCl2(dppf)-$CH_2Cl_2$Adduct (158 mg, 0.193 mmol) and POTASSIUM ACETATE (189 mg, 1.930 mmol) was evacuated and backfilled with $N_2$ (×2). 1,4-Dioxane (4826 µl) was then added via a syringe and the suspension evacuated again and backfilled with $N_2$. The mixture was then stirred at rt for 5 min and then at 75° C. for 2.0 h (dark mixture). The mixture was diluted with EtOAc and filtered. The filtrate was concentrated to afford a brown oil. Purification on the CombiFlash RF MPLC on a 24 g column eluting with 0 to 20% EtOAc/Hexane (30 CV) afforded 242 mg of the title compound, Intermediate 70. Calc'd m/z=425.2. Found m/z=426.2 (M+1).

Intermediate 71

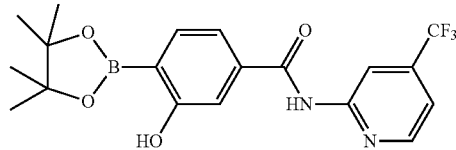 [SMILES: CC1(C)OB(c2ccc(C(=O)Nc3cc(C(F)(F)F)ccn3)cc2O)OC1(C)C]

3-hydroxy-4-(4,4,5,5-tetramethyl-1,3,2-dioxaborolan-2-yl)-N-(4-(trifluoromethyl)pyridin-2-yl)benzamide Step 1: 3-(benzyloxyl)-4-bromo-N-(4-(trifluoromethyl)pyridin-2-yl)benzamide A suspension of 3-(benzyloxy)-4-bromobenzoic acid (2.0 g, 6.51 mmol), in DCM (13.02 ml) under N2 was treated with DMF (0.176 ml, 2.279 mmol) followed by THIONYL CHLORIDE (4.75 ml, 65.1 mmol) via a syringe and the mixture stirred at 35° C. for 18 h. The solvent was evaporated and the residue co-evaporated with DCM and toluene (×2). The resulting residue was then diluted with MeCN (25 ml) and treated with DMAP (1.034 g, 8.47 mmol) and 4-(trifluoromethyl)pyridin-2-amine (1.161 g, 7.16 mmol). The mixture was then stirred at rt for 3 h. The solvent was evaporated and the residue diluted with EtOAc and washed with water (×2). The combined organics was washed with brine, dried ($MgSO_4$) and concentrated. The resulting residue was then purified on the CombiFlash RF on a 80 g column eluting with 0 to 15% EtOAc/Hexane (30 CV) to afford 2.4 g of the title compound as a white solid. Calc'd m/z=451.2. Found m/z=453.2. (M+2).

Step 2: 3-(benzyloxyl)-4-(4,4,5,5-tetramethyl-1,3,2-dioxaborolan-2-yl)-N-(4-(trifluoromethyl)pyridin-2-yl)benzamide A seal vial containing the title compound from step 1, 3-(benzyloxy)-4-bromo-N-(4-(trifluoromethyl)pyridin-2-yl)benzamide (1310 mg, 2.90 mmol), 4,4,4',4',5,5,5',5'-octamethyl-2,2'-bi(1,3,2-dioxaborolane) (811 mg, 3.19 mmol), PdCl2(dppf)-$CH_2Cl_2$Adduct (474 mg, 0.581 mmol) and POTASSIUM ACETATE (570 mg, 5.81 mmol) was evacuated and backfilled with $N_2$. 1,4-Dioxane (1.45E+04 µl) was then added via a syringe and the suspension evacuated again and backfilled with $N_2$. The mixture was then stirred at rt for 5 min and then at 80° C. for 15 h (dark mixture). The mixture was diluted with EtOAc and filtered. The filtrate was concentrated to afford a brown oil which was washed with water (×2) and brine and the layers separated. The combined organic layer was dried ($MgSO_4$) and concentrated to afford an oil. Purification on the CombiFlash RF MPLC on a 80 g column eluting with 0 to 30% EtOAc/Hexane (40 CV) afforded 0.869 g of the title compound. Calc'd m/z=498.3. Found m/z=499.3 (M+1).

Step 3: 3-hydroxy-4-(4,4,5,5-tetramethyl-1,3,2-dioxaborolan-2-yl)-N-(4-(trifluoromethyl)pyridin-2-yl)benzamide A solution of the title compound from step 2, 3-(benzyloxy)-4-(4,4,5,5-tetramethyl-1,3,2-dioxaborolan-2-yl)-N-

(4-(trifluoromethyl)pyridin-2-yl)benzamide (0.4 g, 0.803 mmol), in Ethyl acetate (2.007 ml) and MeOH (2.007 ml) was treated with 10% Pd—C (0.256 g, 0.241 mmol) and the mixture undergo hydrogenolysis at 40 psi on the Parr Shaker over night. The catalyst was filtered off and the filtrate concentrated to afford the title compound, Intermediate 71. Calc'd m/z=408.2. Found m/z=409.2 (M+1).

Intermediate 72

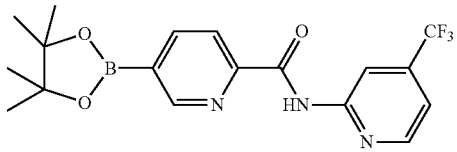 [SMILES: CC1(C)OB(c2ccc(C(=O)Nc3cc(C(F)(F)F)ccn3)nc2)OC1(C)C]

5-(4,4,5,5-tetramethyl-1,3,2-dioxaborolan-2-yl)-N-(4-(trifluoromethyl)pyridin-2-yl)picolinamide Step 1: 5-bromo-N-(4-(trifluoromethyl)pyridin-2-yl)picolinamide A suspension of 5-bromopicolinic acid (1.0 g, 4.95 mmol), in DCM (11. mL) under $N_2$ was treated with DMF (0.134 mL, 1.733 mmol), and THIONYL CHLORIDE (3.61 mL, 49.5 mmol) via a syringe and the mixture stirred at 35° C. for 18 h. The solvent was evaporated and the residue co-evaporated with DCM and toluene (×2). The resulting residue was then diluted with MeCN (12.0 ml) and treated with 5-bromo-N-(4-(trifluoromethyl)pyridin-2-yl)picolinamide (1.35 g, 3.90 mmol, 79% yield) and DMAP (0.786 g, 6.44 mmol). The mixture was then stirred at rt over night and evaporated. The residue was diluted with EtOAc and washed with water (×2) and the layers separated. The combined organics was washed with brine, dried (MgSO$_4$) and concentrated. The resulting residue was purified on the CombiFlash RF MPLC, on a 40 g column eluting with 0 to 10% EtOAc/Hexane (25 CV) to afford 1.35 g of the title compound as a white solid. Calc'd m/z=346.1. Found m/z=347.9 (M+1).

Step 2: 5-(4,4,5,5-tetramethyl-1,3,2-dioxaborolan-2-yl)-N-(4-(trifluoromethyl)pyridin-2-yl)picolinamide A seal vial containing the title compound from step 1, 5-bromo-N-(4-(trifluoromethyl)pyridin-2-yl)picolinamide, (325 mg, 0.939 mmol), 4,4,4',4',5,5,5',5'-octamethyl-2,2'-bi (1,3,2-dioxaborolane) (262 mg, 1.033 mmol), PdCl2(dppf)-CH$_2$Cl$_2$Adduct (153 mg, 0.188 mmol) and POTASSIUM ACETATE (184 mg, 1.878 mmol) was evacuated and backfilled with $N_2$. Dioxane (4695 μl) was then added via a syringe and the suspension evacuated again and backfilled with $N_2$. The mixture was then stirred at rt for 5 min and then at 80° C. for 4 h. The mixture was diluted with EtOAc and filtered. The filtrate was concentrated to afford an oil. Purification on the CombiFlash RF MPLC on a 40 g column eluting with 0 to 30% EtOAc/Hexane afforded 175 mg of the title compound, 5-(4,4,5,5-tetramethyl-1,3,2-dioxaborolan-2-yl)-N-(4-(trifluoromethyl)pyridin-2-yl)picolinamide.

Intermediate 73

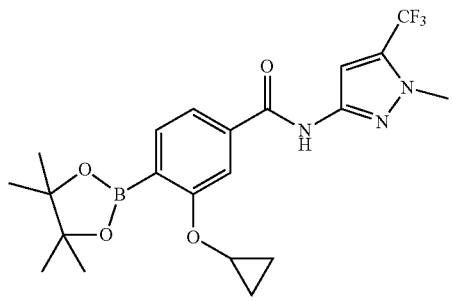

3-cyclopropoxy-N-(1-methyl-5-(trifluoromethyl)-1H-pyrazol-3-yl)-4-(4,4,5,5-tetramethyl-1,3,2-dioxaborolan-2-yl)benzamide Step 1: 4-bromo-3-cyclopropoxy-N-(1-methyl-5-(trifluoromethyl)-1H-pyrazol-3-yl)benzamide A solution of 4-bromo-3-cyclopropoxybenzoic acid (0.3 g, 1.167 mmol) in DMF (6.0 ml) was treated with HATU (0.444 g, 1.167 mmol) and the mixture stirred at rt for 15 min. 1-methyl-5-(trifluoromethyl)-1H-pyrazol-3-amine (0.193 g, 1.167 mmol) was then added followed by DIEA (0.408 ml, 2.334 mmol) and the mixture stirred at room temperature for 15 h. LC-MS showed complete consumption of starting material and formation of desired product. The mixture was diluted with EtOAc and washed with water (×2). The organic layer was then washed with brine, dried (MgSO$_4$) and concentrated to afford an crude oil. Crude was purified by MPLC ISCO Redi sep 24 gr column from 0-30% Hex/EtOAc to afford product 4-bromo-3-cyclopropoxy-N-(1-methyl-5-(trifluoromethyl)-1H-pyrazol-3-yl)benzamide LC-MS (ES, m/z)$C_{15}H_3BrF_3N_3O_2$: 404; Found 406[M+H]$^+$.

Step 2: 3-cyclopropoxy-N-(1-methyl-5-(trifluoromethyl)-1H-pyrazol-3-yl)-4-(4,4,5,5-tetramethyl-1,3,2-dioxaborolan-2-yl)benzamide To a flask was charged with 4-bromo-3-cyclopropoxy-N-(1-methyl-5-(trifluoromethyl)-1H-pyrazol-3-yl)benzamide (0.38 g, 0.94 mmol), 4,4,4',4',5,5,5',5'-octamethyl-2,2'-bi(1, 3,2-dioxaborolane) (0.26 g, 1.03 mmol), potassium acetate (0.27 g, 2.8 mmol), 1,1'-bis(diphenylphosphino)ferrocenedichloro palladium(ii) dichloromethane complex (0.07 g, 0.094 mmol) in dioxane (7.0 ml, 0.13 M). The resulting mixture was degassed with $N_2$ for 10 min and heated in a seal tube at 78° C. 18 hrs. The mixture was diluted with EtOAc and washed with water. Aqueous layer was extracted with EtOAc 1×. Organics were dry over MgSO$_4$, filtered and concentrated in vacuo to give dark brown residue. Crude was purified on 40 gr Redi Sep Rf filter column on CombiFlash with 0-40% Hexane/EtOAc to give product 3-cyclopropoxy-N-(1-methyl-5-(trifluoromethyl)-1H-pyrazol-3-yl)-4-(4,4,5,5-tetramethyl-1,3,2-dioxaborolan-2-yl)benzamide. LC-MS (ES, m/z) $C_{21}H_{25}BF_3N_3O_4$: 451; Found 452[M+H]$^+$.

157
Intermediate 74

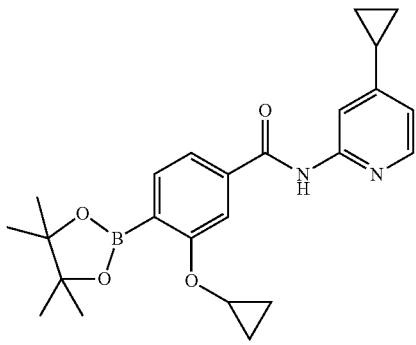 [SMILES: CC1(C)OB(c2ccc(C(=O)Nc3cc(C4CC4)ccn3)cc2OC2CC2)OC1(C)C]

3-cyclopropoxy-N-(4-cyclopropylpyridin-2-yl)-4-(4,4,5,5-tetramethyl-1,3,2-dioxaborolan-2-yl)benzamide

Step 1: 4-bromo-3-cyclopropoxy-N-(4-cyclopropylpyridin-2-yl)benzamide

A solution of 4-bromo-3-cyclopropoxybenzoic acid (0.6 g, 2.334 mmol) and dimethylformamide (0.063 ml, 0.817 mmol) in dichloromethane (12.0 ml) was treated with thionyl chloride (1.703 ml, 23.34 mmol) and the mixture stirred at 35° C. for 18 h. The solvent was evaporated and the residue azeotroped (×2) with toluene. The resulting cream solid was then diluted with MeCN (10 ml) and treated with DMAP (0.371 g, 3.03 mmol). The mixture was stirred at room temperature for 5 min and 4-cyclopropylpyridin-2-amine (0.376 g, 2.80 mmol) was added. The mixture was then stirred at 35 C for 15 h. LC-MS desired product as major product. The solvent was evaporated and the residue diluted with DCM and washed with water (2) and brine. The organic layer was dried (MgSO$_4$) and concentrated to afford a cream solid. Crude was purified on 40 gr Redi Sep Rf filter column on CombiFlash 0-40% Hex/EtOAc to afford product 4-bromo-3-cyclopropoxy-N-(4-cyclopropylpyridin-2-yl)benzamide. LC-MS (ES, m/z) C$_{18}$H$_{17}$BrN$_2$O$_2$: 373; Found 375[M+H]$^+$.

Step 2: 3-cyclopropoxy-N-(4-cyclopropylpyridin-2-yl)-4-(4,4,5,5-tetramethyl-1,3,2-dioxaborolan-2-yl)benzamide In the same procedure as intermediate 73, step 2, 3-cyclopropoxy-N-(4-cyclopropylpyridin-2-yl)-4-(4,4,5,5-tetramethyl-1,3,2-dioxaborolan-2-yl)benzamide was prepared. LC-MS (ES, m/z) C$_{24}$H$_{29}$BN$_2$O$_4$: 420; Found 421 [M+H]$^+$

158
Intermediate 75

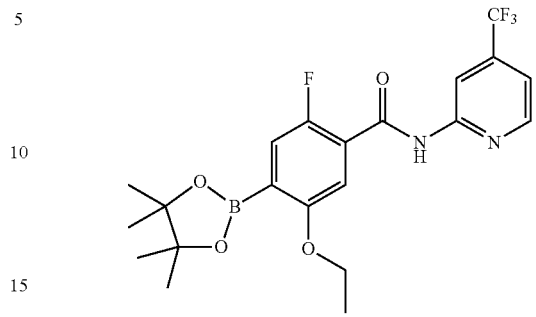

5-ethoxy-2-fluoro-4-(4,4,5,5-tetramethyl-1,3,2-dioxaborolan-2-yl)-N-(4-(trifluoromethyl)pyridin-2-yl)benzamide Step 1: 2-fluoro-5-hydroxy-4-iodobenzoic acid To a 500 ml one neck round bottom flask was charged with 2-fluoro-5-hydroxybenzoic acid (11 g, 70.5 mmol) in ammonia hydrate (14.68 ml, 176 mmol) and water (100 mL). The mixture was stirred and the solid completely dissolved and cooled to 0° C. in an ice water bath. Then a mixture of iodine (17.88 g, 70.5 mmol) and potassium iodide (12.87 g, 78 mmol) in water (100 ml) was added dropwise through a drop funnel in 40 mins. The resulting reaction mixture was stirred at room temperature for 2 hrs. The mixture was then acidified by HCl (conc.) to adjusted the pH to 3 and let sit over night. The solid was filtered and washed with water to afford solid-fluoro-5-hydroxy-4-iodobenzoic acid. LC-MS (ES, m/z) C$_7$H$_4$FIO$_3$: 282; Found 281 [M–H]$^-$.

Step 2: methyl 2-fluoro-5-hydroxy-4-iodobenzoate

To a 250 ml one neck round bottom flask was charged with 2-fluoro-5-hydroxy-4-iodobenzoic acid (12 g, 42.6 mmol) along with a freshly prepared mixture of methanol (100 mL) with sulfurous dichloride (15.19 g, 128 mmol). The resulting reaction mixture was then stirred at room temperature for 15 hours. The methanol was removed by rotary evaporation and the residue was partitioned between NaHCO$_3$(sat, 100 mL) and ethyl acetate (200 mL). The organic layer was separated and the organic layer was extracted with ethyl acetate (3×). The combined organic phases were dried over MgSO$_4$, filtered and concentrated. The crude was then purified by MPLC (80 g silica gel, 0 to 50% ethyl acetate in hexanes, 18 CV) to afford light color solid product methyl 2-fluoro-5-hydroxy-4-iodobenzoate. LC-MS (ES, m/z) C$_8$H$_6$FIO$_3$: 296; Found 297 [M+H]$^+$.

Step 3: methyl 5-ethoxy-2-fluoro-4-iodobenzoate

To a 250 ml one neck round bottom flask was charged with methyl 2-fluoro-5-hydroxy-4-iodobenzoate (2.5 g, 8.44 mmol) along with potassium carbonate (3.50 g, 25.3 mmol) and DMF (15 ml). The mixture was stirred and then iodoethane (1.976 g, 12.67 mmol) was added dropwise via a syringe in 5 min. The resulting reaction mixture was then stirred at room temperature for 18 hrs overnight. The mixture was diluted with ethyl acetate (30 mL) and the solid was filtered and washed with ethyl acetate (3×). The filtrate was then concentrated by rotary evaporation. The residue was purified by MPLC (80 g silica gel, 0-20% ethyl acetate in hexanes, 18 CV) to afford colorless liquid product methyl 5-ethoxy-2-fluoro-4-iodobenzoate. LC-MS (ES, m/z) $C_{10}H_{10}FIO_3$: 324; Found 325 [M+H]+.

Step 4: 5-ethoxy-2-fluoro-4-iodobenzoic acid

To a 250 ml one neck round bottom flask was charged with methyl 5-ethoxy-2-fluoro-4-iodobenzoate (2.700 g, 8.33 mmol) along with lithium hydroxide hydrate (1.748 g, 41.7 mmol) and MeOH (10 ml), THF (10.00 ml), Water (5 ml). The resulting reaction mixture was then stirred and heated in an oil bath of 40° C. for 15 hrs over night The mixture was diluted with water (20 mL) and the pH was adjusted to 2 by HCl (conc.), then extracted with ethyl acetate (3×). The combined organic phases were washed with water, dried over MgSO4, filtered and concentrated to afford white solid product 5-ethoxy-2-fluoro-4-iodobenzoic acid. LC-MS (ES, m/z) $C_9H_8FIO_3$: 310; Found 311 [M+H]+.

Step 5: 5-ethoxy-2-fluoro-4-iodo-N-(4-(trifluoromethyl)pyridin-2-yl)benzamide

To a 100 ml one neck round bottom flask was charged with 5-ethoxy-2-fluoro-4-iodobenzoic acid (1.00 g, 3.23 mmol) along with $CH_2Cl_2$(8 ml) followed by oxalyl dichloride (0.546 ml, 6.45 mmol). The mixture was stirred while a drop of DMF was added to initiate the reaction and air bubble formed right away. The resulting reaction was then stirred at room temperature for 40 min until no air bubble evolved. The mixture was then concentrated.

To a 100 ml one necked round bottom flask was charged with 4-(trifluoromethyl)pyridin-2-amine (0.622 g, 3.84 mmol) along with N,N-dimethylpyridin-4-amine (0.039 g, 0.320 mmol), THF (5 mL) and N-ethyl-N-isopropylpropan-2-amine (0.826 g, 6.39 mmol). The mixture was stirred and then a solution of previously made 5-ethoxy-2-fluoro-4-iodobenzoyl chloride (1.05 g, 3.20 mmol) in THF (5 mL) was added dropwise in 5 min. The resulting reaction mixture was stirred and heated in an oil bath of 40° C. for 15 hrs overnight. The reaction was worked up by basic washing and extraction and the crude was purified by MPLC (120 g silica gel, 0 to 60% ethyl acetate in hexanes, 18 CV) to afford product 5-ethoxy-2-fluoro-4-iodo-N-(4-(trifluoromethyl)pyridin-2-yl)benzamide. LC-MS (ES, m/z) $C_{15}H_{11}F_4IN_2O_2$: 454; Found 455 [M+H]+. 1HNMR (500 MHz, CDCl3, δ); 9.30 (1H, d, J=14 Hz), 8.70 (1H, s), 8.50 (1H, d, J=5 Hz), 7.73 (1H, dd, J=6.0, 3.0 Hz), 7.28 (1H, d, J=11 Hz), 7.13 (1H, dd, J=11, 9.0 Hz), 7.08 (1H, m), 4.09 (2H, q, J=16 Hz), 1.43 (3H, t, J=16 Hz).

Step 6: 5-ethoxy-2-fluoro-4-(4,4,5,5-tetramethyl-1,3,2-dioxaborolan-2-yl)-N-(4-(trifluoromethyl)pyridin-2-yl)benzamide A 5 ml microwave reaction vial containing 5-ethoxy-2-fluoro-4-iodo-N-(4-(trifluoromethyl)pyridin-2-yl)benzamide (200 mg, 0.440 mmol), 4,4,4',4',5,5,5',5'-octamethyl-2,2'-bi(1,3,2-dioxaborolane) (168 mg, 0.661 mmol), potassium acetate (130 mg, 1.321 mmol)) and Pd(dppf)$CH_2Cl_2$(36.0 mg, 0.044 mmol) under a $N_2$ atmosphere was treated with DMSO and immediately evacuated and backfilled with $N_2$ (×3). The resulting red-brown mixture was then stirred at 60° C. for 3 h. The mixture was diluted with ethyl acetate (10 mL) and water (4 mL). The organic layer was separated and the aqueous layer was extracted by ethyl acetate (3×). The combined organic phases were washed with water, dried over MgSO4, filtered and concentrated. The crude was purified by MPLC (24 g gold column, 0 to 60% ethyl acetate in hexanes, 18 CV) to afford white solid product 5-ethoxy-2-fluoro-4-(4,4,5,5-tetramethyl-1,3,2-dioxaborolan-2-yl)-N-(4-(trifluoromethyl)pyridin-2-yl)benzamide. LC-MS (ES, m/z) $C_{21}H_{23}BF_4N_2O_4$: 454; Found 455 [M+H]+.

Intermediate 76

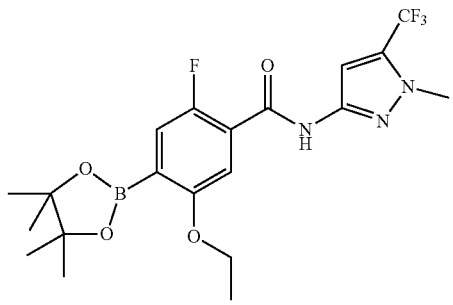

5-ethoxy-2-fluoro-N-(1-methyl-5-(trifluoromethyl)-1H-pyrazol-3-yl)-4-(4,4,5,5-tetramethyl-1,3,2-dioxaborolan-2-yl)benzamide Step 1: 5-ethoxy-2-fluoro-4-iodo-N-(1-methyl-5-(trifluoromethyl)-1H-pyrazol-3-yl)benzamide A solution of 5-ethoxy-2-fluoro-4-iodobenzoic acid, 334660-61B (1.17 g, 3.77 mmol) in DMF (10 ml) was treated with HATU (1.507 g, 3.96 mmol) and the mixture stirred at rt for 15 min. 1-methyl-5-(trifluoromethyl)-1H-pyrazol-3-amine (0.654 g, 3.96 mmol) was then added followed by N-ethyl-N-isopropylpropan-2-amine (1.315 ml, 7.55 mmol) and the mixture stirred at rt for 15 h. The mixture was then diluted with ethyl acetate (50 mL), washed with NaHCO3 (sat, 10 mL) and water, dried over MgSO4, filtered and concentrated. The crude was purified by MPLC (80 g silica gel, 10 to 60% ethyl acetate in hexanes, 18 CV) to afford product 5-ethoxy-2-fluoro-4-iodo-N-(1-methyl-5-(trifluoromethyl)-1H-pyrazol-3-yl)benzamide. LC-MS (ES, m/z) $C_{14}H_{12}F_4IN_3O_2$: 457; Found 458 [M+H]+.

Step 2: 5-ethoxy-2-fluoro-N-(1-methyl-5-(trifluoromethyl)-1H-pyrazol-3-yl)-4-(4,4,5,5-tetramethyl-1,3,2-dioxaborolan-2-yl)benzamide A 20 ml microwave reaction vial containing 5-ethoxy-2-fluoro-4-iodo-N-(1-methyl-5-(trifluoromethyl)-1H-pyrazol-3-yl)benzamide (1500 mg, 3.28 mmol), 4,4,4',4',5,5,5',5'-octamethyl-2,2'-bi(1,3,2-dioxaborolane) (1250 mg, 4.92 mmol), potassium acetate (966 mg, 9.84 mmol)) and Pd(dppf)$CH_2Cl_2$ (268 mg, 0.328 mmol) under a $N_2$ atmosphere was treated with DMSO (15 ml) and immediately evacuated and backfilled with $N_2$ (×3). The resulting red-brown mixture was then stirred at 60° C. for 3 h. The mixture was diluted with ethyl acetate (50 mL) and water (30 mL). The organic layer was separated and the aqueous layer was extracted by ethyl acetate (3×). The combined organic phases were washed with water, dried over MgSO4, filtered and concentrated. The crude was purified by MPLC (80 g gold column, 0 to 60% ethyl acetate in hexanes, 18 CV) to afford white solid product 5-ethoxy-2-fluoro-N-(1-methyl-5-(trifluoromethyl)-1H-pyrazol-3-yl)-4-(4,4,5,5-tetramethyl-1,3,2-dioxaborolan-2-yl)benzamide. LC-MS (ES, m/z) $C_{14}H_{12}F_4IN_3O_2$: 457; Found 458 [M+H]$^+$.

Intermediate 77

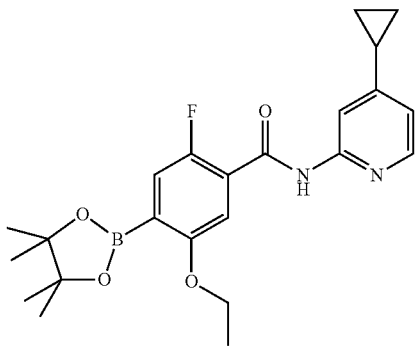 [SMILES: CCOc1cc(C(=O)Nc2cc(C3CC3)ccn2)c(F)cc1B1OC(C)(C)C(C)(C)O1]

N-(4-cyclopropylpyridin-2-1)-5-ethoxy-2-fluoro-4-(4,4,5,5-tetramethyl-1,3,2-dioxaborolan-2-yl)benzamide In the same procedure as intermediate 76 using 4-cyclopropyl-2-pyridineamine as starting material, N-(4-cyclopropylpyridin-2-yl)-5-ethoxy-2-fluoro-4-(4,4,5,5-tetramethyl-1,3,2-dioxaborolan-2-yl)benzamide was prepared. LC-MS (ES, m/z) $C_{14}H_{12}F_4IN_3O_2$: 457; Found 458 [M+H]$^+$.

Intermediate 78

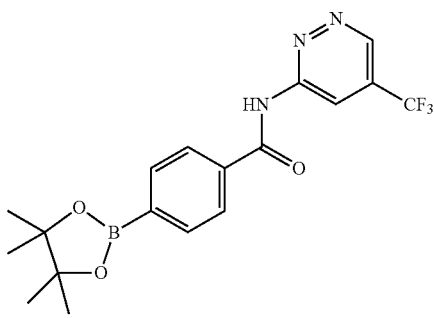 [SMILES: CC1(C)OB(c2ccc(C(=O)Nc3cc(C(F)(F)F)cnn3)cc2)OC1(C)C]

4-(4,4,5,5-tetramethyl-1,3,2-dioxaborolan-2-yl)-N-(5-(trifluoromethyl)pyridazin-3-yl)benzamide Step 1: (E)-2-(3,3,3-trifluoro-2-oxopropylidene)hydrazinecarboxamide To a solution of 3,3-dibromo-1,1,1-trifluoropropan-2-one (22.50 g, 83.33 mmol) in water (220 mL) was added AcONa (27.33 g, 333.32 mmol) and the mixture was heated to 80° C. for 1.5 hrs. After cooling the reaction mixture to room temperature, compound 3 (7.50 g, 100.00 mmol) was added. After stirring the mixture at room temperature for 5 hrs, the precipitate was collected by filtration. After drying the solid, crude (E)-2-(3,3,3-trifluoro-2-oxopropylidene)hydrazinecarboxamide (14.00 g, 77%) was obtained, which used directly to next step without purification.

Step 2: (E)-ethyl 3-((E)-(2-carbamoylhydrazono)methyl)-4,4,4-trifluorobut-2-enoate To a solution of (E)-2-(3,3,3-trifluoro-2-oxopropylidene)hydrazinecarboxamide (8.26 g, 45.115 mmol) in THF (100 mL) was added ethyl 2-(triphenylphosphoranylidene)acetate (15.7 g, 45.115 mmol) at room temperature under N2 protection. The solution was stirred at room temperature overnight. The solvent was removed under reduced pressure and the residue was dissolved in t-butyl methyl ether to remove insoluble matters and the obtained organic layer was dried over anhydrous MgSO$_4$ and concentrated to obtain (E)-ethyl 3-((E)-(2-carbamoylhydrazono)methyl)-4,4,4-trifluorobut-2-enoate (9.00 g, 79%) which did not require further purification.

Step 3: 5-(trifluoromethyl)pyridazin-3(2H)-one

A solution of (E)-ethyl 3-((E)-(2-carbamoylhydrazono)methyl)-4,4,4-trifluorobut-2-enoate (18.00 g, 71.146 mmol) in conc. HCl (100 mL) was heated to reflux for 3 hrs. The result solution was neutralized by Na2CO3, and extracted with DCM (200 mL×3), the organic layer was dried over anhydrous MgSO$_4$ and concentrated. The residue was purified by column chromatography (PE/EA=4/1) to afford the pure 5-(trifluoromethyl)pyridazin-3(2H)-one (5.30 g, 45%) as a white solid.

$^1$H NMR (400 MHz, DMSO-d6) δ ppm 13.61 (br. s, 1 H), 8.18 (d, J=1.57 Hz, 1 H), 7.36 (s, 1 H); MS-ESI (m/z): 165.0 (M+1)+ Acq Method 0-60AB_2 min_220&254.1 cm (0.435 min).

Step 4: 3-chloro-5-(trifluoromethyl)pyridazine

A mixture of 5-(trifluoromethyl)pyridazin-3(2H)-one (2.00 g, 12.195 mmol) and POCl3 (9.33 g, 60.976 mmol) in dioxane (10 mL) was heated at 80° C. for 3 hrs. The volatile was removed, the residue was neutralized by adding saturated Na2CO3 and the mixture was extracted with DCM (20 mL×3). The obtained organic layer was washed with brine (20 mL×3), dried over anhydrous MgSO$_4$, concentrated in vacuo. The residue was purified by column chromatography (PE/EA=60/1) to afford the pure product 3-chloro-5-(trifluoromethyl)pyridazine (300 mg, 14%) as a yellow oil. $^1$H NMR (400 MHz, DMSO-d6) δ ppm 9.71 (d, J=1.17 Hz, 1 H), 8.53 (d, J=0.78 Hz, 1 H); MS-ESI (m/z): 183.1 (M+1)+ Acq Method 0-60AB_2 min_220&254.1 cm (1.032 min).

Step 5: 4-(4,4,5,5-tetramethyl-1,3,2-dioxaborolan-2-yl)-N-(5-(trifluoromethyl)pyridazin-3-yl)benzamide The compound was prepared to the procedure for preparation of 4-(4,4,5,5-tetramethyl-1,3,2-dioxaborolan-2-yl)-N-(4-(trifluoromethyl)pyrimidin-2-yl)benzamide. 1H NMR (400 MHz, DMSO-d6) δ ppm 12.01 (s, 1 H), 9.46 (s, 1 H), 8.70 (s, 1 H), 8.05 (d, J=7.83 Hz, 2 H), 7.80 (d, J=8.22 Hz, 2 H), 1.29 (s, 12 H); MS-ESI (m/z): 394.2 (M+1)+ Acq Method 10-80AB_2 min_220&254.1 cm (1.339 min).

Intermediate 79

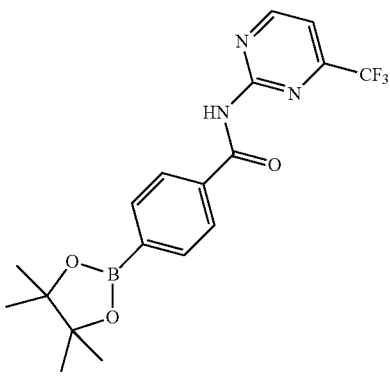 [SMILES: CC1(C)OB(c2ccc(C(=O)Nc3nccc(C(F)(F)F)n3)cc2)OC1(C)C]

4-(4,4,5,5-tetramethyl-1,3,2-dioxaborolan-2-yl)-N-(4-(trifluoromethyl)pyrimidin-2-yl)benzamide To a solution of 4-(4,4,5,5-tetramethyl-1,3,2-dioxaborolan-2-yl)benzamide (400 mg, 1.62 mmol) in t-BuOH (30 mL) was added 2-chloro-4-(trifluoromethyl)pyrimidine (593 mg, 3.24 mmol), Pd2(dba)3 (45 mg, 0.049 mmol), X-phos (24 mg, 0.049 mmol) and Cs2CO3 (1.58 g, 4.86 mmol), and the mixture was heated to reflux under N2 protection for 2 hrs. Water (30 mL) and EtOAc (70 mL) was added, the organic layer was washed with brine (30 mL), dried over anhydrous MgSO$_4$, concentrated in vacuo. The crude was purified by column chromatography (PE/EA=6/1 to 4/1) to give 4-(4,4,5,5-tetramethyl-1,3,2-dioxaborolan-2-yl)-N-(4-(trifluoromethyl)pyrimidin-2-yl)benzamide (500 mg, 79%) as a yellow solid. $^1$H NMR (400 MHz, DMSO-d6) δ ppm 11.53 (br. S, 1 H), 9.07 (d, J=4 Hz, 1 H), 7.94 (d, J=8 Hz, 2 H), 7.76 (d, J=8 Hz, 2 H), 7.71 (d, J=4 Hz, 1 H), 1.29 (s, 12 H); MS-ESI (m/z): 394.2 (M+1)+ Acq Method 10-80AB_2 min_220&254.1 cm (1.282 min).

Intermediate 80

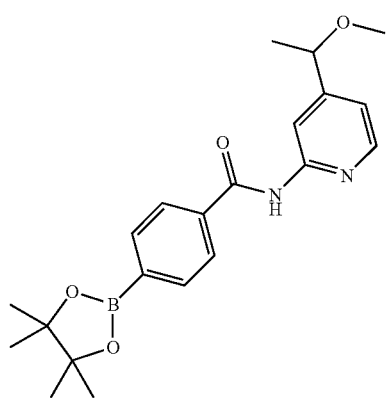

N-(4-(1-methoxyethyl)pyridin-2-yl)-4-(4,4,5,5-tetramethyl-1,3,2-dioxaborolan-2-yl)benzamide (a) 2-chloro-4-(1-methoxyethyl)pyridine A solution of 1-(2-chloropyridin-4-yl)ethanol (100 mg, 0.64 mmol) in DMF (2 mL) was added NaH (18.27 mg, 0.76 mmol). Then the mixture was added iodomethane (135 mg, 0.95 mmol) at 25° C. The mixture was stirred at 25° C. for overnight. The mixture was added water (30 mL) and extracted with EA (50 mL). The organic layer was washed with water (50 mL*3), brine (50 mL), dried over Na2SO4 and evaporation. The residue was purified by TLC to get 2-chloro-4-(1-methoxyethyl)pyridine (40 mg, yield 36.7%). $^1$H NMR (300 MHz, DMSO-d6) δ=8.48-8.22 (m, 1H), 7.45-7.42 (m, 1H), 7.38-7.34 (m, 1H), 4.51-4.25 (m, 1H), 3.19 (s, 3H), 1.36-1.29 (m, 3H).

(b) N-(4-(1-methoxyethyl)pyridin-2-yl)-4-(4,4,5,5-tetramethyl-1,3,2-dioxaborolan-2-yl)benzamide The compound was prepared to the procedure for preparation of N-(4-(2-hydroxypropan-2-yl)pyridin-2-yl)-4-(4,4,5,5-tetramethyl-1,3,2-dioxaborolan-2-yl)benzamide. $^1$H NMR (400 MHz, CHLOROFORM-d) δ=8.69-8.63 (m, 1H), 8.36-8.32 (m, 1H), 8.29 (d, J=5.0 Hz, 1H), 7.98-7.85 (m, 4H), 7.11 (d, J=4.0 Hz, 1H), 4.36 (d, J=6.5 Hz, 1H), 3.30 (s, 3H), 1.46 (d, J=6.5 Hz, 3H), 1.37 (s, 13H).

Intermediate 81

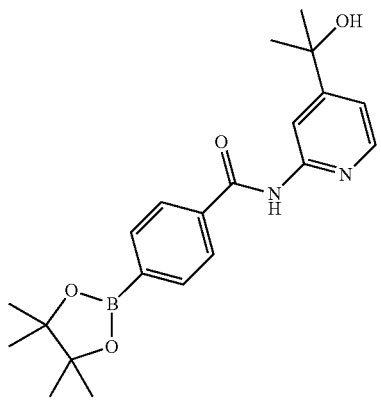 [SMILES: CC(C)(O)c1ccnc(NC(=O)c2ccc(B3OC(C)(C)C(C)(C)O3)cc2)c1]

N-(4-(2-hydroxypropan-2-yl)pyridin-2-yl)-4-(4,4,5,5-tetramethyl-1,3,2-dioxaborolan-2-yl)benzamide Step 1: 2-(2-chloropyridin-4-yl)propan-2-ol To a solution of 2-chloro-4-iodopyridine (2.0 g, 8.36 mmol) in anhydrous THF (20 mL) was added n-BuLi (6.68 mL, 16.72 mmol) at −78° C. The mixture was stirred at −78° C. for 20 min. Then acetone (969 mg, 16.72 mmol) was added at −78° C. and the mixture was stirred at −78° C. for 50 min. The mixture was quenched by sat. NH$_4$Cl (20 mL) and extracted with ethyl acetate (100 mL×3), the combined organic layers were washed with brine (50 mL), dried over sodium sulfate, filtered and concentrated to afford the crude product, which was purified on silica gel chromatography (EA:PE=5%~40%) to afford 2-(2-chloropyridin-4-yl)propan-2-ol (630 mg, yield 44%) as a yellow liquid. LCMS Method: 5-95AB_1.5 min_220.1 cm, Retention time: 0.567, (M+H)+m/z: 171.8.

Step 2: N-(4-(2-hydroxypropan-2-yl)pyridin-2-yl)-4-(4,4,5,5-tetramethyl-1,3,2-dioxaborolan-2-yl)benzamide To a clear solution of 2-(2-chloropyridin-4-yl)propan-2-ol (630 mg, 3.68 mmol) and 4-(4,4,5,5-tetramethyl-1,3,2-dioxaborolan-2-yl)benzamide (911 mg, 3.68 mmol) in dioxane (40 mL) was added Cs2CO3 (2.4 g, 7.368 mmol) and Pd(pddf)Cl2 (catalytic amount) was added under nitrogen protection. Then the mixture was heated to 100° C. stirred for 12 hours. After cooled to room temperature, the mixture was filtered and the filtrate was concentrated in vacuum and purified on silica gel chromatography (EA:PE=5%~40%) to afford N-(4-(2-hydroxypropan-2-yl)pyridin-2-yl)-4-(4,4,5,5-tetramethyl-1,3,2-dioxaborolan-2-yl)benzamide (353 mg, yield 25%) as a yellow liquid.

$^1$H NMR (400 MHz, CHLOROFORM-d) δ=8.60 (s, 1H), 8.48 (s, 1H), 8.28 (d, J=5.3 Hz, 1H), 7.97-7.88 (m, 4H), 7.25 (d, J=1.5 Hz, 1H), 1.90 (s, 1H), 1.62 (s, 6H), 1.37 (s, 12H).

Intermediate 82

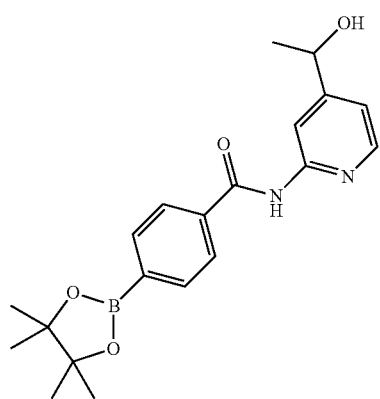 [SMILES: CC(O)c1ccnc(NC(=O)c2ccc(B3OC(C)(C)C(C)(C)O3)cc2)c1]

N-(4-(1-hydroxyethyl)pyridin-2-yl)-4-(4,4,5,5-tetramethyl-1,3,2-dioxaborolan-2-yl)benzamide Step 1: 1-(2-chloropyridin-4-yl)ethanol To a solution of 2-chloro-4-iodopyridine (500 mg, 2.09 mmol) in anhydrous THF (5 mL) was added n-BuLi (1.67 mL, 4.18 mmol) at −78° C. The mixture was stirred at −78° C. for 20 min. Then acetaldehyde (184 mg, 418 mmol) was added at −78° C. and the mixture was stirred at −78° C. for 50 min. The mixture was quenched by sat.NH$_4$Cl (10 mL) and extracted with ethyl acetate (20 mL×3), the combined organic layers were washed with brine, dried over sodium sulfate, filtered and concentrated to afford the crude product, which was purified on silica gel chromatography (EA:PE=5%~40%) to afford 1-(2-chloropyridin-4-yl)ethanol (250 mg, yield 76%) as a yellow liquid.

$^1$H NMR (300 MHz, CHLOROFORM-d) δ=8.38-8.24 (m, 1H), 7.45-7.34 (m, 1H), 7.30-7.20 (m, 1H), 4.92 (dd, J=3.0, 6.2 Hz, 1H), 2.71 (d, J=3.4 Hz, 1H), 1.60-1.44 (m, 3H).

Step 2: N-(4-(1-hydroxyethyl)pyridin-2-yl)-4-(4,4,5,5-tetramethyl-1,3,2-dioxaborolan-2-yl)benzamide The compound was prepared to the procedure for preparation of N-(4-(2-hydroxypropan-2-yl)pyridin-2-yl)-4-(4,4,5,5-tetramethyl-1,3,2-dioxaborolan-2-yl)benzamide. $^1$H NMR (400 MHz, CHLOROFORM-d) δ=8.69-8.64 (m, 1H), 8.38 (s, 1H), 8.29-8.25 (m, 1H), 7.95-7.86 (m, 5H), 7.81 (s, 2H), 7.61-7.42 (m, 1H), 7.16 (d, J=4.3 Hz, 1H), 5.01-4.91 (m, 1H), 3.49 (s, 2H), 2.22-2.19 (m, 1H), 1.66 (br. s, 1H), 1.54 (d, J=6.8 Hz, 3H), 1.36 (d, J=4.0 Hz, 18H).

Intermediate 83

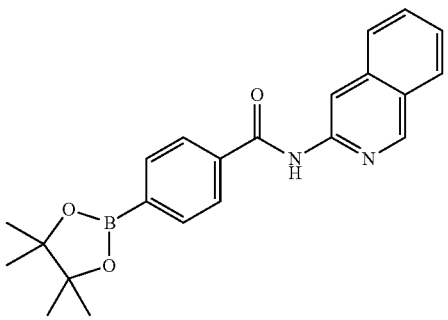 [SMILES: CC1(C)OB(c2ccc(C(=O)Nc3cc4ccccc4cn3)cc2)OC1(C)C]

N-(isoquinolin-3-yl)-4-(4,4,5,5-tetramethyl-1,3,2-dioxaborolan-2-yl)benzamide

To a solution of 4-(4,4,5,5-tetramethyl-1,3,2-dioxaborolan-2-yl)benzoic acid (232 mg, 0.936 mmoL) in anhydrous DCM (10 mL) was added (COCl)$_2$ (356 mg, 2.81 mmol) at 0° C., then DMF (one drop) was added and the mixture was stirred at 25° C. for 1.5 hrs. The mixture was concentrated in vacuo, which then diluted with DCM (5 mL) was added to a solution of isoquinolin-3-amine (90 mg, 0.624 mmol), TEA (158 mg, 1.56 mmol) in DCM (10 mL). The mixture was stirred at 25° C. for 3 hrs, The mixture was quenched by the addition of water (10 mL) at 0° C., the mixture was then extracted with DCM (20 mL×3), the combined organic layers were washed with 1M HCl (5 mL), brine (10 mL), dried over sodium sulfate, filtered and concentrated to give the crude product, which was purified on silica gel column chromatography (EA/PE=10%~40%) (80 mg, yield 34.3%) as a white solid. $^1$H NMR (300 MHz, CHLOROFORM-d) d=9.02 (s, 1H), 8.87 (s, 1H), 8.79 (s, 1H), 8.01-7.86 (m, 6H), 7.68 (t, J=7.1 Hz, 1H), 7.56-7.46 (m, 1H), 1.38 (s, 12H).

Intermediate 84

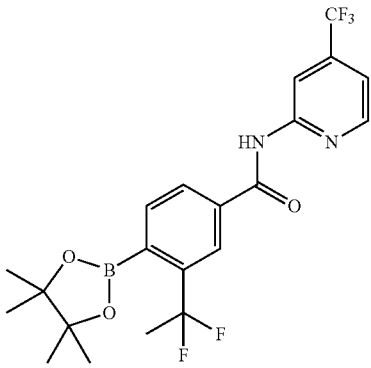 [SMILES: CC(F)(F)c1cc(C(=O)Nc2cc(C(F)(F)F)ccn2)ccc1B1OC(C)(C)C(C)(C)O1]

3-(1,1-difluoroethyl)-4-(4,4,5,5-tetramethyl-1,3,2-dioxaborolan-2-yl)-N-(4-(trifluoromethyl)pyridin-2-yl)benzamide Step 1:
(2-bromo-5-(methoxycarbonyl)phenyl)methylene diacetate CrO3 (18.00 g, 180 mmol) was added in portions over 30 min to 4-bromo-3-methyl-benzoic acid methyl ester (13.8 g, 60 mmol) dissolved in AcOH (99 mL) and Ac2O (102 mL) containing H$_2$SO4 (15 mL) cooled to ice-bath temperature. The mixture was stirred for another hour as the ice bath expired. The reaction mixture was poured onto chilled water (900 mL) and stirred vigorously for 30 mins. The precipitated solid was collected by filtration and washing with water (3×50 mL) to give (2-bromo-5-(methoxycarbonyl)phenyl)methylene diacetate (13.7 g, yield 60%) as a yellow solid. M/Z (ESI) 366.9796 ([M+Na]+.

Step 2: methyl 4-bromo-3-formylbenzoate

4-Bromo-3-diacetoxymethyl-benzoic acid methyl ester (13.7 g, 37.5 mmol) was heated at reflux in MeOH—H2O (1:1, 120 mL) containing H$_2$SO4 (1.5 mL) for 30 mins. The reaction mixture was then diluted with H2O (300 mL) and extracted with EtOAc (3×50 mL). The combined extracts were washed with H2O (50 mL) and brine (50 mL), then dried over Na2SO4. The solvent was removed by rotary evaporation to give a faint-yellow coloured oil. This was a mixture of 4-bromo-3-formylbenzoic acid methyl ester and the dimethyl acetal in an 8.5:1 ratio as found by $^1$H NMR spectroscopy. The oil was taken up in THF (90 mL) and IN HCl (24 mL) and the mixture heated at reflux until complete conversion to the aldehyde was achieved as determined by TLC (Rf~0.9, DCM). The THF was removed by rotary evaporation to give methyl 4-bromo-3-formylbenzoate (8.4 g, Yield 79%) as a white solid. $^1$H NMR (400 MHz, CHLOROFORM-d)=10.38 (s, 1H), 8.54 (d, J=2.3 Hz, 1H), 8.10 (dd, J=2.3, 8.3 Hz, 1H), 7.76 (d, J=8.3 Hz, 1H), 3.95 (s, 3H).

Step 3: methyl 4-bromo-3-(1-hydroxyethyl)benzoate

To a solution of methyl 4-bromo-3-formylbenzoate (1 g, 4.11 mmol) in anhydrous THF (15 mL) at −20° C., MeMgBr (3M in ether, 1.6 mL, 4.93 mmol) was added dropwise. The reaction mixture was stirred at −20° C.~0° C. for 1.5 hrs. The reaction was quenched by saturated ammonium chloride (20 mL) slowly, then the mixture was extracted with EA (20 mL×3), the combined organic layers were washed with brine (20 mL), dried over sodium sulfate, filtered and concentrated to afford the crude product, which was purified on silica gel column chromatograph (EA/PE=0%~25%) to give methyl 4-bromo-3-(1-hydroxyethyl)benzoate (900 mg, yield 84.9%) as a colorless oil. $^1$H NMR (400 MHz, CHLOROFORM-d)=8.23 (d, J=2.0 Hz, 1H), 7.73 (dd, J=2.0, 8.3 Hz, 1H), 7.56 (d, J=8.3 Hz, 1H), 5.22 (dq, J=3.8, 6.3 Hz, 1H), 3.89 (s, 3H), 2.49 (d, J=3.8 Hz, 1H), 1.48 (d, J=6.5 Hz, 3H).

Step 4: methyl 3-acetyl-4-bromobenzoate

To a solution of methyl 4-bromo-3-(1-hydroxyethyl)benzoate (1 g, 3.86 mmol) in anhydrous DCM (20 mL) was added Martin's reagent (3.2 g, 7.72 mmol) at 0° C. portionwise. The mixture was stirred at 0° C. to 25° C. for 2 hours. The mixture was quenched by the addition of a solution of 15% Na2S2O3 in saturated NaHCO3 (30 mL) at 0° C. slowly, the mixture was then separated and the aqueous layer was extracted with DCM (50 mL×2), the combined organic layers were washed with brine (20 mL), dried over sodium sulfate, filtered and concentrated to give methyl 3-acetyl-4-bromobenzoate (900 mg, yield 90.9%) as a yellow oil.

Step 5: methyl 4-bromo-3-(1,1-difluoroethyl)benzoate

To a solution of methyl 3-acetyl-4-bromobenzoate (0.9 g, 3.50 mmol) in anhydrous DCM (20 mL) was added DAST (1.13 g, 7.00 mmol) at −78° C. drop-wise under N2. The mixture was stirred at 0° C. to 25° C. for 16 hours. The mixture was quenched by the addition of saturated NaHCO3 (30 mL) at 0° C. slowly, the mixture was then separated and the aqueous layer was extracted with DCM (50 mL×2), the combined organic layers were washed with brine (20 mL), dried over sodium sulfate, filtered and concentrated to afford the crude product, which was purified on silica gel column chromatograph (EA/PE=0% 15%) to give methyl 4-bromo-3-(1,1-difluoroethyl)benzoate (160 mg, yield 16.4%) as a yellow solid. $^1$H NMR (400 MHz, CHLOROFORM-d) d=8.26 (d, J=1.2 Hz, 1H), 7.94-7.87 (m, 1H), 7.74 (d, J=8.2 Hz, 1H), 3.94 (s, 3H), 2.06 (t, J=18.4 Hz, 3H).

Step 6: 4-bromo-3-(1,1-difluoroethyl)benzoic acid

To a solution of methyl 4-bromo-3-(1,1-difluoroethyl)benzoate (190 mg, 0.680 mmoL) in MeOH/H2O (3:1, 8 mL) was added NaOH (41 mg, 1.02 mmol). The mixture was stirred at 25° C. for 10 hours. Organic solvent was removed and the mixture was diluted with water (10 mL) and EA (10 mL), separated and the aqueous layer was adjust acid to PH=1 with 1M HCl. The white solid was collected via filtration and It was dried to give 4-bromo-3-(1,1-difluoroethyl)benzoic acid (160 mg, yield 93.6%). $^1$H NMR (400 MHz, DMSO-d6)=8.06 (s, 1H), 7.88 (s, 2H), 2.04 (t, J=19.2 Hz, 3H).

Step 7: 4-bromo-3-(1,1-difluoroethyl)-N-(4-(trifluoromethyl)pyridin-2-yl)benzamide To a solution of 4-bromo-3-(1,1-difluoroethyl)benzoic acid (60 mg, 0.226 mmol) in anhydrous DCM (10 mL) was added (COCl)2 (86 mg, 0.679 mmol) at 0° C., then DMF (one drop) was added and the mixture was stirred at 25° C. for 1.5 hrs. The mixture was concentrated in vacuo, which then diluted with THF (10 mL), to the mixture was added a solution of 4-(trifluoromethyl)pyridin-2-amine (74 mg, 0.452 mmol) in THF (1 mL) at 0° C. The mixture was stirred at 80° C. for 16 hrs, then quenched by the addition of water (10 mL) at 0° C., the mixture was then extracted with DCM (50 mL×3), the combined organic layers were washed with brine (20 mL), dried over sodium sulfate, filtered and concentrated to afford the crude product, which was purified on silica gel column chromatograph (EA/PE=0%~35%) to give 4-bromo-3-(1,1-difluoroethyl)-N-(4-(trifluoromethyl)pyridin-2-yl)benzamide (75 mg, 81.5%) as a white solid.

Step 8: 3-(1,1-difluoroethyl)-4-(4,4,5,5-tetramethyl-1,3,2-dioxaborolan-2-yl)-N-(4-(trifluoromethyl)pyridin-2-yl)benzamide To a solution of 4-bromo-3-(1,1-difluoroethyl)-N-(4-(trifluoromethyl)pyridin-2-yl)benzamide (90 mg, 0.22 mmol), KOAc (109 mg, 0.66 mmol) and 4-(4,4,5,5-tetramethyl-1, 3,2-dioxaborolan-2-yl)benzamide (67 mg, 0.26 mmol) in dioxane (6 mL) was added Pd(pddf)Cl2 (catalytic amount) under nitrogen protection. Then the mixture was heated to 100° C. stirred for 3 hours. After cooled to room temperature, the mixture was filtered and the filtrate was concentrated in vacuum and purified on silica gel chromatography (EA/PE=0%~20%) to give 3-(1,1-difluoroethyl)-4-(4,4,5,5-tetramethyl-1,3,2-dioxaborolan-2-yl)-N-(4-(trifluoromethyl)pyridin-2-yl)benzamide (75 mg, yield 75%) as a yellow solid. (ESI): M/Z (M+1): 457.1 (R.T.: 1.328).

Intermediate 85

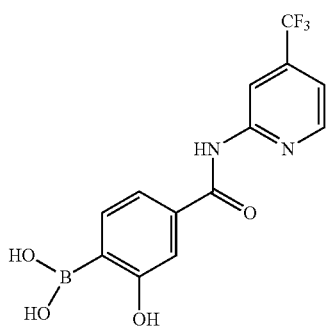 [SMILES: O=C(Nc1cc(C(F)(F)F)ccn1)c1ccc(B(O)O)c(O)c1]

(2-hydroxy-4-((4-(trifluoromethyl)pyridin-2-yl)carbamoyl)phenyl)boronic acid

BBr$_3$ (22.38 mmol, 1.0M in DCM) was added to a stirred mixture of potassium trifluoro(2-methoxy-4-((4-(trifluoromethyl)pyridin-2-yl)carbamoyl)phenyl)borate (5 g, 12.43 mmol) in methylene chloride (10 ml) at 0° C., the resulting reaction mixture was stirred at 0° C. and allowed to rise to room temperature. The yellow precipitate was filtered, washed with methylene chloride and dried by suction under N$_2$ to give (2-hydroxy-4-((4-(trifluoromethyl)pyridin-2-yl)carbamoyl)phenyl)boronic acid (4.25 g, 13.04 mmol), LCMS showed [M+H]$^+$ at 327.

Intermediate 86

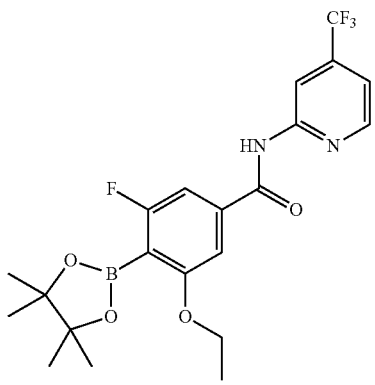 [SMILES: CCOc1cc(C(=O)Nc2cc(C(F)(F)F)ccn2)cc(F)c1B1OC(C)(C)C(C)(C)O1]

3-ethoxy-5-fluoro-4-(4,4,5,5-tetramethyl-1,3,2-dioxaborolan-2-yl)-N-(4-(trifluoromethyl)pyridin-2-yl)benzamide Step a) 3-ethoxy-5-fluorobenzoic acid SODIUM (6.54 g, 285 mmol) was dissolved in EtOH (150 ml) and concentrated to give a white solid. The solid was dissolved in DMSO (100 ml) and then added 3,5-difluorobenzoic acid (18 g, 114 mmol). The mixture was stirred at 80° C. for 12 hours. The mixture was cooled to room temperature and then the mixture was acidified to pH=5 with 2M HCl, extracted with ethyl acetate (50 mL×3). The combined organic layers were washed with brine (20 mL), dried over anhydrous sodium sulfate, concentrated to afford the product 3-ethoxy-5-fluorobenzoic acid.
1H NMR (400 MHz, CHLOROFORM-d) d=7.44-7.33 (m, 2H), 6.83 (d, J=10.2 Hz, 1H), 4.06 (q, J=7.0 Hz, 2H), 1.43 (t, J=7.0 Hz, 3H) ppm.

Step b) 4-borono-3-ethoxy-5-fluorobenzoic acid

To a solution of 3-ethoxy-5-fluorobenzoic acid (4 g, 21.72 mmol) in THF (30 ml) was added LDA (32.6 ml, 65.2 mmol) dropwise at −78° C. under N$_2$ atmosphere. The resultant solution was stirred for 15 min followed by slow addition of triisopropyl borate (4.90 g, 26.1 mmol). The mixture was stirred for 30 min and then hydrolyzed with 1M HCl. Extracted with EA (20 mL×3). The organic layer was washed with water (10 mL), brine (10 mL), dried over Na$_2$SO$_4$, concentrated to afford the crude product. Then the crude product was purified by column chromatography on silica gel eluted with (THF:PE=10%~100%) to give 4-borono-3-ethoxy-5-fluorobenzoic acid (2.45 g, 10.75 mmol, 49.5% yield) as white solid.
$^1$H NMR (400 MHz, DMSO-d$_6$) d=8.40 (s, 1H), 7.21 (s, 1H), 7.14 (d, J=7.8 Hz, 1H), 4.03 (q, J=7.0 Hz, 2H), 1.28 (t, J=6.8 Hz, 3H) ppm.

Step c) 3-ethoxy-5-fluoro-4-(4,4,5,5-tetramethyl-1,3,2-dioxaborolan-2-yl)benzoic acid To a solution of 4-borono-3-ethoxy-5-fluorobenzoic acid (2.45 g, 10.75 mmol) in toluene (50 ml) was added 2,3-dimethylbutane-2,3-diol (1.397 g, 11.82 mmol) in one portion at room temperature under N$_2$ atmosphere. The resultant solution was heated to 120° C. and stirred at this temperature for 14 h. The mixture was cooled to room temperature and concentrated to afford the crude product. Then the crude product was purified by column chromatography on silica gel eluted with (THF:PE=10%~50%) to give 3-ethoxy-5-fluoro-4-(4,4,5,5-tetramethyl-1,3,2-dioxaborolan-2-yl)benzoic acid. $^1$H NMR (400 MHz, CHLOROFORM-d) d=7.34 (d, J=8.2 Hz, 1H), 7.29 (s, 1H), 4.07 (q, J=6.7 Hz, 2H), 1.46-1.31 (m, 15H) ppm.

Step d) 3-ethoxy-5-fluoro-4-(4,4,5,5-tetramethyl-1,3,2-dioxaborolan-2-yl)-N-(4-(trifluoromethyl)pyridin-2-yl)benzamide To a solution of 3-ethoxy-5-fluoro-4-(4,4,5,5-tetramethyl-1,3,2-dioxaborolan-2-yl)benzoic acid (300 mg, 0.967 mmol) in anhydrous DCM (10 ml) was added OXALYL CHLORIDE (614 mg, 4.84 mmol) at 0° C., then DMF (one drop) was added and the mixture was stirred at 20° C. for 1.5 hrs. The mixture was concentrated in vacuo, which then diluted with THF (6 ml), and then to the mixture was added 4-(trifluoromethyl)pyridin-2-amine (314 mg, 1.935 mmol) at 0° C. The mixture was stirred at 80° C. for 16 hrs. After cooled to room temperature, the mixture was concentrated to give the crude product. The crude product was purified by column chromatography on silica gel eluted with (EA: PE=1%~50%) to give 3-ethoxy-5-fluoro-4-(4,4,5,5-tetramethyl-1,3,2-dioxaborolan-2-yl)-N-(4-(trifluoromethyl)pyridin-2-yl)benzamide. $^1$H NMR (400 MHz, CHLOROFORM-d) d=8.71-8.66 (m, 2H), 8.47 (d, J=5.0 Hz, 1H), 7.31 (d, J=5.0 Hz, 1H), 7.18 (s, 1H), 7.12 (dd, J=0.9, 8.2 Hz, 1H), 4.10 (q, J=6.9 Hz, 2H), 1.46-1.38 (m, 15H) ppm.

Intermediate 87E1 and 87 E2

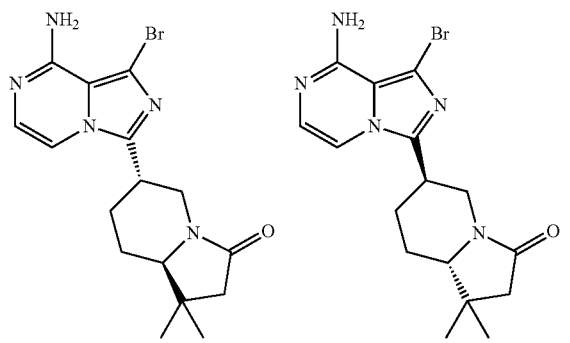 [SMILES: CC1(C)CC(=O)N2C[C@@H](c3nc(Br)c4c(N)nccn34)CC[C@@H]21 ; CC1(C)CC(=O)N2C[C@H](c3nc(Br)c4c(N)nccn34)CC[C@H]21]

(6S,8aR)-6-(8-amino-1-bromoimidazo[1,5-a]pyrazin-3-yl)-1,1-dimethylhexahydroindolizin-3(2H)-one, and (6R,8aS)-6-(8-amino-1-bromoimidazo[1,5-a]pyrazin-3-yl)-1,1-dimethylhexahydroindolizin-3(2H)-one Step (a) methyl 2-(5-bromopyridin-2-yl)-2-methylpropanoate A solution of diisopropylamine (18.05 mL, 127 mmol) in Tetrahydrofuran (360 mL) was cooled to −10° C. under nitrogen and treated with n-BuLi (50.7 mL, 127 mmol, 2.5 M hexane) over a five min period. After 30 min, the solution was cooled to −78° C. and treated with methyl isobutyrate (12.93 g, 127 mmol). After 45 min at −78° C., a solution of 2,5-dibromopyridine (20 g, 84 mmol) in Tetrahydrofuran (40 mL) was added via syringe, resulting in a bright yellow solution. After the addition was complete, the reaction was removed from the cooling bath and warmed to room temperature. After overnight at room temperature, the reaction was quenched by the addition of aqueous NH$_4$Cl (100 mL) and the reaction mixture was extracted with EtOAc. The organic layer was dried over Na$_2$SO$_4$, filtered and concentrated. The crude product was purified by silica gel chromatography (Pet. Ether/EtOAc=90:10) to give methyl 2-(5-bromopyridin-2-yl)-2-methylpropanoate (18.7 g, 86% yield) as a clear oil. MS (ESI) m/z (M+H)$^+$: 260. (LC-MS method C; RET. TIME=1.114 min).

Step (b) 2-(5-bromopyridin-2-yl)-2-methylpropanoic acid

To a solution of methyl 2-(5-bromopyridin-2-yl)-2-methylpropanoate (18.7 g, 72.4 mmol) and NaOH (39.8 ml, 80 mmol) in MeOH (180 mL) was stirred at 50° C. for overnight. The reaction was complete detected by TLC. The organic solvent was removed under reduced pressure, the residual was diluted with EtOAc, acidified with HCl to pH=5, extracted with EtOAc, dried over Na$_2$SO$_4$, concentrated to give 2-(5-bromopyridin-2-yl)-2-methylpropanoic acid (10 g, 56.5% yield) as a light yellow oil.

MS (ESI) m/z (M+H)+: 244. LC-MS method C(Ret time: 0.875 min).

Step (c) 2-(5-bromopyridin-2-yl)-2-methylpropanoyl chloride

To a solution of 2-(5-bromopyridin-2-yl)-2-methylpropanoic acid (1.1 g, 4.51 mmol) in DCM (30 mL) at 0° C. was added OXALYL CHLORIDE (1.183 mL, 13.52 mmol) and DMF (3.49 µL, 0.045 mmol). The mixture was stirred at r.t overnight. The mixture was detected by TLC, and concentrated in vacuuo to give a yellow oil, which was used in next step.

Step (d) 3-(5-bromopyridin-2-yl)-1-diazo-3-methylbutan-2-one

This solution of 2-(5-bromopyridin-2-yl)-2-methylpropanoyl chloride (11 g, 41.9 mmol) in MeCN/THF (30 mL, 1:1) was added dropwise to an ice-water cooled solution of 2M TMS-Diazomethane (41.9 ml, 84 mmol) and Et$_3$N (9.34 mL, 67.0 mmol) in a 1:1 solution of MeCN and THF (70 mL). The resulting yellow mixture was allowed to warm to ambient temperature overnight. The solvent was removed under reduced pressure and the residual was dissolved in EtOAc (50 mL) and washed with water (50 mL), NaHCO$_3$ (50 mL), and brine (50 mL). The combined organic phases was dried over MgSO$_4$ and concentrated to leave a red-brown gum, which was purified by chromatography (PE/AcOEt=10:1) to give 3-(5-bromopyridin-2-yl)-1-diazo-3-methylbutan-2-one.

$^1$H NMR (400 MHz, CHLOROFORM-d) δ=8.64 (d, J=1.57 Hz, 1 H), 7.78 (dd, J=1.96, 8.61 Hz, 1 H), 7.24 (d, J=8.61 Hz, 1 H), 5.14 (s, 1 H), 1.57 (s, 6 H) ppm.

Step (e) methyl 3-(5-bromopyridin-2-yl)-3-methylbutanoate

To a solution of (benzoyloxy)silver (1.025 g, 4.48 mmol) and triethylamine (9.06 g, 90 mmol) in MeOH (50 mL) was added a solution of 3-(5-bromopyridin-2-yl)-1-diazo-3-methylbutan-2-one (6 g, 22.38 mmol) in MeOH (150 mL). The mixture was stirred at r.t. overnight. It was complete detected by LCMS and TLC, concentrated and diluted with EtOAc, washed with saturated NaHCO$_3$ solution and purified with silica gel chromatography (120 g, PE:THF=5:1). Methyl 3-(5-bromopyridin-2-yl)-3-methylbutanoate was obtained as yellow oil.

$^1$H NMR (400 MHz, CHLOROFORM-d) δ=8.58 (d, J=1.56 Hz, 1 H), 7.75 (dd, J=1.96, 8.61 Hz, 1 H), 7.27 (d, J=6.26 Hz, 1 H), 3.55 (s, 3 H), 2.83 (s, 2 H), 1.44 (s, 6 H) ppm.

MS (ESI) m/z (M+H)+: 272. (LC-MS method C; Ret. time=1.046 min).

Step (f) methyl 6-(4-methoxy-2-methyl-4-oxobutan-2-yl)nicotinate

A mixture of Methyl 3-(5-bromopyridin-2-yl)-3-methylbutanoate (4 g, 14.70 mmol), Et$_3$N (6.15 mL, 44.1 mmol), Pd(OAc)$_2$ (0.330 g, 1.470 mmol) and DPPF (1.630 g, 2.94 mmol) in MeOH (20 mL) and DMF (60 mL) was stirred at 90° C. under CO (50 psi) atmosphere overnight. It was detected by LCMS, concentrated and diluted with water, extracted with EtOAc, washed with water and brine, purified with silica gel chromatography (40 g, PE:EA=10:1) to give a yellow oil methyl 6-(4-methoxy-2-methyl-4-oxobutan-2-yl)nicotinate.

$^1$H NMR (400 MHz, CHLOROFORM-d) δ=9.13 (s, 1 H), 8.16-8.29 (m, 1 H), 7.36-7.49 (m, 1 H), 3.94 (s, 3 H), 3.53 (s, 3 H), 2.88 (s, 2 H), 1.40-1.56 (m, 6 H) ppm.

Step (g) methyl 1,1-dimethyl-3-oxooctahydroindolizine-6-carboxylate

To a mixture of methyl 6-(4-methoxy-2-methyl-4-oxobutan-2-yl)nicotinate (500 mg, 1.990 mmol) in AcOH (15 mL) was added NaCNBH$_3$ (375 mg, 5.97 mmol) at 0° C. After stirring at 25° C. overnight, the reaction was detected by TLC, concentrated to remove the solvent, quenched with NaHCO$_3$ solution (pH=8) and extracted with EtOAc (3 times). Dried and concentrated to give a residual. It was dissolved in MeOH and stirred at 70° C. overnight. The reaction was detected by TLC, concentrated and purified with silica gel chromatography (20 g, PE:THF=1:1) to give a colorless oil methyl 1,1-dimethyl-3-oxooctahydroindolizine-6-carboxylate.

$^1$H NMR (400 MHz, CHLOROFORM-d) δ=4.36 (dd, J=3.72, 13.11 Hz, 1 H), 3.65-3.78 (m, 3 H), 2.99 (dd, J=2.93, 11.93 Hz, 1 H), 2.75 (t, J=12.33 Hz, 1 H), 2.36 (tt, J=3.96, 11.88 Hz, 1 H), 2.15-2.28 (m, 3 H), 1.75 (dd, J=3.13, 12.91 Hz, 1 H), 1.57 (dq, J=2.74, 12.91 Hz, 1 H), 1.22-1.33 (m, 1 H), 1.16 (s, 3 H), 1.02 (s, 3 H) ppm.

Step (h) 1,1-dimethyl-3-oxooctahydroindolizine-6-carboxylic acid

A mixture of methyl 1,1-dimethyl-3-oxooctahydroindolizine-6-carboxylate (1.7 g, 7.55 mmol) and LiOH.H$_2$O (0.633 g, 15.09 mmol) in MeOH (20 mL) and Water (7 mL) was stirred at 25° C. overnight. It was detected by TLC, concentrated and acidified with 1N HCl to pH=3, and extracted by DCM, dried over Na$_2$SO$_4$ and concentrated to give a white solid 1,1-dimethyl-3-oxooctahydroindolizine-6-carboxylic acid.

Step (i) N-((3-chloropyrazin-2-yl)methyl)-1,1-dimethyl-3-oxooctahydroindolizine-6-carboxamide To a mixture of 1,1-dimethyl-3-oxooctahydroindolizine-6-carboxylic acid (1.2 g, 5.68 mmol) in DMF (30 mL) was added (3-chloropyrazin-2-yl)methanamine HCl salt (1.023 g, 5.68 mmol), N-ethyl-N-isopropylpropan-2-amine (2.202 g, 17.04 mmol) and HATU (2.160 g, 5.68 mmol) at r.t. After stirring at 25° C. overnight, the reaction was detected by TLC and LCMS, quenched with water and extracted by DCM (3 times), Dried over Na$_2$SO$_4$ and concentrated to give a residual. It was purified with silica gel chromatography (40 g, DCM:MeOH=20:1) to give N-((3-chloropyrazin-2-yl)methyl)-1,1-dimethyl-3-oxooctahydroindolizine-6-carboxamide (1.8 g, 94% yield) as a white solid. MS (ESI) m/z (M$^+$H)$^+$: 337. (LC-MS method C; Ret. time=0.937 min).

Step (j) 6-(8-chloroimidazo[1,5-a]pyrazin-3-yl)-1,1-dimethylhexahydroindolizin-3 (2H)-one PCl$_5$ (2.040 g, 9.80 mmol) was added to a stirred N-((3-chloropyrazin-2-yl)methyl)-1,1-dimethyl-3-oxooctahydroindolizine-6-carboxamide (1.1 g, 3.27 mmol) in Acetonitrile (20 mL) and the mixture was stirred at 25° C. for Overnight. It was detected by TLC and LCMS, quenched with NaHCO$_3$, extracted with DCM, dried over Na$_2$SO$_4$ and concentrated to give 6-(8-chloroimidazo[1,5-a]pyrazin-3-yl)-1,1-dimethylhexahydroindolizin-3(2H)-one (1 g, 96% yield) as a yellow solid. MS (ESI) m/z (M+H)$^+$: 319, (LC-MS method C; Ret. time=0.950 min).

Step (k) 6-(1-bromo-8-chloroimidazo[1,5-a]pyrazin-3-yl)-1,1-dimethylhexahydroindolizin-3 (2H)-one NBS (0.860 g, 4.83 mmol) was added to a stirred 6-(8-chloroimidazo[1,5-a]pyrazin-3-yl)-1,1-dimethylhexahydroindolizin-3(2H)-one (1.4 g, 4.39 mmol) in Acetonitrile (30 mL) and the mixture was stirred at 25° C. for Overnight. It was detected LCMS, quenched with NaHCO$_3$, extracted with EtOAc, dried over Na$_2$SO$_4$ and concentrated to give 6-(1-bromo-8-chloroimidazo[1,5-a]pyrazin-3-yl)-1,1-dimethylhexahydroindolizin-3(2H)-one. MS (ESI) m/z (M+H)$^+$: 399. Acq (LC-MS method C; RET. TIME=1.117 min).

Step (l) 6-(8-amino-1-bromoimidazo[1,5-a]pyrazin-3-yl)-1,1-dimethylhexahydroindolizin-3 (2H)-one 6-(1-bromo-8-chloroimidazo[1,5-a]pyrazin-3-yl)-1,1-dimethylhexahydroindolizin-3(2H)-one (1.7 g, 4.27 mmol) was added to a stirred NH$_3$.H$_2$O (15 mL, 94 mmol) in 2-Propanol (15 mL) and the mixture was stirred at 110° C. overnight. It was detected by LCMS, concentrated, extracted with DCM, dried over Na$_2$SO$_4$ and concentrated to give 6-(8-amino-1-bromoimidazo[1,5-a]pyrazin-3-yl)-1,1-dimethylhexahydroindolizin-3(2H)-one (1.6 g, 99% yield) as a yellow solid. MS (ESI) m/z (M+H)$^+$: 380. (LC-MS method C; RET. TIME=0.854 min).

Step (m) 6-(8-amino-1-bromoimidazo[1,5-a]pyrazin-3-yl)-1,1-dimethylhexahydroindolizin-3 (2H)-one 6-(8-amino-1-bromoimidazo[1,5-a]pyrazin-3-yl)-1,1-dimethylhexahydroindolizin-3(2H)-one (1.5 g, 3.97 mmol, racemic) was separated by SFC separation under the following condition: Column: Chiralpak AS-H 250×4.6 mm I.D., 5 um; Mobile phase: ethanol (0.05% DEA) in CO$_2$ from 5% to 40%; Flow rate: 2.35 mL/min; Wavelength: 220 nm. (6S,8aR)-6-(8-amino-1-bromoimidazo[1,5-a]pyrazin-3-yl)-1,1-dimethylhexahydroindolizin-3(2H)-one (RET. TIME=6.625) and (6R,8aS)-6-(8-amino-1-bromoimidazo[1,5-a]pyrazin-3-yl)-1,1-dimethylhexahydroindolizin-3(2H)-one (Ret. time=8.268) were obtained.

EXAMPLES

Example 1

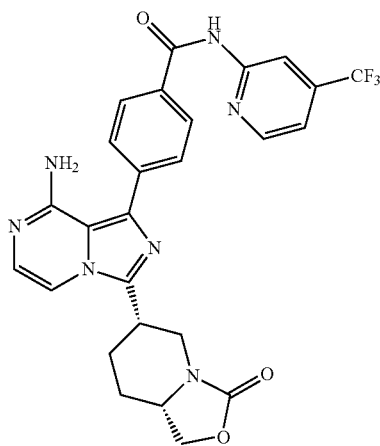 [SMILES: Nc1nccn2c([C@H]3CC[C@H]4COC(=O)N4C3)nc(-c3ccc(C(=O)Nc4cc(C(F)(F)F)ccn4)cc3)c12]

4-(8-amino-3-((6S,8aS)-3-oxohexahydro-1H-oxazolo[3,4-a]pyridin-6-l)imidazo[1,5-a]pyrazin-1-yl)-N-(4-(trifluoromethyl)pyridin-2-yl)benzamide (a) 4-(8-((2,4-dimethoxybenzyl)amino)-3-((3S,6S)-6-(hydroxymethyl)piperidin-3-yl)imidazo[1,5-a]pyrazin-1-yl)-N-(4-(trifluoromethyl)pyridin-2-yl)benzamide To a solution of ((2S,5S)-5-(8-((2,4-dimethoxybenzyl)amino)-1-(4-((4-(trifluoromethyl)pyridin-2-yl)carbamoyl)phenyl)imidazo[1,5-a]pyrazin-3-yl)piperidin-2-yl)methyl acetate (120 mg, 0.17 mmol) in 3 mL of MeOH was added NaOMe (46 mg, 0.85 mmol). The reaction mixture was stirred at room temperature for 3 h under $N_2$. The mixture was poured into aq. $NH_4Cl$, extracted with DCM. The organic layer was dried over $Na_2SO_4$, and concentrated in vacuo to give 110 mg of crude 4-(8-((2,4-dimethoxybenzyl)amino)-3-((3S,6S)-6-(hydroxymethyl)piperidin-3-yl)imidazo[1,5-a]pyrazin-1-yl)-N-(4-(trifluoromethyl)pyridin-2-yl)benzamide, which was used in the next step directly. MS-ESI (m/z): 662.0 (M+1)+ (LC-MS method C; Ret. time: 0.888 min).

(b) 4-(8-((2,4-dimethoxybenzyl)amino)-3-((6S,8aS)-3-oxohexahydro-1H-oxazolo[3,4-a]pyridin-6-yl)imidazo[1,5-a]pyrazin-1-yl)-N-(4-(trifluoromethyl)pyridin-2-yl)benzamide Carbonyldiimidazole (28 mg, 0.17 mmol) and DMAP (5 mg) were added to a solution of compound 4-(8-((2,4-dimethoxybenzyl)amino)-3-((3S,6S)-6-(hydroxymethyl)piperidin-3-yl) imidazo[1,5-a]pyrazin-1-yl)-N-(4-(trifluoromethyl)pyridin-2-yl)benzamide (110 mg crude, 0.17 mmol) in 2 mL of DCM and the resulting mixture was stirred at room temperature for 3 hours. The mixture was diluted with DCM, washed with water and brine, dried over $Na_2SO_4$, filtered, and concentrated in vacuo to give 110 mg of crude of the title compound, 4-(8-((2,4-dimethoxybenzyl)amino)-3-((6S,8aS)-3-oxohexahydro-1H-oxazolo[3,4-a]pyridin-6-yl)imidazo[1,5-a]pyrazin-1-yl)-N-(4-(trifluoromethyl)pyridin-2-yl)benzamide, which was used in the next step directly. MS-ESI (m/z): 688.2 (M+1)+ (LC-MS method C; Ret. time: 1.003 min).

(c) 4-(8-amino-3-((6S,8aS)-3-oxohexahydro-1H-oxazolo[3,4-a]pyridin-6-yl)imidazo[1,5-a]pyrazin-1-yl)-N-(4-(trifluoromethyl)pyridin-2-yl)benzamide A mixture of 4-(8-((2,4-dimethoxybenzyl)amino)-3-((6S,8aS)-3-oxohexahydro-1H-oxazolo[3,4-a]pyridin-6-yl)imidazo[1,5-a]pyrazin-1-yl)-N-(4-(trifluoromethyl)pyridin-2-yl)benzamide (110 mg crude, 0.16 mmol) in 1 mL of trifluoroacetic acid was stirred at 90° C. for 2 h, and concentrated in vacuo. After purification by prep-HPLC, 4-(8-amino-3-((6S,8aS)-3-oxohexahydro-1H-oxazolo[3,4-a]pyridin-6-yl)imidazo[1,5-a]pyrazin-1-yl)-N-(4-(trifluoromethyl)pyridin-2-yl)benzamide (30 mg, yield 34.9%) was obtained. $^1$H NMR (400 MHz, $CD_3OD$): δ=8.63 ~8.66 (m, 2 H), 8.19 (d, J=6.8 Hz, 2 H), 7.92 (d, J=6.8 Hz, 2 H), 7.86 (d, J=6.0 Hz, 1 H), 7.47 (d, J=4.0 Hz, 1 H), 7.05 (d, J=6.0 Hz, 1 H), 4.53 (t, J=8.0 Hz, 1 H), 3.98~4.08 (m, 3 H), 3.69 (s, 1 H), 3.52~3.56 (m, 1 H), 2.34~2.46 (m, 2 H), 2.18~2.23 (m, 1 H), 1.78~1.82 (m, 1 H). LCMS: LC-MS method B; Retention time: 2.452 min. (M+H)+ m/z: 538.2.

Example 2

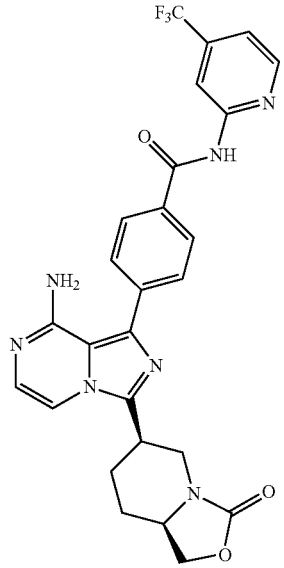 [SMILES: Nc1nccn2c([C@@H]3CC[C@@H]4COC(=O)N4C3)nc(-c3ccc(C(=O)Nc4cc(C(F)(F)F)ccn4)cc3)c12]

4-(8-amino-3-((6R,8aR)-3-oxohexahydro-1H-oxazolo[3,4-a]pyridin-6-yl)imidazol[1,5-a]pyrazin-1-yl)-N-(4-(trifluoromethyl)pyridin-2-yl)benzamide (a) 4-(8-((2,4-dimethoxybenzyl)amino)-3-((6R,8aR)-3-oxohexahydro-1H-oxazolo[3,4-a]pyridin-6-yl)imidazo[1,5-a]pyrazin-1-yl)-N-(4-(trifluoromethyl)pyridin-2-yl)benzamide To a mixture of (2R,5R)-benzyl 5-(8-((2,4-dimethoxybenzyl)amino)-1-(4-((4-(trifluoromethyl)pyridin-2-yl)carbamoyl)phenyl)imidazo[1,5-a]pyrazin-3-yl)-2-(hydroxymethyl)piperidine-1-carboxylate (40 mg) in 3 mL of MeOH was added NaOMe (54 mg, 1 mmol). The reaction mixture was stirred at room temperature for 24 h, and then at 40° C. for 6 hours under N₂. The mixture was poured into aq. NH₄Cl, extracted with DCM (20 mL). The organic layer was dried over Na₂SO₄, and concentrated in vacuo to give 40 mg crude of 4-(8-((2,4-dimethoxybenzyl)amino)-3-((6R,8aR)-3-oxohexahydro-1H-oxazolo[3,4-a]pyridin-6-yl)imidazo[1,5-a]pyrazin-1-yl)-N-(4-(trifluoromethyl)pyridin-2-yl)benzamide, which was used in the next step directly.

MS-ESI (m/z): 688.1 (M+1)⁺ (LC-MS method C; Ret. time: 1.068 min).

(b) 4-(8-amino-3-((6R,8aR)-3-oxohexahydro-1H-oxazolo[3,4-a]pyridin-6-yl)imidazo[1,5-a]pyrazin-1-yl)-N-(4-(trifluoromethyl)pyridin-2-yl)benzamide A mixture of compound 4-(8-((2,4-dimethoxybenzyl)amino)-3-((6R,8aR)-3-oxohexahydro-1H-oxazolo[3,4-a]pyridin-6-yl)imidazo[1,5-a]pyrazin-1-yl)-N-(4-(trifluoromethyl)pyridin-2-yl)benzamide (40 mg crude, 0.06 mmol) in 1 mL of trifluoroacetic acid was stirred at 90° C. for 2 h, and concentrated in vacuo. After purification by prep-HPLC, 4-(8-amino-3-((6R,8aR)-3-oxohexahydro-1H-oxazolo[3,4-a]pyridin-6-yl)imidazo[1,5-a]pyrazin-1-yl)-N-(4-(trifluoromethyl)pyridin-2-yl)benzamide (2 mg, yield 25.6%) was obtained. ¹H NMR (400 MHz, CD₃OD): δ=8.61~8.63 (m, 2 H), 8.16 (d, J=8.4 Hz, 2 H), 7.90 (d, J=8.0 Hz, 2 H), 7.84 (d, J=6.0 Hz, 1 H), 7.44 (d, J=4.8 Hz, 1 H), 7.04 (d, J=5.6 Hz, 1 H), 4.51 (t, J=8.0 Hz, 1 H), 3.96~4.06 (m, 3 H), 3.67 (s, 1 H), 3.50~3.54 (m, 1 H), 2.28~2.42 (m, 2 H), 2.11~2.20 (m, 1 H), 1.76~1.80 (m, 1 H). LCMS: LC-MS method B; Retention time: 2.455 min. (M+H)+ m/z: 538.2.

Example 3

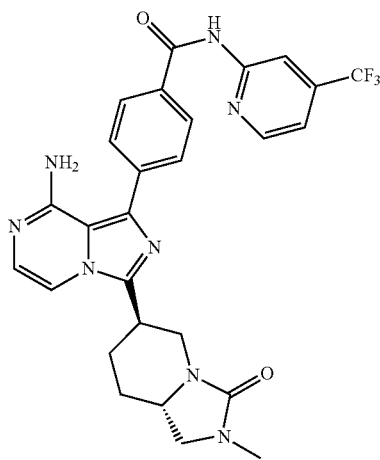 [SMILES: CN1C[C@@H]2CC[C@@H](c3nc(-c4ccc(C(=O)Nc5cc(C(F)(F)F)ccn5)cc4)c4c(N)nccn34)CN2C1=O]

4-(8-amino-3-((6R,8aS)-2-methyl-3-oxooctahydroimidazo[1,5-a]pyridin-6-yl)imidazo[1,5-a]pyrazin-1-yl)-N-(4-(trifluoromethyl)pyridin-2-yl)benzamide (a) (2S,5R)-benzyl 5-(8-amino-1-(4-((4-(trifluoromethyl)pyridin-2-yl)carbamoyl)phenyl)imidazo[1,5-a]pyrazin-3-yl)-2-(methoxymethyl)piperidine-1-carboxylate To a degassed mixture of (2S,5R)-benzyl 5-(8-amino-1-bromoimidazo[1,5-a]pyrazin-3-yl)-2-(methoxymethyl)piperidine-1-carboxylate (50 mg, 0.105 mmol), 4-(4,4,5,5-Tetramethyl-[1,3,2]dioxaborolan-2-yl)-N-(4-trifluoromethyl-pyridin-2-yl)-benzamide (41 mg, 0.105 mmol) and K₂CO₃ (44 mg, 0.316 mmol) in dioxane/H₂O (6 mL, 3:1) was added Pd(dppf)Cl₂ under N₂. The mixture was heated to 100° C. for 1 hour. The reaction mixture was cooled to room temperature and filtered. The filtrate was concentrated, and the residue was purified on silica gel column chromatograph (PE:EA=100%~70%) to give (2S,5R)-benzyl 5-(8-amino-1-(4-((4-(trifluoromethyl)pyridin-2-yl)carbamoyl)phenyl)imidazo[1,5-a]pyrazin-3-yl)-2-(methoxymethyl)piperidine-1-carboxylate (55 mg, yield: 72%).

MS (EI): M/Z (M+1): 660.25. (Condition: 0-60AB_2 MIN; R.T.: 1.216)

(b) 4-(8-amino-3-((3R,6S)-6-(hydroxymethyl)piperidin-3-yl)imidazo[1,5-a]pyrazin-1-yl)-N-(4-(trifluoromethyl)pyridin-2-yl)benzamide A mixture of (2S,5R)-benzyl 5-(8-amino-1-(4-((4-(trifluoromethyl)pyridin-2-yl)carbamoyl)phenyl)imidazo[1,5-a]pyrazin-3-yl)-2-(methoxymethyl)piperidine-1-carboxylate (300 mg, 0.455 mmol) from Step a in dichloromethane (3 mL) was added BBr₃ (608.7 mg, 2.274 mmol) at −78° C. The mixture was stirred at −78° C. for 7 hours. The reaction mixture was quenched with CH₃OH at −78° C. and adjusted to basic pH with NaHCO₃. The mixture was then extracted with dichloromethane/Propan-2-ol (3:1, 50 mL×5). The combined organic layer was washed with brine 3 times, dried over anhydrous sodium sulfate and evaporated to give 4-(8-amino-3-((3R,6S)-6-(hydroxymethyl)piperidin-3-yl)imidazo[1,5-a]pyrazin-1-yl)-N-(4-(trifluoromethyl)pyridin-2-yl)benzamide (220 mg, yield 93%).

MS (EI): M/Z (M+1): 512.19. (Condition: 0-60AB_2 MIN; R.T.: 1.025)

(c) (2S,5R)-5-(8-amino-1-(4-((4-(trifluoromethyl)pyridin-2-yl)carbamoyl)phenyl)imidazo[1,5-a]pyrazin-3-yl)-2-(hydroxymethyl)-N-methylpiperidine-1-carboxamide To a mixture of 4-(8-amino-3-((3R,6S)-6-(hydroxymethyl)piperidin-3-yl)imidazo[1,5-a]pyrazin-1-yl)-N-(4-(trifluoromethyl)pyridin-2-yl)benzamide (70 mg, 0.137 mmol) in tetrahydrofuran was added methylcarbamic chloride (12.8 g, 0.137 mmol) and triethylamine (41.5 g, 0.411 mmol) at 0° C. The mixture was stirred at room temperature for 3 hours. The reaction mixture was concentrated to afford the crude product, which was purified by prep HPLC to give (2S,5R)-5-(8-amino-1-(4-((4-(trifluoromethyl)pyridin-2-yl)carbamoyl)phenyl) imidazo[1,5-a]pyrazin-3-yl)-2-(hydroxymethyl)-N-methylpiperidine-1-carboxamide (11.42 mg, 15% yield). ¹H NMR (400 MHz, CD₃OD): δ=8.64-8.60 (m, 2H), 8.21-8.15 (m, 2H), 7.87 (d, J=8.3 Hz, 2H), 7.81 (d, J=6.0 Hz, 1H), 7.46-7.43 (m, 1H), 7.03 (d, J=5.8 Hz, 1H), 4.26 (d, J=14.3 Hz, 1H), 4.09-4.01 (m, 1H), 3.84-3.77 (m, 1H), 3.75-3.68 (m, 1H), 3.59 (d, J=3.5 Hz, 1H), 3.53 (dd, J=4.6, 14.2 Hz, 1H), 2.60 (s, 3H), 2.33-2.19 (m, 2H), 2.13-2.02 (m, 1H), 1.75-1.64 (m, 1H). MS (ESI): M/Z (M+1): 569.22.

(d) 4-(8-amino-3-((6R,8aS)-2-methyl-3-oxooctahydroimidazo[1,5-a]pyridin-6-yl)imidazo[1,5-a]pyrazin-1-yl)-N-(4-(trifluoromethyl)pyridin-2-yl)benzamide To a mixture of (2S,5R)-5-(8-amino-1-(4-((4-(trifluoromethyl)pyridin-2-yl)carbamoyl)phenyl) imidazo[1,5-a]

pyrazin-3-yl)-2-(hydroxymethyl)-N-methylpiperidine-1-carboxamide (15 mg, 0.026 mmol) in tetrahydrofuran was added SOCl$_2$ (15.56 mg, 0.132 mmol) at 0° C. The mixture was stirred at room temperature for 3 hours. The reaction mixture was concentrated to afford the crude product, which was purified by prep HPLC to give 4-(8-amino-3-((6R,8aS)-2-methyl-3-oxooctahydroimidazo[1,5-a]pyridin-6-yl)imidazo[1,5-a]pyrazin-1-yl)-N-(4-(trifluoromethyl)pyridin-2-yl)benzamide (4.66 mg, 32 yield). $^1$H NMR (400 MHz, CD$_3$OD): δ=8.66-8.60 (m, 2H), 8.20 (d, J=8.3 Hz, 2H), 7.94 (d, J=5.8 Hz, 1H), 7.87 (d, J=8.3 Hz, 2H), 7.45 (d, J=4.5 Hz, 1H), 7.09 (d, J=5.8 Hz, 1H), 5.04 (t, J=8.7 Hz, 1H), 4.52 (t, J=8.5 Hz, 1H), 4.30-4.15 (m, 2H), 3.79-3.68 (m, 1H), 3.67-3.58 (m, 1H), 3.07-2.99 (m, 3H), 2.33 (d, J=12.3 Hz, 1H), 2.22 (dd, J=3.0, 13.1 Hz, 1H), 2.06-1.93 (m, 1H), 1.90-1.77 (m, 1H). MS (ESI): M/Z (M+1): 551.21.

Example 4

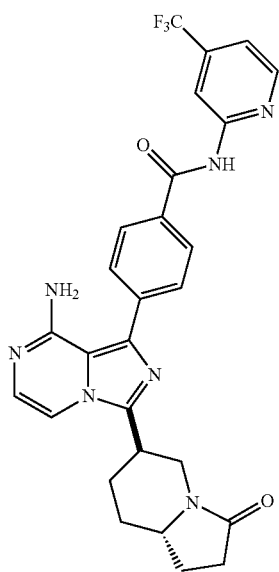 [SMILES: Nc1nccn2c([C@@H]3CC[C@H]4CCC(=O)N4C3)nc(-c3ccc(C(=O)Nc4cc(C(F)(F)F)ccn4)cc3)c12]

4-(8-amino-3-((6R,8aS)-3-oxooctahydroindolizin-6-yl)imidazo[1,5-a]pyrazin-1-yl)-N-(4-(trifluoromethyl)pyridin-2-yl)benzamide Pd(dppf)Cl$_2$ (23.32 mg, 0.029 mmol) was added to a stirred mixture of 4-(4,4,5,5-tetramethyl-1,3,2-dioxaborolan-2-yl)-N-(4-(trifluoromethyl)pyridin-2-yl)benzamide (224 mg, 0.571 mmol), potassium phosphate tribasic (303 mg, 1.428 mmol) and (6R,8aS)-6-(8-amino-1-bromoimidazo[1,5-a]pyrazin-3-yl)hexahydro indolizin-3(2H)-one (100 mg, 0.286 mmol) in 1,4-Dioxane (8 ml) and Water (1 ml). The mixture was degassed back-filled with N$_2$ and stirred at 80° C. for 3 h. and concentrated. The residue was purified by column chromatography on silica gel (ISCO, 40 g), eluting with DCM/MeOH (20/1) to give 4-(8-amino-3-((6R,8aS)-3-oxooctahydroindolizin-6-yl) imidazo[1,5-a]pyrazin-1-yl)-N-(4-(trifluoromethyl)pyridin-2-yl)benzamide (125 mg, 0.233 mmol, 82% yield) as a yellow solid. LCMS data: LC-MS method C; Ret. time 1.21 min; m/z 536.25 (M+H)$^+$; 1H NMR (CDCl$_3$, 500 Hz): delta=8.98 (1H, br s), 8.76 (1H, br, s), 8.52 (1H, d, J=5.5 Hz), 8.10 (1H, d, J=8 Hz), 7.87 (2H, d, J=8 Hz), 7.34 (1H, d, J=5 Hz), 7.16 (1H, d, J=5 Hz), 5.24 (2H, br s), 4.47 (1H, d, J=14 Hz), 3.61-3.67 (1H, m), 3.04-3.16 (2H, m), 2.50 ((2H, t, J=9 Hz), 2.11-2.37 (5H, m), 1.70-1.77 (1H, m), 1.41-1.49 (1H, m).

Example 5

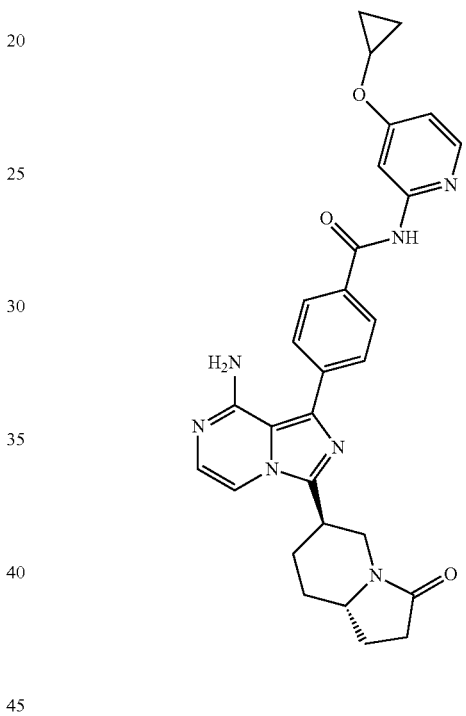

4-(8-amino-3-((6R,8aS)-3-oxooctahydroindolizin-6-yl)imidazo[1,5-a]pyrazin-1-yl)-N-(4-cyclopropoxypyridin-2-yl)benzamide 4-(8-amino-3-((6R,8aS)-3-oxooctahydroindolizin-6-yl) imidazo[1,5-a]pyrazin-1-yl)-N-(4-cyclopropoxypyridin-2-yl)benzamide was prepared following the procedure described for Example 4. LCMS data: LC-MS method C; Ret. time 1.11 min; m/z 524.33 (M+H)$^+$; $^1$H NMR (CDCl$_3$, 500 Hz): 8.26 (1H, d, J=4 Hz), 8.09 (1H, d, J=5.5 Hz), 8.08 (2H, d, J=8 Hz), 7.82 (2H, d, J=8 Hz), 7.32 (1H, d, J=5.5 Hz), 7.11 (1H, d, J=5 Hz), 6.74 (1H, dd, J=5 and 2.5 Hz), 5.16 (1H, br s), 4.43 (1H, d, J=14 Hz), 3.89-3.93 (1H, m), 3.59-3.65 (1H, m), 3.03-3.13 (2H, m), 2.47 ((2H, t, J=9 Hz), 2.09-2.39 (5H, m), 1.67-1.75 (1H, m), 1.39-1.47 (1H, m), 0.84-0.93 (4H, m).

Example 6

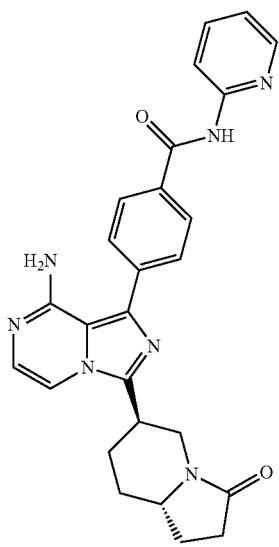 [SMILES: Nc1nccn2c([C@@H]3CC[C@H]4CCC(=O)N4C3)nc(-c3ccc(C(=O)Nc4ccccn4)cc3)c12]

4-(8-amino-3-((6R,8aS)-3-oxooctahydroindolizin-6-yl)imidazo[1,5-a]pyrazin-1-yl)-N-(pyridin-2-yl)benzamide 4-(8-amino-3-((6R,8aS)-3-oxooctahydroindolizin-6-yl)imidazo[1,5-a]pyrazin-1-yl)-N-(pyridin-2-yl)benzamide was prepared following the procedure described for Example 4. LCMS data: LC-MS method E Ret. time 1.22 min; m/z 468.29 (M+H)⁺; ¹H NMR (CDCl₃, 500 Hz): δ=8.84 (1H, br, s), 8.44 (1H, d, J=8.5 Hz), 8.35 (1H, d, J=4 Hz), 8.09 (2H, d, J=8 Hz), 7.85 (2H, d, J=8 Hz), 7.82 (1H, dd, J=9 and 7.5 Hz), 7.33 (1H, d, J=5 Hz), 7.15 (1H, d, J=5 Hz), 7.13 (1H, dd, J=6.5 and 5.5 Hz), 5.28 (1H, br s), 4.47 (1H, d, J=14 Hz), 3.61-3.66 (1H, m), 3.51 (2H, br s), 3.04-3.16 (2H, m), 2.49 ((2H, t, J=9 Hz), 1.41-2.36 (7H, m).

Example 7

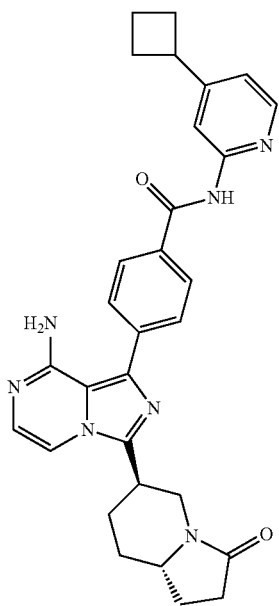 [SMILES: Nc1nccn2c([C@@H]3CC[C@H]4CCC(=O)N4C3)nc(-c3ccc(C(=O)Nc4cc(C5CCC5)ccn4)cc3)c12]

4-(8-amino-3-((6R,8aS)-3-oxooctahydroindolizin-6-yl)imidazo[1,5-a]pyrazin-1-yl)-N-(4-cyclobutylpyridin-2-yl)benzamide 4-(8-amino-3-((6R,8aS)-3-oxooctahydroindolizin-6-yl)imidazo[1,5-a]pyrazin-1-yl)-N-(4-cyclobutylpyridin-2-yl)benzamide was prepared following the standard procedure in Example 4. LCMS data: LC-MS method E Ret. time 1.16 min; m/z 522.40 (M+H)⁺; NMR (CDCl₃, 500 Hz): 8.65 (1H, br s), 8.37 (1H, d, J=8.5 Hz), 8.19 (1H, br s), 8.09 (2H, d, J=8 Hz), 7.85 (2H, d, J=8 Hz), 7.70 (1H, dd, J=8.5 and 2.5 Hz), 7.34 (1H, d, J=5 Hz), 7.18 (1H, d, J=5 Hz), 5.16 (1H, br s), 4.47 (1H, d, J=14 Hz), 3.61-3.66 (2H, m), 3.04-3.16 (2H, m), 2.51 ((2H, t, J=9 Hz), 1.41-2.51 (7H, m).

Example 8

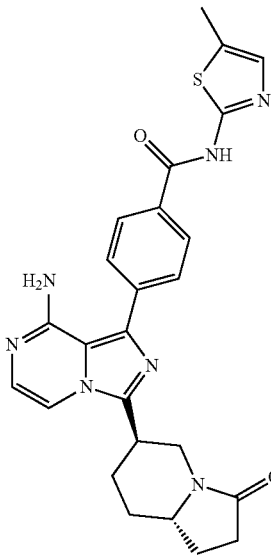

4-(8-amino-3-((6R,8aS)-3-oxooctahydroindolizin-6-yl)imidazo[1,5-a]pyrazin-1-yl)-N-(5-methylthiazol-2-yl)benzamide 4-(8-amino-3-((6R,8aS)-3-oxooctahydroindolizin-6-yl)imidazo[1,5-a]pyrazin-1-yl)-N-(5-methylthiazol-2-yl)benzamide was prepared following the standard procedure describe for Example 4. LCMS data: LC-MS method E Ret. time 1.24 min; m/z 488.29 (M+H)⁺; ¹H NMR (CDCl₃, 500 Hz): delta=8.13 (1H, d, J=8 Hz), 7.87 (1H, d, J=8 Hz), 7.34 (1H, d, J=5 Hz), 7.17 (1H, d, J=5 Hz), 7.09 (1H, br s), 4.47 (1H, d, J=12 Hz), 3.49-3.70 (2H, m), 3.06-3.17 (2H, m), 1.37-2.53 (9H, m).

Example 9

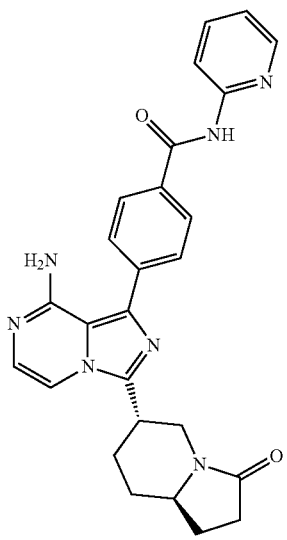 [SMILES: Nc1nccn2c([C@H]3CC[C@@H]4CCC(=O)N4C3)nc(-c3ccc(C(=O)Nc4ccccn4)cc3)c12]

4-(8-amino-3-((6S,8aR)-3-oxooctahydroindolizin-6-yl)imidazo[1,5-a]pyrazin-1-yl)-N-(pyridin-2-yl)benzamide 4-(8-amino-3-((6S,8aR)-3-oxooctahydroindolizin-6-yl)imidazo[1,5-a]pyrazin-1-yl)-N-(pyridin-2-yl)benzamide was prepared follow the standard procedure describe for Example 4. LCMS data: LC-MS method E Ret. time 1.05 min; m/z 468.20 (M+H)+; $^1$HNMR (CDCl$_3$, 500 Hz): delta=8.84 (1H, br, s), 8.44 (1H, d, J=8.5 Hz), 8.35 (1H, d, J=4 Hz), 8.09 (2H, d, J=8 Hz), 7.84 (2H, d, J=8 Hz), 7.82 (1H, dd, J=9 and 7.5 Hz), 7.32 (1H, d, J=5 Hz), 7.15 (1H, d, J=5 Hz), 7.13 (1H, dd, J=6.5 and 5.5 Hz), 5.30 (1H, br s), 4.47 (1H, d, J=14 Hz), 3.61-3.66 (1H, m), 3.04-3.15 (2H, m), 2.49 ((2H, t, J=9 Hz), 1.41-2.36 (7H, m).

Examples 10 and 11

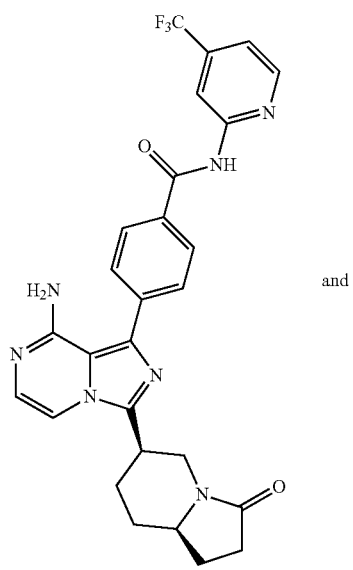

and

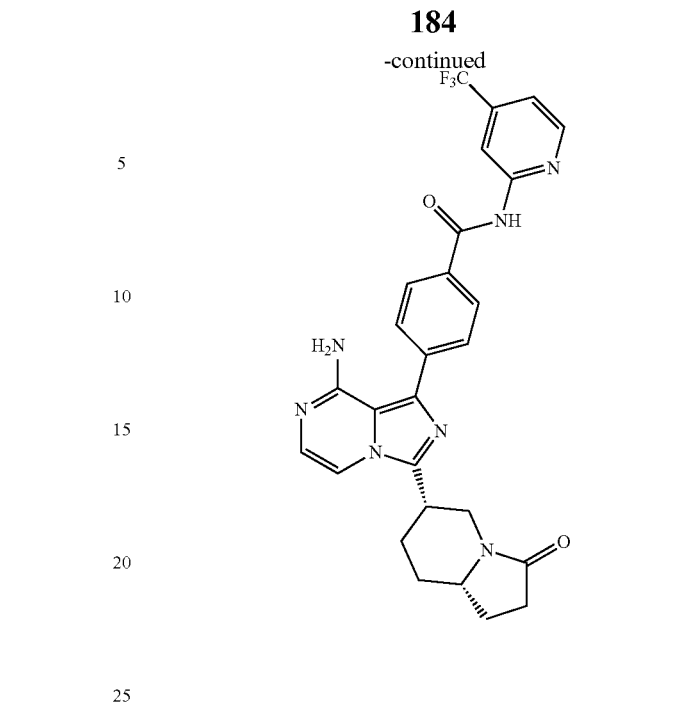

4-(8-amino-3-((6S,8aS)-3-oxooctahydroindolizin-6-yl)imidazo[1,5-a]pyrazin-1-yl)-N-(4-(trifluoromethyl)pyridin-2-yl)benzamide and 4-(8-amino-3-((6R,8aR)-3-oxooctahydroindolizin-6-yl)imidazo[1,5-a]pyrazin-1-yl)-N-(4-(trifluoromethyl)pyridin-2-yl)benzamide (a) cis-3-oxooctahydroindolizine-6-carboxylic acid LiOH (0.826 ml, 1.653 mmol) was added to a stirred mixture of cis-methyl 3-oxooctahydroindolizine-6-carboxylate (163 mg, 0.826 mmol) in Tetrahydrofuran (4 ml) and the mixture stirred at room temperature for 1 h. The mixture was then acidified with 1 N HCl. and concentrated to give cis-3-oxooctahydroindolizine-6-carboxylic acid.

LCMS data: LC-MS method E Ret. time 0.35 min; m/z 184.11 (M+H)+.

(b) cis-N-((3-chloropyrazin-2-yl)methyl)-3-oxooctahydroindolizine-6-carboxamide

HATU (377 mg, 0.991 mmol) was added to a stirred, mixture of cis-3-oxooctahydroindolizine-6-carboxylic acid (151 mg, 0.826 mmol) at ° C. DIPEA (0.433 ml, 2.478 mmol) in DMF (2 ml) was then added followed by (3-chloropyrazin-2-yl)methanamine hydrochloride (164 mg, 0.909 mmol) and the mixture was stirred at room temperature for 1 h. and concentrated. The residue was purified by column chromatography on silica gel (Isco 40 g column), eluting with CH$_2$Cl$_2$/MeOH (30/1) to give cis-N-((3-chloropyrazin-2-yl)methyl)-3-oxooctahydroindolizine-6-carboxamide (185 mg, 0.599 mmol, 72.5% yield) as a white solid. LCMS data: LC-MS method E Ret. time 1.08 min; m/z 309.10 (M+H)+; ¹H NMR (CDCl₃, 500 Hz): delta=8.43 (1H, t, J=4.5 and 2.5 Hz), 8.30 (1H, br s), 7.46 (1H, br s), 4.89-4.93 (1H, m), 4.52-4.57 (m, 2), 3.57-3.59 (m, 1), 3.00 (1H, br d, J=14.5 Hz), 2.71 (1H, br s), 2.30-2.72 (4H, m), 1.69-1.82 (4H, m), 1.49-1.55 m, 1).

(c) cis-6-(8-chloroimidazo[1,5-a]pyrazin-3-yl)hexahydroindolizin-3 (2H)-one

POCl₃ (0.326 ml, 3.50 mmol) was added to a stirred, mixture of cis-N-((3-chloropyrazin-2-yl)methyl)-3-oxooctahydroindolizine-6-carboxamide (180 mg, 0.583 mmol) at 0° C. in Acetonitrile (5 ml). DMF (0.045 ml, 0.583 mmol) was then added, the mixture stirred at room temperature overnight and quenched with iced water and solid NaHCO3. The mixture was extracted with DCM, and the organic layer concentrated. The residue was purified by column chromatography on silica gel (ISCO, 40 g column), eluting with CH₂Cl₂/MeOH (30/1) to give cis-6-(8-chloroimidazo[1,5-a]pyrazin-3-yl)hexahydroindolizin-3(2H)-one (10 mg) as a yellow oil. LCMS data: LC-MS method E Ret. time 1.14 min; m/z 291.1 (M+H)+.

(d) cis-6-(1-bromo-8-chloroimidazo[1,5-a]pyrazin-3-yl)hexahydroindolizin-3(2H)-one NBS (8.26 mg, 0.046 mmol) was added to a stirred mixture of cis-6-(8-chloroimidazo[1,5-a]pyrazin-3-yl)hexahydroindolizin-3(2H)-one (30 mg, 0.031 mmol) in Acetonitrile (5 ml) and the mixture was stirred at room temperature for 1 h. The reaction was quenched with sat. NaHCO₃, extracted with DCM, dried and concentrated. The residue was purified by column chromatography on silica gel (ISCO, 40 g column) (30/1) to give cis-6-(1-bromo-8-chloroimidazo[1,5-a]pyrazin-3-yl)hexahydroindolizin-3(2H)-one (10 mg, 0.027 mmol, 87% yield). LCMS data: LC-MS method E Ret. time 0.97 min; m/z 369.98 and 370.99 (M+H)+.

(e) cis-6-(8-amino-1-bromoimidazo[1,5-a]pyrazin-3-yl)hexahydroindolizin-3(2H)-one A stirred mixture of cis-6-(1-bromo-8-chloroimidazo[1,5-a]pyrazin-3-yl) hexahydroindolizin-3(2H)-one (10 mg, 0.027 mmol) in 15 mL of 2N NH₃ in 2-propanol was heated in a sealed tube at 100° C. overnight and concentrated. The residue was purified by column chromatography on silica gel (ISCO, 40 g), eluting with CH₂Cl₂/MeOH (12/1) to give cis-6-(8-amino-1-bromoimidazo[1,5-a]pyrazin-3-yl)hexahydroindolizin-3(2H)-one (6 mg, 0.017 mmol, 63.3% yield) as a white solid. LCMS Data: LC-MS method E Ret. time 0.97 min; m/z 350.0, and 352.0 (M+H)+.

(f) 4-(8-amino-3-((6S,8aS)-3-oxooctahydroindolizin-6-yl)imidazo[1,5-a]pyrazin-1-yl)-N-(4-(trifluoromethyl)pyridin-2-yl)benzamide and 4-(8-amino-3-((6R,8aR)-3-oxooctahydroindolizin-6-yl)imidazo[1,5-a]pyrazin-1-yl)-N-(4-(trifluoromethyl)pyridin-2-yl)benzamide Pd(dppf)CH₂Cl₂ (3.50 mg, 4.28 μmol) was added to a stirred mixture of 4-(4,4,5,5-tetramethyl-1,3,2-dioxaborolan-2-yl)-N-(4-(trifluoromethyl)pyridin-2-yl)benzamide (16.80 mg, 0.043 mmol), cis-6-(8-amino-1-bromoimidazo[1,5-a]pyrazin-3-yl)hexahydroindolizin-3(2H)-one (15 mg, 0.043 mmol) and Potassium Phosphate Tribasic (45.5 mg, 0.214 mmol) in 1,4-Dioxane (8 ml) and Water (1 ml). The mixture was degassed, back-filled with N₂ and stirred at 85° C. for 3 h. The reaction mixture was concentrated and the residue was purified by column chromatography on silica gel (ISCO, 40 g, column), eluting with (DCM/2N NH₃ in MeOH, 30/1) to give 4-(8-amino-3-((cis)-3-oxooctahydroindolizin-6-yl) imidazo[1,5-a]pyrazin-1-yl)-N-(4-(trifluoromethyl)pyridin-2-yl)benzamide (21.1 mg, 0.039 mmol, 92% yield) as a yellow solid, which was separated on chiral HPLC (4.6×250 mm ChiralCel AD, 2.1 mL/min, 100 bar, 70% MeOH (0.2% DEA1/C02, 35 C., peak one retention time 3.33 min, peak two 5.24 min)) to give 4-(8-amino-3-((6S,8aS)-3-oxooctahydroindolizin-6-yl)imidazo[1,5-a]pyrazin-1-yl)-N-(4-(trifluoromethyl)pyridin-2-yl)benzamide (10.2 mg, 0.019 mmol, 48.6% yield) followed by 4-(8-amino-3-((6R,8aR)-3-oxooctahydroindolizin-6-yl)imidazo[1,5-a]pyrazin-1-yl)-N-(4-(trifluoromethyl)pyridin-2-yl)benzamide (9.7 mg, 0.018 mmol, 46.2% yield). Spectra data for 4-(8-amino-3-((6S,8aS)-3-oxooctahydroindolizin-6-yl)imidazo[1,5-a]pyrazin-1-yl)-N-(4-(trifluoromethyl)pyridin-2-yl)benzamide: LCMS Data: LC-MS method E Ret. time 1.23 min; m/z 536.2 (M+H)+; ¹H NMR (CDCl₃, 500 Hz): 9.14 (1H, br s), 8.76 (1H, s), 8.51 (1H, d, J=5 Hz), 8.06 (2H, d, J=8 Hz), 7.87 (2H, d, J=8 Hz), 7.34 (1H, d, J=5 Hz), 7.22 (1H, d, J=5 Hz), 7.07 (1H, d, J=5 Hz), 5.37 (2H, br s), 4.48 (1H, d, J=14 Hz), 3.62-3.68 (1H, m), 3.42 (1H, br s), 3.21 (1H, dd, J=13.5, 4 Hz), 1.72-2.48 (9H, m).

Spectra data for 4-(8-amino-3-((6R,8aR)-3-oxooctahydroindolizin-6-yl) imidazo[1,5-a]pyrazin-1-yl)-N-(4-(trifluoromethyl)pyridin-2-yl)benzamide: LCMS Data: LC-MS method E Ret. time 1.23 min; m/z 536.2 (M+H)+; ¹H NMR (CDCl₃, 500 Hz): 9.11 (1H, br s), 8.76 (1H, s), 8.51 (1H, d, J=5 Hz), 8.06 (2H, d, J=8 Hz), 7.87 (2H, d, J=8 Hz), 7.34 (1H, d, J=5 Hz), 7.22 (1H, d, J=5 Hz), 7.08 (1H, d, J=5 Hz), 5.34 (2H, br s), 4.48 (1H, d, J=14 Hz), 3.62-3.68 (1H, m), 3.43 (1H, br s), 3.21 (1H, dd, J=13.5, 4 Hz), 1.72-2.52 (9H, m).

The Examples set forth in Table 1 below were prepared using the procedure described for Example 4.

TABLE 1

| Example | Structure | IUPAC Name | Exact Mass [M + H]+ | Retention time (min) (LC-MS method) |
|---------|-----------|------------|---------------------|-------------------------------------|
| 12 | 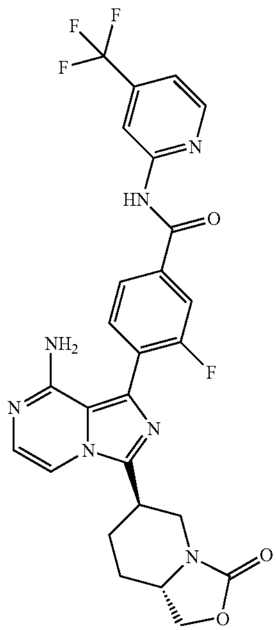 [SMILES: Nc1nccn2c([C@@H]3CC[C@H]4COC(=O)N4C3)nc(-c3ccc(C(=O)Nc4cc(C(F)(F)F)ccn4)cc3F)c12] | 4-(8-amino-3-((6R,8aS)-3-oxohexahydro-1H-oxazolo[3,4-a]pyridin-6-yl)imidazo[1,5-a]pyrazin-1-yl)-3-fluoro-N-(4-(trifluoromethyl)pyridin-2-yl)benzamide | 556.2 | 2.40 (B) |
| 13 | 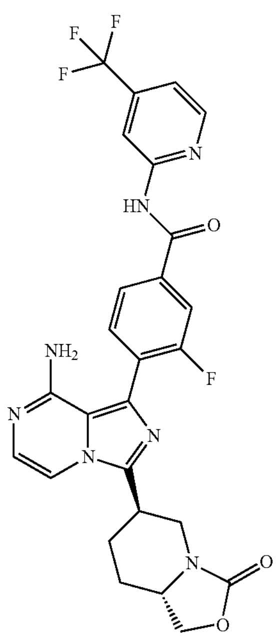 [SMILES: Nc1nccn2c([C@@H]3CC[C@H]4COC(=O)N4C3)nc(-c3ccc(C(=O)Nc4cc(C(F)(F)F)ccn4)cc3F)c12] | 4-(8-amino-3-((6S,8aR)-3-oxohexahydro-1H-oxazolo[3,4-a]pyridin-6-yl)imidazo[1,5-a]pyrazin-1-yl)-3-fluoro-N-(4-(trifluoromethyl)pyridin-2-yl)benzamide | 556.2 | 2.40 (B) |

TABLE 1-continued
| Example | Structure | IUPAC Name | Exact Mass [M + H]+ | Retention time (min) (LC-MS method) |
|---|---|---|---|---|
| 14 | 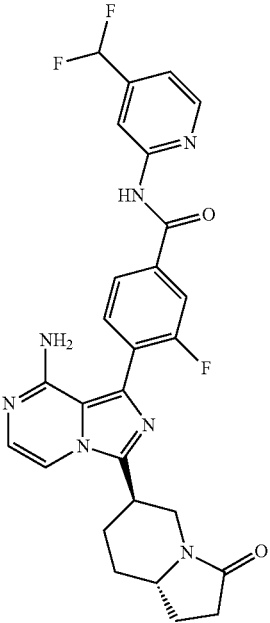 [SMILES: Nc1nccn2c([C@@H]3CC[C@H]4CCC(=O)N4C3)nc(-c3ccc(C(=O)Nc4cc(C(F)F)ccn4)cc3F)c12] | 4-{8-amino-3-[(6R,8aS)-3-oxooctahydroindolizin-6-yl]imidazo[1,5-a]pyrazin-1-yl}-N-[4-(difluoromethyl)pyridin-2-yl]-3-fluorobenzamide | 554.3 | 2.50 (B) |
| 15 | 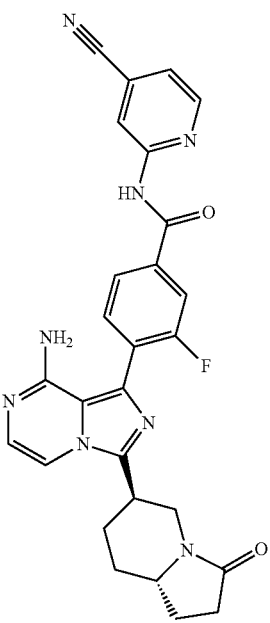 [SMILES: N#Cc1ccnc(NC(=O)c2ccc(-c3nc([C@@H]4CC[C@H]5CCC(=O)N5C4)n4ccnc(N)c34)c(F)c2)c1] | 4-{8-amino-3-[(6R,8aS)-3-oxooctahydroindolizin-6-yl]imidazo[1,5-a]pyrazin-1-yl}-N-(4-cyanopyridin-2-yl)-3-fluorobenzamide | 511.3 | 2.04 (B) |

TABLE 1-continued

| Example | Structure | IUPAC Name | Exact Mass [M + H]+ | Retention time (min) (LC-MS method) |
|---|---|---|---|---|
| 16 | 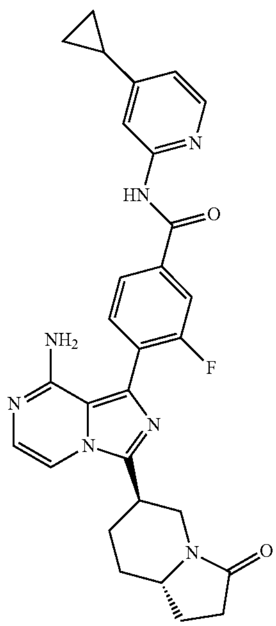 [SMILES: Nc1nccn2c([C@@H]3CC[C@H]4CCC(=O)N4C3)nc(-c3ccc(C(=O)Nc4cc(C5CC5)ccn4)cc3F)c12] | 4-{8-amino-3-[(6R,8aS)-3-oxooctahydroindolizin-6-yl]imidazo[1,5-a]pyrazin-1-yl}-N-(4-cyclopropylpyridin-2-yl)-3-fluorobenzamide | 526.3 | 2.16 (B) |
| 17 | 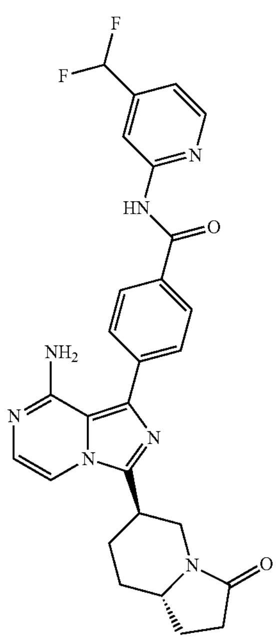 [SMILES: Nc1nccn2c([C@@H]3CC[C@H]4CCC(=O)N4C3)nc(-c3ccc(C(=O)Nc4cc(C(F)F)ccn4)cc3)c12] | 4-{8-amino-3-[(6R,8aS)-3-oxooctahydroindolizin-6-yl]imidazo[1,5-a]pyrazin-1-yl}-N-[4-(difluoromethyl)pyridin-2-yl]benzamide | 518.3 | 2.36 (B) |

TABLE 1-continued

| Example | Structure | IUPAC Name | Exact Mass [M + H]+ | Retention time (min) (LC-MS method) |
|---|---|---|---|---|
| 18 | 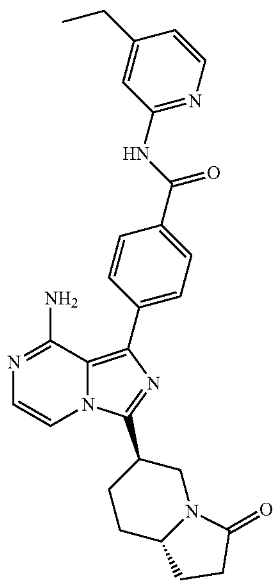 [SMILES: CCc1ccnc(NC(=O)c2ccc(-c3nc([C@@H]4CC[C@H]5CCC(=O)N5C4)n4ccnc(N)c34)cc2)c1] | 4-{8-amino-3-[(6R,8aS)-3-oxooctahydroindolizin-6-yl]imidazo[1,5-a]pyrazin-1-yl}-N-(4-ethylpyridin-2-yl)benzamide | 496.3 | 2.09 (B) |
| 19 | 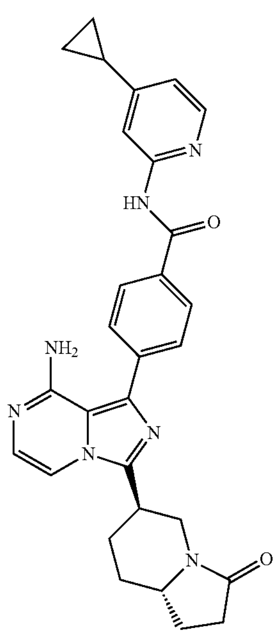 [SMILES: Nc1nccn2c([C@@H]3CC[C@H]4CCC(=O)N4C3)nc(-c3ccc(C(=O)Nc4cc(C5CC5)ccn4)cc3)c12] | 4-{8-amino-3-[(6R,8aS)-3-oxooctahydroindolizin-6-yl]imidazo[1,5-a]pyrazin-1-yl}-N-(4-cyclopropylpyridin-2-yl)benzamide | 508.3 | 2.12 (B) |

TABLE 1-continued

| Example | Structure | IUPAC Name | Exact Mass [M + H]+ | Retention time (min) (LC-MS method) |
|---|---|---|---|---|
| 20 | 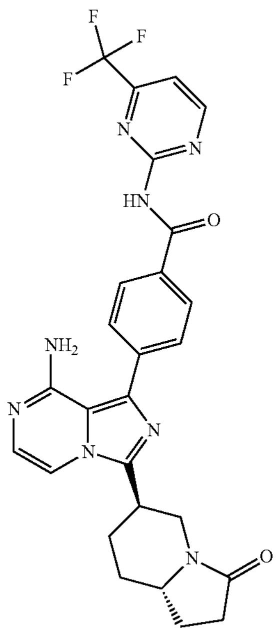 [SMILES: Nc1nccn2c([C@@H]3CC[C@H]4CCC(=O)N4C3)nc(-c3ccc(C(=O)Nc4nccc(C(F)(F)F)n4)cc3)c12] | 4-(8-amino-3-((6R,8aS)-3-oxooctahydroindolizin-6-yl)imidazo[1,5-a]pyrazin-1-yl)-N-(4-(trifluoromethyl)pyrimidin-2-yl)benzamide | 537.4 | 2.26 (B) |
| 21 | 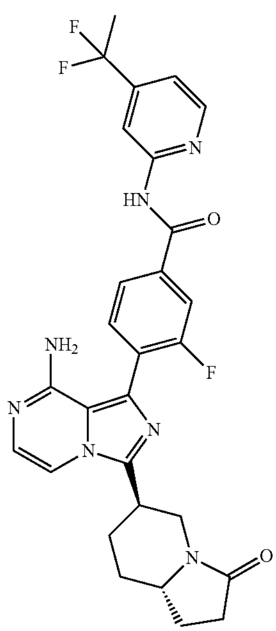 [SMILES: CC(F)(F)c1ccnc(NC(=O)c2ccc(-c3nc([C@@H]4CC[C@H]5CCC(=O)N5C4)n4ccnc(N)c34)c(F)c2)c1] | 4-{8-amino-3-[(6R,8aS)-3-oxooctahydroindolizin-6-yl]imidazo[1,5-a]pyrazin-1-yl}-N-[4-(1,1-difluoroethyl)pyridin-2-yl]-3-fluorobenzamide | 550.3 | 2.42 (B) |

TABLE 1-continued

| Example | Structure | IUPAC Name | Exact Mass [M + H]+ | Retention time (min) (LC-MS method) |
|---|---|---|---|---|
| 22 | 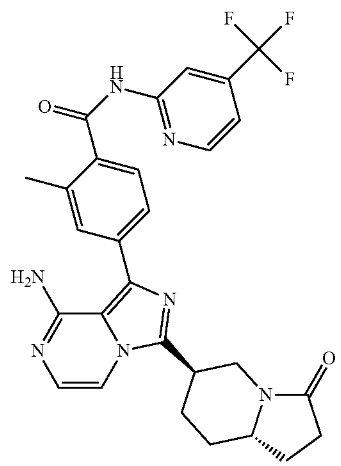 [SMILES: Cc1cc(-c2nc([C@@H]3CC[C@H]4CCC(=O)N4C3)n3ccnc(N)c23)ccc1C(=O)Nc1cc(C(F)(F)F)ccn1] | 4-{8-amino-3-[(6R,8aS)-3-oxooctahydroindolizin-6-yl]imidazo[1,5-a]pyrazin-1-yl}-2-methyl-N-[4-(trifluoromethyl)pyridin-2-yl]benzamide | 550.3 | 2.51 (B) |
| 23 | 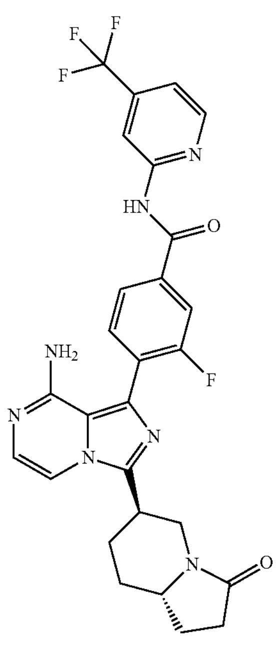 | 4-{8-amino-3-[(6R,8aS)-3-oxooctahydroindolizin-6-yl]imidazo[1,5-a]pyrazin-1-yl}-3-fluoro-N-[4-(trifluoromethyl)pyridin-2-yl]benzamide | 554.3 | 2.50 (B) |

TABLE 1-continued

| Example | Structure | IUPAC Name | Exact Mass [M + H]+ | Retention time (min) (LC-MS method) |
|---|---|---|---|---|
| 24 | 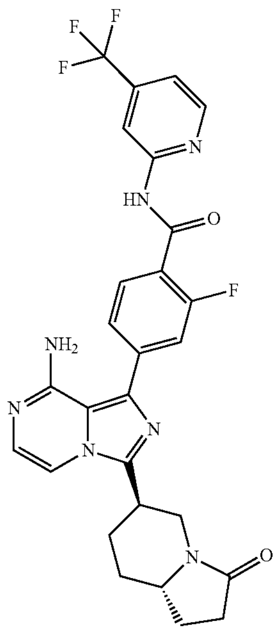 [SMILES: Nc1nccn2c([C@@H]3CC[C@H]4CCC(=O)N4C3)nc(-c3ccc(C(=O)Nc4cc(C(F)(F)F)ccn4)c(F)c3)c12] | 4-{8-amino-3-[(6R,8aS)-3-oxooctahydroindolizin-6-yl]imidazo[1,5-a]pyrazin-1-yl}-2-fluoro-N-[4-(trifluoromethyl)pyridin-2-yl]benzamide | 554.3 | 2.52 (B) |
| 25 | 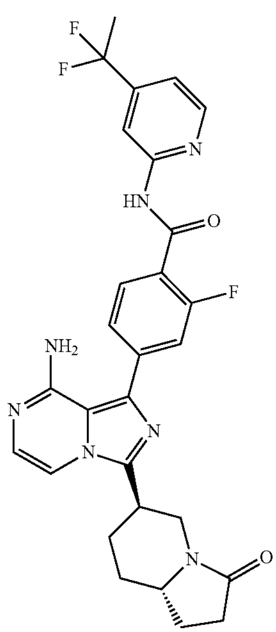 [SMILES: CC(F)(F)c1ccnc(NC(=O)c2ccc(-c3nc([C@@H]4CC[C@H]5CCC(=O)N5C4)n4ccnc(N)c34)cc2F)c1] | 4-{8-amino-3-[(6R,8aS)-3-oxooctahydroindolizin-6-yl]imidazo[1,5-a]pyrazin-1-yl}-N-[4-(1,1-difluoroethyl)pyridin-2-yl]-2-fluorobenzamide | 550.3 | 2.46 (B) |

TABLE 1-continued

| Example | Structure | IUPAC Name | Exact Mass [M + H]+ | Retention time (min) (LC-MS method) |
|---|---|---|---|---|
| 26 | 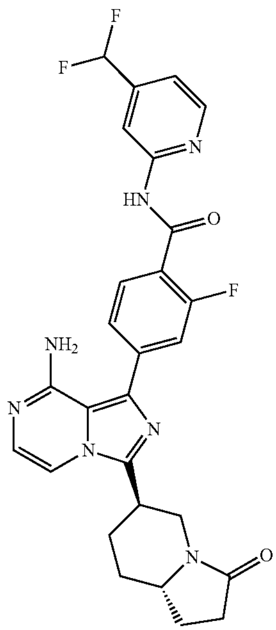 [SMILES: Nc1nccn2c([C@@H]3CC[C@H]4CCC(=O)N4C3)nc(-c3ccc(C(=O)Nc4cc(C(F)F)ccn4)c(F)c3)c12] | 4-{8-amino-3-[(6R,8aS)-3-oxooctahydroindolizin-6-yl]imidazo[1,5-a]pyrazin-1-yl}-N-[4-(difluoromethyl)pyridin-2-yl]-2-fluorobenzamide | 536.3 | 2.42 (B) |
| 27 | 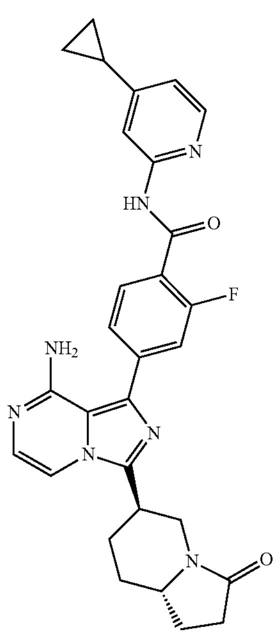 [SMILES: Nc1nccn2c([C@@H]3CC[C@H]4CCC(=O)N4C3)nc(-c3ccc(C(=O)Nc4cc(C5CC5)ccn4)c(F)c3)c12] | 4-{8-amino-3-[(6R,8aS)-3-oxooctahydroindolizin-6-yl]imidazo[1,5-a]pyrazin-1-yl}-N-(4-cyclopropylpyridin-2-yl)-2-fluorobenzamide | 526.3 | 2.20 (B) |

TABLE 1-continued

| Example | Structure | IUPAC Name | Exact Mass [M + H]+ | Retention time (min) (LC-MS method) |
|---|---|---|---|---|
| 28 | 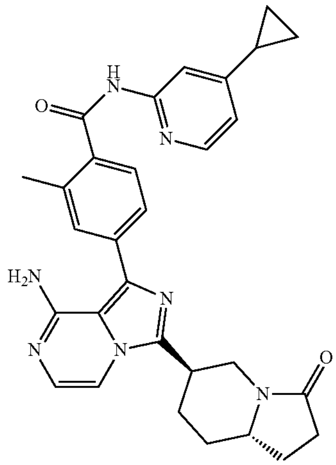 [SMILES: Cc1cc(-c2nc([C@@H]3CC[C@H]4CCC(=O)N4C3)n3ccnc(N)c23)ccc1C(=O)Nc1cc(C2CC2)ccn1] | 4-{8-amino-3-[(6R,8aS)-3-oxooctahydroindolizin-6-yl]imidazo[1,5-a]pyrazin-1-yl}-N-(4-cyclopropylpyridin-2-yl)-2-methylbenzamide | 522.3 | 2.18 (B) |
| 29 | 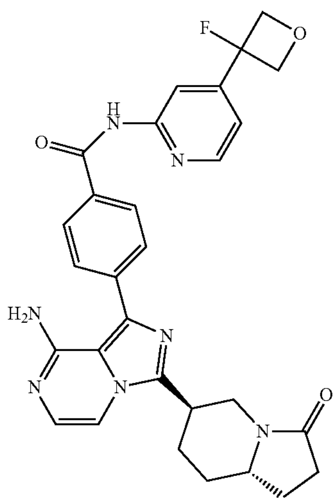 [SMILES: Nc1nccn2c([C@@H]3CC[C@H]4CCC(=O)N4C3)nc(-c3ccc(C(=O)Nc4cc(C5(F)COC5)ccn4)cc3)c12] | 4-{8-amino-3-[(6R,8aS)-3-oxooctahydroindolizin-6-yl]imidazo[1,5-a]pyrazin-1-yl}-N-[4-(3-fluorooxetan-3-yl)pyridin-2-yl]benzamide | 542.3 | 2.25 (B) |
| 30 | 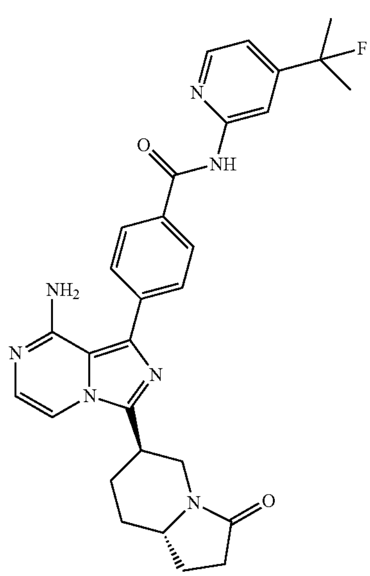 [SMILES: CC(C)(F)c1ccnc(NC(=O)c2ccc(-c3nc([C@@H]4CC[C@H]5CCC(=O)N5C4)n4ccnc(N)c34)cc2)c1] | 4-{8-amino-3-[(6R,8aS)-3-oxooctahydroindolizin-6-yl]imidazo[1,5-a]pyrazin-1-yl}-N-[4-(1-fluoro-1-methylethyl)pyridin-2-yl]benzamide | 528.3 | 2.29 (B) |

TABLE 1-continued

| Example | Structure | IUPAC Name | Exact Mass [M + H]+ | Retention time (min) (LC-MS method) |
|---|---|---|---|---|
| 31 | 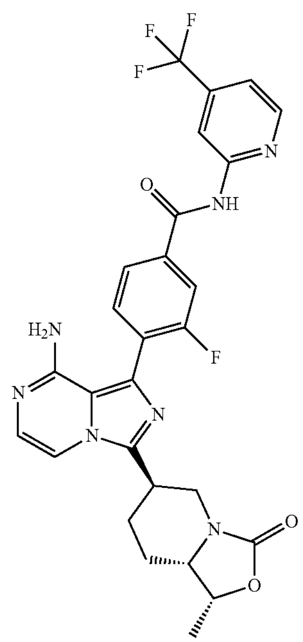 [SMILES: C[C@H]1OC(=O)N2C[C@H](c3nc(-c4ccc(C(=O)Nc5cc(C(F)(F)F)ccn5)cc4F)c4c(N)nccn34)CC[C@@H]12] | 4-{8-amino-3-[(1R,6R,8aS)-1-methyl-3-oxohexahydro[1,3]oxazolo[3,4-a]pyridin-6-yl]imidazo[1,5-a]pyrazin-1-yl}-3-fluoro-N-[4-(trifluoromethyl)pyridin-2-yl]benzamide | 570.3 | 2.21 (B) |
| 32 | 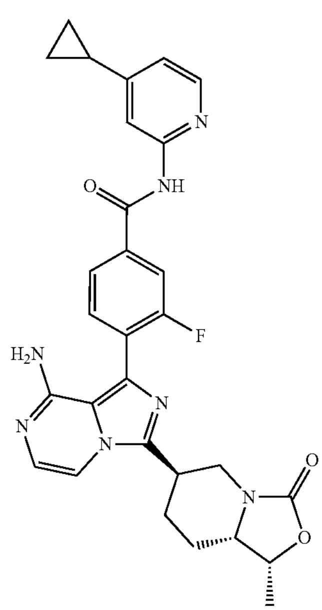 [SMILES: C[C@H]1OC(=O)N2C[C@H](c3nc(-c4ccc(C(=O)Nc5cc(C6CC6)ccn5)cc4F)c4c(N)nccn34)CC[C@@H]12] | 4-{8-amino-3-[(1R,6R,8aS)-1-methyl-3-oxohexahydro[1,3]oxazolo[3,4-a]pyridin-6-yl]imidazo[1,5-a]pyrazin-1-yl}-N-(4-cyclopropylpyridin-2-yl)-3-fluorobenzamide | 542.3 | 1.86 (B) |

TABLE 1-continued

| Example | Structure | IUPAC Name | Exact Mass [M + H]+ | Retention time (min) (LC-MS method) |
|---|---|---|---|---|
| 33 | 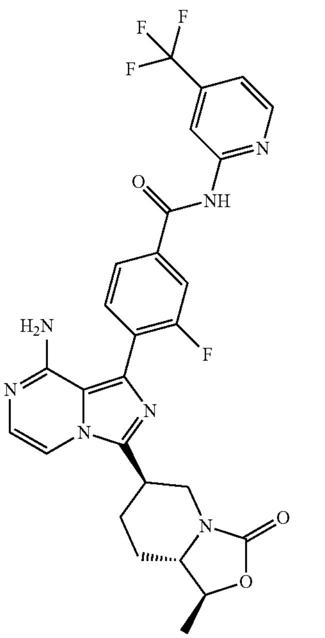 [SMILES: C[C@@H]1OC(=O)N2C[C@H](c3nc(-c4ccc(C(=O)Nc5cc(C(F)(F)F)ccn5)cc4F)c4c(N)nccn34)CC[C@@H]12] | 4-{8-amino-3-[(1S,6R,8aS)-1-methyl-3-oxohexahydro[1,3]oxazolo[3,4-a]pyridin-6-yl]imidazo[1,5-a]pyrazin-1-yl}-3-fluoro-N-[4-(trifluoromethyl)pyridin-2-yl]benzamide | 570.2 | 2.24 (B) |
| 34 | 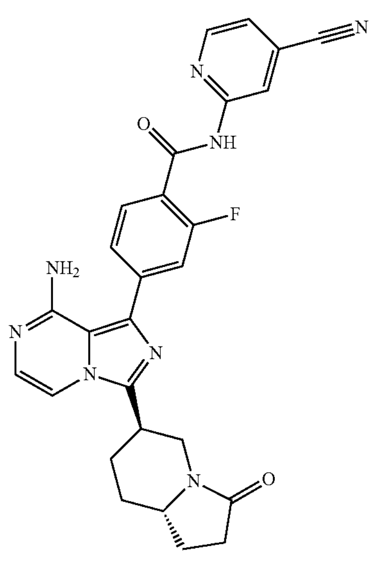 [SMILES: N#Cc1ccnc(NC(=O)c2ccc(-c3nc([C@@H]4CC[C@H]5CCC(=O)N5C4)n4ccnc(N)c34)cc2F)c1] | 4-{8-amino-3-[(6R,8aS)-3-oxooctahydroindolizin-6-yl]imidazo[1,5-a]pyrazin-1-yl}-N-(4-cyanopyridin-2-yl)-2-fluorobenzamide | 511.2 | 2.30 (B) |

TABLE 1-continued

| Example | Structure | IUPAC Name | Exact Mass [M + H]+ | Retention time (min) (LC-MS method) |
|---|---|---|---|---|
| 35 | 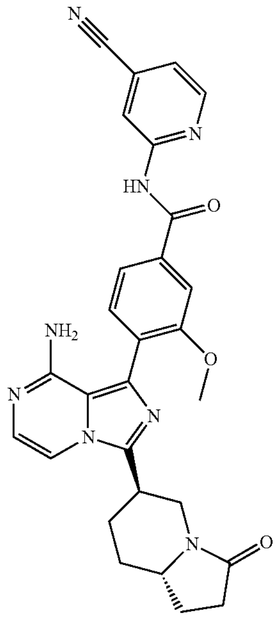 [SMILES: COc1cc(C(=O)Nc2cc(C#N)ccn2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-N-(4-cyanopyridin-2-yl)-3-methoxybenzamide | 523.1 | 1.71 (B) |
| 36 | 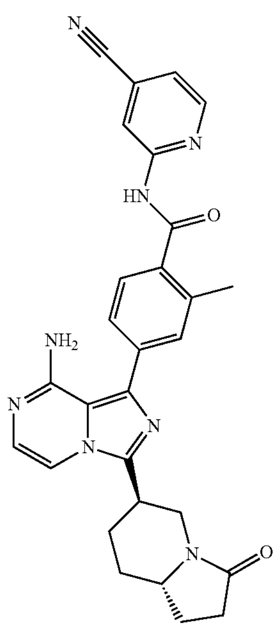 [SMILES: Cc1cc(-c2nc([C@@H]3CC[C@H]4CCC(=O)N4C3)n3ccnc(N)c23)ccc1C(=O)Nc1cc(C#N)ccn1] | 4-{8-amino-3-[(6R,8aS)-3-oxooctahydroindolizin-6-yl]imidazo[1,5-a]pyrazin-1-yl}-N-(4-cyanopyridin-2-yl)-2-methylbenzamide | 507.3 | 2.28 (B) |

TABLE 1-continued

| Example | Structure | IUPAC Name | Exact Mass [M + H]+ | Retention time (min) (LC-MS method) |
|---|---|---|---|---|
| 37 | 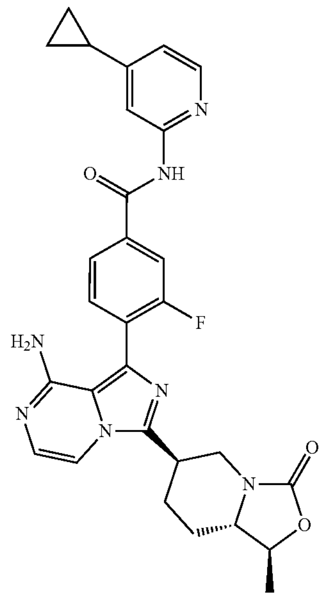 [SMILES: C[C@@H]1OC(=O)N2C[C@H](c3nc(-c4ccc(C(=O)Nc5cc(C6CC6)ccn5)cc4F)c4c(N)nccn34)CC[C@@H]12] | 4-{8-amino-3-[(1S,6R,8aS)-1-methyl-3-oxohexahydro[1,3]oxazolo[3,4-a]pyridin-6-yl]imidazo[1,5-a]pyrazin-1-yl}-N-(4-cyclopropylpyridin-2-yl)-3-fluorobenzamide | 542.2 | 1.37 (B) |
| 38 | 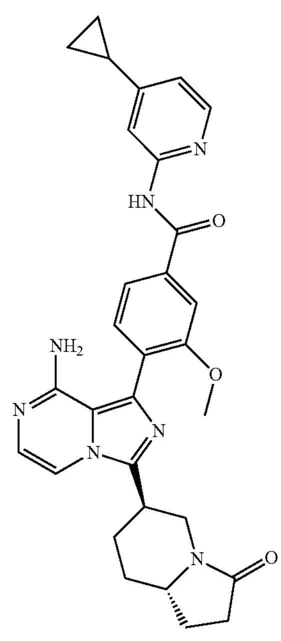 [SMILES: COc1cc(C(=O)Nc2cc(C3CC3)ccn2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-N-(4-cyclopropylpyridin-2-yl)-3-methoxybenzamide | 538.4 | 2.12 (B) |

TABLE 1-continued
| Example | Structure | IUPAC Name | Exact Mass [M + H]+ | Retention time (min) (LC-MS method) |
|---|---|---|---|---|
| 39 | 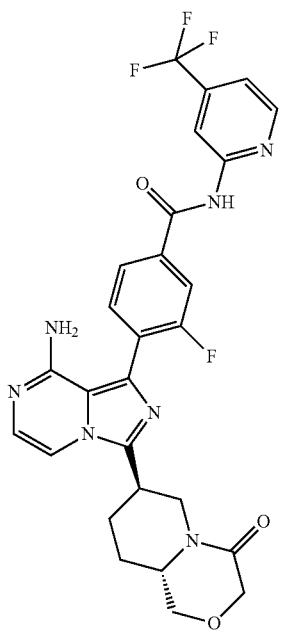 [SMILES: Nc1nccn2c([C@@H]3CC[C@H]4COCC(=O)N4C3)nc(-c3ccc(C(=O)Nc4cc(C(F)(F)F)ccn4)cc3F)c12] | 4-{8-amino-3-[(7R,9aS)-4-oxooctahydropyrido[2,1-c][1,4]oxazin-7-yl]imidazo[1,5-a]pyrazin-1-yl}-3-fluoro-N-[4-(trifluoromethyl)pyridin-2-yl]benzamide | 570.3 | 2.45 (B) |
| 40 | 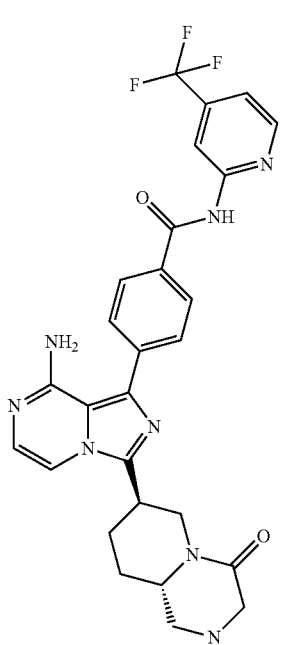 | 4-{8-amino-3-[(7R,9aS)-4-oxooctahydro-2H-pyrido[1,2-a]pyrazin-7-yl]imidazo[1,5-a]pyrazin-1-yl}-N-[4-(trifluoromethyl)pyridin-2-yl]benzamide | 551.4 | 2.11 (B) |

TABLE 1-continued
| Example | Structure | IUPAC Name | Exact Mass [M + H]+ | Retention time (min) (LC-MS method) |
|---|---|---|---|---|
| 41 | 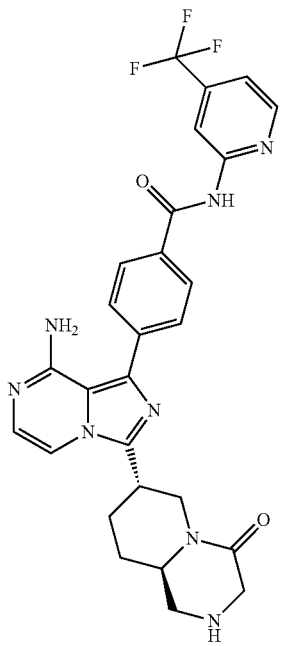 [SMILES: Nc1nccn2c([C@H]3CC[C@@H]4CNCC(=O)N4C3)nc(-c3ccc(C(=O)Nc4cc(C(F)(F)F)ccn4)cc3)c12] | 4-{8-amino-3-[(7S,9aR)-4-oxooctahydro-2H-pyrido[1,2-a]pyrazin-7-yl]imidazo[1,5-a]pyrazin-1-yl}-N-[4-(trifluoromethyl)pyridin-2-yl]benzamide | 551.4 | 2.12 (B) |
| 42 | 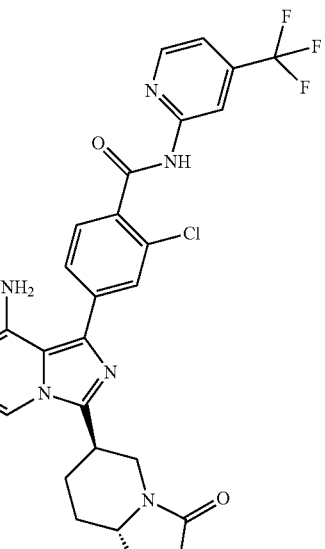 | 4-{8-amino-3-[(6R,8aS)-3-oxooctahydroindolizin-6-yl]imidazo[1,5-a]pyrazin-1-yl}-2-chloro-N-[4-(trifluoromethyl)pyridin-2-yl]benzamide | 570.3 | 2.04 (B) |

TABLE 1-continued

| Example | Structure | IUPAC Name | Exact Mass [M + H]⁺ | Retention time (min) (LC-MS method) |
|---|---|---|---|---|
| 43 | 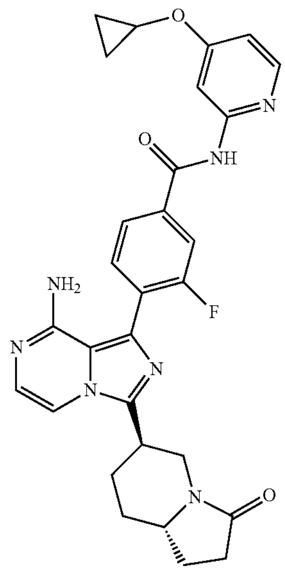 [SMILES: Nc1nccn2c([C@@H]3CC[C@H]4CCC(=O)N4C3)nc(-c3ccc(C(=O)Nc4cc(OC5CC5)ccn4)cc3F)c12] | 4-{8-amino-3-[(6R,8aS)-3-oxooctahydroindolizin-6-yl]imidazo[1,5-a]pyrazin-1-yl}-N-[4-(cyclopropyloxy)pyridin-2-yl]-3-fluorobenzamide | 542.2 | 1.61 (B) |
| 44 | 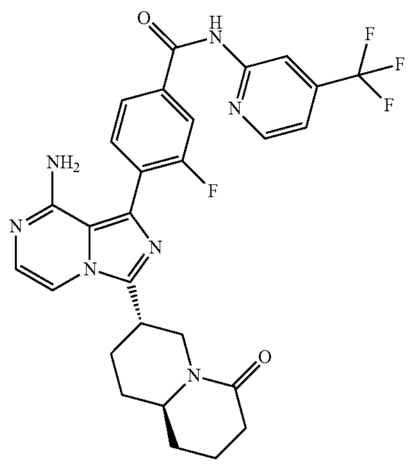 [SMILES: Nc1nccn2c([C@H]3CC[C@@H]4CCCC(=O)N4C3)nc(-c3ccc(C(=O)Nc4cc(C(F)(F)F)ccn4)cc3F)c12] | 4-{8-amino-3-[(3S,9aS)-6-oxooctahydro-2H-quinolizin-3-yl]imidazo[1,5-a]pyrazin-1-yl}-3-fluoro-N-[4-(trifluoromethyl)pyridin-2-yl]benzamide | 568.2 | 2.62 (B) |
| 45 | 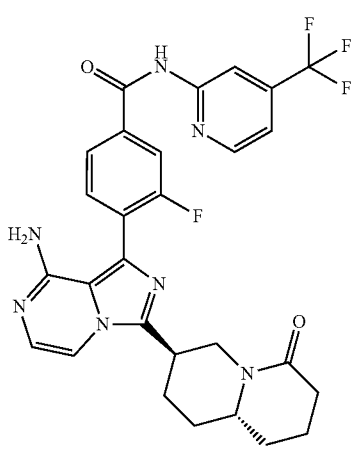 [SMILES: Nc1nccn2c([C@@H]3CC[C@H]4CCCC(=O)N4C3)nc(-c3ccc(C(=O)Nc4cc(C(F)(F)F)ccn4)cc3F)c12] | 4-{8-amino-3-[(3R,9aR)-6-oxooctahydro-2H-quinolizin-3-yl]imidazo[1,5-a]pyrazin-1-yl}-3-fluoro-N-[4-(trifluoromethyl)pyridin-2-yl]benzamide | 568.2 | 2.61 (B) |

TABLE 1-continued

| Example | Structure | IUPAC Name | Exact Mass [M + H]+ | Retention time (min) (LC-MS method) |
|---|---|---|---|---|
| 46 | 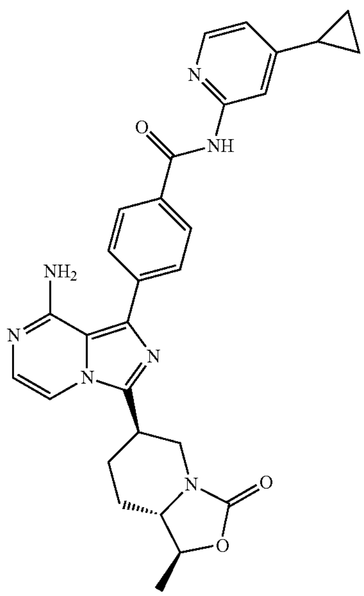 [SMILES: C[C@@H]1OC(=O)N2C[C@H](c3nc(-c4ccc(C(=O)Nc5cc(C6CC6)ccn5)cc4)c4c(N)nccn34)CC[C@@H]12] | 4-{8-amino-3-[(1S,6R,8aS)-1-methyl-3-oxohexahydro[1,3]oxazolo[3,4-a]pyridin-6-yl]imidazo[1,5-a]pyrazin-1-yl}-N-(4-cyclopropylpyridin-2-yl)benzamide | 524.2 | 1.93 (B) |
| 47 | 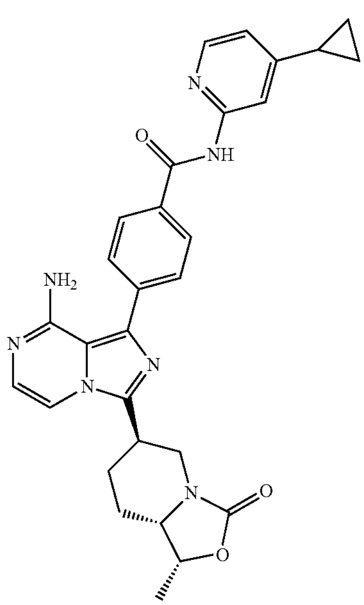 [SMILES: C[C@H]1OC(=O)N2C[C@H](c3nc(-c4ccc(C(=O)Nc5cc(C6CC6)ccn5)cc4)c4c(N)nccn34)CC[C@@H]12] | 4-{8-amino-3-[(1R,6R,8aS)-1-methyl-3-oxohexahydro[1,3]oxazolo[3,4-a]pyridin-6-yl]imidazo[1,5-a]pyrazin-1-yl}-N-(4-cyclopropylpyridin-2-yl)benzamide | 524.2 | 1.91 (B) |

TABLE 1-continued

| Example | Structure | IUPAC Name | Exact Mass [M + H]⁺ | Retention time (min) (LC-MS method) |
|---|---|---|---|---|
| 48 | 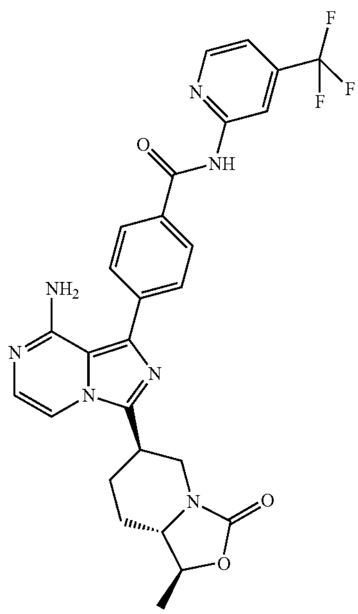 [SMILES: C[C@@H]1OC(=O)N2C[C@H](c3nc(-c4ccc(C(=O)Nc5cc(C(F)(F)F)ccn5)cc4)c4c(N)nccn34)CC[C@@H]12] | 4-{8-amino-3-[(1S,6R,8aS)-1-methyl-3-oxohexahydro[1,3]oxazolo[3,4-a]pyridin-6-yl]imidazo[1,5-a]pyrazin-1-yl}-N-[4-(trifluoromethyl)pyridin-2-yl]benzamide | 552.2 | 2.28 (B) |
| 49 | 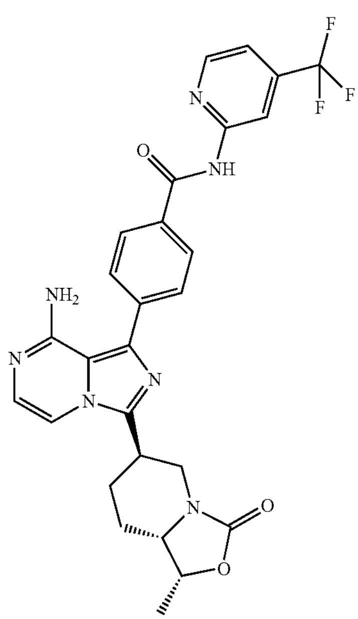 [SMILES: C[C@H]1OC(=O)N2C[C@H](c3nc(-c4ccc(C(=O)Nc5cc(C(F)(F)F)ccn5)cc4)c4c(N)nccn34)CC[C@@H]12] | 4-{8-amino-3-[(1R,6R,8aS)-1-methyl-3-oxohexahydro[1,3]oxazolo[3,4-a]pyridin-6-yl]imidazo[1,5-a]pyrazin-1-yl}-N-[4-(trifluoromethyl)pyridin-2-yl]benzamide | 552.2 | 2.27 (B) |

TABLE 1-continued
| Example | Structure | IUPAC Name | Exact Mass [M + H]+ | Retention time (min) (LC-MS method) |
|---|---|---|---|---|
| 50 | 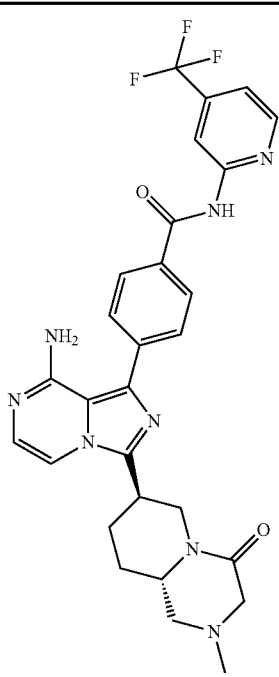 | 4-{8-amino-3-[(7R,9aS)-2-methyl-4-oxooctahydro-2H-pyrido[1,2-a]pyrazin-7-yl]imidazo[1,5-a]pyrazin-1-yl}-N-[4-(trifluoromethyl)pyridin-2-yl]benzamide | 565.2 | 2.00 (B) |
| 51 | 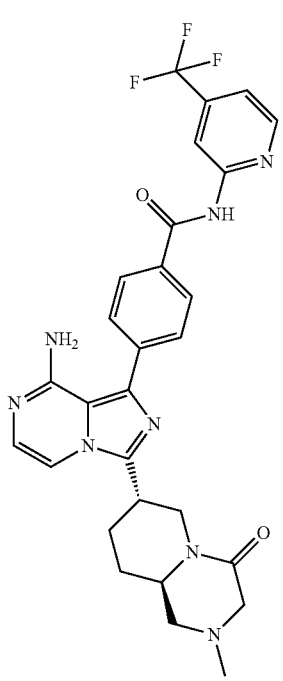 [SMILES: CN1CC(=O)N2C[C@@H](c3nc(-c4ccc(C(=O)Nc5cc(C(F)(F)F)ccn5)cc4)c4c(N)nccn34)CC[C@@H]2C1] | 4-{8-amino-3-[(7S,9aR)-2-methyl-4-oxooctahydro-2H-pyrido[1,2-a]pyrazin-7-yl]imidazo[1,5-a]pyrazin-1-yl}-N-[4-(trifluoromethyl)pyridin-2-yl]benzamide | 565.2 | 1.99 (B) |

TABLE 1-continued

| Example | Structure | IUPAC Name | Exact Mass [M + H]+ | Retention time (min) (LC-MS method) |
|---------|-----------|------------|---------------------|-------------------------------------|
| 52 | 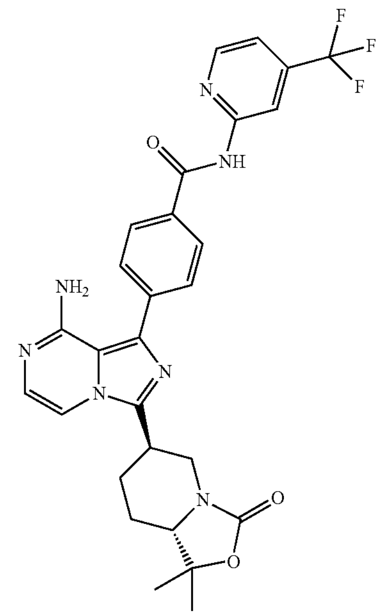 [SMILES: CC1(C)OC(=O)N2C[C@H](c3nc(-c4ccc(C(=O)Nc5cc(C(F)(F)F)ccn5)cc4)c4c(N)nccn34)CC[C@H]21] | 4-{8-amino-3-[(6R,8aS)-1,1-dimethyl-3-oxohexahydro[1,3]oxazolo[3,4-a]pyridin-6-yl]imidazo[1,5-a]pyrazin-1-yl}-N-[4-(trifluoromethyl)pyridin-2-yl]benzamide | 566.2 | 2.33 (B) |
| 53 | 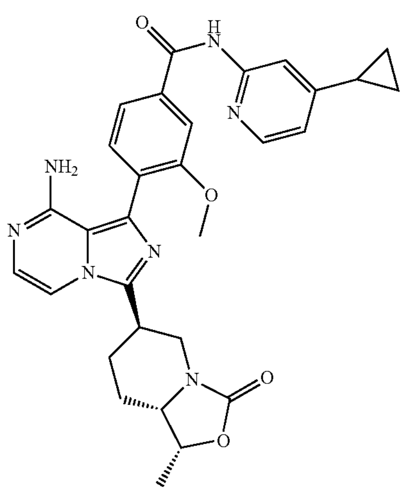 [SMILES: COc1cc(C(=O)Nc2cc(C3CC3)ccn2)ccc1-c1nc([C@@H]2CC[C@H]3[C@@H](C)OC(=O)N3C2)n2ccnc(N)c12] | 4-{8-amino-3-[(1R,6R,8aS)-1-methyl-3-oxohexahydro[1,3]oxazolo[3,4-a]pyridin-6-yl]imidazo[1,5-a]pyrazin-1-yl}-N-(4-cyclopropylpyridin-2-yl)-3-methoxybenzamide | 554.3 | 2.21 (B) |

TABLE 1-continued

| Example | Structure | IUPAC Name | Exact Mass [M + H]+ | Retention time (min) (LC-MS method) |
|---|---|---|---|---|
| 54 | 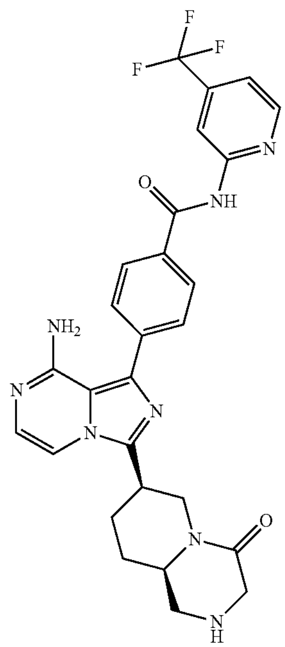 [SMILES: Nc1nccn2c([C@@H]3CC[C@@H]4CNCC(=O)N4C3)nc(-c3ccc(C(=O)Nc4cc(C(F)(F)F)ccn4)cc3)c12] | 4-{8-amino-3-[(7R,9aR)-4-oxooctahydro-2H-pyrido[1,2-a]pyrazin-7-yl]imidazo[1,5-a]pyrazin-1-yl}-N-[4-(trifluoromethyl)pyridin-2-yl]benzamide | 551.2 | 2.23 (B) |
| 55 | 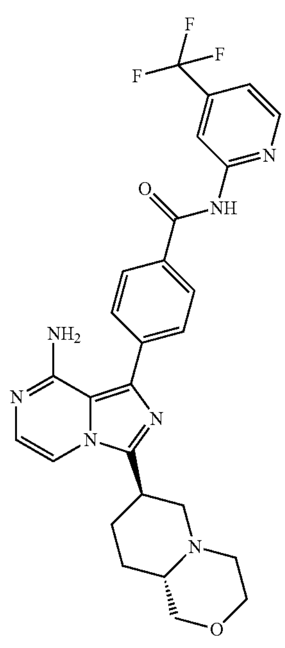 [SMILES: Nc1nccn2c([C@@H]3CC[C@H]4COCCN4C3)nc(-c3ccc(C(=O)Nc4cc(C(F)(F)F)ccn4)cc3)c12] | 4-{8-amino-3-[(7R,9aS)-octahydropyrido[2,1-c][1,4]oxazin-7-yl]imidazo[1,5-a]pyrazin-1-yl}-N-[4-(trifluoromethyl)pyridin-2-yl]benzamide | 538.2 | 2.21 (B) |

TABLE 1-continued
| Example | Structure | IUPAC Name | Exact Mass [M + H]+ | Retention time (min) (LC-MS method) |
|---|---|---|---|---|
| 56 | 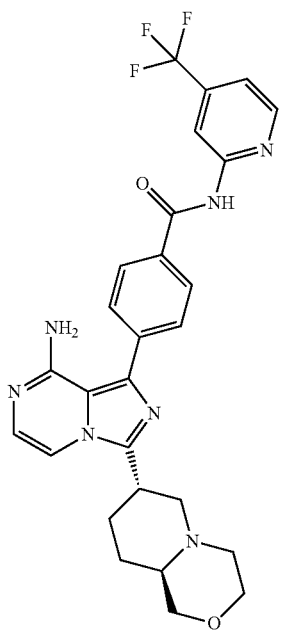 [SMILES: Nc1nccn2c([C@H]3CC[C@@H]4COCCN4C3)nc(-c3ccc(C(=O)Nc4cc(C(F)(F)F)ccn4)cc3)c12] | 4-{8-amino-3-[(7S,9aR)-octahydropyrido[2,1-c][1,4]oxazin-7-yl]imidazo[1,5-a]pyrazin-1-yl}-N-[4-(trifluoromethyl)pyridin-2-yl]benzamide | 538.2 | 2.23 (B) |
| 57 | 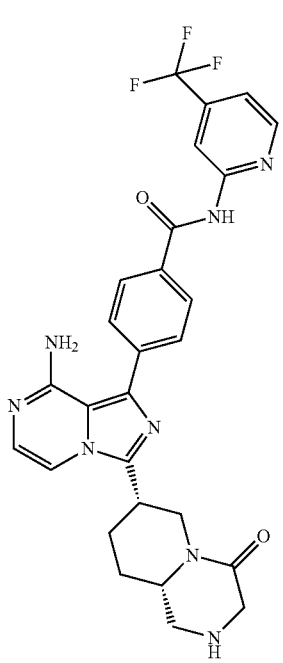 [SMILES: Nc1nccn2c([C@H]3CC[C@H]4CNCC(=O)N4C3)nc(-c3ccc(C(=O)Nc4cc(C(F)(F)F)ccn4)cc3)c12] | 4-{8-amino-3-[(7S,9aS)-4-oxooctahydro-2H-pyrido[1,2-a]pyrazin-7-yl]imidazo[1,5-a]pyrazin-1-yl}-N-[4-(trifluoromethyl)pyridin-2-yl]benzamide | 551.2 | 2.23 (B) |

TABLE 1-continued
| Example | Structure | IUPAC Name | Exact Mass [M + H]+ | Retention time (min) (LC-MS method) |
|---|---|---|---|---|
| 58 | 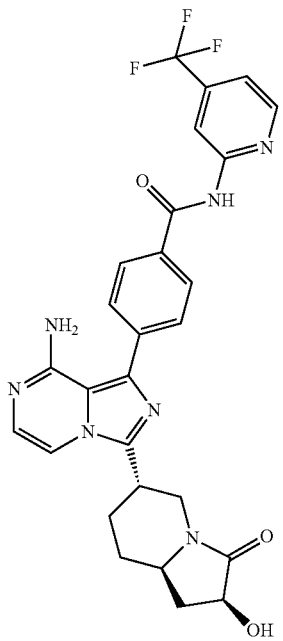 [SMILES: Nc1nccn2c([C@H]3CC[C@@H]4C[C@H](O)C(=O)N4C3)nc(-c3ccc(C(=O)Nc4cc(C(F)(F)F)ccn4)cc3)c12] | 4-{8-amino-3-[(2S,6S,8aR)-2-hydroxy-3-oxooctahydroindolizin-6-yl]imidazo[1,5-a]pyrazin-1-yl}-N-[4-(trifluoromethyl)pyridin-2-yl]benzamide | 552.2 | 2.40 (B) |
| 59 | 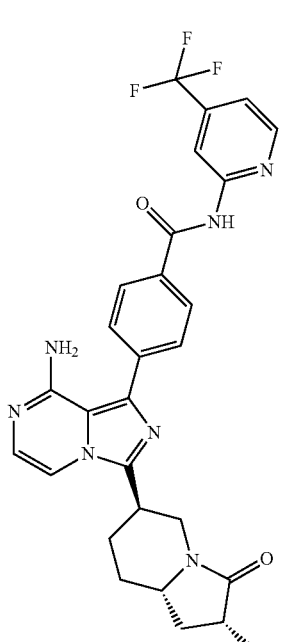 | 4-{8-amino-3-[(2R,6R,8aS)-2-hydroxy-3-oxooctahydroindolizin-6-yl]imidazo[1,5-a]pyrazin-1-yl}-N-[4-(trifluoromethyl)pyridin-2-yl]benzamide | 552.2 | 2.42 (B) |

TABLE 1-continued
| Example | Structure | IUPAC Name | Exact Mass [M + H]+ | Retention time (min) (LC-MS method) |
|---|---|---|---|---|
| 60 | 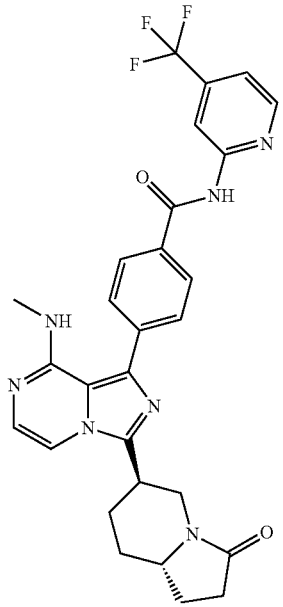 [SMILES: CNc1nccn2c([C@@H]3CC[C@H]4CCC(=O)N4C3)nc(-c3ccc(C(=O)Nc4cc(C(F)(F)F)ccn4)cc3)c12] | 4-{8-(methylamino)-3-[(6R,8aS)-3-oxooctahydroindolizin-6-yl]imidazo[1,5-a]pyrazin-1-yl}-N-[4-(trifluoromethyl)pyridin-2-yl]benzamide | 550.2 | 2.51 (B) |
| 61 | 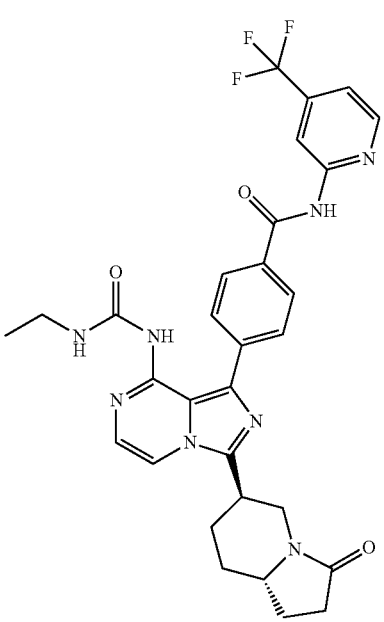 [SMILES: CCNC(=O)Nc1nccn2c([C@@H]3CC[C@H]4CCC(=O)N4C3)nc(-c3ccc(C(=O)Nc4cc(C(F)(F)F)ccn4)cc3)c12] | 4-{8-[(ethylcarbamoyl)amino]-3-[(6R,8aS)-3-oxooctahydroindolizin-6-yl]imidazo[1,5-a]pyrazin-1-yl}-N-[4-(trifluoromethyl)pyridin-2-yl]benzamide | 607.2 | 2.87 (B) |

TABLE 1-continued
| Example | Structure | IUPAC Name | Exact Mass [M + H]⁺ | Retention time (min) (LC-MS method) |
|---|---|---|---|---|
| 62 | 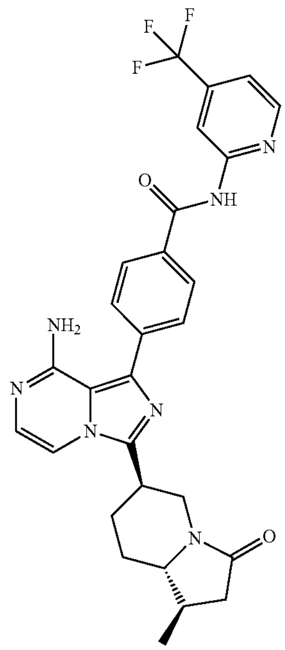 [SMILES: C[C@@H]1CC(=O)N2C[C@H](c3nc(-c4ccc(C(=O)Nc5cc(C(F)(F)F)ccn5)cc4)c4c(N)nccn34)CC[C@@H]12] | 4-{8-amino-3-[(1R,6R,8aS)-1-methyl-3-oxooctahydroindolizin-6-yl]imidazo[1,5-a]pyrazin-1-yl}-N-[4-(trifluoromethyl)pyridin-2-yl]benzamide | 550.2 | 0.97 (C) |
| 63 | 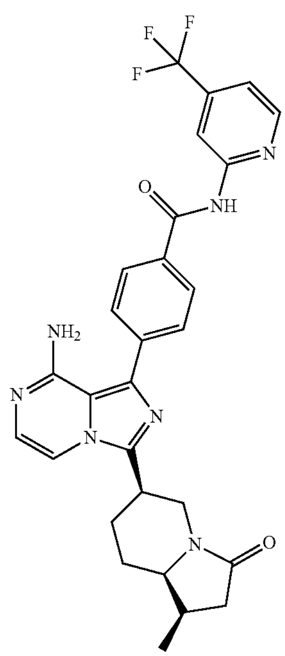 [SMILES: C[C@@H]1CC(=O)N2C[C@H](c3nc(-c4ccc(C(=O)Nc5cc(C(F)(F)F)ccn5)cc4)c4c(N)nccn34)CC[C@H]12] | 4-{8-amino-3-[(1S,6R,8aR)-1-methyl-3-oxooctahydroindolizin-6-yl]imidazo[1,5-a]pyrazin-1-yl}-N-[4-(trifluoromethyl)pyridin-2-yl]benzamide | 550.2 | 0.96 (C) |
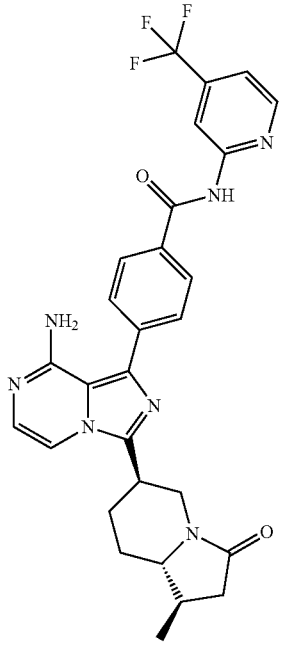

TABLE 1-continued

| Example | Structure | IUPAC Name | Exact Mass [M + H]+ | Retention time (min) (LC-MS method) |
|---|---|---|---|---|
| 64 | 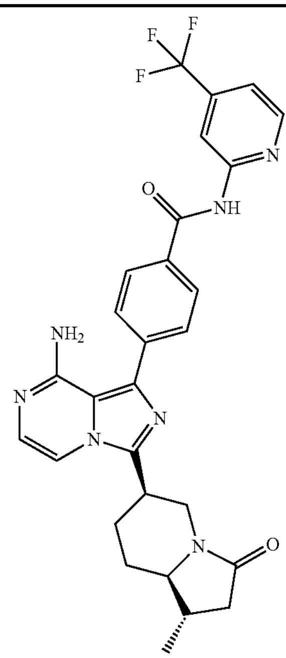 | 4-{8-amino-3-[(1S,6R,8aR)-1-methyl-3-oxooctahydroindolizin-6-yl]imidazo[1,5-a]pyrazin-1-yl}-N-[4-(trifluoromethyl)pyridin-2-yl]benzamide | 550.2 | 0.98 (C) |
| 65 | 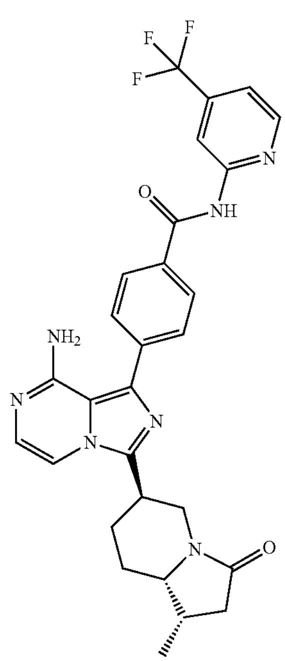 [SMILES: C[C@H]1CC(=O)N2C[C@H](c3nc(-c4ccc(C(=O)Nc5cc(C(F)(F)F)ccn5)cc4)c4c(N)nccn34)CC[C@@H]12] | 4-{8-amino-3-[(1R,6R,8aS)-1-methyl-3-oxooctahydroindolizin-6-yl]imidazo[1,5-a]pyrazin-1-yl}-N-[4-(trifluoromethyl)pyridin-2-yl]benzamide | 550.2 | 0.99 (C) |

TABLE 1-continued

| Example | Structure | IUPAC Name | Exact Mass [M + H]+ | Retention time (min) (LC-MS method) |
|---------|-----------|------------|---------------------|--------------------------------------|
| 66 | 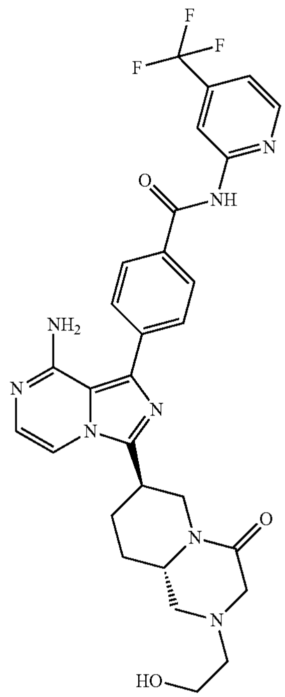 [SMILES: Nc1nccn2c([C@@H]3CC[C@H]4CN(CCO)CC(=O)N4C3)nc(-c3ccc(C(=O)Nc4cc(C(F)(F)F)ccn4)cc3)c12] | 4-{8-amino-3-[(7R,9aS)-2-(2-hydroxyethyl)-4-oxooctahydro-2H-pyrido[1,2-a]pyrazin-7-yl]imidazo[1,5-a]pyrazin-1-yl}-N-[4-(trifluoromethyl)pyridin-2-yl]benzamide | 595.2 | 2.18 (B) |
| 67 | 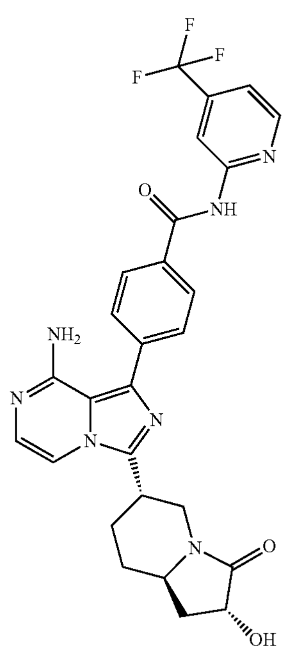 [SMILES: Nc1nccn2c([C@H]3CC[C@@H]4C[C@@H](O)C(=O)N4C3)nc(-c3ccc(C(=O)Nc4cc(C(F)(F)F)ccn4)cc3)c12] | 4-{8-amino-3-[(2R,6S,8aR)-2-hydroxy-3-oxooctahydroindolizin-6-yl]imidazo[1,5-a]pyrazin-1-yl}-N-[4-(trifluoromethyl)pyridin-2-yl]benzamide | 552.2 | 2.39 (B) |

TABLE 1-continued

| Example | Structure | IUPAC Name | Exact Mass [M + H]+ | Retention time (min) (LC-MS method) |
|---|---|---|---|---|
| 68 | 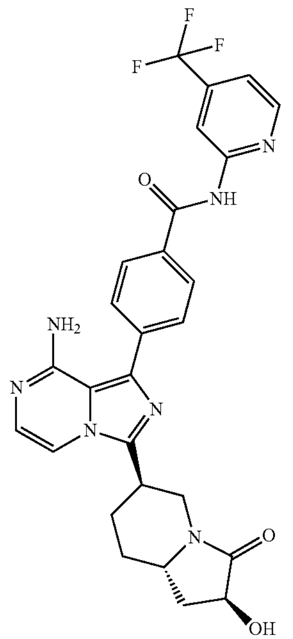 [SMILES: Nc1nccn2c([C@@H]3CC[C@H]4C[C@H](O)C(=O)N4C3)nc(-c3ccc(C(=O)Nc4cc(C(F)(F)F)ccn4)cc3)c12] | 4-{8-amino-3-[(2S,6R,8aS)-2-hydroxy-3-oxooctahydroindolizin-6-yl]imidazo[1,5-a]pyrazin-1-yl}-N-[4-(trifluoromethyl)pyridin-2-yl]benzamide | 552.2 | 2.38 (B) |
| 69 | 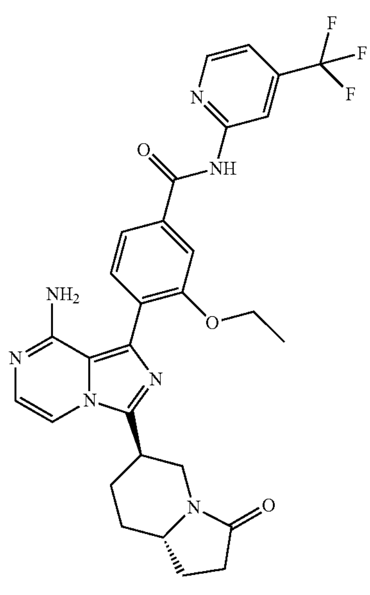 [SMILES: CCOc1cc(C(=O)Nc2cc(C(F)(F)F)ccn2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-ethoxy-N-[4-(trifluoromethyl)pyridin-2-yl]benzamide | 580.2 | 2.57 (B) |

| Example | Structure | IUPAC Name | Exact Mass [M + H]⁺ | Retention time (min) (LC-MS method) |
|---|---|---|---|---|
| 70 | 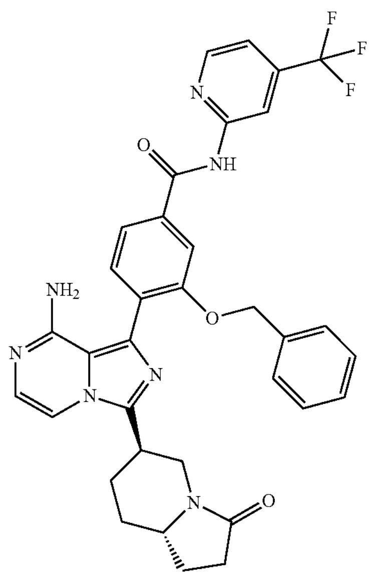 [SMILES: Nc1nccn2c([C@@H]3CC[C@H]4CCC(=O)N4C3)nc(-c3ccc(C(=O)Nc4cc(C(F)(F)F)ccn4)cc3OCc3ccccc3)c12] | 4-{8-amino-3-[(6R,8aS)-3-oxooctahydroindolizin-6-yl]imidazo[1,5-a]pyrazin-1-yl}-3-(benzyloxy)-N-[4-(trifluoromethyl)pyridin-2-yl]benzamide | 642.2 | 2.96 (A) |
| 71 | 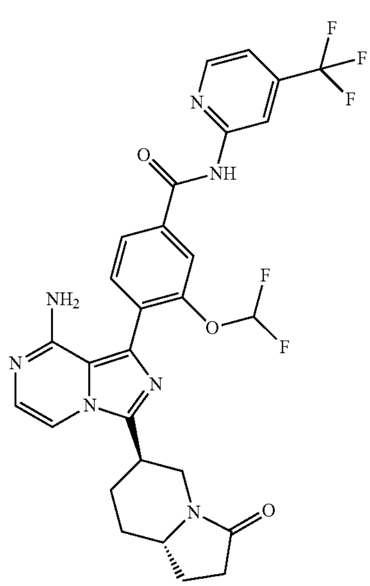 [SMILES: Nc1nccn2c([C@@H]3CC[C@H]4CCC(=O)N4C3)nc(-c3ccc(C(=O)Nc4cc(C(F)(F)F)ccn4)cc3OC(F)F)c12] | 4-{8-amino-3-[(6R,8aS)-3-oxooctahydroindolizin-6-yl]imidazo[1,5-a]pyrazin-1-yl}-3-(difluoromethoxy)-N-[4-(trifluoromethyl)pyridin-2-yl]benzamide | 602.2 | 2.63 (A) |

TABLE 1-continued

| Example | Structure | IUPAC Name | Exact Mass [M + H]+ | Retention time (min) (LC-MS method) |
|---------|-----------|------------|---------------------|-------------------------------------|
| 72 | 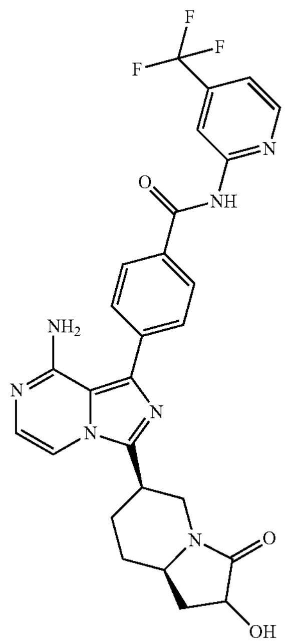 | 4-{8-amino-3-[(2S,6R,8aR)-2-hydroxy-3-oxooctahydroindolizin-6-yl]imidazo[1,5-a]pyrazin-1-yl}-N-[4-(trifluoromethyl)pyridin-2-yl]benzamide | 552.2 | 2.40 (B) |
| 73 | 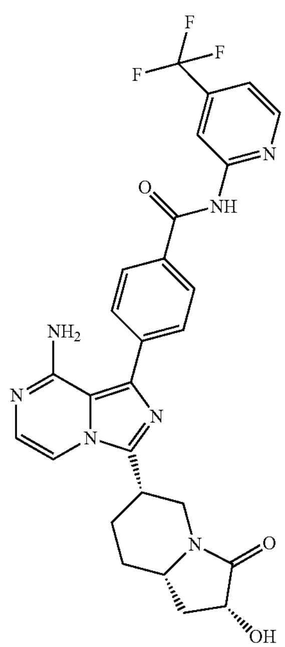 [SMILES: Nc1nccn2c([C@H]3CC[C@H]4C[C@@H](O)C(=O)N4C3)nc(-c3ccc(C(=O)Nc4cc(C(F)(F)F)ccn4)cc3)c12] | 4-{8-amino-3-[(2R,6S,8aS)-2-hydroxy-3-oxooctahydroindolizin-6-yl]imidazo[1,5-a]pyrazin-1-yl}-N-[4-(trifluoromethyl)pyridin-2-yl]benzamide | 552.2 | 2.39 (B) |

TABLE 1-continued

| Example | Structure | IUPAC Name | Exact Mass [M + H]+ | Retention time (min) (LC-MS method) |
|---|---|---|---|---|
| 74 | 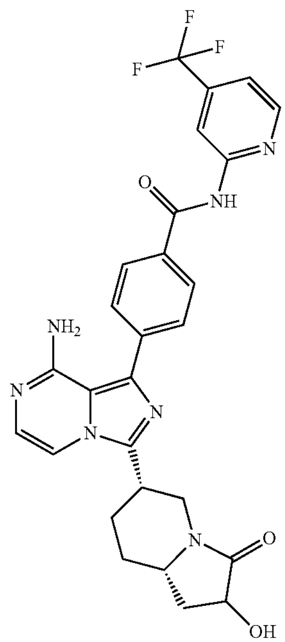 | 4-{8-amino-3-[(2R,6S,8aS)-2-hydroxy-3-oxooctahydroindolizin-6-yl]imidazo[1,5-a]pyrazin-1-yl}-N-[4-(trifluoromethyl)pyridin-2-yl]benzamide | 552.2 | 2.44 (B) |
| 75 | 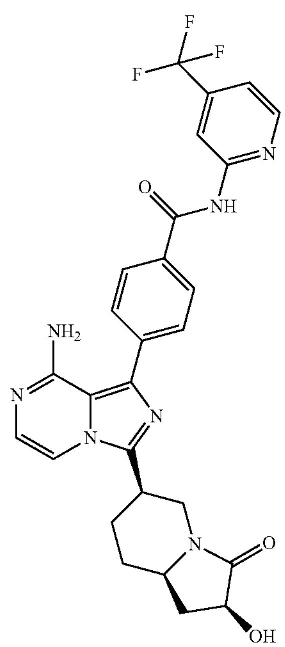 [SMILES: Nc1nccn2c([C@@H]3CC[C@@H]4C[C@H](O)C(=O)N4C3)nc(-c3ccc(C(=O)Nc4cc(C(F)(F)F)ccn4)cc3)c12] | 4-{8-amino-3-[(2S,6R,8aR)-2-hydroxy-3-oxooctahydroindolizin-6-yl]imidazo[1,5-a]pyrazin-1-yl}-N-[4-(trifluoromethyl)pyridin-2-yl]benzamide | 552.2 | 2.44 (B) |

Example 76

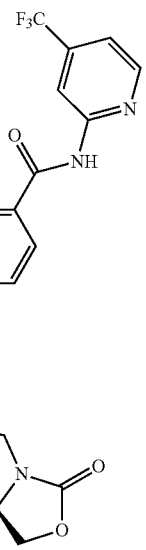

4-(8-amino-3-((6R,8aR)-3-oxohexa hydrooxazolo[4,3-c][1,4]oxazin-6-yl)imidazo[1,5-a]pyrazin-1-yl)-N-(4-(trifluoromethyl)pyridin-2-yl)benzamide (a) (2R,5R)-tert-butyl 5-(((tert-butyldiphenylsilyl)oxy)methyl)-2-(8-((2,4-dimethoxy benzyl)amino)-1-(4-((4-(trifluoromethyl)pyridin-2-yl)carbamoyl)phenyl)imidazo[1,5-a]pyrazin-3-yl)morpholine-4-carboxylate To (2R,5R)-tert-butyl-2-(1-bromo-8-((2,4-dimethoxybenzyl)amino)imidazo[1,5-a]pyrazin-3-yl)-5-(((tert-butyldiphenylsilyl)oxy)methyl)morpholine-4-carboxylate (0.25 g, 0.306 mmol) and 4-(4,4,5,5-tetramethyl-1,3,2-dioxaborolan-2-yl)-N-(4-(trifluoro methyl)pyridin-2-yl)benzamide (0.144 g, 0.918 mmol) in 1,4-Dioxane (6 ml) and Water (0.2 ml) was added, $K_3PO_4$ (0.195 g, 14.63 mmol) and Pd(pddf)Cl2 (0.025 g, 0.031 mmol) and stirred at 80° C. overnight. The reaction mixture was diluted with EtOAc and filtered through celite. The filtrate was washed with water (3×80 mL). The organic phase was dried over $MgSO_4$ and evaporated to dryness. The crude was purified by column chromatography (using 30-60% EtOAc in Hex.) to give (2R,5R)-tert-butyl 5-(((tert-butyldiphenylsilyl)oxy)methyl)-2-(8-((2,4-dimethoxybenzyl)amino)-1-(4-((4-(trifluoromethyl)pyridin-2-yl)carbamoyl)phenyl)imidazo[1,5-a]pyrazin-3-yl)morpholine-4-carboxylate (0.216 g, 70%). LCMS: [M+H]$^+$: 1002.89, LC-MS method A Ret. time=2.86 min.

(b) 4-(8-amino-3-((2R,5S)-5-(hydroxymethyl)morpholin-2-yl)imidazo[1,5-a]pyrazin-1-yl)-N-(4-(trifluoromethyl)pyridin-2-yl)benzamide (2R,5R)-tert-butyl-5-(((tert-butyldiphenylsilyl)oxy)methyl)-2-(8-((2,4-dimethoxybenzyl)amino)-1-(4-((4-(trifluoromethyl)pyridin-2-yl)carbamoyl)phenyl)imidazo[1,5-a]pyrazin-3-yl)morpholine-4-carboxylate (0.5 g, 0.499 mmol) was dissolved in 3 mL TFA and 0.5 mL $H_2O$. The mixture was heated at 80° C. for 3 h, and concentrated. The residue was purified by column chromatography (3-20% MeOH in DCM) to give 4-(8-amino-3-((2R,5S)-5-(hydroxymethyl)morpholin-2-yl)imidazo[1,5-a]pyrazin-1-yl)-N-(4-(trifluoromethyl)pyridin-2-yl)benzamide (204 mg, 80%). LCMS: [M+H]+: 514.07, LC-MS method E Ret. time=1.01 min.

(c) 4-(8-amino-3-((6R,8aR)-3-oxohexa hydrooxazolo[4,3-c][1,4]oxazin-6-yl)imidazo[1,5-a]pyrazin-1-yl)-N-(4-(trifluoromethyl)pyridin-2-yl)benzamide 4-(8-amino-3-((2R,5S)-5-(hydroxymethyl)morpholin-2-yl)imidazo[1,5-a]pyrazin-1-yl)-N-(4-(trifluoromethyl)pyridin-2-yl)benzamide (12 mg, 0.023 mmol) was dissolved in 2 mL of Dichloromethane, and the this was added N-ethyl-N-isopropylpropan-2-amine ((9 mg, 0.070 mmol) and 1,1'-Carbonyldiimidazole (3.8 mg, 0.023 mmol) at 0° C. The mixture was stirred for 30 min and concentrated. The residue was purified using reverse phase column (TFA:CH3CN:$H_2O$ system) to give 4-(8-amino-3-((6R,8aR)-3-oxohexa hydrooxazolo[4,3-c][1,4]oxazin-6-yl)imidazo[1,5-a]pyrazin-1-yl)-N-(4-(trifluoromethyl)pyridin-2-yl)benzamide (6 mg, 48%). LCMS: [M+H]$^+$: 818.31, LC-MS method E Ret. time=1.03 min.

Example 77

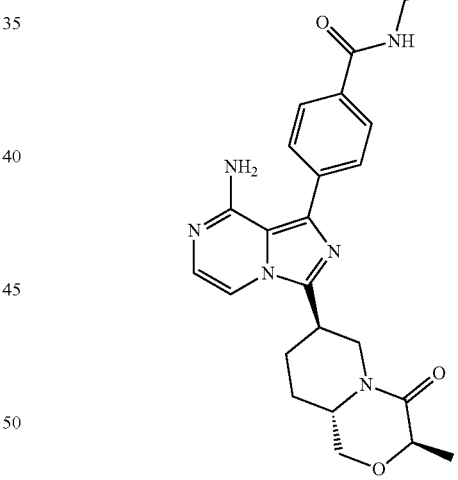

4-(8-amino-3-((3R,7R,9aS)-3-methyl-4-oxooctahydropyrido[2,1-c][1,4]oxazin-7-yl)imidazo[1,5-a]pyrazin-1-yl)-N-(4-(trifluoromethyl)pyridin-2-yl)benzamide To a solution of (3R,7R,9aS)-7-(8-amino-1-bromoimidazo[1,5-a]pyrazin-3-yl)-3-methylhexahydropyrido[2,1-c][1,4]oxazin-4(3H)-one (30 mg, 0.079 mmol), 4-(4,4,5,5-tetramethyl-1,3,2-dioxaborolan-2-yl)-N-(4-(trifluoromethyl)pyridin-2-yl)benzamide (40 mg, 0.102 mmol) and $K_2CO_3$ (32.7 mg, 0.236 mmol) in dioxane/$H_2O$ (2 mL, 3:1) was added Pd(dppf)Cl2 (6 mg, 0.008 mmol) under $N_2$ atmosphere, and stirred at 90-100° C. for 90 min.

The mixture was cooled to room temperature, H₂O (5 mL) was added, and the mixture was extracted with EA (10 mL×2), the organic layers were evaporated to get the crude product, which was separated by prep-HPLC to afford 4-(8-amino-3-((3R,7R,9aS)-3-methyl-4-oxooctahydropyrido[2,1-c][1,4]oxazin-7-yl)imidazo[1,5-a]pyrazin-1-yl)-N-(4-(trifluoromethyl)pyridin-2-yl)benzamide. ¹H NMR (400 MHz, METHANOL-d4) δ=8.68-8.62 (m, 2H), 8.22 (d, J=8.5 Hz, 2H), 7.95-7.87 (m, 3H), 7.47 (d, J=5.0 Hz, 1H), 7.07 (d, J=6.0 Hz, 1H), 4.84 (dd, J=1.9, 13.2 Hz, 1H), 4.25 (q, J=6.7 Hz, 1H), 4.05 (dd, J=4.3, 12.3 Hz, 1H), 3.87 (dd, J=2.5, 12.3 Hz, 1H), 3.57 (d, J=11.5 Hz, 1H), 3.44-3.35 (m, 1H), 3.10 (t, J=12.4 Hz, 1H), 2.36-2.27 (m, 1H), 2.15 (dq, J=4.4, 12.6 Hz, 1H), 2.06-1.87 (m, 2H), 1.48 (d, J=6.8 Hz, 3H). LCMS: Retention time: 2.514 min, (M+H)+ m/z: 566.4.

Example 78

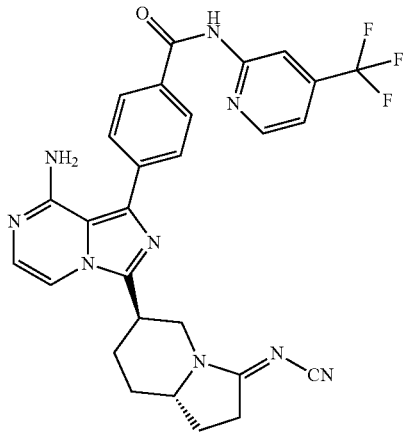 [SMILES: N#C/N=C1\CC[C@@H]2CC[C@@H](c3nc(-c4ccc(C(=O)Nc5cc(C(F)(F)F)ccn5)cc4)c4c(N)nccn34)CN12]

4-(8-amino-3-((6R,8 aS,E)-3-(cyanoimino)octahydroindolizin-6-yl)imidazo[1,5-a]pyrazin-1-yl)-N-(4-(trifluoromethyl)pyridin-2-yl)benzamide Step 1: (6R,8aS)-6-(8-amino-1-bromoimidazo[1,5-a]pyrazin-3-yl)hexahydroindolizine-3 (2H)-thione The mixture of (6R,8aS)-6-(8-amino-1-bromoimidazo[1,5-a]pyrazin-3-yl)hexahydroindolizin-3(2H)-one (50 mg, 0.14 mmol) and Lawesson reagent (31.76 mg, 0.079 mmol) in Toluene/DCM (4 mL/2 ml) was stirred at 65° C. for 3 h. LCMS showed the reaction was complete. The mixture was concentrated in vacuo. The residue was purified by TLC (EA100%) to give (6R,8aS)-6-(8-amino-1-bromoimidazo[1,5-a]pyrazin-3-yl)hexahydroindolizine-3(2H)-thione (25 mg, 47.89 mmol) as a yellow solid. LCMS: Retention time 0.667 min [M+H]⁺ m/z: 365.8

Step 2: (E)-N-((6R,8aS)-6-(8-amino-1-bromoimidazo[1,5-a]pyrazin-3-yl)hexahydroindolizin-3 (2H)-ylidene)cyanamide A solution of (6R,8aS)-6-(8-amino-1-bromoimidazo[1,5-a]pyrazin-3-yl)hexahydroindolizine-3(2H)-thione (23 mg, 0.062 mmol) in ACN (5 mL) was treated with cyanamide (3.77 mg, 0.089 mmol), Hg(Ac)2 (17 mg, 0.053 mmol) and TEA (7.2 mg, 0.07 mmol). The reaction mixture was stirred at 80° C. for 18 h. The mixture was concentrated under vacuum. The residue was partitioned with sat. aq. NaHCO3 (30 mL) and DCM (10 mL×3). The combined organic layer was dried over Na2SO4, filtered, concentrated, and the residue was purified by TLC (pure EA) to give (E)-N-((6R,8aS)-6-(8-amino-1-bromoimidazo[1,5-a]pyrazin-3-yl)hexahydroindolizin-3 (2H)-ylidene)cyanamide (11 mg, 47.0%) as a white solid. LCMS: Retention time: 0.579 min, [M+H]⁺ m/z: 373.8

Step 3: 4-(8-amino-3-((6R,8aS,E)-3-(cyanoimino)octahydroindolizin-6-yl)imidazo[1,5-a]pyrazin-1-yl)-N-(4-(trifluoromethyl)pyridin-2-yl)benzamide To the solution of (E)-N-((6R,8aS)-6-(8-amino-1-bromoimidazo[1,5-a]pyrazin-3-yl)hexahydroindolizin-3(2H)-ylidene)cyanamide (11 mg, 0.029 mmol) in dioxane/H2O (0.8 mL/0.2 mL)) was added Compound 4 (13.84 mg, 0.035 mmol), K2CO3 (12.06 mg, 0.087 mmol) and Pd(dppf)C12 (1.04 mg, 0.002 mmol). The mixture was purged with N2 three times, and stirred at 90° C. for 1 h. The mixture was partitioned with H2O (25 mL) and EA (6 mL×3). The organic layer was dried over Na2SO4, filtered, concentrated, purified by Prep_HPLC to give 4-(8-amino-3-((6R,8aS,E)-3-(cyanoimino)octahydroindolizin-6-yl)imidazo[1,5-a]pyrazin-1-yl)-N-(4-(trifluoromethyl)pyridin-2-yl)benzamide (7 mg, 39.75%) as a white solid.

¹H NMR (400 MHz, CHLOROFORM-d) δ=7.21 (d, J=4.8 Hz, 1H), 7.09 (d, J=5.0 Hz, 1H), 5.79 (br. s, 2H), 4.39 (dd, J=3.1, 13.4 Hz, 1H), 3.85-3.72 (m, 1H), 3.23-3.12 (m, 1H), 3.08-2.90 (m, 3H), 2.41 (tdd, J=5.0, 8.0, 18.0 Hz, 1H), 2.21-2.12 (m, 2H), 1.89-1.75 (m, 2H), 1.47 (dd, J=3.6, 11.9 Hz, 1H), LCMS: LC-MS method B, Retention time: 2.262 min.

Example 79

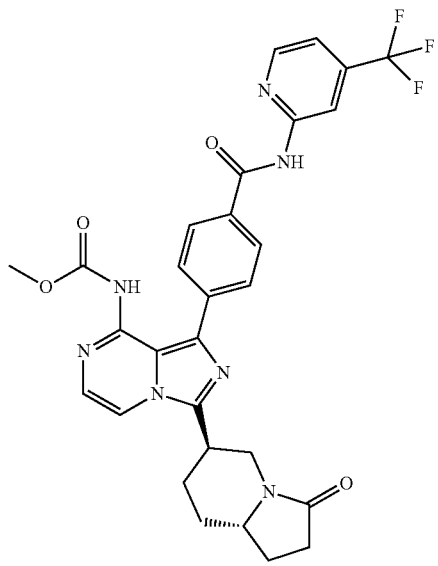 [SMILES: COC(=O)Nc1nccn2c([C@@H]3CC[C@H]4CCC(=O)N4C3)nc(-c3ccc(C(=O)Nc4cc(C(F)(F)F)ccn4)cc3)c12]

methyl (3-((6R,8aS)-3-oxooctahydroindolizin-6-yl)-1-(4-((4-(trifluoromethyl)pyridin-2-yl)carbamoyl)phenyl)imidazo[1,5-a]pyrazin-8-yl)carbamate To a solution of 4-(8-amino-3-((6R,8aS)-3-oxooctahydroindolizin-6-yl)imidazo[1,5-a]pyrazin-1-yl)-N-(4-(trifluoromethyl)pyridin-2-yl)benzamide (40 mg, 0.075 mmol) in DCM (2 mL) was added triethylamine (15.1 mg, 0.15 mmol) and methyl carbonochloridate (100 mg, 1.05 mmol) at 0° C. under N2 atmosphere. The resulting mixture was stirred at 10° C. for 12 hrs. LCMS showed that the reaction was un-complete, methyl carbonochloridate (300 mg, 3.17 mmol) was added slowly to the mixture at 0° C., after addition, the mixture was stirred at 10° C. for 12 hrs. The reaction mixture was evaporated to get the crude product, which was separated by prep-HPLC to afford methyl (3-((6R,8aS)-3-oxooctahydroindolizin-6-yl)-1-(4-((4-(trifluoromethyl)pyridin-2-yl)carbamoyl)phenyl)imidazo[1,5-a]pyrazin-8-yl)carbamate. $^1$H NMR (400 MHz, DMSO-d6) δ=11.36 (s, 1H), 10.06 (br. s, 1H), 8.68 (d, J=5.0 Hz, 1H), 8.54 (s, 1H), 8.18 (d, J=8.0 Hz, 2H), 8.06 (d, J=8.3 Hz, 2H), 7.54 (d, J=4.8 Hz, 1H), 7.13-6.94 (m, 1H), 5.97 (d, J=6.3 Hz, 1H), 4.11 (d, J=12.3 Hz, 1H), 3.66 (s, 3H), 3.51-3.48 (m, 1H), 2.91 (t, J=12.0 Hz, 1H), 2.70-2.59 (m, 1H), 2.24 (t, J=7.7 Hz, 2H), 2.19-2.10 (m, 1H), 2.02 (d, J=13.6 Hz, 1H), 1.91 (d, J=12.8 Hz, 1H), 1.85-1.72 (m, 1H), 1.60-1.49 (m, 1H), 1.25 (q, J=11.2 Hz, 1H). LCMS: LC-MS method B, Retention time: 3.014 min, (M+H)+ m/z: 594.4.

Example 80

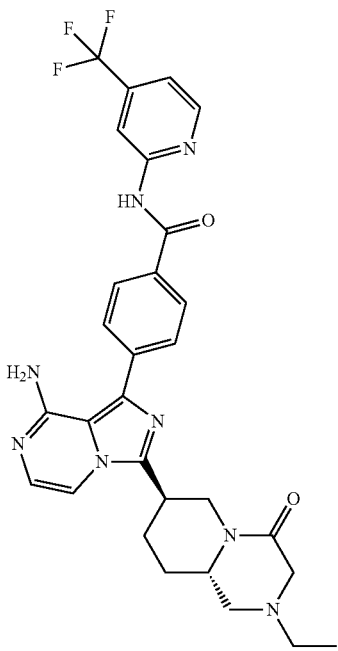 [SMILES: CCN1CC(=O)N2C[C@H](c3nc(-c4ccc(C(=O)Nc5cc(C(F)(F)F)ccn5)cc4)c4c(N)nccn34)CC[C@H]2C1]

4-(8-amino-3-((7R,9aS)-2-ethyl-4-oxooctahydro-1H-pyrido[1,2-a]pyrazin-7-yl)imidazo[1,5-a]pyrazin-1-yl)-N-(4-(trifluoromethyl)pyridin-2-yl)benzamide To a solution of 4-(8-amino-3-((7R,9aS)-4-oxooctahydro-1H-pyrido[1,2-a]pyrazin-7-yl)imidazo[1,5-a]pyrazin-1-yl)-N-(4-(trifluoromethyl)pyridin-2-yl)benzamide (30 mg, 0.055 mmol) in methanol (2 mL) was added acetaldehyde (12 mg, 0.11 mmol), and NaCNBH3 (34.2 mg, 0.55 mmol), and then added HOAc (0.1 mL) under N2. The mixture was stirred for 3 hrs at 25° C. LCMS showed that the reaction was complete, then the mixture was poured into H2O (10 mL), basified with aq. NaHCO3 to pH=8, and the mixture was extracted with DCM (10 mL*3). The organic layer was evaporated to get the crude product, which was then separated by prep-HPLC to get 4-(8-amino-3-((7R,9aS)-2-ethyl-4-oxooctahydro-1H-pyrido[1,2-a]pyrazin-7-yl)imidazo[1,5-a]pyrazin-1-yl)-N-(4-(trifluoromethyl)pyridin-2-yl)benzamide. $^1$H NMR (400 MHz, METHANOL-d4) δ=8.64-8.59 (m, 2H), 8.19 (d, J=8.5 Hz, 2H), 7.91-7.85 (m, 3H), 7.44 (d, J=4.8 Hz, 1H), 7.07 (d, J=5.8 Hz, 1H), 4.10-3.95 (m, 2H), 3.95-3.83 (m, 2H), 3.50-3.39 (m, 1H), 3.38-3.32 (m, 3H), 3.30 (br. s, 1H), 3.12 (t, J=12.5 Hz, 1H), 2.30 (d, J=13.6 Hz, 1H), 2.16-1.98 (m, 2H), 1.73-1.59 (m, 1H), 1.41 (t, J=7.3 Hz, 3H). LCMS: LC-MS method B, Retention time: 1.950 min (M+H)+ m/z: 579.4.

Example 81

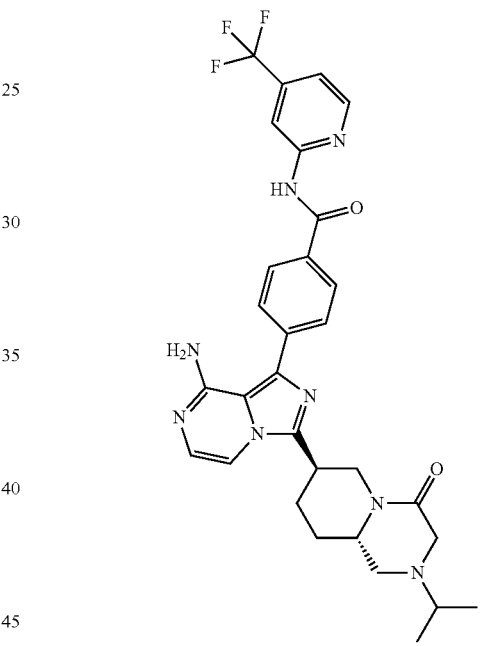

4-(8-amino-3-((7R,9aS)-2-isopropyl-4-oxooctahydro-1H-pyrido[1,2-a]pyrazin-7-yl)imidazo[1,5-a]pyrazin-1-yl)-N-(4-(trifluoromethyl)pyridin-2-yl)benzamide The compound was prepared to the procedure for preparation of 4-(8-amino-3-((7R,9aS)-2-ethyl-4-oxooctahydro-1H-pyrido[1,2-a]pyrazin-7-yl)imidazo[1,5-a]pyrazin-1-yl)-N-(4-(trifluoromethyl)pyridin-2-yl)benzamide.

$^1$H NMR (400 MHz, METHANOL-d4) δ=8.66-8.59 (m, 2H), 8.19 (d, J=8.5 Hz, 2H), 7.93-7.82 (m, 3H), 7.45 (d, J=4.5 Hz, 1H), 7.07 (d, J=6.0 Hz, 1H), 4.09-3.93 (m, 2H), 3.92-3.81 (m, 2H), 3.70 (td, J=6.7, 13.3 Hz, 1H), 3.49-3.37 (m, 1H), 3.36-3.32 (m, 1H), 3.29-3.23 (m, 1H), 3.12 (t, J=12.5 Hz, 1H), 2.31 (d, J=13.1 Hz, 1H), 2.17-1.98 (m, 2H), 1.65 (d, J=12.3 Hz, 1H), 1.43 (dd, J=2.5, 6.5 Hz, 6H). LCMS: LC-MS method B, Retention time: 1.950 min (M+H)+ m/z: 593.5.

Example 82

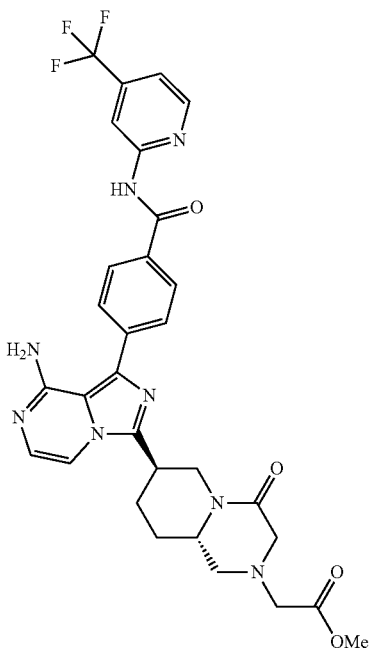 [SMILES: COC(=O)CN1CC(=O)N2C[C@H](c3nc(-c4ccc(C(=O)Nc5cc(C(F)(F)F)ccn5)cc4)c4c(N)nccn34)CC[C@H]2C1]

2-((7R,9aS)-7-(8-amino-1-(4-((4-(trifluoromethyl)
pyridin-2-yl)carbamoyl)phenyl)imidazol[1,5-a]
pyrazin-3-yl)-4-oxohexahydro-1H-pyrido[1,2-a]
pyrazin-2(6H)-yl)acetic acid To a solution of 4-(8-amino-3-((7R,9aS)-4-oxooctahydro-1H-pyrido[1,2-a]pyrazin-7-yl)imidazo[1,5-a]pyrazin-1-yl)-N-(4-(trifluoromethyl)pyridin-2-yl)benzamide (50 mg, 0.09 mmol) in DMF (5 mL) was added NaHCO3 (15.3 mg, 0.18 mmol), and methyl bromoacetate (14 mg, 0.09 mmol) under N2 at 0° C., and the mixture was stirred for 8 hrs. LCMS showed that the reaction was complete, then H2O (10 mL) was added, and the mixture was extracted with ethyl acetate (5 mL*3). The organic layer was evaporated to get the crude product, which was separated by prep-HPLC to get methyl 2-((7R,9aS)-7-(8-amino-1-(4-((4-(trifluoromethyl)pyridin-2-yl)carbamoyl)phenyl)imidazo[1,5-a]pyrazin-3-yl)-4-oxo-hexahydro-1H-pyrido[1,2-a]pyrazin-2(6H)-yl)acetate (39 mg, yield: 69%). $^1$H NMR (400 MHz, METHANOL-d4) δ=8.68-8.60 (m, 2H), 8.21 (d, J=8.3 Hz, 2H), 7.94-7.86 (m, 3H), 7.47 (d, J=4.8 Hz, 1H), 7.07 (d, J=5.8 Hz, 1H), 4.89 (br. s, 1H), 3.79 (s, 3H), 3.76-3.68 (m, 1H), 3.66 (s, 2H), 3.63-3.50 (m, 2H), 3.45-3.35 (m, 2H), 3.08 (t, J=12.4 Hz, 1H), 2.90 (dd, J=7.9, 12.2 Hz, 1H), 2.28 (d, J=13.1 Hz, 1H), 2.15-2.06 (m, 1H), 2.00 (d, J=13.3 Hz, 1H), 1.84-1.70 (m, 1H). LCMS: LC-MS method B, Retention time: 2.160 min, (M+H)+m/z: 623.4.

Examples 83 and 84

Example 84

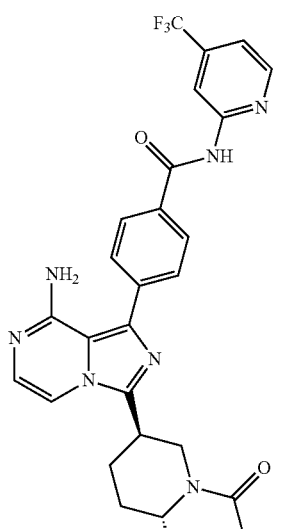

Example 85

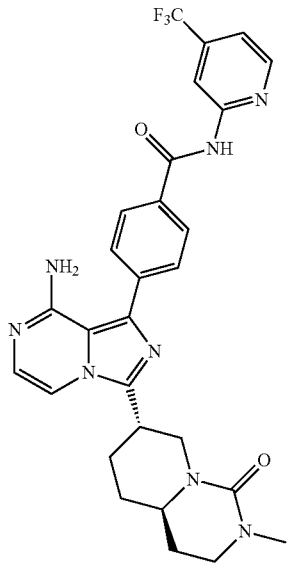

4-(8-amino-3-((4aS,7R)-2-methyl-1-oxooctahydro-
1H-pyrido[1,2-c]pyrimidin-7-yl)imidazol[1,5-a]
pyrazin-1-yl)-N-(4-(trifluoromethyl)pyridin-2-yl)
benzamide and 4-(8-amino-3-((4aR,7S)-2-methyl-1-
oxooctahydro-1H-pyrido[1,2-c]pyrimidin-7-yl)
imidazol[1,5-a]pyrazin-1-yl)-N-(4-(trifluoromethyl)
pyridin-2-yl)benzamide To a solution of trans-7-(8-amino-1-bromoimidazo[1,5-a]pyrazin-3-yl)-2-methyloctahydro-1H-pyrido[1,2-c]pyrimidin-1-one (55 mg, 0.14 mmol) in dioxane/water (2 mL/0.5 mL) was added 4-(4,4,5,5-tetramethyl-1,3,2-dioxaborolan-2-yl)-N-(4-(trifluoromethyl)pyridin-2-yl)benzamide (114 mg, 0.29 mmol), Na2CO3 (46 mg, 0.44 mmol) and Pd(PPh3)2Cl2 (10 mg). The mixture was stirred at 110° C. for 2 h. After cooling the reaction mixture was filtered and the filtrate was purified by pre-HPLC directly to give the trans-mixed product, which was separated by SFC to afford the title compounds.

SFC condition: "Column: Chiralpak AS-H 150*4.6 mm I.D., 5 um Mobile phase: methanol (0.05% DEA) in CO2 from 5% to 40% Flow rate: 3 mL/min Wavelength: 220 nm".

For 4-(8-amino-3-((4aS,7R)-2-methyl-1-oxooctahydro-1H-pyrido[1,2-c]pyrimidin-7-yl)imidazo[1,5-a]pyrazin-1-yl)-N-(4-(trifluoromethyl)pyridin-2-yl)benzamide:

$^1$H NMR (CD$_3$OD, 400 MHz) δ 1.56-1.70 (m, 1 H), 1.84-2.11 (m, 3 H), 2.17-2.29 (m, 2 H), 2.89-3.03 (m, 4 H), 3.31-3.37 (m, 3 H), 3.42-3.50 (m, 1 H), 4.58-4.68 (m, 1 H), 7.04 (d, J=8.0 Hz, 1 H), 7.44 (d, J=4.0 Hz, 1 H), 7.87 (d, J=8.0 Hz, 2 H), 7.91 (d, J=4.0 Hz, 1 H), 8.19 (d, J=8.0 Hz, 2 H), 8.59-8.65 (m, 2 H).

For 4-(8-amino-3-((4aR,7S)-2-methyl-1-oxooctahydro-1H-pyrido[1,2-c]pyrimidin-7-yl)imidazo[1,5-a]pyrazin-1-yl)-N-(4-(trifluoromethyl)pyridin-2-yl)benzamide $^1$H NMR (CD$_3$OD, 400 MHz) δ 1.56-1.70 (m, 1 H), 1.84-2.11 (m, 3 H), 2.17-2.29 (m, 2 H), 2.89-3.03 (m, 4 H), 3.31-3.37 (m, 3 H), 3.42-3.50 (m, 1 H), 4.58-4.68 (m, 1 H), 7.04 (d, J=8.0 Hz, 1 H), 7.44 (d, J=4.0 Hz, 1 H), 7.87 (d, J=8.0 Hz, 2 H), 7.91 (d, J=4.0 Hz, 1 H), 8.19 (d, J=8.0 Hz, 2 H), 8.59-8.65 (m, 2 H).

Example 85

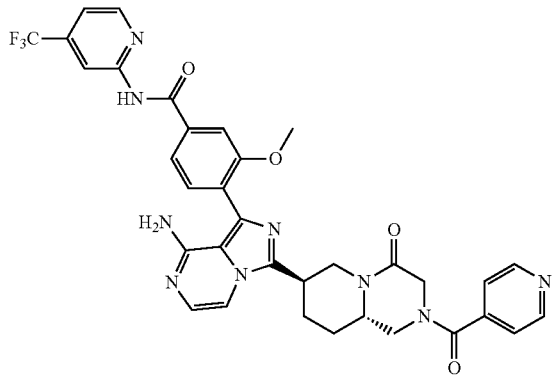 [SMILES: COc1cc(C(=O)Nc2cc(C(F)(F)F)ccn2)ccc1-c1nc([C@@H]2CC[C@H]3CN(C(=O)c4ccncc4)CC(=O)N3C2)n2ccnc(N)c12]

4-(8-amino-3-((7R,9aS)-2-isonicotinoyl-4-oxoocta-hydro-1H-pyrido[1,2-a]pyrazin-7-yl)imidazo[1,5-a]pyrazin-1-yl)-3-methoxy-N-(4-(trifluoromethyl)pyridin-2-yl)benzamide Step 1: 4-(8-amino-3-((7R,9aS)-4-oxooctahydro-1H-pyrido[1,2-a]pyrazin-7-yl)imidazo[1,5-a]pyrazin-1-yl)-3-methoxy-N-(4-(trifluoromethyl)pyridin-2-yl)benzamide To a solution of (7R,9aS)-7-(8-amino-1-bromoimidazo[1,5-a]pyrazin-3-yl)hexahydro-1H-pyrido[1,2-a]pyrazin-4(6H)-one (90 mg, 0.246 mmol), 3-methoxy-4-(4,4,5,5-tetramethyl-1,3,2-dioxaborolan-2-yl)-N-(4-(trifluoromethyl)pyridin-2-yl)benzamide (135 mg, 0.32 mmol) and K2CO3 (102 mg, 0.74 mmol) in dioxane/H2O (4 mL, 3:1) was added Pd(dppf)C12 (14.6 mg, 0.02 mmol) under N2 atmosphere, and stirred at 90-100° C. for 60 min. TLC showed that the reaction was complete, then the mixture was cooled to room temperature, and diluted with H2O (5 mL), and the mixture was extracted with ethyl acetate (10 mL*3). The organic layer was washed with brine (10 mL), dried over Na2SO4, and concentrated in vacuo to give crude product, which was purified by flash chromatography (DCM: MeOH=100~80%) to give 4-(8-amino-3-((7R,9aS)-4-oxooctahydro-1H-pyrido[1,2-a]pyrazin-7-yl)imidazo[1,5-a]pyrazin-1-yl)-3-methoxy-N-(4-(trifluoromethyl)pyridin-2-yl)benzamide (110 mg, yield: 76.9%). $^1$H NMR (400 MHz, CHLOROFORM-d) δ=8.89 (s, 1H), 8.73 (s, 1H), 8.50 (d, J=5.0 Hz, 1H), 7.68 (s, 1H), 7.63-7.56 (m, 2H), 7.33 (d, J=5.0 Hz, 2H), 7.06 (d, J=5.3 Hz, 1H), 5.04 (d, J=11.3 Hz, 1H), 3.92 (s, 3H), 3.62-3.41 (m, 4H), 3.33 (dd, J=4.9, 13.2 Hz, 1H), 3.16-3.04 (m, 1H), 2.90-2.77 (m, 2H), 2.30-2.17 (m, 2H), 1.64 (dt, J=8.0, 12.4 Hz, 1H).

Step 2: 4-(8-amino-3-((7R,9aS)-2-isonicotinoyl-4-oxooctahydro-1H-pyrido[1,2-a]pyrazin-7-yl)imidazo[1,5-a]pyrazin-1-yl)-3-methoxy-N-(4-(trifluoromethyl)pyridin-2-yl)benzamide A mixture of compound 4-(8-amino-3-((7R,9aS)-4-oxooctahydro-1H-pyrido[1,2-a]pyrazin-7-yl)imidazo[1,5-a]pyrazin-1-yl)-3-methoxy-N-(4-(trifluoromethyl)pyridin-2-yl)benzamide (50 mg, 0.086 mmol), triethylamine (26 mg, 0.258 mmol) and isonicotinoyl chloride hydrochloride (15.3 mg, 0.086 mmol) in DCM (2 mL) was stirred at 0° C. for 2 hrs, and then stirred at 20 ~30° C. for 5 hrs. LCMS showed that the reaction was not complete, then isonicotinoyl chloride hydrochloride (15.3 mg, 0.086 mmol) was added, and the mixture was stirred for 12 hrs. The mixture was quenched with 1 mL of methanol, and evaporated to get the crude product, which was then separated by prep-HPLC to get the compound 4-(8-amino-3-((7R,9aS)-2-isonicotinoyl-4-oxooctahydro-1H-pyrido[1,2-a]pyrazin-7-yl)imidazo[1,5-a]pyrazin-1-yl)-3-methoxy-N-(4-(trifluoromethyl)pyridin-2-yl)benzamide. $^1$H NMR (400 MHz, METHANOL-d4) δ=8.86 (d, J=6.0 Hz, 2H), 8.68-8.63 (m, 2H), 7.90-7.78 (m, 5H), 7.70 (d, J=7.8 Hz, 1H), 7.50-7.46 (m, 1H), 7.04 (d, J=6.0 Hz, 1H), 4.63-4.54 (m, 1H), 4.42-4.29 (m, 1H), 4.22-4.09 (m, 1H), 3.99 (s, 3H), 3.94-3.64 (m, 2H), 3.57-3.38 (m, 2H), 3.09 (t, J=12.5 Hz, 1H), 2.26 (d, J=17.3 Hz, 1H), 2.18-1.97 (m, 2H), 1.89-1.59 (m, 2H). LCMS: LC-MS method B, Retention time: 2.347 min, (M+H)+ m/z: 686.4.

Example 86

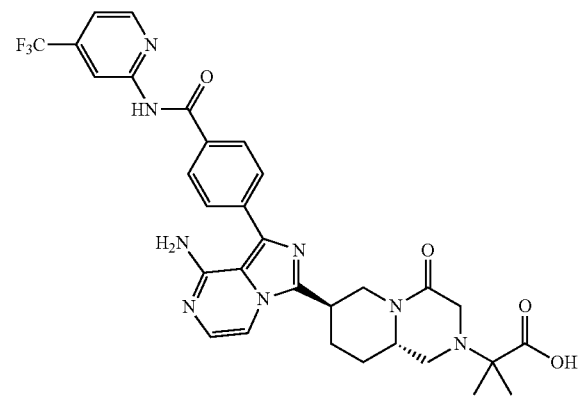 [SMILES: CC(C)(C(=O)O)N1CC(=O)N2C[C@H](c3nc(-c4ccc(C(=O)Nc5cc(C(F)(F)F)ccn5)cc4)c4c(N)nccn34)CC[C@H]2C1]

2-((7R,9aS)-7-(8-amino-1-(4-((4-(trifluoromethyl) pyridin-2-yl)carbamoyl)phenyl)imidazo[1,5-a] pyrazin-3-yl)-4-oxohexahydro-1H-pyrido[1,2-a] pyrazin-2(6H)-yl)-2-methylpropanoic acid

Step 1: tert-butyl 6-(bromomethyl)nicotinate

To a solution of tert-butyl 6-methylnicotinate (10 g, 51.7 mmol) in CCl4 (100 mL) was added NBS (11.9 g, 67.2 mmol) and AIBN (1 g), and the mixture was stirred at 80~90° C. for 12 hrs under N2 atmosphere. The mixture was cooled to room temperature, filtered, and the filtrate was evaporated to get the crude product, which was purified by flash chromatography (PE/EA=100~80%) to get tert-butyl 6-(bromomethyl)nicotinate (3.6 g, yield: 25.7%) as a brown solid. $^1$H NMR (400 MHz, CHLOROFORM-d) δ=9.11 (d, J=1.5 Hz, 1H), 8.25 (dd, J=2.1, 8.2 Hz, 1H), 7.50 (d, J=8.8 Hz, 1H), 4.58 (s, 2H), 1.60 (s, 9H).

(a) tert-butyl 6-((((benzyloxy)carbonyl)(2-methoxy-2-oxoethyl)amino)methyl)nicotinate To a solution of compound Cbz-glycinemethyl ester (1.98 g, 8.8 mmol) in anhydrous THF (50 mL) was added NaH (352 mg, 8.8 mmol) at 0° C., and stirred for 15 min. Then tert-butyl 6-(bromomethyl)nicotinate (2 g, 7.4 mmol) was added in portions. After addition, the mixture was stirred at 0° C. for 5 hrs. Then the reaction was quenched with aq. NH4Cl (20 mL), and extracted with EA (20 mL*3). The organic layer was washed with brine (10 mL), dried over Na2SO4, evaporated to ger the crude product, which was then purified by flash chromatography (PE/EA=100~50%) to get tert-butyl 6-((((benzyloxy)carbonyl)(2-methoxy-2-oxoethyl)amino)methyl)nicotinate (2.5 g, yield: 81.4%) as an oil. $^1$H NMR (400 MHz, CHLOROFORM-d) δ=9.06 (dd, J=1.6, 7.2 Hz, 1H), 8.24-8.10 (m, 1H), 7.44 (d, J=8.3 Hz, 1H), 7.27-7.21 (m, 1H), 5.21-5.13 (m, 2H), 4.72 (d, J=13.8 Hz, 2H), 4.17 (s, 1H), 4.09 (s, 1H), 3.78-3.70 (m, 2H), 3.63 (s, 1H), 1.60 (d, J=2.8 Hz, 9H).

(b) Trans-(7S,9aR)-2-benzyl7-tert-butyl 4-oxohexahydro-1H-pyrido[1,2-a]pyrazine-2,7(6H)-dicarboxylate To a solution of tert-butyl 6-((((benzyloxy)carbonyl)(2-methoxy-2-oxoethyl)amino)methyl)nicotinate (1 g, 2.4 mmol) in HAc (10 mL) was added NaCNBH3 (455 mg, 7.2 mmol) at 10° C. under N2. After addition, the mixture was stirred at 30 ~40° C. for 12 hrs. LCMS showed that the reaction was complete, then the mixture was evaporated, dissolved with H2O (10 mL), basified with aq. NaHCO3 to pH=8, extracted with ethyl acetate (20 mL*3). The organic layer was washed with brine (10 mL), dried over Na2SO4, evaporated to get the crude product, which was then dissolved in 20 mL of methanol, and stirred at 70 ~80° C. for 12 hrs under N2. LCMS showed that the reaction was complete. Then the mixture was evaporated to get the crude product, which was purified by flash chromatography (PE/THF=100 ~50%, 220 nm and 254 nm) to get trans-(7S,9aR)-2-benzyl 7-tert-butyl 4-oxohexahydro-1H-pyrido[1,2-a] pyrazine-2,7(6H)-dicarboxylate (370 mg, yield: 79%). 1H NMR (400 MHz, METHANOL-d4) δ=7.42-7.30 (m, 5H), 5.16 (d, J=6.3 Hz, 2H), 4.98 (d, J=13.6 Hz, 1H), 4.13 (br. s, 2H), 3.84 (d, J=10.3 Hz, 1H), 3.48 (br. s, 2H), 2.81 (dd, J=3.8, 13.6 Hz, 1H), 2.66 (br. s, 1H), 2.19 (d, J=11.8 Hz, 1H), 1.84-1.56 (m, 3H), 1.42 (s, 9H).

(c) Trans-(7S,9aR)-tert-butyl 4-oxooctahydro-1H-pyrido[1,2-a]pyrazine-7-carboxylate To a solution of trans-(7S,9aR)-2-benzyl 7-tert-butyl 4-oxohexahydro-1H-pyrido[1,2-a]pyrazine-2,7(6H)-dicarboxylate (370 mg, 0.95 mmol) in methanol (10 mL) was added Pd/C (90 mg) under H2, and stirred at 10° C. for 1.5 hrs. TLC showed that the reaction was complete, and then the mixture was filtered, and the filtrate was evaporated to get the product trans-(7S,9aR)-tert-butyl 4-oxooctahydro-1H-pyrido[1,2-a]pyrazine-7-carboxylate (200 mg, yield: 82.6%). $^1$H NMR (400 MHz, CHLOROFORM-d) δ=4.98-4.88 (m, 1H), 3.59-3.41 (m, 2H), 3.32-3.20 (m, 2H), 2.78-2.68 (m, 1H), 2.55-2.44 (m, 1H), 2.39-2.25 (m, 1H), 2.17-2.08 (m, 1H), 1.81-1.73 (m, 1H), 1.62-1.53 (m, 1H), 1.44 (s, 9H), 1.40-1.34 (m, 1H).

(d) Trans-(7S,9aR)-tert-butyl 2-(1-methoxy-2-methyl-1-oxopropan-2-yl)-4-oxooctahydro-1H-pyrido[1,2-a]pyrazine-7-carboxylate To compound methyl 2-bromo-2-methylpropanoate (3 mL) was added K2CO3 (920 mg) to pH=8, and compound trans-(7S,9aR)-tert-butyl 4-oxooctahydro-1H-pyrido[1,2-a] pyrazine-7-carboxylate (340 mg, 1.34 mmol) was added to the mixture, followed by DMF (1 mL), and then the mixture was stirred at 60° C. for 12 hrs under N2. The reaction mixture was cooled to room temperature, and diluted with H2O (20 mL), and extracted with EA (10 mL*3). The organic layer was washed with brine (10 mL), dried over Na2SO4, evaporated to get the crude product, which was then purified by flash chromatography (PE/THF=100~80%) to get trans-(7S,9aR)-tert-butyl 2-(1-methoxy-2-methyl-1-oxopropan-2-yl)-4-oxooctahydro-1H-pyrido[1,2-a]pyrazine-7-carboxylate (310 mg, yield: 66%) as a white solid. 1H NMR (400 MHz, CHLOROFORM-d) δ=4.92-4.80 (m, 1H), 3.74-3.67 (m, 3H), 3.52-3.42 (m, 1H), 3.32-3.21 (m, 2H), 2.96 (ddd, J=1.8, 4.5, 12.0 Hz, 1H), 2.52 (t, J=12.4 Hz, 1H), 2.40 (dd, J=7.5, 12.0 Hz, 1H), 2.30 (tt, J=3.8, 12.0 Hz, 1H), 2.16-2.07 (m, 1H), 1.76-1.67 (m, 1H), 1.64 (d, J=4.0 Hz, 1H), 1.59-1.54 (m, 1H), 1.43 (s, 9H), 1.33 (d, J=8.0 Hz, 6H).

(e) Trans-(7S,9aR)-2-(1-methoxy-2-methyl-1-oxopropan-2-yl)-4-oxooctahydro-1H-pyrido[1,2-a]pyrazine-7-carboxylic acid To a solution of compound trans-(7S,9aR)-tert-butyl 2-(1-methoxy-2-methyl-1-oxopropan-2-yl)-4-oxooctahydro-1H-pyrido[1,2-a]pyrazine-7-carboxylate (300 mg, 0.85 mmol) in anhydrous DCM (6 mL) was added TFA (0.5 mL), and stirred at 15° C. for 3 hrs. LCMS showed that the reaction was complete, then the mixture was evaporated to get the crude product trans-(7S,9aR)-2-(1-methoxy-2-methyl-1-oxopropan-2-yl)-4-oxooctahydro-1H-pyrido[1,2-a]pyrazine-7-carboxylic acid (300 mg, yield: 118%) as an oil, which was used in the next step directly. LCMS Method: 0-60AB_2 min_ELSD, Retention time: 0.875 min, (M+H)+ m/z: 298.9.

(f) Trans-methyl 2-((7S,9aR)-7-(((3-chloropyrazin-2-yl)methyl)carbamoyl)-4-oxohexahydro-1H-pyrido[1,2-a]pyrazin-2(6H)-yl)-2-methylpropanoate A mixture of trans-(7S,9aR)-2-(1-methoxy-2-methyl-1-oxopropan-2-yl)-4-oxooctahydro-1H-pyrido[1,2-a]pyrazine-7-carboxylic acid (300 mg, 1 mmol), (3-chloropyrazin- 2-yl)-methanamine (217 mg, 1.2 mmol), HATU (570 mg, 1.5 mmol) and TEA (0.56 mL, 4 mmol) in anhydrous DMF (5 mL) was stirred at 15° C. for 12 hrs. TLC showed that the reaction was complete, then the mixture was diluted with H2O (50 mL), and the mixture was extracted with DCM (10 mL*3). The organic layer was washed with brine (10 mL), dried over Na2SO4, evaporated to get the crude product, which was purified by flash chromatography (PE/THF=100~30%) to give trans-methyl 2-((7S,9aR)-7-(((3-chloropyrazin-2-yl)methyl)carbamoyl)-4-oxohexahydro-1H-pyrido[1,2-a]pyrazin-2(6H)-yl)-2-methylpropanoate (290 mg, yield: 68.4%) as an oil.

$^1$H NMR (400 MHz, CHLOROFORM-d) δ=8.45 (d, J=2.5 Hz, 1H), 8.33 (d, J=2.5 Hz, 1H), 6.96-6.90 (m, 1H), 4.90-4.83 (m, 1H), 4.69 (d, J=4.5 Hz, 2H), 3.76-3.73 (m, 2H), 3.72 (s, 3H), 3.50-3.43 (m, 1H), 2.98 (dd, J=2.9, 12.2 Hz, 1H), 2.70 (t, J=12.5 Hz, 1H), 2.51-2.33 (m, 2H), 2.11-2.03 (m, 1H), 1.84 (d, J=3.3 Hz, 1H), 1.79-1.71 (m, 1H), 1.56-1.47 (m, 1H), 1.34 (d, J=7.3 Hz, 6H).

(g) Trans-methyl 2-((7S,9aR)-7-(8-chloroimidazo[1,5-a]pyrazin-3-yl)-4-oxohexahydro-1H-pyrido[1,2-a]pyrazin-2(6H)-yl)-2-methylpropanoate To a solution of trans-methyl 2-((7S,9aR)-7-(((3-chloropyrazin-2-yl)methyl)carbamoyl)-4-oxohexahydro-1H-pyrido[1,2-a]pyrazin-2(6H)-yl)-2-methylpropanoate (290 mg, 0.68 mmol) in MeCN (15 mL) was added PCl5 (285 mg, 1.37 mmol) in portions, after addition, the mixture was allowed to warm to 15° C., and stirred for 12 hrs. The reaction was poured into an ice-aq.NaHCO3 (50 mL), and extracted with DCM (10 mL*3). The organic layer was washed with brine (10 mL), dried over Na2SO4, evaporated to get the crude product, which was purified by flash chromatography (PE/THF=100~10%) to give trans-methyl 2-((7S,9aR)-7-(8-chloroimidazo[1,5-a]pyrazin-3-yl)-4-oxohexahydro-1H-pyrido[1,2-a]pyrazin-2(6H)-yl)-2-methylpropanoate (140 mg, yield: 50.7%) as an oil. $^1$H NMR (400 MHz, CHLOROFORM-d) δ=7.81 (s, 1H), 7.72 (d, J=5.0 Hz, 1H), 7.37 (d, J=5.0 Hz, 1H), 4.92 (dd, J=3.1, 13.2 Hz, 1H), 3.74 (s, 3H), 3.51-3.36 (m, 3H), 3.10-3.00 (m, 2H), 2.83-2.74 (m, 1H), 2.59 (dd, J=6.8, 12.0 Hz, 1H), 2.26-2.18 (m, 2H), 1.91-1.83 (m, 1H), 1.78-1.66 (m, 1H), 1.38 (d, J=6.3 Hz, 6H).

(h) Trans-methyl 2-((7S,9aR)-7-(1-bromo-8-chloroimidazo[1,5-a]pyrazin-3-yl)-4-oxohexahydro-1H-pyrido[1,2-a]pyrazin-2(6H)-yl)-2-methylpropanoate To a solution of trans-methyl 2-((7S,9aR)-7-(8-chloroimidazo[1,5-a]pyrazin-3-yl)-4-oxohexahydro-1H-pyrido[1,2-a]pyrazin-2(6H)-yl)-2-methylpropanoate (140 mg, 0.35 mmol) in anhydrous DMF (3 mL) was added NBS (74 mg, 0.41 mmol) under N2 atmosphere, and stirred at 15° C. for 60 min. LCMS showed that the reaction was complete, then the mixture was poured into an ice-water (50 mL), and 0.5 mL of aq. NaHCO3 was added, and the mixture was extracted with EA (10 mL*3), the organic layers were then washed with H2O (5 mL*8), brine (10 mL), dried over Na2SO4, and evaporated to get the product trans-methyl 2-((7S,9aR)-7-(1-bromo-8-chloroimidazo[1,5-a]pyrazin-3-yl)-4-oxohexahydro-1H-pyrido[1,2-a]pyrazin-2(6H)-yl)-2-methylpropanoate (140 mg, yield: 82.6%), which was used for next step directly without purification. $^1$H NMR (400 MHz, CHLOROFORM-d) δ=7.72 (d, J=5.0 Hz, 1H), 7.36 (br. s, 1H), 4.87 (d, J=13.3 Hz, 1H), 3.73 (s, 3H), 3.50-3.39 (m, 3H), 3.02 (dd, J=3.9, 12.7 Hz, 2H), 2.79-2.70 (m, 1H), 2.58 (dd, J=6.0, 12.0 Hz, 1H), 2.30-2.14 (m, 2H), 1.89-1.82 (m, 1H), 1.78-1.68 (m, 1H), 1.37 (d, J=6.0 Hz, 6H).

(i) methyl 2-((7R,9aS)-7-(8-amino-1-bromoimidazo[1,5-a]pyrazin-3-yl)-4-oxohexahydro-1H-pyrido[1,2-a]pyrazin-2(6H)-yl)-2-methylpropanoate A mixture of trans-methyl 2-((7S,9aR)-7-(1-bromo-8-chloroimidazo[1,5-a]pyrazin-3-yl)-4-oxohexahydro-1H-pyrido[1,2-a]pyrazin-2(6H)-yl)-2-methylpropanoate (100 mg, 0.206 mmol) in i-PrOH/NH4OH (4 mL, 1:1) was heated at 90~100° C. for 12 hrs in a 30 mL of sealed tube. LCMS showed that the reaction was complete, then the mixture was evaporated to get the crude product, which was then purified by flash chromatography (MeOH:DCM=100~90%) to get the product, which was then separated by SFC (Instrument: Thar 80, Column: AD 250 mm*30 mm, 20 um, Mobile phase: A: Supercritical CO2, B: EtOH (0.05% NH3H2O), A:B=45:55 at 80 ml/min, Column Temp: 38° C., Nozzle Pressure: 100 Bar Nozzle Temp: 60° C., Evaporator Temp: 20° C., Trimmer Temp: 25° C., Wavelength: 220 nm) to give methyl 2-((7R,9aS)-7-(8-amino-1-bromoimidazo[1,5-a]pyrazin-3-yl)-4-oxohexahydro-1H-pyrido[1,2-a]pyrazin-2(6H)-yl)-2-methylpropanoate (30 mg, yield: 62.6%). $^1$H NMR (400 MHz, METHANOL-d4) δ=7.54 (d, J=5.0 Hz, 1H), 6.96 (d, J=3.8 Hz, 1H), 4.75 (d, J=14.3 Hz, 1H), 3.72 (s, 3H), 3.51-3.43 (m, 1H), 3.40-3.34 (m, 2H), 3.23-3.13 (m, 1H), 3.08 (dd, J=4.3, 12.3 Hz, 1H), 2.85 (t, J=12.4 Hz, 1H), 2.61 (dd, J=6.5, 12.3 Hz, 1H), 2.14 (d, J=12.5 Hz, 1H), 2.00-1.81 (m, 2H), 1.79-1.66 (m, 1H), 1.35 (d, J=2.5 Hz, 6H).

(j) methyl 2-((7R,9aS)-7-(8-amino-1-(4-((4-(trifluoromethyl)pyridin-2-yl)carbamoyl)phenyl)imidazo[1,5-a]pyrazin-3-yl)-4-oxohexahydro-1H-pyrido[1,2-a]pyrazin-2(6H)-yl)-2-methylpropanoate To a solution of methyl 2-((7R,9aS)-7-(8-amino-1-bromoimidazo[1,5-a]pyrazin-3-yl)-4-oxohexahydro-1H-pyrido[1,2-a]pyrazin-2(6H)-yl)-2-methylpropanoate (30 mg, 0.064 mmol), 4-(4,4,5,5-tetramethyl-1,3,2-dioxaborolan-2-yl)-N-(4-(trifluoromethyl)pyridin-2-yl)benzamide (32.8 mg, 0.084 mmol) and K2CO3 (26.5 mg, 0.192 mmol) in dioxane/H2O (2 mL, 3:1) was added Pd(dppf)Cl2 (5 mg, 0.006 mmol) under N2 atmosphere, and stirred at 90~100° C. for 60 min. TLC showed that the reaction was complete, then the mixture was cooled to room temperature, and diluted with H2O (5 mL), and the mixture was extracted with EA (10 mL*3). The organic layer which was washed with brine (10 mL), dried over Na2SO4, evaporated to get the crude product, which was then purified by flash chromatography (MeOH: DCM=100~90%) to give methyl 2-((7R,9aS)-7-(8-amino-1-(4-((4-(trifluoromethyl)pyridin-2-yl)carbamoyl)phenyl)imidazo[1,5-a]pyrazin-3-yl)-4-oxohexahydro-1H-pyrido[1,2-a]pyrazin-2(6H)-yl)-2-methylpropanoate (40 mg, yield: 96%). LC-MS method C, Retention time: 0.715 min, (M+H)+ m/z: 651.0.

(k) 2-((7R,9aS)-7-(8-amino-1-(4-((4-(trifluoromethyl)pyridin-2-yl)carbamoyl)phenyl)imidazo[1,5-a]pyrazin-3-yl)-4-oxohexahydro-1H-pyrido[1,2-a]pyrazin-2(6H)-yl)-2-methylpropanoic acid To a solution of methyl 2-((7R,9aS)-7-(8-amino-1-(4-((4-(trifluoromethyl)pyridin-2-yl)carbamoyl)phenyl)imidazo[1,5-a]pyrazin-3-yl)-4-oxohexahydro-1H-pyrido[1,2-a]pyrazin-2(6H)-yl)-2-methylpropanoate (30 mg, 0.046 mmol) in anhydrous DCM (3 mL) was added BBr3 (0.92 mL, 0.92 mmol) at −78° C. under N2. After addition, the mixture was allowed to warm to room temperature (25° C.), and stirred for 20 hrs. The mixture was quenched with 2 mL of methanol at −50° C., and evaporated to get the crude product, which was separated by prep-HPLC to get 2-((7R,9aS)-7-(8-amino-1-(4-((4-(trifluoromethyl)pyridin-2-yl)carbamoyl)phenyl)imidazo[1,5-a]pyrazin-3-yl)-4-oxohexahydro-1H-pyrido[1,2-a]pyrazin-2(6H)-yl)-2-methylpropanoic acid. $^1$H NMR (400 MHz, ACETONITRILE-d3) δ=9.50 (br. s, 1H), 8.65-8.52 (m, 2H), 8.19-8.06 (m, 2H), 7.76 (br. s, 2H), 7.52 (br. s, 1H), 7.42 (d, J=4.8 Hz, 1H), 6.90 (d, J=5.3 Hz, 1H), 4.79 (d, J=1.0 Hz, 1H), 3.80-3.45 (m, 3H), 3.32 (d, J=8.0 Hz, 1H), 3.15 (br. s, 1H), 2.90 (d, J=16.8 Hz, 3H), 2.12 (dd, J=2.4, 4.9 Hz, 1H), 1.91-1.82 (m, 1H), 1.40 (d, J=7.0 Hz, 7H). LCMS: LC-MS method B, Retention time: 2.017 min, (M+H)+ m/z: 637.4.

Example 87

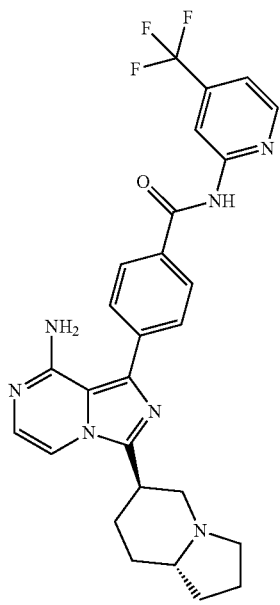 [SMILES: Nc1nccn2c([C@@H]3CC[C@H]4CCCN4C3)nc(-c3ccc(C(=O)Nc4cc(C(F)(F)F)ccn4)cc3)c12]

4-(8-amino-3-((6R,8aS)-octahydroindolizin-6-yl)imidazo[1,5-a]pyrazin-1-yl)-N-(4-(trifluoromethyl)pyridin-2-yl)benzamide Step 1: 1-bromo-3-((6R,8aS)-octahydroindolizin-6-yl)imidazo[1,5-a]pyrazin-8-amine To a suspension of LiAlH4 (23.8 mg, 0.63 mmol) in THF (2.0 mL) in a 20 mL Schlenk tube was added dropwise a solution of (6R,8aS)-6-(8-amino-1-bromoimidazo[1,5-a]pyrazin-3-yl)hexahydroindolizin-3(2H)-one (200.0 mg, 0.57 mmol) in THF (2.0 mL) at 0° C. After stirring at 40° C. for 4 h, the reaction mixture was quenched with H2O (20 mL) and extracted with EtOAc (30 mL×3). The combined organic layer was dried over MgSO4. Evaporation of the solvent followed by purification with Pre-TLC (SiO2, EtOAc/Et3N=95/5) gave 1-bromo-3-((6R,8aS)-octahydroindolizin-6-yl)imidazo[1,5-a]pyrazin-8-amine (100 mg, 52.1% yield) as a pale yellow solid. $^1$H NMR (400 MHz, DMSO-d6) δ=7.67-7.58 (m, 1H), 6.97-6.87 (m, 1H), 6.59 (br. S, 2H), 3.13 (d, J=10.6 Hz, 1H), 2.98-2.90 (m, 1H), 2.19 (t, J=11.0 Hz, 1H), 2.03 (q, J=8.5 Hz, 1H), 1.98-1.90 (m, 1H), 1.83 (br. S, 3H), 1.71-1.58 (m, 2H), 1.57-1.46 (m, 1H), 1.38-1.24 (m, 2H), 1.15 (t, J=7.0 Hz, 1H).

Step 2: 4-(8-amino-3-((6R,8aS)-octahydroindolizin-6-yl)imidazo[1,5-a]pyrazin-1-yl)-N-(4-(trifluoromethyl)pyridin-2-yl)benzamide To a solution of 1-bromo-3-((6R,8aS)-octahydroindolizin-6-yl)imidazo[1,5-a]pyrazin-8-amine (50 mg, 0.15 mmol) and 4-(4,4,5,5-tetramethyl-1,3,2-dioxaborolan-2-yl)-N-(4-(trifluoromethyl)pyridin-2-yl)benzamide (58.3 mg, 0.15 mmol) in 5 mL of dioxane/H2O (4:1) was added K2CO3 (61.7 mg, 0.45 mmol) and Pd(dppf)C12 (catalytic amount, 10 mg) under nitrogen protection. Then the mixture was heated to 90° C. for 2 hour. Then the mixture was poured into water (30 mL) and extracted with EA (50 mL*3). The organic layer was dried with Na2SO4, concentrated in vacuo and purified with pre-HPLC to give 4-(8-amino-3-((6R,8aS)-octahydroindolizin-6-yl)imidazo[1,5-a]pyrazin-1-yl)-N-(4-(trifluoromethyl)pyridin-2-yl)benzamide (30 mg, yield 38.7%) as a white solid. $^1$H NMR (400 MHz, METHANOL-d4) δ=8.67-8.54 (m, 2H), 8.19 (d, J=8.2 Hz, 2H), 7.94-7.82 (m, 3H), 7.45 (d, J=4.7 Hz, 1H), 7.10 (d, J=5.5 Hz, 1H), 3.97 (br. S, 1H), 3.82 (br. S, 1H), 3.72 (br. S, 1H), 3.55 (d, J=11.0 Hz, 1H), 3.19 (br. S, 1H), 2.36 (d, J=10.2 Hz, 3H), 2.18 (d, J=8.6 Hz, 2H), 2.11-1.67 (m, 4H).

Example 88

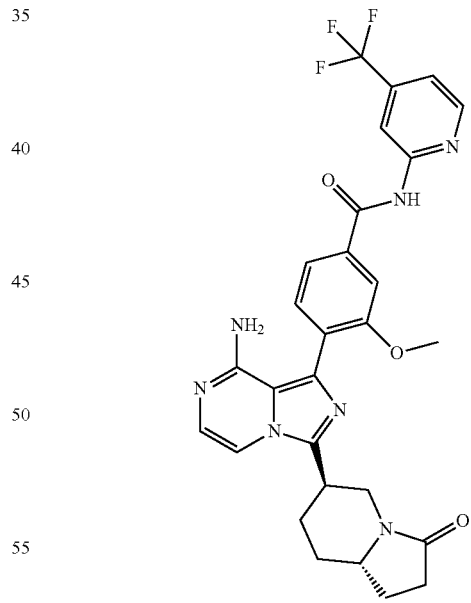

4-(8-amino-3-((6R,8aS)-3-oxooctahydroindolizin-6-yl)imidazo[1,5-a]pyrazin-1-yl)-3-methoxy-N-(4-(trifluoromethyl)pyridin-2-yl)benzamide To a 500 mL flask was added (6R,8aS)-6-(8-amino-1-bromoimidazo[1,5-a]pyrazin-3-yl)hexahydroindolizin-3(2H)-one (10 g, 28.6 mmol), potassium (2-methoxy-4-((4-(trifluoromethyl)pyridin-2-yl)carbamoyl)phenyl)

trifluoroborate (12.06 g, 30.0 mmol), and PdCl2(dppf)-CH₂Cl₂Adduct (1.166 g, 1.428 mmol). The flask was degassed by vacuum and re-filled with N2. Then K2CO3 (2M, 42.8 ml, 86 mmol) and Dioxane (114 ml) were added. The reaction was stirred at 80° C. for a total of 16 hours. After cooling down, the aqueous layer was separated and extracted with EtOAc (50 ml). The organic layers were combined and diluted with EtOAc (150 ml). It was dried over anhydrous Na2SO4, filtered, and concentrated. The product was purified by SiO2 chromatography (240 g, CH₂Cl₂/MeOH 0% to 10%). To afford light color solid product (10.6 g, 65.9%). ¹H NMR (500 MHz, DMSO-D) δ=11.45 (1H, br), 8.70 (1H, d, J=5 Hz), 8.58 (1H, s), 7.83 (1H, s), 7.75 (1H, dd, J=9.0, 1.0 Hz), 7.61 (1H, d, J=5.0 Hz), 7.55 (1H, d, J=5.0 Hz), 7.48 (1H, d, J=8.0 Hz), 7.02 (1H, d, J=5.0 Hz), 5.89 (1H, br), 4.11 (1H, d, J=12, 3.0 Hz), 3.87 (3H, s), 3.53 (1H, m), 3.17 (1H, m), 3.01 (1H, t, J=12.0 Hz), 2.27 (2H, m), 2.17 (1H, m), 2.08 (1H, d, J=12.5 Hz), 1.93 (1H, dd, J=12.5, 3.5 Hz), 1.76 (1H, m), 1.57 (1H, m), 1.40 (1H, m) ppm. LC-MS: C28H₂₆F3N7O3, found [M+1]+: 565.9, LC-MS method B, RET. TIME=1.59 min.

Example 89

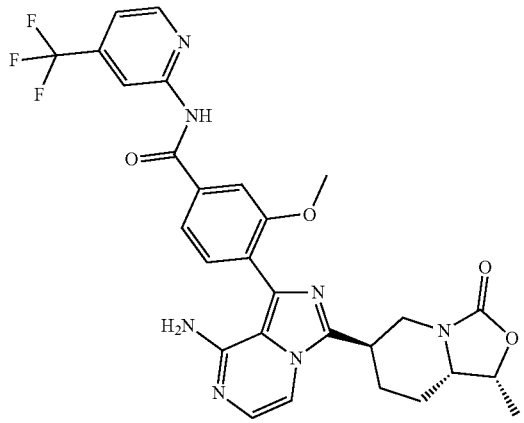 [SMILES: COc1cc(C(=O)Nc2cc(C(F)(F)F)ccn2)ccc1-c1nc([C@@H]2CC[C@H]3[C@@H](C)OC(=O)N3C2)n2ccnc(N)c12]

4-(8-amino-3-((1R,6R,8aS)-1-methyl-3-oxohexahydro-1H-oxazolo[3,4-a]pyridin-6-yl)imidazo[1,5-a]pyrazin-1-yl)-3-methoxy-N-(4-(trifluoromethyl)pyridin-2-yl)benzamide To a solution of (1R,6R,8aS)-6-(8-amino-1-bromoimidazo[1,5-a]pyrazin-3-yl)-1-methyltetrahydro-1H-oxazolo[3,4-a]pyridin-3(5H)-one (50 mg, 0.136 mmol), 3-methoxy-4-(4,4,5,5-tetramethyl-1,3,2-dioxaborolan-2-yl)-N-(4-(trifluoromethyl)pyridin-2-yl)benzamide (75 mg, 0.177 mmol) and K2CO3 (56.6 mg, 0.41 mmol) in dioxane/H2O (2 mL, 3:1) was added Pd(dppf)Cl2 (10.0 mg, 0.013 mmol) under N2 atmosphere, and stirred at 90~100° C. for 60 min. LCMS showed that the reaction was complete, then the mixture was cooled to room temperature, H2O (10 mL) was added and the mixture was extracted with ethyl acetate (10 mL*2). The organic layer was evaporated to get the crude product, which was separated by prep-HPLC to afford 4-(8-amino-3-((1R,6R,8aS)-1-methyl-3-oxohexahydro-1H-oxazolo[3,4-a]pyridin-6-yl)imidazo[1,5-a]pyrazin-1-yl)-3-methoxy-N-(4-(trifluoromethyl)pyridin-2-yl)benzamide. ¹H NMR (400 MHz, METHANOL-d4) δ=8.63 (d, J=7.8 Hz, 2H), 7.87 (d, J=6.0 Hz, 1H), 7.83-7.75 (m, 2H), 7.68 (d, J=7.8 Hz, 1H), 7.45 (d, J=5.0 Hz, 1H), 7.01 (d, J=6.0 Hz, 1H), 4.86-4.77 (m, 1H), 4.10-4.03 (m, 1H), 3.96 (s, 3H), 3.87 (ddd, J=3.5, 7.8, 11.7 Hz, 1H), 3.45-3.35 (m, 2H), 2.28 (d, J=13.6 Hz, 1H), 2.05-1.91 (m, 1H), 1.87-1.79 (m, 1H), 1.78-1.66 (m, 1H), 1.40 (d, J=6.5 Hz, 3H).

LCMS: LC-MS method B, Retention time: 2.516 min, (M+H)+ m/z: 582.4

Example 90

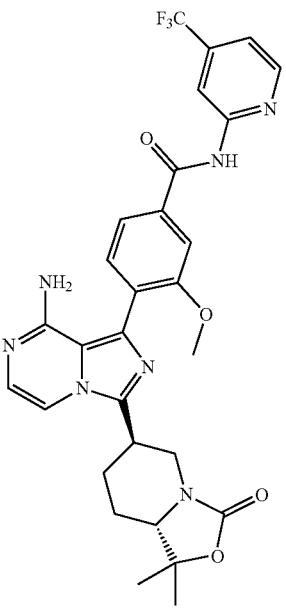 [SMILES: COc1cc(C(=O)Nc2cc(C(F)(F)F)ccn2)ccc1-c1nc([C@@H]2CC[C@@H]3N(C2)C(=O)OC3(C)C)n2ccnc(N)c12]

4-(8-amino-3-((6R,8aS)-1,1-dimethyl-3-oxohexahydro-1H-oxazolo[3,4-a]pyridin-6-yl)imidazo[1,5-a]pyrazin-1-yl)-N-(4-(trifluoromethyl)pyridin-2-yl)benzamide To a solution of (6R,8aS)-6-(8-amino-1-bromoimidazo[1,5-a]pyrazin-3-yl)-1,1-dimethyltetrahydro-1H-oxazolo[3,4-a]pyridin-3(5H)-one (60 mg, 0.131 mmol) and 3-methoxy-4-(4,4,5,5-tetramethyl-1,3,2-dioxaborolan-2-yl)-N-(4-(trifluoromethyl)pyridin-2-yl)benzamide (80 mg, 0.189 mmol) in dioxane (4.5 mL) and water (1.5 mL) was added K2CO3 (65 mg, 0.473 mmol). After degassed with nitrogen for several times, Pd(dppf)Cl2 (cat. amount) was added and the reaction was degassed with nitrogen for several times again, the mixture was heated to 80° C. and stirred under nitrogen for one hour. It was cooled to 20° C., diluted generously with ethyl acetate and filtered through a celite to remove palladium. The cake was washed with ethyl acetate, the combined filtrate was concentrated under reduced pressure and purified by preparative HPLC to give 4-(8-amino-3-((6R,8aS)-1,1-dimethyl-3-oxohexahydro-1H-oxazolo[3,4-a]pyridin-6-yl)imidazo[1,5-a]pyrazin-1-yl)-3-methoxy-N-(4-(trifluoromethyl)pyridin-2-yl)benzamide (56.23 mg, yield 72%) as a white solid. ¹H NMR (400 MHz, METHANOL-d4)=8.63 (d, J=8.0 Hz, 2H), 7.88 (d, J=6.0 Hz, 1H), 7.82-7.76 (m, 2H), 7.68 (d, J=8.0 Hz, 1H), 7.45 (d, J=4.3 Hz, 1H), 7.01 (d, J=5.8 Hz, 1H), 4.07 (d, J=9.8 Hz, 1H), 3.97 (s, 3H), 3.54 (dd, J=3.3, 11.8 Hz, 1H), 3.45-3.34 (m, 2H), 2.28 (d, J=12.8 Hz, 1H), 1.99-1.86 (m, 2H), 1.70 (dd, J=3.1, 12.4 Hz, 1H), 1.50 (s, 3H), 1.42 (s, 3H); (ESI): M/Z (M+1): 596.4.

Example 91

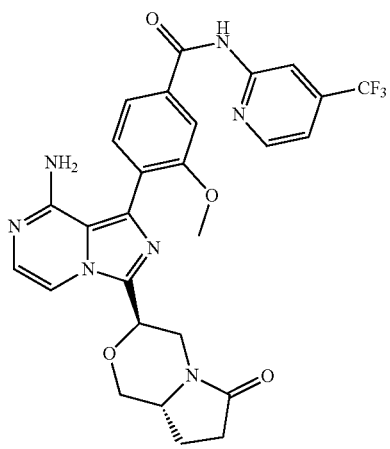 [SMILES: COc1cc(C(=O)Nc2cc(C(F)(F)F)ccn2)ccc1-c1nc([C@H]2CN3C(=O)CC[C@@H]3CO2)n2ccnc(N)c12]

4-(8-amino-3-((3R,8aR)-6-oxohexahydro-1H-pyrrolo[2,1-c][1,4]oxazin-3-yl)imidazo[1,5-a]pyrazin-1-yl)-3-methoxy-N-(4-(trifluoromethyl)pyridin-2-yl)benzamide To a solution of (3R,8aR)-3-(8-amino-1-bromoimidazo[1,5-a]pyrazin-3-yl)tetrahydro-1H-pyrrolo[2,1-c][1,4]oxazin-6(7H)-one (50 mg, 0.142 mmol) and 3-methoxy-4-(4,4,5,5-tetramethyl-1,3,2-dioxaborolan-2-yl)-N-(4-(trifluoromethyl)pyridin-2-yl)benzamide (66 mg, 0.156 mmol) in dioxane (4.5 mL) and water (1.5 mL) was added K2CO3 (59 mg, 0.426 mmol). After degassed with nitrogen for several times, PdCl2(dppf) (cat. amount) was added and the reaction was degassed with nitrogen for several times again, the mixture was heated to 80° C. and stirred under nitrogen for one hour. It was cooled to 20° C., diluted generously with ethyl acetate and filtered through a celite to remove palladium. The cake was washed with ethyl acetate (10 mL), the combined filtrate was concentrated under reduced pressure and purified by preparative HPLC to give 4-(8-amino-3-((3R,8aR)-6-oxohexahydro-1H-pyrrolo[2,1-c][1,4]oxazin-3-yl)imidazo[1,5-a]pyrazin-1-yl)-3-methoxy-N-(4-(trifluoromethyl)pyridin-2-yl)benzamide (13.96 mg, yield 20.8%) as a white solid. $^1$H NMR (400 MHz, METHANOL-d4) δ=8.68-8.62 (m, 2H), 7.95 (d, J=5.8 Hz, 1H), 7.85-7.76 (m, 2H), 7.71 (d, J=7.8 Hz, 1H), 7.47 (d, J=5.3 Hz, 1H), 7.03 (d, J=6.0 Hz, 1H), 4.96 (dd, J=3.3, 11.0 Hz, 1H), 4.42 (dd, J=3.1, 13.4 Hz, 1H), 4.24 (dd, J=4.0, 11.3 Hz, 1H), 3.99 (s, 3H), 3.91 (dtd, J=4.1, 7.3, 10.9 Hz, 1H), 3.58 (q, J=11.3 Hz, 2H), 2.61-2.43 (m, 2H), 2.33-2.22 (m, 1H), 1.78-1.66 (m, 1H); (ESI): M/Z (M+H)+ m/z: 568.4.

The Examples set forth in Table 2 below were prepared using the same chemistry described for Example 88 and corresponding intermediates through Suzuki coupling reactions.

TABLE 2

| Example number | Structure | IUPAC Name | Exact Mass [M + H]+ | Retention time (min) (LC-MS method) |
|---|---|---|---|---|
| 92 | 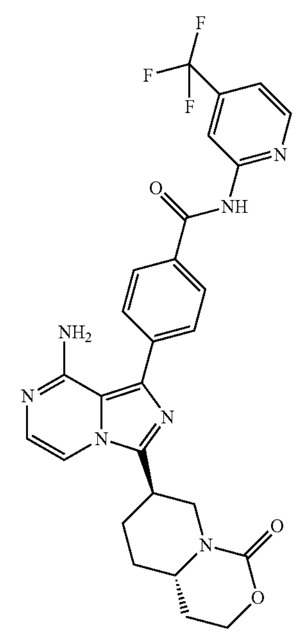 [SMILES: Nc1nccn2c([C@@H]3CC[C@H]4CCOC(=O)N4C3)nc(-c3ccc(C(=O)Nc4cc(C(F)(F)F)ccn4)cc3)c12] | 4-{8-amino-3-[(4aS,7R)-1-oxohexahydro-3H-pyrido[1,2-c][1,3]oxazin-7-yl]imidazo[1,5-a]pyrazin-1-yl}-N-[4-(trifluoromethyl)pyridin-2-yl]benzamide | 552.2 | 2.17 (B) |

TABLE 2-continued
| Example number | Structure | IUPAC Name | Exact Mass [M + H]+ | Retention time (min) (LC-MS method) |
|---|---|---|---|---|
| 93 | 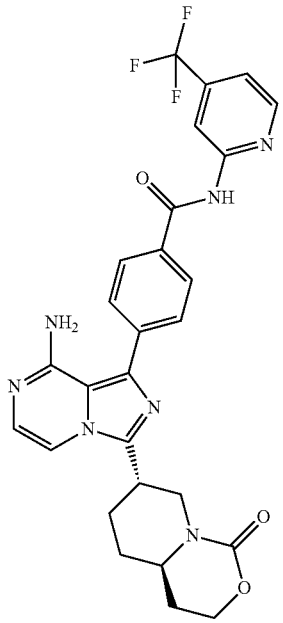 [SMILES: Nc1nccn2c([C@H]3CC[C@@H]4CCOC(=O)N4C3)nc(-c3ccc(C(=O)Nc4cc(C(F)(F)F)ccn4)cc3)c12] | 4-{8-amino-3-[(4aR,7S)-1-oxohexahydro-3H-pyrido[1,2-c][1,3]oxazin-7-yl]imidazo[1,5-a]-pyrazin-1-yl}-N-[4-(trifluoromethyl)pyridin-2-yl]benzamide | 552.2 | 2.17 (B) |
| 94 | 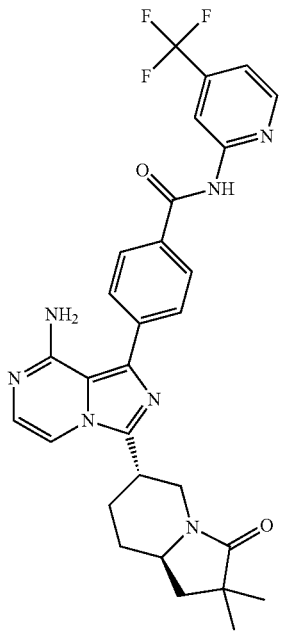 [SMILES: CC1(C)C[C@H]2CC[C@H](c3nc(-c4ccc(C(=O)Nc5cc(C(F)(F)F)ccn5)cc4)c4c(N)nccn34)CN2C1=O] | 4-{8-amino-3-[(6S,8aR)-2,2-dimethyl-3-oxooctahydroindolizin-6-yl]imidazo[1,5-a]pyrazin-1-yl}-N-[4-(trifluoromethyl)pyridin-2-yl]benzamide | 564.2 | 2.22 (B) |

TABLE 2-continued

| Example number | Structure | IUPAC Name | Exact Mass [M + H]+ | Retention time (min) (LC-MS method) |
|---|---|---|---|---|
| 95 | 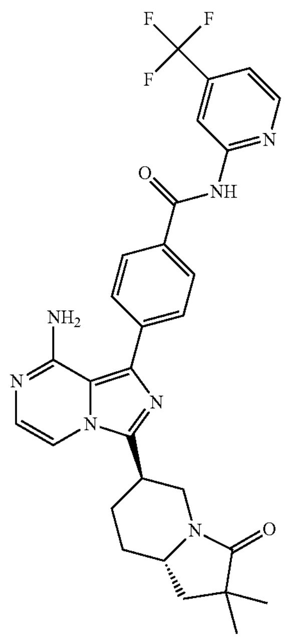 [SMILES: CC1(C)C[C@@H]2CC[C@@H](c3nc(-c4ccc(C(=O)Nc5cc(C(F)(F)F)ccn5)cc4)c4c(N)nccn34)CN2C1=O] | 4-{8-amino-3-[(6R,8aS)-2,2-dimethyl-3-oxooctahydroindolizin-6-yl]imidazo[1,5-a]pyrazin-1-yl}-N-[4-(trifluoromethyl)pyridin-2-yl]benzamide | 564.2 | 2.22 (B) |
| 96 | 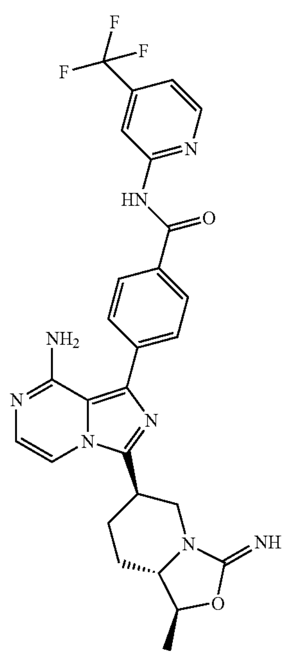 [SMILES: C[C@@H]1OC(=N)N2C[C@H](c3nc(-c4ccc(C(=O)Nc5cc(C(F)(F)F)ccn5)cc4)c4c(N)nccn34)CC[C@@H]12] | 4-{8-amino-3-[(1S,6R,8aS)-3-imino-1-methylhexahydro[1,3]-oxazolo[3,4-a]pyridin-6-yl]imidazo[1,5-a]pyrazin-1-yl}-N-[4-(trifluoromethyl)pyridin-2-yl]benzamide | 551.4 | 2.31 (B) |

TABLE 2-continued

| Example number | Structure | IUPAC Name | Exact Mass [M + H]+ | Retention time (min) (LC-MS method) |
|---|---|---|---|---|
| 97 | 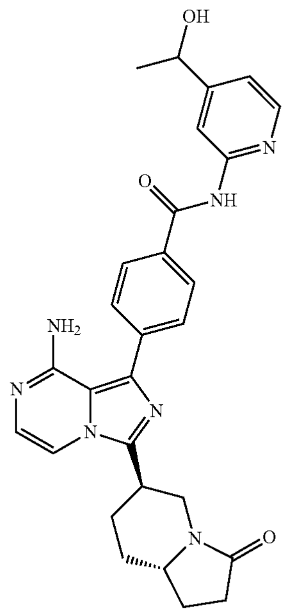 [SMILES: CC(O)c1ccnc(NC(=O)c2ccc(-c3nc([C@@H]4CC[C@H]5CCC(=O)N5C4)n4ccnc(N)c34)cc2)c1] | 4-{8-amino-3-[(6R,8aS)-3-oxooctahydroindolizin-6-yl]imidazo[1,5-a]pyrazin-1-yl}-N-[4-(1-hydroxyethyl)pyridin-2-yl]benzamide | 512.4 | 2.22 (B) |
| 98 | 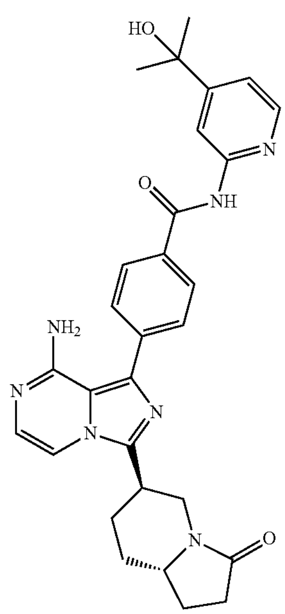 [SMILES: CC(C)(O)c1ccnc(NC(=O)c2ccc(-c3nc([C@@H]4CC[C@H]5CCC(=O)N5C4)n4ccnc(N)c34)cc2)c1] | 4-{8-amino-3-[(6R,8aS)-3-oxooctahydroindolizin-6-yl]imidazo[1,5-a]-pyrazin-1-yl}-N-[4-(1-hydroxy-1-methylethyl)pyridin-2-yl]benzamide | 526.4 | 2.27 (B) |

TABLE 2-continued

| Example number | Structure | IUPAC Name | Exact Mass [M + H]+ | Retention time (min) (LC-MS method) |
|---|---|---|---|---|
| 99 | 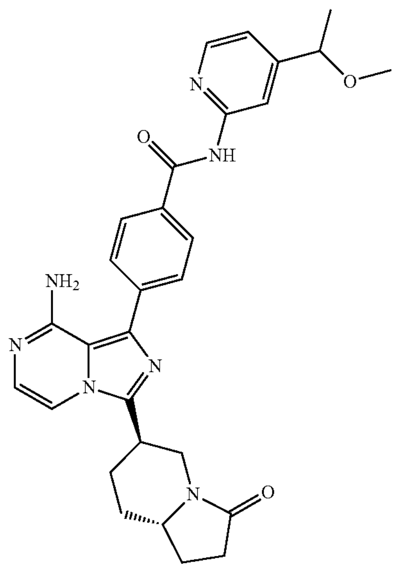 [SMILES: COC(C)c1ccnc(NC(=O)c2ccc(-c3nc([C@@H]4CC[C@H]5CCC(=O)N5C4)n4ccnc(N)c34)cc2)c1] | 4-{8-amino-3-[(6R,8aS)-3-oxooctahydroindolizin-6-yl]imidazo[1,5-a]-pyrazin-1-yl}-N-[4-(1-methoxyethyl)pyridin-2-yl]benzamide | 526.4 | 2.17 (B) |
| 100 | 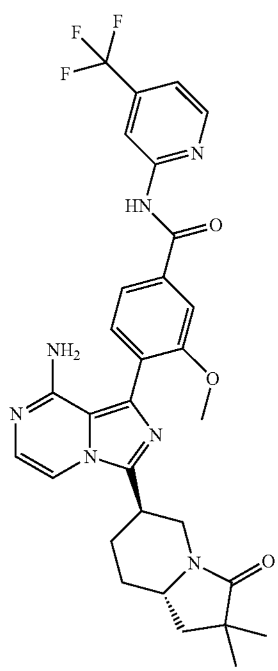 [SMILES: COc1cc(C(=O)Nc2cc(C(F)(F)F)ccn2)ccc1-c1nc([C@@H]2CC[C@H]3CC(C)(C)C(=O)N3C2)n2ccnc(N)c12] | 4-{8-amino-3-[(6R,8aS)-2,2-dimethyl-3-oxooctahydroindolizin-6-yl]imidazo[1,5-a]pyrazin-1-yl}-3-methoxy-N-[4-(trifluoromethyl)pyridin-2-yl]benzamide | 594.2 | 2.18 (B) |

TABLE 2-continued

| Example number | Structure | IUPAC Name | Exact Mass [M + H]+ | Retention time (min) (LC-MS method) |
|---|---|---|---|---|
| 101 | 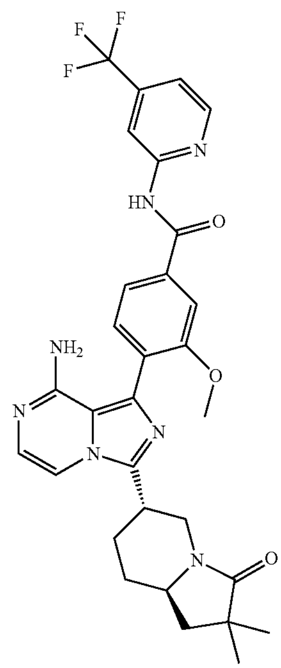 [SMILES: COc1cc(C(=O)Nc2cc(C(F)(F)F)ccn2)ccc1-c1nc([C@H]2CC[C@@H]3CC(C)(C)C(=O)N3C2)n2ccnc(N)c12] | 4-{8-amino-3-[(6S,8aR)-2,2-dimethyl-3-oxooctahydroindolizin-6-yl]imidazo[1,5-a]pyrazin-1-yl}-3-methoxy-N-[4-(trifluoromethyl)pyridin-2-yl]benzamide | 594.2 | 2.28 (B) |
| 102 | 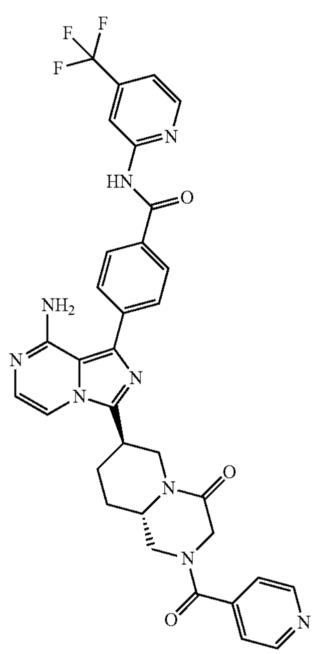 [SMILES: Nc1nccn2c([C@@H]3CC[C@H]4CN(C(=O)c5ccncc5)CC(=O)N4C3)nc(-c3ccc(C(=O)Nc4cc(C(F)(F)F)ccn4)cc3)c12] | 4-{8-amino-3-[(7R,9aS)-4-oxo-2-(pyridin-4-ylcarbonyl)octahydro-2H-pyrido[1,2-a]pyrazin-7-yl]imidazo[1,5-a]pyrazin-1-yl}-N-[4-(trifluoromethyl)pyridin-2-yl]benzamide | 656.4 | 2.32 (B) |

TABLE 2-continued
| Example number | Structure | IUPAC Name | Exact Mass [M + H]+ | Retention time (min) (LC-MS method) |
|---|---|---|---|---|
| 103 | 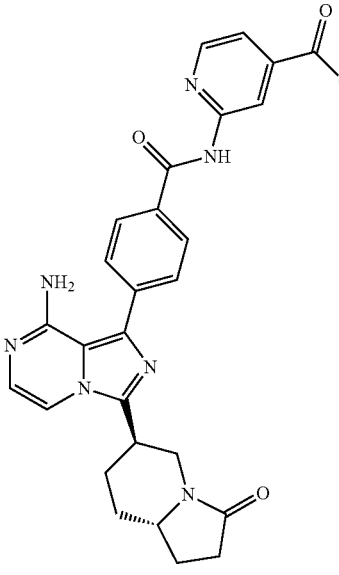 | methyl 2-{[(4-{8-amino-3-[(6R,8aS)-3-oxooctahydroindolizin-6-yl]imidazo[1,5-a]pyrazin-1-yl}phenyl)carbonyl]amino}-pyridine-4-carboxylate | 526.4 | 2.31 (B) |
| 104 | 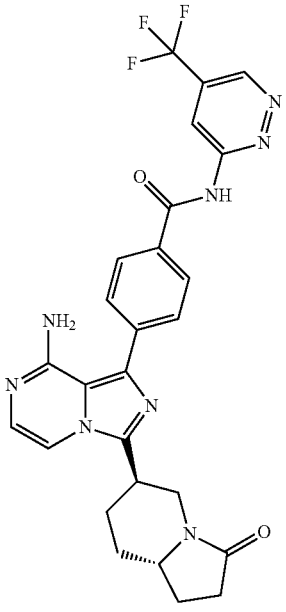 [SMILES: Nc1nccn2c([C@@H]3CC[C@H]4CCC(=O)N4C3)nc(-c3ccc(C(=O)Nc4cc(C(F)(F)F)cnn4)cc3)c12] | 4-{8-amino-3-[(6R,8aS)-3-oxooctahydroindolizin-6-yl]imidazo[1,5-a]-pyrazin-1-yl}-N-[5-(trifluoromethyl)pyridazin-3-yl]benzamide | 537.3 | 2.34 (B) |

TABLE 2-continued

| Example number | Structure | IUPAC Name | Exact Mass [M + H]+ | Retention time (min) (LC-MS method) |
|---|---|---|---|---|
| 105 | 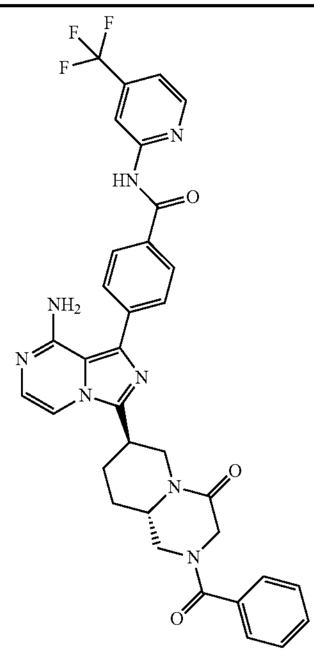 | 4-{8-amino-3-[(7R,9aS)-4-oxo-2-(phenylcarbonyl)octahydro-2H-pyrido[1,2-a]pyrazin-7-yl]imidazo[1,5-a]pyrazin-1-yl}-N-[4-(trifluoromethyl)pyridin-2-yl]benzamide | 655.4 | 2.31 (B) |
| 106 | 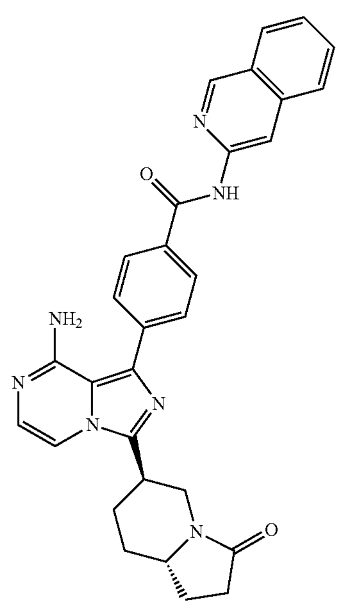 [SMILES: Nc1nccn2c([C@@H]3CC[C@H]4CCC(=O)N4C3)nc(-c3ccc(C(=O)Nc4cc5ccccc5cn4)cc3)c12] | 4-{8-amino-3-[(6R,8aS)-3-oxooctahydroindolizin-6-yl]imidazo[1,5-a]pyrazin-1-yl}-N-isoquinolin-3-ylbenzamide | 518.4 | 2.22 (B) |

TABLE 2-continued

| Example number | Structure | IUPAC Name | Exact Mass [M + H]+ | Retention time (min) (LC-MS method) |
|---|---|---|---|---|
| 107 | 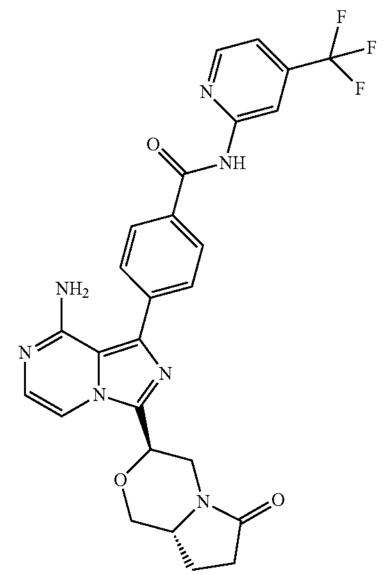 [SMILES: Nc1nccn2c([C@H]3CN4C(=O)CC[C@@H]4CO3)nc(-c3ccc(C(=O)Nc4cc(C(F)(F)F)ccn4)cc3)c12] | 4-{8-amino-3-[(3R,8aR)-6-oxohexahydro-1H-pyrrolo[2,1-c][1,4]oxazin-3-yl]imidazo[1,5-a]pyrazin-1-yl}-N-[4-(trifluoromethyl)pyridin-2-yl]benzamide | 538.4 | 2.40 (B) |
| 108 | 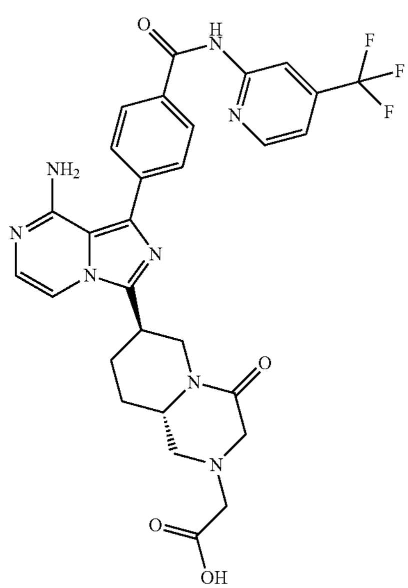 [SMILES: Nc1nccn2c([C@@H]3CC[C@H]4CN(CC(=O)O)CC(=O)N4C3)nc(-c3ccc(C(=O)Nc4cc(C(F)(F)F)ccn4)cc3)c12] | {(7R,9aS)-7-[8-amino-1-(4-{[4-(trifluoromethyl)pyridin-2-yl]carbamoyl}phenyl)-imidazo[1,5-a]pyrazin-3-yl]-4-oxooctahydro-2H-pyrido[1,2-a]pyrazin-2-yl}acetic acid | 609.4 | 2.30 (B) |

TABLE 2-continued
| Example number | Structure | IUPAC Name | Exact Mass [M + H]+ | Retention time (min) (LC-MS method) |
|---|---|---|---|---|
| 109 | 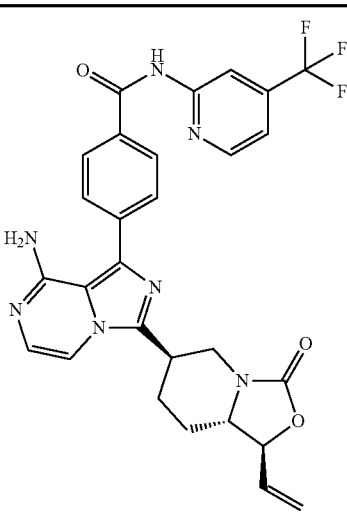 | 4-{8-amino-3-[(1S,6R,8aS)-1-ethenyl-3-oxohexahydro[1,3]oxazolo-[3,4-a]pyridin-6-yl]imidazo[1,5-a]pyrazin-1-yl}-N-[4-(trifluoromethyl)pyridin-2-yl]benzamide | 564.4 | 2.33 (B) |
| 110 | 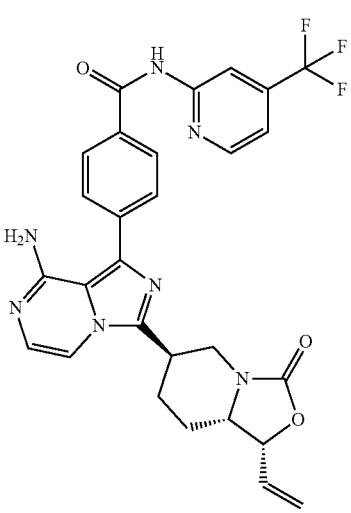 [SMILES: C=C[C@H]1OC(=O)N2C[C@H](c3nc(-c4ccc(C(=O)Nc5cc(C(F)(F)F)ccn5)cc4)c4c(N)nccn34)CC[C@@H]12] | 4-{8-amino-3-[(1R,6R,8aS)-1-ethenyl-3-oxohexahydro[1,3]oxazolo-[3,4-a]pyridin-6-yl]imidazo[1,5-a]pyrazin-1-yl}-N-[4-(trifluoromethyl)pyridin-2-yl]benzamide | 564.4 | 2.36 (B) |

TABLE 2-continued

| Example number | Structure | IUPAC Name | Exact Mass [M + H]+ | Retention time (min) (LC-MS method) |
|---|---|---|---|---|
| 111 | 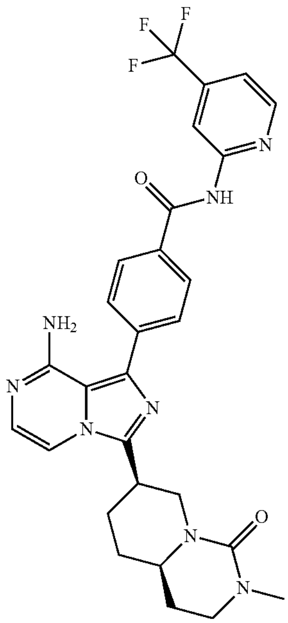 [SMILES: CN1CC[C@H]2CC[C@@H](c3nc(-c4ccc(C(=O)Nc5cc(C(F)(F)F)ccn5)cc4)c4c(N)nccn34)CN2C1=O] | 4-{8-amino-3-[(4aR,7R)-2-methyl-1-oxooctahydro-1H-pyrido[1,2-c]pyrimidin-7-yl]imidazo[1,5-a]pyrazin-1-yl}-N-[4-(trifluoromethyl)pyridin-2-yl]benzamide | 565.2 | 2.27 (B) |
| 112 | 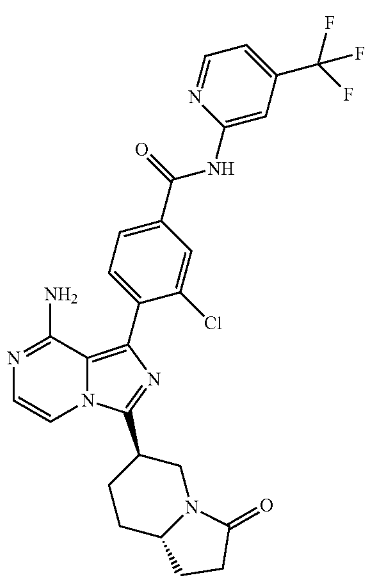 [SMILES: Nc1nccn2c([C@@H]3CC[C@H]4CCC(=O)N4C3)nc(-c3ccc(C(=O)Nc4cc(C(F)(F)F)ccn4)cc3Cl)c12] | 4-{8-amino-3-[(6R,8aS)-3-oxooctahydroindolizin-6-yl]imidazo[1,5-a]-pyrazin-1-yl}-3-chloro-N-[4-(trifluoromethyl)pyridin-2-yl]benzamide | 570.2 | 2.19 (B) |

TABLE 2-continued

| Example number | Structure | IUPAC Name | Exact Mass [M + H]+ | Retention time (min) (LC-MS method) |
|---|---|---|---|---|
| 113 | 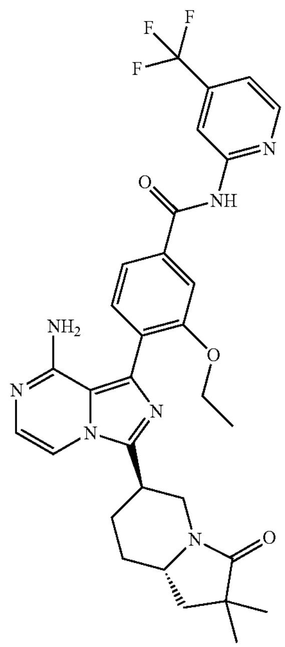 [SMILES: CCOc1cc(C(=O)Nc2cc(C(F)(F)F)ccn2)ccc1-c1nc([C@@H]2CC[C@H]3CC(C)(C)C(=O)N3C2)n2ccnc(N)c12] | 4-{8-amino-3-[(6R,8aS)-2,2-dimethyl-3-oxooctahydroindolizin-6-yl]imidazo[1,5-a]pyrazin-1-yl}-3-ethoxy-N-[4-(trifluoromethyl)pyridin-2-yl]benzamide | 608.3 | 2.26 (B) |
| 114 | 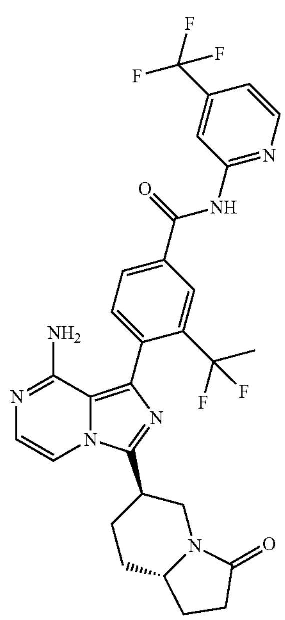 [SMILES: CC(F)(F)c1cc(C(=O)Nc2cc(C(F)(F)F)ccn2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]-pyrazin-1-yl}-3-(1,1-difluoroethyl)-N-[4-(trifluoromethyl)pyridin-2-yl]benzamide | 600.1 | 2.62 (B) |

Example 115

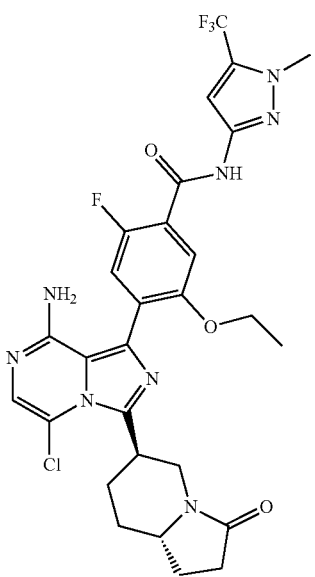 [SMILES: CCOc1cc(C(=O)Nc2cc(C(F)(F)F)n(C)n2)c(F)cc1-c1nc([C@@H]2CC[C@H]3CCC(=O)N3C2)n2c(Cl)cnc(N)c12]

4-(8-amino-5-chloro-3-((6R,8aS)-3-oxooctahydroin-
dolizin-6-yl)imidazo[1,5-a]pyrazin-1-yl)-5-ethoxy-2-
fluoro-N-(1-methyl-5-(trifluoromethyl)-1H-pyrazol-
3-yl)benzamide A 5 ml microwave reaction vial containing (6R,8aS)-6-(8-amino-1-bromo-5-chloroimidazo[1,5-a]pyrazin-3-yl)hexahydroindolizin-3(2H)-one (500 mg, 1.300 mmol), 5-ethoxy-2-fluoro-N-(1-methyl-5-(trifluoromethyl)-1H-pyrazol-3-yl)-4-(4,4,5,5-tetramethyl-1,3,2-dioxaborolan-2-yl)benzamide (713 mg, 1.560 mmol), and Pd(dppf) $CH_2Cl_2$ (53.1 mg, 0.065 mmol) under a $N_2$ atmosphere was treated with Dioxane (10 ml) and potassium phosphate (2M, 1.300 ml, 2.60 mmol). The system was immediately evacuated and backfilled with $N_2$ (×3). The reaction was then exposed to microwave irridiation at 120° C. for 40 min. The mixture was diluted by ethyl acetate, filtered and washed with ethyl acetate. The filtrate was concentrated and the residue was purified by MPLC (40 g silica gel, 0 to 100% ethyl acetate in hexanes, 12 CV and then 0 to 10% methanol in methylenechloride, 18 CV) to afford product (700 mg) which contains small amount of starting material. The product was then repurified again with reverse phase MPLC (130 g C18, 0 to 100% acetonitriel in water) to afford pure product 4-(8-amino-5-chloro-3-((6R,8aS)-3-oxooctahydroindolizin-6-yl)imidazo[1,5-a]pyrazin-1-yl)-5-ethoxy-2-fluoro-N-(1-methyl-5-(trifluoromethyl)-1H-pyrazol-3-yl)benzamide.

LC-MS (ES, m/z) C28H27ClF4N8O3: 634; Found: 635[M+H]$^+$. 1HNMR (500 mHz, CD$_3$OD, δ): 9.49 (1H, d, J=5.8 Hz), 7.36 (1H, d, J=10.4 Hz), 7.17 (1H, s), 7.02 (1H, s), 4.42 (1H, m), 4.13 (2H, m), 3.98 (1H, m), 3.95 (3H, s), 3.67 (1H, m), 3.19 (1H, t, J=12.0 Hz), 2.45 (2H, m), 2.33 (2H, m), 2.08 (1H, m), 2.08 (1H, m), 1.74 (1H, m), 1.48 (1H, m), 1.28 (3H, t, J=7.0 Hz).

The Examples set forth in Table 3 below were prepared using the same chemistry described for Example 115 and corresponding intermediates through Suzuki coupling reaction.

TABLE 3

| Example number | Structure | IUPAC Name | Exact Mass [M + H]+ | Retention time (min) (LC-MS method) |
|---|---|---|---|---|
| 116 | (structure shown) | 4-{8-amino-3-[(6R,8aS)-3-oxooctahydroindolizin-6-yl]imidazo[1,5-a]pyrazin-1-yl}-3-[(~2~H_3_)methyloxy]-N-[4-(trifluoromethyl)pyridin-2-yl]benzamide | 569.3 | 2.46 (A) |

TABLE 3-continued

| Example number | Structure | IUPAC Name | Exact Mass [M + H]+ | Retention time (min) (LC-MS method) |
|---|---|---|---|---|
| 117 | 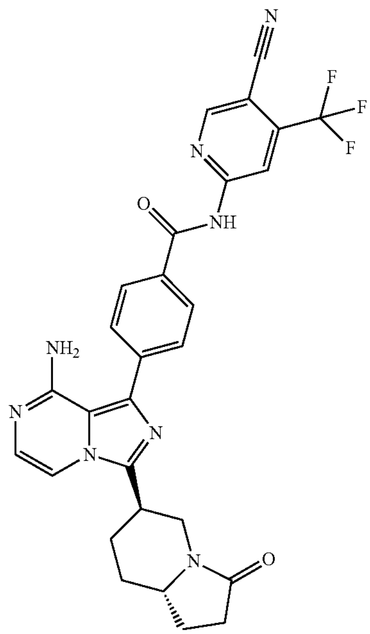 [SMILES: N#Cc1cnc(NC(=O)c2ccc(-c3nc([C@@H]4CC[C@H]5CCC(=O)N5C4)n4ccnc(N)c34)cc2)cc1C(F)(F)F] | 4-{8-amino-3-[(6R,8aS)-3-oxooctahydroindolizin-6-yl]imidazo[1,5-a]pyrazin-1-yl}-N-[5-cyano-4-(trifluoromethyl)pyridin-2-yl]benzamide | 561.2 | 1.19 (E) |
| 118 | 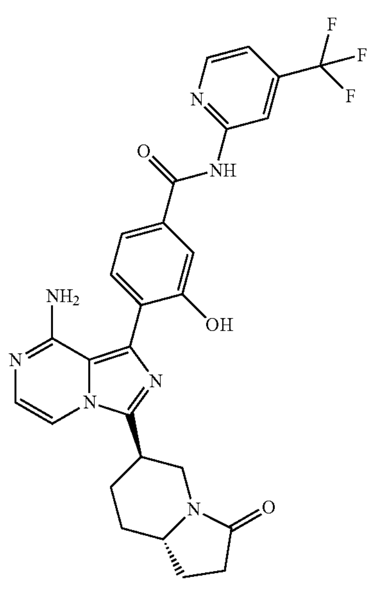 [SMILES: Nc1nccn2c([C@@H]3CC[C@H]4CCC(=O)N4C3)nc(-c3ccc(C(=O)Nc4cc(C(F)(F)F)ccn4)cc3O)c12] | 4-{8-amino-3-[(6R,8aS)-3-oxooctahydroindolizin-6-yl]imidazo[1,5-a]pyrazin-1-yl}-3-hydroxy-N-[4-(trifluoromethyl)pyridin-2-yl]benzamide | 552.2 | 2.89 (A) |

TABLE 3-continued

| Example number | Structure | IUPAC Name | Exact Mass [M + H]+ | Retention time (min) (LC-MS method) |
|---|---|---|---|---|
| 119 | 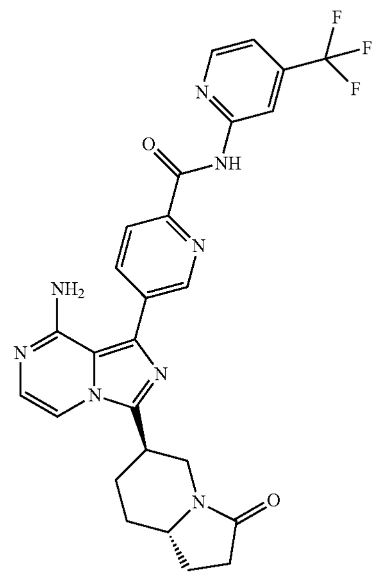 [SMILES: Nc1nccn2c([C@@H]3CC[C@H]4CCC(=O)N4C3)nc(-c3ccc(C(=O)Nc4cc(C(F)(F)F)ccn4)nc3)c12] | 5-{8-amino-3-[(6R,8aS)-3-oxooctahydroindolizin-6-yl]imidazo[1,5-a]pyrazin-1-yl}-N-[4-(trifluoromethyl)pyridin-2-yl]pyridine-2-carboxamide | 537.2 | 2.96 (A) |
| 120 | 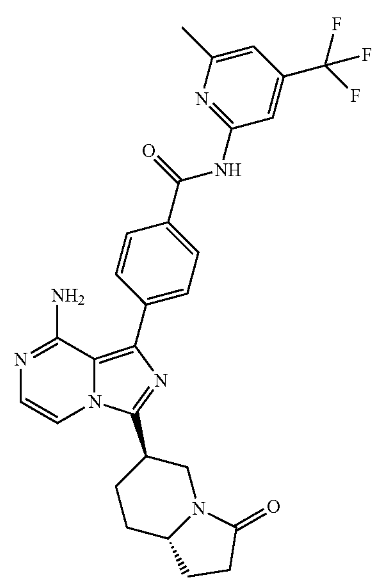 [SMILES: Cc1cc(C(F)(F)F)cc(NC(=O)c2ccc(-c3nc([C@@H]4CC[C@H]5CCC(=O)N5C4)n4ccnc(N)c34)cc2)n1] | 4-{8-amino-3-[(6R,8aS)-3-oxooctahydroindolizin-6-yl]imidazo[1,5-a]pyrazin-1-yl}-N-[6-methyl-4-(trifluoromethyl)pyridin-2-yl]benzamide | 550.2 | 2.69 (A) |

TABLE 3-continued
| Example number | Structure | IUPAC Name | Exact Mass [M + H]+ | Retention time (min) (LC-MS method) |
|---|---|---|---|---|
| 121 | 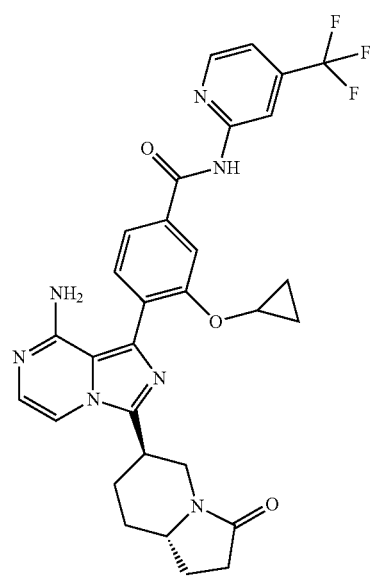 [SMILES: Nc1nccn2c([C@@H]3CC[C@H]4CCC(=O)N4C3)nc(-c3ccc(C(=O)Nc4cc(C(F)(F)F)ccn4)cc3OC3CC3)c12] | 4-{8-amino-3-[(6R,8aS)-3-oxooctahydroindolizin-6-yl]imidazo[1,5-a]pyrazin-1-yl}-3-(cyclopropyloxy)-N-[4-(trifluoromethyl)pyridin-2-yl]benzamide | 592.2 | 2.73 (A) |
| 122 | 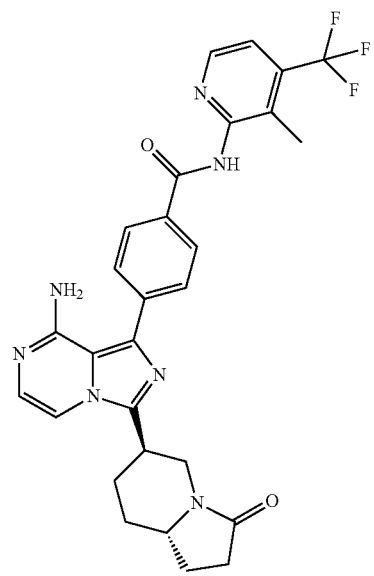 [SMILES: Cc1c(C(F)(F)F)ccnc1NC(=O)c1ccc(-c2nc([C@@H]3CC[C@H]4CCC(=O)N4C3)n3ccnc(N)c23)cc1] | 4-{8-amino-3-[(6R,8aS)-3-oxooctahydroindolizin-6-yl]imidazo[1,5-a]pyrazin-1-yl}-N-[3-methyl-4-(trifluoromethyl)pyridin-2-yl]benzamide | 550.2 | 2.68 (A) |

TABLE 3-continued

| Example number | Structure | IUPAC Name | Exact Mass [M + H]+ | Retention time (min) (LC-MS method) |
|---|---|---|---|---|
| 123 | 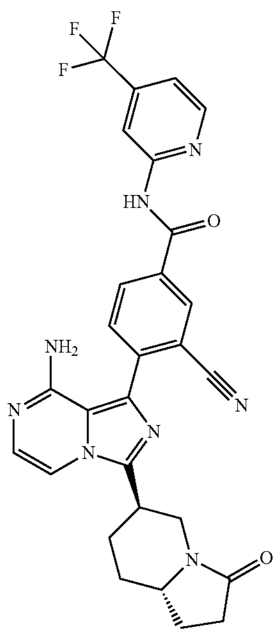 [SMILES: N#Cc1cc(C(=O)Nc2cc(C(F)(F)F)ccn2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-cyano-N-[4-(trifluoromethyl)pyridin-2-yl]benzamide | 561.3 | 2.69 (A) |
| 124 | 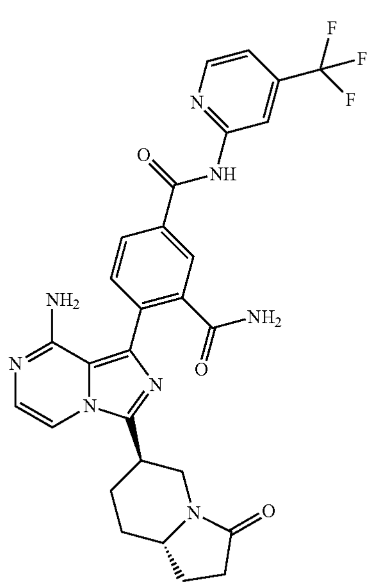 [SMILES: NC(=O)c1cc(C(=O)Nc2cc(C(F)(F)F)ccn2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-N~1~-[4-(trifluoromethyl)pyridin-2-yl]benzene-1,3-dicarboxamide | 579.1 | 2.33 (A) |

TABLE 3-continued

| Example number | Structure | IUPAC Name | Exact Mass [M + H]+ | Retention time (min) (LC-MS method) |
|---|---|---|---|---|
| 125 | 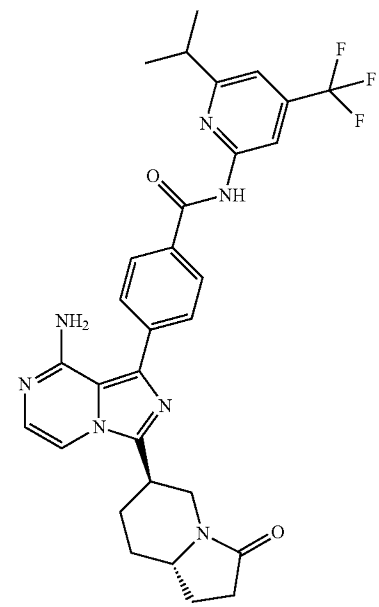 [SMILES: CC(C)c1cc(C(F)(F)F)cc(NC(=O)c2ccc(-c3nc([C@@H]4CC[C@H]5CCC(=O)N5C4)n4ccnc(N)c34)cc2)n1] | 4-{8-amino-3-[(6R,8aS)-3-oxooctahydroindolizin-6-yl]imidazo[1,5-a]pyrazin-1-yl}-N-[6-(1-methylethyl)-4-(trifluoromethyl)pyridin-2-yl]benzamide | 578.5 | 3.13 (A) |
| 126 | 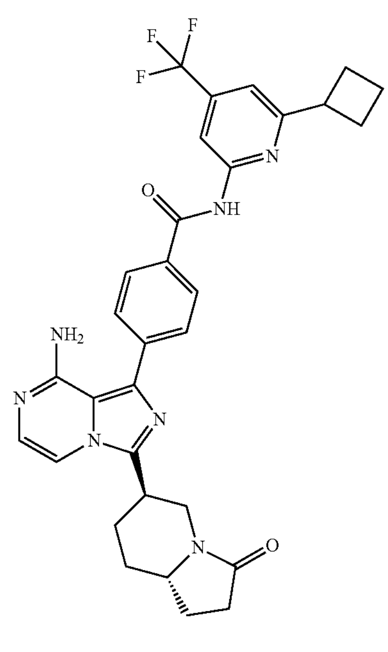 [SMILES: Nc1nccn2c([C@@H]3CC[C@H]4CCC(=O)N4C3)nc(-c3ccc(C(=O)Nc4cc(C(F)(F)F)cc(C5CCC5)n4)cc3)c12] | 4-{8-amino-3-[(6R,8aS)-3-oxooctahydroindolizin-6-yl]imidazo[1,5-a]pyrazin-1-yl}-N-[6-cyclobutyl-4-(trifluoromethyl)pyridin-2-yl]benzamide | 590.5 | 3.28 (A) |

TABLE 3-continued

| Example number | Structure | IUPAC Name | Exact Mass [M + H]+ | Retention time (min) (LC-MS method) |
|---|---|---|---|---|
| 127 | 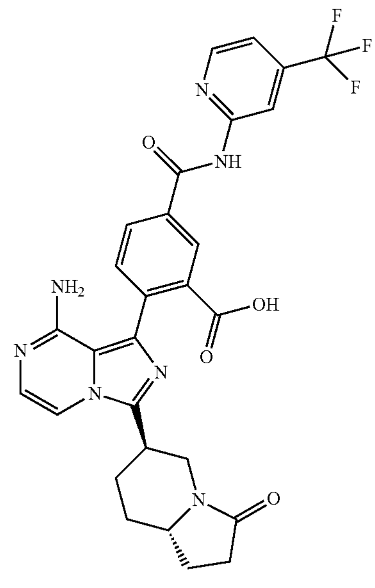 [SMILES: Nc1nccn2c([C@@H]3CC[C@H]4CCC(=O)N4C3)nc(-c3ccc(C(=O)Nc4cc(C(F)(F)F)ccn4)cc3C(=O)O)c12] | 2-{8-amino-3-[(6R,8aS)-3-oxooctahydroindolizin-6-yl]imidazo[1,5-a]pyrazin-1-yl}-5-{[4-(trifluoromethyl)pyridin-2-yl]carbamoyl}benzoic acid | 580.3 | 2.63 (A) |
| 128 | 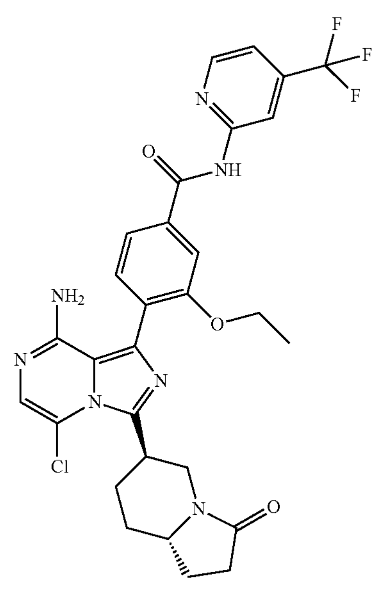 [SMILES: CCOc1cc(C(=O)Nc2cc(C(F)(F)F)ccn2)ccc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-3-ethoxy-N-[4-(trifluoromethyl)pyridin-2-yl]benzamide | 614.4 | 2.98 (A) |

TABLE 3-continued

| Example number | Structure | IUPAC Name | Exact Mass [M + H]+ | Retention time (min) (LC-MS method) |
|---|---|---|---|---|
| 129 | 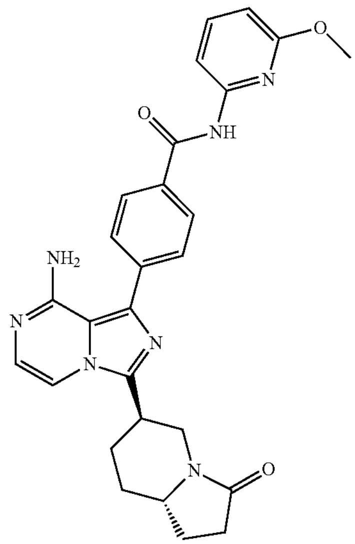 [SMILES: COc1cccc(NC(=O)c2ccc(-c3nc([C@@H]4CC[C@H]5CCC(=O)N5C4)n4ccnc(N)c34)cc2)n1] | 4-{8-amino-3-[(6R,8aS)-3-oxooctahydroindolizin-6-yl]imidazo[1,5-a]pyrazin-1-yl}-N-(6-methoxypyridin-2-yl)benzamide | 498.3 | 2.58 (A) |
| 130 | 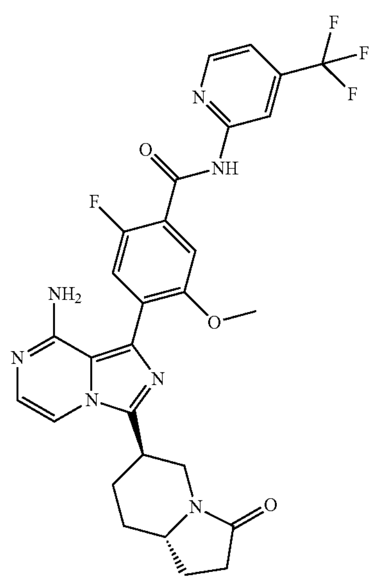 [SMILES: COc1cc(C(=O)Nc2cc(C(F)(F)F)ccn2)c(F)cc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-2-fluoro-5-methoxy-N-[4-(trifluoromethyl)pyridin-2-yl]benzamide | 584.3 | 2.90 (A) |

TABLE 3-continued

| Example number | Structure | IUPAC Name | Exact Mass [M + H]+ | Retention time (min) (LC-MS method) |
|---|---|---|---|---|
| 131 | 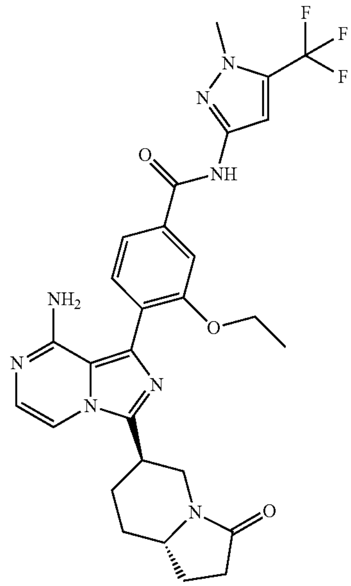 [SMILES: CCOc1cc(C(=O)Nc2cc(C(F)(F)F)n(C)n2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide | 583.4 | 2.88 (A) |
| 132 | 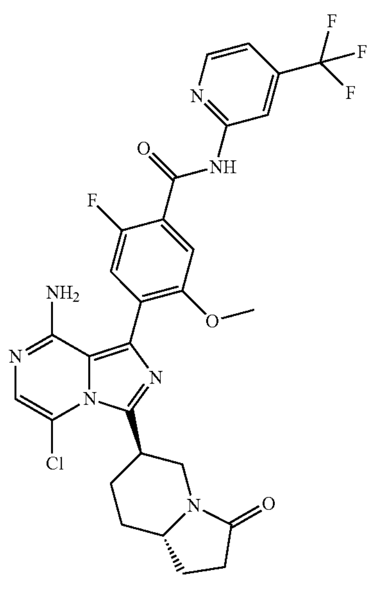 | 4-{8-amino-5-chloro-3-[(6R,8aS)-3-oxooctahydroindolizin-6-yl]imidazo[1,5-a]pyrazin-1-yl}-2-fluoro-5-methoxy-N-[4-(trifluoromethyl)pyridin-2-yl]benzamide | 618.4 | 1.78 (A) |

TABLE 3-continued

| Example number | Structure | IUPAC Name | Exact Mass [M + H]+ | Retention time (min) (LC-MS method) |
|---|---|---|---|---|
| 133 | 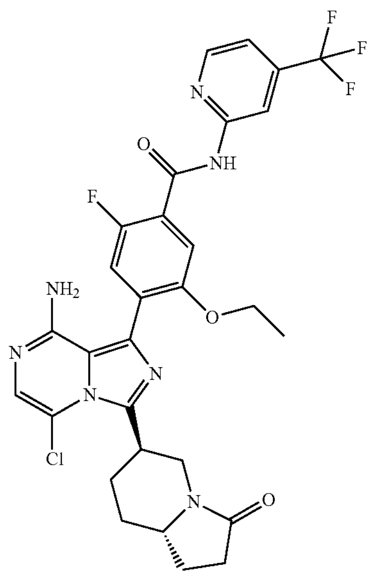 [SMILES: CCOc1cc(C(=O)Nc2cc(C(F)(F)F)ccn2)c(F)cc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-5-ethoxy-2-fluoro-N-[4-(trifluoromethyl)pyridin-2-yl]benzamide | 632.3 | 2.94 (A) |
| 134 | 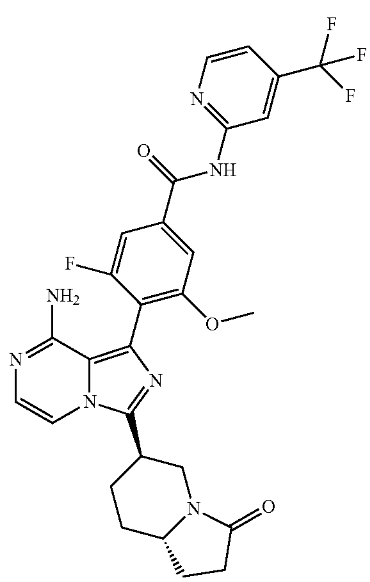 [SMILES: COc1cc(C(=O)Nc2cc(C(F)(F)F)ccn2)cc(F)c1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-fluoro-5-methoxy-N-[4-(trifluoromethyl)pyridin-2-yl]benzamide | 584.3 | 2.66 (A) |

TABLE 3-continued

| Example number | Structure | IUPAC Name | Exact Mass [M + H]+ | Retention time (min) (LC-MS method) |
|---|---|---|---|---|
| 135 | 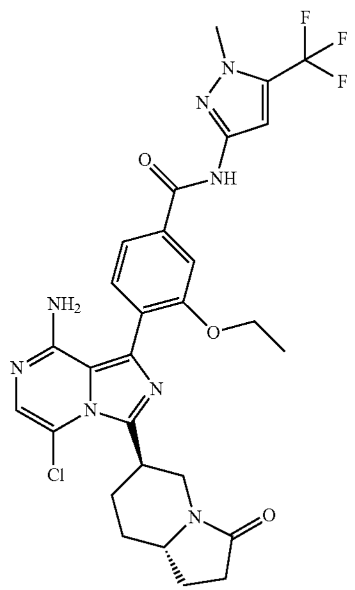 [SMILES: CCOc1cc(C(=O)Nc2cc(C(F)(F)F)n(C)n2)ccc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide | 617.4 | 2.72 (A) |
| 136 | 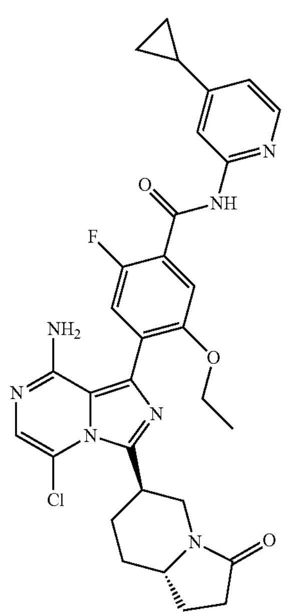 [SMILES: CCOc1cc(C(=O)Nc2cc(C3CC3)ccn2)c(F)cc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-N-(4-cyclopropylpyridin-2-yl)-5-ethoxy-2-fluorobenzamide | 604.5 | 2.37 (A) |

TABLE 3-continued

| Example number | Structure | IUPAC Name | Exact Mass [M + H]+ | Retention time (min) (LC-MS method) |
|---|---|---|---|---|
| 137 | 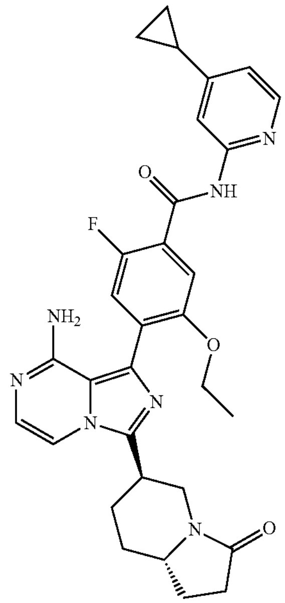 [SMILES: CCOc1cc(C(=O)Nc2cc(C3CC3)ccn2)c(F)cc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-N-(4-cyclopropylpyridin-2-yl)-5-ethoxy-2-fluorobenzamide | 570.5 | 2.26 (A) |
| 138 | 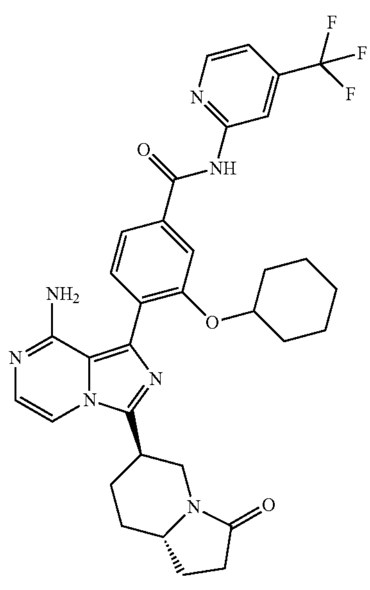 [SMILES: Nc1nccn2c([C@@H]3CC[C@H]4CCC(=O)N4C3)nc(-c3ccc(C(=O)Nc4cc(C(F)(F)F)ccn4)cc3OC3CCCCC3)c12] | 4-{8-amino-3-[(6R,8aS)-3-oxooctahydroindolizin-6-yl]imidazo[1,5-a]pyrazin-1-yl}-3-(cyclohexyloxy)-N-[4-(trifluoromethyl)pyridin-2-yl]benzamide | 634.5 | 3.23 (A) |

TABLE 3-continued
| Example number | Structure | IUPAC Name | Exact Mass [M + H]+ | Retention time (min) (LC-MS method) |
|---|---|---|---|---|
| 139 | 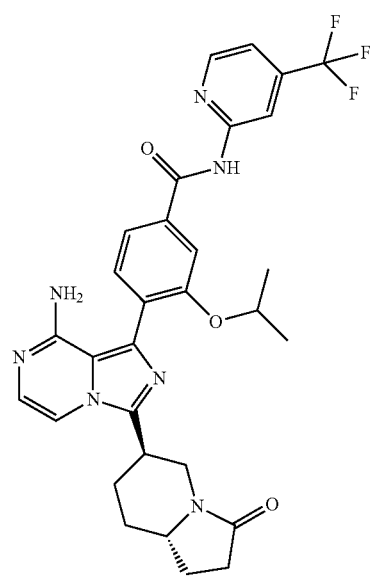 [SMILES: CC(C)Oc1cc(C(=O)Nc2cc(C(F)(F)F)ccn2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-(1-methylethoxy)-N-[4-(trifluoromethyl)pyridin-2-yl]benzamide | 594.5 | 2.97 (A) |
| 140 | 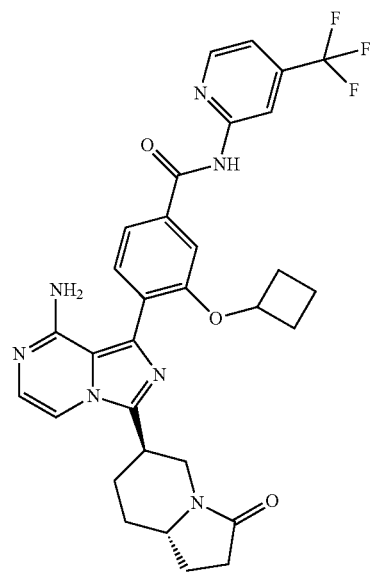 [SMILES: Nc1nccn2c([C@@H]3CC[C@H]4CCC(=O)N4C3)nc(-c3ccc(C(=O)Nc4cc(C(F)(F)F)ccn4)cc3OC3CCC3)c12] | 4-{8-amino-3-[(6R,8aS)-3-oxooctahydroindolizin-6-yl]imidazo[1,5-a]pyrazin-1-yl}-3-(cyclobutyloxy)-N-[4-(trifluoromethyl)pyridin-2-yl]benzamide | 606.5 | 2.88 (A) |

TABLE 3-continued

| Example number | Structure | IUPAC Name | Exact Mass [M + H]+ | Retention time (min) (LC-MS method) |
|---|---|---|---|---|
| 141 | 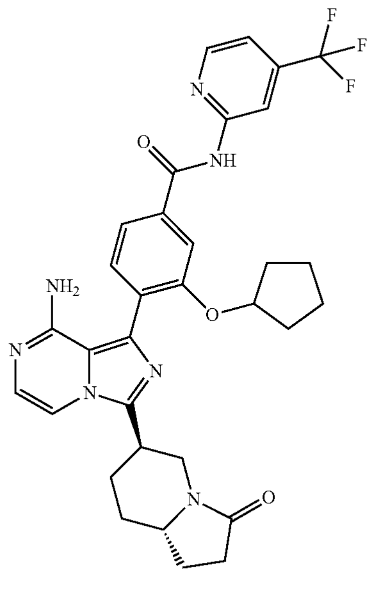 [SMILES: Nc1nccn2c([C@@H]3CC[C@H]4CCC(=O)N4C3)nc(-c3ccc(C(=O)Nc4cc(C(F)(F)F)ccn4)cc3OC3CCCC3)c12] | 4-{8-amino-3-[(6R,8aS)-3-oxooctahydroindolizin-6-yl]imidazo[1,5-a]pyrazin-1-yl}-3-(cyclopentyloxy)-N-[4-(trifluoromethyl)pyridin-2-yl]benzamide | 620.5 | 2.92 (A) |
| 142 | 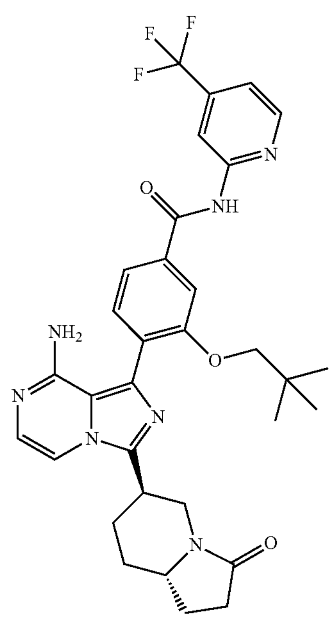 [SMILES: CC(C)(C)COc1cc(C(=O)Nc2cc(C(F)(F)F)ccn2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-(2,2-dimethylpropoxy)-N-[4-(trifluoromethyl)pyridin-2-yl]benzamide | 622.5 | 3.01 (A) |

TABLE 3-continued

| Example number | Structure | IUPAC Name | Exact Mass [M + H]+ | Retention time (min) (LC-MS method) |
|---|---|---|---|---|
| 143 | 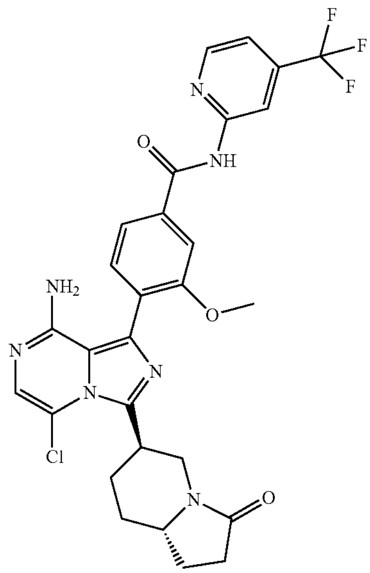 [SMILES: COc1cc(C(=O)Nc2cc(C(F)(F)F)ccn2)ccc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-3-methoxy-N-[4-(trifluoromethyl)pyridin-2-yl]benzamide | 600.5 | 2.72 (A) |
| 144 | 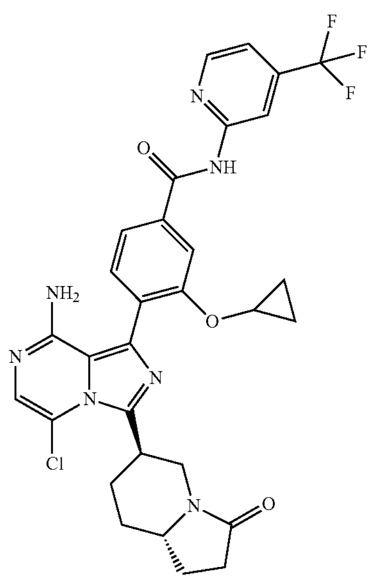 [SMILES: Nc1ncc(Cl)n2c([C@@H]3CC[C@H]4CCC(=O)N4C3)nc(-c3ccc(C(=O)Nc4cc(C(F)(F)F)ccn4)cc3OC3CC3)c12] | 4-{8-amino-5-chloro-3-[(6R,8aS)-3-oxooctahydroindolizin-6-yl]imidazo[1,5-a]pyrazin-1-yl}-3-(cyclopropyloxy)-N-[4-(trifluoromethyl)pyridin-2-yl]benzamide | 626.3 | 2.90 (A) |

TABLE 3-continued

| Example number | Structure | IUPAC Name | Exact Mass [M + H]+ | Retention time (min) (LC-MS method) |
|---|---|---|---|---|
| 145 | 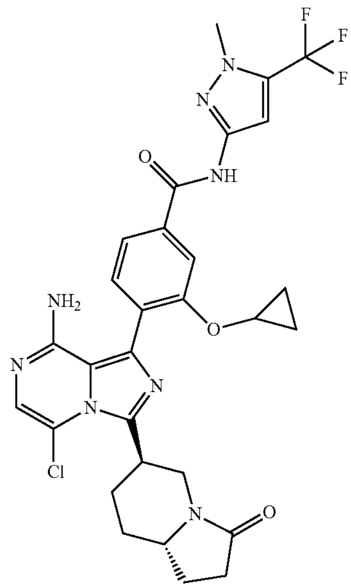 [SMILES: Cn1nc(NC(=O)c2ccc(-c3nc([C@@H]4CC[C@H]5CCC(=O)N5C4)n4c(Cl)cnc(N)c34)c(OC3CC3)c2)cc1C(F)(F)F] | 4-{8-amino-5-chloro-3-[(6R,8aS)-3-oxooctahydroindolizin-6-yl]imidazo[1,5-a]pyrazin-1-yl}-3-(cyclopropyloxy)-N-[1-methyl-5-(trifluoromethyl)-1H-pyrazol-3-yl]benzamide | 629.4 | 2.75 (A) |
| 146 | 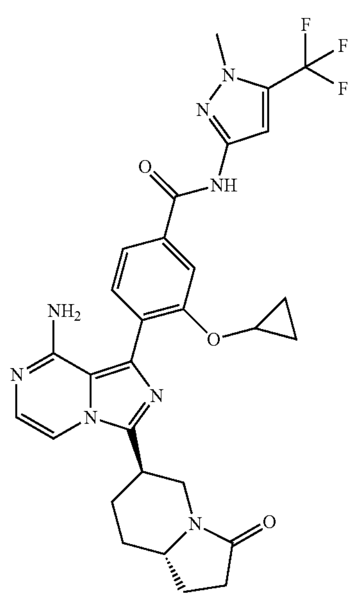 [SMILES: Cn1nc(NC(=O)c2ccc(-c3nc([C@@H]4CC[C@H]5CCC(=O)N5C4)n4ccnc(N)c34)c(OC3CC3)c2)cc1C(F)(F)F] | 4-{8-amino-3-[(6R,8aS)-3-oxooctahydroindolizin-6-yl]imidazo[1,5-a]pyrazin-1-yl}-3-(cyclopropyloxy)-N-[1-methyl-5-(trifluoromethyl)-1H-pyrazol-3-yl]benzamide | 595.4 | 2.60 (A) |

TABLE 3-continued

| Example number | Structure | IUPAC Name | Exact Mass [M + H]+ | Retention time (min) (LC-MS method) |
|---|---|---|---|---|
| 147 | 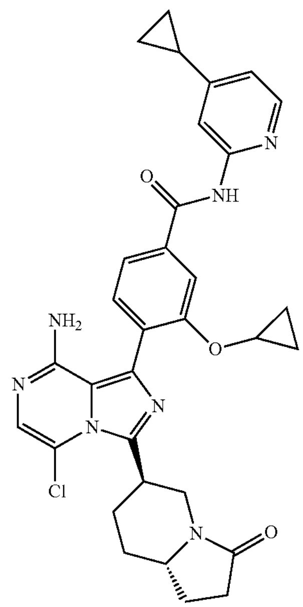 [SMILES: Nc1ncc(Cl)n2c([C@@H]3CC[C@H]4CCC(=O)N4C3)nc(-c3ccc(C(=O)Nc4cc(C5CC5)ccn4)cc3OC3CC3)c12] | 4-{8-amino-5-chloro-3-[(6R,8aS)-3-oxooctahydroindolizin-6-yl]imidazo[1,5-a]pyrazin-1-yl}-3-(cyclopropyloxy)-N-(4-cyclopropylpyridin-2-yl)benzamide | 598.6 | 2.32 (A) |
| 148 | 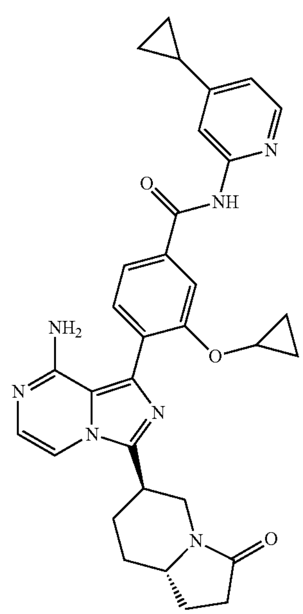 [SMILES: Nc1nccn2c([C@@H]3CC[C@H]4CCC(=O)N4C3)nc(-c3ccc(C(=O)Nc4cc(C5CC5)ccn4)cc3OC3CC3)c12] | 4-{8-amino-3-[(6R,8aS)-3-oxooctahydroindolizin-6-yl]imidazo[1,5-a]pyrazin-1-yl}-3-(cyclopropyloxy)-N-(4-cyclopropylpyridin-2-yl)benzamide | 564.5 | 2.17 (A) |

TABLE 3-continued

| Example number | Structure | IUPAC Name | Exact Mass [M + H]+ | Retention time (min) (LC-MS method) |
|---|---|---|---|---|
| 149 | 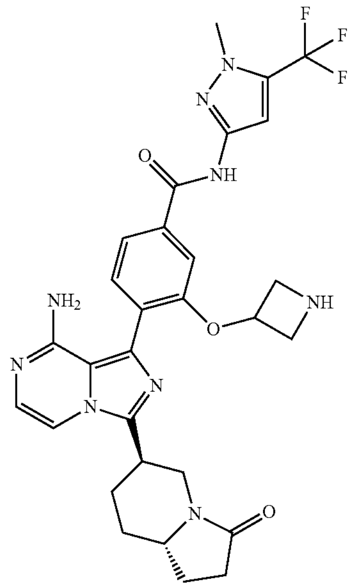 [SMILES: Cn1nc(NC(=O)c2ccc(-c3nc([C@@H]4CC[C@H]5CCC(=O)N5C4)n4ccnc(N)c34)c(OC3CNC3)c2)cc1C(F)(F)F] | 4-{8-amino-3-[(6R,8aS)-3-oxooctahydroindolizin-6-yl]imidazo[1,5-a]pyrazin-1-yl}-3-(azetidin-3-yloxy)-N-[1-methyl-5-(trifluoromethyl)-1H-pyrazol-3-yl]benzamide | 610.5 | 2.18 (A) |
| 150 | 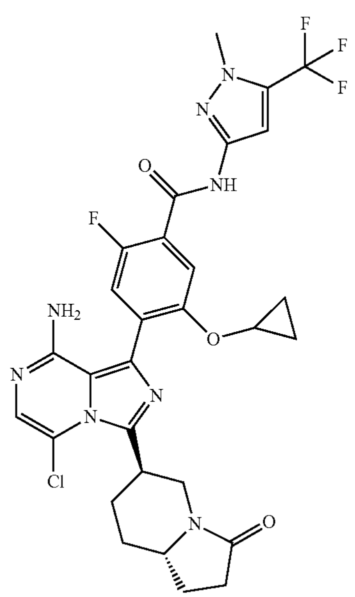 [SMILES: Cn1nc(NC(=O)c2cc(OC3CC3)c(-c3nc([C@@H]4CC[C@H]5CCC(=O)N5C4)n4c(Cl)cnc(N)c34)cc2F)cc1C(F)(F)F] | 4-{8-amino-5-chloro-3-[(6R,8aS)-3-oxooctahydroindolizin-6-yl]imidazo[1,5-a]pyrazin-1-yl}-5-(cyclopropyloxy)-2-fluoro-N-[1-methyl-5-(trifluoromethyl)-1H-pyrazol-3-yl]benzamide | 647.5 | 2.84 (A) |

TABLE 3-continued

| Example number | Structure | IUPAC Name | Exact Mass [M + H]+ | Retention time (min) (LC-MS method) |
|---|---|---|---|---|
| 151 | 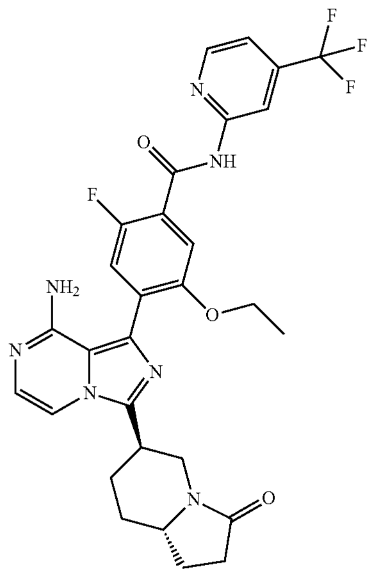 [SMILES: CCOc1cc(C(=O)Nc2cc(C(F)(F)F)ccn2)c(F)cc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-5-ethoxy-2-fluoro-N-[4-(trifluoromethyl)pyridin-2-yl]benzamide | 598.5 | 3.07 (A) |
| 152 | 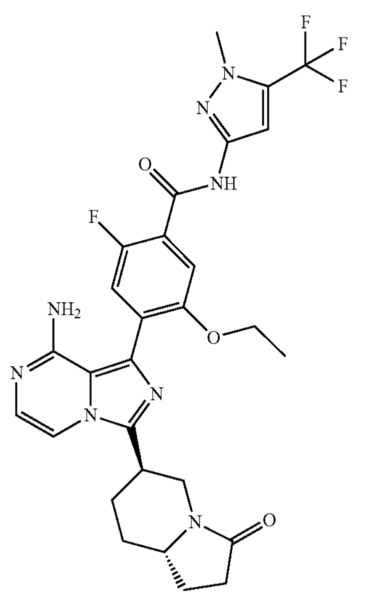 [SMILES: CCOc1cc(C(=O)Nc2cc(C(F)(F)F)n(C)n2)c(F)cc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-5-ethoxy-2-fluoro-N-[1-methyl-5-(trifluoromethyl)-1H-pyrazol-3-yl]benzamide | 601.4 | 2.68 (A) |

TABLE 3-continued

| Example number | Structure | IUPAC Name | Exact Mass [M + H]+ | Retention time (min) (LC-MS method) |
|---|---|---|---|---|
| 153 | 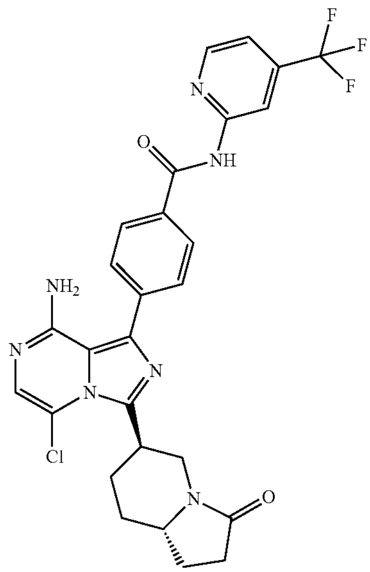 [SMILES: Nc1ncc(Cl)n2c([C@@H]3CC[C@H]4CCC(=O)N4C3)nc(-c3ccc(C(=O)Nc4cc(C(F)(F)F)ccn4)cc3)c12] | 4-{8-amino-5-chloro-3-[(6R,8aS)-3-oxooctahydroindolizin-6-yl]imidazo[1,5-a]pyrazin-1-yl}-N-[4-(trifluoromethyl)pyridin-2-yl]benzamide | 570.2 | 1.33 (E) |
| 154 | 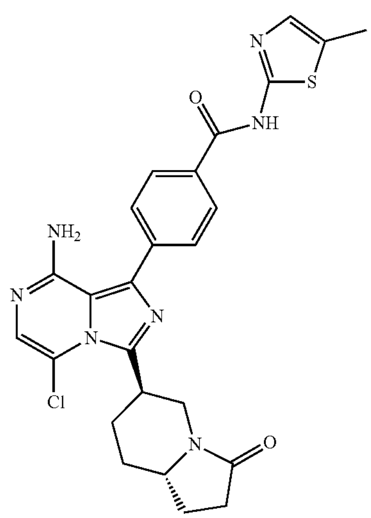 [SMILES: Cc1cnc(NC(=O)c2ccc(-c3nc([C@@H]4CC[C@H]5CCC(=O)N5C4)n4c(Cl)cnc(N)c34)cc2)s1] | 4-{8-amino-5-chloro-3-[(6R,8aS)-3-oxooctahydroindolizin-6-yl]imidazo[1,5-a]pyrazin-1-yl}-N-(5-methyl-1,3-thiazol-2-yl)benzamide | 522.1 | 1.33 (E) |

TABLE 3-continued
| Example number | Structure | IUPAC Name | Exact Mass [M + H]+ | Retention time (min) (LC-MS method) |
|---|---|---|---|---|
| 155 | 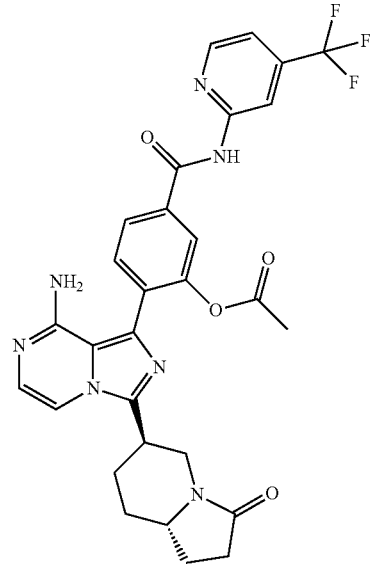 [SMILES: CC(=O)Oc1cc(C(=O)Nc2cc(C(F)(F)F)ccn2)ccc1-c1nc([C@@H]2CC[C@H]3CCC(=O)N3C2)n2ccnc(N)c12] | 2-{8-amino-3-[(6R,8aS)-3-oxooctahydroindolizin-6-yl]imidazo[1,5-a]pyrazin-1-yl}-5-{[4-(trifluoromethyl)pyridin-2-yl]carbamoyl}phenyl acetate | 594.2 | 1.25 (E) |
| 156 | 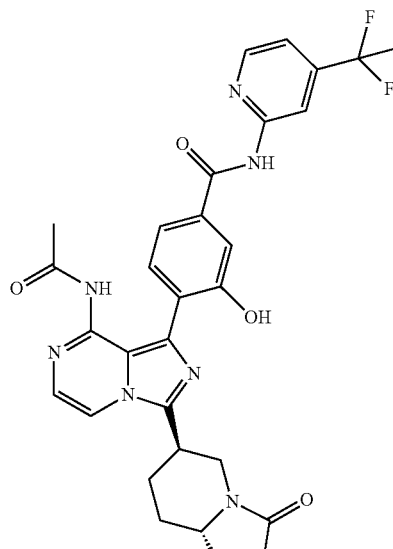 | 4-{8-(acetylamino)-3-[(6R,8aS)-3-oxooctahydroindolizin-6-yl]imidazo[1,5-a]pyrazin-1-yl}-3-hydroxy-N-[4-(trifluoromethyl)pyridin-2-yl]benzamide | 594.2 | 1.26 (E) |

TABLE 3-continued

| Example number | Structure | IUPAC Name | Exact Mass [M + H]+ | Retention time (min) (LC-MS method) |
|---|---|---|---|---|
| 157 | 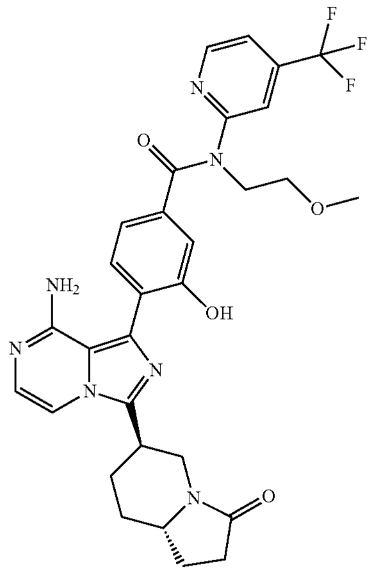 [SMILES: COCCN(C(=O)c1ccc(-c2nc([C@@H]3CC[C@H]4CCC(=O)N4C3)n3ccnc(N)c23)c(O)c1)c1cc(C(F)(F)F)ccn1] | 4-{8-amino-3-[(6R,8aS)-3-oxooctahydroindolizin-6-yl]imidazo[1,5-a]pyrazin-1-yl}-3-hydroxy-N-(2-methoxyethyl)-N-[4-(trifluoromethyl)pyridin-2-yl]benzamide | 610.3 | 1.26 (E) |
| 158 | 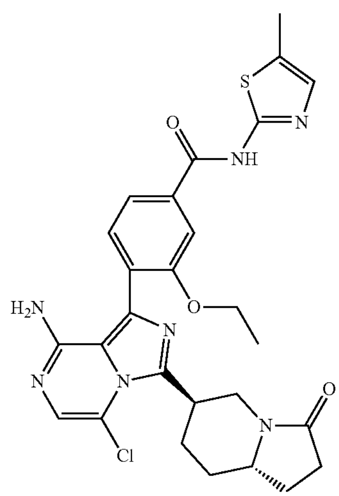 [SMILES: CCOc1cc(C(=O)Nc2ncc(C)s2)ccc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-3-ethoxy-N-(5-methyl-1,3-thiazol-2-yl)benzamide | 566.2 | 1.21 (E) |
| 159 | 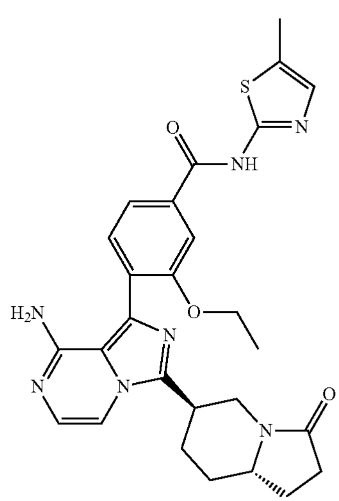 [SMILES: CCOc1cc(C(=O)Nc2ncc(C)s2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-ethoxy-N-(5-methyl-1,3-thiazol-2-yl)benzamide | 532.1 | 1.31 (E) |

TABLE 3-continued

| Example number | Structure | IUPAC Name | Exact Mass [M + H]+ | Retention time (min) (LC-MS method) |
|---|---|---|---|---|
| 160 | 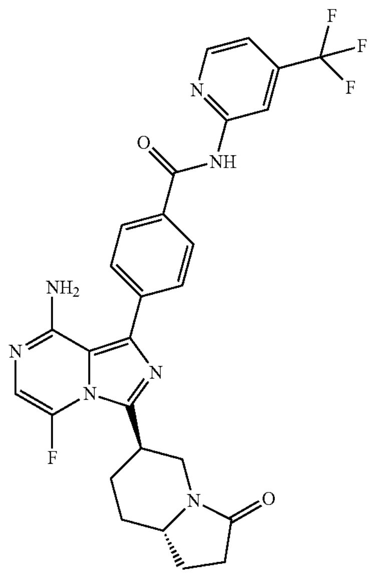 [SMILES: Nc1ncc(F)n2c([C@@H]3CC[C@H]4CCC(=O)N4C3)nc(-c3ccc(C(=O)Nc4cc(C(F)(F)F)ccn4)cc3)c12] | 4-{8-amino-5-fluoro-3-[(6R,8aS)-3-oxooctahydroindolizin-6-yl]imidazo[1,5-a]pyrazin-1-yl}-N-[4-(trifluoromethyl)pyridin-2-yl]benzamide | 554.1 | 1.32 (E) |
| 161 | 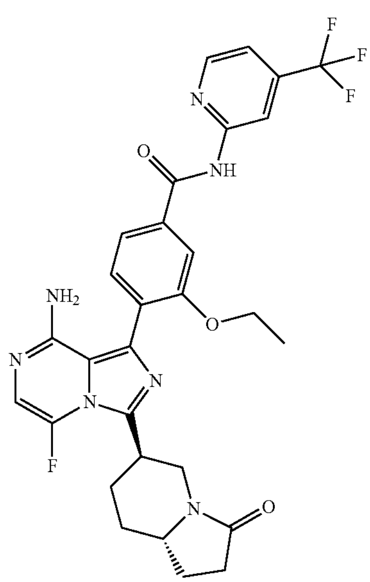 [SMILES: CCOc1cc(C(=O)Nc2cc(C(F)(F)F)ccn2)ccc1-c1nc([C@@H]2CC[C@H]3CCC(=O)N3C2)n2c(F)cnc(N)c12] | 4-{8-amino-5-fluoro-3-[(6R,8aS)-3-oxooctahydroindolizin-6-yl]imidazo[1,5-a]pyrazin-1-yl}-3-ethoxy-N-[4-(trifluoromethyl)pyridin-2-yl]benzamide | 598.2 | 1.26 (E) |

TABLE 3-continued
| Example number | Structure | IUPAC Name | Exact Mass [M + H]+ | Retention time (min) (LC-MS method) |
|---|---|---|---|---|
| 162 | 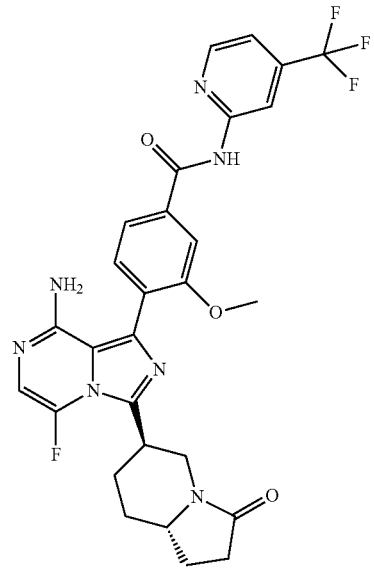 [SMILES: COc1cc(C(=O)Nc2cc(C(F)(F)F)ccn2)ccc1-c1nc([C@@H]2CC[C@H]3CCC(=O)N3C2)n2c(F)cnc(N)c12] | 4-{8-amino-5-fluoro-3-[(6R,8aS)-3-oxooctahydroindolizin-6-yl]imidazo[1,5-a]pyrazin-1-yl}-3-methoxy-N-[4-(trifluoromethyl)pyridin-2-yl]benzamide | 584.3 | 1.22 (E) |
| 163 | 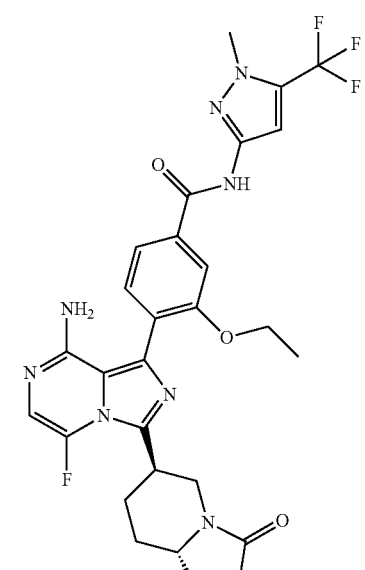 | 4-{8-amino-5-fluoro-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide | 601.2 | 1.29 (E) |

TABLE 3-continued

| Example number | Structure | IUPAC Name | Exact Mass [M + H]+ | Retention time (min) (LC-MS method) |
|---|---|---|---|---|
| 164 | 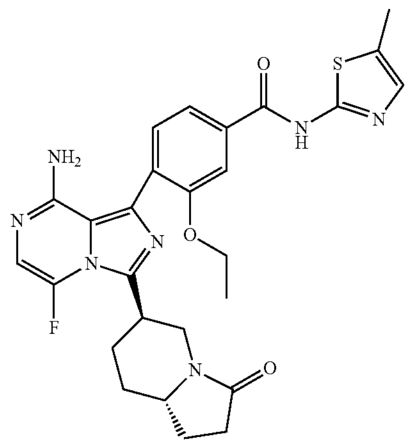 [SMILES: CCOc1cc(C(=O)Nc2ncc(C)s2)ccc1-c1nc([C@@H]2CC[C@H]3CCC(=O)N3C2)n2c(F)cnc(N)c12] | 4-{8-amino-5-fluoro-3-[(6R,8aS)-3-oxooctahydroindolizin-6-yl]imidazo[1,5-a]pyrazin-1-yl}-3-ethoxy-N-(5-methyl-1,3-thiazol-2-yl)benzamide | 550.1 | 1.29 (E) |
| 165 | 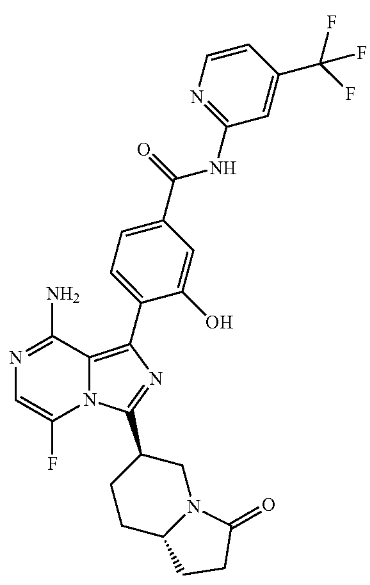 [SMILES: Nc1ncc(F)n2c([C@@H]3CC[C@H]4CCC(=O)N4C3)nc(-c3ccc(C(=O)Nc4cc(C(F)(F)F)ccn4)cc3O)c12] | 4-{8-amino-5-fluoro-3-[(6R,8aS)-3-oxooctahydroindolizin-6-yl]imidazo[1,5-a]pyrazin-1-yl}-3-hydroxy-N-[4-(trifluoromethyl)pyridin-2-yl]benzamide | 572.1 | 1.30 (E) |

TABLE 3-continued

| Example number | Structure | IUPAC Name | Exact Mass [M + H]+ | Retention time (min) (LC-MS method) |
|---|---|---|---|---|
| 166 | 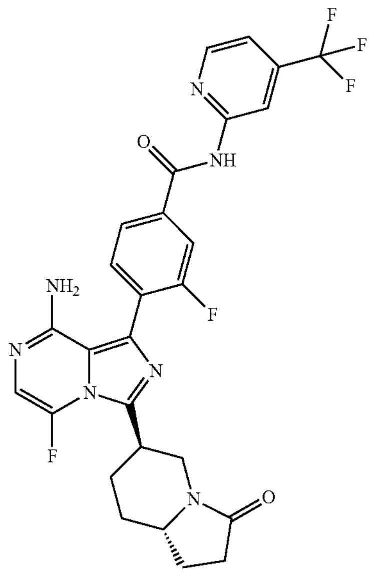 [SMILES: Nc1ncc(F)n2c([C@@H]3CC[C@H]4CCC(=O)N4C3)nc(-c3ccc(C(=O)Nc4cc(C(F)(F)F)ccn4)cc3F)c12] | 4-{8-amino-5-fluoro-3-[(6R,8aS)-3-oxooctahydroindolizin-6-yl]imidazo[1,5-a]pyrazin-1-yl}-3-fluoro-N-[4-(trifluoromethyl)pyridin-2-yl]benzamide | 572.3 | 1.30 (E) |
| 167 | 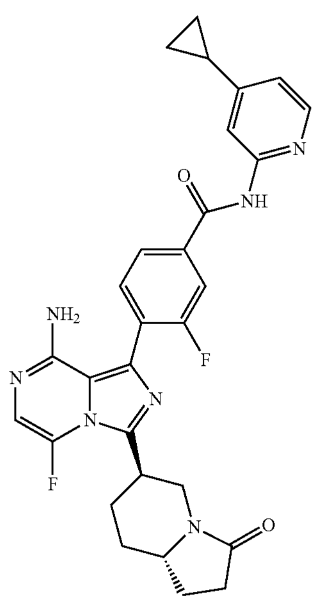 [SMILES: Nc1ncc(F)n2c([C@@H]3CC[C@H]4CCC(=O)N4C3)nc(-c3ccc(C(=O)Nc4cc(C5CC5)ccn4)cc3F)c12] | 4-{8-amino-5-fluoro-3-[(6R,8aS)-3-oxooctahydroindolizin-6-yl]imidazo[1,5-a]pyrazin-1-yl}-N-(4-cyclopropylpyridin-2-yl)-3-fluorobenzamide | 554.1 | 1.26 (E) |

TABLE 3-continued

| Example number | Structure | IUPAC Name | Exact Mass [M + H]+ | Retention time (min) (LC-MS method) |
|---|---|---|---|---|
| 168 | 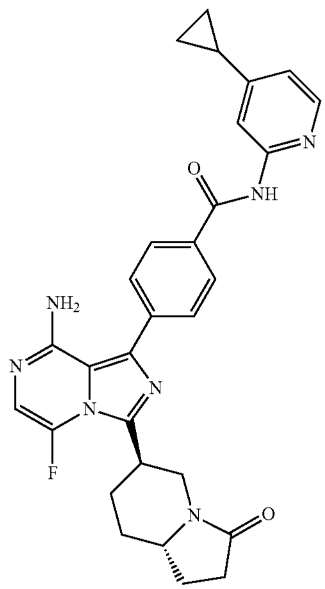 [SMILES: Nc1ncc(F)n2c([C@@H]3CC[C@H]4CCC(=O)N4C3)nc(-c3ccc(C(=O)Nc4cc(C5CC5)ccn4)cc3)c12] | 4-{8-amino-5-fluoro-3-[(6R,8aS)-3-oxooctahydroindolizin-6-yl]imidazo[1,5-a]pyrazin-1-yl}-N-(4-cyclopropylpyridin-2-yl)benzamide | 526.3 | 1.07 (E) |
| 169 | 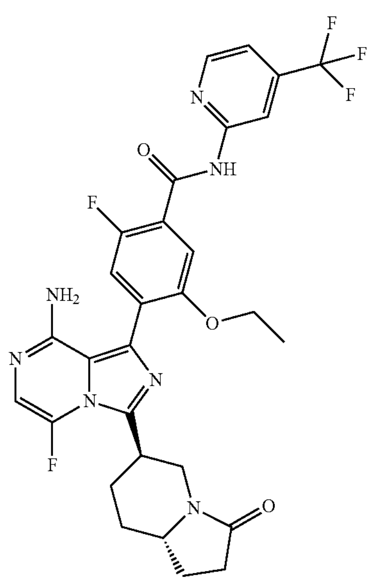 [SMILES: CCOc1cc(C(=O)Nc2cc(C(F)(F)F)ccn2)c(F)cc1-c1nc([C@@H]2CC[C@H]3CCC(=O)N3C2)n2c(F)cnc(N)c12] | 4-{8-amino-5-fluoro-3-[(6R,8aS)-3-oxooctahydroindolizin-6-yl]imidazo[1,5-a]pyrazin-1-yl}-5-ethoxy-2-fluoro-N-[4-(trifluoromethyl)pyridin-2-yl]benzamide | 616.3 | 1.26 (E) |

Example 170

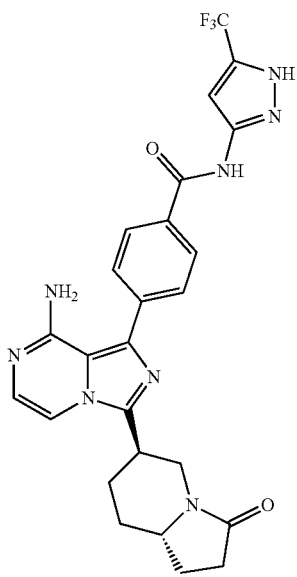 [SMILES: Nc1nccn2c([C@@H]3CC[C@H]4CCC(=O)N4C3)nc(-c3ccc(C(=O)Nc4cc(C(F)(F)F)[nH]n4)cc3)c12]

4-(8-amino-3-((6R,8aS)-3-oxooctahydroindolizin-6-yl)imidazo[1,5-a]pyrazin-1-yl)-N-(5-(trifluoromethyl)-1H-pyrazol-3-yl)benzamide Step 1: lithium 4-(8-amino-3-((6R,8aS)-3-oxooctahydroindolizin-6-yl)imidazo[1,5-a]pyrazin-1-yl)benzoate Potassium carbonate (1184 mg, 8.57 mmol), (6R,8aS)-6-(8-amino-1-bromoimidazo[1,5-a]pyrazin-3-yl)hexahydroindolizin-3(2H)-one (1000 mg, 2.86 mmol), methyl 4-(4,4,5,5-tetramethyl-1,3,2-dioxaborolan-2-yl)benzoate (823 mg, 3.14 mmol), 1,1'-Bis(diphenylphosphino)ferrocene-palladium (II)dichloride dichloromethane complex (233 mg, 0.286 mmol) were mixed in Dioxane (10 ml) and Water (2 ml) in pressure vial, degassed and stirred at 90° C. for 2 hours. Product separated on flash LC 40 g column (B: 10% MeOH, 0.1% NH$_3$OH in CH$_2$Cl$_2$/A: CH$_2$Cl$_2$ (gradient from 0% B to 40% B) to give methyl 4-(8-amino-3-((6R,8aS)-3-oxooctahydroindolizin-6-yl)imidazo[1,5-a]pyrazin-1-yl)benzoate (860 mg, 2.121 mmol). LC-MS: LC-MS method A, RET. TIME=2.09 min., MS found (M)$^+$ m/z=406.23.

Methyl 4-(8-amino-3-((6R,8aS)-3-oxooctahydroindolizin-6-yl)imidazo[1,5-a]pyrazin-1-yl)benzoate (860 mg, 2.121 mmol) and lithium hydroxide (254 mg, 10.61 mmol) were mixed in Tetrahydrofuran (40 ml) and MeOH (5 ml) and Water (2 ml), and stirred for 15 hours at 45° C. Solvents were evaporated to give lithium 4-(8-amino-3-((6R,8aS)-3-oxooctahydroindolizin-6-yl)imidazo[1,5-a]pyrazin-1-yl)benzoate (843 mg, 2.121 mmol, 100% yield).

LC-MS: LC-MS method A, RET. TIME=1.88 min., MS found (M)$^{+\ m/z=}$392.22.

Step 2: 4-(8-amino-3-((6R,8aS)-3-oxooctahydroindolizin-6-yl)imidazo[1,5-a]pyrazin-1-yl)-N-(5-(trifluoromethyl)-1H-pyrazol-3-yl)benzamide N,N-DIISOPROPYLETHYLAMINE (0.022 ml, 0.126 mmol) was added to the mixture of the 3-(TRIFLUOROMETHYL)-1H-PYRAZOL-5-AMINE (19.01 mg, 0.126 mmol), HATU (47.8 mg, 0.126 mmol), lithium 4-(8-amino-3-((6R,8aS)-3-oxooctahydroindolizin-6-yl)imidazo[1,5-a]pyrazin-1-yl)benzoate (Intermediate 20) (50 mg, 0.126 mmol) in DMF (2 ml) and stirred for 30 min. at 0° C.

LC-MS shows completion of the reaction. Product was separated on flash LC on 12 g column (B: 10% MeOH, 0.1% NH$_3$OH in CH$_2$Cl$_2$/A: CH$_2$Cl$_2$ (gradient from 0% B to 40% B) to give 4-(8-amino-3-((6R,8aS)-3-oxooctahydroindolizin-6-yl)imidazo[1,5-a]pyrazin-1-yl)-N-(3-(trifluoromethyl)-1H-pyrazol-5-yl)benzamide (14.3 mg, 0.027 mmol, 21.67% yield). LC-MS: LC-MS method A, RET. TIME=2.41 min., MS found (M)$^+$ m/z=525.26.

The Examples in Table 4 below were synthesized following the methods described for Example 170 using corresponding aromatic amines for the step 2 coupling.

TABLE 4

| Example | Structure | IUPAC Name | (M)+ m/z | UPLC (C) Ret. time (min) (LC-MS method) |
|---|---|---|---|---|
| 171 | 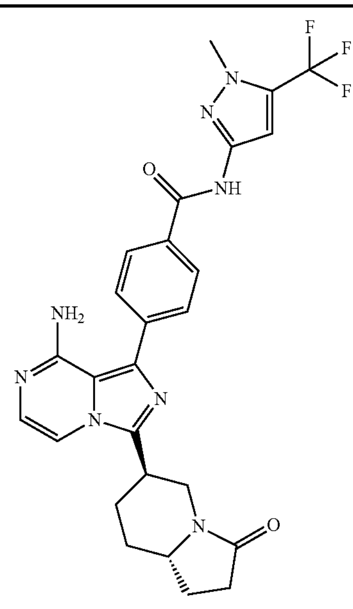 | 4-{8-amino-3-[(6R,8aS)-3-oxooctahydroindolizin-6-yl]imidazo[1,5-a]pyrazin-1-yl}-N-[1-methyl-5-(trifluoromethyl)-1H-pyrazol-3-yl]benzamide | 539.35 | 2.45 (A) |

TABLE 4-continued
| Example | Structure | IUPAC Name | (M)+ m/z | UPLC (C) Ret. time (min) (LC-MS method) |
|---|---|---|---|---|
| 172 | 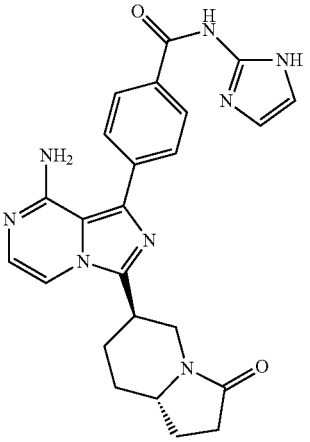 [SMILES: Nc1nccn2c([C@@H]3CC[C@H]4CCC(=O)N4C3)nc(-c3ccc(C(=O)Nc4ncc[nH]4)cc3)c12] | 4-{8-amino-3-[(6R,8aS)-3-oxooctahydroindolizin-6-yl]imidazo[1,5-a]pyrazin-1-yl}-N-1H-imidazol-2-ylbenzamide | 457.25 | 1.67 (A) |
| 173 | 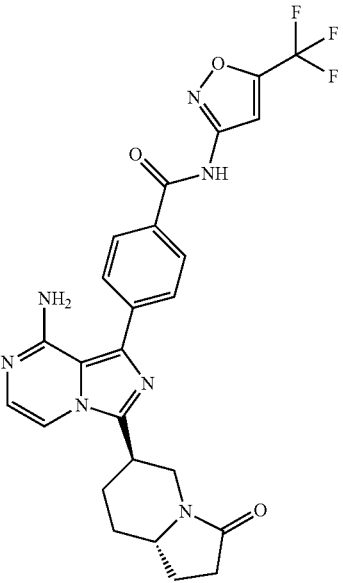 [SMILES: Nc1nccn2c([C@@H]3CC[C@H]4CCC(=O)N4C3)nc(-c3ccc(C(=O)Nc4cc(C(F)(F)F)on4)cc3)c12] | 4-{8-amino-3-[(6R,8aS)-3-oxooctahydroindolizin-6-yl]imidazo[1,5-a]pyrazin-1-yl}-N-[5-(trifluoromethyl)isoxazol-3-yl]benzamide | 526.37 | 2.57 (A) |

TABLE 4-continued
| Example | Structure | IUPAC Name | (M)+ m/z | UPLC (C) Ret. time (min) (LC-MS method) |
|---|---|---|---|---|
| 174 | 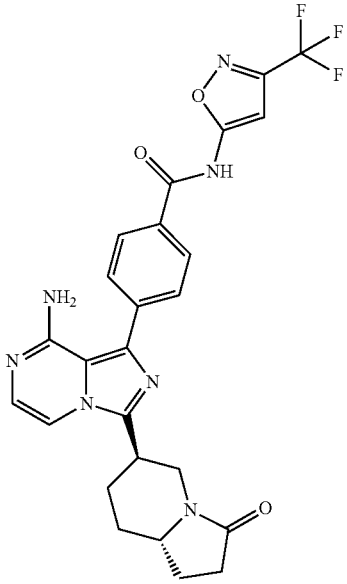 [SMILES: Nc1nccn2c([C@@H]3CC[C@H]4CCC(=O)N4C3)nc(-c3ccc(C(=O)Nc4cc(C(F)(F)F)no4)cc3)c12] | 4-{8-amino-3-[(6R,8aS)-3-oxooctahydroindolizin-6-yl]imidazo[1,5-a]pyrazin-1-yl}-N-[3-(trifluoromethyl)isoxazol-5-yl]benzamide | 526.33 | 2.63 (A) |
| 175 | 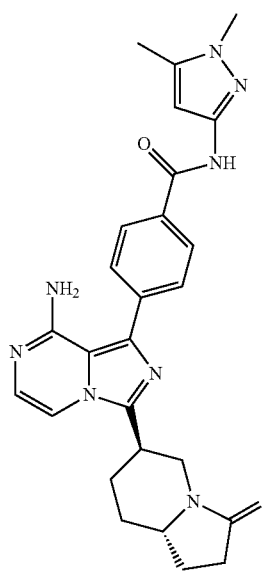 | 4-{8-amino-3-[(6R,8aS)-3-oxooctahydroindolizin-6-yl]imidazo[1,5-a]pyrazin-1-yl}-N-(1,5-dimethyl-1H-pyrazol-3-yl)benzamide | 485.35 | 2.04 (A) |

TABLE 4-continued

| Example | Structure | IUPAC Name | (M)+ m/z | UPLC (C) Ret. time (min) (LC-MS method) |
|---|---|---|---|---|
| 176 | 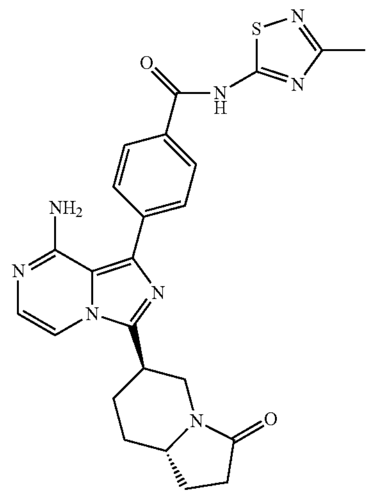 [SMILES: Cc1nsc(NC(=O)c2ccc(-c3nc([C@@H]4CC[C@H]5CCC(=O)N5C4)n4ccnc(N)c34)cc2)n1] | 4-{8-amino-3-[(6R,8aS)-3-oxooctahydroindolizin-6-yl]imidazo[1,5-a]pyrazin-1-yl}-N-(3-methyl-1,2,4-thiadiazol-5-yl)benzamide | 489.28 | 2.15 (A) |
| 177 | 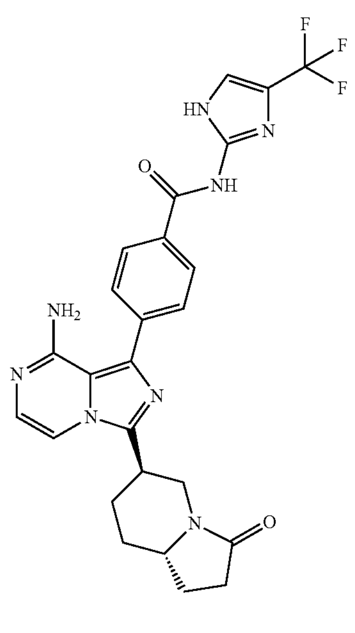 [SMILES: Nc1nccn2c([C@@H]3CC[C@H]4CCC(=O)N4C3)nc(-c3ccc(C(=O)Nc4nc(C(F)(F)F)c[nH]4)cc3)c12] | 4-{8-amino-3-[(6R,8aS)-3-oxooctahydroindolizin-6-yl]imidazo[1,5-a]pyrazin-1-yl}-N-[4-(trifluoromethyl)-1H-imidazol-2-yl]benzamide | 525.33 | 2.29 (A) |

TABLE 4-continued

| Example | Structure | IUPAC Name | (M)+ m/z | UPLC (C) Ret. time (min) (LC-MS method) |
|---------|-----------|------------|----------|------------------------------------------|
| 178 | 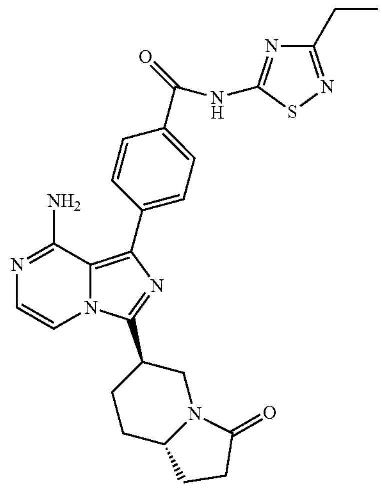 [SMILES: CCc1nsc(NC(=O)c2ccc(-c3nc([C@@H]4CC[C@H]5CCC(=O)N5C4)n4ccnc(N)c34)cc2)n1] | 4-{8-amino-3-[(6R,8aS)-3-oxooctahydroindolizin-6-yl]imidazo[1,5-a]pyrazin-1-yl}-N-(3-ethyl-1,2,4-thiadiazol-5-yl)benzamide | 503.34 | 2.33 (A) |
| 179 | 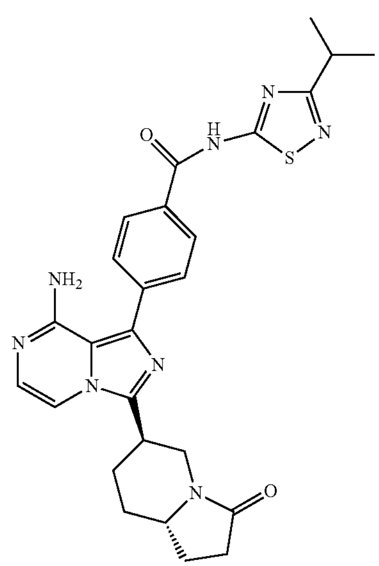 [SMILES: CC(C)c1nsc(NC(=O)c2ccc(-c3nc([C@@H]4CC[C@H]5CCC(=O)N5C4)n4ccnc(N)c34)cc2)n1] | 4-{8-amino-3-[(6R,8aS)-3-oxooctahydroindolizin-6-yl]imidazo[1,5-a]pyrazin-1-yl}-N-[3-(1-methylethyl)-1,2,4-thiadiazol-5-yl]benzamide | 517.33 | 2.68 (A) |

TABLE 4-continued
| Example | Structure | IUPAC Name | (M)+ m/z | UPLC (C) Ret. time (min) (LC-MS method) |
|---|---|---|---|---|
| 180 | 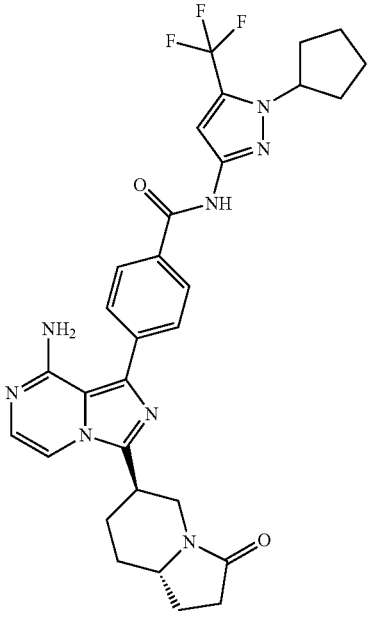 [SMILES: Nc1nccn2c([C@@H]3CC[C@H]4CCC(=O)N4C3)nc(-c3ccc(C(=O)Nc4cc(C(F)(F)F)n(C5CCCC5)n4)cc3)c12] | 4-{8-amino-3-[(6R,8aS)-3-oxooctahydroindolizin-6-yl]imidazo[1,5-a]pyrazin-1-yl}-N-[1-cyclopentyl-5-(trifluoromethyl)-1H-pyrazol-3-yl]benzamide | 593.50 | 2.97 (A) |
| 181 | 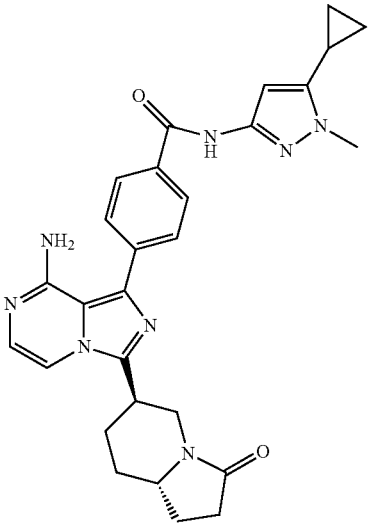 [SMILES: Cn1nc(NC(=O)c2ccc(-c3nc([C@@H]4CC[C@H]5CCC(=O)N5C4)n4ccnc(N)c34)cc2)cc1C1CC1] | 4-{8-amino-3-[(6R,8aS)-3-oxooctahydroindolizin-6-yl]imidazo[1,5-a]pyrazin-1-yl}-N-(5-cyclopropyl-1-methyl-1H-pyrazol-3-yl)benzamide | 511.25 | 3.09 (A) |

TABLE 4-continued

| Example | Structure | IUPAC Name | (M)+ m/z | UPLC (C) Ret. time (min) (LC-MS method) |
|---|---|---|---|---|
| 182 | 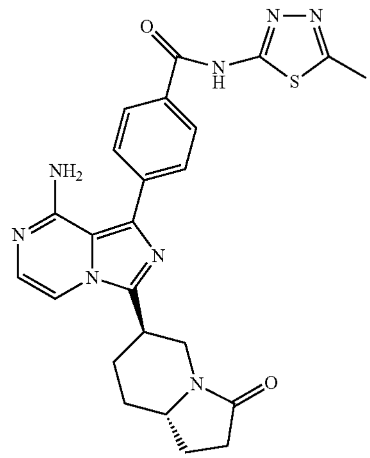 [SMILES: Cc1nnc(NC(=O)c2ccc(-c3nc([C@@H]4CC[C@H]5CCC(=O)N5C4)n4ccnc(N)c34)cc2)s1] | 4-{8-amino-3-[(6R,8aS)-3-oxooctahydroindolizin-6-yl]imidazo[1,5-a]pyrazin-1-yl}-N-(5-methyl-1,3,4-thiadiazol-2-yl)benzamide | 489.27 | 2.19 (A) |

Example 183

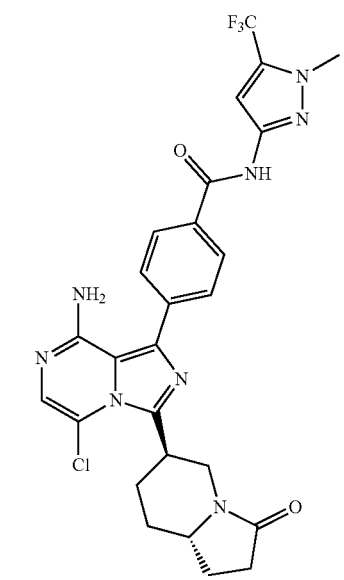 [SMILES: Cn1nc(NC(=O)c2ccc(-c3nc([C@@H]4CC[C@H]5CCC(=O)N5C4)n4c(Cl)cnc(N)c34)cc2)cc1C(F)(F)F]

4-(8-amino-5-chloro-3-((6R,8aS)-3-oxooctahydroindolizin-6-yl)imidazo[1,5-a]pyrazin-1-yl)-N-(1-methyl-5-(trifluoromethyl)-1H-pyrazol-3-yl)benzamide Step 1: (4-((1-methyl-5-(trifluoromethyl)-1H-pyrazol-3-yl)carbamoyl)phenyl)boronic acid 1-methyl-5-(trifluoromethyl)-1H-pyrazol-3-amine (66.6 mg, 0.403 mmol), N-ethyl-N-isopropylpropan-2-amine (0.141 ml, 0.806 mmol), 2-(3H-[1,2,3]triazolo[4,5-b]pyridin-3-yl)-1,1,3,3-tetramethylisouronium hexafluorophosphate(V) (153 mg, 0.403 mmol) were added to the reaction vial with 4-(4,4,5,5-tetramethyl-1,3,2-dioxaborolan-2-yl)benzoic acid (100 mg, 0.403 mmol) and stirred at room temperature in DMF (2 ml) for 15 hours. Reaction mixture was separated on flash LC on 12 g column (Hexane/EtOAc) to give (4-((1-methyl-5-(trifluoromethyl)-1H-pyrazol-3-yl)carbamoyl)phenyl)boronic acid (112 mg, 0.358 mmol, 89% yield). LC-MS: LC-MS method A, RET. TIME=2.72 min., MS found M+ $^{m/z}$=341.13.

Step 2: 4-(8-amino-5-chloro-3-((6R,8aS)-3-oxooctahydroindolizin-6-yl)imidazo[1,5-a]pyrazin-1-yl)-N-(1-methyl-5-(trifluoromethyl)-1H-pyrazol-3-yl)benzamide (6R,8aS)-6-(8-amino-1-bromo-5-chloroimidazo[1,5-a]pyrazin-3-yl)hexahydroindolizin-3(2H)-one (50 mg, 0.130 mmol), 4-((1-methyl-5-(trifluoromethyl)-1H-pyrazol-3-yl)carbamoyl)phenyl)boronic acid (40.7 mg, 0.130 mmol), POTASSIUM CARBONATE (53.9 mg, 0.390 mmol), 1,1'-BIS(DIPHENYLPHOSPHINO)FERROCENE-PALLADIUM(II)DICHLORIDE DICHLOROMETHANE COMPLEX (10.62 mg, 0.013 mmol) were mixed in Dioxane (10 ml) and Water (2 ml) in pressure vial, degassed and stirred at 90° C. for 2 hours. Product was separated on prep HPLC to give 4-(8-amino-5-chloro-3-((6R,8aS)-3-oxooctahydroindolizin-6-yl)imidazo[1,5-a]pyrazin-1-yl)-N-(1-methyl-5-(trifluoromethyl)-1H-pyrazol-3-yl)benzamide, 3TFA (18 mg, 0.019 mmol, 14.38% yield). LC-MS: LC-MS method A, RET. TIME=2.59 min., MS found (M)+ m/z=573.32.

The Examples in Table 5 below were synthesized following the methods described for Example 183 using corresponding aromaticamine and benzoic acids for step 1. The Suzuki coupling of the formed boronic with bromointermediates provide the products.

TABLE 5
| Example | Structure | IUPAC Name | (M)+ m/z | UPLC (C) Ret. time (min) (LC-MS method) |
|---|---|---|---|---|
| 184 | 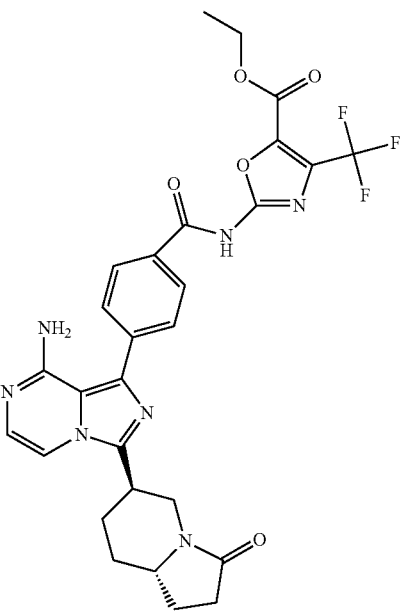 [SMILES: CCOC(=O)c1oc(NC(=O)c2ccc(-c3nc([C@@H]4CC[C@H]5CCC(=O)N5C4)n4ccnc(N)c34)cc2)nc1C(F)(F)F] | ethyl 2-{[(4-{8-amino-3-[(6R,8aS)-3-oxooctahydroindolizin-6-yl]imidazo[1,5-a]pyrazin-1-yl}phenyl)carbonyl]amino}-4-(trifluoromethyl)-1,3-oxazole-5-carboxylate | 598.43 | 2.64 (A) |
| 185 | 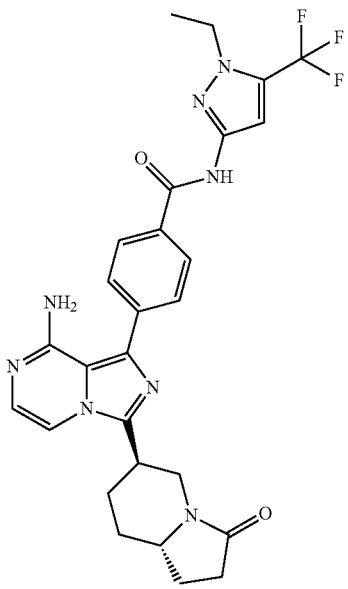 [SMILES: CCn1nc(NC(=O)c2ccc(-c3nc([C@@H]4CC[C@H]5CCC(=O)N5C4)n4ccnc(N)c34)cc2)cc1C(F)(F)F] | 4-{8-amino-3-[(6R,8aS)-3-oxooctahydroindolizin-6-yl]imidazo[1,5-a]pyrazin-1-yl}-N-[1-ethyl-5-(trifluoromethyl)-1H-pyrazol-3-yl]benzamide | 553.41 | 2.51 (A) |

TABLE 5-continued
| Example | Structure | IUPAC Name | (M)+ m/z | UPLC (C) Ret. time (min) (LC-MS method) |
|---|---|---|---|---|
| 186 | 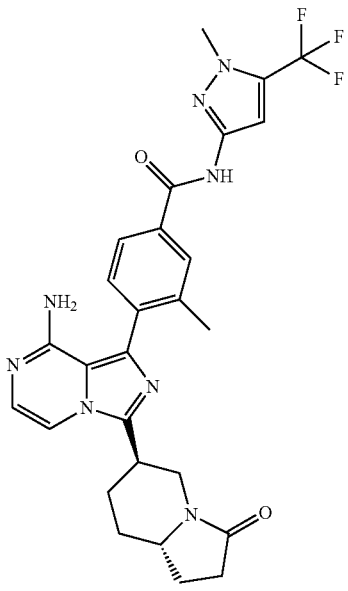 [SMILES: Cc1cc(C(=O)Nc2cc(C(F)(F)F)n(C)n2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-methyl-N-[1-methyl-5-(trifluoromethyl)-1H-pyrazol-3-yl]benzamide | 553.42 | 2.58 (A) |
| 187 | 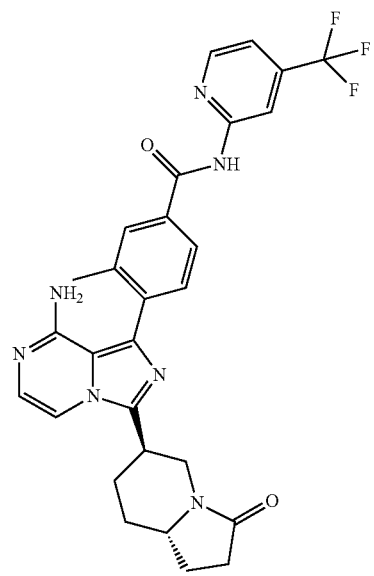 [SMILES: Cc1cc(C(=O)Nc2cc(C(F)(F)F)ccn2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-methyl-N-[4-(trifluoromethyl)pyridin-2-yl]benzamide | 550.41 | 2.70 (A) |

TABLE 5-continued

| Example | Structure | IUPAC Name | (M)+ m/z | UPLC (C) Ret. time (min) (LC-MS method) |
|---|---|---|---|---|
| 188 | 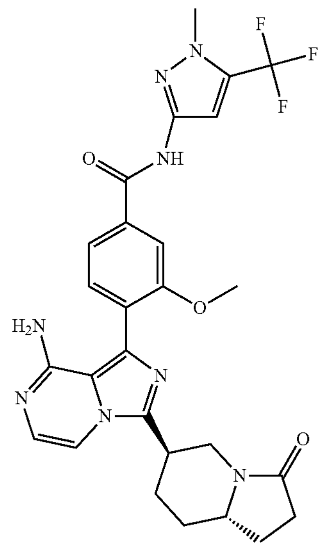 [SMILES: COc1cc(C(=O)Nc2cc(C(F)(F)F)n(C)n2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-methoxy-N-[1-methyl-5-(trifluoromethyl)-1H-pyrazol-3-yl]benzamide | 569.45 | 2.53 (A) |
| 189 | 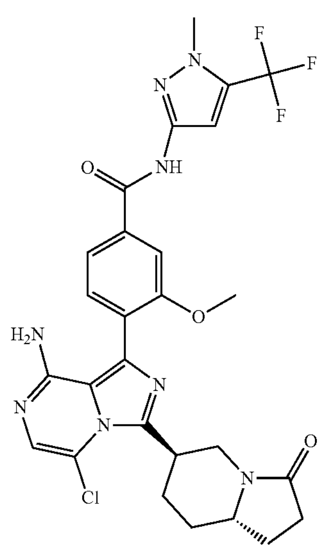 [SMILES: COc1cc(C(=O)Nc2cc(C(F)(F)F)n(C)n2)ccc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-3-methoxy-N-[1-methyl-5-(trifluoromethyl)-1H-pyrazol-3-yl]benzamide | 603.34 | 2.73 (A) |

TABLE 5-continued
| Example | Structure | IUPAC Name | (M)+ m/z | UPLC (C) Ret. time (min) (LC-MS method) |
|---|---|---|---|---|
| 190 | 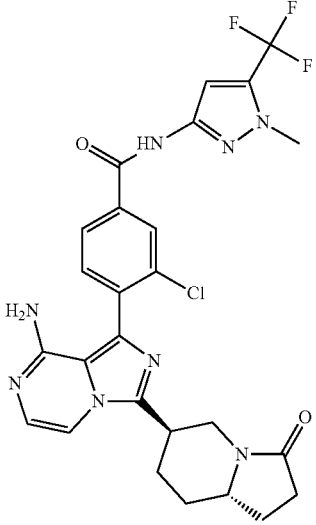 [SMILES: Cn1nc(NC(=O)c2ccc(-c3nc([C@@H]4CC[C@H]5CCC(=O)N5C4)n4ccnc(N)c34)c(Cl)c2)cc1C(F)(F)F] | 4-{8-amino-3-[(6R,8aS)-3-oxooctahydroindolizin-6-yl]imidazo[1,5-a]pyrazin-1-yl}-3-chloro-N-[1-methyl-5-(trifluoromethyl)-1H-pyrazol-3-yl]benzamide | 573.44 | 2.57 (A) |
| 191 | 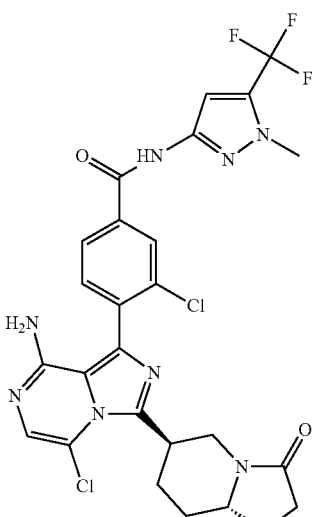 | 4-{8-amino-5-chloro-3-[(6R,8aS)-3-oxooctahydroindolizin-6-yl]imidazo[1,5-a]pyrazin-1-yl}-3-chloro-N-[1-methyl-5-(trifluoromethyl)-1H-pyrazol-3-yl]benzamide | 607.44 | 2.73 (A) |

TABLE 5-continued
| Example | Structure | IUPAC Name | (M)+ m/z | UPLC (C) Ret. time (min) (LC-MS method) |
|---|---|---|---|---|
| 192 | 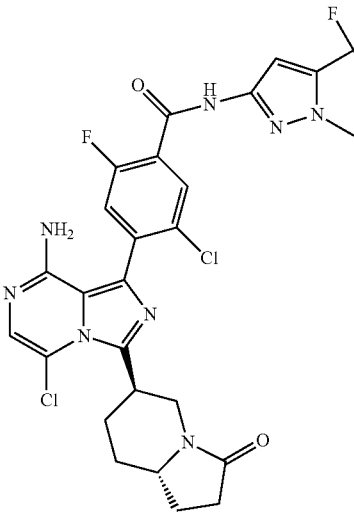 | 4-{8-amino-5-chloro-3-[(6R,8aS)-3-oxooctahydroindolizin-6-yl]imidazo[1,5-a]pyrazin-1-yl}-5-chloro-2-fluoro-N-[1-methyl-5-(trifluoromethyl)-1H-pyrazol-3-yl]benzamide | 625.40 | 2.83 (A) |
| 193 | 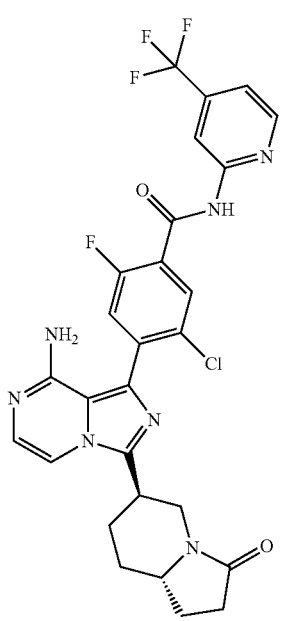 | 4-{8-amino-3-[(6R,8aS)-3-oxooctahydroindolizin-6-yl]imidazo[1,5-a]pyrazin-1-yl}-5-chloro-2-fluoro-N-[4-(trifluoromethyl)pyridin-2-yl]benzamide | 588.36 | 2.80 (A) |

TABLE 5-continued
| Example | Structure | IUPAC Name | (M)+ m/z | UPLC (C) Ret. time (min) (LC-MS method) |
|---|---|---|---|---|
| 194 | 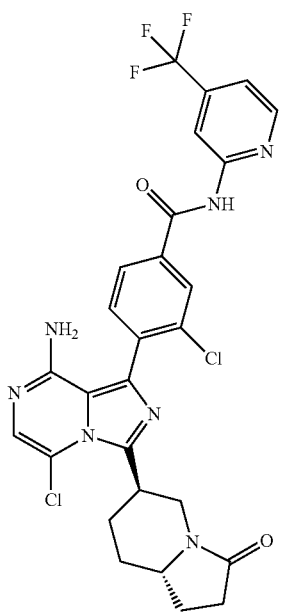 [SMILES: Nc1ncc(Cl)n2c([C@@H]3CC[C@H]4CCC(=O)N4C3)nc(-c3ccc(C(=O)Nc4cc(C(F)(F)F)ccn4)cc3Cl)c12] | 4-{8-amino-5-chloro-3-[(6R,8aS)-3-oxooctahydroindolizin-6-yl]imidazo[1,5-a]pyrazin-1-yl}-3-chloro-N-[4-(trifluoromethyl)pyridin-2-yl]benzamide | 604.04 | 2.89 (A) |
| 195 | 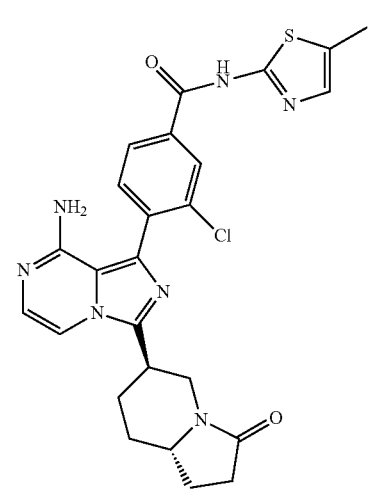 [SMILES: Cc1cnc(NC(=O)c2ccc(-c3nc([C@@H]4CC[C@H]5CCC(=O)N5C4)n4ccnc(N)c34)c(Cl)c2)s1] | 4-(8-amino-3-((6R,8aS)-3-oxooctahydroindolizin-6-yl)imidazo[1,5-a]pyrazin-1-yl)-3-chloro-N-(5-methylthiazol-2-yl)benzamide | 522.27 | 2.39 (A) |

TABLE 5-continued
| Example | Structure | IUPAC Name | (M)+ m/z | UPLC (C) Ret. time (min) (LC-MS method) |
|---|---|---|---|---|
| 196 | 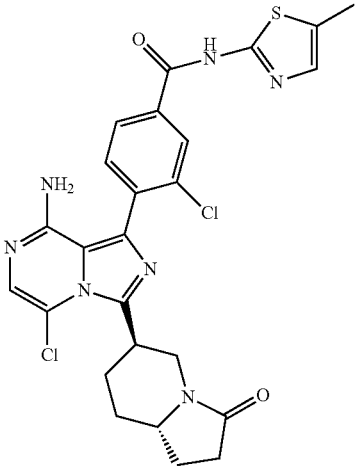 [SMILES: Cc1cnc(NC(=O)c2ccc(-c3nc([C@@H]4CC[C@H]5CCC(=O)N5C4)n4c(Cl)cnc(N)c34)c(Cl)c2)s1] | 4-(8-amino-5-chloro-3-((6R,8aS)-3-oxooctahydroindolizin-6-yl)imidazo[1,5-a]pyrazin-1-yl)-3-chloro-N-(5-methylthiazol-2-yl)benzamide | 556.27 | 2.57 (A) |
| 197 | 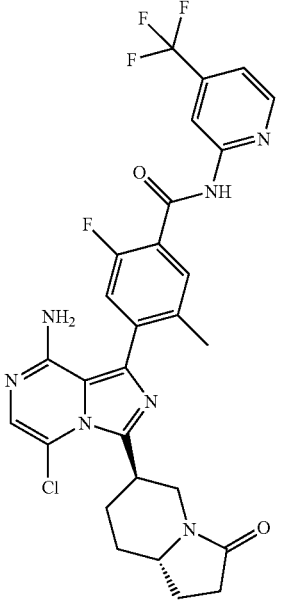 [SMILES: Cc1cc(C(=O)Nc2cc(C(F)(F)F)ccn2)c(F)cc1-c1nc([C@@H]2CC[C@H]3CCC(=O)N3C2)n2c(Cl)cnc(N)c12] | 4-(8-amino-5-chloro-3-((6R,8aS)-3-oxooctahydroindolizin-6-yl)imidazo[1,5-a]pyrazin-1-yl)-2-fluoro-5-methyl-N-(4-(trifluoromethyl)pyridin-2-yl)benzamide | 602.41 | 2.92 (A) |

TABLE 5-continued

| Example | Structure | IUPAC Name | (M)+ m/z | UPLC (C) Ret. time (min) (LC-MS method) |
|---|---|---|---|---|
| 198 | 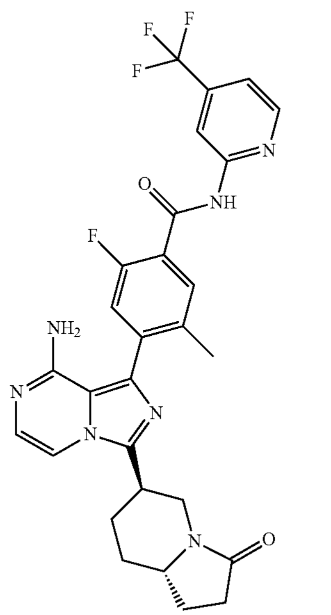 [SMILES: Cc1cc(C(=O)Nc2cc(C(F)(F)F)ccn2)c(F)cc1-c1nc([C@@H]2CC[C@H]3CCC(=O)N3C2)n2ccnc(N)c12] | 4-(8-amino-3-((6R,8aS)-3-oxooctahydroindolizin-6-yl)imidazo[1,5-a]pyrazin-1-yl)-2-fluoro-5-methyl-N-(4-(trifluoromethyl)pyridin-2-yl)benzamide | 568.44 | 2.75 (A) |

Example 199

4-(8-amino-3-((6R,8aS)-3-oxooctahydroindolizin-6-yl)imidazo[1,5-a]pyrazin-1-yl)-3-(2-methoxyethoxy)-N-(3-(trifluoromethyl)phenyl)benzamide Step 1: 4-(8-((2,4-dimethoxybenzyl)amino)-3-((6R,8aS)-3-oxooctahydroindolizin-6-yl)imidazo[1,5-a]pyrazin-1-yl)-3-hydroxy-N-(4-(trifluoromethyl)pyridin-2-yl)benzamide (2-hydroxy-4-((4-(trifluoromethyl)pyridin-2-yl)carbamoyl)phenyl)boronic acid (1.303 g, 4.00 mmol), (6R,8aS)-6-(1-bromo-8-((2,4-dimethoxybenzyl)amino)imidazo[1,5-a]pyrazin-3-yl)hexahydroindolizin-3(2H)-one (1.00 g, 2.00 mmol), potassium phosphate (1.061 g, 5.00 mmol) and Pd(pddf)Cl$_2$ (0.163 g, 0.200 mmol) were stirred in a RBF charged with 1,4-dioxane (40 ml) and water (10 ml). The reaction mixture was degased three times under nitrogen gas atmosphere, and heated at 85° C. for 2 hours, LCMS showed 50% conversion. More boronic acid (1.00 g) was added to the reaction and stirred overnight at 85° C. The reaction mixture was filtered and concentrated to provided a crude, which was purified on Isco (80 g cartridge, 3% MeOH (2 N ammonia) in methylene chloride) to give the desired product, 4-(8-((2,4-dimethoxybenzyl)amino)-3-((6R,8aS)-3-oxooctahydroindolizin-6-yl)imidazo[1,5-a]pyrazin-1-yl)-3-hydroxy-N-(4-(trifluoromethyl)pyridin-2-yl)benzamide, 0.627 g, 44.7%), LCMS showed M+H at 702.

Step 2: 4-(8-((2,4-dimethoxybenzyl)amino)-3-((6R,8aS)-3-oxooctahydroindolizin-6-yl)imidazo[1,5-a]pyrazin-1-yl)-3-(2-methoxyethoxy)-N-(3-(trifluoromethyl)phenyl)benzamide To a 20 ml sample vial was charged with 4-(8-((2,4-dimethoxybenzyl)amino)-3-((6R,8aS)-3-oxooctahydroindolizin-6-yl)imidazo[1,5-a]pyrazin-1-yl)-3-hydroxy-N-(4-(trifluoromethyl)pyridin-2-yl)benzamide (25 mg, 0.036 mmol), cesium carbonate (0.072 mmol) and 1-bromo-2-methoxyethane (5 mg, 0.036 mmol) in dioxane (1 mL), The mixture was stirred and heated in oil bath of 80° C. overnight. The rxn mixture, with 4-(8-((2,4-dimethoxybenzyl)amino)-3-((6R,8aS)-3-oxooctahydroindolizin-6-yl)imidazo[1,5-a]pyrazin-1-yl)-3-(2-methoxyethoxy)-N-(4-(trifluoromethyl)pyridin-2-yl)benzamide (27 mg, 0.036 mmol, 100% yield) was carried on to next step. LC-MS: C40H41F3N6O6, found [M+H]+: 760.

Step 3: 4-(8-amino-3-((6R,8aS)-3-oxooctahydroindolizin-6-yl)imidazo[1,5-a]pyrazin-1-yl)-3-(2-methoxyethoxy)-N-(3-(trifluoromethyl)phenyl)benzamide TFA (5 ml) and TRIETHYLSILANE (0.057 ml, 0.355 mmol) was added to the rxn mixture of step 2, 4-(8-((2,4-dimethoxybenzyl)amino)-3-((6R,8aS)-3-oxooctahydroindolizin-6-yl)imidazo[1,5-a]pyrazin-1-yl)-3-(2-methoxyethoxy)-N-(4-(trifluoromethyl)pyridin-2-yl)benzamide (27 mg, 0.036 mmol) and the mixture was stirred at 90° C. for 2 h. The mixture was rotovaped to dryness, purified by flash chrom (Isco, 10% M, N/D) gave 4-(8-amino-3-((6R,8aS)-3-oxooctahydroindolizin-6-yl)imidazo[1,5-a]pyrazin-1-yl)-3-(2-methoxyethoxy)-N-(4-(trifluoromethyl)pyridin-2-yl)benzamide (16 mg, 0.026 mmol, 73.9% yield). LC-MS: C31H31F3N6O4, found [M+H]+ 610.

The Examples set forth in Table 6 below were prepared using the same chemistry described for Example 115 and corresponding intermediates through Suzuki coupling reaction.

TABLE 6

| Example | Structure | IUPAC Name | Exact Mass [M + H]+ | Retention time (min) (LS-MS method) |
|---|---|---|---|---|
| 200 | 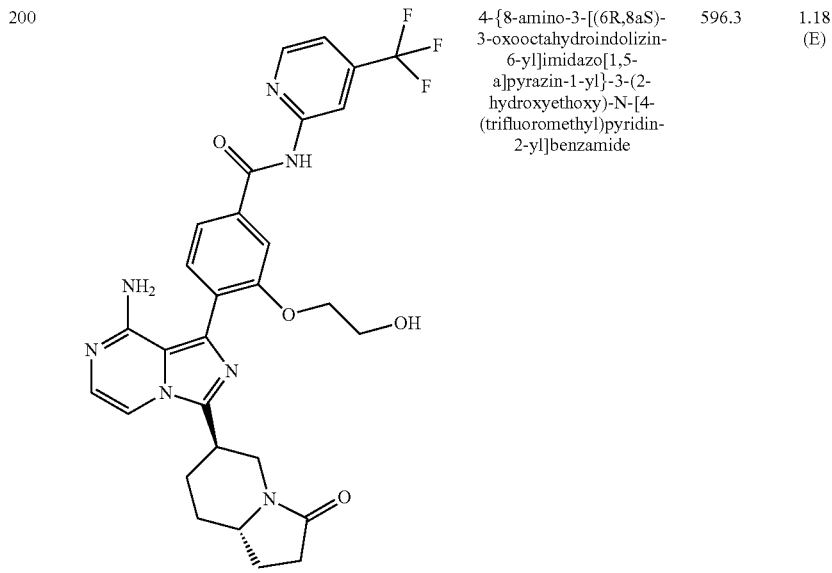 | 4-{8-amino-3-[(6R,8aS)-3-oxooctahydroindolizin-6-yl]imidazo[1,5-a]pyrazin-1-yl}-3-(2-hydroxyethoxy)-N-[4-(trifluoromethyl)pyridin-2-yl]benzamide | 596.3 | 1.18 (E) |

TABLE 6-continued
| Example | Structure | IUPAC Name | Exact Mass [M + H]+ | Retention time (min) (LS-MS method) |
|---|---|---|---|---|
| 201 | 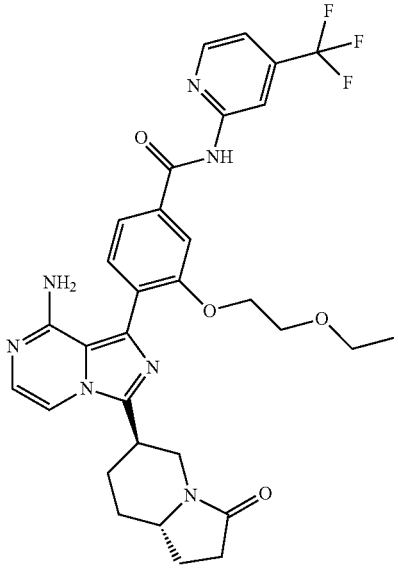 [SMILES: CCOCCOc1cc(C(=O)Nc2cc(C(F)(F)F)ccn2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-(2-ethoxyethoxy)-N-[4-(trifluoromethyl)pyridin-2-yl]benzamide | 624.3 | 1.25 (E) |
| 202 | 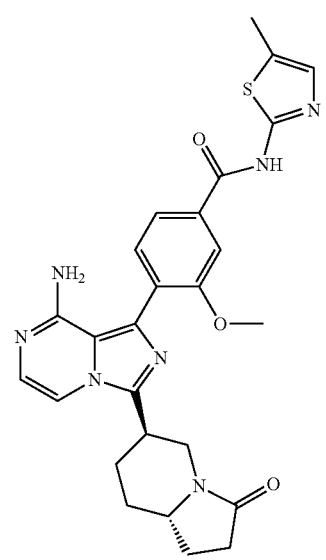 [SMILES: COc1cc(C(=O)Nc2ncc(C)s2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-methoxy-N-(5-methyl-1,3-thiazol-2-yl)benzamide | 518.2 | 1.15 (E) |

TABLE 6-continued

| Example | Structure | IUPAC Name | Exact Mass [M + H]+ | Retention time (min) (LS-MS method) |
|---|---|---|---|---|
| 203 | 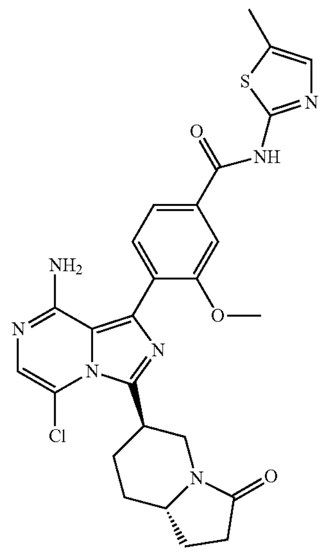 [SMILES: COc1cc(C(=O)Nc2ncc(C)s2)ccc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-3-methoxy-N-(5-methyl-1,3-thiazol-2-yl)benzamide | 552.2 | 1.15 (E) |
| 204 | 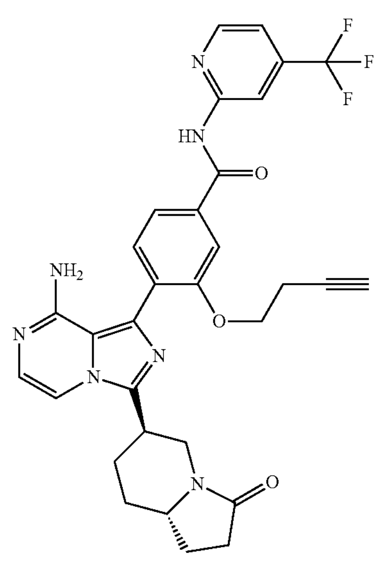 [SMILES: C#CCCOc1cc(C(=O)Nc2cc(C(F)(F)F)ccn2)ccc1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-(but-3-yn-1-yloxy)-N-[4-(trifluoromethyl)pyridin-2-yl]benzamide | 604.2 | 1.02 (E) |

TABLE 6-continued

| Example | Structure | IUPAC Name | Exact Mass [M + H]+ | Retention time (min) (LS-MS method) |
|---------|-----------|------------|---------------------|--------------------------------------|
| 205 | 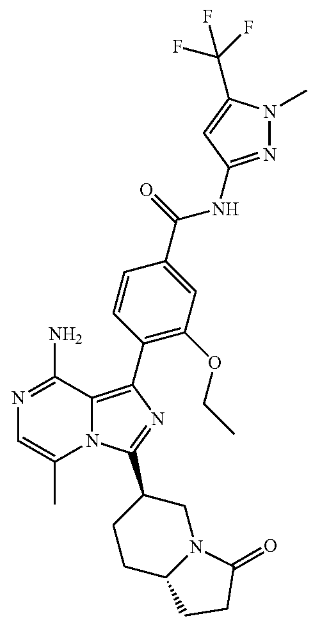 [SMILES: CCOc1cc(C(=O)Nc2cc(C(F)(F)F)n(C)n2)ccc1-c1nc([C@@H]2CC[C@H]3CCC(=O)N3C2)n2c(C)cnc(N)c12] | 4-{8-amino-5-methyl-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide | 597.3 | 2.18 (A) |
| 206 | 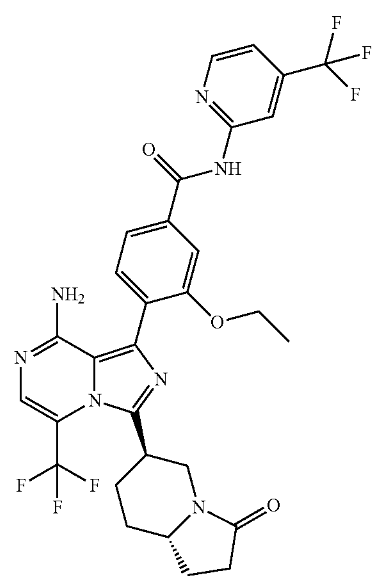 [SMILES: CCOc1cc(C(=O)Nc2cc(C(F)(F)F)ccn2)ccc1-c1nc([C@@H]2CC[C@H]3CCC(=O)N3C2)n2c(C(F)(F)F)cnc(N)c12] | 4-{8-amino-3-[(6R,8aS)-3-oxooctahydroindolizin-6-yl]-5-(trifluoromethyl)imidazo-[1,5-a]pyrazin-1-yl}-3-ethoxy-N-[4-(trifluoromethyl)pyridin-2-yl]benzamide | 648.4 | 1.29 (E) |

TABLE 6-continued

| Example | Structure | IUPAC Name | Exact Mass [M + H]+ | Retention time (min) (LS-MS method) |
|---|---|---|---|---|
| 207 | 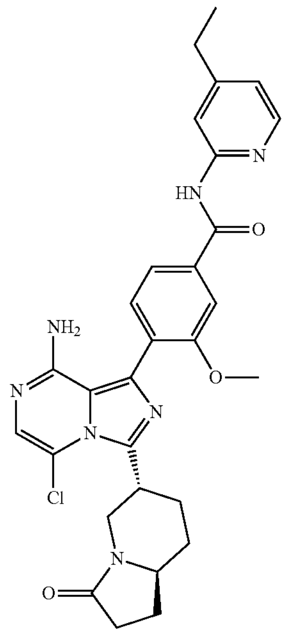 [SMILES: CCc1ccnc(NC(=O)c2ccc(-c3nc([C@@H]4CC[C@H]5CCC(=O)N5C4)n4c(Cl)cnc(N)c34)c(OC)c2)c1] | 4-{8-amino-5-chloro-3-[(6R,8aS)-3-oxooctahydroindolizin-6-yl]imidazo[1,5-a]pyrazin-1-yl}-N-(4-ethylpyridin-2-yl)-3-methoxybenzamide | 560.2 | 0.77 (F) |
| 208 | 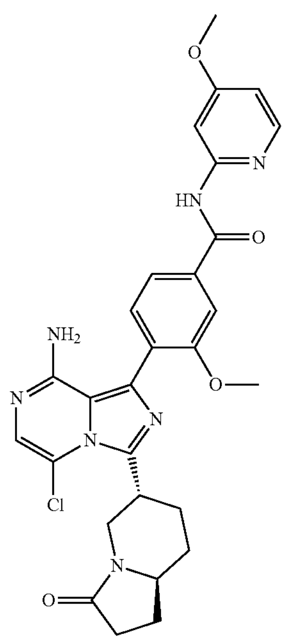 [SMILES: COc1ccnc(NC(=O)c2ccc(-c3nc([C@@H]4CC[C@H]5CCC(=O)N5C4)n4c(Cl)cnc(N)c34)c(OC)c2)c1] | 4-{8-amino-5-chloro-3-[(6R,8aS)-3-oxooctahydroindolizin-6-yl]imidazo[1,5-a]pyrazin-1-yl}-3-methoxy-N-(4-methoxypyridin-2-yl)benzamide | 562.2 | 0.69 (F) |

TABLE 6-continued

| Example | Structure | IUPAC Name | Exact Mass [M + H]+ | Retention time (min) (LS-MS method) |
|---------|-----------|------------|---------------------|--------------------------------------|
| 209 | 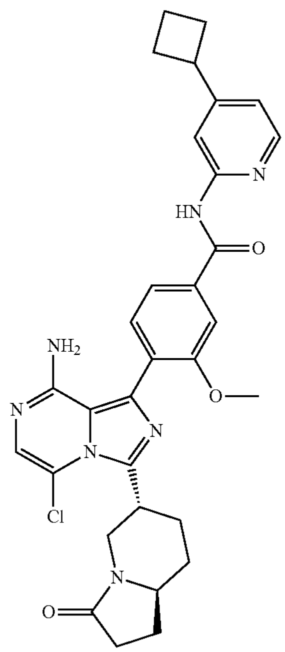 [SMILES: COc1cc(C(=O)Nc2cc(C3CCC3)ccn2)ccc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-N-(4-cyclobutylpyridin-2-yl)-3-methoxybenzamide | 586.2 | 0.86 (F) |
| 210 | 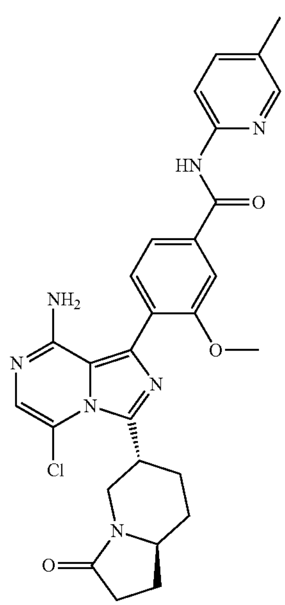 [SMILES: COc1cc(C(=O)Nc2ccc(C)cn2)ccc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-3-methoxy-N-(5-methylpyridin-2-yl)benzamide | 562.2 | 0.70 (F) |

TABLE 6-continued
| Example | Structure | IUPAC Name | Exact Mass [M + H]+ | Retention time (min) (LS-MS method) |
|---|---|---|---|---|
| 211 | 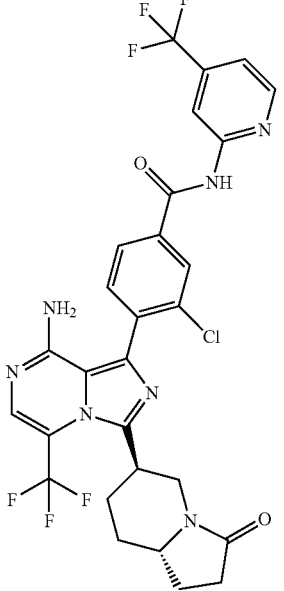 | 4-{8-amino-3-[(6R,8aS)-3-oxooctahydroindolizin-6-yl]-5-(trifluoromethyl)imidazo-[1,5-a]pyrazin-1-yl}-3-chloro-N-[4-(trifluoromethyl)pyridin-2-yl]benzamide | 638.2 | 1.20 (E) |
| 212 | 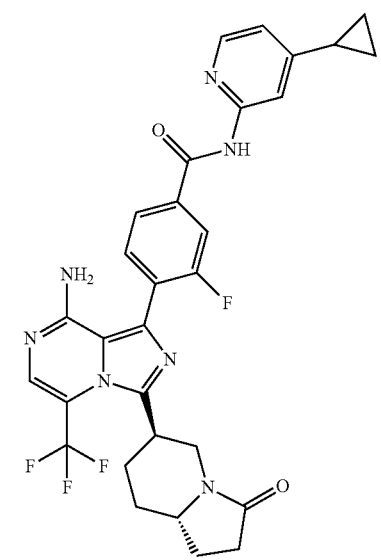 [SMILES: Nc1ncc(C(F)(F)F)n2c([C@@H]3CC[C@H]4CCC(=O)N4C3)nc(-c3ccc(C(=O)Nc4cc(C5CC5)ccn4)cc3F)c12] | 4-{8-amino-3-[(6R,8aS)-3-oxooctahydroindolizin-6-yl]-5-(trifluoromethyl)imidazo-[1,5-a]pyrazin-1-yl}-N-(4-cyclopropylpyridin-2-yl)-3-fluorobenzamide | 594.2 | 1.19 (E) |

TABLE 6-continued

| Example | Structure | IUPAC Name | Exact Mass [M + H]+ | Retention time (min) (LS-MS method) |
|---|---|---|---|---|
| 213 | 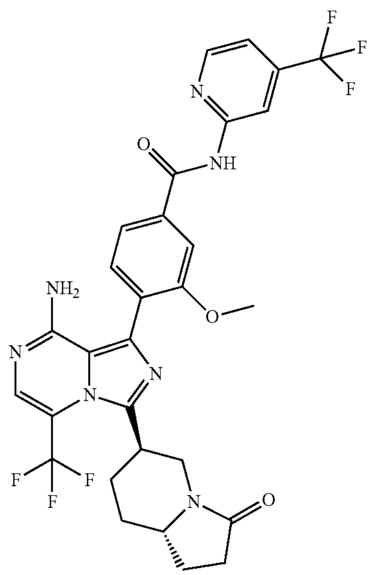 [SMILES: COc1cc(C(=O)Nc2cc(C(F)(F)F)ccn2)ccc1-c1nc([C@@H]2CC[C@H]3CCC(=O)N3C2)n2c(C(F)(F)F)cnc(N)c12] | 4-{8-amino-3-[(6R,8aS)-3-oxooctahydroindolizin-6-yl]-5-(trifluoromethyl)imidazo-[1,5-a]pyrazin-1-yl}-3-methoxy-N-[4-(trifluoromethyl)pyridin-2-yl]benzamide | 634.2 | 1.34 (E) |
| 214 | 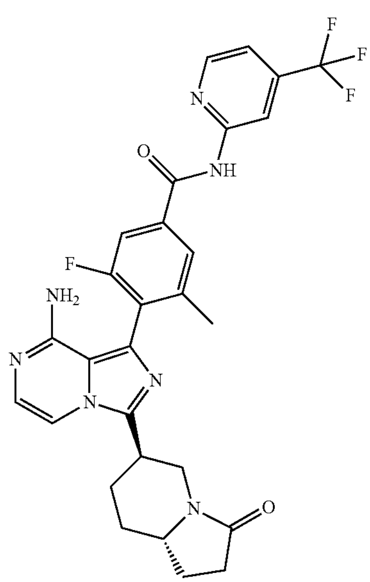 [SMILES: Cc1cc(C(=O)Nc2cc(C(F)(F)F)ccn2)cc(F)c1-c1nc([C@@H]2CC[C@H]3CCC(=O)N3C2)n2ccnc(N)c12] | 4-{8-amino-3-[(6R,8aS)-3-oxooctahydroindolizin-6-yl]imidazo[1,5-a]pyrazin-1-yl}-3-fluoro-5-methyl-N-[4-(trifluoromethyl)pyridin-2-yl]benzamide | 568.4 | 2.74 (A) |

TABLE 6-continued

| Example | Structure | IUPAC Name | Exact Mass [M + H]+ | Retention time (min) (LS-MS method) |
|---------|-----------|------------|---------------------|--------------------------------------|
| 215 | 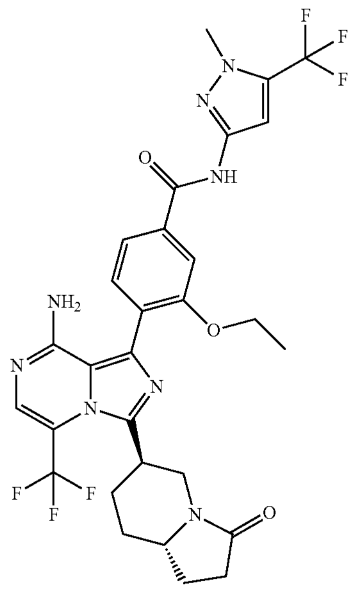 [SMILES: CCOc1cc(C(=O)Nc2cc(C(F)(F)F)n(C)n2)ccc1-c1nc([C@@H]2CC[C@H]3CCC(=O)N3C2)n2c(C(F)(F)F)cnc(N)c12] | 4-{8-amino-3-[(6R,8aS)-3-oxooctahydroindolizin-6-yl]-5-(trifluoromethyl)imidazo-[1,5-a]pyrazin-1-yl}-3-ethoxy-N-[1-methyl-5-(trifluoromethyl)-1H-pyrazol-3-yl]benzamide | 651.2 | 0.94 (E) |
| 216 | 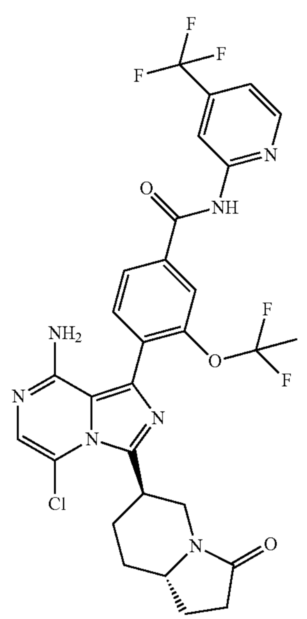 [SMILES: CC(F)(F)Oc1cc(C(=O)Nc2cc(C(F)(F)F)ccn2)ccc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-3-(1,1-difluoroethoxy)-N-[4-(trifluoromethyl)pyridin-2-yl]benzamide | 650.2 | 2.31 (A) |

TABLE 6-continued

| Example | Structure | IUPAC Name | Exact Mass [M + H]+ | Retention time (min) (LS-MS method) |
|---|---|---|---|---|
| 217 | 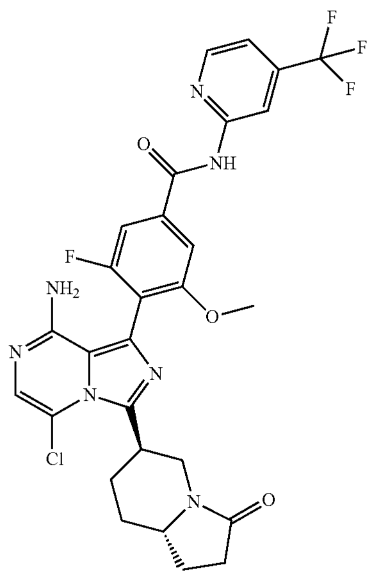 [SMILES: COc1cc(C(=O)Nc2cc(C(F)(F)F)ccn2)cc(F)c1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-3-fluoro-5-methoxy-N-[4-(trifluoromethyl)pyridin-2-yl]benzamide | 618.3 | 2.78 (A) |
| 218 | 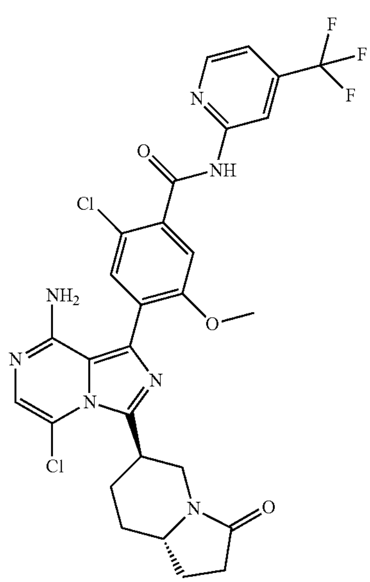 [SMILES: COc1cc(C(=O)Nc2cc(C(F)(F)F)ccn2)c(Cl)cc1-c1nc([C@@H]2CC[C@H]3CCC(=O)N3C2)n2c(Cl)cnc(N)c12] | 4-{8-amino-5-chloro-3-[(6R,8aS)-3-oxooctahydroindolizin-6-yl]imidazo[1,5-a]pyrazin-1-yl}-2-chloro-5-methoxy-N-[4-(trifluoromethyl)pyridin-2-yl]benzamide | 634.2 | 2.86 (A) |

TABLE 6-continued

| Example | Structure | IUPAC Name | Exact Mass [M + H]+ | Retention time (min) (LS-MS method) |
|---|---|---|---|---|
| 219 | 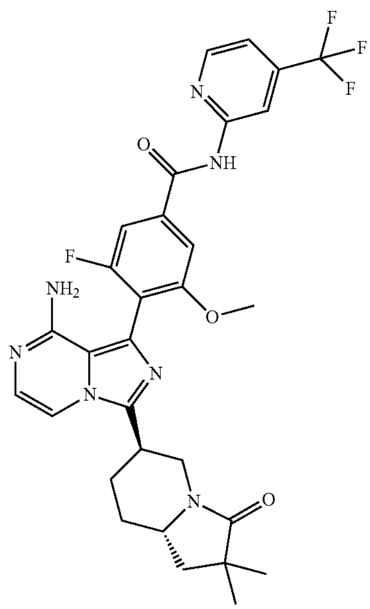 [SMILES: COc1cc(C(=O)Nc2cc(C(F)(F)F)ccn2)cc(F)c1-c1nc([C@@H]2CC[C@H]3CC(C)(C)C(=O)N3C2)n2ccnc(N)c12] | 4-{8-amino-3-[(6R,8aS)-2,2-dimethyl-3-oxooctahydroindolizin-6-yl]imidazo[1,5-a]pyrazin-1-yl}-3-fluoro-5-methoxy-N-[4-(trifluoromethyl)pyridin-2-yl]benzamide | 612.2 | 3.25 (A) |
| 220 | 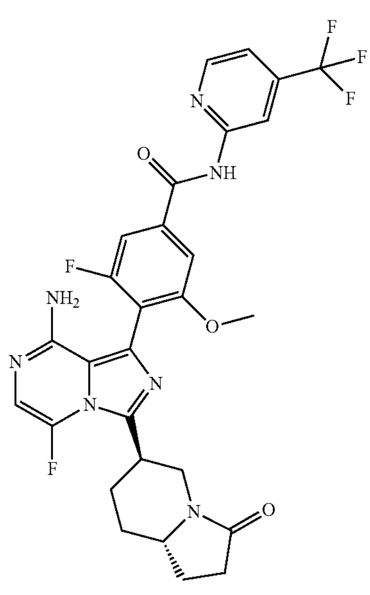 [SMILES: COc1cc(C(=O)Nc2cc(C(F)(F)F)ccn2)cc(F)c1-c1nc([C@@H]2CC[C@H]3CCC(=O)N3C2)n2c(F)cnc(N)c12] | 4-{8-amino-5-fluoro-3-[(6R,8aS)-3-oxooctahydroindolizin-6-yl]imidazo[1,5-a]pyrazin-1-yl}-3-fluoro-5-methoxy-N-[4-(trifluoromethyl)pyridin-2-yl]benzamide | 602.2 | 3.15 (A) |

TABLE 6-continued

| Example | Structure | IUPAC Name | Exact Mass [M + H]+ | Retention time (min) (LS-MS method) |
|---|---|---|---|---|
| 221 | 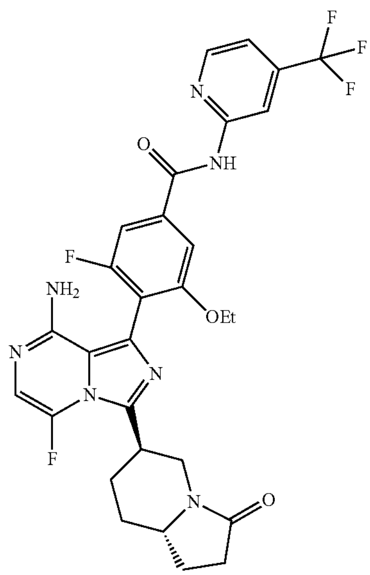 [SMILES: CCOc1cc(C(=O)Nc2cc(C(F)(F)F)ccn2)cc(F)c1-c1nc([C@@H]2CC[C@H]3CCC(=O)N3C2)n2c(F)cnc(N)c12] | 4-(8-amino-5-fluoro-3-((6R,8aS)-3-oxooctahydroindolizin-6-yl)imidazo[1,5-a]pyrazin-1-yl)-3-ethoxy-5-fluoro-N-(4-(trifluoromethyl)pyridin-2-yl)benzamide | 616.2 | 2.63 (A) |
| 222 | 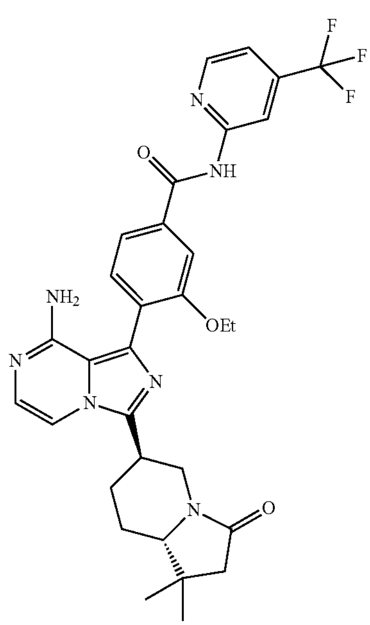 [SMILES: CCOc1cc(C(=O)Nc2cc(C(F)(F)F)ccn2)ccc1-c1nc([C@@H]2CC[C@@H]3N(C2)C(=O)CC3(C)C)n2ccnc(N)c12] | 4-(8-amino-3-((6R,8aS)-1,1-dimethyl-3-oxooctahydroindolizin-6-yl)imidazo[1,5-a]pyrazin-1-yl)-3-ethoxy-N-(4-(trifluoromethyl)pyridin-2-yl)benzamide | 608.2 | 2.23 (B) |

TABLE 6-continued

| Example | Structure | IUPAC Name | Exact Mass [M + H]+ | Retention time (min) (LS-MS method) |
|---|---|---|---|---|
| 223 | 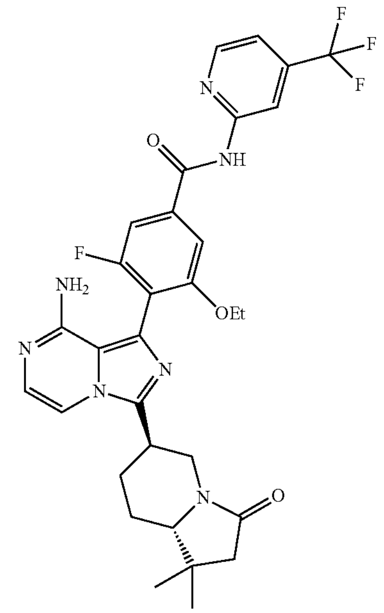 [SMILES: CCOc1cc(C(=O)Nc2cc(C(F)(F)F)ccn2)cc(F)c1-c1nc([C@@H]2CC[C@@H]3N(C2)C(=O)CC3(C)C)n2ccnc(N)c12] | 4-(8-amino-3-((6R,8aS)-1,1-dimethyl-3-oxooctahydroindolizin-6-yl)imidazo[1,5-a]pyrazin-1-yl)-3-ethoxy-5-fluoro-N-(4-(trifluoromethyl)pyridin-2-yl)benzamide | 626.2 | 2.39 (B) |

Btk Enzyme Activity Assay Methods

BTK enzymatic activity was determined with the LANCE (Lanthanide Chelate Excite) TR-FRET (Time-resolved fluorescence resonance energy transfer) assay. In this assay, the potency ($IC_{50}$) of each compound was determined from an eleven point (1:3 serial dilution; final compound concentration range in assay from 1 µM to 0.017 nM) titration curve using the following outlined procedure. To each well of a black non-binding surface Corning 384-well microplate (Corning Catalog #3820), 5 nL of compound (2000 fold dilution in final assay volume of 10 µL) was dispensed, followed by the addition of 7.5 µL of 1× kinase buffer (50 mM Hepes 7.5, 10 mM $MgCl_2$, 0.01% Brij-35, 1 mM EGTA, 0.05% BSA & 1 mM DTT) containing 5.09 pg/µL (66.67 pM) of BTK enzyme (recombinant protein from baculovirus-transfected Sf9 cells: full-length BTK, 6HIS-tag cleaved). Following a 60 minute compound & enzyme incubation, each reaction was initiated by the addition of 2.5 µL 1× kinase buffer containing 8 µM biotinylated "A5" peptide (Biotin-EQEDEPEGDYFEWLE-NH2) (SEQ ID: 1), and 100 µM ATP. The final reaction in each well of 10 µL consists of 50 pM hBTK, 2 µM biotin-A5-peptide, and 25 µM ATP. Phosphorylation reactions were allowed to proceed for 120 minutes. Reactions were immediately quenched by the addition of 20 µL of 1× quench buffer (15 mM EDTA, 25 mM Hepes 7.3, and 0.1% Triton X-100) containing detection reagents (0.626 nM of LANCE-Eu-W1024-anti-phosphoTyrosine antibody, PerkinElmer and 86.8 nM of Streptavidin-conjugated Dylight 650, Dyomics/Thermo-Fisher Scientific). After 60 minutes incubation with detection reagents, reaction plates were read on a PerkinElmer EnVision plate reader using standard TR-FRET protocol. Briefly, excitation of donor molecules (Eu-chelate:anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). $IC_{50}$ values were determined by 4 parameter robust fit of TR-FRET ratio values vs. ($Log_{10}$) compound concentrations.

Table 7 below provides specific $IC_{50}$ values for the Examples described herein. The $IC_{50}$ values set forth below were determined according to the Assay method described above.

TABLE 7

| Example # | $IC_{50}$ BTK activity value (nM) |
|---|---|
| 1 | 5.5 |
| 2 | 15.6 |
| 3 | 7.2 |
| 4 | 0.10 |
| 5 | 0.24 |
| 6 | 2.0 |
| 7 | 60.6 |
| 8 | 2.2 |
| 9 | 194 |
| 10 | 14.7 |
| 11 | 15.3 |
| 12 | 0.083 |
| 13 | 1.3 |
| 14 | 0.12 |
| 15 | 0.21 |
| 16 | 0.20 |
| 17 | 0.31 |
| 18 | 0.16 |
| 19 | 0.18 |
| 20 | 2.2 |
| 21 | 0.21 |

TABLE 7-continued

| Example # | IC$_{50}$ BTK activity value (nM) |
|---|---|
| 22 | 0.41 |
| 23 | 0.11 |
| 24 | 0.45 |
| 25 | 0.54 |
| 26 | 1.5 |
| 27 | 1.1 |
| 28 | 0.64 |
| 29 | 1.9 |
| 30 | 0.85 |
| 31 | 0.096 |
| 32 | 0.21 |
| 33 | 0.17 |
| 34 | 2.5 |
| 35 | 1.1 |
| 36 | 0.98 |
| 37 | 0.39 |
| 38 | 1.9 |
| 39 | 0.12 |
| 40 | 0.22 |
| 41 | 4.0 |
| 42 | 0.52 |
| 43 | 0.13 |
| 44 | 0.095 |
| 45 | 1.7 |
| 46 | 0.53 |
| 47 | 0.17 |
| 48 | 0.14 |
| 49 | 0.11 |
| 50 | 0.26 |
| 51 | 1.6 |
| 52 | 0.13 |
| 53 | 0.50 |
| 54 | 9.6 |
| 55 | 0.30 |
| 56 | 1.8 |
| 57 | 0.28 |
| 58 | 4.1 |
| 59 | 0.13 |
| 60 | 12.7 |
| 61 | 17.7 |
| 62 | 6.7 |
| 63 | 0.058 |
| 64 | 0.77 |
| 65 | 0.085 |
| 66 | 0.13 |
| 67 | 3.7 |
| 68 | 0.081 |
| 69 | 0.16 |
| 70 | 10.7 |
| 71 | 0.48 |
| 72 | 0.45 |
| 73 | 0.93 |
| 74 | 4.6 |
| 75 | 7.6 |
| 76 | 24.9 |
| 77 | 0.13 |
| 78 | 0.46 |
| 79 | 7.3 |
| 80 | 0.27 |
| 81 | 0.29 |
| 82 | 0.19 |
| 83 | 0.092 |
| 84 | 3.0 |
| 85 | 0.89 |
| 86 | 0.45 |
| 87 | 0.67 |
| 88 | 0.19 |
| 89 | 0.13 |
| 90 | 0.18 |
| 91 | 0.52 |
| 92 | 0.075 |
| 93 | 2.6 |
| 94 | 0.14 |
| 95 | 11.4 |
| 96 | 1.3 |
| 97 | 9.7 |
| 98 | 49.3 |
| 99 | 1.5 |
| 100 | 0.51 |
| 101 | 45.4 |
| 102 | 0.21 |
| 103 | 0.40 |
| 104 | 1.2 |
| 105 | 0.23 |
| 106 | 0.19 |
| 107 | 0.26 |
| 108 | 0.22 |
| 109 | 6.3 |
| 110 | 16.8 |
| 111 | 5.2 |
| 112 | 0.57 |
| 113 | 0.54 |
| 114 | 830.9 |
| 115 | 0.67 |
| 116 | 0.22 |
| 117 | 2.1 |
| 118 | 0.58 |
| 119 | 3.3 |
| 120 | 4.8 |
| 121 | 0.58 |
| 122 | 12.4 |
| 123 | 6.3 |
| 124 | 347.5 |
| 125 | 278.3 |
| 126 | 765.9 |
| 127 | 83.5 |
| 128 | 0.27 |
| 129 | 81.2 |
| 130 | 2.5 |
| 131 | 0.74 |
| 132 | 1.2 |
| 133 | 0.55 |
| 134 | 0.28 |
| 135 | 0.23 |
| 136 | 0.78 |
| 137 | 2.0 |
| 138 | 135.3 |
| 139 | 5.7 |
| 140 | 4.6 |
| 141 | 23.7 |
| 142 | 17.5 |
| 143 | 0.22 |
| 144 | 0.50 |
| 145 | 0.44 |
| 146 | 0.59 |
| 147 | 0.75 |
| 148 | 1.4 |
| 149 | 96.7 |
| 150 | 1.8 |
| 151 | 0.75 |
| 152 | 1.3 |
| 153 | 0.16 |
| 154 | 0.81 |
| 155 | 3.9 |
| 156 | 4.4 |
| 157 | 291.6 |
| 158 | 0.45 |
| 159 | 0.63 |
| 160 | 0.28 |
| 161 | 0.99 |
| 162 | 1.3 |
| 163 | 3.1 |
| 164 | 1.9 |
| 165 | 2.3 |
| 166 | 0.34 |
| 167 | 1.3 |
| 168 | 1.5 |
| 169 | 3.7 |
| 170 | 36.9 |
| 171 | 0.41 |
| 172 | 50.7 |
| 173 | 245.4 |

TABLE 7-continued

| Example # | IC$_{50}$ BTK activity value (nM) |
|---|---|
| 174 | 240.6 |
| 175 | 6.5 |
| 176 | 14.9 |
| 177 | 144.2 |
| 178 | 27.6 |
| 179 | 68.9 |
| 180 | 284.9 |
| 181 | 0.93 |
| 182 | 272.1 |
| 183 | 0.64 |
| 184 | 155.3 |
| 185 | 237.4 |
| 186 | 6.9 |
| 187 | 0.46 |
| 188 | 2.7 |
| 189 | 1.5 |
| 190 | 2.2 |
| 191 | 1.9 |
| 192 | 24.6 |
| 193 | 4.6 |
| 194 | 0.39 |
| 195 | 0.63 |
| 196 | 1.5 |
| 197 | 7.8 |
| 198 | 8.2 |
| 199 | 1.9 |
| 200 | 1.1 |
| 201 | 3.2 |
| 202 | 5.2 |
| 203 | 1.7 |
| 204 | 0.75 |
| 205 | 1.2 |
| 206 | 0.72 |
| 207 | 0.58 |
| 208 | 1.6 |
| 209 | 0.41 |
| 210 | 1.4 |
| 211 | 9.0 |
| 212 | 3.8 |
| 213 | 2.7 |
| 214 | 2.2 |
| 215 | 4.0 |
| 216 | 6.6 |
| 217 | 0.17 |
| 218 | 1.8 |
| 219 | 0.28 |
| 220 | 0.40 |
| 221 | |
| 222 | 0.2 |
| 223 | |

[$^3$H]Adenosine Uptake Assay Methods

Compounds are also screened in an adenosine uptake functional cellular assay using the protocol described below. The adenosine uptake inhibition assay may be used to identify compounds with the potential for a negative cardiovascular side effect.

Adenosine uptake activity was determined by monitoring the accumulation of tritiated adenosine into HeLa cells (ATCC catalog #CCL-2) using a PMT-based radiometric detection instrument. In this assay, the potency (IC$_{50}$) of each compound was determined from a ten point (1:3 serial dilution; final compound concentration range in assay from 10 µM to 0.032 nM) titration curve using the following outlined procedure. To each well of a 96-well CytoStar-T scintillating microplate (Perkin Elmer Catalog #RPNQ0163), 25000 HeLa cells in 100 µL of growth medium comprising: Minimum Essential Media (Life Technologies Catalog #11095-080)+10% (v/v) foetal bovine serum (FBS; Sigma Aldrich Catalog #F2442). These cells were incubated overnight at 37° C. in a humidified atmosphere with 5% (v/v) CO$_2$. After this time the growth medium was removed and replaced with 40 µL assay medium comprising: Hanks balanced salts solution (HBSS; Thermo Fisher Catalog #SH30268.01)+5% (v/v) FBS. Compound stock solutions in DMSO were diluted in assay medium to 2.5× final compound concentration maintaining a constant DMSO concentration of 0.25% (v/v). 40 µL of compound in the assay medium was dispensed into individual wells of the Cytostar-T plates and the plates were incubated for 30 minutes under ambient laboratory conditions. Following this incubation, 20 µL of 500 nM [$^3$H] adenosine (American Radiolabeled Chemicals Inc. Catalog #ART0287) was added in the assay medium and incubated for a further 60 minutes under ambient laboratory conditions. The amount of radiolabel accumulation was then determined using a Perkin Elmer Topcount NXT microplate reader. In brief, HeLa cells adhere to the bottom of the Cytostar-T plate, uptake of [$^3$H]adenosine into these cells brings the radiolabel into sufficient proximity to excite the scintillant in the base of the plates. These events are captured by single PMT, time-resolved coincidence counting. IC$_{50}$ values were determined by 4 parameter robust fit of counts per second values vs. (Log$_{10}$) compound concentrations. The potency of some examples in this adenosine uptake inhibition assay are listed in Table 8. The potency of some examples in this assay is not yet determined (denoted "ND").

TABLE 8

| Example number | Adenosine uptake inhibition IC$_{50}$ (nM) |
|---|---|
| 1 | ND |
| 2 | ND |
| 3 | 791.9 |
| 4 | 61.85 |
| 5 | ND |
| 6 | 183.7 |
| 7 | ND |
| 8 | 355.3 |
| 9 | 287.2 |
| 10 | 1345 |
| 11 | 511.3 |
| 12 | ND |
| 13 | ND |
| 14 | ND |
| 15 | 71.89 |
| 16 | 75.11 |
| 17 | ND |
| 18 | 63.48 |
| 19 | 233.2 |
| 20 | 2378 |
| 21 | 234.5 |
| 22 | ND |
| 23 | 4.132 |
| 24 | 67.02 |
| 25 | ND |
| 26 | ND |
| 27 | ND |
| 28 | ND |
| 29 | ND |

TABLE 8-continued

| Example number | Adenosine uptake inhibition IC$_{50}$ (nM) |
| --- | --- |
| 30 | ND |
| 31 | 103.5 |
| 32 | ND |
| 33 | 90.37 |
| 34 | ND |
| 35 | ND |
| 36 | ND |
| 37 | ND |
| 38 | 543.1 |
| 39 | 57.38 |
| 40 | 186 |
| 41 | 793 |
| 42 | 88.05 |
| 43 | ND |
| 44 | 88.83 |
| 45 | 227.2 |
| 46 | 71.34 |
| 47 | 31.83 |
| 48 | 92.64 |
| 49 | 51.75 |
| 50 | 45.13 |
| 51 | 188.2 |
| 52 | 50.1 |
| 53 | 295.5 |
| 54 | ND |
| 55 | ND |
| 56 | 113.8 |
| 57 | 10000 |
| 58 | 810.8 |
| 59 | 397.9 |
| 60 | 44.06 |
| 61 | 19.17 |
| 62 | ND |
| 63 | 71.71 |
| 64 | 114.4 |
| 65 | 132 |
| 66 | 205.8 |
| 67 | 410.4 |
| 68 | 430.5 |
| 69 | 1443 |
| 70 | ND |
| 71 | 731.6 |
| 72 | 729.5 |
| 73 | 973.1 |
| 74 | 1297 |
| 75 | ND |
| 76 | 682 |
| 77 | 31.25 |
| 78 | 132.4 |
| 79 | 294.8 |
| 80 | 82.51 |
| 81 | 68.64 |
| 82 | 78.1 |
| 83 | 123.7 |
| 84 | 154.7 |
| 85 | 2776 |
| 86 | 4187 |
| 87 | 75.45 |
| 88 | 698.9 |
| 89 | 489.5 |
| 90 | 373.2 |
| 91 | 639.2 |
| 92 | 64.56 |
| 93 | 157.5 |
| 94 | 63.2 |
| 95 | ND |
| 96 | 1142 |
| 97 | 5382 |
| 98 | 6323 |
| 99 | 183.5 |
| 100 | 462.9 |
| 101 | 487 |
| 102 | 471.1 |
| 103 | 69.32 |
| 104 | 303.4 |
| 105 | ND |
| 106 | 192.6 |
| 107 | 205.6 |
| 108 | 2877 |
| 109 | 115.5 |
| 110 | 100.5 |
| 111 | 457.6 |
| 112 | 414.7 |
| 113 | ND |
| 114 | 587.2 |
| 115 | 1686 |
| 116 | ND |
| 117 | 102 |
| 118 | 832.5 |
| 119 | 451.1 |
| 120 | 117.1 |
| 121 | 1315 |
| 122 | ND |
| 123 | 718.8 |
| 124 | 10000 |
| 125 | 645.2 |
| 126 | ND |
| 127 | 5159 |
| 128 | 1159 |
| 129 | 39.28 |
| 130 | 728.4 |
| 131 | 2777 |
| 132 | 1490 |
| 133 | ND |
| 134 | 1602 |
| 135 | 2151 |
| 136 | 1433 |
| 137 | 1195 |
| 138 | 1381 |
| 139 | 1275 |
| 140 | 755.8 |
| 141 | 823.6 |
| 142 | 1187 |
| 143 | ND |
| 144 | ND |
| 145 | 2415 |
| 146 | 5003 |
| 147 | 958.8 |
| 148 | 1075 |
| 149 | 10000 |
| 150 | 2301 |
| 151 | 1118 |
| 152 | 1891 |
| 153 | 500.7 |
| 154 | ND |
| 155 | 1529 |
| 156 | 1749 |
| 157 | 1775 |
| 158 | 2068 |
| 159 | 1224 |
| 160 | 290.3 |
| 161 | 1539 |
| 162 | 1538 |
| 163 | 2409 |
| 164 | 817.2 |
| 165 | 1545 |
| 166 | 296.5 |
| 167 | 318 |
| 168 | 284.6 |
| 169 | 2953 |
| 170 | 6754 |
| 171 | ND |
| 172 | ND |

TABLE 8-continued

| Example number | Adenosine uptake inhibition IC$_{50}$ (nM) |
|---|---|
| 173 | ND |
| 174 | ND |
| 175 | 724.8 |
| 176 | 7812 |
| 177 | 3324 |
| 178 | 5490 |
| 179 | 2370 |
| 180 | 229.7 |
| 181 | ND |
| 182 | 3610 |
| 183 | 469.8 |
| 184 | ND |
| 185 | 5394 |
| 186 | ND |
| 187 | 310.1 |
| 188 | 3687 |
| 189 | 1546 |
| 190 | 309.9 |
| 191 | 994.5 |
| 192 | 408 |
| 193 | 212.9 |
| 194 | 225.7 |
| 195 | 174.7 |
| 196 | 741.1 |
| 197 | 198.6 |
| 198 | 252.2 |
| 199 | 7094 |
| 200 | 5446 |
| 201 | 5891 |
| 202 | 6884 |
| 203 | 1730 |
| 204 | 1391 |
| 205 | 2362 |
| 206 | 1112 |
| 207 | 377.3 |
| 208 | 386 |
| 209 | 582 |
| 210 | 1125 |
| 211 | 269 |
| 212 | 86.9 |
| 213 | 699 |
| 214 | 517 |
| 215 | 2473 |
| 216 | 895.3 |
| 217 | 714.1 |
| 218 | 4849 |
| 219 | 726 |
| 220 | 1524 |
| 221 | ND |
| 222 | ND |
| 223 | ND |

The invention claimed is:

1. A compound according to Formula I, or a pharmaceutically acceptable salt thereof,

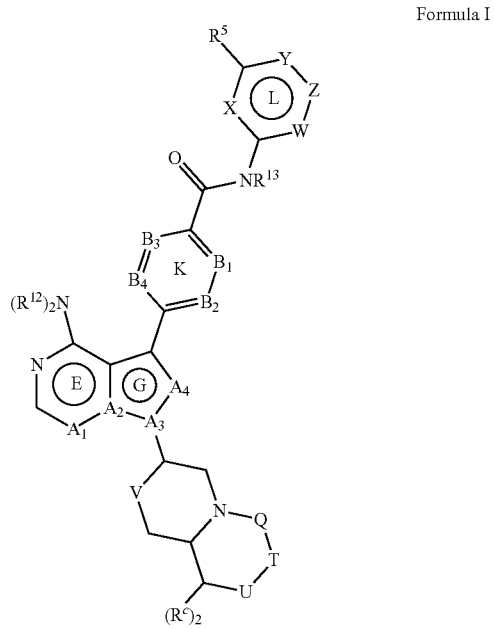

Formula I wherein:

$A_1$, $A_2$, $A_3$, and $A_4$ are independently C, CH, CR$^{11}$ or N and bicyclic ring system E-G is selected from the group consisting of:

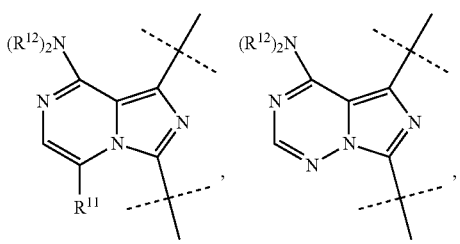

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Biotinylated "A5" peptide

<400> SEQUENCE: 1

Glu Gln Glu Asp Glu Pro Glu Gly Asp Tyr Phe Glu Trp Leu Glu
1               5                   10                  15

-continued

[Chemical structures showing:
- (R¹²)₂N-substituted pyrrolotriazine
- (R¹²)₂N-substituted pyrazolopyrimidine
- (R¹²)₂N-substituted pyrrolopyrimidine
- (R¹²)₂N-substituted pyrazolopyridine with R¹¹
- (R¹²)₂N-substituted pyrrolopyridine with R¹¹]

$R^{11}$ is independently selected from the group consisting of:
a) deuterium,
b) H,
c) halogen,
d) cyano,
e) —CH=CH₂,
f) —COOH,
g) —CO₂(1-6C)alkyl,
h) —CO(1-6C)alkyl,
i) —CONH(1-6C)alkoxy,
j) —CONH(1-6C)alkyl,
k) —CON((1-6C)alkyl)₂,
l) (1-6C)alkyl,
m) (3-7C)cycloalkyl,
n) (1-6C)alkoxy,
o) aryl,
p) (1-5C)heteroaryl,
q) (2-6C)alkenyl,
r) (2-6C)alkynyl, and
s) (4-7C)heterocycloalkyl,
wherein
$R^{11}$ is optionally substituted with one or more groups selected from: halogen, (1-6C)alkyl, (1-5C)alkoxy, OH, or oxo;
$R^{12}$ is independently selected from the group consisting of: H, (1-3C)alkyl, (1-3C)alkylNHC(O), (1-3C)alkylOC(O), and (1-3C)alkylC(O);
$R^{13}$ is independently selected from the group consisting of: H and (1-4C)alkoxy;
wherein in aromatic ring K
$B_1$, $B_2$, $B_3$, $B_4$ together are selected from the following groups:
$B_1$ is $C(R^7)$, $B_2$ is $C(R^8)$, $B_3$ is $C(R^9)$, and $B_4$ is $C(R^{10})$;
$B_1$ is N, $B_2$ is $C(R^8)$, $B_3$ is $C(R^9)$, and $B_4$ is $C(R^{10})$;
$B_1$ is $C(R^7)$, $B_2$ is N, $B_3$ is $C(R^9)$, and $B_4$ is $C(R^{10})$;
$B_1$ is $C(R^7)$, $B_2$ is $C(R^8)$, $B_3$ is N, and $B_4$ is $C(R^{10})$; and
$B_1$ is $C(R^7)$, $B_2$ is $C(R^8)$, $B_3$ is $C(R^9)$, and $B_4$ is N;

$R^7$ is H, halogen, OH, (1-3C)alkyl, (1-6C)alkoxy, (3-6C)cycloalkoxy, (1-5C)heterocycloalkoxy, halo(1-3C)alkyl, or CN; wherein $R^7$ may optionally be substituted with one, two or three halogens, OH, (2-4C)alkynyl, —C(O)NH₂, —C(O)OH, or —C(O)(1-4C)alkyl;
$R^8$ is H, halogen, OH, (1-3C)alkyl, (1-6C)alkoxy, (3-6C)cycloalkoxy, (1-5C)heterocycloalkoxy, halo(1-3C)alkyl, or CN; wherein $R^8$ may optionally be substituted with one, two or three halogens, OH, (2-4C)alkynyl, —C(O)NH₂, —C(O)OH, or —C(O)(1-4C)alkyl;
$R^9$ is H, halogen, OH, (1-3C)alkyl, (1-6C)alkoxy, (3-6C)cycloalkoxy, (1-5C)heterocycloalkoxy, halo(1-3C)alkyl, or CN; wherein $R^9$ may optionally be substituted with one, two or three halogens, OH, (2-4C)alkynyl, —C(O)NH₂, —C(O)OH, or —C(O)(1-4C)alkyl;
$R^{10}$ is H, halogen, OH, (1-3C)alkyl, (1-6C)alkoxy, (3-6C)cycloalkoxy, (1-5C)heterocycloalkoxy, halo(1-3C)alkyl, or CN; wherein $R^{10}$ may optionally be substituted with one, two or three halogens, OH, (2-4C)alkynyl, —C(O)NH₂, —C(O)OH, or —C(O)(1-4C)alkyl;
wherein in ring L
W is CH or N;
X is $C(R^{6a})$, N, O or S;
Y is $C(R^6)$, $N(R^{6b})$, O or S;
Z is $C(R^{6a})$, N or a bond;
$R^5$ is H, halogen, CN, (1-4C)alkyl, (1-5C)alkoxy, (3-6C)cycloalkyl, (3-6C)cycloalkoxy, or —C(O)O(1-3C)alkyl; wherein $R^5$ may optionally be substituted with one, two or three halogens, OH, or (1-3C)alkoxy; or
$R^5$ is aryl, (1-5C)heteroaryl or (2-6C)heterocycloalkyl, wherein $R^5$ may optionally be substituted with halogen, (1-6C)alkyl, or (1-3C)alkoxy;
$R^6$ is H, halogen, CN, (1-6C)alkyl, or (1-6C)alkoxy; wherein $R^6$ may optionally be substituted with one, two or three halogens, or CN;
$R^{6a}$ is H, (1-4C)alkyl or (3-6C)cycloalkyl;
$R^{6b}$ is H, (1-3C)alkyl, (3-6C)cycloalkyl, or —C(O)O(1-4C)alkyl; or
$R^5$ and $R^6$ together can form a carbocyclic or heterocyclic 5- to 6-membered ring, and optionally be unsaturated or aromatic; or $R^5$ and $R^6$ together can form (3-7C)cycloalkenyl or (2-6C)heterocycloalkenyl; each optionally substituted with (1-3C)alkyl or with one or more halogen;
Q is C=O, $C(R^f)_2$ or $C=N(R^h)$;
T is $C(R^e)_2$, O, $NR^e$, or a bond;
U is $C(R^d)_2$, O, or $NR^d$;
V is $C(R^g)_2$, O, or a bond;
$R^c$, $R^d$, $R^e$, and $R^f$ are each independently selected from H, halogen, (1-6C)alkyl, OH, (2-6C)alkenyl, or —C(O)$R^z$, wherein $R^z$ is independently selected from (1-5C)heteroaryl, aryl and OH,
and further wherein any alkyl group of $R^c$, $R^d$, $R^e$, or $R^f$ may optionally be substituted with OH, —C(O)(1-3C)alkoxy or —C(O)OH;
$R^g$ is independently selected from H, halogen, (1-6C)alkyl, (1-6C)alkoxy, halo(1-6C)alkyl, or OH; and
$R^h$ is independently selected from H or CN;
with the proviso that:
1) up to 2 atoms of X, Y, and Z can simultaneously be a heteroatom;
2) when one atom selected from X or Y is O or S, then Z is a bond and the other atom selected from X or Y cannot be O or S;
3) when Z is CH or N, then Y is $C(R^6)$ or N and X is CH, or N;

5) when Q is C(R$^f$)$_2$, then T is C(R$^e$)$_2$;
6) when T is NR$^e$, then R$^e$ is not halogen; and
7) when U is NR$^d$, then R$^d$ is not halogen.

2. The compound of claim 1, or a pharmaceutically acceptable salt thereof, wherein in aromatic ring K, B$_1$, B$_2$, B$_3$ and B$_4$ together are selected from the following groups:
B$_1$ is C(R$^7$), B$_2$ is C(R$^8$), B$_3$ is C(R$^9$), and B$_4$ is C(R$^{10}$);
B$_1$ is N, B$_2$ is C(R$^8$), B$_3$ is C(R$^9$), and B$_4$ is)C(R$^{10}$);
B$_1$ is C(R$^7$), B$_2$ is N, B$_3$ is C(R$^9$), and B$_4$ is)C(R$^{10}$); and
B$_1$ is C(R$^7$), B$_2$ is C(R$^8$), B$_3$ is N, and B$_4$ is)C(R$^{10}$).

3. The compound of claim 2, or a pharmaceutically acceptable salt thereof, wherein in aromatic ring K, B$_1$ is C(R$^7$), B$_2$ is C(R$^8$), B$_3$ is C(R$^9$), and B$_4$ is C(R$^{10}$), wherein R$^7$, R$^8$, R$^9$ and R$^{10}$ are each independently selected from H, halogen, (1-3C)alkyl, (1-3C)alkoxy or halo(1-3C)alkyl; and further wherein any alkoxy may optionally be substituted with one, two or three halogens.

4. The compound of claim 1, or a pharmaceutically acceptable salt thereof, wherein ring L is selected from the group consisting of phenyl, pyridyl, pyrimidyl, pyridazyl, triazinyl, thiazolyl, oxazolyl, isoxazolyl, pyrazolyl, imidazolyl, thiadiazolyl, and isothiazolyl.

5. The compound of claim 4, or a pharmaceutically acceptable salt thereof, wherein ring L is selected from the group consisting of:

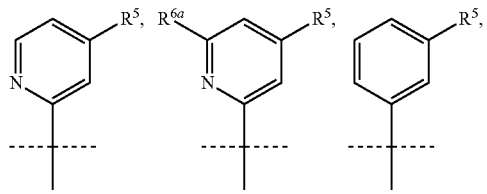

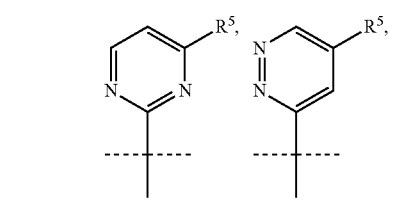

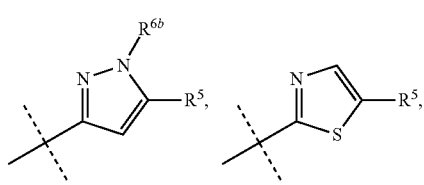

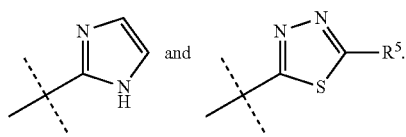

6. The compound of claim 4, or a pharmaceutically acceptable salt thereof, wherein ring L is pyridyl.

7. The compound of claim 1, or a pharmaceutically acceptable salt thereof, wherein R$^5$ is selected from the group consisting of H, fluoro, chloro, CN, cyclopropyl, cyclobutyl, oxetanyl, (1-3C)alkyl, (1-5C)alkoxy, and (3-5C)cycloalkoxy; wherein the alkyl, alkoxy, cycloalkyl and cycloalkoxy of R$^5$ are optionally substituted with one or more halogens.

8. The compound of claim 7, or a pharmaceutically acceptable salt thereof, wherein R$^5$ is selected from the group consisting of H, fluoro, methyl, ethyl, propyl, cyclopropyl, cyclobutyl, cyclopropoxy, and trifluoromethyl.

9. The compound of claim 1, or a pharmaceutically acceptable salt thereof, wherein R$^{11}$ is selected from the group consisting of H, deuterium, fluoro, chloro, bromo, methyl, ethyl, cyclopropyl and vinyl.

10. The compound of claim 9, or a pharmaceutically acceptable salt thereof, wherein R$^{11}$ is selected from the group consisting of H, fluro and chloro.

11. The compound of claim 1, or a pharmaceutically acceptable salt thereof, wherein bicyclic ring system E-G is selected from the group consisting of:

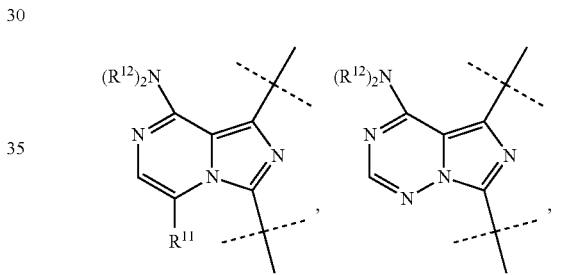

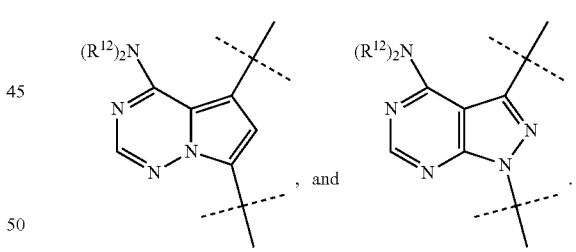

12. A compound of claim 11, or a pharmaceutically acceptable salt thereof, wherein bicyclic ring system E-G is

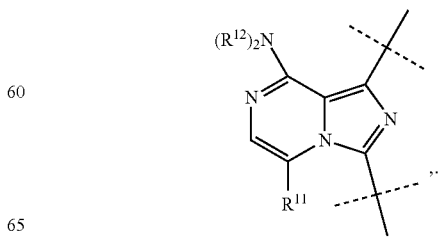

13. The compound of claim 1, having Formula Ie:

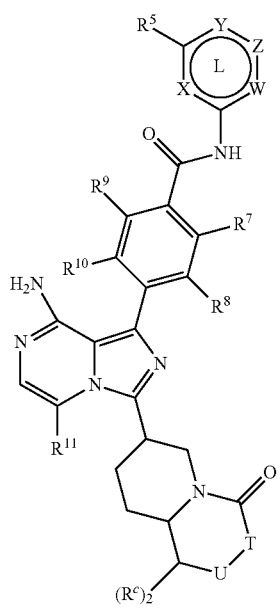

Formula Ie or a pharmaceutically acceptable salt thereof.

14. The compound of claim 13, or a pharmaceutically acceptable salt thereof, wherein
$R^7$, $R^8$, $R^9$, and $R^{10}$ are independently selected from H, halogen, or (1-3C)alkoxy;
$R^{11}$ is H, halogen or (1-3C)alkyl, wherein the alkyl is optionally substituted with one, two or three halogen;
$R^c$ is H or methyl; and
$R^d$ is H or methyl.

15. A pharmaceutical composition which comprises the compound of claim 1, or a pharmaceutically acceptable salt thereof, and one or more pharmaceutically acceptable excipients.

16. The pharmaceutical composition of claim 15, which further comprises at least one additional therapeutically active agent.

17. The pharmaceutical composition of claim 16, wherein the additional therapeutically active agent is an anti-inflammatory agent, an immunosuppressant agent, or a chemotherapeutic agent.

18. A method for modulating Bruton's tyrosine kinase activity in a subject, comprising administering to the subject a therapeutically effective amount of the compound of claim 1, or a pharmaceutically acceptable salt thereof.

19. The method of claim 18, wherein the subject suffers from a Bruton's tyrosine kinase mediated disorder selected from the group consisting of rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis, acute spondylitis, glomerulonephritis with nephrotic syndrome, glomerulonephritis without nephrotic syndrome, autoimmune hematologic disorder, hemolytic anemia, aplasic anemia, idiopathic thrombocytopenia, neutropenia, autoimmune gastritis, autoimmune inflammatory bowel disease, ulcerative colitis, Crohn's disease, host versus graft disease, allograft rejection, chronic thyroiditis, Graves' disease, scleroderma, type I diabetes, type II diabetes, acute active hepatitis, chronic active hepatitis, pancreatitis, primary biliary cirrhosis, myasthenia gravis, multiple sclerosis, systemic lupus erythematosis, psoriasis, atopic dermatitis, contact dermatitis, eczema, skin sunburn, vasculitis, chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease and chronic obstructive pulmonary disease.

20. The method of claim 19, wherein the Bruton's tyrosine kinase mediated disorder is selected from the group consisting of rheumatoid arthritis, psoriatic arthritis and osteoarthritis.

21. A compound according to Formula II, or a pharmaceutically acceptable salt thereof,

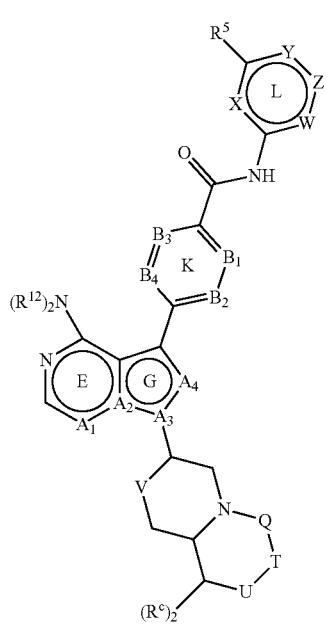

Formula II wherein:
$A_1$, $A_2$, $A_3$, and $A_4$ are independently C, CH, $CR^{11}$ or N and bicyclic ring system E-G is selected from the group consisting of:

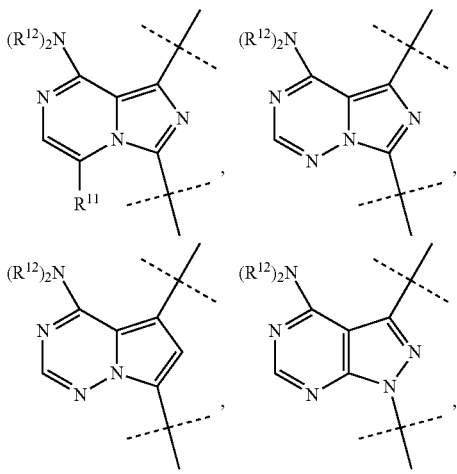

-continued

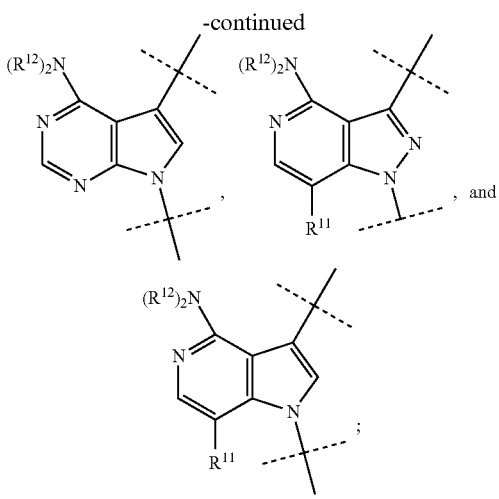

$R^{11}$ is independently selected from the group consisting of:
a) deuterium,
b) H,
c) halogen,
d) cyano,
e) —CH=CH$_2$,
f) —COOH,
g) —CO$_2$(1-6C)alkyl,
h) —CO(1-6C)alkyl,
i) —CONH(1-6C)alkoxy,
j) —CONH(1-6C)alkyl,
k) —CON((1-6C)alkyl)$_2$,
l) (1-6C)alkyl,
m) (3-7C)cycloalkyl,
n) (1-6C)alkoxy,
o) (6-10C)aryl,
p) (1-5C)heteroaryl,
q) (2-6C)alkenyl,
r) (2-6C)alkynyl, and
s) (4-7C)heterocycloalkyl,
wherein
$R^{11}$ is optionally substituted with one or more groups selected from: halogen, (1-6C)alkyl, (1-5C)alkoxy, OH; or oxo;
$R^{12}$ is independently selected from the group consisting of H, (1-3C)alkyl, (1-3C)alkylNHC(O), and (1-3C)alkylOC(O);
wherein in aromatic ring K
$B_1$, $B_2$, $B_3$, $B_4$ together are selected from the following groups:
$B_1$ is C($R^7$), $B_2$ is C($R^8$), $B_3$ is C($R^9$), and $B_4$ is)C($R^{10}$);
$B_1$ is N, $B_2$ is C($R^8$), $B_3$ is C($R^9$), and $B_4$ is C($R^{10}$);
$B_1$ is C($R^7$), $B_2$ is N $B_3$ is C($R^9$), and $B_4$ is C($R^{10}$);
$B_1$ is C($R^7$), $B_2$ is C($R^8$), $B_3$ is N, and $B_4$ is C($R^{10}$); and
$B_1$ is C($R^7$), $B_2$ is C($R^8$), $B_3$ is C($R^9$), and $B_4$ is N;
$R^7$ is H, halogen, OH, (1-3C)alkyl, (1-3C)alkoxy, halo(1-3C)alkyl, or CN; wherein any alkoxy may optionally be substituted with one, two or three halogens;
$R^8$ is H, halogen, OH, (1-3C)alkyl, (1-3C)alkoxy, halo(1-3C)alkyl, or CN; wherein any alkoxy may optionally be substituted with one, two or three halogens;
$R^9$ is H, halogen, OH, (1-3C)alkyl, (1-3C)alkoxy, halo(1-3C)alkyl, or CN; wherein any alkoxy may optionally be substituted with one, two or three halogens;
$R^{10}$ is H, halogen, OH, (1-3C)alkyl, (1-3C)alkoxy, halo(1-3C)alkyl, or CN; wherein any alkoxy may optionally be substituted with one, two or three halogens;
wherein in heteroaromatic ring L
W is CH or N;
X is CH, N, O or S;
Y is C($R^6$), N, O or S;
Z is CH, N or a bond;
$R^5$ is H, halogen, CN, (1-4C)alkyl, (1-5C)alkoxy, (3-6C)cycloalkyl, or (3-6C)cycloalkoxy; wherein any alkyl, alkoxy, cycloalkyl or cycloalkoxy of $R^5$ may optionally be substituted with one, two or three halogens; or
$R^5$ is (6-10C)aryl, (1-5C)heteroaryl or (2-6C)heterocycloalkyl; wherein the aryl or heterocycloalkyl may optionally be substituted with halogen, (1-6C)alkyl, or (1-3C)alkoxy;
$R^6$ is H, halogen, CN, (1-6C)alkyl, or (1-6C)alkoxy; wherein any alkyl or alkoxy of $R^6$ may optionally be substituted with one, two or three halogens, or CN; or
$R^5$ and $R^6$ together may form a 5- to 6-membered fully saturated, partially unsaturated or aromatic carbocyclic or heterocyclic ring; or
$R^5$ and $R^6$ together may form (3-7C)cycloalkenyl or (2-6C)heterocycloalkenyl, wherein each may optionally be substituted with one or more halogens, or (1-3C)alkyl;
Q is C=O or C($R^f$)$_2$;
T is C($R^e$)$_2$, O, NR$^e$, or a bond;
U is C($R^d$)$_2$, O, or NR$^d$;
V is C($R^g$)$_2$, O, or a bond;
$R^c$, $R^d$, $R^e$, and $R^f$ are each independently selected from H, halogen, (1-6C)alkyl, or OH; wherein any alkyl group of $R^c$, $R^d$, $R^e$, or $R^f$ may optionally be substituted with OH; and
$R^g$ is independently selected from H, halogen, (1-6C)alkyl, (1-6C)alkoxy, halo(1-6C)alkyl, and OH;
with the proviso that:
1) up to 2 atoms of X, Y, and Z can simultaneously be a heteroatom;
2) when one atom selected from X or Y is O or S, then Z is a bond and the other atom selected from X or Y cannot be O or S;
3) when Z is CH or N, then Y is C($R^6$) or N and X is CH, or N; and
5) when Q is C($R^f$)$_2$, then T is C($R^e$)$_2$.

22. A compound selected from the group consisting of:
4-{8-amino-3-[(6S,8aS)-3-oxohexahydro[1,3]oxazolo[3,4-a]pyridin-6-yl]imidazo[1,5-a]pyrazin-1-yl}-N-[4-(trifluoromethyl)pyridin-2-yl]benzamide;
4-{8-amino-3-[(6R,8aR)-3-oxohexahydro[1,3]oxazolo[3,4-a]pyridin-6-yl]imidazo[1,5-a]pyrazin-1-yl}-N-[4-(trifluoromethyl)pyridin-2-yl]benzamide;
4-{8-amino-3-[(6R,8aS)-2-methyl-3-oxooctahydroimidazo[1,5-a]pyridin-6-yl]imidazo[1,5-a]pyrazin-1-yl}-N-[4-(trifluoromethyl)pyridin-2-yl]benzamide;
4-{8-amino-3-[(6R,8aS)-3-oxooctahydroindolizin-6-yl]imidazo[1,5-a]pyrazin-1-yl}-N-[4-(trifluoromethyl)pyridin-2-yl]benzamide;
4-{8-amino-3-[(6R,8aS)-3-oxooctahydroindolizin-6-yl]imidazo[1,5-a]pyrazin-1-yl}-N-[4-(cyclopropyloxy)pyridin-2-yl]benzamide;
4-{8-amino-3-[(6R,8aS)-3-oxooctahydroindolizin-6-yl]imidazo[1,5-a]pyrazin-1-yl}-N-pyridin-2-ylbenzamide;
4-{8-amino-3-[(6S,8aR)-3-oxooctahydroindolizin-6-yl]imidazo[1,5-a]pyrazin-1-yl}-N-(4-cyclobutylpyridin-2-yl)benzamide;

4-{8-amino-3-[(6R,8aS)-3-oxooctahydroindolizin-6-yl]
imidazo[1,5-a]pyrazin-1-yl}-N-(5-methyl-1,3-thiazol-
2-yl)benzamide;

4-{8-amino-3-[(6S,8aR)-3-oxooctahydroindolizin-6-yl]
imidazo[1,5-a]pyrazin-1-yl}-N-pyridin-2-ylbenz-
amide;

4-{8-amino-3-[(6S,8aR)-3-oxooctahydroindolizin-6-yl]
imidazo[1,5-a]pyrazin-1-yl}-N-[4-(trifluoromethyl)
pyridin-2-yl]benzamide;

4-{8-amino-3-[(6R,8aR)-3-oxooctahydroindolizin-6-yl]
imidazo[1,5-a]pyrazin-1-yl}-N-[4-(trifluoromethyl)
pyridin-2-yl]benzamide;

4-{8-amino-3-[(6R,8aS)-3-oxohexahydro[1,3]oxazolo[3,
4-a]pyridin-6-yl]imidazo[1,5-a]pyrazin-1-yl}-N-[4-
(trifluoromethyl)pyridin-2-yl]benzamide;

4-{8-amino-3-[(6S,8aR)-3-oxohexahydro[1,3]oxazolo[3,
4-a]pyridin-6-yl]imidazo[1,5-a]pyrazin-1-yl}-N-[4-
(trifluoromethyl)pyridin-2-yl]benzamide;

4-{8-amino-3-[(6R,8aS)-3-oxooctahydroindolizin-6-yl]
imidazo[1,5-a]pyrazin-1-yl}-N-[4-(difluoromethyl)
pyridin-2-yl]-3-fluorobenzamide;

4-{8-amino-3-[(6R,8aS)-3-oxooctahydroindolizin-6-yl]
imidazo[1,5-a]pyrazin-1-yl}-N-(4-cyanopyridin-2-yl)-
3-fluorobenzamide;

4-{8-amino-3-[(6R,8aS)-3-oxooctahydroindolizin-6-yl]
imidazo[1,5-a]pyrazin-1-yl}-N-(4-cyclopropylpyridin-
2-yl)-3-fluorobenzamide;

4-{8-amino-3-[(6R,8aS)-3-oxooctahydroindolizin-6-yl]
imidazo[1,5-a]pyrazin-1-yl}-N-[4-(difluoromethyl)
pyridin-2-yl]benzamide;

4-{8-amino-3-[(6R,8aS)-3-oxooctahydroindolizin-6-yl]
imidazo[1,5-a]pyrazin-1-yl}-N-(4-ethylpyridin-2-yl)
benzamide;

4-{8-amino-3-[(6R,8aS)-3-oxooctahydroindolizin-6-yl]
imidazo[1,5-a]pyrazin-1-yl}-N-(4-cyclopropylpyridin-
2-yl)benzamide;

4-{8-amino-3-[(6R,8aS)-3-oxooctahydroindolizin-6-yl]
imidazo[1,5-a]pyrazin-1-yl}-N-[4-(trifluoromethyl)py-
rimidin-2-yl]benzamide;

4-{8-amino-3-[(6R,8aS)-3-oxooctahydroindolizin-6-yl]
imidazo[1,5-a]pyrazin-1-yl}-N-[4-(1,1-difluoroethyl)
pyridin-2-yl]-3-fluorobenzamide;

4-{8-amino-3-[(6R,8aS)-3-oxooctahydroindolizin-6-yl]
imidazo[1,5-a]pyrazin-1-yl}-2-methyl-N-[4-(trifluo-
romethyl)pyridin-2-yl]benzamide;

4-{8-amino-3-[(6R,8aS)-3-oxooctahydroindolizin-6-yl]
imidazo[1,5-a]pyrazin-1-yl}-3-fluoro-N-[4-(trifluo-
romethyl)pyridin-2-yl]benzamide;

4-{8-amino-3-[(6R,8aS)-3-oxooctahydroindolizin-6-yl]
imidazo[1,5-a]pyrazin-1-yl}-2-fluoro-N-[4-(trifluo-
romethyl)pyridin-2-yl]benzamide;

4-{8-amino-3-[(6R,8aS)-3-oxooctahydroindolizin-6-yl]
imidazo[1,5-a]pyrazin-1-yl}-N-[4-(1,1-difluoroethyl)
pyridin-2-yl]-2-fluorobenzamide;

4-{8-amino-3-[(6R,8aS)-3-oxooctahydroindolizin-6-yl]
imidazo[1,5-a]pyrazin-1-yl}-N-[4-(difluoromethyl)
pyridin-2-yl]-2-fluorobenzamide;

4-{8-amino-3-[(6R,8aS)-3-oxooctahydroindolizin-6-yl]
imidazo[1,5-a]pyrazin-1-yl}-N-(4-cyclopropylpyridin-
2-yl)-2-fluorobenzamide;

4-{8-amino-3-[(6R,8aS)-3-oxooctahydroindolizin-6-yl]
imidazo[1,5-a]pyrazin-1-yl}-N-(4-cyclopropylpyridin-
2-yl)-2-methylbenzamide;

4-{8-amino-3-[(6R,8aS)-3-oxooctahydroindolizin-6-yl]
imidazo[1,5-a]pyrazin-1-yl}-N-[4-(3-fluorooxetan-3-
yl)pyridin-2-yl]benzamide;

4-{8-amino-3-[(6R,8aS)-3-oxooctahydroindolizin-6-yl]
imidazo[1,5-a]pyrazin-1-yl}-N-[4-(1-fluoro-1-methyl-
ethyl)pyridin-2-yl]benzamide;

4-{8-amino-3-[(1R,6R,8aS)-1-methyl-3-oxohexahydro
[1,3]oxazolo[3,4-a]pyridin-6-yl]imidazo[1,5-a]
pyrazin-1-yl}-3-fluoro-N-[4-(trifluoromethyl)pyridin-
2-yl]benzamide;

4-{8-amino-3-[(1R,6R,8aS)-1-methyl-3-oxohexahydro
[1,3]oxazolo[3,4-a]pyridin-6-yl]imidazo[1,5-a]
pyrazin-1-yl}-N-(4-cyclopropylpyridin-2-yl)-3-fluo-
robenzamide;

4-{8-amino-3-[(1S,6R,8aS)-1-methyl-3-oxohexahydro[1,
3]oxazolo[3,4-a]pyridin-6-yl]imidazo[1,5-a]pyrazin-1-
yl}-3-fluoro-N-[4-(trifluoromethyl)pyridin-2-yl]benz-
amide;

4-{8-amino-3-[(6R,8aS)-3-oxooctahydroindolizin-6-yl]
imidazo[1,5-a]pyrazin-1-yl}-N-(4-cyanopyridin-2-yl)-
2-fluorobenzamide;

4-{8-amino-3-[(6R,8aS)-3-oxooctahydroindolizin-6-yl]
imidazo[1,5-a]pyrazin-1-yl}-N-(4-cyanopyridin-2-yl)-
3-methoxybenzamide;

4-{8-amino-3-[(6R,8aS)-3-oxooctahydroindolizin-6-yl]
imidazo[1,5-a]pyrazin-1-yl}-N-(4-cyanopyridin-2-yl)-
2-methylbenzamide;

4-{8-amino-3-[(1 S,6R,8aS)-1-methyl-3-oxohexahydro
[1,3]oxazolo[3,4-a]pyridin-6-yl]imidazo[1,5-a]
pyrazin-1-yl}-N-(4-cyclopropylpyridin-2-yl)-3-fluo-
robenzamide;

4-{8-amino-3-[(6R,8aS)-3-oxooctahydroindolizin-6-yl]
imidazo[1,5-a]pyrazin-1-yl}-N-(4-cyclopropylpyridin-
2-yl)-3-methoxybenzamide;

4-{8-amino-3-[(7R,9aS)-4-oxooctahydropyrido[2,1-c][1,
4]oxazin-7-yl]imidazo[1,5-a]pyrazin-1-yl}-3-fluoro-
N-[4-(trifluoromethyl)pyridin-2-yl]benzamide;

4-{8-amino-3-[(7R,9aS)-4-oxooctahydro-2H-pyrido[1,2-
a]pyrazin-7-yl]imidazo[1,5-a]pyrazin-1-yl}-N-[4-(trif-
luoromethyl)pyridin-2-yl]benzamide;

4-{8-amino-3-[(7S,9aR)-4-oxooctahydro-2H-pyrido[1,2-
a]pyrazin-7-yl]imidazo[1,5-a]pyrazin-1-yl}-N-[4-(trif-
luoromethyl)pyridin-2-yl]benzamide;

4-{8-amino-3-[(6R,8aS)-3-oxooctahydroindolizin-6-yl]
imidazo[1,5-a]pyrazin-1-yl}-2-chloro-N-[4-(trifluo-
romethyl)pyridin-2-yl]benzamide;

4-{8-amino-3-[(6R,8aS)-3-oxooctahydroindolizin-6-yl]
imidazo[1,5-a]pyrazin-1-yl}-N-[4-(cyclopropyloxy)
pyridin-2-yl]-3-fluorobenzamide;

4-{8-amino-3-[(3 S,9aS)-6-oxooctahydro-2H-quinolizin-
3-yl]imidazo[1,5-a]pyrazin-1-yl}-3-fluoro-N-[4-(trif-
luoromethyl)pyridin-2-yl]benzamide;

4-{8-amino-3-[(3R,9aR)-6-oxooctahydro-2H-quinolizin-
3-yl]imidazo[1,5-a]pyrazin-1-yl}-3-fluoro-N-[4-(trif-
luoromethyl)pyridin-2-yl]benzamide;

4-{8-amino-3-[(1 S,6R,8aS)-1-methyl-3-oxohexahydro
[1,3]oxazolo[3,4-a]pyridin-6-yl]imidazo[1,5-a]
pyrazin-1-yl}-N-(4-cyclopropylpyridin-2-yl)benz-
amide;

4-{8-amino-3-[(1R,6R,8aS)-1-methyl-3-oxohexahydro
[1,3]oxazolo[3,4-a]pyridin-6-yl]imidazo[1,5-a]
pyrazin-1-yl}-N-(4-cyclopropylpyridin-2-yl)benz-
amide;

4-{8-amino-3-[(1 S,6R,8aS)-1-methyl-3-oxohexahydro
[1,3]oxazolo[3,4-a]pyridin-6-yl]imidazo[1,5-a]
pyrazin-1-yl}-N-[4-(trifluoromethyl)pyridin-2-yl]ben-
zamide;

4-{8-amino-3-[(1R,6R,8aS)-1-methyl-3-oxohexahydro[1,3]oxazolo[3,4-a]pyridin-6-yl]imidazo[1,5-a]pyrazin-1-yl}-N-[4-(trifluoromethyl)pyridin-2-yl]benzamide;

4-{8-amino-3-[(7R,9aS)-2-methyl-4-oxooctahydro-2H-pyrido[1,2-a]pyrazin-7-yl]imidazo[1,5-a]pyrazin-1-yl}-N-[4-(trifluoromethyl)pyridin-2-yl]benzamide;

4-{8-amino-3-[(7S,9aR)-2-methyl-4-oxooctahydro-2H-pyrido[1,2-a]pyrazin-7-yl]imidazo[1,5-a]pyrazin-1-yl}-N-[4-(trifluoromethyl)pyridin-2-yl]benzamide;

4-{8-amino-3-[(6R,8aS)-1,1-dimethyl-3-oxohexahydro[1,3]oxazolo[3,4-a]pyridin-6-yl]imidazo[1,5-a]pyrazin-1-yl}-N-[4-(trifluoromethyl)pyridin-2-yl]benzamide;

4-{8-amino-3-[(1R,6R,8aS)-1-methyl-3-oxohexahydro[1,3]oxazolo[3,4-a]pyridin-6-yl]imidazo[1,5-a]pyrazin-1-yl}-N-(4-cyclopropylpyridin-2-yl)-3-methoxybenzamide;

4-{8-amino-3-[(7R,9aR)-4-oxooctahydro-2H-pyrido[1,2-a]pyrazin-7-yl]imidazo[1,5-a]pyrazin-1-yl}-N-[4-(trifluoromethyl)pyridin-2-yl]benzamide;

4-{8-amino-3-[(7R,9aS)-octahydropyrido[2,1-c][1,4]oxazin-7-yl]imidazo[1,5-a]pyrazin-1-yl}-N-[4-(trifluoromethyl)pyridin-2-yl]benzamide;

4-{8-amino-3-[(7S,9aR)-octahydropyrido[2,1-c][1,4]oxazin-7-yl]imidazo[1,5-a]pyrazin-1-yl}-N-[4-(trifluoromethyl)pyridin-2-yl]benzamide;

4-{8-amino-3-[(7S,9aS)-4-oxooctahydro-2H-pyrido[1,2-a]pyrazin-7-yl]imidazo[1,5-a]pyrazin-1-yl}-N-[4-(trifluoromethyl)pyridin-2-yl]benzamide;

4-{8-amino-3-[(2S,6S,8aR)-2-hydroxy-3-oxooctahydroindolizin-6-yl]imidazo[1,5-a]pyrazin-1-yl}-N-[4-(trifluoromethyl)pyridin-2-yl]benzamide;

4-{8-amino-3-[(2R,6R,8aS)-2-hydroxy-3-oxooctahydroindolizin-6-yl]imidazo[1,5-a]pyrazin-1-yl}-N-[4-(trifluoromethyl)pyridin-2-yl]benzamide;

4-{8-(methylamino)-3-[(6R,8aS)-3-oxooctahydroindolizin-6-yl]imidazo[1,5-a]pyrazin-1-yl}-N-[4-(trifluoromethyl)pyridin-2-yl]benzamide;

4-{8-[(ethylcarbamoyl)amino]-3-[(6R,8aS)-3-oxooctahydroindolizin-6-yl]imidazo[1,5-a]pyrazin-1-yl}-N-[4-(trifluoromethyl)pyridin-2-yl]benzamide;

4-{8-amino-3-[(1R,6R,8aS)-1-methyl-3-oxooctahydroindolizin-6-yl]imidazo[1,5-a]pyrazin-1-yl}-N-[4-(trifluoromethyl)pyridin-2-yl]benzamide;

4-{8-amino-3-[(1S,6R,8aR)-1-methyl-3-oxooctahydroindolizin-6-yl]imidazo[1,5-a]pyrazin-1-yl}-N-[4-(trifluoromethyl)pyridin-2-yl]benzamide;

4-{8-amino-3-[(1S,6R,8aR)-1-methyl-3-oxooctahydroindolizin-6-yl]imidazo[1,5-a]pyrazin-1-yl}-N-[4-(trifluoromethyl)pyridin-2-yl]benzamide;

4-{8-amino-3-[(1R,6R,8aS)-1-methyl-3-oxooctahydroindolizin-6-yl]imidazo[1,5-a]pyrazin-1-yl}-N-[4-(trifluoromethyl)pyridin-2-yl]benzamide;

4-{8-amino-3-[(7R,9aS)-2-(2-hydroxyethyl)-4-oxooctahydro-2H-pyrido[1,2-a]pyrazin-7-yl]imidazo[1,5-a]pyrazin-1-yl}-N-[4-(trifluoromethyl)pyridin-2-yl]benzamide;

4-{8-amino-3-[(2R,6S,8aR)-2-hydroxy-3-oxooctahydroindolizin-6-yl]imidazo[1,5-a]pyrazin-1-yl}-N-[4-(trifluoromethyl)pyridin-2-yl]benzamide;

4-{8-amino-3-[(2S,6R,8aS)-2-hydroxy-3-oxooctahydroindolizin-6-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-ethoxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(benzyloxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(difluoromethoxy)-N-[4-(trifluoromethyl)pyridin-2-yl]benzamide;

4-{8-amino-3-[(2S,6R,8aR)-2-hydroxy-3-oxooctahydroindolizin-6-yl]imidazo[1,5-a]pyrazin-1-yl}-N-[4-(trifluoromethyl)pyridin-2-yl]benzamide;

4-{8-amino-3-[(2R,6S,8aS)-2-hydroxy-3-oxooctahydroindolizin-6-yl]imidazo[1,5-a]pyrazin-1-yl}-N-[4-(trifluoromethyl)pyridin-2-yl]benzamide;

4-{8-amino-3-[(2R,6S,8aS)-2-hydroxy-3-oxooctahydroindolizin-6-yl]imidazo[1,5-a]pyrazin-1-yl}-N-[4-(trifluoromethyl)pyridin-2-yl]benzamide;

4-{8-amino-3-[(2S,6R,8aR)-2-hydroxy-3-oxooctahydroindolizin-6-yl]imidazo[1,5-a]pyrazin-1-yl}-N-[4-(trifluoromethyl)pyridin-2-yl]benzamide;

4-{8-amino-3-[(6R,8aR)-3-oxotetrahydro-1H-[1,3]oxazolo[4,3-c][1,4]oxazin-6-yl]imidazo[1,5-a]pyrazin-1-yl}-N-[4-(trifluoromethyl)pyridin-2-yl]benzamide;

4-{8-amino-3-[(3R,7R,9aS)-3-methyl-4-oxooctahydropyrido[2,1-c][1,4]oxazin-7-yl]imidazo[1,5-a]pyrazin-1-yl}-N-[4-(trifluoromethyl)pyridin-2-yl]benzamide;

4-{8-amino-3-[(3E,6R,8aS)-3-(cyanoimino)octahydroindolizin-6-yl]imidazo[1,5-a]pyrazin-1-yl}-N-[4-(trifluoromethyl)pyridin-2-yl]benzamide;

methyl{3-[(6R,8aS)-3-oxooctahydroindolizin-6-yl]-1-(4-{[4-(trifluoromethyl)pyridin-2-yl]carbamoyl}phenyl)imidazo[1,5-a]pyrazin-8-yl}carbamate;

4-{8-amino-3-[(7R,9aS)-2-ethyl-4-oxooctahydro-2H-pyrido[1,2-a]pyrazin-7-yl]imidazo[1,5-a]pyrazin-1-yl}-N-[4-(trifluoromethyl)pyridin-2-yl]benzamide;

4-{8-amino-3-[(7R,9aS)-2-(1-methylethyl)-4-oxooctahydro-2H-pyrido[1,2-a]pyrazin-7-yl]imidazo[1,5-a]pyrazin-1-yl}-N-[4-(trifluoromethyl)pyridin-2-yl]benzamide;

methyl{(7R,9aS)-7-[8-amino-1-(4-{[4-(trifluoromethyl)pyridin-2-yl]carbamoyl}phenyl)imidazo[1,5-a]pyrazin-3-yl]-4-oxooctahydro-2H-pyrido[1,2-a]pyrazin-2-yl}acetate;

4-{8-amino-3-[(4aS,7R)-2-methyl-1-oxooctahydro-1H-pyrido[1,2-c]pyrimidin-7-yl]imidazo[1,5-a]pyrazin-1-yl}-N-[4-(trifluoromethyl)pyridin-2-yl]benzamide;

4-{8-amino-3-[(4aR,7S)-2-methyl-1-oxooctahydro-1H-pyrido[1,2-c]pyrimidin-7-yl]imidazo[1,5-a]pyrazin-1-yl}-N-[4-(trifluoromethyl)pyridin-2-yl]benzamide;

4-{8-amino-3-[(7R,9aS)-4-oxo-2-(pyridin-4-ylcarbonyl)octahydro-2H-pyrido[1,2-a]pyrazin-7-yl]imidazo[1,5-a]pyrazin-1-yl}-3-methoxy-N-[4-(trifluoromethyl)pyridin-2-yl]benzamide;

2-{(7R,9aS)-7-[8-amino-1-(4-{[4-(trifluoromethyl)pyridin-2-yl]carbamoyl}phenyl)imidazo[1,5-a]pyrazin-3-yl]-4-oxooctahydro-2H-pyrido[1,2-a]pyrazin-2-yl}-2-methylpropanoic acid;

4-{8-amino-3-[(6R,8aS)-octahydroindolizin-6-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-methoxy-N-[4-(trifluoromethyl)pyridin-2-yl]benzamide;

4-{8-amino-3-[(1R,6R,8aS)-1-methyl-3-oxohexahydro[1,3]oxazolo[3,4-a]pyridin-6-yl]imidazo[1,5-a]pyrazin-1-yl}-3-methoxy-N-[4-(trifluoromethyl)pyridin-2-yl]benzamide;

4-{8-amino-3-[(6R,8aS)-1,1-dimethyl-3-oxohexahydro[1,3]oxazolo[3,4-a]pyrazin-6-yl]imidazo[1,5-a]pyrazin-1-yl}-3-methoxy-N-[4-(trifluoromethyl)pyridin-2-yl]benzamide;

4-{8-amino-3-[(3R,8aR)-6-oxohexahydro-1H-pyrrolo[2,1-c][1,4]oxazin-3-yl]imidazo[1,5-a]pyrazin-1-yl}-3-methoxy-N-[4-(trifluoromethyl)pyridin-2-yl]benzamide;

4-{8-amino-3-[(4aS,7R)-1-oxohexahydro-3H-pyrido[1,2-c][1,3]oxazin-7-yl]imidazo[1,5-a]pyrazin-1-yl}-N-[4-(trifluoromethyl)pyridin-2-yl]benzamide;

4-{8-amino-3-[(4aR,7S)-1-oxohexahydro-3H-pyrido[1,2-c][1,3]oxazin-7-yl]imidazo[1,5-a]pyrazin-1-yl}-N-[4-(trifluoromethyl)pyridin-2-yl]benzamide;

4-{8-amino-3-[(6S,8aR)-2,2-dimethyl-3-oxooctahydroindolizin-6-yl]imidazo[1,5-a]pyrazin-1-yl}-N-[4-(trifluoromethyl)pyridin-2-yl]benzamide;

4-{8-amino-3-[(6R,8aS)-2,2-dimethyl-3-oxooctahydroindolizin-6-yl]imidazo[1,5-a]pyrazin-1-yl}-N-[4-(trifluoromethyl)pyridin-2-yl]benzamide;

4-{8-amino-3-[(1S,6R,8aS)-3-imino-1-methylhexahydro[1,3]oxazolo[3,4-a]pyrazin-6-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[4-(1-hydroxyethyl)pyridin-2-yl]benzamide;

4-{8-amino-3-[(6R,8aS)-3-oxooctahydroindolizin-6-yl]imidazo[1,5-a]pyrazin-1-yl}-N-[4-(1-hydroxy-1-methylethyl)pyridin-2-yl]benzamide;

4-{8-amino-3-[(6R,8aS)-3-oxooctahydroindolizin-6-yl]imidazo[1,5-a]pyrazin-1-yl}-N-[4-(1-methoxyethyl)pyridin-2-yl]benzamide;

4-{8-amino-3-[(6R,8aS)-2,2-dimethyl-3-oxooctahydroindolizin-6-yl]imidazo[1,5-a]pyrazin-1-yl}-3-methoxy-N-[4-(trifluoromethyl)pyridin-2-yl]benzamide;

4-{8-amino-3-[(6S,8aR)-2,2-dimethyl-3-oxooctahydroindolizin-6-yl]imidazo[1,5-a]pyrazin-1-yl}-3-methoxy-N-[4-(trifluoromethyl)pyridin-2-yl]benzamide;

4-{8-amino-3-[(7R,9aS)-4-oxo-2-(pyridin-4-ylcarbonyl)octahydro-2H-pyrido[1,2-a]pyrazin-7-yl]imidazo[1,5-a]pyrazin-1-yl}-N-[4-(trifluoromethyl)pyridin-2-yl]benzamide;

methyl-2-{[(4-{8-amino-3-[(6R,8aS)-3-oxooctahydroindolizin-6-yl]imidazo[1,5-a]pyrazin-1-yl}phenyl)carbonyl]amino}pyridine-4-carboxylate;

4-{8-amino-3-[(6R,8aS)-3-oxooctahydroindolizin-6-yl]imidazo[1,5-a]pyrazin-1-yl}-N-[5-(trifluoromethyl)pyridazin-3-yl]benzamide;

4-{8-amino-3-[(7R,9aS)-4-oxo-2-(phenylcarbonyl)octahydro-2H-pyrido[1,2-a]pyrazin-7-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-isoquinolin-3-ylbenzamide;

4-{8-amino-3-[(3R,8aR)-6-oxohexahydro-1H-pyrrolo[2,1-c][1,4]oxazin-3-yl]imidazo[1,5-a]pyrazin-1-yl}-N-[4-(trifluoromethyl)pyridin-2-yl]benzamide;

{(7R,9aS)-7-[8-amino-1-(4-{[4-(trifluoromethyl)pyridin-2-yl]carbamoyl}phenyl)imidazo[1,5-a]pyrazin-3-yl]-4-oxooctahydro-2H-pyrido[1,2-a]pyrazin-2-yl}acetic acid;

4-{8-amino-3-[(1S,6R,8aS)-1-ethenyl-3-oxohexahydro[1,3]oxazolo[3,4-a]pyrazin-6-yl]imidazo[1,5-a]pyrazin-1-yl}-N-[4-(trifluoromethyl)pyridin-2-yl]benzamide;

4-{8-amino-3-[(1R,6R,8aS)-1-ethenyl-3-oxohexahydro[1,3]oxazolo[3,4-a]pyrazin-6-yl]imidazo[1,5-a]pyrazin-1-yl}-N-[4-(trifluoromethyl)pyridin-2-yl]benzamide;

4-{8-amino-3-[(4aR,7R)-2-methyl-1-oxooctahydro-1H-pyrido[1,2-c]pyrimidin-7-yl]imidazo[1,5-a]pyrazin-1-yl}-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-chloro-N-[4-(trifluoromethyl)pyridin-2-yl]benzamide;

4-{8-amino-3-[(6R,8aS)-2,2-dimethyl-3-oxooctahydroindolizin-6-yl]imidazo[1,5-a]pyrazin-1-yl}-3-ethoxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(1,1-difluoroethyl)-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-5-ethoxy-2-fluoro-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-3-[(~2~-H_3_)methyloxy]-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[5-cyano-4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-hydroxy-N-[4-(trifluoromethyl)pyridin-2-yl]benzamide;

5-{8-amino-3-[(6R,8aS)-3-oxooctahydroindolizin-6-yl]imidazo[1,5-a]pyrazin-1-yl}-N-[4-(trifluoromethyl)pyridin-2-yl]pyridine-2-carboxamide;

4-{8-amino-3-[(6R,8aS)-3-oxooctahydroindolizin-6-yl]imidazo[1,5-a]pyrazin-1-yl}-N-[6-methyl-4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(cyclopropyloxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[3-methyl-4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-cyano-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N~1~-[4-(trifluoromethyl)pyridin-2-yl]benzene-1,3-dicarboxamide;

4-{8-amino-3-[(6R,8aS)-3-oxooctahydroindolizin-6-yl]imidazo[1,5-a]pyrazin-1-yl}-N-[6-(1-methylethyl)-4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[6-cyclobutyl-4-(trifluoromethyl)pyridin-2-yl]benzamide;

2-{8-amino-3-[(6R,8aS)-3-oxooctahydroindolizin-6-yl]imidazo[1,5-a]pyrazin-1-yl}-5-{[4-(trifluoromethyl)pyridin-2-yl]carbamoyl}benzoic acid;

4-{8-amino-5-chloro-3-[(6R,8aS)-3-oxooctahydroindolizin-6-yl]imidazo[1,5-a]pyrazin-1-yl}-3-ethoxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-(6-methoxypyridin-2-yl)benzamide;

4-{8-amino-3-[(6R,8aS)-3-oxooctahydroindolizin-6-yl]imidazo[1,5-a]pyrazin-1-yl}-2-fluoro-5-methoxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-2-fluoro-5-methoxy-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-5-ethoxy-2-fluoro-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-fluoro-5-methoxy-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-N-(4-cyclopropylpyridin-2-yl)-5-ethoxy-2-fluorobenzamide;

4-{8-amino-3-[(6R,8aS)-3-oxooctahydroindolizin-6-yl]imidazo[1,5-a]pyrazin-1-yl}-N-(4-cyclopropylpyridin-2-yl)-5-ethoxy-2-fluorobenzamide;

4-{8-amino-3-[(6R,8aS)-3-oxooctahydroindolizin-6-yl]imidazo[1,5-a]pyrazin-1-yl}-3-(cyclohexyloxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(1-methylethoxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(cyclobutyloxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(cyclopentyloxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(2,2-dimethylpropoxy)-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-methoxy-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-(cyclopropyloxy)-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-(cyclopropyloxy)-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-3-(cyclopropyloxy)-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-3-(cyclopropyloxy)-N-(4-cyclopropylpyridin-2-yl)benzamide;

4-{8-amino-3-[(6R,8aS)-3-oxooctahydroindolizin-6-yl]imidazo[1,5-a]pyrazin-1-yl}-3-(cyclopropyloxy)-N-(4-cyclopropylpyridin-2-yl)benzamide;

4-{8-amino-3-[(6R,8aS)-3-oxooctahydroindolizin-6-yl]imidazo[1,5-a]pyrazin-1-yl}-3-(azetidin-3-yloxy)-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-5-(cyclopropyloxy)-2-fluoro-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-5-ethoxy-2-fluoro-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-5-ethoxy-2-fluoro-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-N-(5-methyl-1,3-thiazol-2-yl)benzamide;

2-{8-amino-3-[(6R,8aS)-3-oxooctahydroindolizin-6-yl]imidazo[1,5-a]pyrazin-1-yl}-5-{[4-(trifluoromethyl)pyridin-2-yl]carbamoyl}phenyl acetate;

4-{8-(acetylamino)-3-[(6R,8aS)-3-oxooctahydroindolizin-6-yl]imidazo[1,5-a]pyrazin-1-yl}-3-hydroxy-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-hydroxy-N-(2-methoxyethyl)-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-ethoxy-N-(5-methyl-1,3-thiazol-2-yl)benzamide;

4-{8-amino-3-[(6R,8aS)-3-oxooctahydroindolizin-6-yl]imidazo[1,5-a]pyrazin-1-yl}-3-ethoxy-N-(5-methyl-1,3-thiazol-2-yl)benzamide;

4-{8-amino-5-fluoro-3-[(6R,8aS)-3-oxooctahydroindolizin-6-yl]imidazo[1,5-a]pyrazin-1-yl}-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-3-ethoxy-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-3-methoxy-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide;

4-{8-amino-5-fluoro-3-[(6R,8aS)-3-oxooctahydroindolizin-6-yl]imidazo[1,5-a]pyrazin-1-yl}-3-ethoxy-N-(5-methyl-1,3-thiazol-2-yl)benzamide;

4-{8-amino-5-fluoro-3-[(6R,8aS)-3-oxooctahydroindolizin-6-yl]imidazo[1,5-a]pyrazin-1-yl}-3-hydroxy-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-3-fluoro-N-[4-(trifluoromethyl)pyridin-2-yl]benzamide;

4-{8-amino-5-fluoro-3-[(6R,8aS)-3-oxooctahydroindolizin-6-yl]imidazo[1,5-a]pyrazin-1-yl}-N-(4-cyclopropylpyridin-2-yl)-3-fluorobenzamide;

4-{8-amino-5-fluoro-3-[(6R,8aS)-3-oxooctahydroindolizin-6-yl]imidazo[1,5-a]pyrazin-1-yl}-N-(4-cyclopropylpyridin-2-yl)benzamide;

4-{8-amino-5-fluoro-3-[(6R,8aS)-3-oxooctahydroindolizin-6-yl]imidazo[1,5-a]pyrazin-1-yl}-5-ethoxy-2-fluoro-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-N-[3-(trifluoromethyl)-1H-pyrazol-5-yl]benzamide;

4-{8-amino-3-[(6R,8aS)-3-oxooctahydroindolizin-6-yl]imidazo[1,5-a]pyrazin-1-yl}-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-N-1H-imidazol-2-ylbenzamide;

4-{8-amino-3-[(6R,8aS)-3-oxooctahydroindolizin-6-yl]imidazo[1,5-a]pyrazin-1-yl}-N-[5-(trifluoromethyl)isoxazol-3-yl]benzamide;

4-{8-amino-3-[(6R,8aS)-3-oxooctahydroindolizin-6-yl]imidazo[1,5-a]pyrazin-1-yl}-N-[3-(trifluoromethyl)isoxazol-5-yl]benzamide;

4-{8-amino-3-[(6R,8aS)-3-oxooctahydroindolizin-6-yl]imidazo[1,5-a]pyrazin-1-yl}-N-(1,5-dimethyl-1H-pyrazol-3-yl)benzamide;

4-{8-amino-3-[(6R,8aS)-3-oxooctahydroindolizin-6-yl]imidazo[1,5-a]pyrazin-1-yl}-N-(3-methyl-1,2,4-thiadiazol-5-yl)benzamide;

4-{8-amino-3-[(6R,8aS)-3-oxooctahydroindolizin-6-yl]imidazo[1,5-a]pyrazin-1-yl}-N-[4-(trifluoromethyl)-1H-imidazol-2-yl]benzamide;

4-{8-amino-3-[(6R,8aS)-3-oxooctahydroindolizin-6-yl]imidazo[1,5-a]pyrazin-1-yl}-N-(3-ethyl-1,2,4-thiadiazol-5-yl)benzamide;

4-{8-amino-3-[(6R,8aS)-3-oxooctahydroindolizin-6-yl]imidazo[1,5-a]pyrazin-1-yl}-N-[3-(1-methylethyl)-1,2,4-thiadiazol-5-yl]benzamide;

4-{8-amino-3-[(6R,8aS)-3-oxooctahydroindolizin-6-yl]imidazo[1,5-a]pyrazin-1-yl}-N-[1-cyclopentyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-N-(5-cyclopropyl-1-methyl-1H-pyrazol-3-yl)benzamide;

4-{8-amino-3-[(6R,8aS)-3-oxooctahydroindolizin-6-yl]imidazo[1,5-a]pyrazin-1-yl}-N-(5-methyl-1,3,4-thiadiazol-2-yl)benzamide;

4-{8-amino-5-chloro-3-[(6R,8aS)-3-oxooctahydroindolizin-6-yl]imidazo[1,5-a]pyrazin-1-yl}-N-[1-methyl-5-(trifluoromethyl)-1H-pyrazol-3-yl]benzamide;

ethyl-2-{[(4-{8-amino-3-[(6R,8aS)-3-oxooctahydroindolizin-6-yl]imidazo[1,5-a]pyrazin-1-yl}phenyl)carbonyl]amino}-4-(trifluoromethyl)-1,3-oxazole-5-carboxylate;

4-{8-amino-3-[(6R,8aS)-3-oxooctahydroindolizin-6-yl]imidazo[1,5-a]pyrazin-1-yl}-N-[1-ethyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-3-methyl-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-3-methyl-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-methoxy-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-3-methoxy-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-3-chloro-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-3-chloro-N-[1-methyl-5-(trifluoromethyl)-1H-pyrazol-3-yl]benzamide;

4-{8-amino-5-chloro-3-[(6R,8aS)-3-oxooctahydroindolizin-6-yl]imidazo[1,5-a]pyrazin-1-yl}-5-chloro-2-fluoro-N-[1-methyl-5-(trifluoromethyl)-1H-pyrazol-3-yl]benzamide;

4-{8-amino-3-[(6R,8aS)-3-oxooctahydroindolizin-6-yl]imidazo[1,5-a]pyrazin-1-yl}-5-chloro-2-fluoro-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-3-chloro-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-chloro-N-(5-methyl-1,3-thiazol-2-yl)benzamide;

4-{8-amino-5-chloro-3-[(6R,8aS)-3-oxooctahydroindolizin-6-yl]imidazo[1,5-a]pyrazin-1-yl}-3-chloro-N-(5-methyl-1,3-thiazol-2-yl)benzamide;

4-{8-amino-5-chloro-3-[(6R,8aS)-3-oxooctahydroindolizin-6-yl]imidazo[1,5-a]pyrazin-1-yl}-2-fluoro-5-methyl-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-2-fluoro-5-methyl-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(2-methoxyethoxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(2-hydroxyethoxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-(2-ethoxyethoxy)-N-[4-(trifluoromethyl)pyridin-2-yl]benzamide;

4-{8-amino-3-[(6R,8aS)-3-oxooctahydroindolizin-6-yl]imidazo[1,5-a]pyrazin-1-yl}-3-methoxy-N-(5-methyl-1,3-thiazol-2-yl)benzamide;

4-{8-amino-5-chloro-3-[(6R,8aS)-3-oxooctahydroindolizin-6-yl]imidazo[1,5-a]pyrazin-1-yl}-3-methoxy-N-(5-methyl-1,3-thiazol-2-yl)benzamide;

4-{8-amino-3-[(6R,8aS)-3-oxooctahydroindolizin-6-yl]imidazo[1,5-a]pyrazin-1-yl}-3-(but-3-yn-1-yloxy)-N-[4-(trifluoromethyl)pyridin-2-yl]benzamide;

4-{8-amino-5-methyl-3-[(6R,8aS)-3-oxooctahydroindolizin-6-yl]imidazo[1,5-a]pyrazin-1-yl}-3-ethoxy-N-[1-methyl-5-(trifluoromethyl)-1H-pyrazol-3-yl]benzamide;

4-{8-amino-3-[(6R,8aS)-3-oxooctahydroindolizin-6-yl]-5-(trifluoromethyl)imidazo[1,5-a]pyrazin-1-yl}-3-ethoxy-N-[4-(trifluoromethyl)pyridin-2-yl]benzamide;

4-{8-amino-5-chloro-3-[(6R,8aS)-3-oxooctahydroindolizin-6-yl]imidazo[1,5-a]pyrazin-1-yl}-N-(4-ethylpyridin-2-yl)-3-methoxybenzamide;

4-{8-amino-5-chloro-3-[(6R,8aS)-3-oxooctahydroindolizin-6-yl]imidazo[1,5-a]pyrazin-1-yl}-3-methoxy-N-(4-methoxypyridin-2-yl)benzamide;

4-{8-amino-5-chloro-3-[(6R,8aS)-3-oxooctahydroindolizin-6-yl]imidazo[1,5-a]pyrazin-1-yl}-N-(4-cyclobutylpyridin-2-yl)-3-methoxybenzamide;

4-{8-amino-5-chloro-3-[(6R,8aS)-3-oxooctahydroindolizin-6-yl]imidazo[1,5-a]pyrazin-1-yl}-3-methoxy-N-(5-methylpyridin-2-yl)benzamide;

4-{8-amino-3-[(6R,8aS)-3-oxooctahydroindolizin-6-yl]-5-(trifluoromethyl)imidazo[1,5-a]pyrazin-1-yl}-3-chloro-N-[4-(trifluoromethyl)pyridin-2-yl]benzamide;

4-{8-amino-3-[(6R,8aS)-3-oxooctahydroindolizin-6-yl]-5-(trifluoromethyl)imidazo[1,5-a]pyrazin-1-yl}-N-(4-cyclopropylpyridin-2-yl)-3-fluorobenzamide;

4-{8-amino-3-[(6R,8aS)-3-oxooctahydroindolizin-6-yl]-5-(trifluoromethyl)imidazo[1,5-a]pyrazin-1-yl}-3-methoxy-N-[4-(trifluoromethyl)pyridin-2-yl]benzamide;

4-{8-amino-3-[(6R,8aS)-3-oxooctahydroindolizin-6-yl]
imidazo[1,5-a]pyrazin-1-yl}-3-fluoro-5-methyl-N-[4-
(trifluoromethyl)pyridin-2-yl]benzamide;

4-{8-amino-3-[(6R,8aS)-3-oxooctahydroindolizin-6-yl]-
5-(trifluoromethyl)imidazo[1,5-a]pyrazin-1-yl}-3-
ethoxy-N-[1-methyl-5-(trifluoromethyl)-1H-pyrazol-
3-yl]benzamide;

4-{8-amino-5-chloro-3-[(6R,8aS)-3-oxooctahydroindol-
izin-6-yl]imidazo[1,5-a]pyrazin-1-yl}-3-(1,1-difluo-
roethoxy)-N-[4-(trifluoromethyl)pyridin-2-yl]benz-
amide;

4-{8-amino-5-chloro-3-[(6R,8aS)-3-oxooctahydroindol-
izin-6-yl]imidazo[1,5-a]pyrazin-1-yl}-3-fluoro-5-
methoxy-N-[4-(trifluoromethyl)pyridin-2-yl]benz-
amide;

4-{8-amino-5-chloro-3-[(6R,8aS)-3-oxooctahydroindol-
izin-6-yl]imidazo[1,5-a]pyrazin-1-yl}-2-chloro-5-
methoxy-N-[4-(trifluoromethyl)pyridin-2-yl]benz-
amide;

4-{8-amino-3-[(6R,8aS)-2,2-dimethyl-3-oxooctahydroin-
dolizin-6-yl]imidazo[1,5-a]pyrazin-1-yl}-3-fluoro-5-
methoxy-N-[4-(trifluoromethyl)pyridin-2-yl]benz-
amide;

4-{8-amino-5-fluoro-3-[(6R,8aS)-3-oxooctahydroindol-
izin-6-yl]imidazo[1,5-a]pyrazin-1-yl}-3-fluoro-5-
methoxy-N-[4-(trifluoromethyl)pyridin-2-yl]benz-
amide;

4-(8-amino-5-fluoro-3-((6R,8aS)-3-oxooctahydroindol-
izin-6-yl)imidazo[1,5-a]pyrazin-1-yl)-3-ethoxy-5-
fluoro-N-(4-(trifluoromethyl)pyridin-2-yl)benzamide;

4-(8-amino-3-((6R,8aS)-1,1-dimethyl-3-oxooctahydroin-
dolizin-6-yl)imidazo[1,5-a]pyrazin-1-yl)-3-ethoxy-N-
(4-(trifluoromethyl)pyridin-2-yl)benzamide; and 4-(8-amino-3-((6R,8aS)-1,1-dimethyl-3-oxooctahydroin-
dolizin-6-yl)imidazo[1,5-a]pyrazin-1-yl)-3-ethoxy-5-
fluoro-N-(4-(trifluoromethyl)pyridin-2-yl)benzamide;

or pharmaceutically acceptable salts thereof.

23. A compound selected from the group consisting of:

4-{8-amino-3-[(6R,8aS)-3-oxooctahydroindolizin-6-yl]
imidazo[1,5-a]pyrazin-1-yl}-N-[4-(trifluoromethyl)
pyridin-2-yl]benzamide;

4-{8-amino-3-[(6R,8aS)-3-oxooctahydroindolizin-6-yl]
imidazo[1,5-a]pyrazin-1-yl}-3-ethoxy-N-[4-(trifluo-
romethyl)pyridin-2-yl]benzamide;

4-{8-amino-3-[(6R,8aS)-1,1-dimethyl-3-oxohexahydro
[1,3]oxazolo[3,4-a]pyridin-6-yl]imidazo[1,5-a]
pyrazin-1-yl}-3-methoxy-N-[4-(trifluoromethyl)pyri-
din-2-yl]benzamide;

4-{8-amino-3-[(6S,8aR)-2,2-dimethyl-3-oxooctahydroin-
dolizin-6-yl]imidazo[1,5-a]pyrazin-1-yl}-N-[4-(trif-
luoromethyl)pyridin-2-yl]benzamide;

4-{8-amino-3-[(6R,8aS)-2,2-dimethyl-3-oxooctahydroin-
dolizin-6-yl]imidazo[1,5-a]pyrazin-1-yl}-3-methoxy-
N-[4-(trifluoromethyl)pyridin-2-yl]benzamide;

4-{8-amino-3-[(6R,8aS)-3-oxooctahydroindolizin-6-yl]
imidazo[1,5-a]pyrazin-1-yl}-3-methoxy-N-[4-(trifluo-
romethyl)pyridin-2-yl]benzamide;

4-{8-amino-3-[(6R,8aS)-2,2-dimethyl-3-oxooctahydroin-
dolizin-6-yl]imidazo[1,5-a]pyrazin-1-yl}-3-ethoxy-N-
[4-(trifluoromethyl)pyridin-2-yl]benzamide;

4-{8-amino-5-chloro-3-[(6R,8aS)-3-oxooctahydroindol-
izin-6-yl]imidazo[1,5-a]pyrazin-1-yl}-5-ethoxy-2-
fluoro-N-[1-methyl-5-(trifluoromethyl)-1H-pyrazol-3-
yl]benzamide;

4-{8-amino-5-chloro-3-[(6R,8aS)-3-oxooctahydroindol-
izin-6-yl]imidazo[1,5-a]pyrazin-1-yl}-3-ethoxy-N-[4-
(trifluoromethyl)pyridin-2-yl]benzamide;

4-{8-amino-3-[(6R,8aS)-3-oxooctahydroindolizin-6-yl]
imidazo[1,5-a]pyrazin-1-yl}-3-fluoro-5-methoxy-N-
[4-(trifluoromethyl)pyridin-2-yl]benzamide;

4-{8-amino-5-chloro-3-[(6R,8aS)-3-oxooctahydroindol-
izin-6-yl]imidazo[1,5-a]pyrazin-1-yl}-3-ethoxy-N-[1-
methyl-5-(trifluoromethyl)-1H-pyrazol-3-yl]benz-
amide;

4-{8-amino-5-chloro-3-[(6R,8aS)-3-oxooctahydroindol-
izin-6-yl]imidazo[1,5-a]pyrazin-1-yl}-3-methoxy-N-
[4-(trifluoromethyl)pyridin-2-yl]benzamide;

4-{8-amino-5-fluoro-3-[(6R,8aS)-3-oxooctahydroindol-
izin-6-yl]imidazo[1,5-a]pyrazin-1-yl}-3-ethoxy-N-[4-
(trifluoromethyl)pyridin-2-yl]benzamide;

4-{8-amino-3-[(6R,8aS)-3-oxooctahydroindolizin-6-yl]-
5-(trifluoromethyl)imidazo[1,5-a]pyrazin-1-yl}-3-
ethoxy-N-[4-(trifluoromethyl)pyridin-2-yl]benzamide;
and 4-(8-amino-5-fluoro-3-((6R,8aS)-3-oxooctahydroindol-
izin-6-yl)imidazo[1,5-a]pyrazin-1-yl)-3-ethoxy-5-
fluoro-N-(4-(trifluoromethyl)pyridin-2-yl)benzamide;

or a pharmaceutically acceptable salt thereof.

* * * * *